(12) United States Patent
Holzapfel et al.

(10) Patent No.: US 11,618,880 B2
(45) Date of Patent: Apr. 4, 2023

(54) COMPOSITIONS COMPRISING BACTERIAL STRAINS AND USE THEREOF IN CONTROLLING PATHOGENIC MICROORGANISMS

(71) Applicant: Better Air International Limited, Central (HK)

(72) Inventors: Wilhelm H. Holzapfel, Gyung-buk (KR); Yosep Ji, Gyung-buk (KR); Yuli Horesh, Tel-Aviv (IL); Michael Hoffman, Moshav Udim (IL); Shimrit Laor, Netanya (IL)

(73) Assignee: Better Air International Limited, Central (HK)

( * ) Notice: Subject to any disclaimer, the term of this patent is extended or adjusted under 35 U.S.C. 154(b) by 171 days.

(21) Appl. No.: 17/019,281

(22) Filed: Sep. 13, 2020

(65) Prior Publication Data
US 2020/0407807 A1    Dec. 31, 2020

Related U.S. Application Data

(63) Continuation of application No. PCT/IB2019/052010, filed on Mar. 12, 2019.

(60) Provisional application No. 62/641,443, filed on Mar. 12, 2018.

(51) Int. Cl.
| | |
|---|---|
| *C12N 1/20* | (2006.01) |
| *A61P 31/04* | (2006.01) |
| *A61K 35/742* | (2015.01) |
| *C12R 1/07* | (2006.01) |
| *A61P 11/00* | (2006.01) |
| *A61K 9/00* | (2006.01) |

(52) U.S. Cl.
CPC ............ *C12N 1/205* (2021.05); *A61K 9/0073* (2013.01); *A61K 35/742* (2013.01); *A61P 11/00* (2018.01); *A61P 31/04* (2018.01); *C12N 1/20* (2013.01); *C12R 2001/07* (2021.05)

(58) Field of Classification Search
None
See application file for complete search history.

(56) References Cited

U.S. PATENT DOCUMENTS

| | | |
|---|---|---|
| 2,293,722 A | 8/1942 | Erickson |
| D221,836 S | 9/1971 | Giles et al. |
| D239,922 S | 5/1976 | Utley |
| D250,394 S | 11/1978 | Menius |
| D279,452 S | 7/1985 | Beechuk |
| D284,362 S | 6/1986 | Biesecker |
| D309,711 S | 8/1990 | Biesecker |
| D376,760 S | 12/1996 | Sykes |
| D433,336 S | 11/2000 | Weber |
| 6,405,944 B1 | 6/2002 | Benahkhoudja |
| D472,471 S | 4/2003 | McClure et al. |
| D473,143 S | 4/2003 | McClure et al. |
| D489,992 S | 5/2004 | Brauner et al. |
| D571,662 S | 6/2008 | Clark et al. |
| 7,858,336 B1 | 12/2010 | Garner et al. |
| D630,946 S | 1/2011 | Crawford |
| D656,599 S | 3/2012 | Browder |
| D663,215 S | 7/2012 | Clay et al. |
| D667,101 S | 9/2012 | Browder |
| D673,253 S | 12/2012 | Mack |
| D678,496 S | 3/2013 | Browder |
| 8,986,610 B2 | 3/2015 | Ben Haim |
| 9,486,552 B1 | 11/2016 | Ansley et al. |
| D805,909 S | 12/2017 | Matsuishi |
| D875,532 S | 2/2020 | Lehanneur |
| D879,613 S | 3/2020 | Lehanneur |
| 2003/0189066 A1 | 10/2003 | Schiller |
| 2005/0160553 A1 | 7/2005 | Gregory |
| 2005/0252930 A1 | 11/2005 | Contadini et al. |
| 2007/0217945 A1 | 9/2007 | Selander |
| 2009/0238716 A1 | 9/2009 | Weening |
| 2009/0324815 A1 | 12/2009 | Nielsen et al. |
| 2010/0021576 A1 | 1/2010 | Chang et al. |
| 2011/0214245 A1 | 9/2011 | Bassett |
| 2012/0152882 A1 | 6/2012 | Tune |
| 2012/0168971 A1 | 7/2012 | Hansen et al. |
| 2013/0015956 A1 | 1/2013 | Wegelin et al. |
| 2013/0068783 A1 | 3/2013 | Gasper et al. |
| 2014/0263426 A1 | 9/2014 | Gasper |
| 2016/0101925 A1 | 4/2016 | Franz et al. |
| 2017/0035262 A1 | 2/2017 | Li et al. |
| 2017/0035925 A1 | 2/2017 | Sevy |
| 2017/0348364 A1 | 12/2017 | Garner et al. |
| 2020/0405781 A1* | 12/2020 | Holzapfel .............. C12N 1/205 |
| 2020/0407808 A1* | 12/2020 | Holzapfel ................ C12N 1/20 |
| 2020/0407809 A1* | 12/2020 | Holzapfel ............ A61K 35/742 |
| 2021/0046256 A1 | 2/2021 | Hoffman et al. |
| 2021/0046497 A1 | 2/2021 | Hoffman et al. |
| 2021/0204774 A1 | 7/2021 | Dery et al. |

FOREIGN PATENT DOCUMENTS

| | | |
|---|---|---|
| CN | 1177636 | 4/1998 |
| CN | 1642827 | 7/2005 |
| CN | 1934241 | 3/2007 |
| CN | 103589655 | 2/2014 |
| CN | 103703121 | 4/2014 |

(Continued)

OTHER PUBLICATIONS

Restriction Official Action dated Jul. 13, 2021 from the US Patent and Trademark Office Re. U.S. Appl. No. 17/019,568. (5 pages).

(Continued)

*Primary Examiner* — Gary B Nickol
*Assistant Examiner* — Jegatheesan Seharaseyon

(57) ABSTRACT

An isolated bacterial strain *Bacillus amyloliquefaciens* 298 is provided. A sample of the strain having been deposited as KCTC 13469BP at the Korean Collection for Type Cultures or a functional homolog of same wherein said isolated microbial strain is purified to a level of at least 99%. Also provided are compositions and articles comprising the bacterial strain and methods of using same.

2 Claims, 6 Drawing Sheets
(2 of 6 Drawing Sheet(s) Filed in Color)
Specification includes a Sequence Listing.

(56) References Cited

FOREIGN PATENT DOCUMENTS

| | | |
|---|---|---|
| CN | 104487566 | 4/2015 |
| CN | 104688895 | 6/2015 |
| CN | 104736162 | 6/2015 |
| CN | 204501790 | 7/2015 |
| CN | 303340433 S | 8/2015 |
| CN | 105087423 | 11/2015 |
| CN | 105219669 | 1/2016 |
| CN | 205032305 | 2/2016 |
| CN | 107567493 | 1/2018 |
| CN | 107723267 | 2/2018 |
| KR | 20-2009-0007893 | 8/2009 |
| KR | 10-2014-0128870 | 11/2014 |
| KR | 10-2017-0130341 | 11/2017 |
| WO | WO 01/34182 | 5/2001 |
| WO | WO 2016/060934 | 4/2016 |
| WO | WO 2016/118864 | 7/2016 |
| WO | WO 2019/175774 | 9/2019 |
| WO | WO 2019/175775 | 9/2019 |
| WO | WO 2019/175777 | 9/2019 |
| WO | WO 2019/175777 A8 | 9/2019 |
| WO | WO 2019/175780 | 9/2019 |
| WO | WO 2019/175782 | 9/2019 |
| WO | WO 2019/175782 A8 | 9/2019 |
| WO | WO 2019/175783 | 9/2019 |
| WO | WO 2019/224691 | 11/2019 |
| WO | WO 2019/175783 A8 | 10/2020 |

OTHER PUBLICATIONS

International Preliminary Report on Patentability dated Dec. 3, 2020 From the International Bureau of WIPO Re. Application No. PCT/IB2019/054141. (9 Pages).
Restriction Official Action dated Jul. 7, 2021 from the US Patent and Trademark Office Re. U.S. Appl. No. 17/019,280. (5 pages).
International Preliminary Report on Patentability dated Sep. 24, 2020 From the International Bureau of WIPO Re. Application No. PCT/IB2019/052007. (6 Pages).
Examination Report dated Sep. 7, 2018 From the Government of India, Patent Office, Intellectual Property Building Re.: Application No. 309690.
Examination Report dated Sep. 11, 2018 From the Government of India, Patent Office, Intellectual Property Building Re.: Application No. 309744.
International Preliminary Report on Patentability dated Sep. 24, 2020 From the International Bureau of WIPO Re. Application No. PCT/IB2019/052016. (7 Pages).
International Preliminary Report on Patentability dated Sep. 24, 2020 From the International Bureau of WIPO Re. Application No. PCT/IB2019/052008. (6 Pages).
International Preliminary Report on Patentability dated Sep. 24, 2020 From the International Bureau of WIPO Re. Application No. PCT/IB2019/052010. (7 Pages).
International Preliminary Report on Patentability dated Sep. 24, 2020 From the International Bureau of WIPO Re. Application No. PCT/IB2019/052014. (7 Pages).
International Preliminary Report on Patentability dated Sep. 24, 2020 From the International Bureau of WIPO Re. Application No. PCT/IB2019/052017. (7 Pages).

International Search Report and the Written Opinion dated Jul. 3, 2019 From the International Searching Authority Re. Application No. PCT/IB2019/052014. (16 Pages).
International Search Report and the Written Opinion dated Jul. 3, 2019 From the International Searching Authority Re. Application No. PCT/IB2019/052017. (14 Pages).
International Search Report and the Written Opinion dated Sep. 17, 2019 From the International Searching Authority Re. Application No. PCT/IB2019/054141. (11 Pages).
International Search Report and the Written Opinion dated Jun. 26, 2019 From the International Searching Authority Re. Application No. PCT/IB2019/052016. (15 Pages).
International Search Report and the Written Opinion dated Jun. 27, 2019 From the International Searching Authority Re. Application No. PCT/IB2019/052007. (12 Pages).
International Search Report and the Written Opinion dated Jun. 27, 2019 From the International Searching Authority Re. Application No. PCT/IB2019/052008. (10 Pages).
International Search Report and the Written Opinion dated Jun. 27, 2019 From the International Searching Authority Re. Application No. PCT/IB2019/052010. (17 Pages).
Notice of Amendment dated Dec. 11, 2018 From the State Intellectual Property Office of the People's Republic of China Re. Application No. 201830508569.8. (2 pages).
Notification of Reason for Rejection dated Jan. 30, 2019 From the Japanese Patent Office Re. Application No. 2018-019747. (2 Pages).
Official Action dated Jun. 12, 2020 from the US Patent and Trademark Office Re. U.S. Appl. No. 29/640,027. (19 pages).
Official Action dated Jun. 12, 2020 from the US Patent and Trademark Office Re. U.S. Appl. No. 29/640,032. (13 pages).
Official Action dated Jun. 25, 2020 from the US Patent and Trademark Office Re. U.S. Appl. No. 29/653,164. (9 pages).
Cho "Characterization of Potential Probiotics Bacillus Subtilis CS90 From Soybean Paste (Doenjang) and Its Antimicrobial Activity Against Food-Borne Pathogens", Journal of Applied Biological Chemistry, 51(5): 285-291, 2008.
Gu et al. "The Preventive Effect and Therapeutic Effect of Spraying Agent of Bacillus Pab02 on Respiratory Infection in Broilers", Proceedings of the 10th in the 4th National Academic Seminar and Animal Micro-Ecology Enterprise Development Forum, p. 450-458, Aug. 1, 2010.
Jeon et al. "Screening and Characterization of Potential Bacillus Starter Cultures for Fermenting Low-Salt Soybean Past (Doenjang)", Journal of Microbiology and Biotechnology, 26(4): 666-674, Apr. 2016.
Ji et al. "Probiotic Bacillus Amyloliquefaciens SC06 Prevents Bacterial Translocation in Weaned Mice", Indian Journal of Microbiology, 53(3): 323-328, Published Online Mar. 16, 2013.
Wong et al. "An Antifungal Protein From Bacillus Amyloliquefaciens", Journal of Applied Microbiology, 105(6): 1888-1898, Dec. 2008.
Xie et al. "Isolation and Characterization of a Bacteriocin Produced by an Isolated Bacillus Subtihs LFB112 That Exhibits Antimicrobial Activity Against Domestic Animal Pathogens", African Journal of Biotechnology, 8(20): 5611-5619, Oct. 19, 2009.
Official Action dated Sep. 22, 2021 from the US Patent and Trademark Office Re. U.S. Appl. No. 17/019,280. (26 pages).

\* cited by examiner

COMPOSITIONS COMPRISING BACTERIAL STRAINS AND USE THEREOF IN CONTROLLING PATHOGENIC MICROORGANISMS

RELATED APPLICATION/S

This application is a US Continuation of PCT Patent Application No. PCT/IB2019/052010 having International filing date of Mar. 12, 2019, which claims the benefit of priority under 35 USC § 119(e) of U.S. Provisional Patent Application No. 62/641,443 filed on Mar. 12, 2018. The contents of the above applications are all incorporated by reference as if fully set forth herein in their entirety.

PCT Patent Application No. PCT/M2019/052010 filed on Mar. 12, 2019 is also related to co-filed PCT Patent Applications Nos. PCT/M2019/052008, PCT/IB2019/052007, PCT/IB2019/052017, PCT/IB2019/052014 and PCT/IB2019/052016 entitled "CARTRIDGE FOR AN AUTOMATED AEROSOL DISPENSING DEVICE"; "ELECTRONIC SAFETY FEATURE FOR AN AUTOMATED AEROSOL DISPENSING DEVICE"; "COMPOSITIONS COMPRISING BACTERIAL STRAINS AND USE THEREOF IN CONTROLLING PATHOGENIC MICROORGANISMS"; "COMPOSITIONS COMPRISING BACTERIAL STRAINS AND USE THEREOF IN CONTROLLING PATHOGENIC MICROORGANISMS" and "COMPOSITIONS COMPRISING BACTERIAL STRAINS AND USE THEREOF IN CONTROLLING PATHOGENIC MICROORGANISMS". The contents of the above applications are all incorporated by reference as if fully set forth herein in their entirety.

SEQUENCE LISTING STATEMENT

The ASCII file, entitled 84592SequenceListing.txt, created on Sep. 13, 2020, comprising 5,109,776 bytes, submitted concurrently with the filing of this application is incorporated herein by reference.

BUDAPEST TREATY DEPOSIT

The biological materials that are the subject of the instant application were deposited and have been accepted by the International Depository Authority under the Budapest Treaty. KCTC 13469BP has been deposited in the Korean Collection for Type Cultures Korea Research Institute of Bioscience and Biotechnology (KRIBB) 181, Ipsin-gil, Jeongeup-si, Jeolllahuk-do 56212, Republic of Korea on Jan. 25, 2018. These materials will be irrevocably and without restriction or condition released to the public upon the issuance of a patent, and the materials will be replaced if useable samples cannot be dispensed by the Depository.

FIELD AND BACKGROUND OF THE INVENTION

The present invention, in some embodiments thereof, relates to compositions comprising bacterial strains and use thereof in controlling pathogenic microorganisms.

A respiratory tract infection (RTI) refers to any of a number of infectious diseases involving the respiratory tract. An infection of this type is normally further classified as an upper respiratory tract infection (URI or URTI) or a lower respiratory tract infection (LRI or LRTI). Lower respiratory infections, such as pneumonia, tend to be far more serious conditions than upper respiratory infections, such as the common cold.

Various *Bacillus subtilis* group strains were reported to antagonize pathogenic bacteria such as *Xanthomonas*, *Pseudomonas* and *Bacillus cereus* group microorganisms and molds such as *Fusarium, Botrytis cinerea, Phoma tracheiphila*. Several bioactive components such as enzymes that degrade fungal structural polymers (protease and chitinase), lipopeptides (iturin, surfactin and fengycin), antibiotics (fengycin, surfactin, iturin and bacillomycin D) and antifungal volatiles have been identified as the main component of antagonistic mode of action (Xu, Park et al. 2016). This pathogen antagonistic characteristic has allowed them to be used as promising biological control agents and implemented in various foods and supplement preparations.

Identifying probiotic microbial strains which can be used in the effective and safe treatment and prophylaxis of respiratory tract infections is therefore highly desired.

Additional background art includes:

Jeon, Jung et al. 2016 J. Microbiol. Biotechnol 26(4): 666-674;

Cho 2008 Journal of Applied Biological Chemistry 51(6): 285-291;

U.S. Publication No. 20170348364;

U.S. Pat. No. 8,986,610.

SUMMARY OF THE INVENTION

According to an aspect of some embodiments of the present invention there is provided an isolated bacterial strain *Bacillus amyloliquefaciens* 298, a sample of which having been deposited as KCTC 13469BP at the Korean Collection for Type Cultures or a functional homolog of same wherein the isolated microbial strain is purified to a level of at least 99%.

According to an aspect of some embodiments of the present invention there is provided an isolated bacterial strain *Bacillus amyloliquefaciens* 298 or a functional homolog thereof comprising a genomic nucleic acid sequence at least 97% identical to the nucleic acid sequence set forth in SEQ ID NO: 4), wherein the isolated microbial strain is purified to a level of at least 99%.

According to an aspect of some embodiments of the present invention there is provided an isolated bacterial strain *Bacillus amyloliquefaciens* 298 or a functional homolog exhibiting:

(i) growth inhibitory effects against bacteria and fungi, as shown in Tables 3 and 4, respectively;

(ii) no lecithinase activity as determined by the absence of a white precipitate when the isolated bacterial strain or functional homolog of same is streaked out onto egg yolk agar and incubated for 24 h at 37° C.; and (iii) gamma hemolytic activity when streaked onto 5% sheep blood agar and incubated for 24 h at 37° C., wherein the isolated microbial strain is purified to a level of at least 99%.

According to some embodiments of the invention, the isolated bacterial strain or functional homolog has no lecithinase activity as determined by the absence of a white precipitate when the isolated bacterial strain or functional homolog of same is streaked out onto egg yolk agar and incubated for 24 h at 37° C.

According to some embodiments of the invention, the isolated bacterial strain or functional homolog exhibits gamma hemolytic activity when streaked onto 5% sheep blood agar and incubated for 24 h at 37° C.

According to some embodiments of the invention, the isolated bacterial strain or functional homolog is sensitive to an antibiotic selected from the group consisting of erythromycin, gentamicin, tetracycline, streptomycin, vancomycin, chloramphenicol, kanamycin and clindamycin according to the European Food Safety Authority MIC breakpoints for *Bacillus* species.

According to some embodiments of the invention, the isolated bacterial strain or functional homolog is incapable of colonizing a mammalian lung.

According to some embodiments of the invention, the isolated bacterial strain or functional homolog exhibits growth inhibitory effects against bacteria and fungi, as shown in Tables 3 and 4, respectively.

According to some embodiments of the invention, the functional homolog is characterized by at least one of:

at least 70% DNA-DNA relatedness to the deposited strain with 5 uC or less DTm;

at least 97% genomic DNA sequence identity to the genomic DNA sequence of the deposited strain;

having an average nucleotide identity (ANI) of at least about 97% with the deposited strain;

having a tetranucleotide signature frequency correlation coefficient of at least about 0.99 with the deposited strain;

having a Dice similarity coefficient;

being of the same ribotype as that of the deposited strain;

having a Pearson correlation coefficient of at least about 0.99 with the deposited strain;

having a multilocus sequence typing (MLST) of at least about 0.99 with the deposited strain;

having a functionality conserved gene that is at least about 97% identical to that of the deposited strain as determined at a level of a single gene or multilocus sequence analysis (MLSA);

having a 16S nucleic acid sequence that is at least about 97% identical to that of the deposited strain;

having substantially the same biochemical profiling as determined by the GEN III redox chemistry;

maintaining the coding and/or non-coding sequence order as that of the deposited strain;

having the same codon usage as that of the deposited strain.

According to an aspect of some embodiments of the present invention there is provided a composition comprising the isolated bacterial strain or functional homolog of same, wherein the composition does not comprise more than 5 different species of microbes.

According to some embodiments of the invention, the composition comprises at least 2 different species of microbes.

According to some embodiments of the invention, the composition comprises at least 3 different species of microbes.

According to some embodiments of the invention, the isolated bacterial strain or functional homolog of same is present in the composition at an amount of at least $10^6$ CFU/gr powder or $10^6$ CFUs/ml.

According to some embodiments of the invention, the composition is formulated as a liquid formulation.

According to some embodiments of the invention, the composition is formulated as a dry formulation.

According to some embodiments of the invention, the composition is formulated as a gel formulation.

According to some embodiments of the invention, the composition is formulated as a sporulated formulation.

According to some embodiments of the invention, the bacterial strain or functional homolog of same is a fermentation product.

According to some embodiments of the invention, the bacterial strain or functional homolog of same is a lysate.

According to some embodiments of the invention, the bacterial strain or functional homolog is viable.

According to an aspect of some embodiments of the present invention there is provided an article of manufacture comprising the isolated bacterial strain or functional homolog of same or the composition.

According to some embodiments of the invention, the bacterial strain or functional homolog of same is attached to a solid support.

According to some embodiments of the invention, the bacterial strain or functional homolog of same is soluble.

According to some embodiments of the invention, the article of manufacture comprises a commodity selected from the group consisting of a food, a feed, a beverage, a pharmaceutical, a nutraceutical, a cosmetic, a filter, a matrix and an aerosol system.

According to an aspect of some embodiments of the present invention there is provided an aerosol dispensing device comprising an effective amount of the bacterial strain or functional homolog of same or composition.

According to an aspect of some embodiments of the present invention there is provided an aerosol dispensing device comprising an effective amount of bacteria of the species *Bacillus amyloliquefaciens*.

According to some embodiments of the invention, the aerosol dispensing device is automated.

According to an aspect of some embodiments of the present invention there is provided a method of controlling a population of pathogenic bacteria and/or fungi in a respiratory system, the method comprising administering to a subject in need thereof an effective amount of bacteria of the species *Bacillus amyloliquefaciens*, thereby controlling the population of pathogenic bacteria and/or fungi in the respiratory system.

According to an aspect of some embodiments of the present invention there is provided a method of controlling a population of pathogenic bacteria and/or fungi, the method comprising providing an effective amount of the isolated bacterial strain or functional homolog of 8 or the composition as described herein, thereby controlling the population of pathogenic bacteria and/or fungi.

According to some embodiments of the invention, the controlling is prophylactic.

According to some embodiments of the invention, the controlling is therapeutic.

According to some embodiments of the invention, the effective amount comprises at least $10^6$ CFU/gr powder $10^6$ CFUs/ml.

According to some embodiments of the invention, the contacting comprises in vivo contacting.

According to some embodiments of the invention, the contacting is by inhalation.

According to some embodiments of the invention, the contacting is by oral administration.

According to some embodiments of the invention, the contacting is by enteral administration.

According to some embodiments of the invention, the contacting is by paraenteral administration.

According to some embodiments of the invention, the contacting comprises in vitro contacting.

According to some embodiments of the invention, the contacting is by using the aerosol dispensing device of any one of claims 24-26.

According to an aspect of some embodiments of the present invention there is provided a method of producing bacteria, the method comprising:

(a) culturing the bacterial strain or functional homolog of same under conditions that allow propagation;

(b) harvesting the bacterial strain or functional homolog of same.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
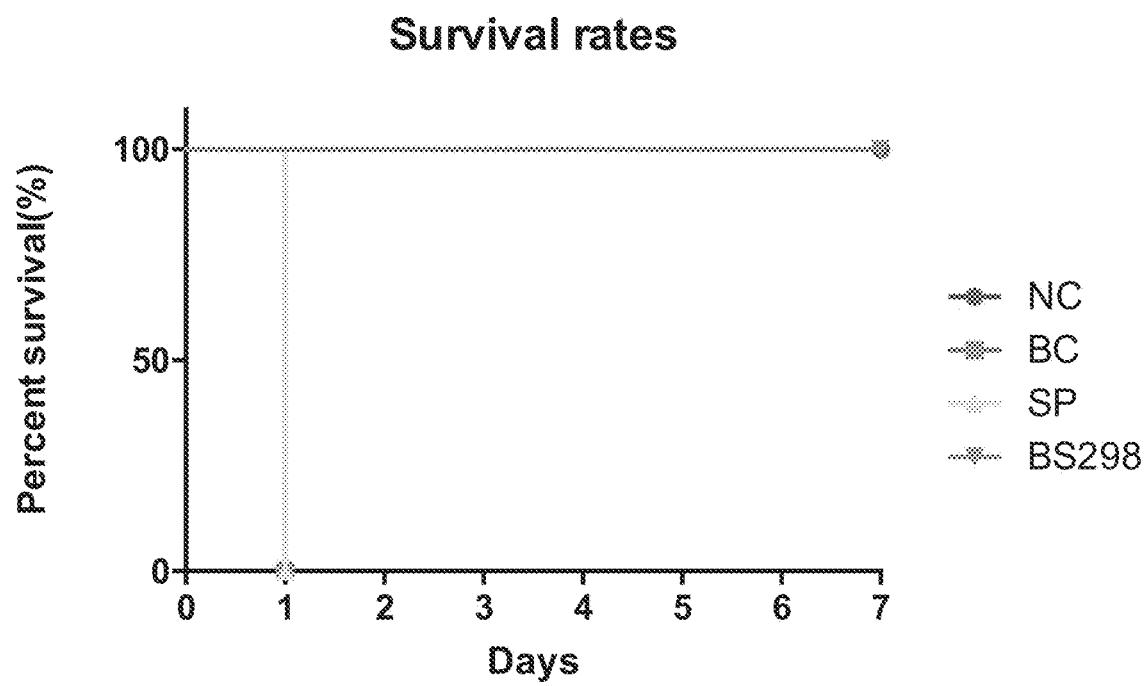
FIG. 1 is a graph showing the survival rates of mice after respiratory tract infection (NC: negative control, BC: *B. cereus*, SP: *S. pneumoniae*, BS298: *B. amyloliquefaciens* 298).
Figure 2:
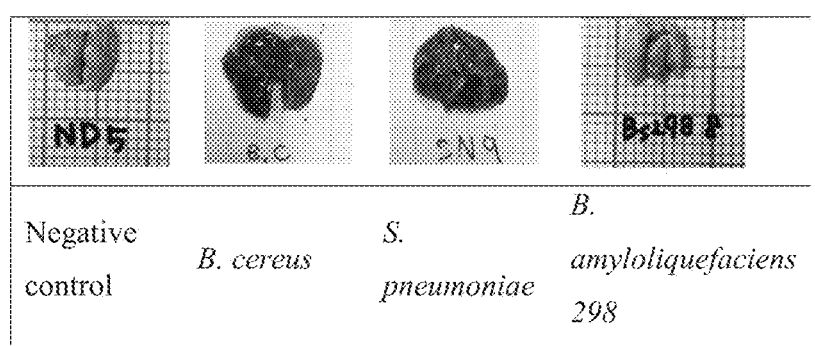
FIG. 2 is a photograph showing the appearance of lungs in each group described in FIG. 1.
Figure 3:
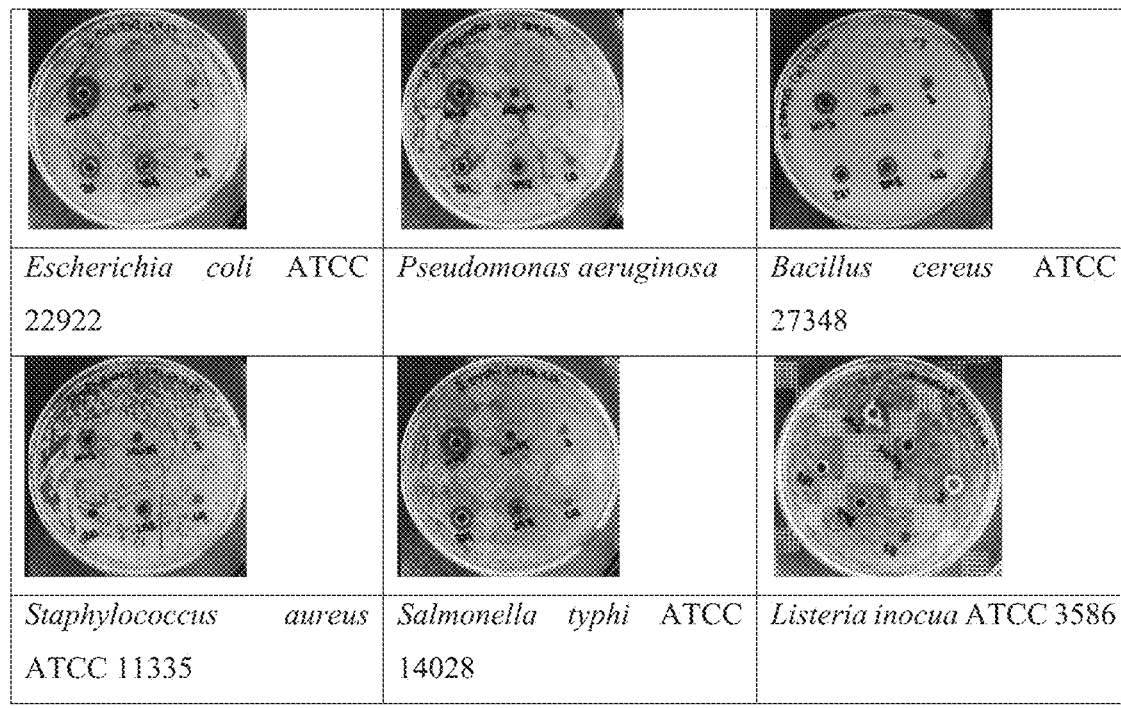
FIG. 3 is a photograph showing antagonism of pathogenic bacteria by *B. amyloliquefaciens* 298.
Figure 4:
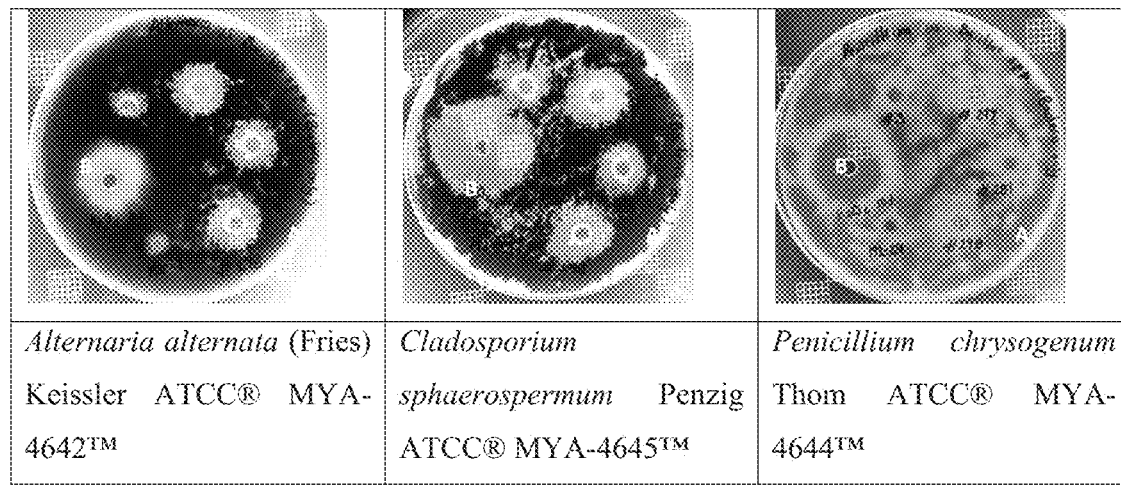
FIG. 4 is a photographic representation of results for the antagonism of test molds using *B. amyloliquefaciens* 298 (A) and 10% hydrogen peroxide (B) as a positive control.

The present invention, in some embodiments thereof, relates to compositions comprising bacterial strains and use thereof in controlling pathogenic microorganisms. Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

In a search for probiotic bacterial strains that can be effectively and safely used in controlling pathogenic microorganisms, the present inventors have identified a novel strain of *Bacillus amyloliquefaciens* (*B. amyloliquefaciens*), termed *B. amyloliquefaciens* strain number 298. The pathogenicity of the strain was assessed using in-vitro methods such as lecithinase activity, hemolysis tests and resistance to therapeutic antibiotics. *B. amyloliquefaciens* 298 safety was also evaluated in-vivo through a lung infection model in mice. Lastly, the efficacy of *Bacillus amyloliquefaciens* 298 in inhibiting the growth of *Escherichia coli*, *Pseudomonas aeruginosa*, *Bacillus cereus*, *Staphylococcus aureus*, *Salmonella Typhimurium*, *Alternaria alternata*, *Cladosporium sphaerospermum* and *Penicillium chrysogenum* was evaluated in-vitro.

Collectively these assays place *B. amyloliquefaciens* 298 as both safe for respiratory tract infection and functional with high potential to be used in various domestic, clinical and industrial applications.

Thus, according to an aspect of the invention there is provided an isolated bacterial strain *Bacillus amyloliquefaciens* 298 or a functional homolog thereof comprising a genomic nucleic acid sequence at least 97% identical to the nucleic acid sequence set forth in SEQ ID NO: 4), wherein said isolated microbial strain is purified to a level of at least 99%.

According to an alternative or an additional aspect of the invention there is provided an isolated bacterial strain *Bacillus amyloliquefaciens* 298 or a functional homolog exhibiting:

(i) growth inhibitory effects against bacteria and fungi, as shown in Tables 3 and 4, respectively;

(ii) no lecithinase activity as determined by the absence of a white precipitate when the isolated bacterial strain or functional homolog of same is streaked out onto egg yolk agar and incubated for 24 h at 37° C.; and (iii) gamma hemolytic activity when streaked onto 5% sheep blood agar and incubated for 24 h at 37° C., wherein said isolated microbial strain is purified to a level of at least 99%.

According to an alternative or an additional aspect of the invention there is provided an isolated bacterial strain *Bacillus amyloliquefaciens* 298, a sample of which having been deposited as KCTC 13469BP a functional homolog of same.

KCTC 13469BP has been deposited in the Korean Collection for Type Cultures, Korea Research Institute of Bioscience and Biotechnology (KRIBB) 181, Ipsin-gil, Jeongeup-si, Jeolllabuk-do 56212, Republic of Korea on Jan. 25, 2018.

The bacterial strain can be as deposited or a variant thereof, also referred to herein as a "functional homolog".

The term "the microbial strain" or "the bacterial strain" can refer to the deposited strain and/or the functional homolog.

As used herein "functional homolog" or "functionally homologous" or "variant" or a grammatical equivalent as used herein, refers to a modification (i.e., at least one mutation) of the deposited microbial strain resulting in a microbial strain that is endowed with substantially the same ensemble of biological activities (+/−10%, 20%, 40%, 50%, 60% when tested under the same conditions) as that of the deposited strain (see hereinbelow and in the Examples section which follows) and can be classified to the same species or strain based on known methods of species/strain classifications.

Following are non-limiting criteria for identifying a functional homolog. These criteria, which are mostly genetic, combined with the functional characteristic as defined hereinbelow and in the Examples section, which follows, will be facilitate the skilled artisan in defining the scope of the functional homolog.

Thus, according to a specific embodiment, the deposited strain and the functional homolog belong to the same operational taxonomic units (OTU).

An "OTU" (or plural, "OTUs") refers to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S-rRNA sequence or a portion of the 16S-rRNA (also referred to herein as "16S") sequence or other functionally conserved genes as listed below. In other embodiments, the entire genomes of two entities are sequenced and compared. In another embodiment, selected regions such as multilocus sequence tags (MLST, MLSA), specific genes, or sets of genes may be genetically compared. In 16S-rRNA embodiments, OTUs that share at least 97% average nucleotide identity across the entire 16S or some variable region of the 16S are considered the same OTU (see e.g. Claesson M J, Wang Q, O'Sullivan O, Greene-Diniz R, Cole J R, Ros R P, and O'Toole P W. 2010. Comparison of two next-generation sequencing technologies for resolving highly complex microbiota composition using tandem variable 16S rRNA gene regions. Nucleic Acids Res 38: e200. Konstantinidis K T, Ramette A, and Tiedje J M. 2006. The bacterial species definition in the genomic era. Philos Trans R Soc Lond B Biol Sci 361: 1929-1940). In embodiments involving the complete genome, MLSTs, specific genes, or sets of genes OTUs that share at least 95% average nucleotide identity are considered the same OTU (see e.g. Achtman M, and Wagner M. 2008. Microbial diversity and the genetic nature of microbial species. Nat. Rev. Microbiol. 6: 431-440. Konstantinidis K T, Ramette A, and Tiedje J M. 2006. The bacterial species definition in the genomic era. Philos Trans R Soc Lond B Biol Sci 361: 1929-1940). OTUs are frequently defined by comparing sequences between organisms. Such characterization employs, e.g., WGS data or a whole genome sequence.

According to a specific embodiment, the classification is based on DNA-DNA pairing data and/or sequence identity to functionally conserved genes or fragments thereof.

According to a specific embodiment a species/strain can be defined by DNA-DNA hybridization involving a pairwise comparison of two entire genomes and reflects the overall sequence similarity between them. According to a specific embodiment, a species is defined as a set of strains with at least about 70%, e.g., at least about 75%, at least about 80%, at least about 85%, at least about 90%, at least about 91%, at least about 92%, at least about 93%, at least about 94%, at least about 95% or more DNA-DNA relatedness and with 5 uC or less DTm and having the activities as defined hereinbelow and in the Examples section which follows.

According to a specific embodiment, the genomic nucleic acid sequence is at least about 97%, at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95% 99.95%, at least about 99.99%, at least about 99.999%, at least about 99.9999%, at least about 99.99999%, at least about 99.999999% or more DNA-DNA relatedness and with 5 uC or less DTm and having the activities hereinbelow and in the Examples section which follows.

Thus, for example, if there is DNA-DNA hybridization on the basis of the article of Goris et al. [Goris, J., Konstantinidis, K. T., Klappenbach, J. A., Coenye, T., Vandamme, P., and Tiedje, J M. (2007). DNA-DNA hybridization values and their relationship to whole-genome sequence similarities. Int J Syst Evol Microbiol 57:81-91], some microorganisms expressing a DNA-DNA relatedness value of 70% or more (as described above) can be regarded as functional homologs according to some embodiments of the invention.

According to a specific embodiment, the reference genomic sequence is as set forth in SEQ ID NO: 4).

As used herein, "sequence identity" or "identity" or grammatical equivalents as used herein in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff JG. [Amino acid substitution matrices from protein blocks. Proc. Natl. Acad. Sci. U.S.A. 1992, 89(22): 10915-9].

Identity can be determined using any homology comparison software, including for example, the BlastN software of the National Center of Biotechnology Information (NCBI) such as by using default parameters.

According to some embodiments of the invention, the identity is a global identity, i.e., an identity over the entire nucleic acid sequences of the invention and not over portions thereof.

According to a specific embodiment, the genomic nucleic acid sequence is at least about 70%, e.g., at least 75%, at least about 80%, at least about 85%, at least about 90%, at least about 91%, at least about 92%, at least about 93%, at least about 94%, at least about 95%, at least about 96% least about 97%, at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95% 99.95%, at least about 99.99%, at least about 99.999%, at least about 99.9999%, at least about 99.99999%, at least about 99.999999% or more to the genomic sequence of the deposited strain (SEQ ID NO: 4).

According to a specific embodiment, the genomic nucleic acid sequence is at least about 97%, at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, 99.95%, at least about 99.99%, at least about 99.999%, at least about 99.9999%, at least about 99.99999%, at least about 99.999999% or more identical to that of the deposited strain (SEQ ID NO: 4).

According to an additional or alternative embodiment, a functional homolog is determined as the average nucleotide identity (ANI), which detects the DNA conservation of the core genome (Konstantinidis K and Tiedje J M, 2005, Proc. Natl. Acad. Sci. USA 102: 2567-2592). In some embodiments, the ANI between the functional homolog and the deposited strain is of at least about 95%, at least about, 96%, at least about 97%, at least about 98%, at least about 99%, at least about 99.1%, at least about 99.5%, at least about 99.6%, at least about 99.7%, at least about 99.8%, at least about 99.9%, at least about 99.99%, at least about 99.999%, at least about 99.9999%, at least about 99.99999%, at least about 99.999999% or more.

According to an additional or alternative embodiment, a functional homolog is determined by the degree of relatedness between the functional homolog and deposited strain determined as the Tetranucleotide Signature Frequency Correlation Coefficient, which is based on oligonucleotide frequencies (Bohlin J. et al. 2008, BMC Genomics, 9:104). In some embodiments, the Tetranucleotide Signature Frequency Correlation coefficient between the variant and the deposited strain is of about 0.99, 0.999, 0.9999, 0.99999, 0.999999, 0.999999 or more.

According to an additional or alternative embodiment, the degree of relatedness between the functional homolog and the deposited strain is determined as the degree of similarity obtained when analyzing the genomes of the parent and of the variant strain by Pulsed-field gel electrophoresis (PFGE) using one or more restriction endonucleases. The degree of similarity obtained by PFGE can be measured by the Dice similarity coefficient. In some embodiments, the Dice similarity coefficient between the variant and the deposited strain is of at least about 96%, at least about 97%, at least about 98%, at least about 99%, at least about 99.1%, at least about 99.5%, at least about 99.6%, at least about 99.7%, at least about 99.8%, at least about 99.9%, at least about 99.99%, at least about 99.999%, at least about 99.9999%, at least about 99.99999%, at least about 99.999999% or more.

According to an additional or alternative embodiment, the functional homolog is defined as having the same ribotype, as obtained using any of the methods known in the art and described, for instance, by Bouchet et al. (Clin. Microbiol. Rev., 2008, 21:262-273).

According to an additional or alternative embodiment, the degree of relatedness between the functional homolog and the deposited strain is determined by the Pearson correlation coefficient obtained by comparing the genetic profiles of both strains obtained by repetitive extragenic palindromic element-based PCR (REP-PCR) (see e.g. Chou and Wang, Int J Food Microbiol. 2006, 110:135-48). In some embodiments, the Pearson correlation coefficient obtained by comparing the REP-PCR profiles of the variant and the deposited strain is of at least about 0.99, at least about 0.999, at least about 0.9999, at least about 0.99999, at least about 0.999999, at least about 0.999999 or more.

According to an additional or alternative embodiment, the degree of relatedness between the functional homolog and the deposited strains is defined by the linkage distance obtained by comparing the genetic profiles of both strains obtained by Multilocus sequence typing (MLST) (see e.g. Maiden, M. C., 1998, Proc. Natl. Acad. Sci. USA 95:3140-3145). In some embodiments, the linkage distance obtained by MLST of the functional homolog and the deposited strain is of at least about 0.99, at least about 0.999, at least about 0.9999, at least about 0.99999, at least about 0.999999, at least about 0.999999 or more.

According to an additional or alternative embodiment, the functional homolog comprises a functionally conserved gene or a fragment thereof e.g., a house-keeping gene e.g., 16S-rRNA or Internal Transcribed Spacer" (ITS), recA, glnII, atpD, gap, glnA, gltA, gyrB, pnp, rpoB, thrC or dnaK that is at least about 97%, at least about 98%, at least about 99%, at least about 99.1%, at least about 99.5%, at least about 99.6%, at least about 99.7%, at least about 99.8%, at least about 99.9%, at least about 99.99%, at least about 99.999%, at least about 99.9999%, at least about 99.99999%, at least about 99.999999% or more identical to that of the deposited strain.

As mentioned, and according to a specific additional or an alternative embodiment, a functional homolog can also be determined on the basis of a multilocus sequence analysis (MLSA) determination of various functionally conserved genes or fragments thereof e.g., at least one, 2, 3, 4, 5, 6, 7, 8, 9, 10, 11, 12, 13, 14, 15 or more functionally conserved genes or fragments thereof, such as of e.g., 16S, ITS, recA, glnII, atpD, gap, glnA, gltA, gyrB, pnp, rpoB, thrC and dnaK.

According to a specific embodiment, the 16S ribosomal RNA (16S-rRNA) nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain (SEQ ID NO: 3).

According to a specific embodiment, the ITS nucleic acid sequence is at least about 97%, e.g. at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the recA nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the atpD nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the dnaK nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the glnII nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the gap nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the glnA nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the gltA nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the gyrB nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the pnp nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the rpoB nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to a specific embodiment, the thrC nucleic acid sequence is at least about 97%, e.g., at least about 97.1%, at least about 97.2%, at least about 97.3%, at least about 97.4%, at least about 97.5%, at least about 97.6%, at least about 97.7%, at least about 97.8%, at least about 97.9%, at least about 98%, at least about 98.1%, at least about 98.2%, at least about 98.3%, at least about 98.4%, at least about 98.5%, at least about 98.6%, at least about 98.7%, at least about 98.8%, at least about 98.9%, at least about 99%, at least about 99.1%, at least about 99.2%, at least about 99.3%, at least about 99.4%, at least about 99.5%, at least about 99.6%, at least about 99.7%, at least about 99.8%, at least about 99.8%, at least about 99.9%, at least about 99.95%, at least about 99.999%, at least about 99.9999%, at least about 99.99999%, at least about 99.999999% or more identical to that of the deposited strain.

According to an additional or alternative embodiment the deposited strain and the functional homolog is characterized by substantially the same (+/− about 10%, 20%, 40%, 50%, 60% when tested under the same conditions) biochemical profiling (e.g., biochemical fingerprinting) using for example, the GEN III redox chemistry (BIOLOG Inc. 21124 Cabot Blvd. Hayward Calif., 94545, USA), which can analyze both Gram-negative and Gram-positive bacteria, for their ability to metabolize all major classes of biochemicals, in addition to determining other important physiological properties such as pH, salt, and lactic acid tolerance. Further details can be obtained in "Modern Phenotypic Microbial Identification", B. R. Bochner, Encyclopedia of Rapid Microbiological Methods, 2006, v.2, Ch. 3, pp. 55-73, which is incorporated herein by reference in its entirety.

Example 7 of the Examples section provides a metabolite analysis of the deposited strain.

According to an additional or alternative embodiment, the functional homolog is defined by a comparison of coding sequences (gene) order.

According to an additional or alternative embodiment, the functional homolog is defined by a comparison of order of non-coding sequences.

According to an additional or alternative embodiment, the functional homolog is defined by a comparison of order of coding and non-coding sequences.

According to some embodiments of the invention, the combined coding region of the functional homolog is such that it maintains the original order of the coding regions as within the genomic sequence of the bacterial isolate yet without the non-coding regions.

Coding sequences of the deposited strain and their annotations are provided in Table 5 of the Examples section which follows.

For example, in case the genomic sequence has the following coding regions, A, B, C, D, E, F, G, each flanked by non-coding sequences (e.g., regulatory elements, introns and the like), the combined coding region will include a single nucleic acid sequence having the A+B+C+D+E+F+G coding regions combined together while maintaining the original order of their genome, yet without the non-coding sequences.

According to some embodiments of the invention, the combined non-coding region of the functional homolog is such that it maintains the original order of the non-coding regions as within the genomic sequence of the bacterial isolate yet without the coding regions as originally present in the bacterial deposit.

According to some embodiments of the invention, the combined non-coding region and coding region (i.e., the genome) of the functional homolog is such that it maintains the original order of the coding and non-coding regions as within the genomic sequence of the microbial deposit.

As used herein "maintains" relate to at least about 90%, 91%, 92%, 93%, 94%, 95%, 96%, 97%, 98%, 99% or 100% is maintained as compared to the deposited strain.

According to an additional or alternative embodiment, the functional homolog is defined by a comparison of gene content.

According to a specific embodiment, the functional homolog comprises a combined coding region where at least about 90%, at least about 91%, at least about 92%, at least about 93%, at least about 94%, at least about 95%, at least about 96%, at least about 97%, at least about 98%, at least about 99%, or more (e.g., 100%) is identical to a combined coding region existing in genome of the deposited strain.

As used herein "combined coding region" refers to a nucleic acid sequence including all of the coding regions of the bacterial isolate yet without the non-coding regions of the bacterial isolate.

According to an additional or alternative embodiment, the functional homolog is defined by a comparison of nucleotide composition and codon usage.

According to an additional or alternative embodiment, the functional homolog is defined by a method based on random genome fragments and DNA microarray technology. These methods are of sufficiently high resolution to for strain-to-species level identification.

One of ordinary skill in the art, based on knowledge of the classification criteria would know how to identify strains that are considered functional homologs.

An additional and more detailed description of species-to-strain classification can be found in:

Cho and Tiedje 2001 Bacterial species determination from DNA-DNA hybridization by using genome fragments and DNA microarrays;

Coenye et al. 2005 Towards a prokaryotic genomic taxonomy. FEMS Microbiol. Rev. 29:147-167;

Konstantinidis and Tiedje (2005) Genomic insights that advance the species definition for prokaryotes. Proc. Natl. Acad. Sci. USA 102:189-197;

Konstantinidis et al. 2006 Toward a more robust assessment of intraspecies diversity using fewer genetic markers. Appl. Environ. Microbiol. 72:7286-7293.

It is to be understood that one or more methods as described herein can be used to identify a functional homolog.

Genomic data can be obtained by methods which are well known in the art e.g., DNA sequencing, bioinformatics, electrophoresis, an enzyme-based mismatch detection assay and a hybridization assay such as PCR, RT-PCR, RNase protection, in-situ hybridization, primer extension, Southern blot, Northern Blot and dot blot analysis.

According to a specific embodiment, the functional homolog and the deposited strain belong to the same species (*Bacillus amyloliquefaciens*).

According to a specific embodiment, the functional homolog and the deposited strain belong to the same subspecies.

As mentioned, the functional homolog is endowed with or maintains (as defined herein) the functional properties of the deposited strain.

Thus according to a specific embodiment, the bacterial strain has no lecithinase activity as determined by the absence of a white precipitate when the isolated bacterial strain or functional homolog of same is streaked out onto egg yolk agar and incubated for 24 h at 37° C.

According to an additional or an alternative embodiment, the bacterial strain exhibits gamma hemolytic activity when streaked onto 5% sheep blood agar and incubated for 24 h at 37° C.

According to an additional or an alternative embodiment, the bacterial strain is sensitive to an antibiotic selected from the group consisting of erythromycin, gentamicin, tetracycline, streptomycin, vancomycin, chloramphenicol, kanamycin and clindamycin according to the European Food Safety Authority MIC breakpoints for *Bacillus* species such as shown in Table 2 hereinbelow.

According to an additional or an alternative embodiment, the bacterial strain is incapable of colonizing a mammalian (e.g., murine) lung.

According to an additional or an alternative embodiment, the bacterial strain is growth inhibitory effects against bacteria and fungi, as shown in Tables 3 and 4, respectively.

According to an additional or an alternative embodiment, the bacterial strain exhibits a secreted metabolome composition as shown in the Examples section which follows. As used herein "isolated" refers to an isolate of bacteria in which the prevalence (i.e., concentration) of the bacterial stain or functional homolog is enriched over that (exceeds that) found in nature (e.g., in Doenjang, a fermented soybean paste). Thus, the present teachings refer to cultures, preparations, compositions (interchangeably used), which comprise the bacterial strain.

The isolated bacterial strain can be comprised in a composition, preparation, formulation, culture, article of manufacture.

According to some embodiments, the composition, preparation, formulation, culture, article of manufacture, comprises more than 1 microbial strains or species.

According to some embodiments, the composition, preparation, formulation, culture, article of manufacture, comprises 2 microbial strains or species.

According to some embodiments, the composition, preparation, formulation, culture, article of manufacture, comprises 3 microbial strains or species.

According to some embodiments, the composition, preparation, formulation, culture, article of manufacture, comprises 4 microbial strains or species.

According to some embodiments, the composition, preparation, formulation, culture, article of manufacture does not comprise more than 5 different species or strains of microbes.

According to some embodiments, the composition, preparation, formulation, culture, article of manufacture does not comprise more than 4 different species or strains of microbes.

According to some embodiments, the composition, preparation, formulation, culture, article of manufacture does not comprise more than 3 different species or strains of microbes.

According to some embodiments, the composition, preparation, formulation, culture, article of manufacture does not comprise more than 2 different species or strains of microbes.

According to some embodiments of the invention, the composition, preparation, formulation, culture, article of manufacture comprises less than 10 microbial species.

According to some embodiments of the invention, the composition, preparation, formulation, culture, article of manufacture comprises less than 9 microbial species.

According to some embodiments of the invention, the composition, preparation, formulation, culture, article of manufacture comprises less than 8 microbial species.

According to some embodiments of the invention, the composition, preparation, formulation, culture, article of manufacture comprises less than 7 microbial species.

According to some embodiments of the invention, the composition, preparation, formulation, culture, article of manufacture comprises less than 6 microbial species.

According to some embodiments of the invention, the composition, preparation, formulation, culture, article of manufacture comprises less than 5 microbial species.

According to some embodiments of the invention, the composition, preparation, formulation, culture, article of manufacture comprises 4 microbial species.

According to some embodiments of the invention, the composition, preparation, formulation, culture, article of manufacture comprises 3 microbial species.

According to some embodiments of the invention, the composition, preparation, formulation, culture, article of manufacture comprises 2 microbial species.

According to some embodiments of the invention, the composition, preparation, formulation, culture, article of manufacture comprises 3 microbial strains.

According to some embodiments of the invention, the composition, preparation, formulation, culture, article of manufacture comprises 2 microbial strains.

According to a specific embodiment of the invention, the composition, preparation, formulation, culture, article of manufacture comprises a single microbial species i.e., the isolated bacterial stain.

According to a specific embodiment, the composition, preparation, formulation, culture, article of manufacture comprises the bacterial strain at a level of purity of at least about 20%, at least about 30%, at least about 40%, at least about 50%, at least about 60%, at least about 70%, at least about 80%, at least about 85%, at least about 90%, at least about 91%, at least about 92%, at least about 93%, at least about 94%, at least about 95%, 96%, at least about, 97%.

According to a specific embodiment, the composition, preparation, formulation, culture, article of manufacture comprises the bacterial strain at a level of purity of at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.95%, at least about 99.99% or more, say 100% pure.

According to a specific embodiment, the microbial strain comprises viable (more than 50%) microbial cells.

As used herein "viable" refers to a microorganism that is alive and capable of regeneration and/or propagation, while in a vegetative, frozen, preserved, or reconstituted state.

According to a specific embodiment, the microbial strain comprises spores of the bacterial strain.

As used herein "spores" or "endospores" refer to microbes that are generally viable, more resistant to environmental influences such as heat and bactericidal than other forms of the same bacterial species, and typically capable of germination and out-growth. Bacteria that are "capable of forming spores" are those bacteria comprising the genes and other necessary abilities to produce spores under suitable environmental conditions.

As used in herein, the term "CFUs" or "Colony Forming Units" refers to the number of microbial cells e.g., bacterial strain, in a defined sample (e g milliliter of liquid, gram of powder) that form colonies and thereafter numbered, on a semi-solid bacteriological growth medium.

According to specific embodiments, the enrichment in the composition, preparation, formulation, culture, article of manufacture is $10^2$ CFUs-$10^9$ CFUs/gr powder or $10^2$ CFUs-$10^9$ CFUs/ml.

According to specific embodiments, the enrichment in the composition, preparation, formulation, culture, article of manufacture is $10^2$ CFUs-$10^8$ CFUs/gr powder or $10^2$ CFUs-$10^8$ CFUs/ml.

According to specific embodiments, the enrichment in the composition, preparation, formulation, culture, article of manufacture is $10^2$ CFUs-$10^7$ CFUs/gr powder or $10^2$ CFUs-$10^7$ CFUs/ml.

According to specific embodiments, the enrichment in the composition, preparation, formulation, culture, article of manufacture is $10^2$ CFUs-$10^6$ CFUs/gr powder or $10^2$ CFUs-$10^6$ CFUs/ml.

According to specific embodiments, the enrichment in the composition, preparation, formulation, culture, article of According to a specific embodiment, the composition, preparation, formulation, culture, article of manufacture comprises the bacterial strain at a level of purity of $10^2$ CFUs-$10^5$ CFUs/gr powder or $10^2$ CFUs-$10^5$ CFUs/ml.

According to specific embodiments, the enrichment in the composition, preparation, formulation, culture, article of manufacture is $10^2$ CFUs-$10^4$ CFUs/gr powder or $10^2$ CFUs-$10^4$ CFUs/ml.

According to specific embodiments, the enrichment in the composition, preparation, formulation, culture, article of manufacture is $10^2$ CFUs-$10^3$ CFUs/gr powder or $10^2$ CFUs-$10^3$ CFUs/ml.

According to specific embodiments, the enrichment in the composition, preparation, formulation, culture, article of manufacture is $10^3$ CFUs-$10^9$ CFUs/gr powder or $10^3$ CFUs-$10^9$ CFUs/ml.

According to specific embodiments, the enrichment in the composition, preparation, formulation, culture, article of manufacture is $10^4$ CFUs-$10^9$ CFUs/gr powder or $10^4$ CFUs-$10^9$ CFUs/ml.

According to specific embodiments, the enrichment in the composition, preparation, formulation, culture, article of manufacture is $10^5$ CFUs-$10^9$ CFUs/gr powder or $10^5$ CFUs-$10^9$ CFUs/ml.

According to specific embodiments, the enrichment in the composition, preparation, formulation, culture, article of manufacture is $10^6$ CFUs-$10^9$ CFUs/gr powder or $10^6$ CFUs-$10^9$ CFUs/ml.

According to specific embodiments, the enrichment in the composition, preparation, formulation, culture, article of manufacture is $10^7$ CFUs-$10^9$ CFUs/gr powder or $10^7$ CFUs-$10^9$ CFUs/ml.

According to specific embodiments, the enrichment in the composition, preparation, formulation, culture, article of manufacture is $10^8$ CFUs-$10^9$ CFUs/gr powder or $10^8$ CFUs-$10^9$ CFUs/ml.

According to specific embodiments, the enrichment in the composition, preparation, formulation, culture, article of manufacture is $10^8$ CFUs-$10^9$ CFUs/gr powder or $10^8$ CFUs-$10^9$ CFUs/ml.

According to a specific embodiment the composition, preparation, formulation, culture, article of manufacture comprises at least about 100 CFUs or spores, at least about $10^2$ CFUs/gr or CFUs/ml, at least about $10^2$ CFUs/gr or CFUs/ml, at least about $10^3$ CFUs/gr or CFUs/ml, at least about $10^4$ CFUs/gr or CFUs/ml, at least about $10^5$ CFUs/gr or CFUs/ml, at least about $10^6$ CFUs/gr or CFUs/ml, at least about $10^7$ CFUs/gr or CFUs/ml, at least about $10^8$ CFUs/gr or CFUs/ml, at least about $10^9$ CFUs/gr or CFUs/ml, at least about $10^{10}$ CFUs/gr or CFUs/ml, at least about $10^{11}$ CFUs/gr or CFUs/ml, at least about $10^{12}$ CFUs/gr or CFUs/ml.

According to a specific embodiment the composition, preparation, formulation, culture, article of manufacture (especially for a liquid formulation) comprises at least about $10^6$ CFUs/gr or CFUs/ml, at least about $10^7$ CFUs/gr or CFUs/ml, at least about $10^8$ CFUs/gr or CFUs/ml, at least about $10^9$ CFUs/gr or CFUs/ml.

According to a specific embodiment the composition, preparation, formulation, culture, article of manufacture (especially for a dry formulation) comprises at least about $10^8$ CFUs/gr or CFUs/ml, at least about $10^9$ CFUs/gr or CFUs/ml, at least about $10^{10}$ CFUs/gr or CFUs/ml, at least about $10^{11}$ CFUs/gr or CFUs/ml, at least about $10^{12}$ CFUs/gr or CFUs/ml.

According to a specific embodiment, the composition, preparation, formulation, culture, article of manufacture is selected from the group consisting of a still culture, whole cultures stored stock of cells (particularly glycerol stocks), agar strip, stored agar plug in glycerol/water, freeze dried stock, and dried stocks such as lyophilisate dried onto filter paper.

According to a specific embodiment, the composition, preparation, culture or formulation is devoid of animal contaminants to render it safe for human use.

As used herein "a culture" refers to a fluid, pellet, scraping, dried sample, lyophilisate or a support, container, or medium such as a plate, paper, filter, matrix, straw, pipette or pipette tip, fiber, needle, gel, swab, tube, vial, particle, etc. that contains the deposited strain or the functional homolog thereof in an amount that exceeds that found in nature, as described hereinabove. In the present invention, an isolated culture of a microbial strain is a culture fluid or a scraping, pellet, dried composition, preparation, formulation, culture, article of manufacture, lyophilisate, or a support, container, or medium that contains the microorganism, in the absence of other organisms (or in combination with other microbes which were preselected and grown for the purpose of combined administration).

According to a specific embodiment, the bacterial strain within the composition, preparation, formulation, culture, article of manufacture is viable.

The bacterial strain can be produced or manufactured using methods which are well known in the art of microbiology.

According to a specific embodiment, the microbial strain is isolated from Doenjang, such as by using Luria Bertani Miller agar (BD, Difco) agar for plating. According to a specific embodiment, representative colonies are picked from plates with the highest dilution still showing colonies. After purification, the strain was stored at −80° C. The stock culture is propagated in LB Miller broth.

According to an aspect, the bacterial strain is cultured under conditions that allow propagation; after which (and/or during which) the bacterial strain is harvested.

Thus, according to some embodiments, cultures of the microbial strain may be prepared using standard static drying and liquid fermentation techniques known in the art. Growth is commonly effected in a bioreactor.

A bioreactor refers to any device or system that supports a biologically active environment. As described herein a bioreactor is a vessel in which microorganisms including the microorganism of the invention can be grown. A bioreactor may be any appropriate shape or size for growing the microorganisms. A bioreactor may range in size and scale from 10 mL (e.g., small scale) to liters to cubic meters (e.g., large scale) and may be made of stainless steel, disposable material (e.g., nylon, plastic bags) or any other appropriate material as known and used in the art. The bioreactor may be a batch type bioreactor, a fed batch type or a continuous-type bioreactor (e.g., a continuous stirred reactor). For example, a bioreactor may be a chemostat as known and used in the art of microbiology for growing and harvesting microorganisms. A bioreactor may be obtained from any commercial supplier (See also Bioreactor System Design, Asenjo & Merchuk, CRC Press, 1995).

For small scale operations, a batch bioreactor may be used, for example, to test and develop new processes, and for processes that cannot be converted to continuous operations.

Microorganisms grown in a bioreactor may be suspended or immobilized. Growth in the bioreactor is generally under aerobic conditions at suitable temperatures and pH for growth. For the organisms of the invention, cell growth can be achieved at temperatures between 5-40° C., with an exemplary temperature range selected from 20 to 10° C., 15 to 28° C., 20 to 30° C., or 15 to 25° C. The pH of the nutrient medium can vary between 4.0 and 9.0. For example, the operating range can be usually slightly acidic to neutral at pH 5.0 to 8.5, or 4.5 to 6.5, or pH 5.0 to 6.0.

According to a specific embodiment, the cell growth is achieved at 20-40° C. at pH of 5.0-8.5.

Typically, maximal cell yield is obtained in 20-72 hours after inoculation. By virtue of the conditions applied in the selection process and general requirements of most microorganisms, a person of ordinary skill in the art would be able to determine essential nutrients and conditions. The microorganisms would typically be grown in aerobic liquid cultures on media which contain sources of carbon, nitrogen, and inorganic salts that can be assimilated by the microorganism and supportive of efficient cell growth. Exemplary carbon sources are hexoses such as glucose, but other sources that are readily assimilated such as amino acids, may be substituted. Many inorganic and proteinaceous materials may be used as nitrogen sources in the growth process. Exemplary nitrogen sources are amino acids and urea but others include gaseous ammonia, inorganic salts of nitrate and ammonium, vitamins, purines, pyrimidines, yeast extract, beef extract, proteose peptone, soybean meal, hydrolysates of casein, distiller's solubles, and the like. Among the inorganic minerals that can be incorporated into the nutrient medium are the customary salts capable of yielding calcium, zinc, iron, manganese, magnesium, copper, cobalt, potassium, sodium, molybdate, phosphate, sulfate, chloride, borate, and like ions.

The culture can be a pure culture, whereby a single microbial strain is included or a mixed culture. This is of course pending the compliance of the microbial strains to co-exist and proliferate under the same culturing conditions. When needed, an antibiotic or other growth-restricting conditions can be employed during culturing to restrict the growth of other microorganisms (contaminants) not desired in the culture/co-culture e.g., temperature, essential nutrients and the like.

According to an alternative or an additional embodiment, the desired combination is produced following culturing, such as when the microbial strains do not share the same or optimal culturing conditions.

The ratio of each type of microorganism in the final product will depend on the intended use (some are listed hereinbelow).

The identity of the microorganism(s) in the culture can be experimentally validated at the nucleic acid level, protein level, metabolite levels, functional level and/or by using classical microbiology tools, e.g., streaking (e.g., with selection).

After production, the microbial strain can be stored or used fresh, either as is or subject to further formulation.

Also contemplated herein are a lysate and/or a fermentation product of the above described methods. Methods of cell lysis of bacterial strains e.g., of the species *B. amyloliquefaciens* are well known in the art.

The formulation of the microbial strain much depends on the intended use. Following is a non-limiting description of various formulations that can be used along with the present teachings.

According to a specific embodiment, the bacterial strain is formulated in a liquid formulation.

According to a specific embodiment, the bacterial strain is formulated in a dry formulation.

According to a specific embodiment, the bacterial strain is formulated in a gel formulation.

Microbial strains formulations used to reduce the incidence of pathogenic microorganisms (bacteria and/or fungi), can be in vivo administered, can be released into the air or in conjunction with an HVAC system, applied to waste, food products, food processing areas, food preparation tools, agricultural products, agricultural water (irrigation water, agricultural soils, agricultural crops) and the like. The formulations of bacteria described herein can be applied in a powder, liquid, foam, gelled, aerosol or solid form. In liquid formulations, the microbial strain formulations may be dispensed from conventional dispensing devices, including pump sprayers, aerosol containers, squirt bottles etc. For application over larger areas, hoses, sprinkler systems or other suitable devices may be used. In the alternative, the formulations can be applied as a dry powder such as lyophilized bacteria or using any of the techniques currently known to a person of skill in the art. The optimal frequency of applications of the microbial strain formulations may depend on the target on which the formulation is to be applied. In certain embodiments, wherein formulations are contemplated, a microorganism is harvested and concentrated using a method that does not markedly decrease the viable cell concentration through centrifugation or filtration.

In embodiments wherein formulations are contemplated for preservation, such preservation may include a process of freezing, freeze-drying and/or spray-drying.

In certain embodiments, the preserved cells can be used in a microbial-based product. The preserved bacterial strain can be provided "as-is" without further dilution or modification. Additionally, in certain embodiments, the bacterial strain can be mixed with a carrier to dilute the concentration of cells to an appropriate concentration for administration. The carrier can be as simple as one element, or a more complex molecule or mixture of molecules in any proportion in order to act as a suitable carrier. This carrier and composition may, in certain instances, have defined properties such as solubility in water or other media. The diluting carrier can be of any composition or combination including but not limited to: lactose, glucose, non-fat dry milk powder, oligosaccharides, glycerol, oil, lecithin, or other materials.

In particular formulations, other chemicals or materials may be used to reduce or absorb moisture and/or oxygen for further protection and preservation of the viable microbial cells. Such chemicals or materials include, but are not limited to: calcium stearate, sodium aluminosilicate, sodium sulfide, sodium carbonate, silica, iron oxides, calcium carbonate, zeolite, bicarbonates, sodium sulfate, silicon dioxide and other silica materials.

In certain embodiments, a microbial strain formulation for administration to a subject or a surface or other target can include a preservation matrix, which contains and preserves the culture. Such a matrix may include a biologically active binding agent, an antioxidant, a polyol, a carbohydrate and a proteinaceous material.

Antioxidants included in a preservation matrix may be provided to retard oxidative damage to the microbial cells during the preservation and storage process.

Polyols (i.e., polyhydric alcohols) included in a preservation matrix may be provided to maintain the native, uncollapsed state of cellular proteins and membranes during the preservation and storage process. In particular, polyols interact with the cell membrane and provide support during the dehydration portion of the preservation process. Examples of polyols include, but are not limited to xylitol, adonitol, glycerol, dulcitol, inositol, mannitol, sorbitol and/or arabitol.

Carbohydrates included in a preservation matrix may be provided to maintain the native, uncollapsed state of cellular proteins and membranes during the preservation and storage process. In particular, carbohydrates provide cell wall integrity during the dehydration portion of the preservation process. Exemplary carbohydrates include, but are not limited to dextrose, lactose, maltose, sucrose, fructose and/or any other monosaccharide, disaccharide or polysaccharide.

A proteinaceous material included in a preservation matrix may provide further protection of the microbial cell during the dehydration portion of the preservation process. Exemplary proteinaceous materials include, but are not limited to skim milk and albumin.

The microbial cells can be preserved within a preservation matrix including coating the cell matrix suspension onto an inert carrier e.g., a maltodextrin bead. The coated beads can then be dried, e.g., by a fluid bed drying method. Fluid bed drying methods are well known in the art. The coated beads can be stored as a powder, placed into gelatin capsules, or pressed into tablets.

In other formulations, the microbial strain contemplated can be formulated as a hard gelatin capsule. Gelatin capsules are commercially available and are well known in the art. In this embodiment, the method further comprises dispensing the cell suspension matrix to a gelatin capsule, chilling the gelatin capsule until the cell suspension matrix forms a non-fluid matrix and to affix the gel to the interior wall of the gelatin capsule, and desiccating the gelatin capsule in a desiccation chamber. Further examples of embodiments of preservation matrices and gelatin capsule formulations may be found in U.S. Pat. No. 6,468,526 which is herein incorporated by reference in its entirety.

In certain applications, the microbial strain may be placed in a microencapsulation formulation. Such microencapsulation formulations may have applicability for example in administration to subjects via oral, nasal, rectal, vaginal or urethral routes. Spray drying is the most commonly used microencapsulation method in the food industry, is economical and flexible, and produces a good quality product. The process involves the dispersion of the core material into a polymer solution, forming an emulsion or dispersion, followed by homogenisation of the liquid, then atomisation of the mixture into the drying chamber. This leads to evaporation of the solvent (water) and hence the formation of matrix type microcapsules.

Examples of microencapsulation can be found for example in U.S. Pat. No. 5,641,209 that is herein incorporated by reference.

An embodiment of preserving by freezing is to prepare frozen beads or pellets comprising the microbial strain. After a suitable fermentation, the liquid is removed from the viable bacteria by a method including but not limited to centrifugation, ultrafiltration, or sedimentation. An additive compound may be added to the bacteria prior to freezing. Suitable additives include but are not limited to, lactose, sucrose, trehalose, maltodextrin, cyclodextrin, spray gum, fish gelatin bloom, and maltitol.

Suitable additives may also serve as cryoprotective agents to improve the stability of the frozen culture. Cryoprotective agents include, but are not limited to, proteins, protein hydrolsates, carbohydrates, or a compound involved in the biosynthesis of nucleic acids. U.S. Publ. Appl. 20070254353. Proteins or protein hydrolysates include but are not limited to, malt extract, milk powder, whey powder, yeast extract, gluten, collagen, gelatin, elastin, keratin, or albumin. Carbohydrates include but are not limited to pentoses (e.g. ribose, xylose), hexoses (e.g. fructose, mannose, sorbose), disaccharides (e.g. sucrose, trehalose, melibiose, lactulose), oligosaccharides (e.g. raffinose), oligofrutoses (e.g. actilight, fribroloses), polysaccharides (e.g. maltodextrins, xanthan gum, pectin, alginate, microcrystalline cellulose, dextran, PEG), and sugar alcohols (sorbitol, manitol). U.S. Publ. Appl. 20070254353.

A foam is defined herein is a composition that is formed by trapping many gas bubbles in a liquid. Methods pertaining to the formulation and administration of foams are set forth in U.S. Pat. Nos. 4,112,942, 5,652,194, 6,140,355, 6,258,374, and 6,558,043, each of which is herein specifically incorporated by reference in its entirety.

A typical foam formulation may, for example, be constructed by introducing a gas into a gel or aqueous pharmaceutical composition such that bubbles of the gas are within the pharmaceutical composition.

A microbial strain formulation can be applied to a surface or simply to the air using an electrostatic spray apparatus. This apparatus should have a chamber for containing the microbial strain formulation and an opening in fluid connection with the chamber through which the microbial strain formulation can be dispensed and deposited on a desired surface. The apparatus should allow for electrically charging the microbial strain formulation. For example, a conductor can be used to connect the chamber to a voltage power source. One of skill in the art would be aware of other suitable devices that can function as such a conductor.

To apply the formulation to a surface or to the air, the formulation is placed into the chamber of the electrostatic spray apparatus. The microbial strain formulation can be pumped into the chamber. When the microbial strain formulation is placed into the chamber, it contacts the conductor, such as a high-voltage DC electrode, and becomes charged. Once the formulation in the chamber is charged, it carries the same charge as the conductor. As a result the formulation and conductor repel each other. This repulsive force discharges the microbial strain formulation through the opening of the nozzle to create streams of droplets. Therefore, no additional gas source is required for atomization of the coating formulation. Accordingly, a cloud of highly charged, highly uniform-sized droplets can be formed.

Since the droplets that are formed carry a charge, when they are deposited on a grounded surface, they will be guided by their electrostatic attraction to the grounded and hence electrically neutral surface. Since the droplets carry the same electrical charge, they will repel each other. This repulsion causes the droplets arriving at the surface to avoid the areas where other droplets have already been deposited and instead land on areas of the surface that have not been coated. In this way, an inherently uniform coating is formed.

One example of a suitable nozzle apparatus that can be used in the method of some embodiments of the invention is an apparatus for electrohydrodynamic spray-coating that is disclosed in U.S. Pat. No. 4,749,125. This apparatus has a metal shim that is placed within the nozzle apparatus to define a plurality of nozzle openings. The metal shim is also connected to a voltage source that allows for the formation of electrically charged droplets of coating formulation.

Aerosol dispending system and automated embodiments thereof are further described hereinbelow.

Lyophilization—Dry microorganism cultures may be prepared according to methods which are well known in the art. In addition to constituents present in the culture medium, the medium may comprise at least one matrix material with or without other stabilizing substances. These materials may be selected from inorganic salts or buffers, at least one other compound which is selected from mono-, oligo- and polysaccharides, polyols, polyethers, amino acids, oligo- and polypeptides, milk-derived compounds, organic carboxylic acids, mineral compounds, organic carrier materials such as wheat semolina bran, alginates, DMSO, PVP (polyvinylpyrrolidone), CMC (carboxymethylcellulose), alpha-tocopherol, beta.-carotene and mixtures thereof.

Examples of suitable saccharide carrier components are sucrose, fructose, maltose, dextrose, lactose and maltodextrin. An example of a suitable polyol is glycerol. Examples of suitable amino acids are glutamic acid, aspartic acid and the salts thereof. An example of a suitable peptide carrier is peptone. An example of a milk-derived compound is sweet whey powder. Suitable organic carboxylic acids are, for example, citric acid, malic acid and L-ascorbic acid. Examples of suitable mineral carriers are montmorillonite and palygorskite.

The microorganism suspension containing the carrier can be dried in various ways. Suitable drying processes are in principle freeze drying, fluidized-bed drying and, spray-drying. Spray-drying also comprises modified spray-drying processes, such as spray-agglomeration or agglomerating spray-drying. The latter process is also known under the name FSD (fluidized spray-dryer) process.

Freeze-drying for preparing dry microorganism cultures according to some embodiments of the present invention can be carried out, for example, on the basis of the freeze-drying process described in U.S. Pat. No. 3,897,307, the contents of which is incorporated completely by reference.

Another drying process contemplated for use according to some embodiments of the present invention is spray-drying. Those methods which can be used according to some embodiments of the present invention are essentially all spray-drying techniques known in the art. The material to be sprayed can, for example, be dried concurrently or countercurrently; spraying can be carried out by means of a single-component or multiple-component nozzle or by means of an atomizer wheel.

The drying process according to some embodiments of the present invention may be carried out in such a manner that a very low residual moisture content is present in the dry material. The percentage water content is typically from about 2 to 3% by weight. This may be achieved by adding a post-drying step subsequently to the spray-drying step. The drying material is, for example, post-dried in a fluidized bed, such as at a temperature in the range of from 15 to 50° C., for a period of, for example, from 15 minutes to 20 hours. Conditioned compressed air or conditioned nitrogen serves as drying gas.

Instead of the above-described physical post-drying processes, it is also conceivable to add specific desiccants to the dry material obtained from the spray-drying. Examples of suitable desiccants are inorganic salts, such as calcium chloride and sodium carbonate, organic polymers, such as the product obtainable under the trade name Kollidion 90 F., and silicon-dioxide-containing desiccants, such as silica gel, zeolites and desiccants which are obtainable under the trade name Tixosil 38, Sipernat 22 S or Aerosil 200.

In certain embodiments, the microbial; strain may be refrigerated after harvesting and concentrating. In certain embodiments, after a suitable fermentation, the liquid is removed from the viable bacteria by a method including but not limited to centrifugation, ultrafiltration, or sedimentation. An additive compound may be added to the bacteria prior to refrigeration. Suitable additives include but are not limited to, lactose, sucrose, trehalose, maltodextrin, cyclodextrin, spray gum, fish gelatin bloom, and maltitol.

Suitable additives may also serve as cryoprotective agents to improve the stability of the refrigerated culture. Cryoprotective agents include, but are not limited to, proteins, protein hydrosolates, carbohydrates, or a compound involved in the biosynthesis of nucleic acids. U.S. Publ.

Appl. 20070254353. Proteins or protein hydrolysates include but are not limited to, malt extract, milk powder, whey powder, yeast extract, gluten, collagen, gelatin, elastin, keratin, or albumin. Carbohydrates include but are not limited to pentoses (e.g. ribose, xylose), hexoses (e.g. fructose, mannose, sorbose), disaccharides (e.g. sucrose, trehalose, melibiose, lactulose), oligosaccharides (e.g. raffinose), oligofrutoses (e.g. actilight, fribroloses), polysaccharides (e.g. maltodextrins, xanthan gum, pectin, alginate, microcrystalline cellulose, dextran, PEG), and sugar alcohols (sorbitol, manitol). U.S. Publ. Appl. 20070254353.

The type of formulation depends on the intended use.

It will be appreciated that the present inventors have identified for the first time certain activities of the bacterial strain *Bacillus amyloliquefaciens*. This bacterial strain was found effective and safe for use in the treatment of respiratory tract infections.

As used herein, the term "treating" includes abrogating, substantially inhibiting, slowing or reversing the progression of a condition, substantially ameliorating clinical or other symptoms of a condition or substantially preventing the appearance of clinical or other symptoms of a condition.

Thus, according to an aspect of the invention there is provided a method of controlling a population of pathogenic bacteria and/or fungi in a respiratory system, the method comprising administering to a subject in need thereof an effective amount of bacteria of the species *Bacillus amyloliquefaciens* or any composition comprising same such as described herein, thereby controlling the population of pathogenic bacteria and/or fungi in the respiratory system.

As used herein "*Bacillus amyloliquefaciens*" refers to a bacterial species in the genus *Bacillus*. It is a gram positive soil bacteria closely related to the species *Bacillus subtilis*. According to a specific embodiment strains of this bacterial species are as described herein, e.g., *Bacillus amyloliquefaciens* 298 and functional homologs thereof.

According to an aspect of the invention there is provided a method of controlling a population of pathogenic bacteria and/or fungi, the method comprising providing an effective amount of the isolated bacterial strain or functional homolog of same or the composition such as described herein, thereby controlling the population of pathogenic bacteria and/or fungi.

As used herein "controlling" refers to preventing or reducing microbial infections such as a bacterial or fungal infection or inhibiting the rate and extent of such infection. Therapeutic treatment is also contemplated.

According to a specific embodiment, the controlling is prevention of an infection.

As described hereinbelow, the present inventors identified the use of the bacterial strain as described herein in controlling various species of microbes.

Thus, according to some embodiments, the present compositions and methods are useful in controlling *E. coli*.

*Escherichia coli* is a Gram-negative, facultatively anaerobic, rod-shaped, coliform bacterium of the genus *Escherichia* that is commonly found in the lower intestine of warm-blooded organisms. Some *E. coli* serotypes can cause serious food poisoning in their hosts, and are occasionally responsible for product recalls due to food contamination. It is most abundant in food and water supply and industrial sites (e.g., paper production).

According to some additional or alternative embodiments, the present compositions and methods are useful in controlling *Pseudomonas aeruginosa*.

*Pseudomonas aeruginosa* is a common Gram-negative, rod-shaped bacterium that can cause disease in plants and animals, including humans. It is the most common cause of infections of burn injuries and of the outer ear (otitis externa), and is the most frequent colonizer of medical devices (e.g., catheters). *Pseudomonas* can be spread by equipment that gets contaminated and is not properly cleaned or on the hands of healthcare workers. *Pseudomonas* can cause community-acquired pneumonias, as well as ventilator-associated pneumonias, being one of the most common agents isolated in several studies. One in ten hospital-acquired infections is from *Pseudomonas*. Cystic fibrosis patients are also predisposed to *P. aeruginosa* infection of the lungs. *P. aeruginosa* may also be a common cause of "hot-tub rash" (dermatitis), caused by lack of proper, periodic attention to water quality. Since these bacteria like moist environments, such as hot tubs and swimming pools, they can cause skin rash or swimmer's ear. *Pseudomonas* is also a common cause of postoperative infection in radial keratotomy surgery patients. The organism is also associated with the skin lesion ecthyma gangrenosum. *P. aeruginosa* is frequently associated with osteomyelitis involving puncture wounds of the foot, believed to result from direct inoculation with *P. aeruginosa* via the foam padding found in tennis shoes, with diabetic patients at a higher risk.

According to some additional or alternative embodiments, the present compositions and methods are useful in controlling *Bacillus cereus*.

*Bacillus cereus* is a Gram-positive, rod-shaped, aerobic, facultatively anaerobic, motile, beta hemolytic bacterium commonly found in soil and food. Some strains are harmful to humans and cause foodborne disease. *Bacillus* foodborne diseases occur due to survival of the bacterial endospores when food is improperly cooked. Cooking temperatures less than or equal to 100° C. (212° F.) allow some *B. cereus* spores to survive. This problem is compounded when food is then improperly refrigerated, allowing the endospores to germinate.

According to some additional or alternative embodiments, the present compositions and methods are useful in controlling *Staphylococcus aureus*.

*Staphylococcus aureus* is a Gram-positive, round-shaped bacterium that is a member of the Firmicutes, and it is a member of the normal flora of the body, frequently found in the nose, respiratory tract, and on the skin. It is often positive for catalase and nitrate reduction and is a facultative anaerobe that can grow without the need for oxygen. It is a common cause of skin infections including abscesses, respiratory infections such as sinusitis, and food poisoning. Pathogenic strains often promote infections by producing virulence factors such as potent protein toxins, and the expression of a cell-surface protein that binds and inactivates antibodies. The emergence of antibiotic-resistant strains of *S. aureus* such as methicillin-resistant *S. aureus* (MRSA) is a worldwide problem in clinical medicine. Despite much research and development there is no approved vaccine for *S. aureus*. Spread of *S. aureus* (including MRSA) generally is through human-to-human contact, although recently some veterinarians have discovered the infection can be spread through pets. Recently, myriad cases of *S. aureus* have been reported in hospitals across America. Transmission of the pathogen is facilitated in medical settings where healthcare worker hygiene is insufficient. *S. aureus* is an incredibly hardy bacterium, as was shown in a study where it survived on polyester for just under three months; polyester is the main material used in hospital privacy curtains. The bacteria are transported on the hands of healthcare workers, who may pick them up from a seemingly healthy patient carrying a benign or commensal strain of *S. aureus*, and then pass it on to the next patient being treated. Introduction of the bacteria into the bloodstream can lead to various complications, including endocarditis, meningitis, and, if it is widespread, sepsis.

According to some additional or alternative embodiments, the present compositions and methods are useful in controlling *Salmonella* Typhimurium.

*Salmonella* Typhimurium. is a serogroup of a rod-shaped, flagellated, facultative anaerobic, Gram-negative bacterium and a member of the genus *Salmonella*. It is a serovar that is a serious human pathogen. The encounter of humans to *S. Typhimurium* is made via fecal-oral route from infected individuals or animals to healthy ones, with food as a common vector. Poor hygiene of patients shedding the organism can lead to secondary infection, as well as consumption of shellfish from polluted bodies of water. Most common source of infection, however, are food of animal origin and drinking water tainted by urine and feces of infected individuals and animals.

According to some additional or alternative embodiments, the present compositions and methods are useful in controlling *Alternaria alternata*.

*Alternaria alternata* is a fungus which has been recorded causing leaf spot and other diseases on over 380 host species of plant. It is an opportunistic pathogen on numerous hosts causing leaf spots, rots and blights on many plant parts. In order to survive, *Alternaria alternata* needs a moist warm environment. It is often found in areas with humid climates, or where there has been significant rainfall. The fungus lives in seeds and seedlings, and is also spread by spores. This disease flourishes in dead plants that have been left in gardens over winter. Additionally, when dead infected debris is added to compost pile it can spread to other vegetables throughout the garden.

According to some additional or alternative embodiments, the present compositions and methods are useful in controlling *Cladosporium sphaerospermum*.

*Cladosporium sphaerospermum* is a fungus belonging to the genus *Cladosporium*. *Cladosporium sphaerospermum* is mainly known as a spoilage agent of harvested fruits and vegetables. *Cladosporium sphaerospermum* is a cosmopolitan fungus that inhabits city buildings and the environment and because of its airborne nature it can move rapidly between locations. *Cladosporium sphaerospermum* is also been shown to inhabit paint films on walls and other surfaces as well as old paintings. This fungus is also able to grow on gypsum-based material with and without paint and wallpaper. Plant materials that are affected include citrus leaves on various other decaying plant leaves, on the stems of herbaceous and woody plants, on fruits and vegetables. The fungus has also been reported from wheat-based bakery items.

According to some additional or alternative embodiments, the pathogenic bacteria and/or fungi are airborne pathogens that typically cause inflammation in the respiratory system e.g., nose, throat, sinuses and the lungs.

Examples of severe infections caused by airborne bacteria include, but are not limited to tuberculosis, pneumonia, and legionellosis.

As mentioned, according to some embodiments, the methods described herein are directed to controlling a population of pathogenic bacteria and/or fungi in a respiratory system which may cause a respiratory tract disease.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

In one embodiment, the composition according to the present invention may be administered in an aerosol, for example by way of a nasal spray, for instance for administration to the respiratory tract.

As used herein the term "respiratory tract disease" refers to diseases of the upper and/or lower respiratory tracts. The term disease as used herein is synonymous with the term disorder.

In one embodiment the respiratory tract disease is an upper respiratory tract disease.

Upper respiratory tract diseases include, for example, one or more of throat soreness, sneezing, blocked nose, runny nose or a cough is a symptom of one or more of the group consisting of: tonsillitis, otitis media rhinitis (inflammation of the nasal mucosa); rhinosinusitis or sinusitis (inflammation of the nares and paranasal sinuses, including frontal, ethmoid, maxillary, and sphenoid); nasopharyngitis, rhinopharyngitis or the common cold (inflammation of the nares, pharynx, hypopharynx, uvula, and tonsils); pharyngitis (inflammation of the pharynx, hypopharynx, uvula, and tonsils); epiglottitis or supraglottitis (inflammation of the superior portion of the larynx and upraglottic area); laryngitis (inflammation of the larynx); laryngotracheitis (inflammation of the larynx, trachea, and subglottic area); and tracheitis (inflammation of the trachea and subglottic area).

In one embodiment the respiratory tract disease is a lower respiratory tract disease.

Lower respiratory tract diseases include, for example, bronchitis, acute bronchitis, pneumonia, lung abscesses.

According to some embodiments, the present teachings are directed at controlling pathogenic microbes which include, but are not limited to, *Salmonella* Typhimurium, *Salmonella enterica*, *Salmonella enteritidis*, *Clostridium botulinum*, *Staphylococcus aureus*, *Campylobacter jejuni*, *Yersinia enterocolitica* and *Yersinia pseudotuberculosis*, *Vibrio cholerae* O1, *Vibrio cholerae* non-O1, *Vibrio parahaemolyticus* and other *Vibrio* spp., *Vibrio vulnificus*, *Clostridium perfringens*, *Bacillus cereus*, *Aeromonas hydrophila*, *Plesiomonas shigelloides*, *Shigella* spp., miscellaneous enteric pathogens, and *Streptococcus* spp.

According to some embodiments the diseases caused by the pathogenic microbes include, but are not limited to, staphylococcal infections (caused, for example, by *Staphylococcus aureus*, *Staphylococcus epidermidis*, or *Staphylococcus saprophyticus*), streptococcal infections (caused, for example, by *Streptococcus pyogenes*, *Streptococcus pneumoniae*, or *Streptococcus agalactiae*), enterococcal infections (caused, for example, by *Enterococcus faecalis*) diphtheria (caused, for example, by *Corynebacterium diptheriae*), anthrax (caused, for example, by *Bacillus anthracis*), listeriosis, gangrene (caused, for example, by *Clostridium perfringens*), tetanus (caused, for example, by *Clostridium tetani*), botulism (caused, for example, by *Clostridium botulinum*), toxic enterocolitis (caused, for example, by *Clostridium difficile*), bacterial meningitis (caused, for example, by *Neisseria meningitidis*), bacteremia (caused, for example, by *Neisseria gonorrhoeae*), *E. coli* infections (colibacilliocis), including urinary tract infections and intestinal infections, shigellosis (caused, for example, by *Shigella* species), salmonellosis (caused, for example, by *Salmonella* species), yersinia infections (caused, for example, by *Yersinia pestis, Yersinia pseudotuberculosis*, or *Yersinia enterocolitica*), cholera (caused, for example, by *Vibrio cholerae*), campylobacteriosis (caused, for example, by *Campylobacter jejuni* or *Campylobacter fetus*), gastritis (caused, for example, by *Helicobacter pylori*), pseudomonas infections (caused, for example, by *Pseudomonas aeruginosa* or *Pseudomonas mallei*), Haemophilus influenzae type B (HIB) meningitis, HIB acute epiglottitis, or HIB cellulitis (caused, for example, by Haemophilus influenzae), pertussis (caused, for example, by *Bordetella pertussis*), mycoplasma pneumonia (caused, for example, by *Mycoplasma pneumoniae*), nongonococcal urethritis (caused, for example, by Ureaplasma urealyticum), legionellosis (caused, for example, by *Legionella pneumophila*), syphillis (caused, for example, by *Treponema pallidum*), leptospirosis (caused, for example, by *Leptospira interrogans*), Lyme borreliosis (caused, for example, by *Borrelia burgdorferi*), tuberculosis (caused, for example, by *Mycobacterium tuberculosis*), leprosy (caused, for example, by *Mycobacterium leprae*), actinomycosis (caused, for example, by *Actinomyces* species), nocardiosis (caused, for example, by *Nocardia* species), chlamydia (caused, for example, by *Chlamydia psittaci, Chlamydia trachomatis*, or *Chlamydia pneumoniae*), Rickettsial diseases, including spotted fever (caused, for example, by *Rickettsia ricketsii*) and Rickettsial pox (caused, for example, by *Rickettsia akari*), typhus (caused, for example, by *Rickettsia prowazekii*), brucellosis (caused, for example, by *Brucella abortus, Brucella melitens*, or *Brucella suis*), and tularemia (caused, for example, by *Francisella tularensis*). Diseases with similar origins and symptoms are also known to affect animals.

According to a specific embodiment, the controlling is prophylactic (reduces the incidence of infection).

According to a specific embodiment, the controlling is therapeutic (reduces the symptoms and/or duration of infection).

The bacterial strains/species can be administered to subjects in need thereof using methods which are well known in the art.

When used as a medicament, the bacterial strains/species of the present invention may be used in any suitable form—whether when alone or when present in a combination with other components or ingredients.

The microorganism of the present invention or composition of the present invention may be used in the form of solid or liquid preparations or alternatives thereof. Examples of solid preparations include, but are not limited to tablets, capsules, dusts, granules and powders which may be wettable, spray-dried or freeze-dried. Examples of liquid preparations include, but are not limited to, aqueous, organic or aqueous-organic solutions, suspensions and emulsions.

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the composition of the present invention is used in a tablet form—such for use as a functional ingredient—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycolate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Exemplary excipients for the forms include lactose, starch, a cellulose, milk sugar or high molecular weight polyethylene glycols.

For aqueous suspensions and/or elixirs, the composition of the present invention may be combined with various sweetening or flavouring agents, colouring matter or dyes, with emulsifying and/or suspending agents and with diluents such as water, propylene glycol and glycerin, and combinations thereof.

The forms may also include gelatin capsules; fibre capsules, fibre tablets etc.; or even beverages.

Further examples of forms are in the form of a cream for example. For some aspects the microorganism may be included in pharmaceutical and/or cosmetic creams such as sun creams and/or after-sun creams for example.

In one aspect, the composition according to the present invention may be administered in an aerosol, for example by way of a nasal spray, for instance for administration to the respiratory tract.

According to a specific embodiment, the microbial species/strains as described herein are dispensed from an aerosol dispensing device (or system).

There are devices known to atomize a liquid and deliver the atomized liquid into the surrounding air.

According to a specific embodiment the aerosol dispensing device is automated.

Such an aerosol dispersing device can work on its own as well as in conjunction with an HVAC system.

Figure 5:
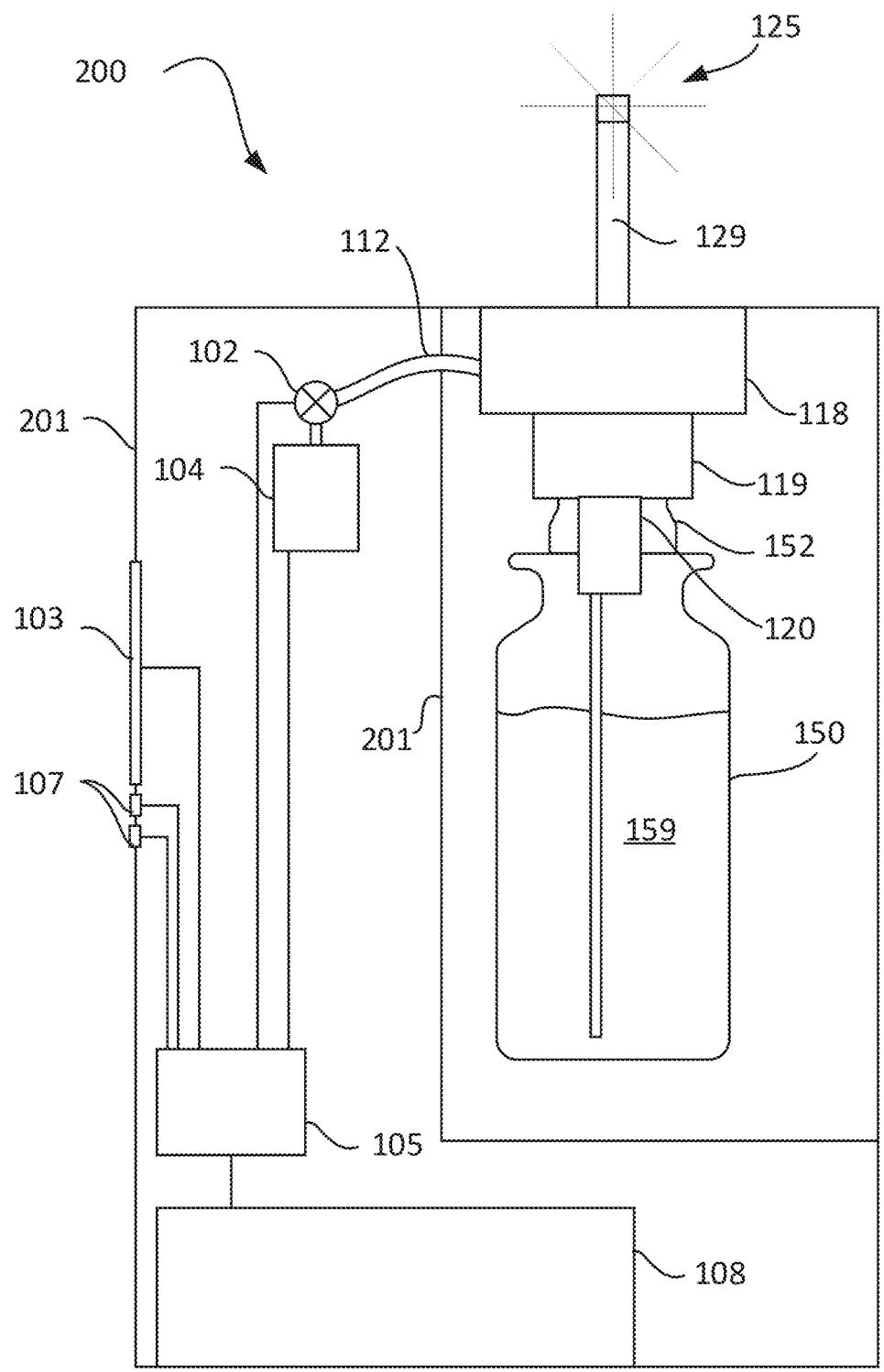
FIG. 5 is a simplified schematic drawing of an example aerosol dispensing device in accordance with some example embodiments.
Figure 6A:
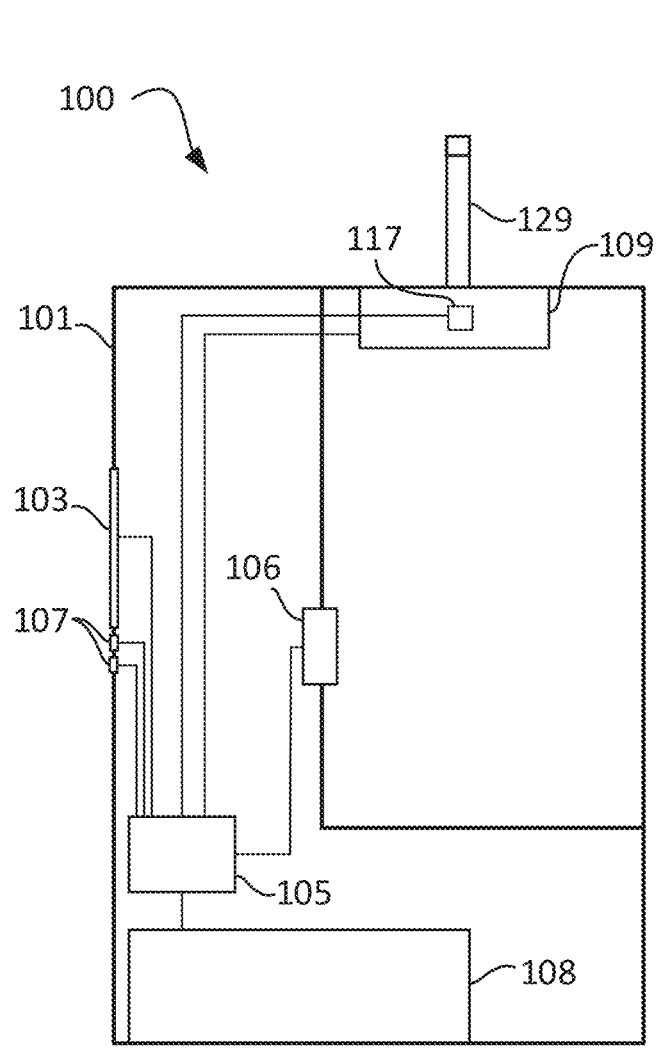
FIGS. 6A and 6B are simplified schematic drawings of an example aerosol dispensing device and an example replaceable cartridge respectively in accordance with some example embodiments.
Figure 6B:
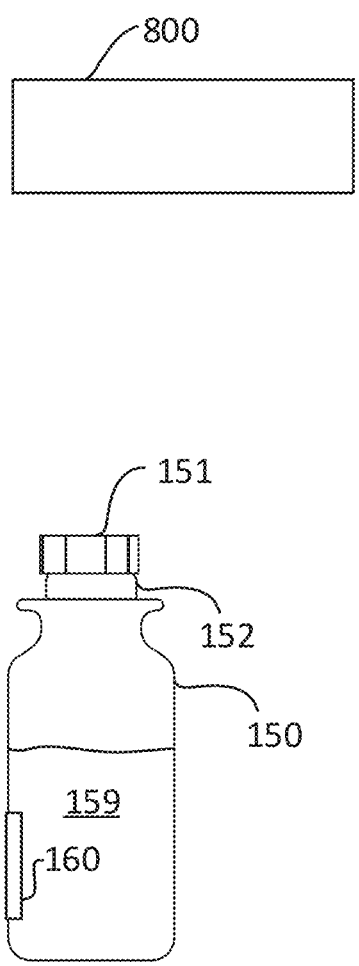
Figure 7:
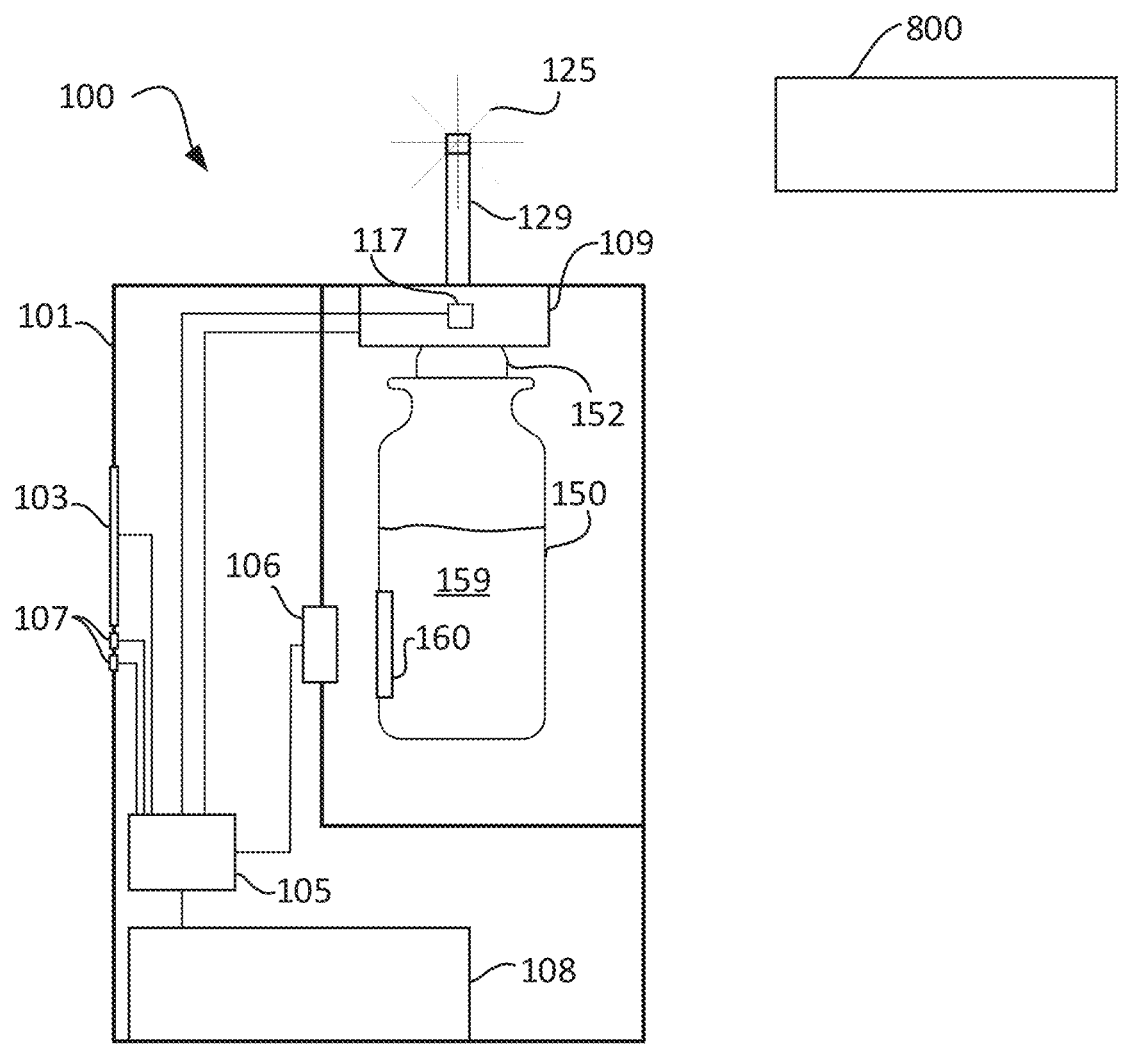
FIG. 7 is a simplified schematic drawing of an example replaceable cartridge installed in an example aerosol dispensing device in accordance with some example embodiments.

Reference is now made to FIG. 5 showing a simplified schematic drawing of an example aerosol dispensing device with a replaceable cartridge that is actuated with compressed air in accordance with some example embodiments. An aerosol dispensing device 200 includes a housing 201 that may house an air compressor 104 to actuate atomizing a liquid 159 contained in a cartridge 150. Pressurized air provided by compressor 104 may be delivered through valve 102 and a channel 112, e.g. a tube to a connector 118. Connector 118 may establish a fluid connection between compressor 104, cartridge 150 and an aerosol outlet 129 from which atomized liquid 125 may be expelled. An atomizer 120 may be integrated in connector 118 or in collar 152 of cartridge 150. Optionally, an adaptor 119 provides a sealed connection between cartridge 150 and connector 118. Although connector 118 and adaptor 119 are shown as two separate elements, it is understood that functionality of these two elements may be integrated into a single part.

According to some example embodiments, at least one of a cartridge for an aerosol dispensing device and the aerosol dispensing device includes a mechanism for stirring liquid contents of the cartridge. Optionally, liquid content in the cartridge may be stirred continuously or periodically during use to maintain a substantially constant concentration of active material over a height of the liquid.

In some example embodiments, device 200 is self-powered with a power source 108. Alternatively, device 200 may be powered by an external power source. In some example embodiments, device 200 includes a user interface including for example a display 103 and one or more user actuated buttons or knobs 107.

Device 200 may be positioned in an indoor environment. The indoor environment may be a public space such as a hospital or a shopping center or may be a personal space such as an office, a home or a vehicle. Optionally, device 200 may be configured to direct aerosol 125 expelled from channel 129 into airflow ducts of a heating, ventilation and air conditioning (HVAC) system. Optionally, circuit 105 is in communication or receives input from an HVAC system and is operated in coordination with the HVAC system. Alternatively, device 200 may be operated independently from an HVAC system and the aerosol may also be dispersed directly into the indoor space, e.g. not through the HVAC ducts.

One such configuration is described in U.S. Pat. No. 8,986,610 entitled "Apparatus and method for dispersing liquid in aerosol," the contents of which is incorporated by reference herein, describes a system and method to deliver an atomized solution to the interior volume of a building or room utilizing a Venturi effect for the atomization. It is described that the solution may contain at least one active material including at least one of a medicament, probiotic, nutraceutical, or combinations thereof. The system includes a solution chamber; a Venturi configuration operatively associated with said solution chamber; an air inlet associated with a pressurized air inlet source; an actuator and a sensor. The solution chamber may be in the form of a replaceable cartridge.

In known automated aerosol dispensing devices, the live organism or active material is typically in the form of a water based solution stored in a replaceable cartridge. A device with embodiments having cartridge replacement embodiments is further described hereinbelow.

Reference is now made to FIGS. 6A and 6B showing a simplified schematic drawing of an example aerosol dispensing device and an example replaceable cartridge respectively and to FIG. 7 showing an example replaceable cartridge installed in an example aerosol dispensing device all in accordance with some example embodiments. An aerosol dispensing device 100 includes a housing 101 that may house an actuator 109 configured to actuate atomization of a liquid 159 in a cartridge 150, an outlet channel 129 from which atomized liquid 125 may be expelled and a circuit 105 configured to control operation of actuator 109. An atomizer 120 for creating aerosol 125 based on actuation with actuator 109, may be integrated as part of actuator 109 or may be integrated in cartridge 150. Optionally, actuator 109 is configured to establish fluid connection with cartridge 150. According to some example embodiments, aerosol dispensing device 100 additionally includes a reader 106 configured to read data on a tag 160 included on cartridge 150.

In some example embodiments, device 100 is self-powered with a power source 108. Alternatively, device 100 may be powered by an external power source. In some example embodiments, device 100 includes a user interface including for example a display 103 and one or more user actuated buttons or knobs 107. Optionally, device 100 additionally includes a sensor 117 configured to sense when cartridge 150 is installed in device 100. Sensor 117 may for example be an opto-coupler sensor that detects a break in a line of sight due to insertion of neck 152 into actuator 109. In another example, sensor 117 may be a button switch that is compressed based on insertion of collar 152 into actuator 109.

Device 100 may be positioned in an indoor environment. The indoor environment may be a public space such as a hospital or a shopping center or may be a personal space such as an office, a home or a vehicle. Optionally, device 100 may be configured to direct aerosol 125 expelled from channel 129 into airflow ducts of a heating, ventilation and air conditioning (HVAC) system. Optionally, circuit 105 is in communication or receives input from an HVAC system and is operated in coordination with the HVAC system. Alternatively, device 100 may be operated independently from an HVAC system and the aerosol may also be dispersed directly into the indoor space, e.g. not through the HVAC ducts.

According to some example embodiments, liquid 159 may include sensitive material such as a pro-biotic, medicament, nutraceutical, or combinations thereof that may be prone to contamination. The material when contaminated may pose a health hazard. Furthermore, any malicious tampering with cartridge 150 may also lead to a hazardous situation. For example an offender may maliciously insert a harmful bacteria or an irritant into cartridge 150. Alternately, an offender may attempt to refill cartridge 150 with unknown or unregulated contents that may not be suitable or safe in general or for a particular indoor space. In other examples, a hazardous situation may be created without malicious intent, for example when a solution in the cartridge has passed its expiration date or when a property of the solution has been altered due to prolonged exposure to humidity or air.

According to some example embodiments, circuit 105 includes safety verification functionality to verify compatibility, authenticity and safety of cartridge 150 when it is inserted into housing 101 and optionally to provide ongoing monitoring while cartridge 150 is maintained in device 100. The verification may be based on input received from reader 106. In some example embodiments, circuit 105 receives data from reader 106 and compares the data received to information stored in memory. Optionally, if an identification code read by reader 106 matches an identification code listed in the memory, verification may be established. The memory may be memory included in circuit 105, memory included in a remote server 800 or memory included in a cloud. Optionally, the information needed to verify authentication of cartridges may be uploaded by a remote server 800 and circuit 105 may access the information based on wireless communication. According to some example embodiments, circuit 105 is configured to terminate dispersion or formation of atomized liquid 125 and provide an alert when cartridge 150 cannot be positively verified.

Reader 106 may be configured to scan a code or interrogate a tag 160 positioned on cartridge 150, when cartridge 150 is installed in device 100 and provide the data to circuit 105. In some examples, reader 106 is or includes a camera or a RFID scanner that is configured to detect data stored on cartridge 150. Preferably, reader 106 is an active reader that is controlled and powered with circuit 105. In some example embodiments, controller 105 activates reader 106 at a defined frequency, e.g. every 5-60 minutes to scan or interrogate tag 160. Additionally or alternatively, controller 105 may activate reader at defined events. For example controller 105 may activate reader when power of device 100 is turned on and during installation of cartridge 150 in the device 100. In some example embodiments communication between reader 106 and tag 160 is wireless or contactless. In other example embodiments, communication between reader 106 and tag 160 is based on electrical contact.

Optionally, cartridge 150 configured for use with device 100 includes tag or code 160 with data to verify its compatibility. Tag or code 160 may be a barcode, e.g. a one dimensional or two dimensional barcode, maybe in passive RFID tag and may be an active RFID tag. Tag or code 160 may be positioned in an inner surface of cartridge 150 that is in contact with fluid 159 or may be positioned on an outer surface of cartridge 150. According to some example embodiments, tag or code 160 may be positioned on cartridge 150 so that it aligns with reader 106 while establishing a sealed connection with actuator 109.

In some example embodiments, tag or code 160 includes passive storage. Information tagged or coded on tag or code 160 may include one or more of the following items: state of a seal on the cartridge, identification data, part number of the product, batch number, production date, expiration date, quantity of material in the cartridge, contents of the cartridge and operating instructions.

Optionally, contents 159 of cartridge 150 are sealed with a seal under cap 151 that is configured to be broken in actuator 109 while inserting cartridge 150 into housing 101. Optionally, breaking of the seal alters data stored in tag or code 160 so that the event may be recorded and detected by reader 106. Optionally, this information may be used to prevent operating device 100 with cartridges that have been refilled. Cartridge 150 may be in the form of a bottle or may be any container that can contain fluid 159 to be dispersed as an aerosol. Typically cartridge 150 is configured to be replaced after its contents have been emptied.

In some example embodiments, tag 160 may be an active tag and reader 106 may transmit data to tag 160 that may be stored in tag 160. Active storage may be a microchip with RAM memory in which case a small power source may be included on cartridge 150. Alternatively, active storage may be an active RFID.

Figure 8:
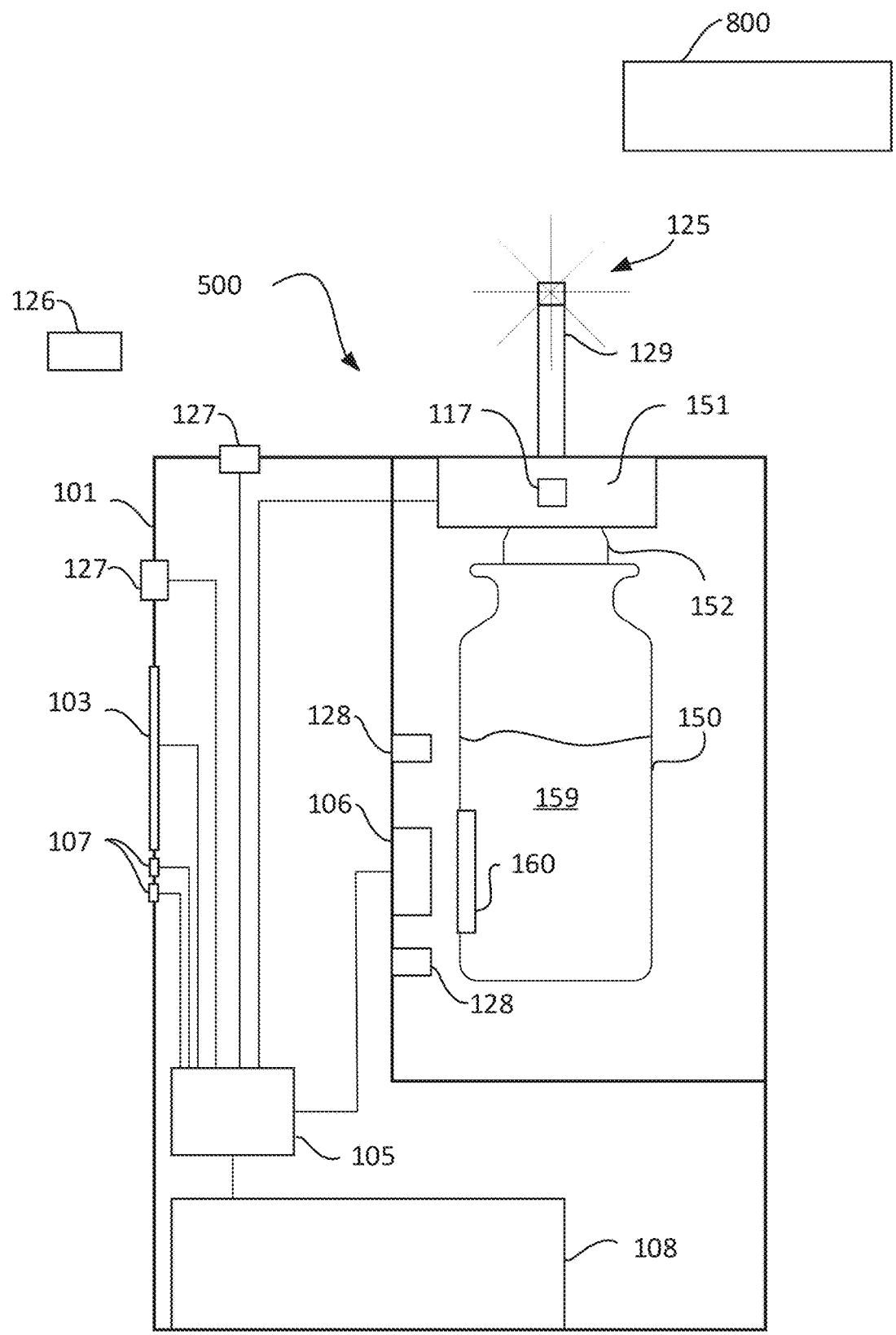
FIG. 8 is simplified schematic drawing of an example aerosol dispensing device including one or more sensors in accordance with some example embodiments.

FIG. 8 shows a simplified schematic drawing of an example aerosol dispensing device including one or more sensors in accordance with some example embodiments. According to some example embodiments, the aerosol dispensing device 500 includes a regulator configured to regulate activity of device 500 installed with a cartridge 150. Functionality of the regulator may be included in circuit 105. Optionally, device 500 includes reader 106 and circuit 105 may regulate activity of device 500 based on information received from reader 106, e.g. instruction that may be specific to liquid 159 contained in the cartridge. Circuit 105 may additionally or alternatively regulate activity of device 500 based on inputs from one or more sensors in communication with circuit 105. In some example embodiment, device 500 includes sensors 128 configured to detect a parameter related to content 159 in cartridge 150. Optionally, sensor 128 is a level sensor for detecting a level of liquid 159 in cartridge 150. Optionally, one sensor 128 may be positioned to sense liquid at 1-3 cm from a bottom of cartridge 150 to detect when contents of cartridge 150 are nearly emptied. In some example embodiments, when contents of cartridge 150 are nearly emptied, circuit 105 may provide an alert on display 103 and may also communicate this information to a remote server 800 in communication with circuit 105. Remote server 800 may then alert a service provider or deliver a new cartridge to the site including device 500.

Device 500 may additionally include sensors 127 that may detect environmental conditions. Optionally, humidity is detected. In some example embodiments, temperature is detected. At times, an expiration date may be adjusted based on the detected environmental conditions. For example an expiration date may be shortened in environments with higher humidity as compared to environments that are more arid. Optionally, frequency or duration of actuation may be adjusted based on output detected from one or more of sensors 127, sensors 128 and based on data read with reader 106.

In some example embodiments, device 500 may be configured to receive input from a stand-alone sensor 126 that is remote from device 500. Input may be received based on tethered or wireless connection. Stand-alone sensor 126 may be for example an air quality probe similar to E4000 indoor air quality probe offered by NanoSense, France, a thermostat associated with an HVAC, or a humidity sensor. Input from remote sensors 126 may similarly be used to adjust an expiration date or to adjust frequency or duration of actuation based on the detected environmental conditions.

According to some example embodiments, the aerosol dispensing device 500 additionally includes safety verification functionality as described herein above to verify compatibility, authenticity and safety of cartridge 150 when it is inserted into device 500 and optionally to provide ongoing monitoring while cartridge 150 is maintained in device 500. In some example embodiments, the safety verification functionality is based on reader 106 reading data on a tag 160 included on cartridge 150 and circuit 105 processing the data.

According to some embodiments the bacterial species/strains as described herein or compositions comprising same are not to be used in the treatment of agricultural water (irrigation water), agricultural soils and agricultural crops.

According to some embodiments, the bacterial species/strains as described herein or compositions comprising same can be used in the treatment of agricultural water (irrigation water), agricultural soils and agricultural crops. In still other embodiments, the formulations of cultured bacteria can be applied in the treatment at food processing facilities. In the case of food processing facilities, agricultural waters and soils, the formulations of cultured bacteria can be applied prophylactically or as a sanitizing agent following an exposure. The product can be used to treat foods including meat and meat products. The meat product can generally be any whole, cut, ground or processed meat product, including, ground beef ("hamburger"), ground turkey, ground chicken, ground pork, beef sausage, pork sausage, chicken sausage, turkey sausage, hot dogs, bologna, salami, cold cuts, game hens, whole chicken, lamb, ham, pork, cube meat, steaks, roasts, fillets, fish, or liver.

Any type of agricultural produce sold in marketplaces, such as those derived from plant or fungi, can be treated by the methods and compositions disclosed herein. Additional types of produce products that can be treated by the disclosed antimicrobial compositions include but are not limited to those derived from leaves, stems, fruit, flowers, seeds, roots, and like components that form the plant, as well as those derived from fungi, including the cap, stem, mycelium and annulus, and like components that form the fungi.

Any type of surface can be treated with the bacterial strains/species as described herein. Examples of surfaces that may be treated include of animate surfaces such, as those of animals or plants, and inanimate surface, such as food, buildings, furniture, objects and the like. Specific examples of surfaces that the composition could be applied to include, but are not limited to the following: meat, grinders, processors, extruders, cutting surfaces, cutting apparatus, blades, seafood, agricultural produce (fruit, vegetables, etc.), nuts, legumes, sprouts, trees, leaves, seeds, bulbs, flowers, animals (livestock and pets), eggs shells, skin, hair, bone, horn, hooves, wool, leather, lawns, fields, soil, floors, walls, countertops, cabinets, toilets, bathtubs, bathrooms (portable and non-portable), sinks, laundry equipment, kitchen appliances (refrigerators, freezers, dishwashers, etc.), heating and refrigeration coils, fans, ceiling fans, heating systems, air conditioning system, ventilation systems, internal and external ducts for ventilation, heating and air conditioning, tabletops, chairs and sofas, desks, luggage, fabrics, clothing, footwear, sports equipment, audio/visual equipment, computers, clocks, boxes (cardboard, wood, etc.), books, paper surfaces, garbage/trash receptacles, building materials, interior and exterior of transportation equipment (automobiles, airplanes, trains, boats, etc.), interior and exterior of spacecraft and other space facilities, trailers, tires, metal, ceramic, tile, linoleum, carpet, wall paper, painted surfaces, plastic, vinyl, polyvinyl chloride (PVC) and the like, plastic, rubber, glass, hose line, plumbing (inside and outside), other application machinery, lighting, heating and cooling filaments, ovens, storage containers, bottles, cans, reception areas, milking parlors, food processing facilities, and the like.

The article of manufacture may be packaged in a form that is appropriate or convenient for shipment, administration, or storage. For example, the product can be placed into a hermetically sealed pouch of plastic, paper, metalized plastic, or metal (e.g. aluminum), bottle, cartridge capsule, plastic bag, or a box.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention.

Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y.

(1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

MATERIALS AND METHODS

Strains

Bacillus strain was isolated from home-made Doenjang using Luria Bertani Miller agar (BD, Difco) agar for plating. Representative colonies were picked from plates with the highest dilution still showing colonies. After purification, the strain was stored at −80° C. The stock culture was propagated first in 10 ml LB Miller broth (in 50 ml Falcon sterile tube) for 18 hours (rotary shaker, 120 RPM), and then the culture was 1% diluted into a fresh media and was propagated in the same conditions as described previously, before each experiment.

Reference strains were obtained from ATCC (American Type Culture Collection) and KACC (Korean Agricultural Culture Collection) and KCTC (Korea, Collection for Type Cultures).

16S rDNA Sequencing

Pure cultures of *Bacillus amyloliquefaciens* 298 was grown on LB Miller agar (BD Difco) at 37° C. for 24 hours. The plate was sent to Solgent Inc. (Deajun, South Korea) for bi-directional 16S rDNA sequencing using (5'-AGA GTT TGATCMTGG CTC AG-3', SEQ ID NO: 1) and 1492R (5'-TAC GGY TAC CTT GTT ACG ACTT-3' SEQ ID NO: 2) primers by (Reysenbach, Giver et al. 1992). Bi-directional sequencing results were assembled using Codon Code Aligner (Codon Code Corporation, USA) and compared with reference sequences of *Bacillus* species on the GenBank database (www(dot)ncbi(dot)nlm(dot)nih(dot)gov/Blastn/).

API Test

Specific sugar fermentation pattern was monitored using API 50 CHB strips (Biomerieux). The *Bacillus* strain pellet was prepared using LB Miller agar (BD Difco) at 37° C. for 24 hours and centrifuged 14,000 rpm for 5 min. The pellet was suspended using the preparation media in the kit and applied on different sugars according to the instruction manual.

Hemolysis Test

*B. amyloliquefaciens* 298 was grown at 37° C. for 18 hours in LB broth and then streaked onto 5% sheep blood agar (Hanil Komed) and incubated for 24 h at 37° C. Alpha (a) hemolysis was considered as the partial decomposition of the hemoglobin of the red blood cells, beta ((3) hemolysis as the complete breakdown of the hemoglobin of the red blood cells observed as a clear zone in the agar plate and gamma (y) hemolysis as the lack of hemolysis. *B. cereus* ATCC 27348 was used as a positive control.

Lecithinase Test

*B. amyloliquefaciens* 298 and *B. cereus* ATCC 27348 (positive control) were grown at 37° C. for 18 hours in LB Miller broth and streaked out onto egg yolk agar. The plates were incubated for 24 h at 37° C. and the formation of a white precipitate around the colonies was considered as positive for lecithinase activity (Hong, Huang et al. 2008, Sorokulova, Pinchuk et al. 2008).

Antibiotic Resistance Test

The basic protocol was followed by CLSI recommendation (Jorgensen and Turnidge 2015). Pure cultures of *B. amyloliquefaciens* 298 were cultivated at 37° C. for 18 hours in LB Miller agar. The agar dilution method was used to assess the minimal inhibitory concentration (MIC) of the antibiotics against the strain. A single colony was resuspended in phosphate buffer saline (PBS) 1× and adjusted 0.01 optical density (OD). Ten microliters ($1\times10^5$ CFU/mL) of strain were inoculated on the plates using multipin-inoculator and incubated at 37 C. for 24 hours. The strain was considered susceptible when they were inhibited at a concentration for a specific antimicrobial equal or lower than the established cut-off value and resistant bacterial strain when it was not inhibited at a concentration of a specific antimicrobial higher than the established cut-off value according to the parameters established by the European Food Safety Authority (EFSA).

Inhalation Infection Test

The animal study was approved by Handong Global University Ethical committee. For the experiment, 40 mice were divided into four groups comprising negative control, two positive controls infected with pathogenic microorganisms of *Streptococcus pneumoniae* ATCC49619 and *Bacillus cereus* ATCC27348 and one group infected with the tested microorganism. Potential probiotic *B. amyloliquefaciens* 298 was infected at a dose of $1\times10^7$ CFU/mouse with pre-treatment of cyclophosphamide to induce immunocompromised status. The cyclophosphamide was used to derive immunocompromised animal model to monitor more emphasized influence of infected microorganims so called worst case scenario (Kong, Hellermann et al. 2005).

The *B. amyloliquefaciens* 298 was grown for 18 hours in LB Miller broth (BD Difco) at 37° C. while *S. pneumoniae* ATCC49619 was cultured on 5% Sheep blood agar and sub-cultured to Brain Heart Infusion broth (BD Difco) and incubated at 37° C. The bacterial solution was diluted using 1× PBS to $1\times10^7$ CFU/mouse. The inoculum concentration was determined by enumeration of cultured bacteria on agar plates.

The animal lung infection model was carried out in 4-week-old female ICR mice (Hyo-chang science). The mice were anesthetized during respiratory infection (*Streptococcus pneumoniae* ATCC49619 and *Bacillus cereus* ATCC27348) using 50 µL of bacterial suspension through intranasal route. After 24 h post infection, 2 mice of each group were selected randomly and sacrificed with diethyl ether for enumeration of viable colonies in lungs. Lungs were extracted and homogenized with Phosphate-buffered saline (PBS). Before homogenization, lungs were monitored visually. The homogenized lung samples were diluted and spread on 5% Sheep blood agar to enumerate number of pathogens in the lungs. The plates were incubated for 18 hours. The rest of the mice were monitored during 1 week to measure their survival rates (Ginsberg, Moldawer et al. 1991).

Efficacy Tests

The agar well diffusion assay was performed to evaluate the antagonistic activity of *B. amyloliquefaciens* 298 against the growth of pathogenic bacteria including *Escherichia coli* ATCC 22922, *Pseudomonas aeruginosa*, *B. cereus* ATCC 27348, *Staphylococcus aureus* ATCC 11335, *Salmonella Typhimurium* ATCC 14028 and *Listeria innocua* ATCC 3586. The antagonistic activity of *B. amyloliquefaciens* 298 was also verified against molds such as *Alternaria alternata* (Fries) Keissler (ATCC® MYA-4642™), *Cladosporium sphaerospermum* Penzig (ATCC® MYA-4645™) and *Penicillium chrysogenum* Thom (ATCC® MYA-4644™). Brain Heart Infusion (BHI) Agar was used for the antagonism against pathogenic microorganisms while the Potato Dextrose Agar (PDA) was used for evaluation against molds. Reference pathogens were prepared using BHI broth at 37° C. for 18 hours while *B. amyloliquefaciens* 298 was grown using LB broth at 37° C. for 18 hours. Molds were prepared using PDA at 25° C. with 85% HR for 7 days. Mold spores, pathogens and *B. amyloliquefaciens* 298 were harvested and resuspended in PBS. Pathogens and *B. amyloliquefaciens* 298 were adjusted to an optical density of 0.2 and 100 uL of pathogen suspended in PBS was spread on BHI agar plates. The same amount of mold spore suspension was inoculated on PDA. Wells were made in all the plates and 20 μL of *B. amyloliquefaciens* 298 suspensions were inoculated in the wells while the BHI plates were incubated at 37° C. for 24 hours and PDA plates at 25° C. for 72 hours. The inhibition of pathogens and molds was observed as a clear zone around the *bacillus* strain inoculated wells and 10% hydrogen peroxide served as a positive control.

16S rDNA Sequence

The identity of the strain was confirmed as *B. subtilis* according to the National Center for Biotechnology Information (NCBI) database according to the 16S-rRNA (SEQ ID NO: 3) sequencing result.

Complete Genome Sequence

The complete genome sequence of *B. amyloliquefaciens* 298 was generated using the PacBio RS platform with single-molecule real-time (SMRT) sequencing at Theragenetex (Seoul, South Korea). Annotations were performed by merging the results obtained from the Rapid Annotations using Subsystems Technology (RAST) server, Glimmer 3.02 modeling software, tRNAscan-SE 2.0, and RNAmmer 1.2. In addition, the contigs were searched against the KEGG, UniProt, and Clusters of Orthologous Groups (COG) databases to annotate the gene description.

Metabolite Analysis

Total protein was extracted from growth media of *B. amyloliquefaciens* 298 after 18 hours at 37° C. incubation to evaluate the secreted metabolites of *B. amyloliquefaciens* 298. A stock solution was prepared dissolving 500 g of Trichloroacetic acid (TCA) into 350 ml of distilled water. 1 volume of TCA stock solution was added to 4 volumes of *B. amyloliquefaciens* 298 growth media and incubated at 4° C. for 10 min. The tube was centrifuged at 14,000 rpm for 5 min and supernatant was removed to concentrate the protein pellet. The pellet was washed with 200 μl cold acetone and again concentrated by 14,000 rpm centrifugation for 5 min. This step was repeated for three times and the pellet was sent to be analyzed using LC-LTQ-Orbitrap at Technopark Biocenter (Pohang, South Korea). The raw data was analyzed using UniProt database to match predicted proteins from the growth media of *B. amyloliquefaciens* 298.

Example 1

In-Vitro Safety Evaluation of Lecithinase and Hemolysis Activity

*B. amyloliquefaciens* 298 did not show lecithinase activity observed as the absence of a white precipitate around the *Bacillus* colonies and all *B. amyloliquefaciens* 298 showed negative reaction for hemolysis as well.

TABLE 1

Lecithinase and hemolysis activity of *B. amyloliquefaciens* 298 and *B. cereus* ATCC 27348.

| Strain | Lecithinase activity | Hemolysis activity |
| --- | --- | --- |
| *Bacillus amyloliquefaciens* 298 | Negative | Gamma |
| *Bacillus cereus* ATCC 27348 (positive control) | Positive | Beta |

Example 2

In-vitro Evaluation of Antibiotic Resistance

The agar dilution was used to evaluate the minimal inhibitory concentration (MIC) of antibiotics. *B. amyloliquefaciens* 298 was found to be sensitive to erythromycin, gentamicin, tetracycline, streptomycin, vancomycin, chloramphenicol, kanamycin and clindamycin according to the European Food Safety Authority MIC breakpoints for *Bacillus* species. The determined MIC values are clearly below or equal to the EFSA breakpoint values (Table 2).

TABLE 2

Minimum inhibitory concentrations (MIC) of *B. amyloliquefaciens* 298. Antibiotic resistance test

| | Minimum inhibitory concentration (mg/L) of antibiotics | | | | | | | |
| --- | --- | --- | --- | --- | --- | --- | --- | --- |
| Strain | Ery | Gen | Tet | Str | Van | Chl | Kan | Cli |
| *B. amyloliquefaciens* 298 | ≤0.125 | ≤2 | ≤0.125 | 8 | 0.25 | ≤4 | ≤4 | 0.5 |
| EFSA breakpoint | 4 | 4 | 8 | 8 | 4 | 8 | 8 | 4 |

Ery: Erythromycin;
Gen: Gentamicin;
Tet: Tetracycline;
Str: Streptomycin;
Vm: Vancomycin;
Chl: Chloramphenicol;
Kan: Kanamycin;
Cli: Clindamycin.

Example 3

Respiratory Tract Infection Test

The survival rate after respiratory tract infection of *B. amyloliquefaciens* 298 was 100% while the positive control of pathogenic bacteria infected groups including *S. pneumoniae* and *B. cereus* showed 100% mortality after 24 hours (FIG. 1). Lung pictures were taken and showed strong damage in pathogen infected positive groups while lung of *B. amyloliquefaciens* 298 infected groups showed similar lung status as negative control group (FIG. 2) and any colony of *Bacillus* was found from the homogenized lung of *B. amyloliquefaciens* 298 infected group (data not shown). These data demonstrate that *B. amyloliquefaciens* 298 does not infect lung probably due to lack of colonization in the lung.

Example 4

Efficacy Tests

The antagonism test results of *B. amyloliquefaciens* 298 showed inhibited growth of *E. coli* ATCC 22922, *P. aeruginosa, B. cereus* ATCC 27348 and *S. Typhimurium* ATCC 14028 at different degrees (FIG. 3 and Table 3).

TABLE 3

Antagonistic activity of *Bacillus amyloliquefaciens* 298 against pathogens.

| Pathogens | *B. amyloliquefaciens* 298 |
|---|---|
| *Escherichia coli* ATCC 22922 | 2 |
| *Pseudomonas aeruginosa* | 1 |
| *Bacillus cereus* ATCC 27348 | 2 |
| *Staphylococcus aureus* ATCC 11335 | 1 |
| *Salmonella Typhimurium* ATCC 14028 | 2 |
| *Listeria innocua* ATCC 3586 | NA |

NA: No antagonism was observed

*B. amyloliquefaciens* 298 antagonism against mold indicates positive antagonism against *Alternaria alternata* (Fries) Keissler (ATCC® MYA-4642™) and *Cladosporium sphaerospermum* Penzig (ATCC® MYA-4645™) at variable level (Table 4). The inhibition of the mold growth is evidently expressed as a clear zone around the wells inoculated with the *B. amyloliquefaciens* 298 (FIG. 4). *Penicillium chrysogenum* Thom (ATCC® MYA-4644™) was not inhibited at all for any of the strains used on this experiment, however the mycelium color around the well inoculated with *B. amyloliquefaciens* 298 show and slightly decrease in the intensity (data not shown) from green to white.

TABLE 4

Antifungal activity of *Bacillus amyloliquefaciens* 298 against molds.

| | Inhibition zone (mm) | | |
|---|---|---|---|
| Strain | *Alternaria alternata* (Fries) Keissler (ATCC MYA-4642) | *Cladosporium sphaerospermum* Penzig (ATCC MYA-4645) | *Penicillium chrysogenum* Thom (ATCC MYA-4644) |
| *Bacillus amyloliquefaciens* 298 | 6 | 6 | NA |
| Hydrogen peroxide 10% | 8 | 12 | 10 |

NA: No antagonism was observed

Example 5

Taxonomic Identification

The identity of the strain was confirmed as *B. subtilis* according to the National Center for Biotechnology Information (NCBI) database. API results were monitored for further identification of physiological characteristics.

Example 6

Complete Genome Sequence

A Single run of PacBio provided total number of 151,771 reads which comprises in total of 1,368,609,189 bases. Raw data was assembled using Canu v1.6 and single contig was produced in size of 3,928,316 base pairs (Separate attached text file of "*Bacillus* amyloliquefaciens 298.fasta"). Total number of genes were 3,854 (3,740 coding sequences) and 3,044 annotated genes were found which calculated as 81.39% of total genes (gene annotations are listed in Table 5 below).

TABLE 5

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 387 | 1676 | + | GENE_00001 | Prodigal: 2.6 | CDS | — | — | — | — | O07553 | nhaC_1 | — | — | Na(+)/H(+) antiporter NhaC |
| Contig1 | 1714 | 3096 | − | GENE_00002 | Prodigal: 2.6 | CDS | — | — | — | — | P94426 | gabR_1 | — | — | HTH-type transcriptional regulatory protein GabR |
| Contig1 | 3215 | 3835 | + | GENE_00003 | Prodigal: 2.6 | CDS | — | — | — | — | P21341 | paiB_1 | — | — | Protease synthase and sporulation protein PAI 2 |
| Contig1 | 3884 | 4246 | − | GENE_00004 | Prodigal: 2.6 | CDS | — | — | — | — | — | — | — | — | hypothetical protein |
| Contig1 | 4463 | 5653 | − | GENE_00005 | Prodigal: 2.6 | CDS | — | — | — | — | P43531 | yntM_1 | — | — | Inner membrane transport protein YnfM |
| Contig1 | 5898 | 6476 | + | GENE_00006 | Prodigal: 2.6 | CDS | — | — | — | — | P43506 | bm3R1_1 | — | — | HTH-type transcriptional repressor Bm3R1 |
| Contig1 | 6669 | 6968 | − | GENE_00007 | Prodigal: 2.6 | CDS | — | — | — | — | P23261 | cotF_1 | — | — | Spore coat protein F precursor |
| Contig1 | 6983 | 7180 | − | GENE_00008 | Prodigal: 2.6 | CDS | — | — | — | — | — | — | — | — | hypothetical protein |
| Contig1 | 7199 | 8335 | − | GENE_00009 | Prodigal: 2.6 | CDS | 1.2.99.4 | — | — | — | Q52078 | fdm_1 | — | — | Formaldehyde dismutase |
| Contig1 | 8354 | 8722 | − | GENE_00010 | Prodigal: 2.6 | CDS | — | — | — | — | P23261 | cotF_2 | — | — | Spore coat protein F precursor |
| Contig1 | 8740 | 8985 | − | GENE_00011 | Prodigal: 2.6 | CDS | — | — | — | — | — | — | — | — | hypothetical protein |
| Contig1 | 9336 | 10613 | + | GENE_00012 | Prodigal: 2.6 | CDS | 2.7.13.3 | — | — | — | O32198 | liaS_1 | — | — | Sensor histidine kinase LiaS |
| Contig1 | 10606 | 11241 | + | GENE_00013 | Prodigal: 2.6 | CDS | — | — | — | — | Q7A4R9 | vraR_1 | — | — | Response regulator protein VraR |
| Contig1 | 11340 | 13493 | + | GENE_00014 | Prodigal: 2.6 | CDS | — | — | — | — | P96687 | ydfJ_1 | — | — | Membrane protein YdfJ |
| Contig1 | 13527 | 14249 | − | GENE_00015 | Prodigal: 2.6 | CDS | 2.4.2.- | — | — | — | O33341 | — | — | — | Putative glutamine amidotransferase |
| Contig1 | 14386 | 16014 | − | GENE_00016 | Prodigal: 2.6 | CDS | — | — | — | — | P63389 | yheS_1 | — | — | putative ABC transporter ATP-binding protein YheS |
| Contig1 | 16293 | 16820 | − | GENE_00017 | Prodigal: 2.6 | CDS | 2.3.1.57 | — | — | — | P0A951 | speG | — | — | Spermidine N(1)-acetyltransferase |
| Contig1 | 16939 | 17796 | − | GENE_00018 | Prodigal: 2.6 | CDS | — | PRK04164 | — | — | — | — | — | — | hypothetical protein |
| Contig1 | 18109 | 19212 | + | GENE_00019 | Prodigal: 2.6 | CDS | 1.1.1.6 | — | — | — | P32816 | gldA_1 | — | — | Glycerol dehydrogenase |
| Contig1 | 19359 | 20570 | + | GENE_00020 | Prodigal: 2.6 | CDS | — | — | — | — | P28246 | bcr_1 | — | — | Bicyclomycin resistance protein |
| Contig1 | 20599 | 21834 | − | GENE_00021 | Prodigal: 2.6 | CDS | 2.3.1.179 | — | — | — | P73283 | fabF_1 | — | — | 3-oxoacyl-[acyl-carrier-protein] synthase 2 |
| Contig1 | 21943 | 22782 | + | GENE_00022 | Prodigal: 2.6 | CDS | — | PRK10621 | — | — | — | — | — | — | hypothetical protein |
| Contig1 | 22824 | 23567 | − | GENE_00023 | Prodigal: 2.6 | CDS | — | — | — | — | — | — | — | — | hypothetical protein |
| Contig1 | 23726 | 24184 | − | GENE_00024 | Prodigal: 2.6 | CDS | 2.3.1.57 | — | — | — | P39909 | bltD | — | — | Spermine/spermidine acetyltransferase |
| Contig1 | 24317 | 25138 | + | GENE_00025 | Prodigal: 2.6 | CDS | — | — | — | — | P0A4T9 | tipA | — | — | HTH-type transcriptional activator TipA |
| Contig1 | 25353 | 26225 | + | GENE_00026 | Prodigal: 2.6 | CDS | — | — | — | — | P0ABT8 | yijE | — | — | putative inner membrane transporter YijE |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 26325 | 27008 | + | GENE_00027 | Prodigal: 2.6 | CDS | — | — | PF12535.2 | — | — | — | — | Hydrolase of X-linked nucleoside diphosphate N terminal | hypothetical protein |
| Contig1 | 27140 | 28045 | − | GENE_00028 | Prodigal: 2.6 | CDS | 3.8.1.3 | — | — | — | Q01398 | dehH1 | — | — | Haloacetate dehalogenase H-1 |
| Contig1 | 28067 | 29122 | − | GENE_00029 | Prodigal: 2.6 | CDS | 1.1.1.83 | — | — | — | P76251 | dmlA | — | — | D-malate dehydrogenase [decarboxylating] |
| Contig1 | 29305 | 29991 | + | GENE_00030 | Prodigal: 2.6 | CDS | — | — | — | — | P0ACM2 | ydfH_1 | — | — | putative HTH-type transcriptional regulator YdfH |
| Contig1 | 30131 | 31324 | + | GENE_00031 | Prodigal: 2.6 | CDS | 2.4.1.- | — | — | — | Q53685 | oleD_1 | — | — | Oleandomycin glycosyltransferase |
| Contig1 | 31382 | 31636 | − | GENE_00032 | Prodigal: 2.6 | CDS | — | — | — | — | — | — | — | — | hypothetical protein |
| Contig1 | 31870 | 32139 | + | GENE_00033 | Prodigal: 2.6 | CDS | — | — | — | — | — | — | — | — | hypothetical protein |
| Contig1 | 32276 | 33634 | + | GENE_00034 | Prodigal: 2.6 | CDS | — | — | — | — | P32959 | pbpE | — | — | Penicillin-binding protein 4* |
| Contig1 | 33687 | 33860 | − | GENE_00035 | Prodigal: 2.6 | CDS | — | — | — | — | — | — | — | — | hypothetical protein |
| Contig1 | 34056 | 34622 | + | GENE_00036 | Prodigal: 2.6 | CDS | — | — | — | — | — | — | — | — | hypothetical protein |
| Contig1 | 34674 | 35834 | − | GENE_00037 | Prodigal: 2.6 | CDS | — | — | — | — | Q0CQS6 | pbuE_1 | — | — | Purine efflux pump PbuE |
| Contig1 | 36166 | 36882 | + | GENE_00038 | Prodigal: 2.6 | CDS | — | — | — | — | O05509 | gmuR | — | — | HTH-type transcriptional regulator GmuR |
| Contig1 | 37004 | 37690 | + | GENE_00039 | Prodigal: 2.6 | CDS | — | — | — | — | P0ACL9 | pdhR | — | — | Pyruvate dehydrogenase complex repressor |
| Contig1 | 37680 | 38894 | + | GENE_00040 | Prodigal: 2.6 | CDS | — | — | — | — | P37482 | yycB | — | — | putative transporter YycB |
| Contig1 | 38954 | 39268 | − | GENE_00041 | Prodigal: 2.6 | CDS | — | — | — | — | O69279 | sugE_1 | — | — | Quaternary ammonium compound-resistance protein SugE |
| Contig1 | 39268 | 39597 | − | GENE_00042 | Prodigal: 2.6 | CDS | — | — | — | — | O69279 | sugE_2 | — | — | Quaternary ammonium compound-resistance protein SugE |
| Contig1 | 39670 | 40251 | − | GENE_00043 | Prodigal: 2.6 | CDS | — | — | — | — | O07001 | yvdT | — | — | putative HTH-type transcriptional regulator YvdT |
| Contig1 | 40368 | 41930 | − | GENE_00044 | Prodigal: 2.6 | CDS | — | — | — | — | O07002 | yveA_1 | — | — | Aspartate-proton symporter |
| Contig1 | 42168 | 43022 | − | GENE_00045 | Prodigal: 2.6 | CDS | 1.11.1.6 | — | — | — | P80878 | — | — | — | putative manganese catalase |
| Contig1 | 43134 | 43595 | − | GENE_00046 | Prodigal: 2.6 | CDS | — | — | PF08327.5 | — | O07615 | ydbD_1 | — | Activator of Hsp90 ATPase homolog 1-like protein | hypothetical protein |
| Contig1 | 43723 | 44724 | + | GENE_00047 | Prodigal: 2.6 | CDS | 1.6.5.- | — | — | — | O07615 | yhfP | — | — | Putative quinone oxido-reductase YhfP |
| Contig1 | 45155 | 46573 | + | GENE_00048 | Prodigal: 2.6 | CDS | — | — | — | — | O34718 | iolT | — | — | Major myo-inositol transporter IolT |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 46877 | 46953 | + | GENE_00049 | Aragorn: 1.2 | tRNA | — | — | — | — | — | — | — | — | tRNA-Arg(acg) |
| Contig1 | 46962 | 47035 | + | GENE_00050 | Aragorn: 1.2 | tRNA | — | — | — | — | — | — | — | — | tRNA-Gly(tcc) |
| Contig1 | 47200 | 48746 | + | GENE_00051 | — | rRNA | — | — | — | — | — | — | — | — | 16S ribosomal RNA |
| Contig1 | 48982 | 51906 | + | GENE_00052 | — | rRNA | — | — | — | — | — | — | — | — | 23S ribosomal RNA |
| Contig1 | 51961 | 52071 | + | GENE_00053 | — | rRNA | — | — | — | — | — | — | — | — | 5S ribosomal RNA |
| Contig1 | 52094 | 52170 | + | GENE_00054 | Aragorn: 1.2 | tRNA | — | — | — | — | — | — | — | — | tRNA-Met(cat) |
| Contig1 | 52181 | 52257 | + | GENE_00055 | Aragorn: 1.2 | tRNA | — | — | — | — | — | — | — | — | tRNA-Asp(gtc) |
| Contig1 | 52439 | 53416 | + | GENE_00056 | Prodigal: 2.6 | CDS | 2.7.4.16 | — | — | — | P0AGG0 | thiL | — | — | Thiamine-monophosphate kinase |
| Contig1 | 53432 | 53908 | + | GENE_00057 | Prodigal: 2.6 | CDS | — | — | — | — | O05515 | tsaE | — | — | tRNA threonylcarbamoyl-adenosine biosynthesis protein TsaE |
| Contig1 | 53889 | 54578 | + | GENE_00058 | Prodigal: 2.6 | CDS | — | — | — | — | O05516 | tsaB | — | — | tRNA threonylcarbamoyl-adenosine biosynthesis protein TsaB |
| Contig1 | 54589 | 55044 | + | GENE_00059 | Prodigal: 2.6 | CDS | 2.3.1.- | — | — | — | P21340 | paiA_1 | — | — | Protease synthase and sporulation negative regulatory protein PAI 1 |
| Contig1 | 55037 | 56077 | + | GENE_00060 | Prodigal: 2.6 | CDS | 2.3.1.- | — | — | — | O05518 | tsaD | — | — | tRNA N6-adenosine threonylcarbamoyl-transferase |
| Contig1 | 56300 | 58228 | − | GENE_00061 | Prodigal: 2.6 | CDS | — | — | — | — | P63389 | yheS_2 | — | — | putative ABC transporter ATP-binding protein YheS |
| Contig1 | 58368 | 58880 | + | GENE_00062 | Prodigal: 2.6 | CDS | — | — | — | — | Q5L3F4 | moaC | — | — | Cyclic pyranopterin monophosphate synthase accessory protein |
| Contig1 | 58877 | 59524 | + | GENE_00063 | Prodigal: 2.6 | CDS | — | — | — | — | O05521 | rex | — | — | Redox-sensing transcriptional repressor Rex |
| Contig1 | 59543 | 59713 | + | GENE_00064 | Prodigal: 2.6 | CDS | — | — | — | — | O05522 | tatAy | — | — | Sec-independent protein translocase protein TatAy |
| Contig1 | 59729 | 60478 | + | GENE_00065 | Prodigal: 2.6 | CDS | — | — | — | — | O05523 | tatC2 | — | — | Sec-independent protein translocase protein TatCy |
| Contig1 | 60520 | 60711 | − | GENE_00066 | Prodigal: 2.6 | CDS | — | — | — | — | — | — | — | — | hypothetical protein |
| Contig1 | 60708 | 61442 | − | GENE_00067 | Prodigal: 2.6 | CDS | — | — | PF02517.10 | — | — | — | — | — | CAAX amino terminal protease self-immunity |
| Contig1 | 61679 | 61963 | + | GENE_00068 | Prodigal: 2.6 | CDS | — | — | — | — | P28599 | groS | — | — | 10 kDa chaperonin |
| Contig1 | 62005 | 63639 | + | GENE_00069 | Prodigal: 2.6 | CDS | — | — | — | — | P28598 | groL | — | — | 60 kDa chaperonin |
| Contig1 | 63872 | 64231 | − | GENE_00070 | Prodigal: 2.6 | CDS | — | — | — | — | — | — | — | — | hypothetical protein |
| Contig1 | 64253 | 66145 | − | GENE_00071 | Prodigal: 2.6 | CDS | 3.1.-.- | — | — | — | O31998 | yokI_1 | — | — | putative ribonuclease YokI |
| Contig1 | 66563 | 67132 | + | GENE_00072 | Prodigal: 2.6 | CDS | — | — | PF01420.13 | — | — | — | — | — | Type I restriction modification DNA specificity domain protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 67153 | 68745 | + | GENE_00073 | Prodigal: 2.6 | CDS | 2.1.1.72 | — | — | — | Q89Z59 | — | — | — | putative type I restriction enzymeP M protein |
| Contig1 | 68735 | 69967 | + | GENE_00074 | Prodigal: 2.6 | CDS | — | PRK09737 | — | — | — | — | — | — | EcoKI restriction-modification system protein HsdS |
| Contig1 | 69989 | 73147 | + | GENE_00075 | Prodigal: 2.6 | CDS | 3.1.21.3 | — | — | — | Q7A801 | hsdR | — | — | Type-1 restriction enzyme R protein |
| Contig1 | 73243 | 75732 | – | GENE_00076 | Prodigal: 2.6 | CDS | — | — | PF07719.11 | — | — | — | — | — | Tetratricopeptide repeat protein |
| Contig1 | 75933 | 76994 | + | GENE_00077 | Prodigal: 2.6 | CDS | 1.1.1.14 | — | — | — | Q06004 | gutB_1 | — | — | Sorbitol dehydrogenase |
| Contig1 | 77068 | 78444 | + | GENE_00078 | Prodigal: 2.6 | CDS | — | — | — | — | P31435 | yicJ | — | — | Inner membrane symporter YicJ |
| Contig1 | 78546 | 79508 | + | GENE_00079 | Prodigal: 2.6 | CDS | 2.7.1.92 | — | — | — | Q9KAG8 | iolC_1 | — | — | 5-dehydro-2-deoxygluconokinase |
| Contig1 | 79742 | 80059 | + | GENE_00080 | Prodigal: 2.6 | CDS | — | — | — | — | — | — | — | — | hypothetical protein |
| Contig1 | 80174 | 80860 | + | GENE_00081 | Prodigal: 2.6 | CDS | — | — | — | — | P54617 | — | — | Phage shock protein A homolog | hypothetical protein |
| Contig1 | 80911 | 81936 | + | GENE_00082 | Prodigal: 2.6 | CDS | — | — | PF08271.6 | — | — | — | — | — | TFHB zinc-binding protein |
| Contig1 | 81936 | 82697 | + | GENE_00083 | Prodigal: 2.6 | CDS | — | — | — | — | — | — | — | — | hypothetical protein |
| Contig1 | 82724 | 83728 | + | GENE_00084 | Prodigal: 2.6 | CDS | — | — | — | — | — | — | — | — | hypothetical protein |
| Contig1 | 83771 | 85702 | + | GENE_00085 | Prodigal: 2.6 | CDS | 2.3.1.- | — | — | — | Q7A3D6 | oatA | — | — | O-acetyltransferase OatA |
| Contig1 | 85974 | 86834 | – | GENE_00086 | Prodigal: 2.6 | CDS | — | — | — | — | O05403 | rsiV | — | — | Anti-sigma-V factor RsiV |
| Contig1 | 86834 | 87331 | – | GENE_00087 | Prodigal: 2.6 | CDS | — | — | — | — | O05404 | sigV_1 | — | — | RNA polymerase sigma factor SigV |
| Contig1 | 87520 | 88560 | – | GENE_00088 | Prodigal: 2.6 | CDS | 1.1.1.14 | — | — | — | Q06004 | gutB_2 | — | — | Sorbitol dehydrogenase |
| Contig1 | 88920 | 89288 | + | GENE_00089 | Prodigal: 2.6 | CDS | — | — | PF03330.12 | — | — | — | — | — | Rare lipoprotein A (RlpA)-like double-psi beta-barrel |
| Contig1 | 89354 | 90400 | + | GENE_00090 | Prodigal: 2.6 | CDS | — | — | — | MF_00671 | — | tolB | — | — | Protein TolB |
| Contig1 | 90431 | 90589 | – | GENE_00091 | Prodigal: 2.6 | CDS | — | — | — | — | — | — | — | — | hypothetical protein |
| Contig1 | 90688 | 90897 | – | GENE_00092 | Prodigal: 2.6 | CDS | — | — | — | — | — | — | — | — | hypothetical protein |
| Contig1 | 91105 | 92643 | – | GENE_00093 | Prodigal: 2.6 | CDS | — | — | PF07726.5 | — | P07788 | cotA | — | — | Spore coat protein A |
| Contig1 | 92753 | 94138 | + | GENE_00094 | Prodigal: 2.6 | CDS | — | — | — | — | P46349 | gabP_1 | — | — | GABA permease |
| Contig1 | 94475 | 95437 | + | GENE_00095 | Prodigal: 2.6 | CDS | — | — | — | — | — | — | — | — | ATPase family associated with various cellular activities (AAA) |
| Contig1 | 95437 | 96606 | + | GENE_00096 | Prodigal: 2.6 | CDS | — | — | — | — | — | — | — | — | hypothetical protein |
| Contig1 | 96625 | 98832 | + | GENE_00097 | Prodigal: 2.6 | CDS | 2.3.2.13 | — | — | — | Q9HZX3 | tgpA | — | — | Protein-glutamine gamma-glutamyltransferase |
| Contig1 | 98987 | 100537 | + | GENE_00098 | Prodigal: 2.6 | CDS | 6.3.5.2 | — | — | — | P99105 | guaA | — | — | GMP synthase [glutamine-hydrolyzing] |
| Contig1 | 100734 | 101501 | – | GENE_00099 | Prodigal: 2.6 | CDS | — | — | — | — | — | — | — | — | hypothetical protein |
| Contig1 | 101831 | 102364 | + | GENE_00100 | Prodigal: 2.6 | CDS | — | — | — | — | O05404 | sigV_2 | — | — | RNA polymerase sigma factor SigV |
| Contig1 | 102346 | 103788 | + | GENE_00101 | Prodigal: 2.6 | CDS | — | — | — | — | — | — | — | — | hypothetical protein |
| Contig1 | 104147 | 105469 | + | GENE_00102 | Prodigal: 2.6 | CDS | — | — | — | — | O34987 | pbuG | — | — | Guanine/hypoxanthine permease PbuG |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 105667 | 106449 | + | GENE_00103 | Prodigal: 2.6 | CDS | — | — | — | — | — | — | — | — | hypothetical protein |
| Contig1 | 106579 | 106761 | + | GENE_00104 | Prodigal: 2.6 | CDS | — | — | — | — | — | — | — | — | hypothetical protein |
| Contig1 | 106883 | 107432 | + | GENE_00105 | Prodigal: 2.6 | CDS | — | — | — | — | — | — | — | — | hypothetical protein |
| Contig1 | 107431 | 107628 | + | GENE_00106 | Prodigal: 2.6 | CDS | — | — | — | — | — | — | — | — | hypothetical protein |
| Contig1 | 107941 | 108429 | + | GENE_00107 | Prodigal: 2.6 | CDS | 5.4.99.18 | — | — | — | Q9WYS7 | purE | — | — | N5-carboxyaminoimidazole ribonucleotide mutase |
| Contig1 | 108383 | 109564 | + | GENE_00108 | Prodigal: 2.6 | CDS | 6.3.4.18 | PRK04164 | — | — | Q7A695 | purK | — | — | N5-carboxyaminoimidazole ribonucleotide synthase |
| Contig1 | 109564 | 110856 | + | GENE_00109 | Prodigal: 2.6 | CDS | 4.3.2.2 | — | — | — | P12047 | purB | — | — | Adenylosuccinate lyase |
| Contig1 | 110932 | 111651 | + | GENE_00110 | Prodigal: 2.6 | CDS | 6.3.2.6 | — | — | — | P12046 | purC | — | — | Phosphoribosyl-aminoimidazole-succinocarboxamide synthase |
| Contig1 | 111651 | 111905 | + | GENE_00111 | Prodigal: 2.6 | CDS | — | — | — | — | — | — | — | — | Phosphoribosylformyl-glycinamidine synthase subunit PurS |
| Contig1 | 111902 | 112585 | + | GENE_00112 | Prodigal: 2.6 | CDS | 6.3.5.3 | PRK05974 | — | — | P99166 | purQ | — | — | Phosphoribosylformyl-glycinamidine synthase 1 |
| Contig1 | 112569 | 114797 | + | GENE_00113 | Prodigal: 2.6 | CDS | 6.3.5.3 | — | — | — | P65901 | purL | — | — | Phosphoribosylformyl-glycinamidine synthase 2 |
| Contig1 | 114773 | 116203 | + | GENE_00114 | Prodigal: 2.6 | CDS | 2.4.2.14 | — | — | — | P00497 | purF | — | — | Amidophosphoribosyl-transferase precursor |
| Contig1 | 116295 | 117335 | + | GENE_00115 | Prodigal: 2.6 | CDS | 6.3.3.1 | — | — | — | Q81ZH0 | purM | — | — | Phosphoribosylformyl-glycinamidine cyclo-ligase |
| Contig1 | 117332 | 117919 | + | GENE_00116 | Prodigal: 2.6 | CDS | 2.1.2.2 | — | — | — | P99162 | purN | — | — | Phosphoribosyl-glycinamide formyltransferase |
| Contig1 | 117916 | 119454 | + | GENE_00117 | Prodigal: 2.6 | CDS | — | — | — | — | P67544 | purH | — | — | Bifunctional purine biosynthesis protein PurH |
| Contig1 | 119468 | 120736 | + | GENE_00118 | Prodigal: 2.6 | CDS | 6.3.4.13 | — | — | — | P12039 | purD | — | — | Phosphoribosylamine-glycine ligase |
| Contig1 | 120873 | 121106 | − | GENE_00119 | Prodigal: 2.6 | CDS | — | — | — | — | — | — | — | — | hypothetical protein |
| Contig1 | 121225 | 122967 | + | GENE_00120 | Prodigal: 2.6 | CDS | 3.5.4.2 | — | — | — | O34909 | yerA | — | — | Putative adenine deaminase YerA |
| Contig1 | 122992 | 123987 | + | GENE_00121 | Prodigal: 2.6 | CDS | — | — | — | — | O34968 | yerB | — | — | Putative lipoprotein YerB precursor |
| Contig1 | 123990 | 124301 | + | GENE_00122 | Prodigal: 2.6 | CDS | — | — | PF01371.13 | — | P39812 | — | — | — | Trp repressor protein |
| Contig1 | 124336 | 125910 | − | GENE_00123 | Prodigal: 2.6 | CDS | 1.4.1.13 | — | — | — | — | gltA_1 | — | — | Glutamate synthase [NADPH] large chain |
| Contig1 | 126106 | 126795 | + | GENE_00124 | Prodigal: 2.6 | CDS | 2.5.1.- | — | — | — | O34790 | pcrB | — | — | Heptaprenylglyceryl phosphate synthase |
| Contig1 | 126853 | 129072 | + | GENE_00125 | Prodigal: 2.6 | CDS | 3.6.4.12 | — | — | — | O34580 | pcrA | — | — | ATP-dependent DNA helicase PcrA |
| Contig1 | 129094 | 131103 | + | GENE_00126 | Prodigal: 2.6 | CDS | 6.5.1.2 | — | — | — | O87703 | ligA | — | — | DNA ligase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 131119 | 132315 | + | GENE_00127 | Prodigal: 2.6 | CDS | — | — | PF07537.5 | — | — | — | — | — | CamS sex pheromone cAM373 precursor |
| Contig1 | 132552 | 133547 | + | GENE_00128 | Prodigal: 2.6 | CDS | 2.7.1.39 | — | — | MF_00301 | — | thrB_1 | — | — | Homoserine kinase |
| Contig1 | 133584 | 134276 | - | GENE_00129 | Prodigal: 2.6 | CDS | — | PRK09977 | — | — | — | — | — | — | putative Mg(2+) transport ATPase |
| Contig1 | 134397 | 135875 | - | GENE_00130 | Prodigal: 2.6 | CDS | — | — | — | — | Q7A4Q7 | putP_1 | — | — | Sodium/proline symporter |
| Contig1 | 136296 | 136586 | + | GENE_00131 | Prodigal: 2.6 | CDS | 6.3.5.- | — | — | — | P68808 | gate | — | — | Aspartyl/glutamyl-tRNA(Asn/Gln) amidotransferase subunit C |
| Contig1 | 136601 | 138058 | + | GENE_00132 | Prodigal: 2.6 | CDS | 6.3.5.- | — | — | — | P63489 | gatA | — | — | Glutamyl-tRNA(Gln) amidotransferase subunit A |
| Contig1 | 138072 | 139502 | + | GENE_00133 | Prodigal: 2.6 | CDS | 6.3.5.- | — | — | — | O30509 | gatB | — | — | Aspartyl/glutamyl-tRNA(Asn/Gln) amidotransferase subunit B |
| Contig1 | 139565 | 140413 | - | GENE_00134 | Prodigal: 2.6 | CDS | — | — | — | — | P0ACS9 | acrR | — | — | HTH-type transcriptional regulator AcrR |
| Contig1 | 140542 | 143685 | + | GENE_00135 | Prodigal: 2.6 | CDS | — | — | — | — | O31501 | swrC | — | — | Swarming motility protein SwrC |
| Contig1 | 143838 | 144749 | + | GENE_00136 | Prodigal: 2.6 | CDS | 2.7.1.107 | — | — | — | O31502 | dagK | — | — | Diacylglycerol kinase |
| Contig1 | 144897 | 146273 | + | GENE_00137 | Prodigal: 2.6 | CDS | 2.1.1.189 | — | — | — | O31503 | rlmCD_1 | — | — | 23S rRNA (uracil-C(5))-methyltransferase RlmCD |
| Contig1 | 147055 | 150009 | + | GENE_00138 | Prodigal: 2.6 | CDS | — | — | — | — | — | — | — | — | hypothetical protein |
| Contig1 | 151010 | 151405 | - | GENE_00139 | Prodigal: 2.6 | CDS | — | — | — | — | — | — | — | — | hypothetical protein |
| Contig1 | 151418 | 151699 | - | GENE_00140 | Prodigal: 2.6 | CDS | — | — | — | — | — | — | — | — | hypothetical protein |
| Contig1 | 151831 | 152130 | - | GENE_00141 | Prodigal: 2.6 | CDS | — | — | — | — | — | — | — | — | hypothetical protein |
| Contig1 | 152313 | 152855 | - | GENE_00142 | Prodigal: 2.6 | CDS | — | — | — | — | — | — | — | — | hypothetical protein |
| Contig1 | 152988 | 153461 | - | GENE_00143 | Prodigal: 2.6 | CDS | — | — | — | — | C0H3X4 | yezG | — | — | putative antitoxin YezG |
| Contig1 | 153466 | 155472 | - | GENE_00144 | Prodigal: 2.6 | CDS | 3.1.-.- | — | — | — | O31506 | yeeF | — | — | Putative ribonuclease YeeF |
| Contig1 | 155771 | 156490 | + | GENE_00145 | Prodigal: 2.6 | CDS | — | — | — | — | P67181 | — | — | — | putative transcriptional regulatory protein |
| Contig1 | 156670 | 156972 | + | GENE_00146 | Prodigal: 2.6 | CDS | — | — | — | — | — | — | — | — | hypothetical protein |
| Contig1 | 157149 | 158018 | + | GENE_00147 | Prodigal: 2.6 | CDS | 2.7.7.- | — | — | — | P17585 | aadK | — | — | Aminoglycoside 6-adenylyltransferase |
| Contig1 | 158152 | 158400 | + | GENE_00148 | Prodigal: 2.6 | CDS | — | — | PF11007.2 | — | — | — | — | — | Spore coat associated protein JA (CotJA) |
| Contig1 | 158384 | 158647 | + | GENE_00149 | Prodigal: 2.6 | CDS | — | — | PF12652.1 | — | — | — | — | — | CotJB protein |
| Contig1 | 158662 | 159231 | + | GENE_00150 | Prodigal: 2.6 | CDS | 1.11.1.6 | — | — | — | P603555 | — | — | — | Manganese catalase |
| Contig1 | 159320 | 159853 | + | GENE_00151 | Prodigal: 2.6 | CDS | — | PRK03624 | — | — | — | — | — | — | putative acetyltransferase |
| Contig1 | 159884 | 160162 | + | GENE_00152 | Prodigal: 2.6 | CDS | — | — | — | — | — | — | — | — | hypothetical protein |
| Contig1 | 160277 | 160966 | + | GENE_00153 | Prodigal: 2.6 | CDS | — | — | — | — | — | — | — | — | hypothetical protein |
| Contig1 | 160999 | 161325 | - | GENE_00154 | Prodigal: 2.6 | CDS | 1.14.99.3 | — | — | — | O31534 | hmoA | — | — | Heme-degrading monooxygenase HmoA |
| Contig1 | 161410 | 161775 | - | GENE_00155 | Prodigal: 2.6 | CDS | — | — | PF12681.1 | — | — | — | — | — | Glyoxalase-like domain protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 161934 | 162800 | + | GENE_00156 | Prodigal: 2.6 | CDS | — | — | — | — | P54504 | rsbRD_1 | — | — | RsbT co-antagonist protein RsbRD |
| Contig1 | 163082 | 164110 | + | GENE_00157 | Prodigal: 2.6 | CDS | — | — | — | — | P0AG78 | sbp | — | — | Sulfate-binding protein precursor |
| Contig1 | 164126 | 164962 | + | GENE_00158 | Prodigal: 2.6 | CDS | — | — | — | — | P27367 | cysT | — | — | Sulfate transport system permease protein CysT |
| Contig1 | 164973 | 165836 | + | GENE_00159 | Prodigal: 2.6 | CDS | — | — | — | — | P27370 | cysW | — | — | Sulfate transport system permease protein CysW |
| Contig1 | 165850 | 166920 | + | GENE_00160 | Prodigal: 2.6 | CDS | 3.6.3.25 | — | — | — | P14788 | cysA | — | — | Sulfate/thiosulfate import ATP-binding protein CysA |
| Contig1 | 167039 | 167212 | + | GENE_00161 | Prodigal: 2.6 | CDS | — | — | — | — | — | — | — | — | hypothetical protein |
| Contig1 | 167242 | 167544 | + | GENE_00162 | Prodigal: 2.6 | CDS | 2.7.1.26 | — | — | — | P94465 | ribR | — | — | RNA-binding riboflavin kinase RibR |
| Contig1 | 167635 | 168279 | — | GENE_00163 | Prodigal: 2.6 | CDS | — | — | — | — | P0AAC4 | ybhL | — | — | Inner membrane protein YbhL |
| Contig1 | 168318 | 168830 | + | GENE_00164 | Prodigal: 2.6 | CDS | — | — | — | — | P0ACR9 | mprA | — | — | Transcriptional repressor MprA |
| Contig1 | 168981 | 170102 | + | GENE_00165 | Prodigal: 2.6 | CDS | 1.14.13.114 | — | — | — | P86491 | — | — | — | 6-hydroxynicotinate 3-monooxygenase precursor |
| Contig1 | 170139 | 171209 | — | GENE_00166 | Prodigal: 2.6 | CDS | — | — | — | — | — | — | — | — | hypothetical protein |
| Contig1 | 171374 | 174556 | + | GENE_00167 | Prodigal: 2.6 | CDS | — | — | — | — | P14779 | — | — | — | Bifunctional P-450/NADPH-P450 reductase |
| Contig1 | 175021 | 175614 | + | GENE_00168 | Prodigal: 2.6 | CDS | — | — | — | — | — | — | — | — | hypothetical protein |
| Contig1 | 175607 | 175918 | + | GENE_00169 | Prodigal: 2.6 | CDS | — | — | PF12840.1 | — | — | — | — | — | Helix-turn-helix domain protein |
| Contig1 | 175919 | 176809 | + | GENE_00170 | Prodigal: 2.6 | CDS | 3.6.3.- | — | — | — | P32010 | drrA_1 | — | — | Daunorubicin/doxorubicin resistance ATP-binding protein DrrA |
| Contig1 | 176824 | 177564 | + | GENE_00171 | Prodigal: 2.6 | CDS | — | — | — | — | P0AFP9 | ybhR_1 | — | — | Inner membrane transport permease YbhR |
| Contig1 | 177621 | 177761 | + | GENE_00172 | Prodigal: 2.6 | CDS | — | — | — | — | — | — | — | — | hypothetical protein |
| Contig1 | 178340 | 180268 | + | GENE_00173 | Prodigal: 2.6 | CDS | — | — | — | — | Q797B3 | ltaS1 | — | — | Lipoteichoic acid synthase 1 |
| Contig1 | 180484 | 181248 | + | GENE_00174 | Prodigal: 2.6 | CDS | 2.7.7.33 | — | — | — | Q8Z5I4 | rfbF | — | — | Glucose-1-phosphate cytidylyltransferase |
| Contig1 | 181321 | 182223 | + | GENE_00175 | Prodigal: 2.6 | CDS | 4.2.1.45 | — | — | — | P26397 | rfbG | — | — | CDP-glucose 4,6-dehydratase |
| Contig1 | 182248 | 183159 | + | GENE_00176 | Prodigal: 2.6 | CDS | — | — | PF03407.10 | — | — | — | — | — | Nucleotide-diphospho-sugar transferase |
| Contig1 | 183188 | 184348 | + | GENE_00177 | Prodigal: 2.6 | CDS | 2.4.1.212 | — | — | — | Q7BLV3 | hyaD | — | — | Hyaluronan synthase |
| Contig1 | 184361 | 185302 | + | GENE_00178 | Prodigal: 2.6 | CDS | — | — | — | — | — | — | — | — | hypothetical protein |
| Contig1 | 185331 | 186560 | — | GENE_00179 | Prodigal: 2.6 | CDS | — | — | — | — | P52067 | fsr | — | — | Fosmidomycin resistance protein |
| Contig1 | 186678 | 188063 | — | GENE_00180 | Prodigal: 2.6 | CDS | — | — | — | — | O07576 | yhdG_1 | — | — | putative amino acid permease YhdG |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 188308 | 189765 | + | GENE_00181 | Prodigal: 2.6 | CDS | 1.2.1.3 | — | — | — | O06478 | yfmT | — | — | Putative aldehyde dehydrogenase YfmT |
| Contig1 | 189781 | 190635 | + | GENE_00182 | Prodigal: 2.6 | CDS | — | — | — | — | O06477 | yfmS | — | — | Putative sensory transducer protein YfmS |
| Contig1 | 190766 | 191665 | + | GENE_00183 | Prodigal: 2.6 | CDS | 1.-.-.- | — | — | — | P0AG84 | yghA | — | — | putative oxidoreductase YghA |
| Contig1 | 191713 | 192780 | − | GENE_00184 | Prodigal: 2.6 | CDS | 2.4.1.- | — | — | — | O31986 | sunS_1 | — | — | SPBc2 prophage-derived glycosyltransferase SunS |
| Contig1 | 192939 | 194828 | + | GENE_00185 | Prodigal: 2.6 | CDS | — | — | — | — | P43672 | uup | — | — | ABC transporter ATP-binding protein uup |
| Contig1 | 195017 | 195439 | + | GENE_00186 | Prodigal: 2.6 | CDS | — | — | — | — | O06474 | yfmP | — | — | HTH-type transcriptional regulator YfmP |
| Contig1 | 195503 | 196687 | + | GENE_00187 | Prodigal: 2.6 | CDS | — | — | — | — | O06473 | yfmO | — | — | Multidrug efflux protein YfmO |
| Contig1 | 196731 | 198287 | − | GENE_00188 | Prodigal: 2.6 | CDS | — | — | — | — | P63389 | yheS_3 | — | — | putative ABC transporter ATP-binding protein YheS |
| Contig1 | 198459 | 199589 | + | GENE_00189 | Prodigal: 2.6 | CDS | 3.6.4.13 | — | — | — | P54475 | cshB_1 | — | — | DEAD-box ATP-dependent RNA helicase CshB |
| Contig1 | 199663 | 200109 | + | GENE_00190 | Prodigal: 2.6 | CDS | — | — | PF00583.18 | — | — | — | — | — | Acetyltransferase (GNAT) family protein |
| Contig1 | 200160 | 201179 | − | GENE_00191 | Prodigal: 2.6 | CDS | 1.-.-.- | — | — | — | O34812 | yfmj | — | — | Putative NADP-dependent oxidoreductase YfmJ |
| Contig1 | 201308 | 201679 | − | GENE_00192 | Prodigal: 2.6 | CDS | — | — | — | — | — | — | — | — | hypothetical protein |
| Contig1 | 201849 | 202196 | + | GENE_00193 | Prodigal: 2.6 | CDS | — | — | — | — | P80241 | yflT | — | — | General stress protein 17M |
| Contig1 | 202360 | 203625 | + | GENE_00194 | Prodigal: 2.6 | CDS | 4.2.2.2 | — | — | — | P39116 | pel | — | — | Pectate lyase precursor |
| Contig1 | 203750 | 205186 | + | GENE_00195 | Prodigal: 2.6 | CDS | — | — | — | — | O34726 | yflS | — | — | Putative malate transporter YflS |
| Contig1 | 205251 | 205991 | + | GENE_00196 | Prodigal: 2.6 | CDS | — | — | PF01391.12 | — | — | — | — | — | Collagen triple helix repeat (20 copies) |
| Contig1 | 206444 | 211927 | − | GENE_00197 | Prodigal: 2.6 | CDS | — | — | — | — | — | — | — | — | hypothetical protein |
| Contig1 | 212093 | 212272 | − | GENE_00198 | Prodigal: 2.6 | CDS | — | — | — | — | — | — | — | — | hypothetical protein |
| Contig1 | 212536 | 212685 | − | GENE_00199 | Prodigal: 2.6 | CDS | — | — | — | — | — | — | — | — | hypothetical protein |
| Contig1 | 212678 | 214927 | − | GENE_00200 | Prodigal: 2.6 | CDS | — | — | — | — | — | — | — | — | hypothetical protein |
| Contig1 | 214931 | 215116 | − | GENE_00201 | Prodigal: 2.6 | CDS | — | — | — | — | — | — | — | — | hypothetical protein |
| Contig1 | 215132 | 215323 | − | GENE_00202 | Prodigal: 2.6 | CDS | — | — | — | — | — | — | — | — | hypothetical protein |
| Contig1 | 215619 | 217223 | + | GENE_00203 | Prodigal: 2.6 | CDS | 2.7.13.3 | — | — | — | O34427 | citS | — | — | Sensor protein CitS |
| Contig1 | 217220 | 217900 | + | GENE_00204 | Prodigal: 2.6 | CDS | — | — | — | — | O34534 | citT | — | — | Transcriptional regulatory protein CitT |
| Contig1 | 217913 | 218875 | + | GENE_00205 | Prodigal: 2.6 | CDS | — | — | PF03401.8 | — | — | — | — | — | Tripartite tricarboxylate transporter family receptor |
| Contig1 | 219068 | 220366 | + | GENE_00206 | Prodigal: 2.6 | CDS | — | — | — | — | P55069 | citM | — | — | Mg(2+)citrate complex secondary transporter |
| Contig1 | 220418 | 221212 | + | GENE_00207 | Prodigal: 2.6 | CDS | 3.-.-.- | — | — | — | O34409 | yflN_1 | — | — | putative metallo-hydrolase YflN |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 221336 | 222427 | + | GENE_00208 | Prodigal: 2.6 | CDS | 1.14.13.165 | — | — | — | O34453 | nos | — | — | Nitric oxide synthase oxygenase |
| Contig1 | 222421 | 222693 | — | GENE_00209 | Prodigal: 2.6 | CDS | 3.6.1.7 | PRK11536 | — | — | O35031 | acyP | — | — | Acylphosphatase |
| Contig1 | 222761 | 223420 | + | GENE_00210 | Prodigal: 2.6 | CDS | — | — | — | — | — | — | — | — | 6-N-hydroxylaminopurine resistance protein |
| Contig1 | 223461 | 223595 | — | GENE_00211 | Prodigal: 2.6 | CDS | — | — | — | — | — | — | — | — | hypothetical protein |
| Contig1 | 223775 | 223930 | — | GENE_00212 | Prodigal: 2.6 | CDS | — | — | — | — | — | — | — | — | hypothetical protein |
| Contig1 | 224013 | 224324 | — | GENE_00213 | Prodigal: 2.6 | CDS | — | — | — | — | — | — | — | — | hypothetical protein |
| Contig1 | 224381 | 225130 | — | GENE_00214 | Prodigal: 2.6 | CDS | 3.4.11.18 | — | — | — | O34484 | mapB | — | — | Methionine aminopeptidase 2 |
| Contig1 | 225295 | 226677 | + | GENE_00215 | Prodigal: 2.6 | CDS | — | — | — | — | P69786 | ptsG_1 | — | — | PTS system glucose-specific EIICB component |
| Contig1 | 226803 | 227246 | + | GENE_00216 | Prodigal: 2.6 | CDS | — | — | PF10787.3 | — | — | — | — | — | putative protein from bacillus cereus group |
| Contig1 | 227287 | 229224 | — | GENE_00217 | Prodigal: 2.6 | CDS | — | — | — | — | O34952 | ltaS2_1 | — | — | Lipoteichoic acid synthase 2 |
| Contig1 | 229470 | 229847 | + | GENE_00218 | Prodigal: 2.6 | CDS | — | PRK10203 | — | — | — | — | — | — | hypothetical protein |
| Contig1 | 229857 | 230288 | — | GENE_00219 | Prodigal: 2.6 | CDS | — | — | — | — | P96698 | cotP_1 | — | — | Spore coat protein P |
| Contig1 | 230304 | 230546 | — | GENE_00220 | Prodigal: 2.6 | CDS | — | — | PF10676.3 | — | — | — | — | — | Spore germination protein gerPA/gerPF |
| Contig1 | 230561 | 230821 | — | GENE_00221 | Prodigal: 2.6 | CDS | — | — | PF10676.3 | — | — | — | — | — | Spore germination protein gerPA/gerPF |
| Contig1 | 231094 | 232509 | + | GENE_00222 | Prodigal: 2.6 | CDS | — | — | — | — | — | — | — | — | PTS system trehalose-specific EIIBC component |
| Contig1 | 232585 | 234270 | + | GENE_00223 | Prodigal: 2.6 | CDS | 3.2.1.93 | — | — | — | P36672 | treB | — | — | Trehalose-6-phosphate hydrolase |
| Contig1 | 234294 | 235010 | + | GENE_00224 | Prodigal: 2.6 | CDS | — | — | — | — | P39795 | treA | — | — | Trehalose operon transcriptional repressor |
| Contig1 | 235144 | 235809 | + | GENE_00225 | Prodigal: 2.6 | CDS | 1.-.-.- | — | — | — | P39796 | treR | — | — | Putative NAD(P)H nitroreductase YfkO |
| Contig1 | 235845 | 236606 | — | GENE_00226 | Prodigal: 2.6 | CDS | — | — | PF07907.5 | — | O34475 | yfkO | — | — | YibE/F-like protein |
| Contig1 | 236603 | 237742 | — | GENE_00227 | Prodigal: 2.6 | CDS | — | — | PF07907.5 | — | — | — | — | — | YibE/F-like protein |
| Contig1 | 237953 | 242245 | — | GENE_00228 | Prodigal: 2.6 | CDS | — | — | — | — | O34313 | yfkN | — | — | Trifunctional nucleotide phosphoesterase protein YfkN precursor |
| Contig1 | 242466 | 242981 | + | GENE_00229 | Prodigal: 2.6 | CDS | 3.2.-.- | — | — | — | P80876 | yfkM | — | — | General stress protein 18 |
| Contig1 | 243002 | 244033 | — | GENE_00230 | Prodigal: 2.6 | CDS | — | — | — | — | P46828 | ccpA_1 | — | — | Catabolite control protein A |
| Contig1 | 244170 | 245054 | — | GENE_00231 | Prodigal: 2.6 | CDS | 1.1.1.25 | — | — | — | Q8Y9N5 | aroE_1 | — | — | Shikimate dehydrogenase |
| Contig1 | 245119 | 245880 | — | GENE_00232 | Prodigal: 2.6 | CDS | 4.2.1.10 | — | — | — | P24670 | aroD | — | — | 3-dehydroquinate dehydratase |
| Contig1 | 245907 | 247100 | — | GENE_00233 | Prodigal: 2.6 | CDS | — | — | — | — | P76197 | ydiM | — | — | Inner membrane transport protein YdiM |
| Contig1 | 247436 | 247651 | — | GENE_00234 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 247807 | 248280 | + | GENE_00235 | Prodigal: 2.6 | CDS | 3.1.3.48 | — | — | — | O35016 | yfkJ | — | — | Low molecular weight protein-tyrosine-phosphatase YfkJ |
| Contig1 | 248294 | 248620 | + | GENE_00236 | Prodigal: 2.6 | CDS | — | — | — | — | — | — | — | — | hypothetical protein |
| Contig1 | 248632 | 249471 | + | GENE_00237 | Prodigal: 2.6 | CDS | — | PRK01637 | — | — | — | — | — | — | hypothetical protein |
| Contig1 | 249515 | 249622 | + | GENE_00238 | Prodigal: 2.6 | CDS | — | — | — | — | — | — | — | — | hypothetical protein |
| Contig1 | 249657 | 250835 | − | GENE_00239 | Prodigal: 2.6 | CDS | — | — | — | — | P21503 | ycaD | — | — | putative MFS-type transporter YcaD |
| Contig1 | 250994 | 252049 | + | GENE_00240 | Prodigal: 2.6 | CDS | — | — | — | — | O34840 | yfkE | — | — | Putative cation exchanger YfkE |
| Contig1 | 252123 | 252914 | + | GENE_00241 | Prodigal: 2.6 | CDS | — | — | — | — | — | — | — | — | hypothetical protein |
| Contig1 | 252942 | 253775 | − | GENE_00242 | Prodigal: 2.6 | CDS | — | — | — | — | O35043 | yfkC | — | — | putative MscS family protein YfkC |
| Contig1 | 253782 | 254903 | − | GENE_00243 | Prodigal: 2.6 | CDS | 4.3.99.3 | — | — | MF_00917 | — | queE_1 | — | — | 7-carboxy-7-deazaguanine synthase |
| Contig1 | 255050 | 255235 | + | GENE_00244 | Prodigal: 2.6 | CDS | — | — | — | — | — | — | — | — | hypothetical protein |
| Contig1 | 255336 | 256127 | + | GENE_00245 | Prodigal: 2.6 | CDS | 3.5.1.- | — | — | — | O34928 | pdaA_1 | — | — | Peptidoglycan-N-acetylmuramic acid deacetylase PdaA precursor |
| Contig1 | 256162 | 257022 | − | GENE_00246 | Prodigal: 2.6 | CDS | 1.1.1.60 | — | — | — | P0ABQ2 | garR_1 | — | — | 2-hydroxy-3-oxopropionate reductase |
| Contig1 | 257073 | 257720 | − | GENE_00247 | Prodigal: 2.6 | CDS | — | — | — | — | — | — | — | — | hypothetical protein |
| Contig1 | 257784 | 258743 | − | GENE_00248 | Prodigal: 2.6 | CDS | — | — | — | — | Q9WZ31 | corA_1 | — | — | Magnesium transport protein CorA |
| Contig1 | 258850 | 259713 | + | GENE_00249 | Prodigal: 2.6 | CDS | 3.2.2.21 | — | — | — | P37878 | alkA | — | — | DNA-3-methyladenine glycosylase |
| Contig1 | 259858 | 261258 | + | GENE_00250 | Prodigal: 2.6 | CDS | 2.1.1.189 | — | — | — | O31503 | rlmCD_2 | — | — | 23S rRNA (uracil-C(5))-methyltransferase RlmCD |
| Contig1 | 263169 | 264152 | + | GENE_00251 | Prodigal: 2.6 | CDS | 1.-.-.- | — | — | — | P67717 | dus | — | — | putative tRNA-dihydrouridine synthase |
| Contig1 | 264310 | 264789 | + | GENE_00252 | Prodigal: 2.6 | CDS | — | — | — | — | — | — | — | — | hypothetical protein |
| Contig1 | 265064 | 266065 | + | GENE_00253 | Prodigal: 2.6 | CDS | 1.1.1.- | — | — | — | O31404 | acoA | — | — | Acetoin:2,6-dichlorophenol-indophenol oxidoreductase subunit alpha |
| Contig1 | 266067 | 267095 | + | GENE_00254 | Prodigal: 2.6 | CDS | 1.1.1.- | — | — | — | P27746 | acoB | — | — | Acetoin:2,6-dichlorophenol-indophenol oxidoreductase subunit beta |
| Contig1 | 267110 | 268303 | + | GENE_00255 | Prodigal: 2.6 | CDS | 2.3.1.12 | — | — | — | P65636 | pdhC_1 | — | — | Dihydrolipoyllysine-residue acetyltransferase component of pyruvate dehydrogenase complex |
| Contig1 | 268318 | 269697 | + | GENE_00256 | Prodigal: 2.6 | CDS | 1.8.1.4 | — | — | — | P11959 | pdhD_1 | — | — | Dihydrolipoyl dehydrogenase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 269804 | 271612 | + | GENE_00257 | Prodigal: 2.6 | CDS | — | — | — | — | O31551 | acoR | — | — | Acetoin dehydrogenase operon transcriptional activator AcoR |
| Contig1 | 271678 | 271860 | + | GENE_00258 | Prodigal: 2.6 | CDS | — | — | — | — | O31552 | sspH | — | — | Small, acid-soluble spore protein H |
| Contig1 | 272031 | 273380 | + | GENE_00259 | Prodigal: 2.6 | CDS | 3.2.1.122 | — | — | — | P54716 | glvA | — | — | Maltose-6′-phosphate glucosidase |
| Contig1 | 273449 | 274210 | + | GENE_00260 | Prodigal: 2.6 | CDS | — | — | — | — | P54717 | glvR | — | — | HTH-type transcriptional regulator GlvR |
| Contig1 | 274227 | 275813 | + | GENE_00261 | Prodigal: 2.6 | CDS | — | — | — | — | P54715 | malP | — | — | PTS system maltose-specific EIICB component |
| Contig1 | 276002 | 278326 | + | GENE_00262 | Prodigal: 2.6 | CDS | 5.1.3.- | — | — | — | Q44492 | algE5 | — | — | Poly(beta-D-mannuronate) C5 epimerase 5 |
| Contig1 | 278624 | 280357 | + | GENE_00263 | Prodigal: 2.6 | CDS | 3.6.3.- | — | — | — | Q99T13 | — | — | — | Putative multidrug export ATP-binding/permease protein |
| Contig1 | 280338 | 282155 | + | GENE_00264 | Prodigal: 2.6 | CDS | — | — | — | — | Q9WYC4 | — | — | — | putative ABC transporter ATP-binding protein |
| Contig1 | 282322 | 282726 | + | GENE_00265 | Prodigal: 2.6 | CDS | 1.-.-.- | — | — | — | P54720 | catD | — | — | Putative oxidoreductase CatD |
| Contig1 | 282743 | 283600 | + | GENE_00266 | Prodigal: 2.6 | CDS | 1.13.11.2 | — | — | — | P54721 | catE | — | — | Catechol-2,3-dioxygenase |
| Contig1 | 283991 | 284938 | + | GENE_00267 | Prodigal: 2.6 | CDS | 2.5.1.- | — | — | — | O31652 | ctaB1 | — | — | Protoheme IX farnesyltransferase 1 |
| Contig1 | 284976 | 285527 | - | GENE_00268 | Prodigal: 2.6 | CDS | — | — | PF03551.8 | — | — | — | — | — | Transcriptional regulator PadR-like family protein |
| Contig1 | 285761 | 286363 | + | GENE_00269 | Prodigal: 2.6 | CDS | — | — | — | MF_01216 | — | azoR | — | — | FMN-dependent NADH-azoreductase |
| Contig1 | 286354 | 287442 | + | GENE_00270 | Prodigal: 2.6 | CDS | — | — | — | — | Q5HKP7 | icaC | — | — | putative poly-beta-1,6-N-acetyl-D-glucosamine export protein |
| Contig1 | 287299 | 287580 | - | GENE_00271 | Prodigal: 2.6 | CDS | — | — | — | — | — | — | — | — | hypothetical protein |
| Contig1 | 287699 | 290110 | + | GENE_00272 | Prodigal: 2.6 | CDS | — | — | — | — | Q0VZ70 | cmdD_1 | — | — | Chondramide synthase cmdD |
| Contig1 | 290133 | 290405 | + | GENE_00273 | Prodigal: 2.6 | CDS | — | — | — | — | P11540 | — | — | — | Barstar |
| Contig1 | 290431 | 290973 | + | GENE_00274 | Prodigal: 2.6 | CDS | 3.-.-.- | — | — | — | O31562 | yfiT | — | — | Putative metal-dependent hydrolase YfiT |
| Contig1 | 290933 | 292525 | - | GENE_00275 | Prodigal: 2.6 | CDS | — | — | — | — | P96712 | bmr3_1 | — | — | Multidrug resistance protein 3 |
| Contig1 | 292634 | 293116 | - | GENE_00276 | Prodigal: 2.6 | CDS | — | — | — | — | O34777 | ohrR_1 | — | — | Organic hydroperoxide resistance transcriptional regulator |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 293285 | 295855 | + | GENE_00277 | Prodigal: 2.6 | CDS | 2.3.2.3 | — | — | — | C0H3X7 | mprF | — | — | Phosphatidylglycerol lysyltransferase |
| Contig1 | 295948 | 296832 | + | GENE_00278 | Prodigal: 2.6 | CDS | 5.1.-.- | — | — | — | P37757 | yddE | — | — | putative isomerase YddE |
| Contig1 | 296909 | 297493 | + | GENE_00279 | Prodigal: 2.6 | CDS | 1.-.-.- | — | — | — | P0ACY1 | ydjA | — | — | Putative NAD(P)H nitroreductase YdjA |
| Contig1 | 297532 | 297723 | − | GENE_00280 | Prodigal: 2.6 | CDS | — | — | — | — | — | — | — | — | hypothetical protein |
| Contig1 | 297794 | 297904 | − | GENE_00281 | Prodigal: 2.6 | CDS | — | — | — | — | — | — | — | — | hypothetical protein |
| Contig1 | 297962 | 298861 | − | GENE_00282 | Prodigal: 2.6 | CDS | — | — | — | — | Q7A6Q5 | — | — | — | Epimerase family protein |
| Contig1 | 298952 | 299743 | + | GENE_00283 | Prodigal: 2.6 | CDS | — | — | — | — | P66003 | recX | — | — | Regulatory protein RecX |
| Contig1 | 299750 | 300061 | + | GENE_00284 | Prodigal: 2.6 | CDS | — | — | — | — | — | — | — | — | hypothetical protein |
| Contig1 | 300202 | 301401 | + | GENE_00285 | Prodigal: 2.6 | CDS | — | — | — | — | P77389 | ydhP_1 | — | — | Inner membrane transport protein YdhP |
| Contig1 | 301441 | 301830 | − | GENE_00286 | Prodigal: 2.6 | CDS | — | — | — | — | — | — | — | — | hypothetical protein |
| Contig1 | 301793 | 302704 | − | GENE_00287 | Prodigal: 2.6 | CDS | 3.4.21.- | — | — | — | P39790 | mpr | — | — | Extracellular metalloprotease precursor |
| Contig1 | 303126 | 303395 | + | GENE_00288 | Prodigal: 2.6 | CDS | — | — | — | — | — | — | — | — | hypothetical protein |
| Contig1 | 303527 | 304054 | + | GENE_00289 | Prodigal: 2.6 | CDS | — | — | — | — | P96729 | ywsB_1 | — | — | Cell wall-binding protein YwsB precursor |
| Contig1 | 304140 | 304475 | + | GENE_00290 | Prodigal: 2.6 | CDS | — | — | — | — | — | — | — | — | hypothetical protein |
| Contig1 | 304468 | 305328 | + | GENE_00291 | Prodigal: 2.6 | CDS | 3.3.2.10 | — | — | — | O52866 | — | — | — | Soluble epoxide hydrolase |
| Contig1 | 305539 | 306519 | + | GENE_00292 | Prodigal: 2.6 | CDS | 2.4.-.- | — | — | — | Q45539 | csbB | — | — | Putative glycosyltransferase CsbB |
| Contig1 | 306556 | 309141 | + | GENE_00293 | Prodigal: 2.6 | CDS | — | — | PF09586 | — | — | — | — | — | Bacterial membrane protein YfhO |
| Contig1 | 309138 | 310121 | + | GENE_00294 | Prodigal: 2.6 | CDS | — | — | — | — | — | — | — | — | hypothetical protein |
| Contig1 | 310347 | 311441 | + | GENE_00295 | Prodigal: 2.6 | CDS | 3.2.2. | — | — | — | O31584 | yfhQ | — | — | putative A/G-specific adenine glycosylase YfhQ |
| Contig1 | 311448 | 311672 | − | GENE_00296 | Prodigal: 2.6 | CDS | — | — | — | — | — | — | — | — | hypothetical protein |
| Contig1 | 311754 | 312506 | + | GENE_00297 | Prodigal: 2.6 | CDS | 1.3.1.104 | — | PF04632.6 | — | P71079 | fabL | — | — | Enoyl-[acyl-carrier-protein] reductase [NADPH] FabL |
| Contig1 | 312572 | 312742 | + | GENE_00298 | Prodigal: 2.6 | CDS | — | — | — | — | P84585 | — | — | — | Small, acid-soluble spore protein gamma-type |
| Contig1 | 312903 | 313169 | + | GENE_00299 | Prodigal: 2.6 | CDS | — | — | — | — | — | — | — | — | hypothetical protein |
| Contig1 | 313305 | 313835 | + | GENE_00300 | Prodigal: 2.6 | CDS | — | — | — | — | — | — | — | — | hypothetical protein |
| Contig1 | 313917 | 315659 | + | GENE_00301 | Prodigal: 2.6 | CDS | 3.6.3.- | — | — | — | Q99T13 | — | — | — | Putative multidrug export ATP-binding/permease protein |
| Contig1 | 315739 | 316803 | − | GENE_00302 | Prodigal: 2.6 | CDS | — | — | — | — | — | — | — | — | Fusaric acid resistance protein family protein |
| Contig1 | 317013 | 318302 | − | GENE_00303 | Prodigal: 2.6 | CDS | 5.4.3.8 | — | — | — | Q81YV0 | hemL1 | — | — | Glutamate-1-semialdehyde 2,1-aminomutase 1 |
| Contig1 | 318460 | 318933 | + | GENE_00304 | Prodigal: 2.6 | CDS | 1.11.1.15 | — | — | — | Q83CY8 | bcp | — | — | Putative peroxiredoxin bcp |
| Contig1 | 319058 | 319495 | + | GENE_00305 | Prodigal: 2.6 | CDS | — | — | — | — | P71086 | perR | — | — | Peroxide operon regulator |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 319530 | 319883 | − | GENE_00306 | Prodigal: 2.6 | CDS | — | PRK02935 | — | — | — | — | — | — | hypothetical protein |
| Contig1 | 320086 | 320970 | + | GENE_00307 | Prodigal: 2.6 | CDS | — | — | — | — | — | — | — | — | hypothetical protein |
| Contig1 | 321265 | 322812 | + | GENE_00308 | — | rRNA | — | — | — | — | — | — | — | — | 16S ribosomal RNA |
| Contig1 | 322990 | 325915 | + | GENE_00309 | — | rRNA | — | — | — | — | — | — | — | — | 23S ribosomal RNA |
| Contig1 | 326021 | 326131 | + | GENE_00310 | — | rRNA | — | — | — | — | — | — | — | — | 5S ribosomal RNA |
| Contig1 | 326144 | 326218 | + | GENE_00311 | Aragorn: 1.2 | tRNA | — | — | — | — | — | — | — | — | tRNA-Asn(gtt) |
| Contig1 | 326224 | 326314 | + | GENE_00312 | Aragorn: 1.2 | tRNA | — | — | — | — | — | — | — | — | tRNA-Ser(gga) |
| Contig1 | 326351 | 326423 | + | GENE_00313 | Aragorn: 1.2 | tRNA | — | — | — | — | — | — | — | — | tRNA-Glu(ttc) |
| Contig1 | 326433 | 326508 | + | GENE_00314 | Aragorn: 1.2 | tRNA | — | — | — | — | — | — | — | — | tRNA-Val(tac) |
| Contig1 | 326516 | 326592 | + | GENE_00315 | Aragorn: 1.2 | tRNA | — | — | — | — | — | — | — | — | tRNA-Met(cat) |
| Contig1 | 326601 | 326677 | + | GENE_00316 | Aragorn: 1.2 | tRNA | — | — | — | — | — | — | — | — | tRNA-Asp(gtc) |
| Contig1 | 326688 | 326763 | + | GENE_00317 | Aragorn: 1.2 | tRNA | — | — | — | — | — | — | — | — | tRNA-Phe(gaa) |
| Contig1 | 326767 | 326840 | + | GENE_00318 | Aragorn: 1.2 | tRNA | — | — | — | — | — | — | — | — | tRNA-Thr(tgt) |
| Contig1 | 326851 | 326935 | + | GENE_00319 | Aragorn: 1.2 | tRNA | — | — | — | — | — | — | — | — | tRNA-Tyr(gta) |
| Contig1 | 326946 | 327019 | + | GENE_00320 | Aragorn: 1.2 | tRNA | — | — | — | — | — | — | — | — | tRNA-Trp(cca) |
| Contig1 | 327049 | 327124 | + | GENE_00321 | Aragorn: 1.2 | tRNA | — | — | — | — | — | — | — | — | tRNA-His(gtg) |
| Contig1 | 327133 | 327206 | + | GENE_00322 | Aragorn: 1.2 | tRNA | — | — | — | — | — | — | — | — | tRNA-Gln(ttg) |
| Contig1 | 327259 | 327333 | + | GENE_00323 | Aragorn: 1.2 | tRNA | — | — | — | — | — | — | — | — | tRNA-Gly(gcc) |
| Contig1 | 327339 | 327409 | + | GENE_00324 | Aragorn: 1.2 | tRNA | — | — | — | — | — | — | — | — | tRNA-Cys(gca) |
| Contig1 | 327417 | 327505 | + | GENE_00325 | Aragorn: 1.2 | tRNA | — | — | — | — | — | — | — | — | tRNA-Leu(taa) |
| Contig1 | 327752 | 327835 | + | GENE_00326 | Aragorn: 1.2 | tRNA | — | — | — | — | — | — | — | — | tRNA-Leu(caa) |
| Contig1 | 328053 | 328574 | + | GENE_00327 | Prodigal: 2.6 | CDS | — | — | PF03553.8 | — | — | — | — | — | Na+/H+ antiporter family protein |
| Contig1 | 328648 | 329346 | + | GENE_00328 | Prodigal: 2.6 | CDS | 3.4.21.- | — | — | — | P58495 | — | — | — | putative peptidase |
| Contig1 | 329627 | 331399 | + | GENE_00329 | Prodigal: 2.6 | CDS | 4.1.99.17 | — | — | — | P45740 | thiC | — | — | Phosphomethyl-pyrimidine synthase |
| Contig1 | 331440 | 332795 | − | GENE_00330 | Prodigal: 2.6 | CDS | 1.21.-.- | — | — | — | O06997 | yvdP_1 | — | — | putative FAD-linked oxidoreductase YvdP |
| Contig1 | 333050 | 333229 | + | GENE_00331 | Prodigal: 2.6 | CDS | — | — | — | — | — | — | — | — | hypothetical protein |
| Contig1 | 333232 | 334953 | + | GENE_00332 | Prodigal: 2.6 | CDS | — | — | — | — | P42061 | appA_1 | — | — | Oligopeptide-binding protein AppA precursor |
| Contig1 | 335022 | 335978 | + | GENE_00333 | Prodigal: 2.6 | CDS | — | — | — | — | P0AEF8 | dppB_1 | — | — | Dipeptide transport system permease protein DppB |
| Contig1 | 335991 | 336896 | + | GENE_00334 | Prodigal: 2.6 | CDS | — | — | — | — | P75799 | gsiD | — | — | Glutathione transport system permease protein GsiD |
| Contig1 | 336893 | 337879 | + | GENE_00335 | Prodigal: 2.6 | CDS | — | — | — | — | P24136 | oppD_1 | — | — | Oligopeptide transport ATP-binding protein OppD |
| Contig1 | 337872 | 338231 | + | GENE_00336 | Prodigal: 2.6 | CDS | — | — | — | — | P24137 | oppF_1 | — | — | Oligopeptide-binding ATP-binding protein OppF |
| Contig1 | 338228 | 338836 | + | GENE_00337 | Prodigal: 2.6 | CDS | — | — | — | — | P24137 | oppF_2 | — | — | Oligopeptide transport ATP-binding protein OppF |
| Contig1 | 338909 | 340354 | − | GENE_00338 | Prodigal: 2.6 | CDS | 1.11.1.6 | — | — | — | P26901 | katA_1 | — | — | Vegetative catalase |
| Contig1 | 340611 | 341546 | + | GENE_00339 | Prodigal: 2.6 | CDS | — | — | PF04909.8 | — | — | — | — | — | Amidohydrolase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 341770 | 342537 | + | GENE_00340 | Prodigal: 2.6 | CDS | 3.6.3.- | — | — | — | P97027 | ssuB_1 | — | — | Aliphatic sulfonates import ATP-binding protein SsuB |
| Contig1 | 342553 | 343542 | + | GENE_00341 | Prodigal: 2.6 | CDS | — | — | — | — | P40400 | ssuA | — | — | Putative aliphatic sulfonates-binding protein precursor |
| Contig1 | 343542 | 344375 | + | GENE_00342 | Prodigal: 2.6 | CDS | — | — | — | — | P40401 | ssuC_1 | — | — | Putative aliphatic sulfonates transport permease protein SsuC |
| Contig1 | 344400 | 345536 | + | GENE_00343 | Prodigal: 2.6 | CDS | 1.14.14.5 | — | — | — | P40402 | ssuD | — | — | Alkanesulfonate monooxygenase |
| Contig1 | 345711 | 345980 | + | GENE_00344 | Prodigal: 2.6 | CDS | — | — | — | — | O31587 | rpsN2 | — | — | Alternate 30S ribosomal protein S14 |
| Contig1 | 346001 | 346468 | − | GENE_00345 | Prodigal: 2.6 | CDS | — | — | — | — | — | — | — | — | hypothetical protein |
| Contig1 | 346465 | 346671 | − | GENE_00346 | Prodigal: 2.6 | CDS | — | — | PF01381.16 | — | — | — | — | — | Helix-turn-helix |
| Contig1 | 346857 | 346930 | + | GENE_00347 | Aragorn: 1.2 | tRNA | — | — | — | — | — | — | — | — | tRNA-Gly(tcc) |
| Contig1 | 347020 | 347643 | + | GENE_00348 | Prodigal: 2.6 | CDS | — | — | — | — | — | — | — | — | hypothetical protein |
| Contig1 | 347728 | 348888 | + | GENE_00349 | Prodigal: 2.6 | CDS | 1.1.-.- | — | — | — | P97030 | queG | — | — | Epoxyqueuosine reductase |
| Contig1 | 348963 | 349874 | + | GENE_00350 | Prodigal: 2.6 | CDS | — | — | PF12671.1 | — | — | — | — | — | Putative amidase domain protein |
| Contig1 | 349920 | 350393 | + | GENE_00351 | Prodigal: 2.6 | CDS | 2.1.1.207 | — | — | — | P44868 | trmL | — | — | tRNA (cytidine(34)-2'-O)-methyltransferase |
| Contig1 | 350530 | 351162 | + | GENE_00352 | Prodigal: 2.6 | CDS | — | — | PF04519.7 | — | — | — | — | — | Polymer-forming cytoskeletal |
| Contig1 | 351153 | 351866 | + | GENE_00353 | Prodigal: 2.6 | CDS | — | — | — | — | — | — | — | — | hypothetical protein |
| Contig1 | 351878 | 352588 | + | GENE_00354 | Prodigal: 2.6 | CDS | — | — | — | — | — | — | — | — | hypothetical protein |
| Contig1 | 352645 | 352734 | − | GENE_00355 | Prodigal: 2.6 | CDS | — | — | PF08298.5 | — | — | — | — | — | PrkA AAA domain protein |
| Contig1 | 352947 | 354842 | + | GENE_00356 | Prodigal: 2.6 | CDS | — | — | — | — | — | — | — | — | hypothetical protein |
| Contig1 | 355033 | 356211 | + | GENE_00357 | Prodigal: 2.6 | CDS | — | — | — | — | P45742 | — | — | Stress response UPF0229 protein YhbH | hypothetical protein |
| Contig1 | 356397 | 356861 | + | GENE_00358 | Prodigal: 2.6 | CDS | — | — | — | — | O32181 | yusO_1 | — | — | putative HTH-type transcriptional regulator YusO |
| Contig1 | 356931 | 357563 | + | GENE_00359 | Prodigal: 2.6 | CDS | — | — | — | — | P52599 | emrK | — | — | putative multidrug resistance protein EmrK |
| Contig1 | 357604 | 359199 | + | GENE_00360 | Prodigal: 2.6 | CDS | — | — | — | — | P0AEJ0 | emrB_1 | — | — | Multidrug export protein EmrB |
| Contig1 | 359224 | 359757 | + | GENE_00361 | Prodigal: 2.6 | CDS | 1.6.5.2 | — | — | — | C1I202 | pmpB | — | — | p-benzoquinone reductase |
| Contig1 | 359770 | 360141 | + | GENE_00362 | Prodigal: 2.6 | CDS | — | — | — | — | — | — | — | — | hypothetical protein |
| Contig1 | 360261 | 361028 | + | GENE_00363 | Prodigal: 2.6 | CDS | — | — | — | — | — | — | — | — | hypothetical protein |
| Contig1 | 361031 | 361408 | + | GENE_00364 | Prodigal: 2.6 | CDS | — | — | — | — | O34712 | ytrA_1 | — | — | HTH-type transcriptional repressor YtrA |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 361398 | 362114 | + | GENE_00365 | Prodigal: 2.6 | CDS | 3.6.3.- | — | — | — | P94374 | yxlF_1 | — | — | putative ABC transporter ATP-binding protein YxlF |
| Contig1 | 362115 | 363032 | + | GENE_00366 | Prodigal: 2.6 | CDS | 3.6.3.- | — | — | — | P94374 | yxlF_2 | — | — | putative ABC transporter ATP-binding protein YxlF |
| Contig1 | 363025 | 363972 | + | GENE_00367 | Prodigal: 2.6 | CDS | — | — | — | — | — | — | — | — | ABC-2 family transporter protein |
| Contig1 | 364064 | 364264 | − | GENE_00368 | Prodigal: 2.6 | CDS | — | — | PF12730.1 | — | P32081 | cspB | — | — | Cold shock protein CspB |
| Contig1 | 364647 | 365477 | + | GENE_00369 | Prodigal: 2.6 | CDS | — | — | — | — | O32167 | metQ_1 | — | — | Methionine-binding lipoprotein MetQ precursor |
| Contig1 | 365494 | 366573 | − | GENE_00370 | Prodigal: 2.6 | CDS | 2.7.7.65 | — | — | — | P76330 | yedQ_1 | — | — | putative diguanylate cyclase YedQ |
| Contig1 | 366725 | 368116 | + | GENE_00371 | Prodigal: 2.6 | CDS | — | — | — | — | P54596 | tcyP | — | — | L-cystine uptake protein TcyP |
| Contig1 | 368184 | 368756 | − | GENE_00372 | Prodigal: 2.6 | CDS | — | — | — | — | — | — | — | — | hypothetical protein |
| Contig1 | 368901 | 369440 | + | GENE_00373 | Prodigal: 2.6 | CDS | — | — | — | — | P54598 | yhcN | — | — | Lipoprotein YhcN precursor |
| Contig1 | 369561 | 370505 | − | GENE_00374 | Prodigal: 2.6 | CDS | — | — | — | — | — | — | — | — | hypothetical protein |
| Contig1 | 370465 | 371130 | − | GENE_00375 | Prodigal: 2.6 | CDS | — | — | PF07875.6 | — | — | — | — | — | Coat F domain protein |
| Contig1 | 371323 | 373377 | + | GENE_00376 | Prodigal: 2.6 | CDS | 3.1.31.- | — | — | — | P54602 | yhcR_1 | — | — | Endonuclease YhcR precursor |
| Contig1 | 373374 | 373970 | + | GENE_00377 | Prodigal: 2.6 | CDS | — | — | PF04203.7 | — | — | — | — | — | Sortase family protein |
| Contig1 | 373967 | 374875 | − | GENE_00378 | Prodigal: 2.6 | CDS | 5.4.99.23 | — | — | — | P33643 | rluD_1 | — | — | Ribosomal large subunit pseudouridine synthase D |
| Contig1 | 374985 | 375380 | + | GENE_00379 | Prodigal: 2.6 | CDS | — | — | — | — | — | — | — | — | hypothetical protein |
| Contig1 | 375511 | 375933 | + | GENE_00380 | Prodigal: 2.6 | CDS | — | — | — | — | O06186 | hrp1_1 | — | — | Hypoxic response protein 1 |
| Contig1 | 376061 | 376750 | + | GENE_00381 | Prodigal: 2.6 | CDS | 3.1.3.68 | — | — | — | P77247 | yniC | — | — | 2-deoxyglucose-6-phosphate phosphatase |
| Contig1 | 376743 | 378281 | + | GENE_00382 | Prodigal: 2.6 | CDS | 3.5.1.100 | — | — | — | Q75SP7 | ramA | — | — | (R)-stereoselective amidase |
| Contig1 | 378464 | 379876 | + | GENE_00383 | Prodigal: 2.6 | CDS | 2.6.1.77 | — | — | — | Q9APM5 | tpa_1 | — | — | Taurine-pyruvate aminotransferase |
| Contig1 | 379893 | 380468 | + | GENE_00384 | Prodigal: 2.6 | CDS | — | — | PF04309.6 | — | — | — | — | — | Glycerol-3-phosphate responsive antiterminator |
| Contig1 | 380641 | 381468 | + | GENE_00385 | Prodigal: 2.6 | CDS | — | — | — | — | P18156 | glpF | — | — | Glycerol uptake facilitator protein |
| Contig1 | 381485 | 382975 | + | GENE_00386 | Prodigal: 2.6 | CDS | 2.7.1.30 | — | — | — | P18157 | glpK | — | — | Glycerol kinase |
| Contig1 | 383117 | 384781 | + | GENE_00387 | Prodigal: 2.6 | CDS | 1.1.5.3 | — | — | — | P18158 | glpD | — | — | Aerobic glycerol-3-phosphate dehydrogenase |
| Contig1 | 384921 | 386663 | + | GENE_00388 | Prodigal: 2.6 | CDS | 5.4.2.2 | — | — | — | P18159 | pgcA | — | — | Phosphoglucomutase |
| Contig1 | 386809 | 387945 | + | GENE_00389 | Prodigal: 2.6 | CDS | 2.7.13.3 | — | — | — | Q99SZ7 | vraS | — | — | Sensor protein VraS |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 387945 | 388592 | + | GENE_00390 | Prodigal: 2.6 | CDS | — | — | — | — | O32197 | liaR_1 | — | — | Transcriptional regulatory protein LiaR |
| Contig1 | 388589 | 389113 | + | GENE_00391 | Prodigal: 2.6 | CDS | 1.7.-.- | — | — | — | O07529 | azr_1 | — | — | FMN-dependent NADPH-azoreductase |
| Contig1 | 389127 | 389369 | − | GENE_00392 | Prodigal: 2.6 | CDS | — | — | — | — | — | — | — | — | hypothetical protein |
| Contig1 | 389561 | 389884 | + | GENE_00393 | Prodigal: 2.6 | CDS | — | — | — | — | — | — | — | — | hypothetical protein |
| Contig1 | 389927 | 391372 | − | GENE_00394 | Prodigal: 2.6 | CDS | 3.4.-.- | — | — | — | O07532 | lytF | — | — | Peptidoglycan endopeptidase LytF precursor |
| Contig1 | 391552 | 391986 | − | GENE_00395 | Prodigal: 2.6 | CDS | — | — | — | — | Q9L132 | nsrR | — | — | HTH-type transcriptional repressor NsrR |
| Contig1 | 392121 | 393635 | − | GENE_00396 | Prodigal: 2.6 | CDS | — | — | PF05552.6 | — | — | — | — | Conserved TM helix | hypothetical protein |
| Contig1 | 393805 | 395211 | + | GENE_00397 | Prodigal: 2.6 | CDS | — | PRK11767 | — | — | — | — | — | — | SpoVR family protein |
| Contig1 | 395249 | 396628 | − | GENE_00398 | Prodigal: 2.6 | CDS | 3.1.3.1 | — | — | — | P19406 | phoA | — | — | Alkaline phosphatase 4 precursor |
| Contig1 | 397087 | 397911 | + | GENE_00399 | Prodigal: 2.6 | CDS | 3.4.-.- | — | — | — | P54421 | lytE | — | — | putative peptidoglycan endopeptidase LytE precursor |
| Contig1 | 397979 | 398854 | − | GENE_00400 | Prodigal: 2.6 | CDS | — | — | — | — | P39647 | cysL_1 | — | — | HTH-type transcriptional regulator CysL |
| Contig1 | 398958 | 400067 | + | GENE_00401 | Prodigal: 2.6 | CDS | 2.3.3.1 | — | — | — | P39119 | citA | — | — | Citrate synthase 1 |
| Contig1 | 400147 | 401016 | + | GENE_00402 | Prodigal: 2.6 | CDS | 1.-.-.- | — | — | — | P80873 | ydaD_1 | — | — | General stress protein 39 |
| Contig1 | 401346 | 402749 | + | GENE_00403 | Prodigal: 2.6 | CDS | — | — | — | — | O07576 | yhdG_2 | — | — | putative amino acid permease YhdG |
| Contig1 | 402912 | 404219 | + | GENE_00404 | Prodigal: 2.6 | CDS | — | — | PF00209.12 | — | — | — | — | — | Sodium:neurotransmitter symporter family protein |
| Contig1 | 404256 | 404546 | − | GENE_00405 | Prodigal: 2.6 | CDS | — | — | — | — | O07580 | yhdK | — | — | putative anti-sigma-M factor YhdK |
| Contig1 | 404534 | 405607 | − | GENE_00406 | Prodigal: 2.6 | CDS | — | — | — | — | O07581 | yhdL | — | — | putative anti-sigma-M factor YhdL |
| Contig1 | 405600 | 406091 | − | GENE_00407 | Prodigal: 2.6 | CDS | — | — | — | — | O07582 | sigM | — | — | RNA polymerase sigma factor SigM |
| Contig1 | 406330 | 406929 | + | GENE_00408 | Prodigal: 2.6 | CDS | 2.3.1.- | — | — | — | O07584 | plsC | — | — | 1-acyl-sn-glycerol-3-phosphate acyltransferase |
| Contig1 | 406975 | 408309 | − | GENE_00409 | Prodigal: 2.6 | CDS | — | — | — | — | O05961 | tlyC | — | — | Hemolysin C |
| Contig1 | 408371 | 408796 | − | GENE_00410 | Prodigal: 2.6 | CDS | — | — | — | — | P22853 | merR1 | — | — | Mercuric resistance operon regulatory protein |
| Contig1 | 408976 | 410160 | + | GENE_00411 | Prodigal: 2.6 | CDS | 2.6.1.1 | — | — | — | Q9X0Y2 | aspC | — | — | Aspartate aminotransferase |
| Contig1 | 410193 | 411413 | + | GENE_00412 | Prodigal: 2.6 | CDS | 4.1.1.87 | — | — | — | P40804 | pksF | — | — | Polyketide biosynthesis malonyl-ACP decarboxylase PksF |
| Contig1 | 411666 | 413054 | + | GENE_00413 | Prodigal: 2.6 | CDS | — | — | — | — | P0AE78 | corC_1 | — | — | Magnesium and cobalt efflux protein CorC |
| Contig1 | 413068 | 413427 | − | GENE_00414 | Prodigal: 2.6 | CDS | — | — | — | — | P37002 | crcB_1 | — | — | Putative fluoride ion transporter CrcB |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 413424 | 413819 | − | GENE_00415 | Prodigal: 2.6 | CDS | — | — | — | — | P37002 | crcB_2 | — | — | Putative fluoride ion transporter CrcB |
| Contig1 | 413821 | 414537 | − | GENE_00416 | Prodigal: 2.6 | CDS | 3.1.4.46 | — | — | — | P10908 | ugpQ_1 | — | — | Glycerophosphoryl diester phosphodiesterase |
| Contig1 | 414707 | 414811 | + | GENE_00417 | Prodigal: 2.6 | CDS | — | — | — | — | — | — | — | — | hypothetical protein |
| Contig1 | 414974 | 416089 | + | GENE_00418 | Prodigal: 2.6 | CDS | — | — | — | — | P0AEB5 | ynaI | — | — | Low conductance mechanosensitive channel YnaI |
| Contig1 | 416141 | 416884 | + | GENE_00419 | Prodigal: 2.6 | CDS | 3.5.1.- | — | — | — | Q9WYW0 | cobB | — | — | NAD-dependent protein deacetylase |
| Contig1 | 416918 | 417766 | − | GENE_00420 | Prodigal: 2.6 | CDS | 3.5.1.104 | — | — | — | Q8DP63 | pgdA_1 | — | — | Peptidoglycan-N-acetylglucosamine deacetylase |
| Contig1 | 418023 | 418874 | + | GENE_00421 | Prodigal: 2.6 | CDS | 2.6.1.21 | — | — | — | P19938 | dat_1 | — | — | D-alanine aminotransferase |
| Contig1 | 418917 | 419423 | − | GENE_00422 | Prodigal: 2.6 | CDS | — | — | — | — | P17446 | betI | — | — | HTH-type transcriptional regulator BetI |
| Contig1 | 419610 | 420161 | + | GENE_00423 | Prodigal: 2.6 | CDS | — | — | — | — | — | — | — | — | hypothetical protein |
| Contig1 | 420201 | 420701 | − | GENE_00424 | Prodigal: 2.6 | CDS | — | — | — | — | O07552 | nhaX_1 | — | — | Stress response protein NhaX |
| Contig1 | 420995 | 421099 | + | GENE_00425 | Prodigal: 2.6 | CDS | — | — | — | — | — | — | — | — | hypothetical protein |
| Contig1 | 421123 | 422919 | + | GENE_00426 | Prodigal: 2.6 | CDS | 3.6.3.- | — | — | — | O07550 | yheI | — | — | putative multidrug resistance ABC transporter ATP-binding/permease protein YheI |
| Contig1 | 422876 | 424897 | + | GENE_00427 | Prodigal: 2.6 | CDS | 3.6.3.- | — | — | — | O07549 | yheH | — | — | putative multidrug resistance ABC transporter ATP-binding/permease protein YheH |
| Contig1 | 424938 | 425558 | − | GENE_00428 | Prodigal: 2.6 | CDS | 1.2.1.11 | — | — | MF_02121 | — | asd_1 | — | — | Aspartate-semialdehyde dehydrogenase |
| Contig1 | 425587 | 425712 | − | GENE_00429 | Prodigal: 2.6 | CDS | — | — | — | — | — | — | — | — | hypothetical protein |
| Contig1 | 425814 | 426020 | − | GENE_00430 | Prodigal: 2.6 | CDS | — | — | — | — | P84584 | — | — | — | Small, acid-soluble spore protein 2 |
| Contig1 | 426245 | 426451 | − | GENE_00431 | Prodigal: 2.6 | CDS | — | — | — | — | — | — | — | — | hypothetical protein |
| Contig1 | 426543 | 427901 | − | GENE_00432 | Prodigal: 2.6 | CDS | — | — | — | — | O07545 | yheD_1 | — | — | Endospore coat-associated protein YheD |
| Contig1 | 427891 | 428982 | − | GENE_00433 | Prodigal: 2.6 | CDS | — | — | — | — | O07545 | yheD_2 | — | — | Endospore coat-associated protein YheD |
| Contig1 | 429220 | 430353 | + | GENE_00434 | Prodigal: 2.6 | CDS | — | — | — | — | — | — | — | — | hypothetical protein |
| Contig1 | 430439 | 430789 | + | GENE_00435 | Prodigal: 2.6 | CDS | — | — | — | — | — | — | — | — | hypothetical protein |
| Contig1 | 430828 | 431967 | − | GENE_00436 | Prodigal: 2.6 | CDS | — | — | — | — | — | — | — | — | hypothetical protein |
| Contig1 | 432351 | 433217 | + | GENE_00437 | Prodigal: 2.6 | CDS | — | — | — | — | O07539 | yhaX | — | — | Stress response protein YhaX |
| Contig1 | 433330 | 434832 | + | GENE_00438 | Prodigal: 2.6 | CDS | 1.3.99.22 | — | — | — | Q796V8 | hemZ | — | — | Oxygen-independent coproporphyrinogen-III oxidase 2 |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 434934 | 436223 | + | GENE_00439 | Prodigal: 2.6 | CDS | 1.14.13.59 | — | — | — | P11295 | iucD | — | — | L-lysine N6-monooxygenase |
| Contig1 | 436249 | 437463 | — | GENE_00440 | Prodigal: 2.6 | CDS | — | — | — | — | O07536 | yhaU | — | — | K(+)/H(+) antiporter YhaU |
| Contig1 | 437471 | 437968 | — | GENE_00441 | Prodigal: 2.6 | CDS | — | — | — | — | O07535 | khtT_1 | — | — | K(+)/H(+) antiporter subunit KhtT |
| Contig1 | 437996 | 438349 | — | GENE_00442 | Prodigal: 2.6 | CDS | — | — | — | — | — | — | — | — | hypothetical protein |
| Contig1 | 438534 | 439301 | + | GENE_00443 | Prodigal: 2.6 | CDS | 4.2.1.17 | — | — | — | P76082 | paaF | — | — | 2,3-dehydroadipyl-CoA hydratase |
| Contig1 | 439326 | 439511 | — | GENE_00444 | Prodigal: 2.6 | CDS | — | — | — | — | — | — | — | — | hypothetical protein |
| Contig1 | 439617 | 440513 | + | GENE_00445 | Prodigal: 2.6 | CDS | 3.6.3.- | — | — | — | P45073 | lptB | — | — | Lipopolysaccharide export system ATP-binding protein LptB |
| Contig1 | 440506 | 441765 | + | GENE_00446 | Prodigal: 2.6 | CDS | — | — | PF12698.1 | — | — | — | — | — | ABC-2 family transporter protein |
| Contig1 | 441876 | 443099 | + | GENE_00447 | Prodigal: 2.6 | CDS | — | — | — | — | O07522 | yhaO | — | — | putative metallophoesterase YhaO |
| Contig1 | 443096 | 445978 | + | GENE_00448 | Prodigal: 2.6 | CDS | — | — | — | — | — | — | — | — | hypothetical protein |
| Contig1 | 446052 | 446996 | + | GENE_00449 | Prodigal: 2.6 | CDS | 3.1.-.- | — | — | — | O07521 | yhaM | — | — | 3'-5' exoribonuclease YhaM |
| Contig1 | 447111 | 447338 | + | GENE_00450 | Prodigal: 2.6 | CDS | — | — | — | — | O07520 | yhaL | — | — | Sporulation protein YhaL |
| Contig1 | 447377 | 448228 | — | GENE_00451 | Prodigal: 2.6 | CDS | 5.2.1.8 | — | — | — | P24327 | prsA | — | — | Foldase protein PrsA precursor |
| Contig1 | 449020 | 449550 | + | GENE_00452 | Prodigal: 2.6 | CDS | — | — | — | — | — | — | — | — | hypothetical protein |
| Contig1 | 449771 | 450103 | + | GENE_00453 | Prodigal: 2.6 | CDS | — | — | — | — | — | — | — | — | hypothetical protein |
| Contig1 | 450100 | 450711 | — | GENE_00454 | Prodigal: 2.6 | CDS | — | — | — | — | P11065 | hpr | — | — | HTH-type transcriptional regulator Hpr |
| Contig1 | 450891 | 451247 | + | GENE_00455 | Prodigal: 2.6 | CDS | — | — | PF12732.1 | — | — | — | — | — | YtxH-like protein |
| Contig1 | 451377 | 451556 | + | GENE_00456 | Prodigal: 2.6 | CDS | — | — | — | — | — | — | — | — | hypothetical protein |
| Contig1 | 451614 | 452132 | — | GENE_00457 | Prodigal: 2.6 | CDS | — | — | — | — | O07515 | trpP | — | — | putative tryptophan transport protein |
| Contig1 | 452253 | 453332 | — | GENE_00458 | Prodigal: 2.6 | CDS | 2.6.1.52 | — | — | — | P80862 | serC | — | — | Phosphoserine aminotransferase |
| Contig1 | 453469 | 453906 | — | GENE_00459 | Prodigal: 2.6 | CDS | 3.-.-.- | — | — | — | P44956 | — | — | — | HIT-like protein |
| Contig1 | 454396 | 455139 | + | GENE_00460 | Prodigal: 2.6 | CDS | — | — | — | — | P55339 | ecsA_1 | — | — | ABC-type transporter ATP-binding protein EcsA |
| Contig1 | 455132 | 456358 | + | GENE_00461 | Prodigal: 2.6 | CDS | — | — | PF05975.6 | — | — | — | — | — | Bacterial ABC transporter protein EcsB |
| Contig1 | 456401 | 457105 | + | GENE_00462 | Prodigal: 2.6 | CDS | — | — | PF12787.1 | — | — | — | — | — | EcsC protein family protein |
| Contig1 | 457126 | 458313 | — | GENE_00463 | Prodigal: 2.6 | CDS | 3.5.1.14 | — | — | — | P37112 | amaA | — | — | N-acyl-L-amino acid amidohydrolase |
| Contig1 | 458382 | 459107 | — | GENE_00464 | Prodigal: 2.6 | CDS | — | — | — | — | — | — | — | — | hypothetical protein |
| Contig1 | 459050 | 459766 | — | GENE_00465 | Prodigal: 2.6 | CDS | — | — | — | — | — | — | — | — | hypothetical protein |
| Contig1 | 459884 | 460384 | — | GENE_00466 | Prodigal: 2.6 | CDS | 1.14.99.3 | — | — | — | P38049 | hmoB | — | — | Heme-degrading monooxygenase HmoB |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 460507 | 462648 | + | GENE_00467 | Prodigal: 2.6 | CDS | — | — | — | — | P38050 | pbpF | — | — | Penicillin-binding protein 1F |
| Contig1 | 462721 | 463833 | + | GENE_00468 | Prodigal: 2.6 | CDS | 4.1.1.37 | — | — | — | P32395 | hemE | — | — | Uroporphyrinogen decarboxylase |
| Contig1 | 463909 | 464844 | + | GENE_00469 | Prodigal: 2.6 | CDS | 4.99.1.1 | — | — | — | P32396 | hemH | — | — | Ferrochelatase |
| Contig1 | 464872 | 466305 | + | GENE_00470 | Prodigal: 2.6 | CDS | 1.3.3.4 | — | — | — | P32397 | hemY | — | — | Protoporphyrinogen oxidase |
| Contig1 | 466453 | 467025 | + | GENE_00471 | Prodigal: 2.6 | CDS | — | — | — | — | P43506 | bm3R1_2 | — | — | HTH-type transcriptional repressor Bm3R1 |
| Contig1 | 467100 | 469433 | + | GENE_00472 | Prodigal: 2.6 | CDS | — | — | — | MF_01894 | — | smc_1 | — | — | Chromosome partition protein Smc |
| Contig1 | 469484 | 470461 | − | GENE_00473 | Prodigal: 2.6 | CDS | 2.3.1.180 | — | — | — | O07600 | fabHB | — | — | 3-oxoacyl-[acyl-carrier-protein] synthase 3 protein 2 |
| Contig1 | 470599 | 470820 | − | GENE_00474 | Prodigal: 2.6 | CDS | — | — | — | — | — | — | — | — | Putative hypothetical protein |
| Contig1 | 470943 | 471983 | + | GENE_00475 | Prodigal: 2.6 | CDS | 3.4.11.- | — | — | — | P94521 | ysdC_1 | — | — | Putative aminopeptidase YsdC |
| Contig1 | 472024 | 473313 | − | GENE_00476 | Prodigal: 2.6 | CDS | — | — | — | — | P24943 | gltT_1 | — | — | Proton/sodium-glutamate symport protein |
| Contig1 | 473840 | 474574 | + | GENE_00477 | Prodigal: 2.6 | CDS | 3.1.26.11 | — | — | MF_01818 | — | rbn | — | — | Ribonuclease BN |
| Contig1 | 474587 | 475582 | + | GENE_00478 | Prodigal: 2.6 | CDS | 2.7.7.63 | — | — | — | O07608 | lplJ | — | — | Lipoate-protein ligase LplJ |
| Contig1 | 475663 | 476307 | + | GENE_00479 | Prodigal: 2.6 | CDS | 4.-.-.- | — | — | — | O07609 | yhfK | — | — | putative sugar epimerase YhfK |
| Contig1 | 476439 | 477980 | + | GENE_00480 | Prodigal: 2.6 | CDS | 6.2.1.3 | — | — | — | O07610 | lcfB_1 | — | — | Long-chain-fatty-acid-CoA ligase |
| Contig1 | 478028 | 478423 | − | GENE_00481 | Prodigal: 2.6 | CDS | — | — | — | — | — | — | — | — | hypothetical protein |
| Contig1 | 478578 | 479828 | + | GENE_00482 | Prodigal: 2.6 | CDS | — | — | — | — | — | htpX_1 | — | — | Protease HtpX |
| Contig1 | 479873 | 481021 | + | GENE_00483 | Prodigal: 2.6 | CDS | 3.4.21.62 | — | — | MF_00188 | P00782 | apr | — | — | Subtilisin BPN' precursor |
| Contig1 | 481509 | 481769 | − | GENE_00484 | Prodigal: 2.6 | CDS | — | — | — | — | C0SP94 | yhfQ_1 | — | — | Putative ABC transporter substrate-binding lipoprotein YhfQ precursor |
| Contig1 | 481766 | 482386 | + | GENE_00485 | Prodigal: 2.6 | CDS | — | — | — | — | C0SP94 | yhfQ2 | — | — | Putative ABC transporter substrate-binding lipoprotein YhfQ precursor |
| Contig1 | 482401 | 482976 | − | GENE_00486 | Prodigal: 2.6 | CDS | 3.1.3.3 | — | — | — | D3DFP8 | pspB | — | — | Putative phosphoserine phosphatase 2 |
| Contig1 | 483027 | 484118 | − | GENE_00487 | Prodigal: 2.6 | CDS | 2.3.1.- | — | — | — | O07618 | yhfS | — | — | Putative acetyl-CoA C-acetyltransferase YhfS |
| Contig1 | 484106 | 485542 | − | GENE_00488 | Prodigal: 2.6 | CDS | 6.2.1.- | — | — | — | O07619 | yhfT | — | — | putative acyl-CoA ligase YhfT |
| Contig1 | 485554 | 486111 | − | GENE_00489 | Prodigal: 2.6 | CDS | — | — | — | — | O07620 | bioY_1 | — | — | putative biotin transporter BioY |
| Contig1 | 486242 | 487534 | − | GENE_00490 | Prodigal: 2.6 | CDS | — | — | — | — | O07621 | hemAT | — | — | Heme-based aerotactic transducer HemAT |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 487657 | 489180 | − | GENE_00491 | Prodigal: 2.6 | CDS | 1.4.3.- | — | — | — | P37906 | puuB | — | — | Gamma-glutamylputrescine oxidoreductase |
| Contig1 | 489305 | 490162 | + | GENE_00492 | Prodigal: 2.6 | CDS | 1.-.-.- | PRK03057 | — | — | P80873 | ydaD_2 | — | — | General stress protein 39 |
| Contig1 | 490193 | 490426 | − | GENE_00493 | Prodigal: 2.6 | CDS | — | — | — | — | — | — | — | — | hypothetical protein |
| Contig1 | 490742 | 491320 | + | GENE_00494 | Prodigal: 2.6 | CDS | — | — | — | — | P40396 | comK | — | — | Competence transcription factor |
| Contig1 | 491466 | 491834 | + | GENE_00495 | Prodigal: 2.6 | CDS | — | — | — | — | — | — | — | — | hypothetical protein |
| Contig1 | 491861 | 492232 | + | GENE_00496 | Prodigal: 2.6 | CDS | — | — | — | — | — | — | — | — | hypothetical protein |
| Contig1 | 492232 | 492372 | + | GENE_00497 | Prodigal: 2.6 | CDS | — | — | — | — | — | — | — | — | hypothetical protein |
| Contig1 | 492365 | 493075 | + | GENE_00498 | Prodigal: 2.6 | CDS | — | — | — | — | — | — | — | — | hypothetical protein |
| Contig1 | 493271 | 493540 | + | GENE_00499 | Prodigal: 2.6 | CDS | — | — | PF05901.5 | — | — | — | — | — | Excalibur calcium-binding domain protein |
| Contig1 | 493573 | 493890 | − | GENE_00500 | Prodigal: 2.6 | CDS | — | — | — | — | — | — | — | — | hypothetical protein |
| Contig1 | 493931 | 495400 | − | GENE_00501 | Prodigal: 2.6 | CDS | — | PRK00967 | — | — | O34745 | yodF_1 | — | — | putative symporter YodF |
| Contig1 | 495397 | 495597 | − | GENE_00502 | Prodigal: 2.6 | CDS | — | — | — | — | — | — | — | — | hypothetical protein |
| Contig1 | 495718 | 496077 | − | GENE_00503 | Prodigal: 2.6 | CDS | — | — | — | — | — | — | — | — | hypothetical protein |
| Contig1 | 496229 | 496855 | + | GENE_00504 | Prodigal: 2.6 | CDS | — | — | — | — | P76221 | ydjZ_1 | — | — | TVP38/TMEM64 family inner membrane protein YdjZ |
| Contig1 | 496852 | 497367 | + | GENE_00505 | Prodigal: 2.6 | CDS | 3.4.21.89 | — | — | — | O07560 | sipV | — | — | Signal peptidase I V |
| Contig1 | 497512 | 498993 | + | GENE_00506 | Prodigal: 2.6 | CDS | 1.14.13.50 | — | — | — | P42535 | pcpB | — | — | Pentachlorophenol 4-monooxygenase |
| Contig1 | 499083 | 499604 | + | GENE_00507 | Prodigal: 2.6 | CDS | — | — | PF01047.16 | — | — | — | — | — | MarR family protein |
| Contig1 | 499641 | 500798 | − | GENE_00508 | Prodigal: 2.6 | CDS | — | — | PF05145.6 | — | — | — | — | — | Putative ammonia monooxygenase |
| Contig1 | 500966 | 502162 | − | GENE_00509 | Prodigal: 2.6 | CDS | — | — | — | — | P02980 | tetA_1 | — | — | Tetracycline resistance protein, class B |
| Contig1 | 502178 | 502798 | − | GENE_00510 | Prodigal: 2.6 | CDS | — | — | — | — | P0A0N5 | qacR | — | — | HTH-type transcriptional regulator QacR |
| Contig1 | 503049 | 503567 | − | GENE_00511 | Prodigal: 2.6 | CDS | — | — | PF02915.11 | — | — | — | — | — | Rubrerythrin |
| Contig1 | 503636 | 504349 | − | GENE_00512 | Prodigal: 2.6 | CDS | — | — | — | — | — | — | — | — | hypothetical protein |
| Contig1 | 504491 | 507991 | + | GENE_00513 | Prodigal: 2.6 | CDS | 3.1.-.- | — | — | — | P23477 | addB | — | — | ATP-dependent helicase/deoxyribonuclease subunit B |
| Contig1 | 507978 | 511682 | + | GENE_00514 | Prodigal: 2.6 | CDS | 3.1.-.- | — | — | — | P23478 | addA_1 | — | — | ATP-dependent helicase/nuclease subunit A |
| Contig1 | 511747 | 512919 | + | GENE_00515 | Prodigal: 2.6 | CDS | — | — | — | — | A6QGP7 | sbcD | — | — | Nuclease SbcCD subunit D |
| Contig1 | 512916 | 516308 | + | GENE_00516 | Prodigal: 2.6 | CDS | — | — | — | — | Q7A5S6 | sbcC | — | — | Nuclease SbcCD subunit C |
| Contig1 | 516324 | 516617 | + | GENE_00517 | Prodigal: 2.6 | CDS | — | — | — | — | — | — | — | — | hypothetical protein |
| Contig1 | 516661 | 516879 | − | GENE_00518 | Prodigal: 2.6 | CDS | — | — | — | — | O06716 | gerPF_1 | — | — | putative spore germination protein GerPF |
| Contig1 | 516919 | 517314 | − | GENE_00519 | Prodigal: 2.6 | CDS | — | — | — | — | O06717 | gerPE | — | — | putative spore germination protein GerPE |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 517314 | 517490 | – | GENE_00520 | Prodigal: 2.6 | CDS | — | — | — | — | O06718 | gerPD | — | — | putative spore germination protein GerPD |
| Contig1 | 517487 | 518104 | – | GENE_00521 | Prodigal: 2.6 | CDS | — | — | — | — | O06719 | gerPC | — | — | putative spore germination protein GerPC |
| Contig1 | 518140 | 518376 | – | GENE_00522 | Prodigal: 2.6 | CDS | — | — | — | — | O06720 | gerPB | — | — | putative spore germination protein GerPB |
| Contig1 | 518389 | 518610 | – | GENE_00523 | Prodigal: 2.6 | CDS | — | — | — | — | O06721 | gerPA | — | — | putative spore germination protein GerPA |
| Contig1 | 518801 | 519010 | – | GENE_00524 | Prodigal: 2.6 | CDS | 3.1.3.- | — | — | — | O06722 | yisI | — | — | Aspartyl-phosphate phosphatase YisI |
| Contig1 | 519226 | 520131 | + | GENE_00525 | Prodigal: 2.6 | CDS | 4.3.2.3 | — | — | — | Q39BA7 | — | — | — | Ureidoglycolate lyase |
| Contig1 | 520225 | 520581 | + | GENE_00526 | Prodigal: 2.6 | CDS | — | — | — | — | — | — | — | — | hypothetical protein |
| Contig1 | 520834 | 521376 | – | GENE_00527 | Prodigal: 2.6 | CDS | — | — | — | — | — | — | — | — | hypothetical protein |
| Contig1 | 521552 | 523393 | + | GENE_00528 | Prodigal: 2.6 | CDS | 6.3.5.4 | — | — | — | O05272 | asnO | — | — | Asparagine synthetase [glutamine-hydrolyzing] 3 |
| Contig1 | 523479 | 524219 | + | GENE_00529 | Prodigal: 2.6 | CDS | 2.5.1.99 | — | — | — | P37294 | crtB | — | — | All-trans-phytoene synthase |
| Contig1 | 524255 | 525652 | – | GENE_00530 | Prodigal: 2.6 | CDS | — | — | — | — | O82855 | norM_1 | — | — | Multidrug resistance protein NorM |
| Contig1 | 525745 | 526608 | + | GENE_00531 | Prodigal: 2.6 | CDS | — | — | — | — | P0A9E0 | araC | — | — | Arabinose operon regulatory protein |
| Contig1 | 526644 | 527669 | + | GENE_00532 | Prodigal: 2.6 | CDS | — | — | — | — | P37947 | degA_1 | — | — | HTH-type transcriptional regulator DegA |
| Contig1 | 527893 | 528924 | + | GENE_00533 | Prodigal: 2.6 | CDS | 1.1.1.18 | — | — | — | O68965 | idhA | — | — | Inositol 2-dehydrogenase |
| Contig1 | 528970 | 529464 | – | GENE_00534 | Prodigal: 2.6 | CDS | — | — | PF05163.6 | — | — | — | — | — | DinB family protein |
| Contig1 | 529519 | 530127 | – | GENE_00535 | Prodigal: 2.6 | CDS | — | — | — | — | P11667 | argO | — | — | Arginine exporter protein ArgO |
| Contig1 | 530253 | 531695 | + | GENE_00536 | Prodigal: 2.6 | CDS | — | — | — | — | Q2G1P1 | norG_1 | — | — | HTH-type transcriptional regulator NorG |
| Contig1 | 531703 | 532329 | – | GENE_00537 | Prodigal: 2.6 | CDS | — | — | PF00805.16 | — | — | — | — | — | Pentapeptide repeats (8 copies) |
| Contig1 | 532528 | 532968 | – | GENE_00538 | Prodigal: 2.6 | CDS | — | — | PF00583.18 | — | — | — | — | — | Acetyltransferase (GNAT) family protein |
| Contig1 | 533051 | 534892 | – | GENE_00539 | Prodigal: 2.6 | CDS | — | — | — | — | O06745 | yitJ | — | — | Bifunctional homocysteine S-methyltransferase/5,10-methylenetetra-hydrofolate reductase |
| Contig1 | 535205 | 535696 | – | GENE_00540 | Prodigal: 2.6 | CDS | — | PRK05412 | — | — | — | — | — | — | putative nucleotide-binding protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 535844 | 536692 | + | GENE_00541 | Prodigal: 2.6 | CDS | — | — | — | — | Q7A5Q1 | — | — | Conserved virulence factor B | hypothetical protein |
| Contig1 | 536864 | 537841 | + | GENE_00542 | Prodigal: 2.6 | CDS | — | — | — | — | P29724 | tmpC_1 | — | — | Membrane lipoprotein TmpC precursor |
| Contig1 | 537838 | 539487 | + | GENE_00543 | Prodigal: 2.6 | CDS | — | — | — | — | P39214 | mcpA_1 | — | — | Methyl-accepting chemotaxis protein McpA |
| Contig1 | 539548 | 539670 | − | GENE_00544 | Prodigal: 2.6 | CDS | — | — | — | — | — | — | — | — | hypothetical protein |
| Contig1 | 539719 | 540570 | − | GENE_00545 | Prodigal: 2.6 | CDS | — | — | — | — | Q9X1H9 | — | — | — | Fatty acid-binding protein |
| Contig1 | 540695 | 541537 | + | GENE_00546 | Prodigal: 2.6 | CDS | — | — | — | — | — | — | — | — | hypothetical protein |
| Contig1 | 541552 | 542013 | + | GENE_00547 | Prodigal: 2.6 | CDS | — | — | — | — | P39804 | ipi | — | — | Intracellular proteinase inhibitor |
| Contig1 | 542051 | 542248 | − | GENE_00548 | Prodigal: 2.6 | CDS | — | — | — | — | — | — | — | — | hypothetical protein |
| Contig1 | 542248 | 542397 | − | GENE_00549 | Prodigal: 2.6 | CDS | — | — | — | — | — | — | — | — | hypothetical protein |
| Contig1 | 542483 | 543295 | − | GENE_00550 | Prodigal: 2.6 | CDS | 3.1.3.23 | — | — | — | P0A8Y5 | yidA_1 | — | — | Sugar phosphatase YidA |
| Contig1 | 543416 | 544183 | + | GENE_00551 | Prodigal: 2.6 | CDS | — | — | — | — | — | — | — | — | esterase |
| Contig1 | 544246 | 544554 | + | GENE_00552 | Prodigal: 2.6 | CDS | 2.5.1.- | — | — | — | O31817 | fosB | — | — | hypothetical protein Metallothiol transferase FosB |
| Contig1 | 544664 | 545086 | − | GENE_00553 | Prodigal: 2.6 | CDS | — | — | — | — | — | — | — | — | |
| Contig1 | 545428 | 546864 | + | GENE_00554 | Prodigal: 2.6 | CDS | 1.-.-.- | PRK10566 | — | — | P72056 | dprE1 | — | — | putative decaprenylphosphoryl-beta-D-ribose oxidase |
| Contig1 | 546861 | 547403 | + | GENE_00555 | Prodigal: 2.6 | CDS | — | — | — | MF_01528 | — | mdtG | — | — | Multidrug resistance protein MdtG |
| Contig1 | 547570 | 548607 | + | GENE_00556 | Prodigal: 2.6 | CDS | 1.2.1.38 | — | — | — | Q07906 | argC | — | — | N-acetyl-gamma-glutamyl-phosphate reductase |
| Contig1 | 548630 | 549847 | + | GENE_00557 | Prodigal: 2.6 | CDS | — | — | — | — | Q07908 | arg J | — | — | Arginine biosynthesis bifunctional protein ArgJ |
| Contig1 | 549862 | 550638 | + | GENE_00558 | Prodigal: 2.6 | CDS | 2.7.2.8 | — | — | — | Q9X2A4 | argB | — | — | Acetylglutamate kinase |
| Contig1 | 550635 | 551792 | + | GENE_00559 | Prodigal: 2.6 | CDS | 2.6.1.11 | — | — | — | O66442 | argD_1 | — | — | Acetylornithine aminotransferase |
| Contig1 | 551861 | 552919 | + | GENE_00560 | Prodigal: 2.6 | CDS | 6.3.5.5 | — | — | — | P54324 | carA_1 | — | — | Carbamoyl-phosphate synthase arginine-specific small chain |
| Contig1 | 552912 | 556007 | + | GENE_00561 | Prodigal: 2.6 | CDS | 6.3.5.5 | — | — | — | Q9ZB63 | carB_1 | — | — | Carbamoyl-phosphate synthase arginine-specific large chain |
| Contig1 | 555995 | 556966 | + | GENE_00562 | Prodigal: 2.6 | CDS | 2.1.3.3 | — | — | — | P18186 | argF | — | — | Ornithine carbamoyltransferase |
| Contig1 | 557042 | 557221 | + | GENE_00563 | Prodigal: 2.6 | CDS | — | — | — | — | — | — | — | — | hypothetical protein |
| Contig1 | 557258 | 557443 | − | GENE_00564 | Prodigal: 2.6 | CDS | — | — | — | — | — | — | — | — | hypothetical protein |
| Contig1 | 557704 | 558438 | + | GENE_00565 | Prodigal: 2.6 | CDS | — | — | — | — | — | — | — | — | hypothetical protein |
| Contig1 | 558521 | 559087 | + | GENE_00566 | Prodigal: 2.6 | CDS | — | — | — | — | — | — | — | — | hypothetical protein |
| Contig1 | 559270 | 560130 | + | GENE_00567 | Prodigal: 2.6 | CDS | — | — | — | — | Q2YKI6 | — | — | — | Purine-binding protein precursor |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 560143 | 560334 | + | GENE_00568 | Prodigal: 2.6 | CDS | — | — | PF10815.2 | — | — | — | — | — | ComZ |
| Contig1 | 560364 | 560582 | − | GENE_00569 | Prodigal: 2.6 | CDS | — | — | — | — | — | — | — | — | hypothetical protein |
| Contig1 | 560750 | 561688 | + | GENE_00570 | Prodigal: 2.6 | CDS | 2.3.1.180 | — | — | — | O34746 | fabHA | — | — | 3-oxoacyl-[acyl-carrier-protein] synthase 3 protein 1 |
| Contig1 | 561711 | 562949 | + | GENE_00571 | Prodigal: 2.6 | CDS | 2.3.1.179 | — | — | — | Q7A6F8 | fabF_2 | — | — | 3-oxoacyl-[acyl-carrier-protein] synthase 2 |
| Contig1 | 563033 | 563818 | + | GENE_00572 | Prodigal: 2.6 | CDS | — | — | — | — | — | — | — | — | hypothetical protein |
| Contig1 | 563992 | 564978 | + | GENE_00573 | Prodigal: 2.6 | CDS | — | — | — | — | P24136 | oppD_2 | — | — | Oligopeptide transport ATP-binding protein OppD |
| Contig1 | 564975 | 565964 | + | GENE_00574 | Prodigal: 2.6 | CDS | — | — | — | — | P24137 | oppF_3 | — | — | Oligopeptide transport ATP-binding protein OppF |
| Contig1 | 566042 | 567670 | + | GENE_00575 | Prodigal: 2.6 | CDS | — | — | — | — | P42061 | appA_2 | — | — | Oligopeptide-binding protein AppA precursor |
| Contig1 | 567737 | 568687 | + | GENE_00576 | Prodigal: 2.6 | CDS | — | — | — | — | P0AEF8 | dppB_2 | — | — | Dipeptide transport system permease protein DppB |
| Contig1 | 568709 | 569623 | + | GENE_00577 | Prodigal: 2.6 | CDS | — | — | — | — | P24139 | oppC_1 | — | — | Oligopeptide transport system permease protein OppC |
| Contig1 | 569771 | 570523 | + | GENE_00578 | Prodigal: 2.6 | CDS | — | — | — | — | — | — | — | — | hypothetical protein |
| Contig1 | 570557 | 571549 | − | GENE_00579 | Prodigal: 2.6 | CDS | 6.1.1.2 | — | — | — | P21656 | trpS | — | — | Tryptophan-tRNA ligase |
| Contig1 | 572293 | 573927 | + | GENE_00580 | Prodigal: 2.6 | CDS | — | — | — | — | P24141 | oppA | — | — | Oligopeptide-binding protein OppA precursor |
| Contig1 | 574034 | 574969 | + | GENE_00581 | Prodigal: 2.6 | CDS | — | — | — | — | P24138 | oppB | — | — | Oligopeptide transport system permease protein OppB |
| Contig1 | 574973 | 575890 | + | GENE_00582 | Prodigal: 2.6 | CDS | — | — | — | — | P24139 | oppC_2 | — | — | Oligopeptide transport system permease protein OppC |
| Contig1 | 575903 | 576979 | + | GENE_00583 | Prodigal: 2.6 | CDS | — | — | — | — | P24136 | oppD_3 | — | — | Oligopeptide transport ATP-binding protein OppD |
| Contig1 | 576972 | 577889 | + | GENE_00584 | Prodigal: 2.6 | CDS | — | — | — | — | P24137 | oppF_4 | — | — | Oligopeptide transport ATP-binding protein OppF |
| Contig1 | 577996 | 579183 | + | GENE_00585 | Prodigal: 2.6 | CDS | 2.3.1.- | — | — | — | — | — | — | — | hypothetical protein |
| Contig1 | 579301 | 579879 | + | GENE_00586 | Prodigal: 2.6 | CDS | — | — | — | — | O31601 | yjbC | — | — | Putative acetyltransferase YjbC |
| Contig1 | 580058 | 580453 | + | GENE_00587 | Prodigal: 2.6 | CDS | — | — | — | — | O31602 | spxA | — | — | Regulatory protein Spx |
| Contig1 | 580511 | 581167 | − | GENE_00588 | Prodigal: 2.6 | CDS | — | — | PF03741.10 | — | — | — | — | — | Integral membrane protein TerC family protein |
| Contig1 | 581350 | 582099 | + | GENE_00589 | Prodigal: 2.6 | CDS | — | — | — | — | P37958 | mecA | — | — | Adapter protein MecA 1 |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 582250 | 583410 | + | GENE_00590 | Prodigal: 2.6 | CDS | — | — | PF06054.5 | — | — | — | — | — | Competence protein CoiA-like family protein |
| Contig1 | 583407 | 585467 | + | GENE_00591 | Prodigal: 2.6 | CDS | 3.4.24.- | — | — | — | P54124 | pepF1_1 | — | — | Oligoendopeptidase F, plasmid |
| Contig1 | 585505 | 585672 | — | GENE_00592 | Prodigal: 2.6 | CDS | — | — | — | — | — | — | — | — | hypothetical protein |
| Contig1 | 585958 | 586860 | — | GENE_00593 | Prodigal: 2.6 | CDS | — | — | PF01323.14 | — | — | — | — | — | DSBA-like thioredoxin domain protein |
| Contig1 | 586857 | 587255 | — | GENE_00594 | Prodigal: 2.6 | CDS | — | — | — | — | O31607 | yjbI | — | — | Group 2 truncated hemoglobin YjbI |
| Contig1 | 587484 | 588158 | — | GENE_00595 | Prodigal: 2.6 | CDS | 4.2.2.- | — | — | — | P0AGC3 | slt | — | — | Soluble lytic murein transglycosylase precursor |
| Contig1 | 588163 | 588738 | + | GENE_00596 | Prodigal: 2.6 | CDS | — | — | PF01928.15 | — | — | — | — | — | CYTH domain protein |
| Contig1 | 588865 | 589230 | + | GENE_00597 | Prodigal: 2.6 | CDS | — | — | — | — | — | — | — | — | hypothetical protein |
| Contig1 | 589258 | 589893 | + | GENE_00598 | Prodigal: 2.6 | CDS | 27.6.5 | — | — | — | O31611 | yjbM | — | — | GTP pyrophosphokinase YjbM |
| Contig1 | 589911 | 590711 | + | GENE_00599 | Prodigal: 2.6 | CDS | 2.7.1.23 | — | — | — | P65777 | ppnK | — | — | putative inorganic polyphosphate/ATP-NAD kinase |
| Contig1 | 590726 | 591619 | + | GENE_00600 | Prodigal: 2.6 | CDS | 5.4.99.23 | — | — | — | P33643 | rluD_2 | — | — | Ribosomal large subunit pseudouridine synthase D |
| Contig1 | 591652 | 592401 | — | GENE_00601 | Prodigal: 2.6 | CDS | 3.6.1.17 | — | — | — | O31614 | prpE | — | — | Bis(5'-nucleosyl)-tetraphosphatase PrpE [asymmetrical] |
| Contig1 | 592629 | 594473 | + | GENE_00602 | Prodigal: 2.6 | CDS | — | — | — | — | P03819 | kefC | — | — | Glutathione-regulated potassium-efflux system protein KefC |
| Contig1 | 594720 | 595430 | + | GENE_00603 | Prodigal: 2.6 | CDS | 3.5.99.2 | — | — | — | P25052 | tenA | — | — | Thiaminase-2 |
| Contig1 | 595408 | 596025 | + | GENE_00604 | Prodigal: 2.6 | CDS | — | — | — | — | P25053 | tenI | — | — | Regulatory protein TenI |
| Contig1 | 596009 | 597118 | + | GENE_00605 | Prodigal: 2.6 | CDS | 1.4.3.19 | — | — | — | O31616 | thiO | — | — | Glycine oxidase |
| Contig1 | 597115 | 597318 | + | GENE_00606 | Prodigal: 2.6 | CDS | — | — | — | — | O31617 | thiS | — | — | Sulfur carrier protein ThiS |
| Contig1 | 597321 | 598085 | + | GENE_00607 | Prodigal: 2.6 | CDS | 2.8.1.10 | — | — | — | O31618 | thiG | — | — | Thiazole synthase |
| Contig1 | 598082 | 599092 | + | GENE_00608 | Prodigal: 2.6 | CDS | 2.7.7.73 | — | — | — | P30138 | thiF_1 | — | — | Sulfur carrier protein ThiS adenylyltransferase |
| Contig1 | 599115 | 599927 | + | GENE_00609 | Prodigal: 2.6 | CDS | 2.7.1.49 | — | — | — | O31620 | thiD_1 | — | — | Hydroxymethyl pyrimidine/phospho-methylpyrimidine kinase |
| Contig1 | 600058 | 600834 | + | GENE_00610 | Prodigal: 2.6 | CDS | 1.3.1.9 | — | — | — | P54616 | fabI | — | — | Enoyl-[acyl-carrier-protein] reductase [NADH] FabI |
| Contig1 | 600932 | 601540 | + | GENE_00611 | Prodigal: 2.6 | CDS | — | — | — | — | — | — | — | — | hypothetical protein |
| Contig1 | 601599 | 602042 | — | GENE_00612 | Prodigal: 2.6 | CDS | — | — | — | — | Q08312 | cotZ | — | — | Spore coat protein Z |
| Contig1 | 602190 | 602672 | — | GENE_00613 | Prodigal: 2.6 | CDS | — | — | — | — | Q08311 | cotY | — | — | Spore coat protein Y |
| Contig1 | 602823 | 603323 | — | GENE_00614 | Prodigal: 2.6 | CDS | — | — | — | — | Q08313 | cotX | — | — | Spore coat protein X |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 603416 | 603730 | - | GENE_00615 | Prodigal: 2.6 | CDS | — | — | — | — | Q08310 | cotW | — | — | Spore coat protein W |
| Contig1 | 603768 | 604154 | - | GENE_00616 | Prodigal: 2.6 | CDS | — | — | — | — | Q08309 | cotV | — | — | Spore coat protein V |
| Contig1 | 604325 | 604681 | + | GENE_00617 | Prodigal: 2.6 | CDS | — | — | — | — | O31623 | yjcA_1 | — | — | Sporulation protein YjcA |
| Contig1 | 604757 | 604876 | + | GENE_00618 | Prodigal: 2.6 | CDS | — | — | — | — | — | — | — | — | hypothetical protein |
| Contig1 | 604967 | 605164 | + | GENE_00619 | Prodigal: 2.6 | CDS | — | — | — | — | — | — | — | — | hypothetical protein |
| Contig1 | 605256 | 605414 | + | GENE_00620 | Prodigal: 2.6 | CDS | — | — | PF09680.4 | — | — | — | — | — | Protein of unknown function (Tiny_TM_bacill) |
| Contig1 | 605581 | 605835 | + | GENE_00621 | Prodigal: 2.6 | CDS | — | — | — | — | — | — | — | — | hypothetical protein |
| Contig1 | 605904 | 608189 | - | GENE_00622 | Prodigal: 2.6 | CDS | 3.6.4.12 | — | — | — | O31626 | yjcD | — | — | Putative ATP-dependent DNA helicase YjcD |
| Contig1 | 608310 | 608564 | + | GENE_00623 | Prodigal: 2.6 | CDS | — | — | — | — | — | — | — | — | hypothetical protein |
| Contig1 | 608633 | 609382 | + | GENE_00624 | Prodigal: 2.6 | CDS | 3.5.2.6 | — | — | — | — | — | — | — | Beta-lactamase 2 precursor |
| Contig1 | 609424 | 610146 | - | GENE_00625 | Prodigal: 2.6 | CDS | — | — | PF01061.18 | — | P04190 | blm | — | — | ABC-2 type transporter |
| Contig1 | 610139 | 610876 | - | GENE_00626 | Prodigal: 2.6 | CDS | 3.6.3.- | — | — | — | P32010 | drrA_2 | — | — | Daunorubicin/doxorubicin resistance ATP-binding protein DrrA |
| Contig1 | 610877 | 611110 | - | GENE_00627 | Prodigal: 2.6 | CDS | — | — | PF04014.12 | — | — | — | — | — | SpoVT/AbrB like domain protein |
| Contig1 | 611133 | 611228 | - | GENE_00628 | Prodigal: 2.6 | CDS | — | — | — | — | — | — | — | — | hypothetical protein |
| Contig1 | 611271 | 611702 | - | GENE_00629 | Prodigal: 2.6 | CDS | 2.3.1.- | — | — | — | — | — | — | — | putative N-acetyltransferase YjcF |
| Contig1 | 611707 | 612222 | - | GENE_00630 | Prodigal: 2.6 | CDS | — | — | PF02834.10 | — | O31628 | yjcF1 | — | — | 2',5' RNA ligase family |
| Contig1 | 612248 | 612784 | - | GENE_00631 | Prodigal: 2.6 | CDS | — | PRK10439 | — | — | — | — | — | — | enterobactin/ferric enterobactin esterase |
| Contig1 | 613339 | 614460 | + | GENE_00632 | Prodigal: 2.6 | CDS | 2.5.1.- | — | — | — | O31631 | metI | — | — | Cystathionine gamma-synthase/O-acetylhomoserine (thiol)-lyase |
| Contig1 | 614453 | 615628 | + | GENE_00633 | Prodigal: 2.6 | CDS | 4.4.1.8 | — | — | — | O31632 | metC | — | — | Cystathionine beta-lyase MetC |
| Contig1 | 615766 | 615840 | + | GENE_00634 | Aragorn: 1.2 | tRNA | — | — | — | — | — | — | — | — | tRNA-Val(gac) |
| Contig1 | 616129 | 616419 | - | GENE_00635 | Prodigal: 2.6 | CDS | — | — | — | — | — | — | — | — | hypothetical protein |
| Contig1 | 616436 | 617101 | - | GENE_00636 | Prodigal: 2.6 | CDS | — | — | — | — | — | — | — | — | hypothetical protein |
| Contig1 | 618368 | 618670 | - | GENE_00637 | Prodigal: 2.6 | CDS | — | — | — | — | — | — | — | — | hypothetical protein |
| Contig1 | 618677 | 620545 | - | GENE_00638 | Prodigal: 2.6 | CDS | 3.1.-.- | — | — | — | O31998 | yokI_2 | — | — | putative ribonuclease YokI |
| Contig1 | 621064 | 621426 | + | GENE_00639 | Prodigal: 2.6 | CDS | — | — | — | — | — | — | — | — | hypothetical protein |
| Contig1 | 621739 | 622653 | + | GENE_00640 | Prodigal: 2.6 | CDS | 3.5.2.6 | — | PF03992.10 | — | P39824 | penP | — | — | Beta-lactamase precursor |
| Contig1 | 622764 | 623045 | + | GENE_00641 | Prodigal: 2.6 | CDS | — | — | — | — | — | — | — | — | Antibiotic biosynthesis monooxygenase |
| Contig1 | 623145 | 624557 | - | GENE_00642 | Prodigal: 2.6 | CDS | — | — | — | — | P0AEJ0 | emrB_2 | — | — | Multidrug export protein EmrB |
| Contig1 | 624700 | 625173 | - | GENE_00643 | Prodigal: 2.6 | CDS | — | — | PF01047.16 | — | — | — | — | — | MarR family protein |

TABLE 5-continued

| # ContigID | Start | End | Strand | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|
| Contig1 | 625443 | 626555 | − | GENE_00644 Prodigal: 2.6 | CDS | 3.2.1.89 | — | — | — | Q65CX5 | ganB | — | — | Arabinogalactan endo-1,4-beta-galactosidase precursor |
| Contig1 | 626607 | 628106 | − | GENE_00645 Prodigal: 2.6 | CDS | 2.7.7.12 | — | — | — | E8MF11 | galT_1 | — | — | Galactose-1-phosphate uridylyltransferase |
| Contig1 | 628108 | 629100 | − | GENE_00646 Prodigal: 2.6 | CDS | 5.1.3.2 | — | — | — | Q7WTB1 | galE | — | — | UDP-glucose 4-epimerase |
| Contig1 | 629104 | 630273 | − | GENE_00647 Prodigal: 2.6 | CDS | 2.7.1.6 | — | — | — | Q9R7D7 | galK | — | — | Galactokinase |
| Contig1 | 630289 | 631986 | − | GENE_00648 Prodigal: 2.6 | CDS | — | — | — | — | Q99S77 | lacE | — | — | PTS system lactose-specific EIICB component |
| Contig1 | 631998 | 632312 | − | GENE_00649 Prodigal: 2.6 | CDS | 2.7.1.- | — | — | — | P23532 | lacF_1 | — | — | Lactose-specific phosphotransferase enzyme IIA component |
| Contig1 | 632375 | 633775 | − | GENE_00650 Prodigal: 2.6 | CDS | 3.2.1.85 | — | — | — | C7N8L9 | lacG | — | — | 6-phospho-beta-galactosidase |
| Contig1 | 634022 | 634789 | + | GENE_00651 Prodigal: 2.6 | CDS | — | — | — | — | P67744 | lacR_1 | — | — | Lactose phosphotransferase system repressor |
| Contig1 | 634807 | 635490 | + | GENE_00652 Prodigal: 2.6 | CDS | 3.1.3.- | — | — | — | P77475 | yqaB | — | — | Fructose-1-phosphate phosphatase YqaB |
| Contig1 | 635680 | 636027 | − | GENE_00653 Prodigal: 2.6 | CDS | — | PRK09272 | — | — | — | — | — | — | hypothetical protein |
| Contig1 | 636011 | 636436 | − | GENE_00654 Prodigal: 2.6 | CDS | — | — | PF01047.16 | — | — | — | — | — | MarR family protein |
| Contig1 | 636799 | 637434 | + | GENE_00655 Prodigal: 2.6 | CDS | — | PRK09977 | — | — | — | — | — | — | putative Mg(2+) transport ATPase |
| Contig1 | 637562 | 637795 | + | GENE_00656 Prodigal: 2.6 | CDS | — | — | — | — | — | — | — | — | hypothetical protein |
| Contig1 | 637775 | 637948 | − | GENE_00657 Prodigal: 2.6 | CDS | — | — | — | — | — | — | — | — | hypothetical protein |
| Contig1 | 637992 | 638393 | − | GENE_00658 Prodigal: 2.6 | CDS | — | — | — | — | — | — | — | — | hypothetical protein |
| Contig1 | 638493 | 639062 | − | GENE_00659 Prodigal: 2.6 | CDS | — | — | — | — | — | — | — | — | hypothetical protein |
| Contig1 | 639152 | 642142 | + | GENE_00660 Prodigal: 2.6 | CDS | 1.2.1.2 | — | — | — | Q99RW4 | — | — | — | Putative formate dehydrogenase |
| Contig1 | 642135 | 642677 | + | GENE_00661 Prodigal: 2.6 | CDS | — | — | — | — | — | — | — | — | hypothetical protein |
| Contig1 | 642885 | 644105 | + | GENE_00662 Prodigal: 2.6 | CDS | 1.14.14.- | — | — | — | P14762 | — | — | — | Cytochrome P450(BM-1) |
| Contig1 | 644102 | 645286 | + | GENE_00663 Prodigal: 2.6 | CDS | 2.4.1.- | — | — | — | Q35685 | oleD_2 | — | — | Oleandomycin glycosyltransferase |
| Contig1 | 645325 | 645510 | + | GENE_00664 Prodigal: 2.6 | CDS | — | — | — | — | — | — | — | — | hypothetical protein |
| Contig1 | 645686 | 646504 | + | GENE_00665 Prodigal: 2.6 | CDS | — | PRK05928 | — | — | — | — | — | — | uroporphyrinogen-III synthase |
| Contig1 | 646529 | 647290 | − | GENE_00666 Prodigal: 2.6 | CDS | — | — | — | — | — | — | — | — | hypothetical protein |
| Contig1 | 647292 | 648029 | − | GENE_00667 Prodigal: 2.6 | CDS | 3.6.3.27 | — | — | — | P0A2V9 | pstB3_1 | — | — | Phosphate import ATP-binding protein PstB 3 |
| Contig1 | 648055 | 649038 | + | GENE_00668 Prodigal: 2.6 | CDS | — | — | — | — | — | — | — | — | hypothetical protein |
| Contig1 | 649168 | 649665 | + | GENE_00669 Prodigal: 2.6 | CDS | — | — | PF07883.5 | — | — | — | — | — | Cupin domain protein |
| Contig1 | 650052 | 650468 | + | GENE_00670 Prodigal: 2.6 | CDS | — | — | — | — | — | — | — | — | hypothetical protein |
| Contig1 | 650508 | 651686 | + | GENE_00671 Prodigal: 2.6 | CDS | 1.6.99.- | — | — | — | P80861 | yjiD | — | — | NADH dehydrogenase-like protein YjlD |
| Contig1 | 651873 | 653270 | + | GENE_00672 Prodigal: 2.6 | CDS | 5.3.1.12 | — | — | — | O34808 | uxaC | — | — | Uronate isomerase |
| Contig1 | 653295 | 654686 | + | GENE_00673 Prodigal: 2.6 | CDS | — | — | — | — | O34961 | yjmB | — | — | putative symporter YjmB |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 654757 | 655755 | + | GENE_00674 | Prodigal: 2.6 | CDS | — | — | — | — | Q9JMQ1 | exuR | — | — | putative HTH-type transcriptional repressor ExuR |
| Contig1 | 655831 | 657264 | + | GENE_00675 | Prodigal: 2.6 | CDS | 1.1.1.58 | — | — | — | O34354 | uxaB | — | — | Altronate oxidoreductase |
| Contig1 | 657277 | 658770 | + | GENE_00676 | Prodigal: 2.6 | CDS | 4.2.1.7 | — | PF01925.13 | — | O34673 | uxaA | — | — | Altronate dehydratase |
| Contig1 | 658804 | 659568 | − | GENE_00677 | Prodigal: 2.6 | CDS | — | — | — | — | — | — | — | — | Sulfite exporter TauE/SafE |
| Contig1 | 659717 | 660184 | − | GENE_00678 | Prodigal: 2.6 | CDS | 3.1.-.- | — | PF05163.6 | — | — | — | — | — | DinB family protein |
| Contig1 | 660394 | 661524 | + | GENE_00679 | Prodigal: 2.6 | CDS | — | — | — | — | Q00828 | rapA_1 | — | — | Response regulator aspartate phosphatase A |
| Contig1 | 661514 | 661648 | + | GENE_00680 | Prodigal: 2.6 | CDS | — | — | — | — | — | — | — | — | hypothetical protein |
| Contig1 | 661790 | 662743 | + | GENE_00681 | Prodigal: 2.6 | CDS | 3.5.1.28 | — | — | — | P24808 | cwlA | — | — | N-acetylmuramoyl-L-alanine amidase CwlA precursor |
| Contig1 | 662782 | 663159 | − | GENE_00682 | Prodigal: 2.6 | CDS | — | — | — | — | — | — | — | — | hypothetical protein |
| Contig1 | 663268 | 663873 | + | GENE_00683 | Prodigal: 2.6 | CDS | — | — | — | — | — | — | — | — | hypothetical protein |
| Contig1 | 663863 | 664012 | − | GENE_00684 | Prodigal: 2.6 | CDS | — | — | — | — | — | — | — | — | hypothetical protein |
| Contig1 | 664028 | 664618 | − | GENE_00685 | Prodigal: 2.6 | CDS | — | — | — | — | — | — | — | — | hypothetical protein |
| Contig1 | 664767 | 665105 | − | GENE_00686 | Prodigal: 2.6 | CDS | — | — | — | — | P23789 | xre_1 | — | — | HTH-type transcriptional regulator Xre |
| Contig1 | 665297 | 665476 | + | GENE_00687 | Prodigal: 2.6 | CDS | — | — | — | — | — | — | — | — | hypothetical protein |
| Contig1 | 666193 | 666993 | + | GENE_00688 | Prodigal: 2.6 | CDS | — | — | — | MF_00377 | — | dnaA_1 | — | — | Chromosomal replication initiator protein DnaA |
| Contig1 | 666993 | 667160 | + | GENE_00689 | Prodigal: 2.6 | CDS | — | — | — | — | — | — | — | — | hypothetical protein |
| Contig1 | 667258 | 667599 | + | GENE_00690 | Prodigal: 2.6 | CDS | — | — | — | — | — | — | — | — | hypothetical protein |
| Contig1 | 667589 | 667792 | + | GENE_00691 | Prodigal: 2.6 | CDS | — | — | — | — | — | — | — | — | hypothetical protein |
| Contig1 | 667906 | 668418 | + | GENE_00692 | Prodigal: 2.6 | CDS | — | PRK06930 | — | — | — | — | — | — | positive control sigma-like factor |
| Contig1 | 668531 | 669328 | + | GENE_00693 | Prodigal: 2.6 | CDS | — | — | PF03592.10 | — | — | — | — | — | Terminase small subunit |
| Contig1 | 669325 | 670623 | + | GENE_00694 | Prodigal: 2.6 | CDS | — | — | PF04466.7 | — | — | — | — | — | Phage terminase large subunit |
| Contig1 | 670627 | 672051 | + | GENE_00695 | Prodigal: 2.6 | CDS | — | — | PF04860.6 | — | — | — | — | — | Phage portal protein |
| Contig1 | 672083 | 672928 | + | GENE_00696 | Prodigal: 2.6 | CDS | — | — | — | — | — | — | — | — | hypothetical protein |
| Contig1 | 672955 | 673890 | + | GENE_00697 | Prodigal: 2.6 | CDS | — | — | — | — | — | — | — | — | Phage-like element PBSX protein XkdG |
| Contig1 | 673907 | 674290 | + | GENE_00698 | Prodigal: 2.6 | CDS | — | — | — | — | — | — | — | — | XkdG protein |
| Contig1 | 674287 | 674643 | + | GENE_00699 | Prodigal: 2.6 | CDS | — | — | — | — | — | — | — | — | hypothetical protein |
| Contig1 | 674640 | 675143 | + | GENE_00700 | Prodigal: 2.6 | CDS | — | — | — | — | P54327 | xkdG | — | — | Phage-like element PBSX protein XkdH |
| Contig1 | 675140 | 675586 | + | GENE_00701 | Prodigal: 2.6 | CDS | — | — | — | — | P54328 | xkdH | — | — | hypothetical protein |
| Contig1 | 675583 | 675792 | + | GENE_00702 | Prodigal: 2.6 | CDS | — | — | — | — | — | — | — | — | hypothetical protein |
| Contig1 | 675792 | 677189 | + | GENE_00703 | Prodigal: 2.6 | CDS | — | — | PF04984.8 | — | — | — | — | — | Phage tail sheath protein |
| Contig1 | 677191 | 677634 | + | GENE_00704 | Prodigal: 2.6 | CDS | — | — | — | — | — | — | — | — | Phage-like element PBSX protein XkdM |
| Contig1 | 677710 | 678156 | + | GENE_00705 | Prodigal: 2.6 | CDS | — | — | PF08890.5 | — | P54332 | xkdM | — | — | Phage XkdN-like protein |
| Contig1 | 678180 | 678350 | + | GENE_00706 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 678338 | 683377 | + | GENE_00707 | Prodigal: 2.6 | CDS | — | — | PF01464.14 | — | — | — | — | — | Transglycosylase SLT domain protein |
| Contig1 | 683370 | 684029 | + | GENE_00708 | Prodigal: 2.6 | CDS | — | PRK11198 | — | — | — | — | — | — | LysM domain/BON superfamily protein |
| Contig1 | 684043 | 685020 | + | GENE_00709 | Prodigal: 2.6 | CDS | — | — | PF05954.5 | — | — | — | — | — | Phage late control gene D protein (GPD) |
| Contig1 | 685020 | 685286 | + | GENE_00710 | Prodigal: 2.6 | CDS | — | — | — | — | — | — | — | — | hypothetical protein |
| Contig1 | 685390 | 685815 | + | GENE_00711 | Prodigal: 2.6 | CDS | — | — | — | — | — | — | — | — | hypothetical protein |
| Contig1 | 685808 | 686854 | + | GENE_00712 | Prodigal: 2.6 | CDS | — | — | PF04865.8 | — | — | — | — | — | Baseplate J-like protein |
| Contig1 | 686838 | 687416 | + | GENE_00713 | Prodigal: 2.6 | CDS | — | — | — | — | — | — | — | — | hypothetical protein |
| Contig1 | 687413 | 687685 | + | GENE_00714 | Prodigal: 2.6 | CDS | — | — | — | — | — | — | — | — | hypothetical protein |
| Contig1 | 687688 | 689277 | + | GENE_00715 | Prodigal: 2.6 | CDS | — | — | — | — | — | — | — | — | hypothetical protein |
| Contig1 | 689290 | 689715 | + | GENE_00716 | Prodigal: 2.6 | CDS | — | — | PF09636.4 | — | — | — | — | — | XkdW protein |
| Contig1 | 689720 | 689917 | + | GENE_00717 | Prodigal: 2.6 | CDS | — | — | — | — | — | — | — | — | hypothetical protein |
| Contig1 | 689974 | 690735 | + | GENE_00718 | Prodigal: 2.6 | CDS | — | — | — | — | — | — | — | — | hypothetical protein |
| Contig1 | 690787 | 691050 | + | GENE_00719 | Prodigal: 2.6 | CDS | — | — | PF10779.3 | — | — | — | — | — | Haemolysin XhlA |
| Contig1 | 691064 | 691327 | + | GENE_00720 | Prodigal: 2.6 | CDS | — | — | PF04688.7 | — | — | — | — | — | Phage lysis protein, holin |
| Contig1 | 691341 | 692219 | + | GENE_00721 | Prodigal: 2.6 | CDS | 3.5.1.28 | — | — | — | P39800 | xlyA | — | — | N-acetylmuramoyl-L-alanine amidase XlyA precursor |
| Contig1 | 692476 | 692646 | − | GENE_00722 | Prodigal: 2.6 | CDS | — | — | — | — | O34800 | spoIISB | — | — | Stage II sporulation protein SB |
| Contig1 | 692647 | 693393 | − | GENE_00723 | Prodigal: 2.6 | CDS | — | — | — | — | O34853 | spoIISA | — | — | Stage II sporulation protein SA |
| Contig1 | 693498 | 694496 | − | GENE_00724 | Prodigal: 2.6 | CDS | — | — | — | — | P0AFJ7 | pitA | — | — | Low-affinity inorganic phosphate transporter 1 |
| Contig1 | 694509 | 695126 | − | GENE_00725 | Prodigal: 2.6 | CDS | — | — | — | — | O30498 | — | — | — | Putative pit accessory protein |
| Contig1 | 695412 | 696728 | − | GENE_00726 | Prodigal: 2.6 | CDS | — | — | — | — | O34739 | steT | — | — | Serine/threonine exchanger SteT |
| Contig1 | 697052 | 698002 | + | GENE_00727 | Prodigal: 2.6 | CDS | 1.13.11.- | — | — | — | O34689 | mhqA | — | — | Putative ring-cleaving dioxygenase MhqA |
| Contig1 | 698186 | 700324 | + | GENE_00728 | Prodigal: 2.6 | CDS | 2.4.2.43 | — | — | MF_01165 | — | arnT | — | — | Undecaprenyl phosphate-alpha-4-amino-4-deoxy-L-arabinose arabinosyl transferase |
| Contig1 | 700336 | 701307 | + | GENE_00729 | Prodigal: 2.6 | CDS | — | — | — | — | P77293 | — | — | Bactoprenol glucosyl transferase homolog from prophage CPS-53 | hypothetical protein |
| Contig1 | 701394 | 701570 | − | GENE_00730 | Prodigal: 2.6 | CDS | — | — | — | — | — | — | — | — | hypothetical protein |
| Contig1 | 701671 | 703023 | − | GENE_00731 | Prodigal: 2.6 | CDS | 3.4.21.10 | — | — | — | O34358 | htrA_1 | — | — | Serine protease Do-like HtrA |
| Contig1 | 703308 | 704867 | + | GENE_00732 | Prodigal: 2.6 | CDS | — | — | — | — | P31474 | hsrA_1 | — | — | putative transport protein HsrA |
| Contig1 | 705023 | 705847 | + | GENE_00733 | Prodigal: 2.6 | CDS | 3.4.11.- | — | — | — | P26902 | dppA | — | — | D-aminopeptidase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 705862 | 706788 | + | GENE_00734 | Prodigal: 2.6 | CDS | — | — | — | — | P26903 | dppB_3 | — | — | Dipeptide transport system permease protein DppB |
| Contig1 | 706794 | 707741 | + | GENE_00735 | Prodigal: 2.6 | CDS | — | — | — | — | P26904 | dppC | — | — | Dipeptide transport system permease protein DppC |
| Contig1 | 707747 | 708775 | + | GENE_00736 | Prodigal: 2.6 | CDS | — | — | — | — | P24136 | oppD_4 | — | — | Oligopeptide transport ATP-binding protein OppD |
| Contig1 | 708772 | 710391 | + | GENE_00737 | Prodigal: 2.6 | CDS | — | — | — | — | P26906 | dppE | — | — | Dipeptide-binding protein DppE precursor |
| Contig1 | 710479 | 711414 | + | GENE_00738 | Prodigal: 2.6 | CDS | 3.4.16.- | — | — | — | O34851 | ykfA_1 | — | — | putative murein peptide carboxypeptidase |
| Contig1 | 711421 | 712518 | + | GENE_00739 | Prodigal: 2.6 | CDS | 5.1.1.- | — | — | — | O34508 | ykfB | — | — | L-Ala-D/L-Glu epimerase |
| Contig1 | 712515 | 713414 | + | GENE_00740 | Prodigal: 2.6 | CDS | 3.4.-.- | — | — | — | O35010 | ykfC | — | — | Gamma-D-glutamyl-L-lysine endopeptidase |
| Contig1 | 713418 | 714389 | + | GENE_00741 | Prodigal: 2.6 | CDS | — | — | — | — | P24137 | oppF_5 | — | — | Oligopeptide transport ATP-binding protein OppF |
| Contig1 | 714416 | 715465 | − | GENE_00742 | Prodigal: 2.6 | CDS | 3.1.1.31 | — | — | — | O34499 | pgl | — | — | 6-phosphogluconolactonase |
| Contig1 | 715536 | 716396 | − | GENE_00743 | Prodigal: 2.6 | CDS | 3.5.3.18 | — | — | — | Q9I4E3 | — | — | — | N(G),N(G)-dimethylarginine dimethylaminohydrolase |
| Contig1 | 716585 | 717103 | + | GENE_00744 | Prodigal: 2.6 | CDS | 3.1.2.- | — | — | — | P44886 | — | — | — | putative acyl-CoA thioester hydrolase |
| Contig1 | 717203 | 717748 | + | GENE_00745 | Prodigal: 2.6 | CDS | — | PRK09585 | — | — | — | — | — | — | anhydro-N-acetyl-muramic acid kinase |
| Contig1 | 717936 | 718274 | + | GENE_00746 | Prodigal: 2.6 | CDS | — | — | — | — | P49856 | ykkC | — | — | Multidrug resistance protein YkkC |
| Contig1 | 718274 | 718588 | + | GENE_00747 | Prodigal: 2.6 | CDS | — | — | — | — | P49857 | ykkD | — | — | Multidrug resistance protein YkkD |
| Contig1 | 718662 | 719564 | + | GENE_00748 | Prodigal: 2.6 | CDS | 3.5.1.10 | — | — | — | P37051 | purU | — | — | Formyltetrahydrofolate deformylase |
| Contig1 | 719934 | 721046 | + | GENE_00749 | Prodigal: 2.6 | CDS | 2.7.2.11 | — | — | — | P39820 | proB_1 | — | — | Glutamate 5-kinase 1 |
| Contig1 | 721043 | 722290 | + | GENE_00750 | Prodigal: 2.6 | CDS | 1.2.1.41 | — | — | — | Q9WYC9 | proA | — | — | Gamma-glutamyl phosphate reductase |
| Contig1 | 722404 | 722829 | + | GENE_00751 | Prodigal: 2.6 | CDS | — | — | — | — | O34762 | ohrA | — | — | Organic hydroperoxide resistance protein OhrA |
| Contig1 | 722857 | 723381 | − | GENE_00752 | Prodigal: 2.6 | CDS | — | — | — | — | O34777 | ohrR_2 | — | — | Organic hydroperoxide resistance transcriptional regulator |
| Contig1 | 723441 | 723851 | + | GENE_00753 | Prodigal: 2.6 | CDS | — | — | — | — | P80242 | ohrB_1 | — | — | Organic hydroperoxide resistance protein OhrB |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 723992 | 724576 | + | GENE_00754 | Prodigal: 2.6 | CDS | — | — | — | — | P27951 | bag | — | — | IgA FC receptor precursor |
| Contig1 | 724596 | 725060 | + | GENE_00755 | Prodigal: 2.6 | CDS | — | — | — | — | — | — | — | — | hypothetical protein |
| Contig1 | 725065 | 726192 | + | GENE_00756 | Prodigal: 2.6 | CDS | 2.4.1.- | — | — | — | O31986 | sunS_2 | — | — | SPBc2 prophage-derived glycosyltransferase SunS |
| Contig1 | 726214 | 727329 | − | GENE_00757 | Prodigal: 2.6 | CDS | — | — | PF01391.12 | — | — | — | — | — | Collagen triple helix repeat (20 copies) |
| Contig1 | 727570 | 728169 | − | GENE_00758 | Prodigal: 2.6 | CDS | — | — | — | — | Q47142 | hcaT_1 | — | — | putative 3-phenylpropionic acid transporter |
| Contig1 | 728147 | 728767 | − | GENE_00759 | Prodigal: 2.6 | CDS | — | — | — | — | Q47142 | hcaT_2 | — | — | putative 3-phenylpropionic acid transporter |
| Contig1 | 728819 | 729520 | + | GENE_00760 | Prodigal: 2.6 | CDS | — | — | — | — | P0A9E9 | yeiL | — | — | Regulatory protein YeiL |
| Contig1 | 729567 | 731855 | − | GENE_00761 | Prodigal: 2.6 | CDS | 2.1.1.14 | — | — | — | P80877 | metE_1 | — | — | 5-methyltetra-hydropteroyl-triglutamate-homocysteine methyltransferase |
| Contig1 | 732233 | 733192 | − | GENE_00762 | Prodigal: 2.6 | CDS | 3.4.21.- | — | — | — | P11018 | isp | — | — | Major intracellular serine protease precursor |
| Contig1 | 733412 | 734245 | + | GENE_00763 | Prodigal: 2.6 | CDS | — | — | — | — | O34860 | rsbRB | — | — | RsbT co-antagonist protein RsbRB |
| Contig1 | 734291 | 735052 | − | GENE_00764 | Prodigal: 2.6 | CDS | — | — | — | — | O34572 | ykoC | — | — | Putative HMP/thiamine permease protein YkoC |
| Contig1 | 735027 | 736664 | − | GENE_00765 | Prodigal: 2.6 | CDS | 3.6.3.- | — | — | — | O34362 | ykoD | — | — | Putative HMP/thiamine import ATP-binding protein YkoD |
| Contig1 | 736651 | 737250 | − | GENE_00766 | Prodigal: 2.6 | CDS | — | — | — | — | O34738 | ykoE | — | — | Putative HMP/thiamine permease protein YkoE |
| Contig1 | 737695 | 738957 | + | GENE_00767 | Prodigal: 2.6 | CDS | 3.2.-.- | — | — | — | O05495 | ydhD | — | — | Putative sporulation-specific glycosylase YdhD |
| Contig1 | 739048 | 739185 | + | GENE_00768 | Prodigal: 2.6 | CDS | — | — | PF11132.2 | — | — | — | — | — | Transcriptional regulator protein (SplA) |
| Contig1 | 739692 | 741047 | + | GENE_00769 | Prodigal: 2.6 | CDS | — | — | — | — | Q830V1 | mgtE | — | — | Magnesium transporter MgtE |
| Contig1 | 741083 | 741415 | − | GENE_00770 | Prodigal: 2.6 | CDS | — | — | — | — | Q45666 | tnrA | — | — | HTH-type transcriptional regulator TnrA |
| Contig1 | 741610 | 741765 | + | GENE_00771 | Prodigal: 2.6 | CDS | — | — | — | — | — | — | — | — | hypothetical protein |
| Contig1 | 741854 | 742036 | + | GENE_00772 | Prodigal: 2.6 | CDS | — | — | — | — | O34763 | ykoL | — | — | Stress response protein YkoL |
| Contig1 | 742179 | 742643 | + | GENE_00773 | Prodigal: 2.6 | CDS | — | — | — | — | O31672 | mhqR_1 | — | — | HTH-type transcriptional regulator MhqR |
| Contig1 | 742822 | 743376 | + | GENE_00774 | Prodigal: 2.6 | CDS | — | — | — | — | — | — | — | — | hypothetical protein |
| Contig1 | 743386 | 745221 | − | GENE_00775 | Prodigal: 2.6 | CDS | 6.5.1.1 | — | — | — | O34398 | ykoU | — | — | putative ATP-dependent DNA ligase YkoU |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 745224 | 746105 | − | GENE_00776 | Prodigal: 2.6 | CDS | — | — | — | — | O34859 | ykoV | — | — | putative DNA repair protein YkoV |
| Contig1 | 746771 | 747340 | + | GENE_00777 | Prodigal: 2.6 | CDS | — | PRK10847 | — | — | — | — | — | — | hypothetical protein |
| Contig1 | 747587 | 748369 | + | GENE_00778 | Prodigal: 2.6 | CDS | — | — | PF03741.10 | — | — | — | — | — | Integral membrane protein TerC family protein |
| Contig1 | 748646 | 749401 | + | GENE_00779 | Prodigal: 2.6 | CDS | — | — | — | — | O31654 | sigI | — | — | RNA polymerase sigma factor SigI |
| Contig1 | 749398 | 750576 | + | GENE_00780 | Prodigal: 2.6 | CDS | — | — | — | — | O31655 | rsgI | — | — | Anti-sigma-I factor RsgI |
| Contig1 | 750583 | 750777 | − | GENE_00781 | Prodigal: 2.6 | CDS | — | — | — | — | P04833 | sspD | — | — | Small, acid-soluble spore protein D |
| Contig1 | 750913 | 751614 | − | GENE_00782 | Prodigal: 2.6 | CDS | 3.4.24.- | — | — | — | — | — | — | — | hypothetical protein |
| Contig1 | 751763 | 752656 | + | GENE_00783 | Prodigal: 2.6 | CDS | — | — | — | — | P23894 | htpX2 | — | — | Protease HtpX |
| Contig1 | 752816 | 754168 | + | GENE_00784 | Prodigal: 2.6 | CDS | — | — | — | — | O32081 | ktrB | — | — | Ktr system potassium uptake protein B |
| Contig1 | 754264 | 754938 | − | GENE_00785 | Prodigal: 2.6 | CDS | — | — | — | — | — | — | — | — | hypothetical protein |
| Contig1 | 754940 | 755110 | + | GENE_00786 | Prodigal: 2.6 | CDS | — | — | — | — | — | — | — | — | hypothetical protein |
| Contig1 | 755150 | 756172 | + | GENE_00787 | Prodigal: 2.6 | CDS | — | — | — | — | — | — | — | — | Acyltransferase family protein |
| Contig1 | 756428 | 758647 | + | GENE_00788 | Prodigal: 2.6 | CDS | 2.7.13.3 | — | — | — | O31661 | kinE | — | — | Sporulation kinase E |
| Contig1 | 758644 | 759141 | + | GENE_00789 | Prodigal: 2.6 | CDS | 2.1.1.63 | — | PF01757.16 | — | P11742 | ogt_1 | — | — | Methylated-DNA--protein-cysteine methyltransferase, constitutive |
| Contig1 | 759232 | 759351 | + | GENE_00790 | Prodigal: 2.6 | CDS | — | — | — | — | — | — | — | — | hypothetical protein |
| Contig1 | 759383 | 760444 | − | GENE_00791 | Prodigal: 2.6 | CDS | 5.3.1.23 | — | — | — | O31662 | mtnA | — | — | Methylthioribose-1-phosphate isomerase |
| Contig1 | 760451 | 761635 | − | GENE_00792 | Prodigal: 2.6 | CDS | 2.7.1.100 | — | — | — | O31663 | mtnK | — | — | Methylthioribose kinase |
| Contig1 | 761993 | 762772 | − | GENE_00793 | Prodigal: 2.6 | CDS | 3.5.1.111 | — | — | — | Q93NG1 | — | — | — | 2-oxoglutaramate amidase |
| Contig1 | 762865 | 764037 | + | GENE_00794 | Prodigal: 2.6 | CDS | 2.6.1.83 | — | — | — | A0LEA5 | dapL_1 | — | — | LL-diaminopimelate aminotransferase |
| Contig1 | 764279 | 765493 | + | GENE_00795 | Prodigal: 2.6 | CDS | 5.3.2.5 | — | — | — | O31666 | mtnW | — | — | 2,3-diketo-5-methylthiopentyl-1-phosphate enolase |
| Contig1 | 765490 | 766194 | + | GENE_00796 | Prodigal: 2.6 | CDS | 3.1.3.87 | — | — | — | O31667 | mtnX | — | — | 2-hydroxy-3-keto-5-methylthiopentenyl-1-phosphate phosphatase |
| Contig1 | 766152 | 766781 | + | GENE_00797 | Prodigal: 2.6 | CDS | 4.2.1.109 | — | — | — | O31668 | mtnB | — | — | Methylthioribulose-1-phosphate dehydratase |
| Contig1 | 766797 | 767333 | + | GENE_00798 | Prodigal: 2.6 | CDS | 1.13.11.54 | — | — | — | Q9ZFE7 | mtnD | — | — | Acireductone dioxygenase |
| Contig1 | 767614 | 767874 | + | GENE_00799 | Prodigal: 2.6 | CDS | 3.1.3.- | — | — | — | P05043 | spo0E | — | — | Aspartyl-phosphate phosphatase Spo0E |
| Contig1 | 768085 | 769446 | − | GENE_00800 | Prodigal: 2.6 | CDS | 2.7.13.3 | — | — | — | O31671 | kinD | — | — | Sporulation kinase D |
| Contig1 | 769800 | 770246 | + | GENE_00801 | Prodigal: 2.6 | CDS | — | — | — | — | O31672 | mhqR_2 | — | — | HTH-type transcriptional regulator MhqR |
| Contig1 | 770282 | 771073 | − | GENE_00802 | Prodigal: 2.6 | CDS | — | — | — | — | P56427 | motB_1 | — | — | Motility protein B |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 771045 | 771869 | − | GENE_00803 | Prodigal: 2.6 | CDS | — | — | — | — | O06873 | pomA_1 | — | — | Chemotaxis protein PomA |
| Contig1 | 772029 | 774125 | − | GENE_00804 | Prodigal: 2.6 | CDS | — | — | — | — | O31673 | clpE | — | — | ATP-dependent Clp protease ATP-binding subunit ClpE |
| Contig1 | 774527 | 775564 | + | GENE_00805 | Prodigal: 2.6 | CDS | — | — | — | — | — | — | — | — | hypothetical protein |
| Contig1 | 775662 | 776783 | + | GENE_00806 | Prodigal: 2.6 | CDS | — | — | — | — | — | — | — | — | hypothetical protein |
| Contig1 | 777033 | 777692 | + | GENE_00807 | Prodigal: 2.6 | CDS | 6.3.4.20 | — | — | — | O31675 | queC | — | — | 7-cyano-7-deazaguanine synthase |
| Contig1 | 777693 | 778133 | + | GENE_00808 | Prodigal: 2.6 | CDS | 4.1.2.50 | — | — | — | O31676 | queD | — | — | 6-carboxy-5,6,7,8-tetrahydropterin synthase |
| Contig1 | 778126 | 778857 | + | GENE_00809 | Prodigal: 2.6 | CDS | 4.3.99.3 | — | — | — | O31677 | queE_2 | — | — | 7-carboxy-7-deazaguanine synthase |
| Contig1 | 778875 | 779369 | + | GENE_00810 | Prodigal: 2.6 | CDS | 1.7.1.13 | — | — | — | O31678 | queF | — | — | NADPH-dependent 7-cyano-7-deazaguanine reductase |
| Contig1 | 780085 | 780564 | + | GENE_00811 | Prodigal: 2.6 | CDS | — | — | PF00583.18 | — | — | — | — | — | Acetyltransferase (GNAT) family protein |
| Contig1 | 781116 | 781391 | + | GENE_00812 | Prodigal: 2.6 | CDS | — | — | — | — | — | — | — | — | hypothetical protein |
| Contig1 | 781464 | 781649 | − | GENE_00813 | Prodigal: 2.6 | CDS | — | — | — | — | — | — | — | — | hypothetical protein |
| Contig1 | 781813 | 782007 | + | GENE_00814 | Prodigal: 2.6 | CDS | — | — | — | — | — | — | — | — | hypothetical protein |
| Contig1 | 782281 | 782904 | + | GENE_00815 | Prodigal: 2.6 | CDS | — | — | — | — | P0A3V0 | sleB_1 | — | — | Spore cortex-lytic enzyme precursor |
| Contig1 | 783020 | 784360 | + | GENE_00816 | Prodigal: 2.6 | CDS | — | — | — | — | O31686 | ykvU | — | — | Sporulation protein YkvU |
| Contig1 | 784423 | 784917 | + | GENE_00817 | Prodigal: 2.6 | CDS | — | — | — | — | O31687 | stoA | — | — | Sporulation thiol-disulfide oxidoreductase A precursor |
| Contig1 | 785161 | 787074 | + | GENE_00818 | Prodigal: 2.6 | CDS | 3.6.3.- | — | — | — | O31688 | zosA | — | — | Zinc-transporting ATPase |
| Contig1 | 787187 | 788281 | + | GENE_00819 | Prodigal: 2.6 | CDS | 3.4.-.- | — | — | — | Q7A552 | — | — | — | putative peptidase |
| Contig1 | 788339 | 788464 | − | GENE_00820 | Prodigal: 2.6 | CDS | — | — | — | — | — | — | — | — | hypothetical protein |
| Contig1 | 788564 | 789529 | + | GENE_00821 | Prodigal: 2.6 | CDS | — | — | — | — | P37517 | ccpB_1 | — | — | Catabolite control protein B |
| Contig1 | 789601 | 790446 | + | GENE_00822 | Prodigal: 2.6 | CDS | — | — | — | — | O31691 | glcT | — | — | PtsGHI operon antiterminator |
| Contig1 | 790677 | 792773 | + | GENE_00823 | Prodigal: 2.6 | CDS | — | — | — | — | P20166 | ptsG_2 | — | — | PTS system glucose-specific EIICBA component |
| Contig1 | 792870 | 793136 | + | GENE_00824 | Prodigal: 2.6 | CDS | 2.7.11.- | — | — | — | P08877 | ptsH | — | — | Phosphocarrier protein HPr |
| Contig1 | 793136 | 794851 | + | GENE_00825 | Prodigal: 2.6 | CDS | 27.3.9 | — | — | — | P08838 | ptsI | — | — | Phosphoenolpyruvate-protein phosphotransferase |
| Contig1 | 794939 | 795178 | + | GENE_00826 | Prodigal: 2.6 | CDS | — | — | PF11132.2 | — | — | — | — | — | Transcriptional regulator protein (SplA) |
| Contig1 | 795265 | 796293 | + | GENE_00827 | Prodigal: 2.6 | CDS | 4.1.99.14 | — | — | — | P37956 | splB | — | — | Spore photoproduct lyase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 796421 | 798388 | + | GENE_00828 | Prodigal: 2.6 | CDS | — | — | — | — | P54576 | mcpC | — | — | Methyl-accepting chemotaxis protein McpC |
| Contig1 | 798469 | 799335 | + | GENE_00829 | Prodigal: 2.6 | CDS | 1.1.1.60 | — | — | — | P0ABQ2 | garR_2 | — | — | 2-hydroxy-3-oxopropionate reductase |
| Contig1 | 799373 | 800149 | − | GENE_00830 | Prodigal: 2.6 | CDS | — | — | PF00188.20 | — | — | — | — | — | Cysteine-rich secretory protein family protein |
| Contig1 | 800486 | 802618 | + | GENE_00831 | Prodigal: 2.6 | CDS | — | — | — | — | Q796K8 | pbpH_1 | — | — | Penicillin-binding protein H |
| Contig1 | 802796 | 804616 | + | GENE_00832 | Prodigal: 2.6 | CDS | 2.7.13.3 | — | — | — | P16497 | kinA_1 | — | — | Sporulation kinase A |
| Contig1 | 804642 | 805811 | − | GENE_00833 | Prodigal: 2.6 | CDS | 2.6.1.- | — | — | — | P16524 | patA_1 | — | — | Putative N-acetyl-LL-diaminopimelate aminotransferase |
| Contig1 | 806012 | 806173 | − | GENE_00834 | Prodigal: 2.6 | CDS | — | — | — | — | — | — | — | — | hypothetical protein |
| Contig1 | 806362 | 807273 | + | GENE_00835 | Prodigal: 2.6 | CDS | — | — | — | — | P37599 | cheV | — | — | Chemotaxis protein CheV |
| Contig1 | 807316 | 807780 | − | GENE_00836 | Prodigal: 2.6 | CDS | — | — | — | — | — | — | — | — | hypothetical protein |
| Contig1 | 807903 | 809195 | − | GENE_00837 | Prodigal: 2.6 | CDS | — | PRK08633 | — | — | — | — | — | — | 2-acyl-glycerophosphoethanolamine acyltransferase |
| Contig1 | 809271 | 809771 | − | GENE_00838 | Prodigal: 2.6 | CDS | 2.-.-.- | — | — | — | O34816 | ykuD_1 | — | — | Putative L,D-transpeptidase YkuD |
| Contig1 | 809840 | 810703 | − | GENE_00839 | Prodigal: 2.6 | CDS | 3.1.-.- | — | — | — | Q9PP77 | — | — | — | putative metallophosphoesterase |
| Contig1 | 810844 | 811608 | + | GENE_00840 | Prodigal: 2.6 | CDS | 1.3.1.34 | — | — | — | O34717 | fadH | — | — | putative 2,4-dienoyl-CoA reductase |
| Contig1 | 811719 | 811958 | + | GENE_00841 | Prodigal: 2.6 | CDS | — | — | — | — | — | — | — | — | hypothetical protein |
| Contig1 | 812411 | 813631 | + | GENE_00842 | Prodigal: 2.6 | CDS | — | — | — | — | O35014 | ykuI | — | — | putative EAL-domain containing protein YkuI |
| Contig1 | 814076 | 814315 | + | GENE_00843 | Prodigal: 2.6 | CDS | — | — | — | — | — | — | — | — | hypothetical protein |
| Contig1 | 814438 | 814956 | + | GENE_00844 | Prodigal: 2.6 | CDS | — | — | — | — | — | — | — | — | hypothetical protein |
| Contig1 | 815097 | 815288 | + | GENE_00845 | Prodigal: 2.6 | CDS | — | — | — | — | — | — | — | — | hypothetical protein |
| Contig1 | 815432 | 815875 | + | GENE_00846 | Prodigal: 2.6 | CDS | — | — | — | — | O31698 | ykuL | — | — | CBS domain-containing protein YkuL |
| Contig1 | 816016 | 816897 | + | GENE_00847 | Prodigal: 2.6 | CDS | — | — | — | — | P06614 | cysB_1 | — | — | HTH-type transcriptional regulator CysB |
| Contig1 | 817009 | 817482 | + | GENE_00848 | Prodigal: 2.6 | CDS | — | — | — | — | Q01095 | — | — | — | Flavodoxin |
| Contig1 | 817472 | 818365 | + | GENE_00849 | Prodigal: 2.6 | CDS | — | — | — | — | — | — | — | — | hypothetical protein |
| Contig1 | 818392 | 818847 | + | GENE_00850 | Prodigal: 2.6 | CDS | — | — | — | — | P00323 | — | — | — | Flavodoxin |
| Contig1 | 818929 | 819639 | + | GENE_00851 | Prodigal: 2.6 | CDS | 2.3.1.89 | — | — | — | O34981 | dapH_1 | — | — | 2,3,4,5-tetrahydropyridine-2,6-dicarboxylate N-acetyltransferase |
| Contig1 | 819710 | 820834 | + | GENE_00852 | Prodigal: 2.6 | CDS | 3.5.1.47 | — | — | — | O34916 | ykuR | — | — | N-acetyldiaminopimelate deacetylase |
| Contig1 | 820895 | 821140 | + | GENE_00853 | Prodigal: 2.6 | CDS | — | — | — | — | — | — | — | — | hypothetical protein |
| Contig1 | 821174 | 821980 | − | GENE_00854 | Prodigal: 2.6 | CDS | — | PRK03094 | — | — | O34897 | ykuT | — | — | putative MscS family protein YkuT |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 822268 | 822726 | + | GENE_00855 | Prodigal: 2.6 | CDS | 1.8.-.- | — | — | — | O31699 | ykuV | — | — | Thiol-disulfide oxidoreductase YkuV |
| Contig1 | 823178 | 823774 | + | GENE_00856 | Prodigal: 2.6 | CDS | — | — | — | — | O34857 | rok | — | — | Repressor rok |
| Contig1 | 823795 | 824787 | − | GENE_00857 | Prodigal: 2.6 | CDS | — | — | — | — | O31700 | — | — | — | Sporulation protein cse15 |
| Contig1 | 824933 | 825535 | + | GENE_00858 | Prodigal: 2.6 | CDS | 2.7.7.77 | — | — | — | P65405 | mobA | — | — | putative molybdenum cofactor guanylyltransferase |
| Contig1 | 825587 | 826606 | + | GENE_00859 | Prodigal: 2.6 | CDS | 2.7.7.73 | — | — | — | P30138 | thiF_2 | — | — | Sulfur carrier protein ThiS adenylyltransferase |
| Contig1 | 826624 | 827916 | + | GENE_00860 | Prodigal: 2.6 | CDS | 2.10.1.1 | — | — | — | P99139 | moeA | — | — | Molybdopterin molybdenumtransferase |
| Contig1 | 827877 | 828398 | + | GENE_00861 | Prodigal: 2.6 | CDS | — | — | — | — | P44902 | mobB | — | — | Molybdopterin-guanine dinucleotide biosynthesis adapter protein |
| Contig1 | 828399 | 828869 | + | GENE_00862 | Prodigal: 2.6 | CDS | 2.8.1.12 | — | — | — | P65401 | moaE | — | — | Molybdopterin synthase catalytic subunit |
| Contig1 | 828866 | 829099 | + | GENE_00863 | Prodigal: 2.6 | CDS | — | — | — | — | P30748 | moaD | — | — | Molybdopterin synthase sulfur carrier subunit |
| Contig1 | 829423 | 830121 | + | GENE_00864 | Prodigal: 2.6 | CDS | — | — | PF04893.11 | — | — | — | — | — | YipI domain protein |
| Contig1 | 830123 | 831259 | + | GENE_00865 | Prodigal: 2.6 | CDS | — | — | — | — | O31710 | yknX | — | — | Putative efflux system component YknX |
| Contig1 | 831260 | 831952 | + | GENE_00866 | Prodigal: 2.6 | CDS | 3.6.3.- | — | — | — | P75831 | macB_1 | — | — | Macrolide export ATP-binding/permease protein MacB |
| Contig1 | 831949 | 833142 | + | GENE_00867 | Prodigal: 2.6 | CDS | — | — | — | — | O31712 | yknZ | — | — | putative ABC transporter permease YknZ |
| Contig1 | 833424 | 834179 | + | GENE_00868 | Prodigal: 2.6 | CDS | — | — | — | — | P67744 | lacR_2 | — | — | Lactose phosphotransferase system repressor |
| Contig1 | 834176 | 835087 | + | GENE_00869 | Prodigal: 2.6 | CDS | 2.7.1.144 | — | — | — | Q833W9 | lacC | — | — | Tagatose-6-phosphate kinase |
| Contig1 | 835102 | 837006 | + | GENE_00870 | Prodigal: 2.6 | CDS | — | — | — | — | P71012 | fruA | — | — | PTS system fructose-specific EIIABC component |
| Contig1 | 837137 | 837718 | + | GENE_00871 | Prodigal: 2.6 | CDS | 3.4.21.89 | — | — | — | P71013 | sipT | — | — | Signal peptidase I T |
| Contig1 | 837756 | 838025 | − | GENE_00872 | Prodigal: 2.6 | CDS | — | — | — | — | — | — | — | — | hypothetical protein |
| Contig1 | 838188 | 839807 | + | GENE_00873 | Prodigal: 2.6 | CDS | — | — | — | — | P63389 | yheS_4 | — | — | putative ABC transporter ATP-binding protein YheS |
| Contig1 | 839920 | 840828 | + | GENE_00874 | Prodigal: 2.6 | CDS | 1.1.1.169 | — | — | — | P37402 | panE_1 | — | — | 2-dehydropantoate 2-reductase |
| Contig1 | 840858 | 842090 | − | GENE_00875 | Prodigal: 2.6 | CDS | 3.4.11.- | — | — | — | P24828 | — | — | — | Aminopeptidase 2 |
| Contig1 | 842191 | 842325 | − | GENE_00876 | Prodigal: 2.6 | CDS | — | — | — | — | — | — | — | — | hypothetical protein |
| Contig1 | 842397 | 843416 | − | GENE_00877 | Prodigal: 2.6 | CDS | — | — | — | — | P0A9X4 | mreB_1 | — | — | Rod shape-determining protein MreB |
| Contig1 | 843673 | 843957 | + | GENE_00878 | Prodigal: 2.6 | CDS | — | — | — | — | P39758 | abh | — | — | Putative transition state regulator Abh |
| Contig1 | 844615 | 845433 | + | GENE_00879 | Prodigal: 2.6 | CDS | 2.7.13.3 | — | — | — | P16497 | kinA_2 | — | — | Sporulation kinase A |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 845435 | 846262 | + | GENE_00880 | Prodigal: 2.6 | CDS | 2.3.2.- | — | — | — | P39759 | ykqA | — | — | Putative gamma-glutamylcyclotransferase YkqA |
| Contig1 | 846303 | 846968 | + | GENE_00881 | Prodigal: 2.6 | CDS | — | — | — | — | O32080 | ktrA_1 | — | — | Ktr system potassium uptake protein A |
| Contig1 | 847117 | 848850 | – | GENE_00882 | Prodigal: 2.6 | CDS | 3.5.4.2 | — | — | — | P39761 | adeC | — | — | Adenine deaminase |
| Contig1 | 848882 | 850549 | – | GENE_00883 | Prodigal: 2.6 | CDS | 3.1.-.- | — | — | — | Q45493 | rnjA | — | — | Ribonuclease J 1 |
| Contig1 | 850555 | 850767 | – | GENE_00884 | Prodigal: 2.6 | CDS | — | — | — | — | — | — | — | — | hypothetical protein |
| Contig1 | 851119 | 851892 | + | GENE_00885 | Prodigal: 2.6 | CDS | — | — | — | — | Q5XAQ1 | — | — | — | Putative bifunctional phosphatase/peptidyl-prolyl cis-trans isomerase |
| Contig1 | 851928 | 852482 | – | GENE_00886 | Prodigal: 2.6 | CDS | 3.5.1.88 | — | — | — | Q45495 | defB | — | — | Peptide deformylase 2 |
| Contig1 | 852595 | 852771 | – | GENE_00887 | Prodigal: 2.6 | CDS | — | — | PF09680.4 | — | — | — | — | — | Protein of unknown function (Tiny TM bacil1) |
| Contig1 | 853012 | 853656 | + | GENE_00888 | Prodigal: 2.6 | CDS | — | — | PF10368.3 | — | — | — | — | — | Putative cell-wall binding lipoprotein |
| Contig1 | 854104 | 856410 | + | GENE_00889 | Prodigal: 2.6 | CDS | — | — | — | — | A7A4Y0 | baeE_1 | — | — | Polyketide biosynthesis protein BaeE |
| Contig1 | 856432 | 868686 | + | GENE_00890 | Prodigal: 2.6 | CDS | — | — | — | — | P40806 | pksJ_1 | — | — | Polyketide synthase PksJ |
| Contig1 | 868686 | 873455 | + | GENE_00891 | Prodigal: 2.6 | CDS | — | — | — | — | Q05470 | pksL_1 | — | — | Polyketide synthase PksL |
| Contig1 | 873503 | 875746 | + | GENE_00892 | Prodigal: 2.6 | CDS | — | — | — | — | Q05470 | pksL_2 | — | — | Polyketide synthase PksL |
| Contig1 | 875692 | 882210 | + | GENE_00893 | Prodigal: 2.6 | CDS | 2.3.1.- | — | — | — | O31782 | pksN_1 | — | — | Polyketide synthase PksN |
| Contig1 | 882203 | 889204 | + | GENE_00894 | Prodigal: 2.6 | CDS | — | — | — | — | P40806 | pksJ_2 | — | — | Polyketide synthase PksJ |
| Contig1 | 889228 | 894939 | + | GENE_00895 | Prodigal: 2.6 | CDS | — | — | — | — | Q05470 | pksL_3 | — | — | Polyketide synthase PksL |
| Contig1 | 894939 | 902318 | + | GENE_00896 | Prodigal: 2.6 | CDS | — | — | — | — | Q05470 | pksL_4 | — | — | Polyketide synthase PksL |
| Contig1 | 902369 | 906223 | + | GENE_00897 | Prodigal: 2.6 | CDS | — | — | — | — | P40806 | pksJ_3 | — | — | Polyketide synthase PksJ |
| Contig1 | 906256 | 907347 | + | GENE_00898 | Prodigal: 2.6 | CDS | — | — | — | — | O31773 | pbpX_1 | — | — | Putative penicillin-binding protein PbpX |
| Contig1 | 907819 | 908934 | + | GENE_00899 | Prodigal: 2.6 | CDS | 1.2.4.1 | — | — | — | P21881 | pdhA | — | — | Pyruvate dehydrogenase E1 component subunit alpha |
| Contig1 | 908938 | 909915 | + | GENE_00900 | Prodigal: 2.6 | CDS | 1.2.4.1 | — | — | — | P21874 | pdhB | — | — | Pyruvate dehydrogenase E1 component subunit beta |
| Contig1 | 910040 | 911368 | + | GENE_00901 | Prodigal: 2.6 | CDS | 2.3.1.12 | — | — | — | P21883 | pdhC_2 | — | — | Dihydrolipoyllysine-residue acetyltransferase component of pyruvate dehydrogenase complex |
| Contig1 | 911373 | 912785 | + | GENE_00902 | Prodigal: 2.6 | CDS | 1.8.1.4 | — | — | — | P11959 | pdhD_2 | — | — | Dihydrolipoyl dehydrogenase |
| Contig1 | 912833 | 913207 | – | GENE_00903 | Prodigal: 2.6 | CDS | — | — | — | — | — | — | — | — | hypothetical protein |
| Contig1 | 913456 | 914247 | + | GENE_00904 | Prodigal: 2.6 | CDS | — | — | — | — | P83513 | — | — | — | Bifunctional xylanase/deacetylase precursor |
| Contig1 | 914528 | 916000 | – | GENE_00905 | Prodigal: 2.6 | CDS | 4.1.1.19 | — | — | — | P21885 | speA_1 | — | — | Arginine decarboxylase |
| Contig1 | 916180 | 916446 | + | GENE_00906 | Prodigal: 2.6 | CDS | — | — | — | — | — | — | — | — | hypothetical protein |
| Contig1 | 916482 | 917114 | – | GENE_00907 | Prodigal: 2.6 | CDS | — | PRK04387 | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 917363 | 917539 | + | GENE_00908 | Prodigal: 2.6 | CDS | — | — | — | — | — | — | — | — | hypothetical protein |
| Contig1 | 917673 | 918470 | + | GENE_00909 | Prodigal: 2.6 | CDS | 3.1.3.25 | — | — | — | P0ADG4 | suhB | — | — | Inositol-1-monophosphatase |
| Contig1 | 918457 | 918909 | — | GENE_00910 | Prodigal: 2.6 | CDS | — | — | — | — | — | — | — | — | hypothetical protein |
| Contig1 | 918961 | 920526 | — | GENE_00911 | Prodigal: 2.6 | CDS | 3.4.24.28 | — | — | — | P06832 | npr | — | — | Bacillolysin precursor |
| Contig1 | 921024 | 921317 | — | GENE_00912 | Prodigal: 2.6 | CDS | — | — | — | — | — | — | — | — | hypothetical protein |
| Contig1 | 921355 | 921972 | — | GENE_00913 | Prodigal: 2.6 | CDS | — | — | — | — | — | — | — | — | hypothetical protein |
| Contig1 | 922284 | 922472 | — | GENE_00914 | Prodigal: 2.6 | CDS | — | — | — | — | — | — | — | — | hypothetical protein |
| Contig1 | 922584 | 924422 | + | GENE_00915 | Prodigal: 2.6 | CDS | — | — | — | — | P32132 | typA | — | — | GTP-binding protein TypA/BipA |
| Contig1 | 924479 | 924799 | — | GENE_00916 | Prodigal: 2.6 | CDS | — | — | — | — | — | — | — | — | hypothetical protein |
| Contig1 | 924840 | 925049 | — | GENE_00917 | Prodigal: 2.6 | CDS | — | — | — | — | — | — | — | — | hypothetical protein |
| Contig1 | 925151 | 925774 | — | GENE_00918 | Prodigal: 2.6 | CDS | — | — | PF09580.4 | — | — | — | — | — | Sporulation lipoprotein YhcN/YlaJ (Spore_YhcN_YlaJ) |
| Contig1 | 925929 | 927257 | + | GENE_00919 | Prodigal: 2.6 | CDS | — | — | — | — | P0A9K3 | ybeZ_1 | — | — | PhoH-like protein |
| Contig1 | 927252 | 927728 | — | GENE_00920 | Prodigal: 2.6 | CDS | — | — | — | — | — | — | — | — | hypothetical protein |
| Contig1 | 927833 | 928762 | + | GENE_00921 | Prodigal: 2.6 | CDS | 3.5.1.2 | — | — | — | O07637 | glsA2 | — | — | Glutaminase 2 |
| Contig1 | 928870 | 929151 | + | GENE_00922 | Prodigal: 2.6 | CDS | — | — | — | — | — | — | — | — | hypothetical protein |
| Contig1 | 929357 | 930568 | + | GENE_00923 | Prodigal: 2.6 | CDS | — | — | — | — | O07639 | ftsW_1 | — | — | Lipid II flippase FtsW |
| Contig1 | 930644 | 934090 | + | GENE_00924 | Prodigal: 2.6 | CDS | 6.4.1.7 | — | — | — | D3DJ42 | cflB_1 | — | — | 2-oxoglutarate carboxylase small subunit |
| Contig1 | 934187 | 935113 | — | GENE_00925 | Prodigal: 2.6 | CDS | 1.3.-.- | — | — | — | P12946 | ctaA | — | — | Heme A synthase |
| Contig1 | 935457 | 936374 | + | GENE_00926 | Prodigal: 2.6 | CDS | 2.5.1.- | — | — | — | P24009 | ctaB2 | — | — | Protoheme IX farnesyltransferase 2 |
| Contig1 | 936592 | 937662 | + | GENE_00927 | Prodigal: 2.6 | CDS | 1.9.3.1 | — | — | — | Q03438 | ctaC | — | — | Cytochrome c oxidase subunit 2 precursor |
| Contig1 | 937694 | 939562 | + | GENE_00928 | Prodigal: 2.6 | CDS | 1.9.3.1 | — | — | — | P16262 | ctaD | — | — | Cytochrome c oxidase subunit 1 |
| Contig1 | 939562 | 940185 | + | GENE_00929 | Prodigal: 2.6 | CDS | 1.9.3.1 | — | — | — | Q03439 | ctaE | — | — | Cytochrome c oxidase subunit 3 |
| Contig1 | 940188 | 940520 | + | GENE_00930 | Prodigal: 2.6 | CDS | 1.9.3.1 | — | — | — | Q03440 | caaD | — | — | Cytochrome c oxidase subunit 4B |
| Contig1 | 940545 | 941429 | + | GENE_00931 | Prodigal: 2.6 | CDS | — | — | PF09678.4 | — | — | — | — | — | Cytochrome c oxidase caa3 assembly factor (Caa3_CtaG) |
| Contig1 | 941464 | 941823 | — | GENE_00932 | Prodigal: 2.6 | CDS | — | — | PF08868.4 | — | O06186 | hrp1_2 | — | — | YugN-like family protein |
| Contig1 | 941964 | 942407 | + | GENE_00933 | Prodigal: 2.6 | CDS | — | — | PF00188.20 | — | — | — | — | — | Hypoxic response protein 1 |
| Contig1 | 942492 | 943532 | + | GENE_00934 | Prodigal: 2.6 | CDS | — | — | — | — | — | — | — | — | Cysteine-rich secretory protein family protein |
| Contig1 | 943697 | 944107 | + | GENE_00935 | Prodigal: 2.6 | CDS | — | — | — | — | — | — | — | — | hypothetical protein |
| Contig1 | 944123 | 944362 | + | GENE_00936 | Prodigal: 2.6 | CDS | — | — | — | — | — | — | — | — | hypothetical protein |
| Contig1 | 944433 | 944882 | + | GENE_00937 | Prodigal: 2.6 | CDS | — | PRK02886 | — | — | — | — | — | — | hypothetical protein |
| Contig1 | 944938 | 945213 | + | GENE_00938 | Prodigal: 2.6 | CDS | — | — | — | — | — | — | — | — | hypothetical protein |
| Contig1 | 945213 | 945513 | + | GENE_00939 | Prodigal: 2.6 | CDS | — | — | — | — | — | — | — | — | hypothetical protein |
| Contig1 | 945513 | 946067 | + | GENE_00940 | Prodigal: 2.6 | CDS | 2.1.1.171 | — | — | — | P44869 | rsmD | — | — | Ribosomal RNA small subunit methyltransferase D |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 946072 | 946554 | + | GENE_00941 | Prodigal: 2.6 | CDS | 2.7.7.3 | — | — | — | O34797 | coaD | — | — | Phosphopantetheine adenylyltransferase |
| Contig1 | 946573 | 947799 | − | GENE_00942 | Prodigal: 2.6 | CDS | | — | — | — | O34765 | ylbJ | — | — | Sporulation integral membrane protein YlbJ |
| Contig1 | 947979 | 948758 | + | GENE_00943 | Prodigal: 2.6 | CDS | | — | — | — | P0AFR0 | rssA | — | — | NTE family protein RssA |
| Contig1 | 948764 | 949786 | + | GENE_00944 | Prodigal: 2.6 | CDS | 3.4.21.53 | — | — | — | O69300 | lon | — | — | Lon protease |
| Contig1 | 949805 | 951052 | − | GENE_00945 | Prodigal: 2.6 | CDS | | — | — | — | — | — | — | — | hypothetical protein |
| Contig1 | 951261 | 951779 | + | GENE_00946 | Prodigal: 2.6 | CDS | | — | — | — | — | — | — | — | hypothetical protein |
| Contig1 | 951801 | 951980 | + | GENE_00947 | Prodigal: 2.6 | CDS | | — | — | — | O34687 | rpmF | — | — | 50S ribosomal protein L32 |
| Contig1 | 952140 | 952715 | + | GENE_00948 | Prodigal: 2.6 | CDS | | — | — | — | P39650 | rsfA_1 | — | — | Prespore-specific transcriptional regulator RsfA |
| Contig1 | 952756 | 953238 | − | GENE_00949 | Prodigal: 2.6 | CDS | 2.3.1.- | — | — | — | O34468 | ylbP | — | — | putative N-acetyltransferase YlbP |
| Contig1 | 953362 | 954282 | + | GENE_00950 | Prodigal: 2.6 | CDS | 1.1.1.169 | — | — | — | O34661 | panE_2 | — | — | putative 2-dehydropantoate 2-reductase |
| Contig1 | 954312 | 955988 | + | GENE_00951 | Prodigal: 2.6 | CDS | | — | — | — | — | — | — | — | hypothetical protein |
| Contig1 | 956081 | 956545 | + | GENE_00952 | Prodigal: 2.6 | CDS | | — | — | MF_01008 | — | mraZ | — | — | Protein MraZ |
| Contig1 | 956615 | 957550 | + | GENE_00953 | Prodigal: 2.6 | CDS | 2.1.1.199 | — | — | — | P60392 | rsmH_1 | — | — | Ribosomal RNA small subunit methyltransferase H |
| Contig1 | 957590 | 957943 | + | GENE_00954 | Prodigal: 2.6 | CDS | | — | — | — | Q07867 | ftsL | — | — | Cell division protein FtsL |
| Contig1 | 957950 | 960094 | + | GENE_00955 | Prodigal: 2.6 | CDS | | — | — | — | Q07868 | pbpB | — | — | Penicillin-binding protein 2B |
| Contig1 | 960208 | 962127 | + | GENE_00956 | Prodigal: 2.6 | CDS | | — | — | — | Q03524 | spoVD | — | — | Stage V sporulation protein D |
| Contig1 | 962323 | 963795 | + | GENE_00957 | Prodigal: 2.6 | CDS | 6.3.2.7 | — | — | — | Q2FZP6 | murE | — | — | UDP-N-acetylmuramoyl-L-alanyl-D-glutamate--L-lysine ligase |
| Contig1 | 963903 | 964877 | + | GENE_00958 | Prodigal: 2.6 | CDS | 2.7.8.13 | — | — | — | Q2FZ93 | mraY | — | — | Phospho-N-acetylmuramoyl-pentapeptide-transferase |
| Contig1 | 964878 | 966233 | + | GENE_00959 | Prodigal: 2.6 | CDS | 6.3.2.9 | — | — | — | P0A090 | murD | — | — | UDP-N-acetylmuramoylalanine-D-glutamate ligase |
| Contig1 | 966367 | 967392 | + | GENE_00960 | Prodigal: 2.6 | CDS | | — | — | — | P0ABG4 | ftsW_2 | — | — | Lipid II flippase FtsW |
| Contig1 | 967509 | 968600 | + | GENE_00961 | Prodigal: 2.6 | CDS | 2.4.1.227 | — | — | — | Q9HW01 | murG_1 | — | — | UDP-N-acetylglucosamine--N-acetylmuramyl-(penta peptide) pyrophosphoryl-undecaprenol N-acetylglucosamine transferase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 968626 | 969537 | + | GENE_00962 | Prodigal: 2.6 | CDS | 1.3.1.98 | — | — | — | Q8Y776 | murB | — | — | UDP-N-acetylenolpyruvoyl-glucosamine reductase |
| Contig1 | 969667 | 970455 | + | GENE_00963 | Prodigal: 2.6 | CDS | — | — | — | — | P16655 | divIB | — | — | Cell division protein DivIB |
| Contig1 | 971004 | 972317 | + | GENE_00964 | Prodigal: 2.6 | CDS | — | — | — | — | P28264 | ftsA | — | — | Cell division protein FtsA |
| Contig1 | 972353 | 973501 | + | GENE_00965 | Prodigal: 2.6 | CDS | — | — | — | — | P17865 | ftsZ | — | — | Cell division protein FtsZ |
| Contig1 | 973776 | 978071 | + | GENE_00966 | Prodigal: 2.6 | CDS | 3.4.21.- | — | PF03419.7 | — | P16397 | bpr | — | — | Bacillopeptidase F precursor |
| Contig1 | 978287 | 979216 | + | GENE_00967 | Prodigal: 2.6 | CDS | — | — | — | — | — | — | — | — | Sporulation factor SpoIIGA |
| Contig1 | 979274 | 979993 | + | GENE_00968 | Prodigal: 2.6 | CDS | — | — | — | — | P06222 | sigE | — | — | RNA polymerase sigma-E factor precursor |
| Contig1 | 980134 | 980916 | + | GENE_00969 | Prodigal: 2.6 | CDS | — | — | — | — | P07860 | sigF_1 | — | — | RNA polymerase sigma-F factor |
| Contig1 | 981045 | 981842 | + | GENE_00970 | Prodigal: 2.6 | CDS | 3.6.3.- | — | — | — | O31723 | ylmA | — | — | putative ABC transporter ATP-binding protein YlmA |
| Contig1 | 981872 | 983308 | + | GENE_00971 | Prodigal: 2.6 | CDS | 3.5.1.- | — | — | — | Q9K9G9 | — | — | — | N-formyl-4-amino-5-aminomethyl-2-methylpyrimidine deformylase |
| Contig1 | 983369 | 983620 | + | GENE_00972 | Prodigal: 2.6 | CDS | — | — | PF05239.10 | — | — | — | — | — | PRC-barrel domain protein |
| Contig1 | 983775 | 984611 | + | GENE_00973 | Prodigal: 2.6 | CDS | — | — | — | — | — | — | — | Alanine racemase, N-terminal domain | Laccase domain protein |
| Contig1 | 984616 | 985308 | + | GENE_00974 | Prodigal: 2.6 | CDS | — | — | PF01168.14 | — | Q99US8 | — | — | — | hypothetical protein |
| Contig1 | 985305 | 985763 | + | GENE_00975 | Prodigal: 2.6 | CDS | — | — | — | — | O31728 | sepF | — | — | Cell division protein SepF |
| Contig1 | 985770 | 986048 | + | GENE_00976 | Prodigal: 2.6 | CDS | — | — | PF02325.11 | — | — | — | — | — | YGGT family protein |
| Contig1 | 986110 | 986880 | + | GENE_00977 | Prodigal: 2.6 | CDS | — | — | PF01479.19 | — | — | — | — | — | S4 domain protein |
| Contig1 | 986975 | 987469 | + | GENE_00978 | Prodigal: 2.6 | CDS | — | — | — | — | P71021 | divIVA | — | — | Septum site-determining protein DivIVA |
| Contig1 | 987811 | 990576 | + | GENE_00979 | Prodigal: 2.6 | CDS | 6.1.1.5 | — | — | — | P41972 | ileS | — | — | Isoleucine-tRNA ligase |
| Contig1 | 990726 | 991097 | + | GENE_00980 | Prodigal: 2.6 | CDS | — | — | — | — | P80872 | yocK_1 | — | — | General stress protein 160 |
| Contig1 | 991199 | 991660 | + | GENE_00981 | Prodigal: 2.6 | CDS | 3.4.23.36 | — | — | — | P00804 | lspA | — | — | Lipoprotein signal peptidase |
| Contig1 | 991662 | 992576 | + | GENE_00982 | Prodigal: 2.6 | CDS | 5.4.99.23 | — | — | — | P33643 | rluD_3 | — | — | Ribosomal large subunit pseudouridine synthase D |
| Contig1 | 992765 | 993310 | + | GENE_00983 | Prodigal: 2.6 | CDS | — | — | — | — | P39765 | pyrR | — | — | Bifunctional protein PyrR |
| Contig1 | 993465 | 994775 | + | GENE_00984 | Prodigal: 2.6 | CDS | — | — | — | — | P39766 | pyrP | — | — | Uracil permease |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 994917 | 995831 | + | GENE_00985 | Prodigal: 2.6 | CDS | 2.1.3.2 | — | — | — | P05654 | pyrB | — | — | Aspartate carbamoyltransferase |
| Contig1 | 995815 | 997101 | + | GENE_00986 | Prodigal: 2.6 | CDS | 3.5.2.3 | — | — | — | Q81WF0 | pyrC | — | — | Dihydroorotase |
| Contig1 | 997098 | 998192 | + | GENE_00987 | Prodigal: 2.6 | CDS | 6.3.5.5 | — | — | — | P99147 | carA_2 | — | — | Carbamoyl-phosphate synthase small chain |
| Contig1 | 998177 | 1001392 | + | GENE_00988 | Prodigal: 2.6 | CDS | 6.3.5.5 | — | — | — | P63740 | carB_2 | — | — | Carbamoyl-phosphate synthase large chain |
| Contig1 | 1001389 | 1002159 | + | GENE_00989 | Prodigal: 2.6 | CDS | — | — | — | — | P25983 | pyrK | — | — | Dihydroorotate dehydrogenase B (NAD(+)), electron transfer subunit |
| Contig1 | 1002159 | 1003094 | + | GENE_00990 | Prodigal: 2.6 | CDS | 1.3.1.14 | — | — | — | P25996 | pyrD | — | — | Dihydroorotate dehydrogenase B (NAD(+)), catalytic subunit |
| Contig1 | 1003063 | 1003782 | + | GENE_00991 | Prodigal: 2.6 | CDS | 4.1.1.23 | — | — | — | P25971 | pyrF | — | — | Orotidine 5'-phosphate decarboxylase |
| Contig1 | 1003779 | 1004411 | + | GENE_00992 | Prodigal: 2.6 | CDS | 2.4.2.10 | — | — | — | Q81WF6 | pyrE | — | — | Orotate phosphoribosyltransferase |
| Contig1 | 1004745 | 1005446 | + | GENE_00993 | Prodigal: 2.6 | CDS | 1.8.4.8 | — | — | — | P94498 | cysH | — | — | Phosphoadenosine phosphosulfate reductase |
| Contig1 | 1005459 | 1006523 | + | GENE_00994 | Prodigal: 2.6 | CDS | — | — | — | — | O34734 | cysP | — | — | Sulfate permease CysP |
| Contig1 | 1006572 | 1007720 | + | GENE_00995 | Prodigal: 2.6 | CDS | 2.7.7.4 | — | — | — | O34764 | sat | — | — | Sulfate adenylyltransferase |
| Contig1 | 1007734 | 1008327 | + | GENE_00996 | Prodigal: 2.6 | CDS | 2.7.1.25 | — | — | — | O34577 | cysC | — | — | putative adenylyl-sulfate kinase |
| Contig1 | 1008452 | 1009225 | + | GENE_00997 | Prodigal: 2.6 | CDS | 2.1.1.107 | — | — | — | O34744 | sumT | — | — | Uroporphyrinogen-III C-methyltransferase |
| Contig1 | 1009226 | 1010011 | + | GENE_00998 | Prodigal: 2.6 | CDS | 4.99.1.4 | — | — | — | O34632 | sirB | — | — | Sirohydrochlorin ferrochelatase |
| Contig1 | 1009992 | 1010480 | + | GENE_00999 | Prodigal: 2.6 | CDS | 1.3.1.76 | — | — | — | O34813 | sirC | — | — | Precorrin-2 dehydrogenase |
| Contig1 | 1010458 | 1010766 | + | GENE_01000 | Prodigal: 2.6 | CDS | — | — | PF05833.5 | — | — | — | — | Fibronectin-binding protein A N-terminus (FbpA) | hypothetical protein |
| Contig1 | 1010873 | 1012588 | − | GENE_01001 | Prodigal: 2.6 | CDS | — | — | — | — | — | — | — | — | hypothetical protein |
| Contig1 | 1012699 | 1015371 | + | GENE_01002 | Prodigal: 2.6 | CDS | 3.6.3.8 | — | — | — | O34431 | yloB | — | — | Calcium-transporting ATPase |
| Contig1 | 1015444 | 1016328 | + | GENE_01003 | Prodigal: 2.6 | CDS | — | PRK11820 | — | — | — | — | — | — | hypothetical protein |
| Contig1 | 1016405 | 1016674 | + | GENE_01004 | Prodigal: 2.6 | CDS | — | PRK04323 | — | — | — | — | — | — | hypothetical protein |
| Contig1 | 1016682 | 1017296 | + | GENE_01005 | Prodigal: 2.6 | CDS | 2.7.4.8 | — | — | — | Q8Y672 | gmk | — | — | Guanylate kinase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1017300 | 1017503 | + | GENE_01006 | Prodigal: 2.6 | CDS | 2.7.7.6 | — | — | — | Q5XAP2 | rpoZ | — | — | DNA-directed RNA polymerase subunit omega |
| Contig1 | 1017594 | 1018814 | + | GENE_01007 | Prodigal: 2.6 | CDS | — | — | — | — | P0ABQ0 | coaBC | — | — | Coenzyme A biosynthesis bifunctional protein CoaBC |
| Contig1 | 1018811 | 1021222 | + | GENE_01008 | Prodigal: 2.6 | CDS | 3.6.4.- | — | — | — | P17888 | priA | — | — | Primosomal protein N' |
| Contig1 | 1021247 | 1021729 | + | GENE_01009 | Prodigal: 2.6 | CDS | 3.5.1.88 | — | — | — | Q819U0 | deff | — | — | Peptide deformylase 1 |
| Contig1 | 1021752 | 1022687 | + | GENE_01010 | Prodigal: 2.6 | CDS | 2.1.2.9 | — | — | — | Q81WH2 | fmt | — | — | Methionyl-tRNA formyltransferase |
| Contig1 | 1022674 | 1024017 | + | GENE_01011 | Prodigal: 2.6 | CDS | 2.1.1.176 | — | — | — | P36929 | rsmB | — | — | Ribosomal RNA small subunit methyltransferase B |
| Contig1 | 1024021 | 1025112 | + | GENE_01012 | Prodigal: 2.6 | CDS | 2.1.1 | — | — | — | Q7A600 | rlmN | — | — | putative dual-specificity RNA methyltransferase RlmN |
| Contig1 | 1025118 | 1025879 | + | GENE_01013 | Prodigal: 2.6 | CDS | 3.1.3.16 | — | — | — | Q8Y678 | stp_1 | — | — | Serine/threonine phosphatase stp |
| Contig1 | 1025873 | 1027816 | + | GENE_01014 | Prodigal: 2.6 | CDS | 2.7.11.1 | — | — | — | O34507 | prkC_1 | — | — | Serine/threonine-protein kinase PrkC |
| Contig1 | 1027831 | 1028721 | + | GENE_01015 | Prodigal: 2.6 | CDS | 3.6.1.- | — | — | — | O34530 | rsgA | — | — | Putative ribosome biogenesis GTPase RsgA |
| Contig1 | 1028723 | 1029376 | + | GENE_01016 | Prodigal: 2.6 | CDS | 5.1.3.1 | — | — | — | P74061 | rpe | — | — | Ribulose-phosphate 3-epimerase |
| Contig1 | 1029442 | 1030086 | + | GENE_01017 | Prodigal: 2.6 | CDS | 2.7.6.2 | — | — | — | O34664 | thiN | — | — | Thiamine pyrophosphokinase |
| Contig1 | 1030331 | 1030519 | − | GENE_01018 | Prodigal: 2.6 | CDS | — | — | — | — | P23374 | rpmB | — | — | 50S ribosomal protein L28 |
| Contig1 | 1030778 | 1031140 | + | GENE_01019 | Prodigal: 2.6 | CDS | — | — | PF02734.11 | — | — | — | — | — | hypothetical protein DAK2 domain protein |
| Contig1 | 1031156 | 1032823 | + | GENE_01020 | Prodigal: 2.6 | CDS | — | — | — | — | — | — | — | — | |
| Contig1 | 1032966 | 1033628 | + | GENE_01021 | Prodigal: 2.6 | CDS | 4.3.1.17 | — | — | — | P33074 | sdhB | — | — | L-serine dehydratase, beta chain |
| Contig1 | 1033649 | 1034551 | + | GENE_01022 | Prodigal: 2.6 | CDS | 4.3.1.17 | — | — | — | P33073 | sdhA | — | — | L-serine dehydratase, alpha chain |
| Contig1 | 1034529 | 1036677 | + | GENE_01023 | Prodigal: 2.6 | CDS | 3.6.4.12 | — | — | — | P64325 | recG | — | — | ATP-dependent DNA helicase RecG |
| Contig1 | 1036684 | 1037250 | + | GENE_01024 | Prodigal: 2.6 | CDS | — | — | — | — | O34835 | fapR | — | — | Transcription factor FapR |
| Contig1 | 1037264 | 1038262 | + | GENE_01025 | Prodigal: 2.6 | CDS | 2.3.1.- | — | — | — | P71018 | plsX | — | — | Phosphate acyltransferase |
| Contig1 | 1038281 | 1039234 | + | GENE_01026 | Prodigal: 2.6 | CDS | 2.3.1.39 | — | — | — | Q7A5Z3 | fabD | — | — | Malonyl CoA-acyl carrier protein transacylase |
| Contig1 | 1039227 | 1039967 | + | GENE_01027 | Prodigal: 2.6 | CDS | 1.1.1.100 | — | — | — | P99093 | fabG_1 | — | — | 3-oxoacyl-[acyl-carrier-protein] reductase FabG |
| Contig1 | 1040052 | 1040285 | + | GENE_01028 | Prodigal: 2.6 | CDS | — | — | — | — | P80643 | acpA | — | — | Acyl carrier protein |
| Contig1 | 1040424 | 1041173 | + | GENE_01029 | Prodigal: 2.6 | CDS | 3.1.26.3 | — | — | — | P51833 | rnc | — | — | Ribonuclease 3 |
| Contig1 | 1041275 | 1044835 | + | GENE_01030 | Prodigal: 2.6 | CDS | — | — | — | — | P51834 | smc_2 | — | — | Chromosome partition protein Smc |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1044855 | 1045844 | + | GENE_01031 | Prodigal: 2.6 | CDS | — | — | — | — | P51835 | ftsY | — | — | Signal recognition particle receptor FtsY |
| Contig1 | 1045928 | 1046698 | + | GENE_01032 | Prodigal: 2.6 | CDS | — | — | PF01636.17 | — | — | — | — | — | Phosphotransferase enzyme family protein |
| Contig1 | 1046818 | 1047150 | + | GENE_01033 | Prodigal: 2.6 | CDS | — | PRK00118 | — | — | — | — | — | — | putative DNA-binding protein |
| Contig1 | 1047164 | 1048504 | + | GENE_01034 | Prodigal: 2.6 | CDS | — | — | — | — | P37105 | ffh | — | — | Signal recognition particle protein |
| Contig1 | 1048610 | 1048882 | + | GENE_01035 | Prodigal: 2.6 | CDS | — | — | — | — | P21474 | rpsP | — | — | 30S ribosomal protein S16 |
| Contig1 | 1048882 | 1049127 | + | GENE_01036 | Prodigal: 2.6 | CDS | — | PRK00468 | — | — | — | — | — | — | hypothetical protein |
| Contig1 | 1049218 | 1049604 | + | GENE_01037 | Prodigal: 2.6 | CDS | — | — | — | — | — | — | — | — | hypothetical protein |
| Contig1 | 1049609 | 1050133 | + | GENE_01038 | Prodigal: 2.6 | CDS | — | — | — | — | P66656 | rimM | — | — | Ribosome maturation factor RimM |
| Contig1 | 1050130 | 1050861 | + | GENE_01039 | Prodigal: 2.6 | CDS | 2.1.1.228 | — | — | — | Q6GHJ5 | trmD | — | — | tRNA (guanine-N(1))-methyltransferase |
| Contig1 | 1051002 | 1051349 | + | GENE_01040 | Prodigal: 2.6 | CDS | — | — | — | — | O31742 | rplS | — | — | 50S ribosomal protein L19 |
| Contig1 | 1051492 | 1052340 | + | GENE_01041 | Prodigal: 2.6 | CDS | — | — | — | — | O31743 | rbgA | — | — | Ribosome biogenesis GTPase A |
| Contig1 | 1052413 | 1053180 | + | GENE_01042 | Prodigal: 2.6 | CDS | 3.1.26.4 | — | — | — | O31744 | rnhB | — | — | Ribonuclease HH |
| Contig1 | 1053197 | 1054900 | + | GENE_01043 | Prodigal: 2.6 | CDS | — | — | — | — | — | — | — | — | hypothetical protein |
| Contig1 | 1054897 | 1055178 | + | GENE_01044 | Prodigal: 2.6 | CDS | — | — | — | — | P76299 | flhB_1 | — | — | Flagellar biosynthetic protein FlhB |
| Contig1 | 1055353 | 1056510 | + | GENE_01045 | Prodigal: 2.6 | CDS | 6.2.1.5 | — | — | — | P80886 | sucC | — | — | Succinyl-CoA ligase [ADP-forming] subunit beta |
| Contig1 | 1056539 | 1057441 | + | GENE_01046 | Prodigal: 2.6 | CDS | 6.2.1.5 | — | — | — | P80865 | sucD | — | — | Succinyl-CoA ligase [ADP-forming] subunit alpha |
| Contig1 | 1057506 | 1058405 | + | GENE_01047 | Prodigal: 2.6 | CDS | — | — | — | — | — | — | — | — | hypothetical protein |
| Contig1 | 1058587 | 1060662 | + | GENE_01048 | Prodigal: 2.6 | CDS | 5.99.1.2 | PRK10736 | — | — | Q7A5Y5 | topA | — | — | DNA topoisomerase 1 |
| Contig1 | 1060727 | 1062034 | + | GENE_01049 | Prodigal: 2.6 | CDS | 2.1.1.74 | — | — | — | P39815 | trmFO | — | — | Methylenetetrahydrofolate tRNA-(uracil-5-)-methyltransferase TrmFO |
| Contig1 | 1062104 | 1063021 | + | GENE_01050 | Prodigal: 2.6 | CDS | — | — | — | — | P39776 | xerC_1 | — | — | Tyrosine recombinase XerC |
| Contig1 | 1063037 | 1063582 | + | GENE_01051 | Prodigal: 2.6 | CDS | 3.4.21.- | — | — | — | P39070 | clpQ | — | — | ATP-dependent protease subunit ClpQ |
| Contig1 | 1063599 | 1065002 | + | GENE_01052 | Prodigal: 2.6 | CDS | — | — | — | — | P39778 | clpY | — | — | ATP-dependent protease ATPase subunit ClpY |
| Contig1 | 1065040 | 1065819 | + | GENE_01053 | Prodigal: 2.6 | CDS | — | — | — | — | P39779 | codY | — | — | GTP-sensing transcriptional pleiotropic repressor CodY |
| Contig1 | 1066171 | 1066560 | + | GENE_01054 | Prodigal: 2.6 | CDS | — | — | — | — | P24500 | flgB | — | — | Flagellar basal body rod protein FlgB |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1066560 | 1067012 | + | GENE_01055 | Prodigal: 2.6 | CDS | — | — | — | — | P0A1I7 | flgC | — | — | Flagellar basal-body rod protein FlgC |
| Contig1 | 1067023 | 1067343 | + | GENE_01056 | Prodigal: 2.6 | CDS | — | — | — | — | P26462 | fliE | — | — | Flagellar hook-basal body complex protein FliE |
| Contig1 | 1067386 | 1068996 | + | GENE_01057 | Prodigal: 2.6 | CDS | — | — | — | — | P15928 | fliF | — | — | Flagellar M-ring protein |
| Contig1 | 1069009 | 1070025 | + | GENE_01058 | Prodigal: 2.6 | CDS | — | — | — | — | Q9WY63 | fliG | — | — | Flagellar motor switch protein FliG |
| Contig1 | 1070018 | 1070773 | + | GENE_01059 | Prodigal: 2.6 | CDS | — | PRK06669 | — | — | — | — | — | — | flagellar assembly protein H |
| Contig1 | 1070770 | 1072086 | + | GENE_01060 | Prodigal: 2.6 | CDS | 3.6.3.14 | — | — | — | P40291 | yscN | — | — | putative ATP synthase YscN |
| Contig1 | 1072092 | 1072535 | + | GENE_01061 | Prodigal: 2.6 | CDS | — | — | — | — | P20487 | fliJ | — | — | Flagellar FliJ protein |
| Contig1 | 1072547 | 1073161 | + | GENE_01062 | Prodigal: 2.6 | CDS | — | — | PF03448.11 | — | — | — | — | — | MgtE intracellular N domain protein |
| Contig1 | 1073168 | 1074511 | + | GENE_01063 | Prodigal: 2.6 | CDS | — | — | PF02120.10 | — | — | — | — | — | Flagellar hook-length control protein FliK |
| Contig1 | 1074512 | 1074952 | + | GENE_01064 | Prodigal: 2.6 | CDS | — | — | — | — | P0A1J9 | flgD | — | — | Basal-body rod modification protein FlgD |
| Contig1 | 1074977 | 1075753 | + | GENE_01065 | Prodigal: 2.6 | CDS | — | — | — | — | P0A1J3 | flgG_1 | — | — | Flagellar basal-body rod protein FlgG |
| Contig1 | 1076005 | 1076424 | + | GENE_01066 | Prodigal: 2.6 | CDS | — | PRK07718 | — | — | — | — | — | — | flagellar basal body-associated protein FliL |
| Contig1 | 1076458 | 1077456 | + | GENE_01067 | Prodigal: 2.6 | CDS | — | — | — | — | P23453 | fliM | — | — | Flagellar motor switch protein FliM |
| Contig1 | 1077446 | 1078564 | + | GENE_01068 | Prodigal: 2.6 | CDS | — | — | — | — | P15070 | fliN | — | — | Flagellar motor switch protein FliN |
| Contig1 | 1078591 | 1078953 | + | GENE_01069 | Prodigal: 2.6 | CDS | — | — | — | — | P24072 | cheY_1 | — | — | Chemotaxis protein CheY |
| Contig1 | 1078968 | 1079621 | + | GENE_01070 | Prodigal: 2.6 | CDS | — | — | PF04347.7 | — | — | — | — | — | Flagellar biosynthesis protein, FliO |
| Contig1 | 1079614 | 1080279 | + | GENE_01071 | Prodigal: 2.6 | CDS | — | — | — | — | P54700 | fliP | — | — | Flagellar biosynthetic protein FliP precursor |
| Contig1 | 1080294 | 1080563 | + | GENE_01072 | Prodigal: 2.6 | CDS | — | — | — | — | P74931 | fliQ | — | — | Flagellar biosynthetic protein FliQ |
| Contig1 | 1080570 | 1081349 | + | GENE_01073 | Prodigal: 2.6 | CDS | — | — | — | — | P74932 | fliR | — | — | Flagellar biosynthetic protein FliR |
| Contig1 | 1081346 | 1082428 | + | GENE_01074 | Prodigal: 2.6 | CDS | — | — | — | — | P40727 | flhB_2 | — | — | Flagellar biosynthesis protein FlhB |
| Contig1 | 1082462 | 1084495 | + | GENE_01075 | Prodigal: 2.6 | CDS | — | — | — | — | P35620 | flhA | — | — | Flagellar biosynthesis protein FlhA |
| Contig1 | 1084495 | 1085586 | + | GENE_01076 | Prodigal: 2.6 | CDS | — | — | — | — | Q01960 | flhF | — | — | Flagellar biosynthesis protein FlhF |
| Contig1 | 1085583 | 1086476 | + | GENE_01077 | Prodigal: 2.6 | CDS | — | — | — | — | P40742 | ylxH | — | — | Flagellum site-determining protein YlxH |
| Contig1 | 1086473 | 1087540 | + | GENE_01078 | Prodigal: 2.6 | CDS | 3.1.1.61 | — | — | — | Q9WYN9 | cheB | — | — | Chemotaxis response regulator protein-glutamate methylesterase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1087546 | 1089564 | + | GENE_01079 | Prodigal: 2.6 | CDS | 2.7.13.3 | — | — | — | P29072 | cheA | — | — | Chemotaxis protein CheA |
| Contig1 | 1089587 | 1090060 | + | GENE_01080 | Prodigal: 2.6 | CDS | — | — | — | — | P39802 | cheW | — | — | Chemotaxis protein CheW |
| Contig1 | 1090076 | 1090705 | + | GENE_01081 | Prodigal: 2.6 | CDS | 3.-.-.- | — | — | — | P40403 | cheC | — | — | CheY-P phosphatase CheC |
| Contig1 | 1090702 | 1091202 | + | GENE_01082 | Prodigal: 2.6 | CDS | 3.5.1.44 | — | — | — | P40404 | cheD | — | — | Chemoreceptor glutamine deamidase CheD |
| Contig1 | 1091229 | 1091918 | + | GENE_01083 | Prodigal: 2.6 | CDS | — | — | — | — | P10726 | sigD | — | — | RNA polymerase sigma-D factor |
| Contig1 | 1092021 | 1092494 | + | GENE_01084 | Prodigal: 2.6 | CDS | — | — | — | — | — | — | — | — | hypothetical protein |
| Contig1 | 1092638 | 1093378 | + | GENE_01085 | Prodigal: 2.6 | CDS | — | — | — | — | P21464 | rpsB | — | — | 30S ribosomal protein S2 |
| Contig1 | 1093478 | 1094359 | + | GENE_01086 | Prodigal: 2.6 | CDS | — | — | — | — | P80700 | tsf | — | — | Elongation factor Ts |
| Contig1 | 1094505 | 1095227 | + | GENE_01087 | Prodigal: 2.6 | CDS | 2.7.4.22 | — | — | — | O31749 | pyrH | — | — | Uridylate kinase |
| Contig1 | 1095230 | 1095787 | + | GENE_01088 | Prodigal: 2.6 | CDS | — | — | — | — | P81101 | frr | — | — | Ribosome-recycling factor |
| Contig1 | 1095913 | 1096695 | + | GENE_01089 | Prodigal: 2.6 | CDS | 2.5.1.31 | — | — | — | O82827 | uppS | — | — | Ditrans, polycis-undecaprenyl-diphosphate synthase ((2E,6E)-farnesyl-diphosphate specific) |
| Contig1 | 1096708 | 1097496 | + | GENE_01090 | Prodigal: 2.6 | CDS | 2.7.7.41 | — | — | — | P0ABG1 | cdsA | — | — | Phosphatidate cytidylyltransferase |
| Contig1 | 1097552 | 1098703 | + | GENE_01091 | Prodigal: 2.6 | CDS | 1.1.1.267 | — | — | — | Q9RCT1 | dxr | — | — | 1-deoxy-D-xylulose 5-phosphate reductoisomerase |
| Contig1 | 1098716 | 1099978 | + | GENE_01092 | Prodigal: 2.6 | CDS | 3.4.24.- | — | — | — | O31754 | rasP | — | — | Regulator of sigma-W protease RasP |
| Contig1 | 1100010 | 1101704 | + | GENE_01093 | Prodigal: 2.6 | CDS | 6.1.1.15 | — | — | — | Q7A5Y3 | proS | — | — | Proline tRNA ligase |
| Contig1 | 1101816 | 1105079 | + | GENE_01094 | Prodigal: 2.6 | CDS | 2.7.7.7 | — | — | — | P13267 | polC_1 | — | — | DNA polymerase III PolC-type |
| Contig1 | 1105121 | 1106128 | + | GENE_01095 | Prodigal: 2.6 | CDS | 2.7.7.7 | — | — | — | P13267 | polC_2 | — | — | DNA polymerase III PolC-type |
| Contig1 | 1106368 | 1106838 | + | GENE_01096 | Prodigal: 2.6 | CDS | — | — | — | — | P67220 | rimP | — | — | Ribosome maturation factor RimP |
| Contig1 | 1106878 | 1107999 | + | GENE_01097 | Prodigal: 2.6 | CDS | — | PRK09190 | — | — | P0A5M2 | — | — | Transcription termination/antitermination protein NusA | hypothetical protein |
| Contig1 | 1108013 | 1108288 | + | GENE_01098 | Prodigal: 2.6 | CDS | — | — | — | — | — | — | — | — | hypothetical protein |
| Contig1 | 1108290 | 1108592 | + | GENE_01099 | Prodigal: 2.6 | CDS | — | — | — | — | P32729 | rplGA | — | — | putative ribosomal protein YlxQ |
| Contig1 | 1108612 | 1110759 | + | GENE_01100 | Prodigal: 2.6 | CDS | — | — | — | — | P04766 | infB | — | — | Translation initiation factor IF-2 |
| Contig1 | 1110756 | 1111034 | + | GENE_01101 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1111051 | 1111404 | + | GENE_01102 | Prodigal: 2.6 | CDS | — | — | — | — | P65967 | rbfA | — | — | Ribosome-binding factor A |
| Contig1 | 1111488 | 1112417 | + | GENE_01103 | Prodigal: 2.6 | CDS | 5.4.99.25 | — | — | — | P65855 | truB | — | — | tRNA pseudouridine synthase B |
| Contig1 | 1112437 | 1113378 | + | GENE_01104 | Prodigal: 2.6 | CDS | — | — | — | — | P0AG40 | ribF | — | — | Riboflavin biosynthesis protein RibF |
| Contig1 | 1113544 | 1113813 | + | GENE_01105 | Prodigal: 2.6 | CDS | — | — | — | — | P21473 | rpsO | — | — | 30S ribosomal protein S15 |
| Contig1 | 1113988 | 1116111 | + | GENE_01106 | Prodigal: 2.6 | CDS | 27.7.8 | — | — | — | P50849 | pnp | — | — | Polyribonucleotide nucleotidyltransferase |
| Contig1 | 1116224 | 1117183 | + | GENE_01107 | Prodigal: 2.6 | CDS | 3.5.1.- | — | — | — | O34928 | pdaA_2 | — | — | Peptidoglycan-N-acetylmuramic acid deacetylase PdaA precursor |
| Contig1 | 1117223 | 1118458 | + | GENE_01108 | Prodigal: 2.6 | CDS | 3.4.24.55 | — | — | — | P05458 | ptrA | — | — | Protease 3 precursor |
| Contig1 | 1118537 | 1118794 | + | GENE_01109 | Prodigal: 2.6 | CDS | — | — | PF05239.10 | — | — | — | — | — | PRC-barrel domain protein |
| Contig1 | 1118951 | 1119841 | + | GENE_01110 | Prodigal: 2.6 | CDS | 1.3.1.- | — | — | — | Q04809 | dpaA | — | — | Dipicolinate synthase subunit A |
| Contig1 | 1119844 | 1120434 | + | GENE_01111 | Prodigal: 2.6 | CDS | 1.3.1.- | — | — | — | Q04810 | dpaB | — | — | Dipicolinate synthase subunit B |
| Contig1 | 1120569 | 1121609 | + | GENE_01112 | Prodigal: 2.6 | CDS | 1.2.1.11 | — | — | — | Q04797 | asd_2 | — | — | Aspartate-semialdehyde dehydrogenase |
| Contig1 | 1121698 | 1122912 | + | GENE_01113 | Prodigal: 2.6 | CDS | 27.2.4 | — | — | — | P08495 | lysC_1 | — | — | Aspartokinase 2 |
| Contig1 | 1122943 | 1123812 | + | GENE_01114 | Prodigal: 2.6 | CDS | 4.3.3.7 | — | — | — | Q04796 | dapA_1 | — | — | 4-hydroxy-tetrahydrodipicolinate synthase |
| Contig1 | 1123958 | 1125658 | + | GENE_01115 | Prodigal: 2.6 | CDS | 3.1.-.- | — | — | — | O31760 | rnjB | — | — | Ribonuclease J 2 |
| Contig1 | 1125786 | 1126511 | + | GENE_01116 | Prodigal: 2.6 | CDS | — | — | — | — | Q99171 | tepA | — | — | Translocation-enhancing protein TepA |
| Contig1 | 1126508 | 1126717 | + | GENE_01117 | Prodigal: 2.6 | CDS | — | — | — | — | — | — | — | — | hypothetical protein |
| Contig1 | 1126852 | 1129212 | + | GENE_01118 | Prodigal: 2.6 | CDS | — | — | — | — | P21458 | spoIIIE | — | — | DNA translocase SpoIIIE |
| Contig1 | 1129337 | 1130062 | + | GENE_01119 | Prodigal: 2.6 | CDS | — | — | — | — | O34817 | yvoA_1 | — | — | HTH-type transcriptional repressor YvoA |
| Contig1 | 1130253 | 1131404 | + | GENE_01120 | Prodigal: 2.6 | CDS | — | — | — | — | O31762 | ymfD | — | — | Bacillibactin exporter |
| Contig1 | 1131506 | 1131961 | + | GENE_01121 | Prodigal: 2.6 | CDS | — | — | — | — | O32181 | yusO_2 | — | — | putative HTH-type transcriptional regulator YusO |
| Contig1 | 1131961 | 1135080 | + | GENE_01122 | Prodigal: 2.6 | CDS | — | — | — | — | P96706 | ydgH | — | — | Putative membrane protein YdgH |
| Contig1 | 1135232 | 1136512 | + | GENE_01123 | Prodigal: 2.6 | CDS | — | — | — | — | P71007 | albE | — | — | Antilisterial bacteriocin subtilosin biosynthesis protein AlbE |
| Contig1 | 1136509 | 1137795 | + | GENE_01124 | Prodigal: 2.6 | CDS | 3.4.24.- | — | — | — | P71006 | albF | — | — | Putative zinc protease AlbF |
| Contig1 | 1137854 | 1138582 | + | GENE_01125 | Prodigal: 2.6 | CDS | 1.1.1.100 | — | — | — | O67610 | fabG_2 | — | — | 3-oxoacyl-[acyl-carrier-protein] reductase FabG |
| Contig1 | 1138657 | 1138914 | + | GENE_01126 | Prodigal: 2.6 | CDS | — | — | — | — | — | — | — | — | hypothetical protein |
| Contig1 | 1139042 | 1139833 | + | GENE_01127 | Prodigal: 2.6 | CDS | — | — | PF01842.19 | — | — | — | — | — | ACT domain protein |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1139852 | 1140778 | + | GENE_01128 | Prodigal: 2.6 | CDS | — | PRK10856 | — | — | — | — | — | — | cytoskeletal protein RodZ |
| Contig1 | 1140825 | 1141406 | + | GENE_01129 | Prodigal: 2.6 | CDS | 27.8.5 | — | — | — | P63756 | pgsA_1 | — | — | CDP-diacylglycerol--glycerol-3-phosphate 3-phosphatidyltransferase |
| Contig1 | 1141424 | 1142674 | + | GENE_01130 | Prodigal: 2.6 | CDS | — | — | — | — | P54184 | cinA | — | — | Putative competence-damage inducible protein |
| Contig1 | 1142845 | 1143888 | + | GENE_01131 | Prodigal: 2.6 | CDS | — | — | — | MF_00268 | — | recA | — | — | Protein RecA |
| Contig1 | 1144056 | 1145237 | + | GENE_01132 | Prodigal: 2.6 | CDS | — | — | — | — | O31773 | pbpX_2 | — | — | Putative penicillin-binding protein PbpX |
| Contig1 | 1145530 | 1147089 | + | GENE_01133 | Prodigal: 2.6 | CDS | 3.1.-.- | — | — | — | — | rny | — | — | Ribonuclease Y |
| Contig1 | 1147150 | 1147944 | + | GENE_01134 | Prodigal: 2.6 | CDS | — | — | PF00149.22 | — | O31774 | — | — | — | Calcineurin-like phosphoesterase |
| Contig1 | 1148144 | 1148404 | + | GENE_01135 | Prodigal: 2.6 | CDS | — | — | — | — | P45693 | spoVS | — | — | Stage V sporulation protein S |
| Contig1 | 1148662 | 1149708 | + | GENE_01136 | Prodigal: 2.6 | CDS | 1.1.1.103 | — | — | — | Q5SKS4 | tdh | — | — | L-threonine 3-dehydrogenase |
| Contig1 | 1149724 | 1150899 | + | GENE_01137 | Prodigal: 2.6 | CDS | 2.3.1.29 | — | — | — | Q5SHZ8 | — | — | — | 8-amino-7-oxononanoate synthase/2-amino-3-ketobutyrate coenzyme A ligase |
| Contig1 | 1151042 | 1152571 | + | GENE_01138 | Prodigal: 2.6 | CDS | 2.-.-.- | — | — | — | O31778 | miaB | — | — | (Dimethylallyl)adenosine tRNA methylthiotransferase MiaB |
| Contig1 | 1152574 | 1153005 | + | GENE_01139 | Prodigal: 2.6 | CDS | — | — | — | — | — | — | — | — | hypothetical protein |
| Contig1 | 1153259 | 1153804 | + | GENE_01140 | Prodigal: 2.6 | CDS | — | — | — | — | P14016 | cotE | — | — | Spore coat protein E |
| Contig1 | 1153920 | 1156508 | + | GENE_01141 | Prodigal: 2.6 | CDS | — | — | — | — | Q93I88 | mutS | — | — | DNA mismatch repair protein MutS |
| Contig1 | 1156524 | 1158401 | + | GENE_01142 | Prodigal: 2.6 | CDS | — | — | — | — | P49850 | mutL | — | — | DNA mismatch repair protein MutL |
| Contig1 | 1158413 | 1158775 | - | GENE_01143 | Prodigal: 2.6 | CDS | — | — | — | — | — | — | — | — | hypothetical protein |
| Contig1 | 1159533 | 1160291 | - | GENE_01144 | Prodigal: 2.6 | CDS | — | — | — | — | — | — | — | — | hypothetical protein |
| Contig1 | 1160592 | 1160909 | + | GENE_01145 | Prodigal: 2.6 | CDS | — | — | — | — | — | — | — | — | hypothetical protein |
| Contig1 | 1160906 | 1161442 | + | GENE_01146 | Prodigal: 2.6 | CDS | — | — | — | — | — | — | — | — | hypothetical protein |
| Contig1 | 1162106 | 1162231 | - | GENE_01147 | Prodigal: 2.6 | CDS | — | — | — | — | — | — | — | — | hypothetical protein |
| Contig1 | 1162577 | 1162786 | - | GENE_01148 | Prodigal: 2.6 | CDS | — | — | — | — | — | — | — | — | hypothetical protein |
| Contig1 | 1163404 | 1164096 | + | GENE_01149 | Prodigal: 2.6 | CDS | 3.-.-.- | — | — | — | A7Z4X7 | baeB | — | — | putative polyketide biosynthesis zinc-dependent hydrolase BaeB |
| Contig1 | 1164411 | 1165280 | + | GENE_01150 | Prodigal: 2.6 | CDS | 2.3.1.39 | — | — | — | A7Z4X8 | baeC | — | — | Polyketide biosynthesis malonyl CoA-acyl carrier protein transacylase BaeC |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1165417 | 1166391 | + | GENE_01151 | Prodigal: 2.6 | CDS | — | — | — | — | A7Z4X9 | — | — | Polyketide biosynthesis acyl-transferase homolog BaeD | hypothetical protein |
| Contig1 | 1166393 | 1168633 | + | GENE_01152 | Prodigal: 2.6 | CDS | — | — | — | — | A7Z4Y0 | baeE_2 | — | — | Polyketide biosynthesis protein BaeE |
| Contig1 | 1168699 | 1168947 | + | GENE_01153 | Prodigal: 2.6 | CDS | — | — | — | — | Q7PC63 | acpK | — | — | Polyketide biosynthesis acyl-carrier-protein AcpK |
| Contig1 | 1168998 | 1170260 | + | GENE_01154 | Prodigal: 2.6 | CDS | 2.3.3.- | — | — | — | P40830 | pksG_1 | — | — | Polyketide biosynthesis 3-hydroxy-3-methylglutaryl-ACP synthase PksG |
| Contig1 | 1170257 | 1171030 | + | GENE_01155 | Prodigal: 2.6 | CDS | 4.2.1.- | — | — | — | P40805 | pksH | — | — | putative polyketide biosynthesis enoyl-CoA hydratase PksH |
| Contig1 | 1171040 | 1171789 | + | GENE_01156 | Prodigal: 2.6 | CDS | 4.-.-.- | — | — | — | P40802 | pksL_1 | — | — | Putative polyketide biosynthesis enoyl-CoA isomerase PksI |
| Contig1 | 1171829 | 1172773 | + | GENE_01157 | Prodigal: 2.6 | CDS | — | — | — | — | P40806 | pksJ_4 | — | — | Polyketide synthase PksJ |
| Contig1 | 1172758 | 1186776 | + | GENE_01158 | Prodigal: 2.6 | CDS | — | — | — | — | P40806 | pksJ_5 | — | — | Polyketide synthase PksJ |
| Contig1 | 1186778 | 1200205 | + | GENE_01159 | Prodigal: 2.6 | CDS | — | — | — | — | Q05470 | pksL_5 | — | — | Polyketide synthase PksL |
| Contig1 | 1200223 | 1210764 | + | GENE_01160 | Prodigal: 2.6 | CDS | — | — | — | — | P40872 | pksM_1 | — | — | Polyketide synthase PksM |
| Contig1 | 1210754 | 1227061 | + | GENE_01161 | Prodigal: 2.6 | CDS | 2.3.1.- | — | — | — | O31782 | pksN_2 | — | — | Polyketide synthase PksN |
| Contig1 | 1227075 | 1234532 | + | GENE_01162 | Prodigal: 2.6 | CDS | 2.3.1.- | — | — | — | O31784 | pksR_1 | — | — | Polyketide synthase PksR |
| Contig1 | 1234667 | 1235878 | - | GENE_01163 | Prodigal: 2.6 | CDS | 1.14.-.- | — | — | — | P33271 | — | — | — | Cytochrome P450 107B1 |
| Contig1 | 1236167 | 1236601 | + | GENE_01164 | Prodigal: 2.6 | CDS | 3.-.-.- | — | — | — | P42983 | nucB_1 | — | — | Sporulation-specific extracellular nuclease precursor |
| Contig1 | 1236721 | 1237416 | + | GENE_01165 | Prodigal: 2.6 | CDS | — | — | — | — | — | — | — | — | hypothetical protein |
| Contig1 | 1237450 | 1237812 | - | GENE_01166 | Prodigal: 2.6 | CDS | — | — | — | — | — | — | — | — | hypothetical protein |
| Contig1 | 1238005 | 1239333 | + | GENE_01167 | Prodigal: 2.6 | CDS | 3.4.21.- | — | — | — | O31788 | aprX | — | — | Serine protease AprX |
| Contig1 | 1239512 | 1239745 | + | GENE_01168 | Prodigal: 2.6 | CDS | — | — | — | — | — | — | — | — | hypothetical protein |
| Contig1 | 1240001 | 1240708 | + | GENE_01169 | Prodigal: 2.6 | CDS | — | — | — | — | — | — | — | — | hypothetical protein |
| Contig1 | 1240769 | 1241221 | + | GENE_01170 | Prodigal: 2.6 | CDS | — | — | PF02566.13 | — | — | — | — | — | OsmC-like protein |
| Contig1 | 1241235 | 1241588 | - | GENE_01171 | Prodigal: 2.6 | CDS | — | — | — | — | P0CW83 | ebrB | — | — | Multidrug resistance protein EbrB |
| Contig1 | 1241605 | 1241937 | - | GENE_01172 | Prodigal: 2.6 | CDS | — | — | — | — | P0CW81 | ebrA | — | — | Multidrug resistance protein EbrA |
| Contig1 | 1242058 | 1242363 | - | GENE_01173 | Prodigal: 2.6 | CDS | — | — | — | — | — | — | — | — | hypothetical protein |
| Contig1 | 1242464 | 1242868 | + | GENE_01174 | Prodigal: 2.6 | CDS | — | — | PF12788.1 | — | — | — | — | — | YmaF family protein |
| Contig1 | 1242967 | 1243911 | + | GENE_01175 | Prodigal: 2.6 | CDS | 2.5.1.75 | — | — | — | Q9KAC3 | miaA | — | — | tRNA dimethylallyltransferase |
| Contig1 | 1243951 | 1244172 | + | GENE_01176 | Prodigal: 2.6 | CDS | — | — | — | — | O31796 | hfq | — | — | RNA-binding protein Hfq |
| Contig1 | 1244269 | 1244544 | + | GENE_01177 | Prodigal: 2.6 | CDS | — | — | — | — | — | — | — | — | hypothetical protein |
| Contig1 | 1244627 | 1244842 | + | GENE_01178 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1245102 | 1245494 | + | GENE_01179 | Prodigal: 2.6 | CDS | 1.17.4.1 | — | — | MF_00128 | P0CH00 | nrdI | — | — | Protein NrdI |
| Contig1 | 1245454 | 1247556 | + | GENE_01180 | Prodigal: 2.6 | CDS | 1.17.4.1 | — | — | — | — | nrdE2 | — | — | Ribonucleoside-diphosphate reductase subunit alpha 2 |
| Contig1 | 1247574 | 1248563 | + | GENE_01181 | Prodigal: 2.6 | CDS | 1.17.4.1 | — | — | — | P50621 | nrdF | — | — | Ribonucleoside-diphosphate reductase subunit beta |
| Contig1 | 1248612 | 1249232 | + | GENE_01182 | Prodigal: 2.6 | CDS | — | — | — | — | — | — | — | — | hypothetical protein |
| Contig1 | 1249282 | 1250040 | − | GENE_01183 | Prodigal: 2.6 | CDS | 3.5.1.28 | — | — | — | Q06320 | cwlC | — | — | Sporulation-specific N-acetylmuramoyl-L-alanine amidase |
| Contig1 | 1250347 | 1251315 | + | GENE_01184 | Prodigal: 2.6 | CDS | — | — | — | — | P27643 | spoVK | — | — | Stage V sporulation protein K |
| Contig1 | 1251445 | 1252707 | + | GENE_01185 | Prodigal: 2.6 | CDS | — | — | — | — | P25519 | hflX | — | — | GTPase HflX |
| Contig1 | 1252724 | 1253989 | + | GENE_01186 | Prodigal: 2.6 | CDS | 4.4.1.11 | — | — | — | P13254 | mdeA | — | — | Methionine gamma-lyase |
| Contig1 | 1254099 | 1254503 | + | GENE_01187 | Prodigal: 2.6 | CDS | — | — | — | — | P37582 | glnR | — | — | HTH-type transcriptional regulator GlnR |
| Contig1 | 1254561 | 1255895 | + | GENE_01188 | Prodigal: 2.6 | CDS | 6.3.1.2 | — | — | — | P12425 | glnA | — | — | Glutamine synthetase |
| Contig1 | 1256122 | 1257216 | − | GENE_01189 | Prodigal: 2.6 | CDS | — | — | PF03022.10 | — | — | — | — | — | Major royal jelly protein |
| Contig1 | 1257763 | 1259154 | + | GENE_01190 | Prodigal: 2.6 | CDS | — | — | — | — | P0CE45 | uidB | — | — | Glucuronide carrier protein |
| Contig1 | 1259197 | 1260798 | + | GENE_01191 | Prodigal: 2.6 | CDS | 3.2.1.37 | — | — | — | P94489 | xynB | — | — | Beta-xylosidase |
| Contig1 | 1260961 | 1262115 | − | GENE_01192 | Prodigal: 2.6 | CDS | — | — | — | — | P0AF20 | nagC | — | — | N-acetylglucosamine repressor |
| Contig1 | 1262379 | 1263716 | + | GENE_01193 | Prodigal: 2.6 | CDS | 5.3.1.5 | — | — | — | P54273 | xylA | — | — | Xylose isomerase |
| Contig1 | 1263850 | 1265349 | + | GENE_01194 | Prodigal: 2.6 | CDS | 2.7.1.17 | — | — | — | P35850 | xylB_1 | — | — | Xylulose kinase |
| Contig1 | 1265812 | 1268133 | + | GENE_01195 | Prodigal: 2.6 | CDS | 2.7.9.2 | — | — | — | Q9K0I2 | ppsA_1 | — | — | Phosphoenolpyruvate synthase |
| Contig1 | 1268962 | 1269060 | − | GENE_01196 | Prodigal: 2.6 | CDS | — | — | PF09680.4 | — | — | — | — | — | Protein of unknown function (Tiny_TM_bacill) |
| Contig1 | 1269874 | 1270059 | − | GENE_01197 | Prodigal: 2.6 | CDS | — | — | — | — | — | — | — | — | hypothetical protein |
| Contig1 | 1270304 | 1271320 | − | GENE_01198 | Prodigal: 2.6 | CDS | 1.1.1.1 | — | — | — | Q7A742 | adh | — | — | Alcohol dehydrogenase |
| Contig1 | 1271921 | 1272385 | + | GENE_01199 | Prodigal: 2.6 | CDS | — | — | — | — | — | — | — | — | hypothetical protein |
| Contig1 | 1272418 | 1273056 | + | GENE_01200 | Prodigal: 2.6 | CDS | — | — | — | — | — | — | — | — | hypothetical protein |
| Contig1 | 1273557 | 1274318 | + | GENE_01201 | Prodigal: 2.6 | CDS | — | PRK10809 | PF00583.18 | — | — | — | — | — | Acetyltransferase (GNAT) family protein |
| Contig1 | 1274536 | 1275078 | + | GENE_01202 | Prodigal: 2.6 | CDS | — | — | — | — | — | — | — | — | ribosomal-protein-S5-alanine N-acetyltransferase |
| Contig1 | 1275729 | 1276361 | + | GENE_01203 | Prodigal: 2.6 | CDS | — | — | — | — | — | — | — | — | hypothetical protein |
| Contig1 | 1276587 | 1277660 | + | GENE_01204 | Prodigal: 2.6 | CDS | 1.14.13.107 | — | — | — | Q9EUT9 | limB_1 | — | — | Limonene 1,2-monooxygenase |
| Contig1 | 1277874 | 1278494 | + | GENE_01205 | Prodigal: 2.6 | CDS | — | — | — | — | Q9KLD5 | gbpA | — | — | GlcNAc-binding protein A precursor |
| Contig1 | 1278659 | 1278757 | − | GENE_01206 | Prodigal: 2.6 | CDS | — | — | PF09680.4 | — | — | — | — | — | Protein of unknown function (Tiny_TM_bacill) |
| Contig1 | 1279030 | 1279533 | − | GENE_01207 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1279546 | 1280082 | − | GENE_01208 | Prodigal: 2.6 | CDS | — | — | — | — | O32211 | yvgO_1 | — | — | Stress response protein YvgO precursor |
| Contig1 | 1280367 | 1280513 | — | GENE_01209 | Prodigal: 2.6 | CDS | — | — | — | — | — | — | — | — | hypothetical protein |
| Contig1 | 1280682 | 1283099 | — | GENE_01210 | Prodigal: 2.6 | CDS | — | — | PF12708.1 | — | — | — | — | — | Pectate lyase superfamily protein |
| Contig1 | 1283477 | 1283911 | + | GENE_01211 | Prodigal: 2.6 | CDS | 3.6.1.23 | — | — | — | O31801 | yncF | — | — | putative deoxyuridine 5′-triphosphate nucleotidohydrolase YncF |
| Contig1 | 1284187 | 1285008 | + | GENE_01212 | Prodigal: 2.6 | CDS | — | — | — | — | — | — | — | — | hypothetical protein |
| Contig1 | 1285117 | 1285266 | + | GENE_01213 | Prodigal: 2.6 | CDS | — | — | — | — | — | — | — | — | hypothetical protein |
| Contig1 | 1285253 | 1286083 | + | GENE_01214 | Prodigal: 2.6 | CDS | — | — | PF01145.19 | — | — | — | — | — | SPFH domain/Band 7 family protein |
| Contig1 | 1286111 | 1286560 | − | GENE_01215 | Prodigal: 2.6 | CDS | — | — | — | — | — | — | — | — | hypothetical protein |
| Contig1 | 1286702 | 1287130 | + | GENE_01216 | Prodigal: 2.6 | CDS | — | — | — | — | — | — | — | — | hypothetical protein |
| Contig1 | 1287469 | 1288089 | + | GENE_01217 | Prodigal: 2.6 | CDS | 3.4.21.88 | — | — | — | P31080 | lexA | — | — | LexA repressor |
| Contig1 | 1288246 | 1288557 | + | GENE_01218 | Prodigal: 2.6 | CDS | — | — | — | — | Q45056 | yneA | — | — | Cell division suppressor protein YneA |
| Contig1 | 1288573 | 1289223 | + | GENE_01219 | Prodigal: 2.6 | CDS | — | — | — | — | Q45057 | — | — | Resolvase homolog YneB | hypothetical protein |
| Contig1 | 1289292 | 1289525 | + | GENE_01220 | Prodigal: 2.6 | CDS | — | — | — | — | — | — | — | — | hypothetical protein |
| Contig1 | 1289692 | 1291695 | + | GENE_01221 | Prodigal: 2.6 | CDS | 2.2.1.1 | PRK02539 | — | — | P99161 | tkt | — | — | Transketolase |
| Contig1 | 1291847 | 1292293 | + | GENE_01222 | Prodigal: 2.6 | CDS | — | — | — | — | P45707 | sirA | — | — | Sporulation inhibitor of replication protein SirA |
| Contig1 | 1292379 | 1292597 | + | GENE_01223 | Prodigal: 2.6 | CDS | — | — | — | — | — | — | — | — | hypothetical protein |
| Contig1 | 1292671 | 1292844 | − | GENE_01224 | Prodigal: 2.6 | CDS | 3.1.3.- | PRK01844 | — | — | O31819 | ynzD | — | — | Aspartyl-phosphate phosphatase YnzD |
| Contig1 | 1293049 | 1293753 | + | GENE_01225 | Prodigal: 2.6 | CDS | — | — | PF02683.9 | — | — | — | — | — | Cytochrome C biogenesis protein transmembrane region |
| Contig1 | 1293838 | 1293987 | + | GENE_01226 | Prodigal: 2.6 | CDS | — | — | — | — | Q56312 | cheY_2 | — | — | Chemotaxis protein CheY |
| Contig1 | 1293984 | 1294199 | + | GENE_01227 | Prodigal: 2.6 | CDS | — | — | — | — | Q56312 | cheY_3 | — | — | Chemotaxis protein CheY |
| Contig1 | 1294288 | 1294770 | − | GENE_01228 | Prodigal: 2.6 | CDS | — | — | — | — | — | — | — | — | hypothetical protein |
| Contig1 | 1294798 | 1295226 | + | GENE_01229 | Prodigal: 2.6 | CDS | — | — | — | — | — | — | — | — | hypothetical protein |
| Contig1 | 1295460 | 1295831 | − | GENE_01230 | Prodigal: 2.6 | CDS | — | — | — | — | Q45058 | cotM | — | — | Spore coat protein M |
| Contig1 | 1295926 | 1296072 | − | GENE_01231 | Prodigal: 2.6 | CDS | — | — | — | — | P71032 | sspP | — | — | Small, acid-soluble spore protein P |
| Contig1 | 1296102 | 1296248 | − | GENE_01233 | Prodigal: 2.6 | CDS | — | — | — | — | P71031 | sspO | — | — | Small, acid-soluble spore protein O |
| Contig1 | 1296480 | 1299206 | + | GENE_01234 | Prodigal: 2.6 | CDS | 4.2.1.3 | — | — | — | P09339 | citB | — | — | Aconitate hydratase |
| Contig1 | 1299268 | 1299777 | + | GENE_01235 | Prodigal: 2.6 | CDS | — | — | — | — | Q81SZ9 | resA_1 | — | — | Thiol-disulfide oxidoreductase ResA |
| Contig1 | 1299856 | 1299981 | + | GENE_01236 | Prodigal: 2.6 | CDS | — | — | — | — | — | — | — | — | hypothetical protein |
| Contig1 | 1300045 | 1300191 | + | GENE_01237 | Prodigal: 2.6 | CDS | — | — | — | — | Q7WY69 | sspN | — | — | Small, acid-soluble spore protein N |
| Contig1 | 1300216 | 1300458 | + | GENE_01237 | Prodigal: 2.6 | CDS | — | — | — | — | Q45060 | tip | — | — | Small, acid-soluble spore protein Tip |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1300545 | 1300961 | + | GENE_01238 | Prodigal: 2.6 | CDS | 3.1.2.- | — | — | — | P0A8Z3 | ybgC | — | — | Acyl-CoA thioester hydrolase YbgC |
| Contig1 | 1300977 | 1301276 | + | GENE_01239 | Prodigal: 2.6 | CDS | — | — | PF01521.14 | — | — | — | — | — | hypothetical protein |
| Contig1 | 1301306 | 1301593 | — | GENE_01240 | Prodigal: 2.6 | CDS | — | — | — | — | — | — | — | — | Iron-sulphur cluster biosynthesis |
| Contig1 | 1301682 | 1302263 | — | GENE_01241 | Prodigal: 2.6 | CDS | 2.3.1.- | — | — | — | Q45064 | plsY | — | — | Glycerol-3-phosphate acyltransferase |
| Contig1 | 1302415 | 1302822 | + | GENE_01242 | Prodigal: 2.6 | CDS | — | — | — | — | — | — | — | — | hypothetical protein |
| Contig1 | 1303247 | 1305214 | + | GENE_01243 | Prodigal: 2.6 | CDS | 5.99.1.3 | — | — | — | P66939 | parE | — | — | DNA topoisomerase 4 subunit B |
| Contig1 | 1305217 | 1307640 | + | GENE_01244 | Prodigal: 2.6 | CDS | 5.99.1.3 | — | — | — | Q93KF4 | parC | — | — | DNA topoisomerase 4 subunit A |
| Contig1 | 1307687 | 1307812 | — | GENE_01245 | Prodigal: 2.6 | CDS | — | — | — | — | — | — | — | — | hypothetical protein |
| Contig1 | 1307837 | 1308190 | — | GENE_01246 | Prodigal: 2.6 | CDS | — | — | — | — | — | — | — | — | hypothetical protein |
| Contig1 | 1308567 | 1309985 | + | GENE_01247 | Prodigal: 2.6 | CDS | — | — | — | — | Q45068 | alsT_1 | — | — | Amino-acid carrier protein AlsT |
| Contig1 | 1310189 | 1311145 | + | GENE_01248 | Prodigal: 2.6 | CDS | 2.7.1.45 | — | — | — | Q53W83 | kdgK | — | — | 2-dehydro-3-deoxygluconokinase |
| Contig1 | 1311175 | 1312194 | + | GENE_01249 | Prodigal: 2.6 | CDS | 1.-.-.- | — | — | — | O35045 | yjmD | — | — | putative zinc-type alcohol dehydrogenase-like protein YjmD |
| Contig1 | 1312208 | 1312693 | + | GENE_01250 | Prodigal: 2.6 | CDS | — | — | — | — | P50846 | kdgA | — | — | KHG/KDPG aldolase |
| Contig1 | 1312699 | 1313469 | + | GENE_01251 | Prodigal: 2.6 | CDS | 4.2.1.8 | — | — | — | O34346 | uxuA_1 | — | — | Mannonate dehydratase |
| Contig1 | 1313584 | 1313919 | + | GENE_01252 | Prodigal: 2.6 | CDS | 4.2.1.8 | — | — | — | O34346 | uxuA_2 | — | — | Mannonate dehydratase |
| Contig1 | 1313916 | 1314752 | + | GENE_01253 | Prodigal: 2.6 | CDS | 1.-.-.- | — | — | — | O34896 | uxuB | — | — | putative oxidoreductase UxuB |
| Contig1 | 1314836 | 1315837 | + | GENE_01254 | Prodigal: 2.6 | CDS | — | — | — | — | P50844 | kdgR | — | — | HTH-type transcriptional regulator KdgR |
| Contig1 | 1315904 | 1316368 | + | GENE_01255 | Prodigal: 2.6 | CDS | — | — | — | — | O34456 | exuT_1 | — | — | Hexuronate transporter |
| Contig1 | 1316365 | 1317177 | + | GENE_01256 | Prodigal: 2.6 | CDS | — | — | — | — | O34456 | exuT_2 | — | — | Hexuronate transporter |
| Contig1 | 1317296 | 1318111 | + | GENE_01257 | Prodigal: 2.6 | CDS | — | — | — | — | — | — | — | — | hypothetical protein |
| Contig1 | 1318108 | 1318716 | + | GENE_01258 | Prodigal: 2.6 | CDS | — | — | — | — | — | — | — | — | hypothetical protein |
| Contig1 | 1318710 | 1320338 | + | GENE_01259 | Prodigal: 2.6 | CDS | — | — | — | — | — | — | — | — | hypothetical protein |
| Contig1 | 1321270 | 1322406 | — | GENE_01260 | Prodigal: 2.6 | CDS | — | — | PF03403.1 | — | — | — | — | — | hypothetical protein isoform II |
| Contig1 | 1322603 | 1324102 | + | GENE_01261 | Prodigal: 2.6 | CDS | 3.2.1.4 | — | — | — | P10475 | eglS | — | — | Endoglucanase precursor |
| Contig1 | 1324566 | 1324877 | + | GENE_01262 | Prodigal: 2.6 | CDS | — | — | — | — | — | — | — | — | hypothetical protein |
| Contig1 | 1324927 | 1326327 | — | GENE_01263 | Prodigal: 2.6 | CDS | 2.7.13.3 | — | — | — | Q45614 | yycG_1 | — | — | Sensor histidine kinase YycG |
| Contig1 | 1326330 | 1327037 | — | GENE_01264 | Prodigal: 2.6 | CDS | — | — | — | — | P39663 | sphR | — | — | Alkaline phosphatase synthesis transcriptional regulatory protein SphR |
| Contig1 | 1327180 | 1328451 | — | GENE_01265 | Prodigal: 2.6 | CDS | 3.2.1.136 | — | — | — | Q45070 | xynC | — | — | Glucuronoxylanase XynC precursor |
| Contig1 | 1328504 | 1329649 | — | GENE_01266 | Prodigal: 2.6 | CDS | 3.2.1.55 | — | — | — | Q45071 | xynD_1 | — | — | Arabinoxylan arabinofuranohydrolase precursor |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1329646 | 1330038 | − | GENE_01267 | Prodigal: 2.6 | CDS | 3.2.1.55 | — | — | — | Q45071 | xynD_2 | — | — | Arabinoxylan arabinofuranohydrolase precursor |
| Contig1 | 1330212 | 1338080 | − | GENE_01268 | Prodigal: 2.6 | CDS | — | — | — | — | Q70LM4 | lgrD_1 | — | — | Linear gramicidin synthase subunit D |
| Contig1 | 1338164 | 1354255 | − | GENE_01269 | Prodigal: 2.6 | CDS | — | — | — | — | P0C064 | grsB | — | — | Gramicidin S synthase 2 |
| Contig1 | 1354300 | 1366248 | − | GENE_01270 | Prodigal: 2.6 | CDS | — | — | — | — | O30409 | tycC | — | — | Tyrocidine synthase 3 |
| Contig1 | 1366268 | 1367470 | − | GENE_01271 | Prodigal: 2.6 | CDS | 2.3.1.39 | — | — | — | Q9R9J2 | fenF_1 | — | — | Malonyl CoA-acyl carrier protein transacylase |
| Contig1 | 1368028 | 1368813 | − | GENE_01272 | Prodigal: 2.6 | CDS | 1.1.1.30 | — | — | — | O86034 | bdhA_1 | — | — | D-beta-hydroxybutyrate dehydrogenase |
| Contig1 | 1368826 | 1369488 | − | GENE_01273 | Prodigal: 2.6 | CDS | 2.8.3.5 | — | — | — | P42316 | scoB_1 | — | — | putative succinyl-CoA:3-ketoacid coenzyme A transferase subunit B |
| Contig1 | 1369506 | 1370189 | − | GENE_01274 | Prodigal: 2.6 | CDS | 2.8.3.5 | — | — | — | P42315 | scoA | — | — | putative succinyl-CoA:3-ketoacid coenzyme A transferase subunit A |
| Contig1 | 1370232 | 1371677 | − | GENE_01275 | Prodigal: 2.6 | CDS | — | PRK09821 | — | — | P53554 | — | — | — | putative transporter |
| Contig1 | 1371980 | 1373176 | − | GENE_01276 | Prodigal: 2.6 | CDS | 1.14.15.12 | — | — | — | — | bioI | — | — | Biotin biosynthesis cytochrome P450 |
| Contig1 | 1373178 | 1374197 | − | GENE_01277 | Prodigal: 2.6 | CDS | 2.8.1.6 | — | — | — | P19206 | bioB_1 | — | — | Biotin synthase |
| Contig1 | 1374200 | 1374901 | − | GENE_01278 | Prodigal: 2.6 | CDS | 6.3.3.3 | — | — | — | P13000 | bioD1 | — | — | ATP-dependent dethiobiotin synthetase BioD 1 |
| Contig1 | 1374898 | 1376058 | − | GENE_01279 | Prodigal: 2.6 | CDS | 2.3.1.47 | — | — | — | P53556 | bioF | — | — | 8-amino-7-oxononanoate synthase 2 |
| Contig1 | 1376048 | 1377394 | − | GENE_01280 | Prodigal: 2.6 | CDS | 2.6.1.- | — | — | — | P53555 | bioK | — | — | L-Lysine-8-amino-7-oxononanoate aminotransferase |
| Contig1 | 1377391 | 1378161 | − | GENE_01281 | Prodigal: 2.6 | CDS | 6.2.1.14 | — | — | — | P22822 | bioW | — | — | 6-carboxyhexanoate--CoA ligase |
| Contig1 | 1378440 | 1378847 | + | GENE_01282 | Prodigal: 2.6 | CDS | — | — | PF04138.8 | — | — | — | — | — | GtrA-like protein |
| Contig1 | 1378854 | 1379747 | + | GENE_01283 | Prodigal: 2.6 | CDS | 2.7.7.9 | — | — | — | Q05852 | gtaB_1 | — | — | UTP--glucose-1-phosphate uridylyltransferase |
| Contig1 | 1379822 | 1380412 | + | GENE_01284 | Prodigal: 2.6 | CDS | — | — | — | — | P30149 | yabI | — | — | Inner membrane protein YabI |
| Contig1 | 1380465 | 1381994 | − | GENE_01285 | Prodigal: 2.6 | CDS | 2.1.3.1 | — | — | — | Q8GBW6 | — | — | — | Methylmalonyl-CoA carboxyltransferase 12S subunit |
| Contig1 | 1382012 | 1382791 | − | GENE_01286 | Prodigal: 2.6 | CDS | 4.2.1.17 | — | — | — | P64016 | echA8 | — | — | putative enoyl-CoA hydratase echA8 |
| Contig1 | 1382805 | 1383704 | − | GENE_01287 | Prodigal: 2.6 | CDS | 4.1.3.4 | — | — | — | O34873 | yngG | — | — | Hydroxymethylglutaryl-CoA lyase YngG |
| Contig1 | 1383720 | 1383932 | − | GENE_01288 | Prodigal: 2.6 | CDS | — | — | — | — | C0H419 | yngHB | — | — | Biotin/lipoyl attachment protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1383929 | 1385278 | − | GENE_01289 | Prodigal: 2.6 | CDS | 6.4.1.7 | — | — | — | D3DJ42 | cfiB_2 | — | — | 2-oxoglutarate carboxylase small subunit |
| Contig1 | 1385300 | 1386940 | − | GENE_01290 | Prodigal: 2.6 | CDS | 6.2.1.3 | — | — | — | O07610 | lcfB_2 | — | — | Long-chain-fatty-acid-CoA ligase |
| Contig1 | 1386985 | 1388127 | − | GENE_01291 | Prodigal: 2.6 | CDS | 1.3.99.- | — | — | — | P45867 | acdA | — | — | Acyl-CoA dehydrogenase |
| Contig1 | 1388268 | 1389806 | − | GENE_01292 | Prodigal: 2.6 | CDS | — | — | — | — | — | — | — | — | hypothetical protein |
| Contig1 | 1389928 | 1390308 | − | GENE_01293 | Prodigal: 2.6 | CDS | — | — | — | — | O31623 | yjcA_2 | — | — | Sporulation protein YjcA |
| Contig1 | 1390384 | 1394187 | − | GENE_01294 | Prodigal: 2.6 | CDS | 2.3.1.- | — | — | — | O31827 | PPsE | — | — | Plipastatin synthase subunit E |
| Contig1 | 1394206 | 1404981 | − | GENE_01295 | Prodigal: 2.6 | CDS | 2.3.1.- | — | — | — | P94459 | ppsD | — | — | Plipastatin synthase subunit D |
| Contig1 | 1405007 | 1410124 | − | GENE_01296 | Prodigal: 2.6 | CDS | 2.3.1.- | — | — | — | P39847 | ppsC_1 | — | — | Plipastatin synthase subunit C |
| Contig1 | 1410184 | 1412655 | − | GENE_01297 | Prodigal: 2.6 | CDS | 2.3.1.- | — | — | — | P39847 | ppsC_2 | — | — | Plipastatin synthase subunit C |
| Contig1 | 1412671 | 1420368 | − | GENE_01298 | Prodigal: 2.6 | CDS | 2.3.1.- | — | — | — | P39846 | ppsB_1 | — | — | Plipastatin synthase subunit B |
| Contig1 | 1420394 | 1428052 | − | GENE_01299 | Prodigal: 2.6 | CDS | 2.3.1.- | — | — | — | P39845 | ppsA_2 | — | — | Plipastatin synthase subunit A |
| Contig1 | 1428532 | 1430007 | − | GENE_01300 | Prodigal: 2.6 | CDS | 3.4.16.4 | — | — | — | P39844 | dacC | — | — | D-alanyl-D-alanine carboxypeptidase DacC precursor |
| Contig1 | 1430025 | 1431000 | − | GENE_01301 | Prodigal: 2.6 | CDS | 5.1.3.3 | — | — | — | P39840 | galM | — | — | Aldose 1-epimerase |
| Contig1 | 1431110 | 1432498 | − | GENE_01302 | Prodigal: 2.6 | CDS | — | — | — | — | Q7A7N0 | mepA | — | — | Multidrug export protein MepA |
| Contig1 | 1432727 | 1433269 | + | GENE_01303 | Prodigal: 2.6 | CDS | — | — | — | — | — | — | — | — | hypothetical protein |
| Contig1 | 1433415 | 1433487 | − | GENE_01304 | Aragorn: 1.2 | tRNA | — | — | — | — | — | — | — | — | tRNA-Arg(cct) |
| Contig1 | 1433530 | 1434075 | − | GENE_01305 | Prodigal: 2.6 | CDS | — | — | — | MF_01808 | — | xerC_2 | — | — | Tyrosine recombinase XerC |
| Contig1 | 1434391 | 1434621 | − | GENE_01306 | Prodigal: 2.6 | CDS | — | — | PF12728.1 | — | — | — | — | — | Helix-turn-helix domain protein |
| Contig1 | 1434865 | 1436640 | + | GENE_01307 | Prodigal: 2.6 | CDS | 2.32.2 | — | — | — | P54422 | ggt | — | — | Gamma-glutamyltranspeptidase precursor |
| Contig1 | 1436687 | 1437862 | − | GENE_01308 | Prodigal: 2.6 | CDS | — | PRK10141 | — | — | Q797E3 | pbuE_2 | — | — | Purine efflux pump PbuE |
| Contig1 | 1438006 | 1438308 | − | GENE_01309 | Prodigal: 2.6 | CDS | — | — | — | — | — | — | — | — | DNA-binding transcriptional repressor ArsR |
| Contig1 | 1438346 | 1440274 | − | GENE_01310 | Prodigal: 2.6 | CDS | 6.1.1.3 | — | — | — | P18256 | thrZ | — | — | Threonine-tRNA ligase 2 |
| Contig1 | 1440920 | 1441786 | − | GENE_01311 | Prodigal: 2.6 | CDS | — | — | — | — | O34685 | yofA_1 | — | — | HTH-type transcriptional regulator YofA |
| Contig1 | 1441905 | 1442885 | + | GENE_01312 | Prodigal: 2.6 | CDS | 1.3.1.86 | — | — | — | Q82LU9 | ccrA2 | — | — | Crotonyl-CoA reductase |
| Contig1 | 1443261 | 1444742 | − | GENE_01313 | Prodigal: 2.6 | CDS | 1.4.1.13 | — | — | — | O34399 | gltB | — | — | Glutamate synthase [NADPH] small chain |
| Contig1 | 1444759 | 1449318 | − | GENE_01314 | Prodigal: 2.6 | CDS | 1.4.1.13 | — | — | — | P39812 | gltA_2 | — | — | Glutamate synthase [NADPH] large chain |
| Contig1 | 1449455 | 1450366 | + | GENE_01315 | Prodigal: 2.6 | CDS | — | — | — | — | P20668 | gltC_1 | — | — | HTH-type transcriptional regulator GltC |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1450427 | 1451545 | − | GENE_01316 | Prodigal: 2.6 | CDS | 2.7.2.11 | — | — | — | P39820 | proB_2 | — | — | Glutamate 5-kinase 1 |
| Contig1 | 1451570 | 1452367 | − | GENE_01317 | Prodigal: 2.6 | CDS | 1.5.1.2 | — | — | — | P22008 | proC_1 | — | — | Pyrroline-5-carboxylate reductase |
| Contig1 | 1452595 | 1452972 | − | GENE_01318 | Prodigal: 2.6 | CDS | — | — | — | — | P0CI76 | — | — | Replication termination protein | hypothetical protein |
| Contig1 | 1453249 | 1453965 | − | GENE_01319 | Prodigal: 2.6 | CDS | 1.1.1.100 | — | — | — | P99093 | fabG_3 | — | — | 3-oxoacyl-[acyl-carrier-protein] reductase FabG |
| Contig1 | 1454095 | 1454400 | + | GENE_01320 | Prodigal: 2.6 | CDS | — | — | — | — | — | — | — | — | hypothetical protein |
| Contig1 | 1454466 | 1455227 | + | GENE_01321 | Prodigal: 2.6 | CDS | — | — | — | — | — | — | — | — | hypothetical protein |
| Contig1 | 1455259 | 1456506 | − | GENE_01322 | Prodigal: 2.6 | CDS | — | — | — | — | O34864 | yoaB | — | — | Putative transporter YoaB |
| Contig1 | 1456554 | 1458020 | − | GENE_01323 | Prodigal: 2.6 | CDS | 2.7.1.- | — | — | — | O34861 | yoaC | — | — | Putative sugar kinase YoaC |
| Contig1 | 1458013 | 1459029 | − | GENE_01324 | Prodigal: 2.6 | CDS | 1.1.1.- | — | — | — | O34815 | yoaD | — | — | Putative 2-hydroxyacid dehydrogenase YoaD |
| Contig1 | 1459391 | 1461454 | + | GENE_01325 | Prodigal: 2.6 | CDS | 1.8.5.3 | — | — | — | P18775 | dmsA_1 | — | — | Dimethyl sulfoxide reductase DmsA precursor |
| Contig1 | 1461538 | 1461822 | + | GENE_01326 | Prodigal: 2.6 | CDS | — | — | — | — | — | — | — | — | hypothetical protein |
| Contig1 | 1461866 | 1462081 | + | GENE_01327 | Prodigal: 2.6 | CDS | — | — | — | — | — | — | — | — | hypothetical protein |
| Contig1 | 1462280 | 1462858 | + | GENE_01328 | Prodigal: 2.6 | CDS | — | — | PF12802.1 | — | — | — | — | — | MarR family protein |
| Contig1 | 1462851 | 1463132 | + | GENE_01329 | Prodigal: 2.6 | CDS | — | — | — | — | — | — | — | — | hypothetical protein |
| Contig1 | 1463515 | 1464261 | − | GENE_01330 | Prodigal: 2.6 | CDS | 1.1.1.47 | — | — | — | P12310 | gdh_1 | — | — | Glucose 1-dehydrogenase |
| Contig1 | 1464430 | 1464786 | + | GENE_01331 | Prodigal: 2.6 | CDS | — | — | — | — | O34533 | ytcD_1 | — | — | putative HTH-type transcriptional regulator YtcD |
| Contig1 | 1465386 | 1465718 | − | GENE_01332 | Prodigal: 2.6 | CDS | 6.1.1.10 | — | — | — | P67579 | metG_1 | — | — | Methionine--tRNA ligase |
| Contig1 | 1465787 | 1466497 | − | GENE_01333 | Prodigal: 2.6 | CDS | — | — | — | — | P40408 | btr_1 | — | — | HTH-type transcriptional activator Btr |
| Contig1 | 1466548 | 1467114 | − | GENE_01334 | Prodigal: 2.6 | CDS | — | — | PF00440.17 | — | — | — | — | — | Bacterial regulatory proteins, tetR family |
| Contig1 | 1467114 | 1467494 | − | GENE_01335 | Prodigal: 2.6 | CDS | — | — | — | — | — | — | — | — | hypothetical protein |
| Contig1 | 1467455 | 1467832 | − | GENE_01336 | Prodigal: 2.6 | CDS | 3.-.-.- | — | — | — | Q5XD24 | — | — | — | putative metallo-hydrolase |
| Contig1 | 1468056 | 1468577 | + | GENE_01337 | Prodigal: 2.6 | CDS | — | — | — | — | — | — | — | — | hypothetical protein |
| Contig1 | 1468607 | 1468939 | − | GENE_01338 | Prodigal: 2.6 | CDS | — | — | — | — | O31844 | czrA | — | — | HTH-type transcriptional repressor CzrA |
| Contig1 | 1469131 | 1469796 | + | GENE_01339 | Prodigal: 2.6 | CDS | — | — | — | — | — | — | — | — | hypothetical protein |
| Contig1 | 1469861 | 1470397 | + | GENE_01340 | Prodigal: 2.6 | CDS | — | — | — | — | — | — | — | — | hypothetical protein |
| Contig1 | 1470542 | 1471324 | − | GENE_01341 | Prodigal: 2.6 | CDS | — | — | — | — | — | — | — | — | hypothetical protein |
| Contig1 | 1471519 | 1472016 | + | GENE_01342 | Prodigal: 2.6 | CDS | — | — | — | — | — | — | — | — | hypothetical protein |
| Contig1 | 1472080 | 1473057 | + | GENE_01343 | Prodigal: 2.6 | CDS | 3.4.16.- | — | — | — | O34851 | ykfA_2 | — | — | putative murein peptide carboxypeptidase |
| Contig1 | 1473089 | 1473514 | − | GENE_01344 | Prodigal: 2.6 | CDS | — | — | — | — | — | — | — | — | hypothetical protein |
| Contig1 | 1473643 | 1474515 | − | GENE_01345 | Prodigal: 2.6 | CDS | — | — | — | — | O34669 | yocH_1 | — | — | Cell wall-binding protein YocH precursor |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1474751 | 1476529 | − | GENE_01346 | Prodigal: 2.6 | CDS | 3.6.4.12 | — | — | — | P15043 | recQ_1 | — | — | ATP-dependent DNA helicase RecQ |
| Contig1 | 1477037 | 1477663 | − | GENE_01347 | Prodigal: 2.6 | CDS | 1.7.-.- | — | — | — | O35022 | azoR1 | — | — | FMN-dependent NADH-azoreductase 1 |
| Contig1 | 1477687 | 1477788 | − | GENE_01348 | Prodigal: 2.6 | CDS | — | — | — | — | — | — | — | — | hypothetical protein |
| Contig1 | 1477808 | 1478299 | − | GENE_01349 | Prodigal: 2.6 | CDS | — | — | — | — | P80872 | yocK2 | — | — | General stress protein 160 |
| Contig1 | 1478383 | 1478730 | − | GENE_01350 | Prodigal: 2.6 | CDS | — | — | — | — | — | — | — | — | hypothetical protein |
| Contig1 | 1478856 | 1479089 | + | GENE_01351 | Prodigal: 2.6 | CDS | — | — | — | — | — | — | — | — | hypothetical protein |
| Contig1 | 1479076 | 1479558 | + | GENE_01352 | Prodigal: 2.6 | CDS | — | — | — | — | P96698 | cotP_2 | — | — | Spore coat protein P |
| Contig1 | 1479629 | 1479901 | + | GENE_01353 | Prodigal: 2.6 | CDS | — | — | — | — | — | — | — | — | hypothetical protein |
| Contig1 | 1479898 | 1480131 | + | GENE_01354 | Prodigal: 2.6 | CDS | — | — | — | — | — | — | — | — | hypothetical protein |
| Contig1 | 1480176 | 1480520 | − | GENE_01355 | Prodigal: 2.6 | CDS | — | — | — | — | — | — | — | — | hypothetical protein |
| Contig1 | 1480813 | 1480953 | − | GENE_01356 | Prodigal: 2.6 | CDS | — | — | — | — | — | — | — | — | hypothetical protein |
| Contig1 | 1481019 | 1481222 | − | GENE_01357 | Prodigal: 2.6 | CDS | — | — | — | — | — | — | — | — | hypothetical protein |
| Contig1 | 1481405 | 1482892 | + | GENE_01358 | Prodigal: 2.6 | CDS | 1.2.1.39 | — | — | — | P80668 | feaB | — | — | Phenylacetaldehyde dehydrogenase |
| Contig1 | 1482988 | 1484871 | + | GENE_01359 | Prodigal: 2.6 | CDS | 4.2.1.137 | — | — | — | Q796C3 | sqhC | — | — | Sporulenol synthase |
| Contig1 | 1484868 | 1485713 | + | GENE_01360 | Prodigal: 2.6 | CDS | 1.15.1.1 | — | — | — | P80293 | sodA_1 | — | — | Superoxide dismutase [Mn/Fe] |
| Contig1 | 1485754 | 1487091 | − | GENE_01361 | Prodigal: 2.6 | CDS | — | — | PF00209.12 | — | — | — | — | — | Sodium:neurotransmitter symporter family protein |
| Contig1 | 1487295 | 1488263 | + | GENE_01362 | Prodigal: 2.6 | CDS | — | — | PF01758.10 | — | — | — | — | — | Sodium Bile acid symporter family protein |
| Contig1 | 1488291 | 1489037 | − | GENE_01363 | Prodigal: 2.6 | CDS | 3.-.-.- | — | — | — | O34409 | yflN_2 | — | — | putative metallo-hydrolase YflN |
| Contig1 | 1489111 | 1490358 | − | GENE_01364 | Prodigal: 2.6 | CDS | 2.3.1.61 | — | — | — | Q7A5N4 | odhB | — | — | Dihydrolipoyllysine-residue succinyltransferase component of 2-oxoglutarate dehydrogenase complex |
| Contig1 | 1490374 | 1493228 | − | GENE_01365 | Prodigal: 2.6 | CDS | 1.2.4.2 | — | — | — | Q931R8 | odhA | — | — | 2-oxoglutarate dehydrogenase E1 component |
| Contig1 | 1493436 | 1495352 | − | GENE_01366 | Prodigal: 2.6 | CDS | — | — | PF11775.2 | — | — | — | — | — | Cobalamin biosynthesis protein CobT VWA domain protein |
| Contig1 | 1495363 | 1496253 | − | GENE_01367 | Prodigal: 2.6 | CDS | — | — | — | — | Q02441 | nirQ | — | — | Denitrification regulatory protein NirQ |
| Contig1 | 1496331 | 1496921 | − | GENE_01368 | Prodigal: 2.6 | CDS | — | — | — | — | O31851 | yojM | — | — | Superoxide dismutase-like protein YojM precursor |
| Contig1 | 1497005 | 1498246 | − | GENE_01369 | Prodigal: 2.6 | CDS | 3.4.19.11 | — | — | — | O31852 | cwlS | — | — | D-gamma-glutamyl-meso-diaminopimelic acid endopeptidase CwlS precursor |
| Contig1 | 1498567 | 1499778 | − | GENE_01370 | Prodigal: 2.6 | CDS | 2.4.1.- | — | — | — | Q53685 | oleD_3 | — | — | Oleandomycin glycosyltransferase |
| Contig1 | 1499897 | 1500523 | − | GENE_01371 | Prodigal: 2.6 | CDS | 2.7.7.85 | — | — | MF_01438 | — | disA_1 | — | — | DNA integrity scanning protein DisA |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1500616 | 1500726 | + | GENE_01372 | Prodigal: 2.6 | CDS | — | — | — | — | — | — | — | — | hypothetical protein |
| Contig1 | 1500801 | 1502162 | + | GENE_01373 | Prodigal: 2.6 | CDS | — | — | — | — | O82855 | norM_2 | — | — | Multidrug resistance protein NorM |
| Contig1 | 1502176 | 1503024 | + | GENE_01374 | Prodigal: 2.6 | CDS | — | — | — | — | O31856 | rsbRC | — | — | RsbT co-antagonist protein RsbRC |
| Contig1 | 1503052 | 1503717 | − | GENE_01375 | Prodigal: 2.6 | CDS | 3.5.1.103 | — | — | — | Q9F344 | mshB_1 | — | — | 1 D-myo-inositol 2-acetamido-2-deoxy-alpha-D-glucopyranoside deacetylase |
| Contig1 | 1503735 | 1504085 | − | GENE_01376 | Prodigal: 2.6 | CDS | — | — | — | — | — | — | — | — | hypothetical protein |
| Contig1 | 1504082 | 1504360 | − | GENE_01377 | Prodigal: 2.6 | CDS | — | — | — | — | — | — | — | — | hypothetical protein |
| Contig1 | 1504428 | 1505324 | − | GENE_01378 | Prodigal: 2.6 | CDS | — | — | — | — | — | — | — | — | putative DMT superfamily transporter inner membrane protein |
| Contig1 | 1505422 | 1505886 | + | GENE_01379 | Prodigal: 2.6 | CDS | — | — | — | — | Q7WY67 | gerT | — | — | Spore germination protein GerT |
| Contig1 | 1505921 | 1506160 | − | GENE_01380 | Prodigal: 2.6 | CDS | — | — | — | — | — | — | — | — | hypothetical protein |
| Contig1 | 1506314 | 1506703 | + | GENE_01381 | Prodigal: 2.6 | CDS | — | — | PF01361.1 | — | — | — | — | — | Tautomerase enzyme |
| Contig1 | 1506756 | 1507124 | + | GENE_01382 | Prodigal: 2.6 | CDS | — | — | — | — | — | — | — | — | hypothetical protein |
| Contig1 | 1507164 | 1507493 | − | GENE_01383 | Prodigal: 2.6 | CDS | — | — | — | — | O34844 | yodB_1 | — | — | HTH-type transcriptional regulator YodB |
| Contig1 | 1507635 | 1508243 | + | GENE_01384 | Prodigal: 2.6 | CDS | 1.-.-.- | — | — | — | P81102 | yodC_1 | — | — | Putative NAD(P)H nitroreductase YodC |
| Contig1 | 1508287 | 1508889 | − | GENE_01385 | Prodigal: 2.6 | CDS | 3.1.-.- | — | — | — | O34842 | mhqD | — | — | Putative hydrolase MhqD |
| Contig1 | 1508892 | 1509815 | − | GENE_01386 | Prodigal: 2.6 | CDS | 1.13.11.- | — | — | — | O34543 | mhqE | — | — | Putative ring-cleaving dioxygenase MhqE |
| Contig1 | 1510001 | 1510201 | + | GENE_01387 | Prodigal: 2.6 | CDS | — | — | — | — | — | — | — | — | hypothetical protein |
| Contig1 | 1510201 | 1511703 | + | GENE_01388 | Prodigal: 2.6 | CDS | — | — | — | — | O34745 | yodF_2 | — | — | putative symporter YodF |
| Contig1 | 1511738 | 1513216 | − | GENE_01389 | Prodigal: 2.6 | CDS | — | — | PF02055.10 | — | — | — | — | — | O-Glycosyl hydrolase family 30 |
| Contig1 | 1513364 | 1514806 | − | GENE_01390 | Prodigal: 2.6 | CDS | 3.2.1.86 | — | — | — | P42973 | bglA | — | — | Aryl-phospho-beta-D-glucosidase BglA |
| Contig1 | 1515056 | 1515781 | + | GENE_01391 | Prodigal: 2.6 | CDS | — | — | — | — | Q45591 | yydK | — | — | putative HTH-type transcriptional regulator YydK |
| Contig1 | 1515842 | 1517245 | − | GENE_01392 | Prodigal: 2.6 | CDS | 3.4.21.102 | — | — | — | O34666 | ctpA | — | — | Carboxy-terminal processing protease CtpA precursor |
| Contig1 | 1517392 | 1518093 | + | GENE_01393 | Prodigal: 2.6 | CDS | 2.1.1.197 | — | — | — | P36571 | bioC | — | — | Malonyl-[acyl-carrier protein] O-methyltransferase |
| Contig1 | 1518186 | 1518440 | + | GENE_01394 | Prodigal: 2.6 | CDS | — | — | — | — | — | — | — | — | hypothetical protein |
| Contig1 | 1518484 | 1519302 | − | GENE_01395 | Prodigal: 2.6 | CDS | 3.4.16.4 | — | — | — | Q47746 | vanYB | — | — | D-alanyl-D-alanine carboxypeptidase |
| Contig1 | 1519386 | 1520084 | − | GENE_01396 | Prodigal: 2.6 | CDS | 2.4.2.1 | — | — | — | O34925 | deoD | — | — | Purine nucleoside phosphorylase DeoD-type |
| Contig1 | 1520220 | 1520345 | + | GENE_01397 | Prodigal: 2.6 | CDS | — | — | — | — | — | — | — | — | hypothetical protein |
| Contig1 | 1520400 | 1520720 | − | GENE_01398 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1520780 | 1521448 | − | GENE_01399 | Prodigal: 2.6 | CDS | — | PRK10699 | — | — | — | — | — | — | phosphatidylglycero-phosphatase B |
| Contig1 | 1521464 | 1521637 | − | GENE_01400 | Prodigal: 2.6 | CDS | — | — | — | — | — | — | — | — | hypothetical protein |
| Contig1 | 1521755 | 1521898 | + | GENE_01401 | Prodigal: 2.6 | CDS | — | — | — | — | — | — | — | — | hypothetical protein |
| Contig1 | 1521895 | 1522575 | − | GENE_01402 | Prodigal: 2.6 | CDS | — | — | — | — | — | — | — | — | hypothetical protein |
| Contig1 | 1522321 | 1522645 | − | GENE_01403 | Prodigal: 2.6 | CDS | — | — | — | — | — | — | — | — | hypothetical protein |
| Contig1 | 1523620 | 1523898 | − | GENE_01404 | Prodigal: 2.6 | CDS | — | — | — | — | — | — | — | — | hypothetical protein |
| Contig1 | 1523895 | 1525316 | − | GENE_01405 | Prodigal: 2.6 | CDS | 5.4.3.2 | — | — | — | O34676 | kamA | — | — | L-lysine 2,3-aminomutase |
| Contig1 | 1525313 | 1526179 | − | GENE_01406 | Prodigal: 2.6 | CDS | 2.3.1.- | — | — | — | O34895 | yodP | — | — | N-acetyltransferase YodP |
| Contig1 | 1526148 | 1526606 | − | GENE_01407 | Prodigal: 2.6 | CDS | 3.5.1.- | — | — | — | Q9K9G9 | — | — | — | N-formyl-4-amino-5-aminomethyl-2-methylpyrimidine deformylase |
| Contig1 | 1526615 | 1527448 | − | GENE_01408 | Prodigal: 2.6 | CDS | 3.5.1.- | — | — | — | Q9K9G9 | — | — | — | N-formyl-4-amino-5-aminomethyl-2-methylpyrimidine deformylase |
| Contig1 | 1527420 | 1528115 | − | GENE_01409 | Prodigal: 2.6 | CDS | 2.8.3.5 | — | — | — | P42316 | scoB_2 | — | — | putative succinyl-CoA:3-ketoacid coenzyme A transferase subunit B |
| Contig1 | 1528100 | 1528789 | − | GENE_01410 | Prodigal: 2.6 | CDS | 2.8.3.8 | — | — | — | P76458 | atoD | — | — | Acetate CoA-transferase subunit alpha |
| Contig1 | 1528796 | 1530127 | − | GENE_01411 | Prodigal: 2.6 | CDS | 2.6.1.77 | — | — | — | Q9APM5 | tpa_2 | — | — | Taurine–pyruvate aminotransferase |
| Contig1 | 1530689 | 1530841 | − | GENE_01412 | Prodigal: 2.6 | CDS | — | — | PF09680.4 | — | — | — | — | — | hypothetical protein |
| Contig1 | 1530979 | 1531125 | − | GENE_01413 | Prodigal: 2.6 | CDS | — | — | — | — | — | — | — | — | Protein of unknown function (Tiny_TM_bacill) |
| Contig1 | 1531204 | 1531983 | − | GENE_01414 | Prodigal: 2.6 | CDS | — | — | PF00583.18 | — | — | — | — | — | Acetyltransferase (GNAT) family protein |
| Contig1 | 1532022 | 1533293 | − | GENE_01415 | Prodigal: 2.6 | CDS | — | — | — | — | P39621 | spsA_1 | — | — | Spore coat polysaccharide biosynthesis protein SpsA |
| Contig1 | 1533358 | 1533657 | − | GENE_01416 | Prodigal: 2.6 | CDS | — | — | — | — | — | — | — | — | hypothetical protein |
| Contig1 | 1533869 | 1534300 | + | GENE_01417 | Prodigal: 2.6 | CDS | — | — | — | — | — | — | — | — | hypothetical protein |
| Contig1 | 1534307 | 1535263 | − | GENE_01418 | Prodigal: 2.6 | CDS | — | — | — | — | O31681 | ykvP | — | — | Spore protein YkvP |
| Contig1 | 1535313 | 1536464 | − | GENE_01419 | Prodigal: 2.6 | CDS | 3.1.3.8 | — | — | — | O66037 | phy | — | — | 3-phytase precursor |
| Contig1 | 1536780 | 1537205 | + | GENE_01420 | Prodigal: 2.6 | CDS | 5.1.3.2 | — | — | — | Q9ZDJ5 | capD | — | — | UDP-glucose 4-epimerase |
| Contig1 | 1537239 | 1537415 | − | GENE_01421 | Prodigal: 2.6 | CDS | — | — | — | — | — | — | — | — | hypothetical protein |
| Contig1 | 1537767 | 1538024 | − | GENE_01422 | Prodigal: 2.6 | CDS | — | — | — | — | — | — | — | — | hypothetical protein |
| Contig1 | 1538331 | 1538498 | + | GENE_01423 | Prodigal: 2.6 | CDS | — | — | — | — | — | — | — | — | hypothetical protein |
| Contig1 | 1538523 | 1538723 | − | GENE_01424 | Prodigal: 2.6 | CDS | — | — | — | — | — | — | — | — | hypothetical protein |
| Contig1 | 1539367 | 1539741 | − | GENE_01425 | Prodigal: 2.6 | CDS | — | — | — | — | — | — | — | — | hypothetical protein |
| Contig1 | 1539973 | 1540425 | + | GENE_01426 | Prodigal: 2.6 | CDS | — | — | — | — | — | — | — | — | hypothetical protein |
| Contig1 | 1540768 | 1541904 | + | GENE_01427 | Prodigal: 2.6 | CDS | 3.1.-.- | — | — | — | Q00828 | rapA_2 | — | — | Response regulator aspartate phosphatase A |
| Contig1 | 1541858 | 1542076 | + | GENE_01428 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1542403 | 1543194 | + | GENE_01429 | Prodigal: 2.6 | CDS | — | — | — | — | — | — | — | — | hypothetical protein |
| Contig1 | 1543488 | 1543847 | − | GENE_01430 | Prodigal: 2.6 | CDS | — | — | — | — | — | — | — | — | hypothetical protein |
| Contig1 | 1544059 | 1544517 | − | GENE_01431 | Prodigal: 2.6 | CDS | — | — | — | — | — | — | — | — | Antitoxin YobK |
| Contig1 | 1544533 | 1546332 | − | GENE_01432 | Prodigal: 2.6 | CDS | 3.1.-.- | — | — | — | O34596 | yobK | — | — | Ribonuclease YobL |
| Contig1 | 1546369 | 1546803 | − | GENE_01433 | Prodigal: 2.6 | CDS | — | — | PF09346 | — | O34330 | yobL | — | — | SMI1/KNR4 family protein |
| Contig1 | 1546743 | 1546901 | − | GENE_01434 | Prodigal: 2.6 | CDS | — | — | — | — | — | — | — | — | hypothetical protein |
| Contig1 | 1547065 | 1548045 | + | GENE_01435 | Prodigal: 2.6 | CDS | 3.1.-.- | — | — | — | O32001 | yokF | — | — | SPBc2 prophage-derived endonuclease YokF precursor |
| Contig1 | 1548174 | 1548494 | − | GENE_01436 | Prodigal: 2.6 | CDS | — | — | — | — | — | — | — | — | hypothetical protein |
| Contig1 | 1548518 | 1549081 | − | GENE_01437 | Prodigal: 2.6 | CDS | — | — | — | — | — | — | — | — | hypothetical protein |
| Contig1 | 1549455 | 1551122 | + | GENE_01438 | Prodigal: 2.6 | CDS | — | — | PF07508.7 | — | — | — | — | — | Recombinase |
| Contig1 | 1551163 | 1551735 | + | GENE_01439 | Prodigal: 2.6 | CDS | 4.2.1.115 | — | — | — | Q0P8W4 | pseB | — | — | UDP-N-acetylglucosamine 4,6-dehydratase (inverting) |
| Contig1 | 1551776 | 1552210 | − | GENE_01440 | Prodigal: 2.6 | CDS | 1.8.4.12 | — | — | — | P54155 | msrB | — | — | Peptide methionine sulfoxide reductase MsrB |
| Contig1 | 1552212 | 1552745 | − | GENE_01441 | Prodigal: 2.6 | CDS | 1.8.4.11 | — | — | — | P54154 | msrA | — | — | Peptide methionine sulfoxide reductase MsrA |
| Contig1 | 1552895 | 1553299 | + | GENE_01442 | Prodigal: 2.6 | CDS | — | — | — | — | O32181 | yusO_3 | — | — | putative HTH-type transcriptional regulator YusO |
| Contig1 | 1553350 | 1553916 | − | GENE_01443 | Prodigal: 2.6 | CDS | — | — | — | — | — | — | — | — | hypothetical protein |
| Contig1 | 1553923 | 1554678 | − | GENE_01444 | Prodigal: 2.6 | CDS | 3.-.-.- | — | — | — | P42969 | lipC_1 | — | — | Spore germination lipase LipC |
| Contig1 | 1554756 | 1555379 | − | GENE_01445 | Prodigal: 2.6 | CDS | — | — | — | — | P54178 | — | — | SCO1 protein homolog precursor | hypothetical protein |
| Contig1 | 1555436 | 1555687 | − | GENE_01446 | Prodigal: 2.6 | CDS | — | — | — | — | — | — | — | — | hypothetical protein |
| Contig1 | 1555780 | 1557048 | − | GENE_01447 | Prodigal: 2.6 | CDS | 4.3.1.19 | — | — | — | P04968 | ilvA | — | — | L-threonine dehydratase biosynthetic IlvA |
| Contig1 | 1557233 | 1558225 | + | GENE_01448 | Prodigal: 2.6 | CDS | — | — | — | — | P41789 | glnG | — | — | Nitrogen regulation protein NR(I) |
| Contig1 | 1558242 | 1558880 | + | GENE_01449 | Prodigal: 2.6 | CDS | — | — | PF03006.14 | — | — | — | — | — | Haemolysin-III related |
| Contig1 | 1558922 | 1559545 | − | GENE_01450 | Prodigal: 2.6 | CDS | — | — | — | — | — | — | — | — | hypothetical protein |
| Contig1 | 1559561 | 1560046 | − | GENE_01451 | Prodigal: 2.6 | CDS | 1.5.1.3 | — | — | — | P11045 | dfrA | — | — | Dihydrofolate reductase |
| Contig1 | 1560043 | 1560837 | − | GENE_01452 | Prodigal: 2.6 | CDS | 2.1.1.45 | — | — | — | P11044 | thyA2 | — | — | Thymidylate synthase 2 |
| Contig1 | 1560937 | 1561545 | − | GENE_01453 | Prodigal: 2.6 | CDS | — | — | — | — | — | — | — | — | hypothetical protein |
| Contig1 | 1561808 | 1562578 | − | GENE_01454 | Prodigal: 2.6 | CDS | 2.1.1.242 | — | — | — | Q7UAV7 | rsmj | — | — | Ribosomal RNA small subunit methyltransferase J |
| Contig1 | 1562618 | 1563052 | − | GENE_01455 | Prodigal: 2.6 | CDS | — | — | — | — | — | — | — | — | hypothetical protein |
| Contig1 | 1563134 | 1564810 | − | GENE_01456 | Prodigal: 2.6 | CDS | 4.2.1.9 | — | — | — | P51785 | ilvD | — | — | Dihydroxy-acid dehydratase |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1565069 | 1566202 | − | GENE_01457 | Prodigal: 2.6 | CDS | — | — | — | — | Q931R7 | — | — | Conserved virulence factor C | hypothetical protein |
| Contig1 | 1566271 | 1566879 | − | GENE_01458 | Prodigal: 2.6 | CDS | — | PRK10119 | — | — | — | — | — | — | putative hydrolase |
| Contig1 | 1566891 | 1567373 | − | GENE_01459 | Prodigal: 2.6 | CDS | — | — | — | — | P99097 | — | — | Glutathione peroxidase homolog BsaA | hypothetical protein |
| Contig1 | 1567654 | 1568562 | + | GENE_01460 | Prodigal: 2.6 | CDS | 2.3.1.46 | — | — | — | Q72X44 | metA | — | — | Homoserine O-succinyltransferase |
| Contig1 | 1568787 | 1569929 | + | GENE_01461 | Prodigal: 2.6 | CDS | 2.4.1.- | — | — | — | P54166 | ugtP | — | — | Processive diacylglycerol beta-glucosyltransferase |
| Contig1 | 1570151 | 1570351 | + | GENE_01462 | Prodigal: 2.6 | CDS | — | — | — | — | P51777 | cspD | — | — | Cold shock protein CspD |
| Contig1 | 1570403 | 1570585 | + | GENE_01463 | Prodigal: 2.6 | CDS | — | — | — | — | P68731 | degR | — | — | Regulatory protein DegR |
| Contig1 | 1570747 | 1571004 | + | GENE_01464 | Prodigal: 2.6 | CDS | — | — | — | — | — | — | — | — | hypothetical protein |
| Contig1 | 1571031 | 1571213 | − | GENE_01465 | Prodigal: 2.6 | CDS | — | — | — | — | — | — | — | — | hypothetical protein |
| Contig1 | 1571216 | 1571887 | − | GENE_01466 | Prodigal: 2.6 | CDS | 3.1.26.4 | — | — | MF_00042 | — | mhA_1 | — | — | Ribonuclease H |
| Contig1 | 1571969 | 1572649 | − | GENE_01467 | Prodigal: 2.6 | CDS | — | — | — | — | P37619 | yhhQ | — | — | Inner membrane protein YhhQ |
| Contig1 | 1572653 | 1573048 | + | GENE_01468 | Prodigal: 2.6 | CDS | — | — | — | — | P54162 | mhA_2 | — | — | 14.7 kDa ribonuclease H-like protein |
| Contig1 | 1573100 | 1573228 | + | GENE_01469 | Prodigal: 2.6 | CDS | — | — | — | — | Q7WY66 | sspL | — | — | Small, acid-soluble spore protein L |
| Contig1 | 1573234 | 1574121 | − | GENE_01470 | Prodigal: 2.6 | CDS | 3.1.11.- | — | — | — | P54161 | ypcP | — | — | 5'-3' exonuclease |
| Contig1 | 1574217 | 1574360 | − | GENE_01471 | Prodigal: 2.6 | CDS | — | — | — | — | — | — | — | — | hypothetical protein |
| Contig1 | 1574437 | 1574694 | − | GENE_01472 | Prodigal: 2.6 | CDS | — | — | — | — | — | — | — | — | hypothetical protein |
| Contig1 | 1574762 | 1578346 | − | GENE_01473 | Prodigal: 2.6 | CDS | 3.6.5.5 | — | — | — | B2IZD3 | — | — | — | Bacterial dynamin-like protein |
| Contig1 | 1578697 | 1579203 | − | GENE_01474 | Prodigal: 2.6 | CDS | — | — | PF04140.8 | — | — | — | — | — | Isoprenylcysteine carboxyl methyltransferase (ICMT) family protein |
| Contig1 | 1579203 | 1580303 | − | GENE_01475 | Prodigal: 2.6 | CDS | 2.3.1.- | — | — | — | O06587 | — | — | — | Alpha-pyrone synthesis polyketide synthase-like Pks11 |
| Contig1 | 1580469 | 1580915 | + | GENE_01476 | Prodigal: 2.6 | CDS | — | — | — | — | — | — | — | — | hypothetical protein |
| Contig1 | 1581107 | 1581415 | − | GENE_01477 | Prodigal: 2.6 | CDS | 2.1.1.63 | — | — | MF_00772 | — | ogt_2 | — | — | Methylated-DNA--protein-cysteine methyltransferase |
| Contig1 | 1581637 | 1581900 | + | GENE_01478 | Prodigal: 2.6 | CDS | — | — | — | — | — | — | — | — | hypothetical protein |
| Contig1 | 1582247 | 1582447 | + | GENE_01479 | Prodigal: 2.6 | CDS | — | — | — | — | — | — | — | — | hypothetical protein |
| Contig1 | 1582453 | 1582830 | + | GENE_01480 | Prodigal: 2.6 | CDS | — | — | — | — | — | — | — | — | hypothetical protein |
| Contig1 | 1583035 | 1583601 | + | GENE_01481 | Prodigal: 2.6 | CDS | 3.5.2.19 | — | — | — | Q1MW86 | sttH | — | — | Streptothricin hydrolase |
| Contig1 | 1583936 | 1584211 | + | GENE_01482 | Prodigal: 2.6 | CDS | — | — | — | — | — | — | — | — | hypothetical protein |
| Contig1 | 1584603 | 1585907 | − | GENE_01483 | Prodigal: 2.6 | CDS | — | — | — | — | O32140 | pucK | — | — | Uric acid permease PucK |
| Contig1 | 1585904 | 1586488 | − | GENE_01484 | Prodigal: 2.6 | CDS | 2.4.2.22 | — | — | — | P42085 | xpt | — | — | Xanthine phosphoribosyltransferase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1586821 | 1588323 | − | GENE_01485 | Prodigal: 2.6 | CDS | 3.4.24.- | — | — | — | P50848 | ypwA | — | — | Putative metalloprotease YpwA |
| Contig1 | 1588435 | 1590354 | − | GENE_01486 | Prodigal: 2.6 | CDS | 3.6.4.12 | — | — | — | P27296 | dinG | — | — | putative ATP-dependent helicase DinG |
| Contig1 | 1590459 | 1590650 | − | GENE_01487 | Prodigal: 2.6 | CDS | — | — | — | — | — | — | — | — | hypothetical protein |
| Contig1 | 1590817 | 1590969 | + | GENE_01488 | Prodigal: 2.6 | CDS | — | — | — | — | — | — | — | — | hypothetical protein |
| Contig1 | 1591028 | 1592176 | − | GENE_01489 | Prodigal: 2.6 | CDS | — | — | — | — | P75864 | rlmL | — | — | Ribosomal RNA large subunit methyltransferase K/L |
| Contig1 | 1592710 | 1593009 | − | GENE_01490 | Prodigal: 2.6 | CDS | — | — | — | — | P0CI74 | gpsB | — | — | Cell cycle protein GpsB |
| Contig1 | 1593089 | 1593637 | − | GENE_01491 | Prodigal: 2.6 | CDS | — | — | — | — | — | — | — | — | hypothetical protein |
| Contig1 | 1593726 | 1593962 | − | GENE_01492 | Prodigal: 2.6 | CDS | — | — | PF11122.2 | — | — | — | — | — | Inner spore coat protein D |
| Contig1 | 1594046 | 1594141 | − | GENE_01493 | Prodigal: 2.6 | CDS | — | — | — | — | — | — | — | — | hypothetical protein |
| Contig1 | 1594275 | 1595513 | − | GENE_01494 | Prodigal: 2.6 | CDS | — | — | — | — | — | — | — | — | hypothetical protein |
| Contig1 | 1595533 | 1597779 | − | GENE_01495 | Prodigal: 2.6 | CDS | 3.6.4.13 | — | — | MF_00965 | — | dbpA_1 | — | — | ATP-dependent RNA helicase DbpA |
| Contig1 | 1597878 | 1598384 | − | GENE_01496 | Prodigal: 2.6 | CDS | 2.7.1.- | — | — | — | P60857 | err | — | — | Glucose-specific phosphotransferase enzyme HA component |
| Contig1 | 1598523 | 1598936 | + | GENE_01497 | Prodigal: 2.6 | CDS | — | — | — | — | — | — | — | — | hypothetical protein |
| Contig1 | 1598966 | 1599367 | − | GENE_01498 | Prodigal: 2.6 | CDS | — | — | — | — | — | — | — | — | hypothetical protein |
| Contig1 | 1599554 | 1599736 | + | GENE_01499 | Prodigal: 2.6 | CDS | — | — | — | — | — | — | — | — | hypothetical protein |
| Contig1 | 1599775 | 1600143 | − | GENE_01500 | Prodigal: 2.6 | CDS | — | — | — | — | — | — | — | — | hypothetical protein |
| Contig1 | 1600189 | 1600434 | − | GENE_01501 | Prodigal: 2.6 | CDS | — | — | — | — | — | — | — | — | hypothetical protein |
| Contig1 | 1600640 | 1600744 | + | GENE_01502 | Prodigal: 2.6 | CDS | — | — | — | — | Q7WY65 | sspM | — | — | Small, acid-soluble spore protein M |
| Contig1 | 1600788 | 1601753 | − | GENE_01503 | Prodigal: 2.6 | CDS | — | — | — | — | — | — | — | — | hypothetical protein |
| Contig1 | 1601795 | 1602403 | + | GENE_01504 | Prodigal: 2.6 | CDS | 3.1.22.- | — | — | — | P39792 | recU | — | — | Holliday junction resolvase RecU |
| Contig1 | 1602442 | 1605225 | + | GENE_01505 | Prodigal: 2.6 | CDS | — | — | — | — | P39793 | ponA | — | — | Penicillin-binding protein 1A/1B |
| Contig1 | 1605304 | 1605795 | − | GENE_01506 | Prodigal: 2.6 | CDS | — | — | — | — | — | — | — | — | hypothetical protein |
| Contig1 | 1605792 | 1606451 | − | GENE_01507 | Prodigal: 2.6 | CDS | 4.2.99.18 | — | — | — | P0AB83 | nth | — | — | Endonuclease III |
| Contig1 | 1606470 | 1607168 | − | GENE_01508 | Prodigal: 2.6 | CDS | — | — | — | — | P39787 | dnaD | — | — | DNA replication protein DnaD |
| Contig1 | 1607263 | 1608555 | − | GENE_01509 | Prodigal: 2.6 | CDS | 6.1.1.22 | — | — | — | P67572 | asnS | — | — | Asparagine--tRNA ligase |
| Contig1 | 1608690 | 1609337 | − | GENE_01510 | Prodigal: 2.6 | CDS | 2.6.1.1 | — | — | — | P23034 | — | — | — | Aspartate aminotransferase |
| Contig1 | 1609403 | 1609870 | − | GENE_01511 | Prodigal: 2.6 | CDS | 2.6.1.1 | — | — | — | P23034 | — | — | — | Aspartate aminotransferase |
| Contig1 | 1609893 | 1610378 | − | GENE_01512 | Prodigal: 2.6 | CDS | — | — | — | — | — | — | — | — | hypothetical protein |
| Contig1 | 1610388 | 1610558 | − | GENE_01513 | Prodigal: 2.6 | CDS | — | — | — | — | — | — | — | — | hypothetical protein |
| Contig1 | 1610706 | 1613492 | − | GENE_01514 | Prodigal: 2.6 | CDS | — | — | — | — | Q7A5K4 | — | — | Probable ATP-dependent helicase DinG homolog | hypothetical protein |
| Contig1 | 1613614 | 1613997 | − | GENE_01515 | Prodigal: 2.6 | CDS | 4.1.1.11 | — | — | — | A4JQ59 | panD | — | — | Aspartate 1-decarboxylase precursor |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1613999 | 1614859 | − | GENE_01516 | Prodigal: 2.6 | CDS | 6.3.2.1 | — | — | — | Q6GDK5 | panC | — | — | Pantothenate synthetase |
| Contig1 | 1614863 | 1615696 | − | GENE_01517 | Prodigal: 2.6 | CDS | 2.1.2.11 | — | — | — | P65656 | panB | — | — | 3-methyl-2-oxobutanoate hydroxymethyltransferase |
| Contig1 | 1615941 | 1616918 | − | GENE_01518 | Prodigal: 2.6 | CDS | 6.3.4.15 | — | — | — | P0CI75 | birA | — | — | Bifunctional ligase/repressor BirA |
| Contig1 | 1616903 | 1618093 | − | GENE_01519 | Prodigal: 2.6 | CDS | 2.7.7.72 | — | — | — | Q7SIB1 | cca | — | — | CCA-adding enzyme |
| Contig1 | 1618098 | 1619231 | − | GENE_01520 | Prodigal: 2.6 | CDS | 2.4.1.250 | — | — | — | A0QQZ8 | mshA_1 | — | — | D-inositol 3-phosphate glycosyltransferase |
| Contig1 | 1619228 | 1619941 | − | GENE_01521 | Prodigal: 2.6 | CDS | 3.5.1.103 | — | — | MF_0169 | — | mshB_2 | — | — | 1D-myo-inositol 2-acetamido-2-deoxy-alpha-D-glucopyranoside deacetylase |
| Contig1 | 1619934 | 1620347 | − | GENE_01522 | Prodigal: 2.6 | CDS | 4.2.3.3 | — | — | — | Q5SHD6 | mgsA | — | — | Methylglyoxal synthase |
| Contig1 | 1620370 | 1621173 | − | GENE_01523 | Prodigal: 2.6 | CDS | 1.17.1.8 | — | — | — | P63895 | dapB | — | — | 4-hydroxy-tetrahydrodipicolinate reductase |
| Contig1 | 1621182 | 1621517 | − | GENE_01524 | Prodigal: 2.6 | CDS | — | PRK09562 | — | — | — | — | — | — | nucleoside triphosphate pyrophosphohydrolase |
| Contig1 | 1621660 | 1622532 | + | GENE_01525 | Prodigal: 2.6 | CDS | — | PRK04164 | — | — | — | — | — | — | hypothetical protein |
| Contig1 | 1622556 | 1623731 | − | GENE_01526 | Prodigal: 2.6 | CDS | 4.1.1.2 | — | — | — | O34714 | oxdC_1 | — | — | Oxalate decarboxylase OxdC |
| Contig1 | 1623761 | 1624543 | − | GENE_01527 | Prodigal: 2.6 | CDS | — | — | PF09577.4 | — | — | — | — | — | Sporulation protein YpjB (SpoYpjB) |
| Contig1 | 1624611 | 1625204 | − | GENE_01528 | Prodigal: 2.6 | CDS | — | — | — | — | — | — | — | — | hypothetical protein |
| Contig1 | 1625312 | 1626079 | − | GENE_01529 | Prodigal: 2.6 | CDS | — | — | — | — | Q56247 | cccA_1 | — | — | Cytochrome c-551 precursor |
| Contig1 | 1626111 | 1626785 | − | GENE_01530 | Prodigal: 2.6 | CDS | — | — | — | — | P46912 | qcrB | — | — | Menaquinol-cytochrome c reductase cytochrome b subunit |
| Contig1 | 1626787 | 1627146 | − | GENE_01531 | Prodigal: 2.6 | CDS | 1.10.9.1 | — | — | — | Q46136 | petC | — | — | Cytochrome b6-f complex iron-sulfur subunit |
| Contig1 | 1627167 | 1627289 | − | GENE_01532 | Prodigal: 2.6 | CDS | — | — | — | — | — | — | — | — | hypothetical protein |
| Contig1 | 1627427 | 1627873 | − | GENE_01533 | Prodigal: 2.6 | CDS | — | — | — | — | — | — | — | — | hypothetical protein |
| Contig1 | 1627928 | 1628467 | − | GENE_01534 | Prodigal: 2.6 | CDS | — | PRK03636 | — | — | — | — | — | — | hypothetical protein |
| Contig1 | 1628541 | 1629812 | − | GENE_01535 | Prodigal: 2.6 | CDS | — | PRK11788 | — | — | — | — | — | — | tetratricopeptide repeat protein |
| Contig1 | 1630131 | 1631417 | − | GENE_01536 | Prodigal: 2.6 | CDS | 2.5.1.19 | — | — | — | Q9KCA6 | aroA1 | — | — | 3-phosphoshikimate 1-carboxyvinyltransferase 1 |
| Contig1 | 1631429 | 1632535 | − | GENE_01537 | Prodigal: 2.6 | CDS | — | PRK06545 | — | — | — | — | — | — | prephenate dehydrogenase |
| Contig1 | 1632596 | 1633678 | − | GENE_01538 | Prodigal: 2.6 | CDS | 2.6.1.9 | — | — | — | Q92A83 | hisC | — | — | Histidinol-phosphate aminotransferase |
| Contig1 | 1633690 | 1634487 | − | GENE_01539 | Prodigal: 2.6 | CDS | 4.2.1.20 | — | — | — | P16608 | trpA | — | — | Tryptophan synthase alpha chain |
| Contig1 | 1634480 | 1635682 | − | GENE_01540 | Prodigal: 2.6 | CDS | 4.2.1.20 | — | — | — | Q81TL8 | trpB | — | — | Tryptophan synthase beta chain |
| Contig1 | 1635663 | 1636316 | − | GENE_01541 | Prodigal: 2.6 | CDS | 5.3.1.24 | — | — | — | Q56320 | trpF | — | — | N-(5'-phosphoribosyl)anthranilate isomerase |
| Contig1 | 1636321 | 1637073 | − | GENE_01542 | Prodigal: 2.6 | CDS | 4.1.1.48 | — | — | — | Q2YRR4 | trpC | — | — | Indole-3-glycerol phosphate synthase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1637066 | 1638082 | − | GENE_01543 | Prodigal: 2.6 | CDS | 2.4.2.18 | — | — | — | P00500 | trpD | — | — | Anthranilate phosphoribosyltransferase |
| Contig1 | 1638054 | 1639601 | − | GENE_01544 | Prodigal: 2.6 | CDS | 4.1.3.27 | — | — | — | A0QX93 | trpE | — | — | Anthranilate synthase component 1 |
| Contig1 | 1639825 | 1640208 | − | GENE_01545 | Prodigal: 2.6 | CDS | 5.4.99.5 | — | — | — | P19080 | aroH | — | — | Chorismate mutase AroH |
| Contig1 | 1640205 | 1641293 | − | GENE_01546 | Prodigal: 2.6 | CDS | 4.2.3.4 | — | — | — | Q6GGU4 | aroB | — | — | 3-dehydroquinate synthase |
| Contig1 | 1641293 | 1642465 | − | GENE_01547 | Prodigal: 2.6 | CDS | 4.2.3.5 | — | — | — | P31104 | aroF_1 | — | — | Chorismate synthase |
| Contig1 | 1642537 | 1643307 | − | GENE_01548 | Prodigal: 2.6 | CDS | 2.1.1.80 | — | — | — | Q88ER1 | cheR2 | — | — | Chemotaxis protein methyltransferase Cher2 |
| Contig1 | 1643497 | 1643943 | − | GENE_01549 | Prodigal: 2.6 | CDS | 2.7.4.6 | — | — | — | P31103 | ndk | — | — | Nucleoside diphosphate kinase |
| Contig1 | 1644064 | 1645113 | − | GENE_01550 | Prodigal: 2.6 | CDS | 2.5.1.30 | — | — | — | P31114 | hepT | — | — | Heptaprenyl diphosphate synthase component 2 |
| Contig1 | 1645055 | 1645756 | − | GENE_01551 | Prodigal: 2.6 | CDS | 2.1.1.163 | — | — | — | P31113 | ubiE | — | — | Demethylmenaquinone methyltransferase |
| Contig1 | 1645762 | 1646526 | − | GENE_01552 | Prodigal: 2.6 | CDS | 2.5.1.30 | — | — | — | P31112 | hepS | — | — | Heptaprenyl diphosphate synthase component 1 |
| Contig1 | 1646674 | 1646901 | − | GENE_01553 | Prodigal: 2.6 | CDS | — | — | — | — | P19466 | mtrB | — | — | Transcription attenuation protein MtrB |
| Contig1 | 1646922 | 1647494 | − | GENE_01554 | Prodigal: 2.6 | CDS | 3.5.4.16 | — | — | — | P19465 | folE | — | — | GTP cyclohydrolase 1 |
| Contig1 | 1647681 | 1647959 | − | GENE_01555 | Prodigal: 2.6 | CDS | — | — | — | — | P08821 | hupA | — | — | DNA-binding protein HU 1 |
| Contig1 | 1648333 | 1649811 | − | GENE_01556 | Prodigal: 2.6 | CDS | 3.6.1.3 | — | — | — | P35149 | spoIVA | — | — | Stage IV sporulation protein A |
| Contig1 | 1649997 | 1650731 | − | GENE_01557 | Prodigal: 2.6 | CDS | — | — | — | — | — | — | — | — | hypothetical protein |
| Contig1 | 1650751 | 1650954 | − | GENE_01558 | Prodigal: 2.6 | CDS | — | — | — | — | — | — | — | — | hypothetical protein |
| Contig1 | 1651273 | 1652310 | + | GENE_01559 | Prodigal: 2.6 | CDS | 1.1.1.94 | — | — | — | Q97NF1 | gpsA | — | — | Glycerol-3-phosphate dehydrogenase [NAD(P)+] |
| Contig1 | 1652328 | 1653638 | − | GENE_01560 | Prodigal: 2.6 | CDS | — | — | — | — | P50743 | der_1 | — | — | GTPase Der |
| Contig1 | 1653831 | 1654433 | − | GENE_01561 | Prodigal: 2.6 | CDS | — | — | — | — | — | — | — | — | hypothetical protein |
| Contig1 | 1654510 | 1654641 | − | GENE_01562 | Prodigal: 2.6 | CDS | — | — | — | — | — | — | — | — | hypothetical protein |
| Contig1 | 1654676 | 1655725 | − | GENE_01563 | Prodigal: 2.6 | CDS | 5.3.3.2 | — | — | — | P50740 | fni | — | — | Isopentenyl-diphosphate delta-isomerase |
| Contig1 | 1655740 | 1656888 | − | GENE_01564 | Prodigal: 2.6 | CDS | — | — | — | — | P38494 | — | — | 30S ribosomal protein S1 homolog | hypothetical protein |
| Contig1 | 1657117 | 1657791 | − | GENE_01565 | Prodigal: 2.6 | CDS | 2.7.4.25 | — | — | — | P38493 | cmk | — | — | Cytidylate kinase |
| Contig1 | 1657870 | 1658046 | − | GENE_01566 | Prodigal: 2.6 | CDS | — | — | — | — | — | — | — | — | hypothetical protein |
| Contig1 | 1658093 | 1658470 | − | GENE_01567 | Prodigal: 2.6 | CDS | — | — | — | MF_01457 | — | ycgR | — | — | Flagellar brake protein YcgR |
| Contig1 | 1658467 | 1658748 | − | GENE_01568 | Prodigal: 2.6 | CDS | — | — | PF12945.1 | — | — | — | — | — | Flagellar protein YcgR |
| Contig1 | 1658836 | 1660185 | − | GENE_01569 | Prodigal: 2.6 | CDS | — | — | — | — | P38490 | ypeB | — | — | Sporulation protein YpeB |
| Contig1 | 1660210 | 1661079 | − | GENE_01570 | Prodigal: 2.6 | CDS | — | — | — | — | P50739 | sleB_2 | — | — | Spore cortex-lytic enzyme precursor |
| Contig1 | 1661212 | 1661868 | − | GENE_01571 | Prodigal: 2.6 | CDS | 3.4.-.- | — | — | — | P50738 | prsW | — | — | Protease PrsW |
| Contig1 | 1661965 | 1662948 | − | GENE_01572 | Prodigal: 2.6 | CDS | 1.18.1.2 | — | — | — | Q8KCB2 | — | — | — | Ferredoxin--NADP reductase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1663054 | 1664328 | − | GENE_01573 | Prodigal: 2.6 | CDS | 1.4.1.2 | — | — | — | P50735 | gudB | — | — | Cryptic catabolic NAD-specific glutamate dehydrogenase GudB |
| Contig1 | 1664489 | 1665073 | − | GENE_01574 | Prodigal: 2.6 | CDS | — | — | — | — | P50734 | mecB | — | — | Adapter protein MecA 2 |
| Contig1 | 1665224 | 1666012 | − | GENE_01575 | Prodigal: 2.6 | CDS | 3.1.-.- | — | — | — | Q9PP77 | — | — | — | putative metallophosphoesterase |
| Contig1 | 1666099 | 1666557 | − | GENE_01576 | Prodigal: 2.6 | CDS | — | — | — | — | — | — | — | — | hypothetical protein |
| Contig1 | 1666626 | 1667396 | − | GENE_01577 | Prodigal: 2.6 | CDS | — | — | — | — | Q7A5I6 | ebpS | — | — | Elastin-binding protein EbpS |
| Contig1 | 1667374 | 1667961 | − | GENE_01578 | Prodigal: 2.6 | CDS | — | — | PF02517.10 | — | — | — | — | — | CAAX amino terminal protease self-immunity |
| Contig1 | 1667976 | 1669394 | − | GENE_01579 | Prodigal: 2.6 | CDS | 3.6.4.12 | — | — | — | P15043 | recQ_2 | — | — | ATP-dependent DNA helicase RecQ |
| Contig1 | 1669459 | 1670517 | − | GENE_01580 | Prodigal: 2.6 | CDS | — | — | — | — | — | — | — | — | hypothetical protein |
| Contig1 | 1670786 | 1671034 | + | GENE_01581 | Prodigal: 2.6 | CDS | — | — | — | — | P50727 | fer | — | — | Ferredoxin |
| Contig1 | 1671174 | 1671746 | − | GENE_01582 | Prodigal: 2.6 | CDS | — | — | — | — | P50726 | fmnP | — | — | Riboflavin transporter FmnP |
| Contig1 | 1672233 | 1673816 | + | GENE_01583 | Prodigal: 2.6 | CDS | 1.1.1.95 | — | — | — | P0A544 | serA | — | — | D-3-phosphoglycerate dehydrogenase |
| Contig1 | 1673863 | 1674960 | − | GENE_01584 | Prodigal: 2.6 | CDS | — | — | — | — | P35166 | rsiX | — | — | Sigma-X negative effector |
| Contig1 | 1674899 | 1675483 | − | GENE_01585 | Prodigal: 2.6 | CDS | — | — | — | — | P35165 | sigX | — | — | RNA polymerase sigma factor SigX |
| Contig1 | 1675675 | 1677456 | − | GENE_01586 | Prodigal: 2.6 | CDS | 2.7.13.3 | — | — | — | Q5HFT1 | srrB | — | — | Sensor protein SrrB |
| Contig1 | 1677464 | 1678174 | − | GENE_01587 | Prodigal: 2.6 | CDS | — | — | — | — | Q9L524 | srrA_1 | — | — | Transcriptional regulatory protein SrrA |
| Contig1 | 1678256 | 1679431 | − | GENE_01588 | Prodigal: 2.6 | CDS | — | — | — | — | P72978 | ccsA_1 | — | — | Cytochrome c biogenesis protein CcsA |
| Contig1 | 1679450 | 1681078 | − | GENE_01589 | Prodigal: 2.6 | CDS | — | — | — | — | P73912 | ccsB | — | — | Cytochrome c biogenesis protein CcsB |
| Contig1 | 1681075 | 1681614 | − | GENE_01590 | Prodigal: 2.6 | CDS | — | — | — | — | P35160 | resA_2 | — | — | Thiol-disulfide oxidoreductase ResA |
| Contig1 | 1681699 | 1682433 | − | GENE_01591 | Prodigal: 2.6 | CDS | 5.4.99.22 | — | — | — | P35159 | rluB | — | — | Ribosomal large subunit pseudouridine synthase B |
| Contig1 | 1682527 | 1683063 | − | GENE_01592 | Prodigal: 2.6 | CDS | — | — | — | — | P35158 | spmB | — | — | Spore maturation protein B |
| Contig1 | 1683068 | 1683658 | − | GENE_01593 | Prodigal: 2.6 | CDS | — | — | — | — | P35157 | spmA | — | — | Spore maturation protein A |
| Contig1 | 1683646 | 1684797 | − | GENE_01594 | Prodigal: 2.6 | CDS | 3.4.16.4 | — | — | — | P35150 | dacB | — | — | D-alanyl-D-alanine carboxypeptidase DacB precursor |
| Contig1 | 1684910 | 1685440 | − | GENE_01595 | Prodigal: 2.6 | CDS | — | — | — | — | — | — | — | — | hypothetical protein |
| Contig1 | 1685485 | 1686078 | − | GENE_01596 | Prodigal: 2.6 | CDS | — | — | — | — | P35155 | scpB | — | — | Segregation and condensation protein B |
| Contig1 | 1686068 | 1686823 | − | GENE_01597 | Prodigal: 2.6 | CDS | — | — | — | — | P35154 | scpA | — | — | Segregation and condensation protein A |
| Contig1 | 1687031 | 1687120 | + | GENE_01598 | Prodigal: 2.6 | CDS | — | — | PF09680.4 | — | — | — | — | — | Protein of unknown function (Tiny_TM_bacill) |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1687207 | 1687728 | + | GENE_01599 | Prodigal: 2.6 | CDS | — | — | — | — | — | — | — | — | hypothetical protein |
| Contig1 | 1687794 | 1688168 | − | GENE_01600 | Prodigal: 2.6 | CDS | — | — | PF00583.18 | — | — | — | — | — | Acetyltransferase (GNAT) family protein |
| Contig1 | 1688285 | 1688749 | − | GENE_01601 | Prodigal: 2.6 | CDS | 2.5.1.78 | — | — | — | P11998 | ribH | — | — | 6,7-dimethyl-8-ribityllumazine synthase |
| Contig1 | 1688782 | 1689978 | − | GENE_01602 | Prodigal: 2.6 | CDS | — | — | — | — | Q99TA0 | ribBA | — | — | Riboflavin biosynthesis protein RibBA |
| Contig1 | 1689993 | 1690640 | − | GENE_01603 | Prodigal: 2.6 | CDS | 2.5.1.9 | — | — | — | P16440 | ribE | — | — | Riboflavin synthase |
| Contig1 | 1690621 | 1691736 | − | GENE_01604 | Prodigal: 2.6 | CDS | — | — | — | — | P17618 | ribD | — | — | Riboflavin biosynthesis protein RibD |
| Contig1 | 1692134 | 1692478 | − | GENE_01605 | Prodigal: 2.6 | CDS | — | — | — | — | — | — | — | — | hypothetical protein |
| Contig1 | 1692726 | 1693286 | − | GENE_01606 | Prodigal: 2.6 | CDS | 3.4.21.89 | — | — | — | P28628 | sipS | — | — | Signal peptidase I S |
| Contig1 | 1693382 | 1693873 | − | GENE_01607 | Prodigal: 2.6 | CDS | — | — | — | — | — | — | — | — | hypothetical protein |
| Contig1 | 1694023 | 1694454 | − | GENE_01608 | Prodigal: 2.6 | CDS | 5.2.1.8 | — | — | — | P35137 | ppiB | — | — | Peptidyl-prolyl cis-trans isomerase B |
| Contig1 | 1694739 | 1695638 | + | GENE_01609 | Prodigal: 2.6 | CDS | — | — | — | — | — | — | — | — | hypothetical protein |
| Contig1 | 1695683 | 1697002 | − | GENE_01610 | Prodigal: 2.6 | CDS | 4.1.1.20 | — | — | — | P09890 | lysA | — | — | Diaminopimelate decarboxylase |
| Contig1 | 1697127 | 1698608 | − | GENE_01611 | Prodigal: 2.6 | CDS | — | — | — | — | Q9ZFB4 | gerXA | — | — | Spore germination protein XA |
| Contig1 | 1698562 | 1699167 | − | GENE_01612 | Prodigal: 2.6 | CDS | — | — | — | — | — | — | — | — | hypothetical protein |
| Contig1 | 1699174 | 1699524 | − | GENE_01613 | Prodigal: 2.6 | CDS | — | — | PF03862.7 | — | — | — | — | — | SpoVA protein |
| Contig1 | 1699525 | 1700541 | − | GENE_01614 | Prodigal: 2.6 | CDS | — | — | — | — | P40869 | spoVAD | — | — | Stage V sporulation protein AD |
| Contig1 | 1700553 | 1701005 | − | GENE_01615 | Prodigal: 2.6 | CDS | — | — | PF03862.7 | — | — | — | — | — | SpoVA protein |
| Contig1 | 1701018 | 1701389 | − | GENE_01616 | Prodigal: 2.6 | CDS | — | — | — | — | — | — | — | — | hypothetical protein |
| Contig1 | 1701433 | 1702053 | − | GENE_01617 | Prodigal: 2.6 | CDS | — | — | PF12164.2 | — | — | — | — | — | Stage V sporulation protein AA |
| Contig1 | 1702180 | 1702947 | − | GENE_01618 | Prodigal: 2.6 | CDS | 2.7.11.1 | — | — | — | P07860 | sigF_2 | — | — | RNA polymerase sigma-F factor |
| Contig1 | 1702959 | 1703399 | − | GENE_01619 | Prodigal: 2.6 | CDS | — | — | — | — | P10728 | spoIIAB | — | — | Anti-sigma F factor |
| Contig1 | 1703396 | 1703749 | − | GENE_01620 | Prodigal: 2.6 | CDS | — | — | — | — | P10727 | spoIIAA | — | — | Anti-sigma F factor antagonist |
| Contig1 | 1703845 | 1705014 | − | GENE_01621 | Prodigal: 2.6 | CDS | 3.4.16.4 | — | — | — | P38422 | dacF | — | — | D-alanyl-D-alanine carboxypeptidase DacF precursor |
| Contig1 | 1705151 | 1705969 | − | GENE_01622 | Prodigal: 2.6 | CDS | 2.4.2.1 | — | — | — | P46354 | punA | — | — | Purine nucleoside phosphorylase 1 |
| Contig1 | 1705982 | 1707166 | − | GENE_01623 | Prodigal: 2.6 | CDS | 5.4.2.7 | — | — | — | Q81ZN9 | deoB | — | — | Phosphopentomutase |
| Contig1 | 1707335 | 1708225 | − | GENE_01624 | Prodigal: 2.6 | CDS | — | — | — | — | P0A0P0 | xerD | — | — | Tyrosine recombinase XerD |
| Contig1 | 1708233 | 1708460 | − | GENE_01625 | Prodigal: 2.6 | CDS | — | — | — | — | — | — | — | — | hypothetical protein |
| Contig1 | 1708575 | 1709024 | − | GENE_01626 | Prodigal: 2.6 | CDS | — | — | — | — | P54574 | fur | — | — | Ferric uptake regulation protein |
| Contig1 | 1709137 | 1709781 | − | GENE_01627 | Prodigal: 2.6 | CDS | — | — | — | — | P37873 | spoIIM | — | — | Stage II sporulation protein M |
| Contig1 | 1709815 | 1709919 | − | GENE_01628 | Prodigal: 2.6 | CDS | — | — | — | — | — | — | — | — | hypothetical protein |
| Contig1 | 1709858 | 1710085 | − | GENE_01629 | Prodigal: 2.6 | CDS | — | — | — | — | — | — | — | — | hypothetical protein |
| Contig1 | 1710143 | 1710433 | − | GENE_01630 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1710546 | 1711859 | − | GENE_01631 | Prodigal: 2.6 | CDS | 1.1.1.38 | — | — | — | P16468 | — | — | — | NAD-dependent malic enzyme |
| Contig1 | 1711872 | 1713278 | − | GENE_01632 | Prodigal: 2.6 | CDS | — | — | — | — | P54571 | mleN | — | — | Malate-2H(+)/Na(+)-lactate antiporter |
| Contig1 | 1713420 | 1714847 | − | GENE_01633 | Prodigal: 2.6 | CDS | 4.3.1.1 | — | — | — | P0AC38 | aspA | — | — | Aspartate ammonia-lyase |
| Contig1 | 1714885 | 1715874 | − | GENE_01634 | Prodigal: 2.6 | CDS | 3.5.1.1 | — | — | — | P26900 | ansA | — | — | L-asparaginase 1 |
| Contig1 | 1716051 | 1716404 | + | GENE_01635 | Prodigal: 2.6 | CDS | — | — | — | — | P23789 | xre_2 | — | — | HTH-type transcriptional regulator Xre |
| Contig1 | 1716415 | 1717578 | − | GENE_01636 | Prodigal: 2.6 | CDS | — | — | — | — | — | — | — | — | hypothetical protein |
| Contig1 | 1717578 | 1718135 | − | GENE_01637 | Prodigal: 2.6 | CDS | 3.6.1.13 | — | — | — | P54570 | nudF | — | — | ADP-ribose pyrophosphatase |
| Contig1 | 1718211 | 1718333 | + | GENE_01638 | Prodigal: 2.6 | CDS | — | — | — | — | — | — | — | — | hypothetical protein |
| Contig1 | 1718396 | 1719316 | + | GENE_01639 | Prodigal: 2.6 | CDS | 1.1.1.- | — | — | — | P80874 | yhdN_1 | — | — | General stress protein 69 |
| Contig1 | 1719349 | 1719576 | + | GENE_01640 | Prodigal: 2.6 | CDS | — | — | — | — | — | — | — | — | hypothetical protein |
| Contig1 | 1719696 | 1720610 | + | GENE_01641 | Prodigal: 2.6 | CDS | — | — | — | MF_00832 | — | rutD_1 | — | — | Putative aminoacrylate hydrolase RutD |
| Contig1 | 1720650 | 1720889 | − | GENE_01642 | Prodigal: 2.6 | CDS | — | — | — | — | — | — | — | — | hypothetical protein |
| Contig1 | 1720864 | 1721226 | − | GENE_01643 | Prodigal: 2.6 | CDS | — | — | — | — | — | — | — | — | hypothetical protein |
| Contig1 | 1721299 | 1722267 | − | GENE_01644 | Prodigal: 2.6 | CDS | — | PRK03333 | — | — | — | — | — | — | dephospho-CoA kinase/protein folding accessory domain-containing protein |
| Contig1 | 1722264 | 1722608 | − | GENE_01645 | Prodigal: 2.6 | CDS | — | — | PF03992.10 | — | — | — | — | — | Antibiotic biosynthesis monooxygenase |
| Contig1 | 1722621 | 1723091 | − | GENE_01646 | Prodigal: 2.6 | CDS | — | — | — | MF_01127 | Q47155 | ypeA | — | — | Acetyltransferase YpeA |
| Contig1 | 1723307 | 1724533 | + | GENE_01647 | Prodigal: 2.6 | CDS | 2.7.7.7 | — | — | — | — | dinB_1 | — | — | DNA polymerase IV |
| Contig1 | 1724548 | 1724892 | + | GENE_01648 | Prodigal: 2.6 | CDS | — | — | PF08863.4 | — | — | — | — | — | YoID-like protein |
| Contig1 | 1724989 | 1725198 | + | GENE_01649 | Prodigal: 2.6 | CDS | — | — | — | — | — | — | — | — | hypothetical protein |
| Contig1 | 1725889 | 1726341 | + | GENE_01650 | Prodigal: 2.6 | CDS | — | PRK12287 | — | — | — | — | — | — | pheromone autoinducer 2 transporter |
| Contig1 | 1726433 | 1726600 | + | GENE_01651 | Prodigal: 2.6 | CDS | — | — | — | — | — | — | — | — | hypothetical protein |
| Contig1 | 1726602 | 1726994 | − | GENE_01652 | Prodigal: 2.6 | CDS | — | — | PF00903.19 | — | — | — | — | — | Glyoxalase/Bleomycin resistance protein/Dioxygenase superfamily protein |
| Contig1 | 1727016 | 1727975 | − | GENE_01653 | Prodigal: 2.6 | CDS | 2.7.1.33 | — | — | — | P63810 | coaA | — | — | Pantothenate kinase |
| Contig1 | 1728051 | 1729400 | − | GENE_01654 | Prodigal: 2.6 | CDS | 4.3.1.18 | — | — | — | Q82L08 | dsdA | — | — | D-serine dehydratase |
| Contig1 | 1729417 | 1730193 | − | GENE_01655 | Prodigal: 2.6 | CDS | 1.-.-.- | — | — | — | Q99RF5 | — | — | — | — | putative oxidoreductase |
| Contig1 | 1730199 | 1731158 | − | GENE_01656 | Prodigal: 2.6 | CDS | 3.1.2.6 | — | — | MF_01374 | — | gloB_1 | — | — | Hydroxyacylglutathione hydrolase |
| Contig1 | 1731554 | 1732396 | + | GENE_01657 | Prodigal: 2.6 | CDS | 1.5.1.2 | — | — | — | P22008 | proC_2 | — | — | Pyrroline-5-carboxylate reductase |
| Contig1 | 1732430 | 1733176 | − | GENE_01658 | Prodigal: 2.6 | CDS | 4.-.-.- | — | — | — | P40802 | pksI_2 | — | — | Putative polyketide biosynthesis enoyl-CoA isomerase PksI |
| Contig1 | 1733226 | 1734533 | − | GENE_01659 | Prodigal: 2.6 | CDS | 2.3.3.- | — | — | — | P40830 | pksG_2 | — | — | Polyketide biosynthesis 3-hydroxy-3-methylglutaryl-ACP synthase PksG |
| Contig1 | 1734530 | 1735684 | − | GENE_01660 | Prodigal: 2.6 | CDS | 1.14.99.- | — | — | — | Q06069 | — | — | — | Cytochrome P450(MEG) |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1735766 | 1736614 | − | GENE_01661 | Prodigal: 2.6 | CDS | 2.3.1.− | — | — | — | O31784 | pksR_2 | — | — | Polyketide synthase PksR |
| Contig1 | 1736611 | 1741980 | − | GENE_01662 | Prodigal: 2.6 | CDS | — | — | — | — | Q05470 | pksL_6 | — | — | Polyketide synthase PksL |
| Contig1 | 1741977 | 1743908 | − | GENE_01663 | Prodigal: 2.6 | CDS | 2.3.1.− | — | — | — | O31782 | pksN_3 | — | — | Polyketide synthase PksN |
| Contig1 | 1743965 | 1748131 | − | GENE_01664 | Prodigal: 2.6 | CDS | — | — | — | — | Q05470 | pksL_7 | — | — | Polyketide synthase PksL |
| Contig1 | 1748154 | 1752545 | − | GENE_01665 | Prodigal: 2.6 | CDS | — | — | — | — | P40806 | pksJ_6 | — | — | Polyketide synthase PksJ |
| Contig1 | 1752512 | 1755871 | − | GENE_01666 | Prodigal: 2.6 | CDS | 2.3.1.− | — | — | — | O31782 | pksN_4 | — | — | Polyketide synthase PksN |
| Contig1 | 1755876 | 1764896 | − | GENE_01667 | Prodigal: 2.6 | CDS | 2.3.1.− | — | — | — | O31782 | pksN_5 | — | — | Polyketide synthase PksN |
| Contig1 | 1764857 | 1771486 | − | GENE_01668 | Prodigal: 2.6 | CDS | — | — | — | — | P40872 | pksM_2 | — | — | Polyketide synthase PksM |
| Contig1 | 1771538 | 1777264 | − | GENE_01669 | Prodigal: 2.6 | CDS | — | — | — | — | Q05470 | pksL_8 | — | — | Polyketide synthase PksL |
| Contig1 | 1777304 | 1783600 | − | GENE_01670 | Prodigal: 2.6 | CDS | — | — | — | — | P40806 | pksJ_7 | — | — | Polyketide synthase PksJ |
| Contig1 | 1783619 | 1796200 | − | GENE_01671 | Prodigal: 2.6 | CDS | 2.3.1.− | — | — | — | O31782 | pksN_6 | — | — | Polyketide synthase PksN |
| Contig1 | 1796240 | 1796977 | − | GENE_01672 | Prodigal: 2.6 | CDS | 1.1.1.100 | — | — | — | Q9KQH7 | fabG_4 | — | — | 3-oxoacyl-[acyl-carrier-protein] reductase FabG |
| Contig1 | 1796992 | 1798356 | − | GENE_01673 | Prodigal: 2.6 | CDS | 6.2.1.3 | — | — | — | O07610 | lcfB_3 | — | — | Long-chain-fatty-acid-CoA ligase |
| Contig1 | 1798353 | 1798625 | − | GENE_01674 | Prodigal: 2.6 | CDS | — | — | — | MF_01217 | — | acpP | — | — | Acyl carrier protein |
| Contig1 | 1798650 | 1799630 | − | GENE_01675 | Prodigal: 2.6 | CDS | — | — | — | — | — | — | — | — | hypothetical protein |
| Contig1 | 1799670 | 1801928 | − | GENE_01676 | Prodigal: 2.6 | CDS | — | — | — | — | O34787 | pksE | — | — | Polyketide biosynthesis protein PksE |
| Contig1 | 1802663 | 1803193 | + | GENE_01677 | Prodigal: 2.6 | CDS | — | — | — | — | P0AFG0 | — | — | Transcription termination/antitermination protein NusG | hypothetical protein |
| Contig1 | 1803534 | 1804412 | − | GENE_01678 | Prodigal: 2.6 | CDS | — | — | — | — | Q55459 | cmpR_1 | — | — | HTH-type transcriptional activator CmpR |
| Contig1 | 1804551 | 1804874 | + | GENE_01679 | Prodigal: 2.6 | CDS | — | — | PF06942.6 | — | — | — | — | — | GlpM protein |
| Contig1 | 1805014 | 1806030 | + | GENE_01680 | Prodigal: 2.6 | CDS | 1.6.99.1 | — | — | — | P54550 | namA | — | — | NADPH dehydrogenase |
| Contig1 | 1806144 | 1806917 | + | GENE_01681 | Prodigal: 2.6 | CDS | — | — | — | MF_00832 | — | rutD_2 | — | — | Putative aminoacrylate hydrolase RutD |
| Contig1 | 1807195 | 1808121 | − | GENE_01682 | Prodigal: 2.6 | CDS | 3.1.26.11 | — | — | — | P54548 | rnz | — | — | Ribonuclease Z |
| Contig1 | 1808330 | 1809799 | + | GENE_01683 | Prodigal: 2.6 | CDS | 1.1.1.49 | — | — | — | P54547 | zwf | — | — | Glucose-6-phosphate 1-dehydrogenase |
| Contig1 | 1809891 | 1811300 | − | GENE_01684 | Prodigal: 2.6 | CDS | 1.1.1.44 | — | — | — | P80859 | gndA | — | — | 6-phosphogluconate dehydrogenase, NADP(+)-dependent, decarboxylating |
| Contig1 | 1811409 | 1812653 | − | GENE_01685 | Prodigal: 2.6 | CDS | 2.7.7.7 | — | — | — | Q47155 | dinB_2 | — | — | DNA polymerase IV |
| Contig1 | 1812729 | 1813010 | + | GENE_01686 | Prodigal: 2.6 | CDS | — | — | — | — | Q7WY64 | miM | — | — | Membrane protein insertion and folding monitor |
| Contig1 | 1813043 | 1813879 | + | GENE_01687 | Prodigal: 2.6 | CDS | — | — | — | — | P54544 | misCB | — | — | Membrane protein insertase MisCB precursor |
| Contig1 | 1813999 | 1815114 | − | GENE_01688 | Prodigal: 2.6 | CDS | 3.4.11.4 | — | — | — | P29745 | pepT_1 | — | — | Peptidase T |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1815131 | 1816654 | − | GENE_01689 | Prodigal: 2.6 | CDS | 2.1.3.1 | — | — | — | Q8GBW6 | — | — | — | Methylmalonyl-CoA carboxyltransferase 12S subunit |
| Contig1 | 1816641 | 1817069 | − | GENE_01690 | Prodigal: 2.6 | CDS | — | — | PF12681.1 | — | — | — | — | — | Glyoxalase-like domain protein |
| Contig1 | 1817163 | 1817258 | + | GENE_01691 | Prodigal: 2.6 | CDS | — | — | — | — | — | — | — | — | hypothetical protein |
| Contig1 | 1817272 | 1817802 | − | GENE_01692 | Prodigal: 2.6 | CDS | 2.-.-.- | — | — | — | O34816 | ykuD_2 | — | — | Putative L,D-transpeptidase YkuD |
| Contig1 | 1817872 | 1818825 | − | GENE_01693 | Prodigal: 2.6 | CDS | — | — | — | — | — | — | — | — | hypothetical protein |
| Contig1 | 1818902 | 1819624 | − | GENE_01694 | Prodigal: 2.6 | CDS | — | — | — | — | P54537 | artM | — | — | Arginine transport ATP-binding protein ArtM |
| Contig1 | 1819617 | 1820276 | − | GENE_01695 | Prodigal: 2.6 | CDS | — | — | — | — | P54536 | artQ | — | — | Arginine transport system permease protein ArtQ |
| Contig1 | 1820338 | 1821105 | − | GENE_01696 | Prodigal: 2.6 | CDS | — | — | — | — | P54535 | artP | — | — | Arginine-binding extracellular protein ArtP precursor |
| Contig1 | 1821351 | 1821788 | − | GENE_01697 | Prodigal: 2.6 | CDS | — | — | — | — | — | — | — | — | hypothetical protein |
| Contig1 | 1821966 | 1822862 | + | GENE_01698 | Prodigal: 2.6 | CDS | 2.7.1.- | — | — | — | P39074 | bmrU | — | — | Putative lipid kinase BmrU |
| Contig1 | 1822906 | 1824168 | − | GENE_01699 | Prodigal: 2.6 | CDS | 2.3.1.12 | — | — | — | P65636 | pdhC_3 | — | — | Dihydrolipoyllysine-residue acetyltransferase component of pyruvate dehydrogenase complex |
| Contig1 | 1824190 | 1825173 | − | GENE_01700 | Prodigal: 2.6 | CDS | 1.2.4.4 | — | — | — | P37941 | bfmBAB | — | — | 2-oxoisovalerate dehydrogenase subunit beta |
| Contig1 | 1825186 | 1826178 | − | GENE_01701 | Prodigal: 2.6 | CDS | 1.2.4.4 | — | — | — | P37940 | bfmBAA | — | — | 2-oxoisovalerate dehydrogenase subunit alpha |
| Contig1 | 1826201 | 1827622 | − | GENE_01702 | Prodigal: 2.6 | CDS | 1.8.1.4 | — | — | — | Q8NTE1 | lpd | — | — | Dihydrolipoyl dehydrogenase |
| Contig1 | 1827612 | 1828721 | − | GENE_01703 | Prodigal: 2.6 | CDS | 27.2.7 | — | — | — | Q97II1 | buk2 | — | — | Butyrate kinase 2 |
| Contig1 | 1828745 | 1829839 | − | GENE_01704 | Prodigal: 2.6 | CDS | 1.4.1.9 | — | — | — | P13154 | ldh_1 | — | — | Leucine dehydrogenase |
| Contig1 | 1829853 | 1830746 | − | GENE_01705 | Prodigal: 2.6 | CDS | 2.3.1.8 | — | — | — | Q9X0L4 | pta_1 | — | — | Phosphate acetyltransferase |
| Contig1 | 1830869 | 1832938 | − | GENE_01706 | Prodigal: 2.6 | CDS | — | — | — | — | P38022 | rocR_1 | — | — | Arginine utilization regulatory protein RocR |
| Contig1 | 1833092 | 1833334 | + | GENE_01707 | Prodigal: 2.6 | CDS | — | — | — | — | — | — | — | — | hypothetical protein |
| Contig1 | 1833363 | 1834268 | − | GENE_01708 | Prodigal: 2.6 | CDS | 4.1.3.30 | — | — | — | Q56062 | prpB | — | — | Methylisocitrate lyase |
| Contig1 | 1834287 | 1835714 | − | GENE_01709 | Prodigal: 2.6 | CDS | 4.2.1.79 | — | — | — | P45859 | prpD | — | — | 2-methylcitrate dehydratase |
| Contig1 | 1835740 | 1836837 | − | GENE_01710 | Prodigal: 2.6 | CDS | 2.3.3.5 | — | — | — | P45858 | mmgD | — | — | 2-methylcitrate synthase |
| Contig1 | 1836861 | 1837994 | − | GENE_01711 | Prodigal: 2.6 | CDS | 1.3.99.- | — | — | — | P45857 | mmgC | — | — | Acyl-CoA dehydrogenase |
| Contig1 | 1838024 | 1838875 | − | GENE_01712 | Prodigal: 2.6 | CDS | 1.1.1.157 | — | — | — | P45856 | mmgB | — | — | putative 3-hydroxybutyryl-CoA dehydrogenase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1838895 | 1840076 | − | GENE_01713 | Prodigal: 2.6 | CDS | 2.3.1.9 | — | — | — | P45855 | mmgA | — | — | Acetyl-CoA acetyltransferase |
| Contig1 | 1840217 | 1840954 | − | GENE_01714 | Prodigal: 2.6 | CDS | 3.1.4.46 | — | — | — | P10908 | ugpQ_2 | — | — | Glycerophosphoryl diester phosphodiesterase |
| Contig1 | 1841042 | 1841668 | − | GENE_01715 | Prodigal: 2.6 | CDS | 3.5.1.28 | — | — | — | Q02114 | lytC_1 | — | — | N-acetylmuramoyl-L-alanine amidase LytC precursor |
| Contig1 | 1841687 | 1841980 | − | GENE_01716 | Prodigal: 2.6 | CDS | — | — | — | — | — | — | — | — | hypothetical protein |
| Contig1 | 1842314 | 1842937 | − | GENE_01717 | Prodigal: 2.6 | CDS | — | — | — | MF_01521 | — | mntP_1 | — | — | Putative manganese efflux pump MntP |
| Contig1 | 1843084 | 1843716 | + | GENE_01718 | Prodigal: 2.6 | CDS | — | — | PF01381.16 | — | — | — | — | — | Helix-turn-helix |
| Contig1 | 1843837 | 1843932 | + | GENE_01719 | Prodigal: 2.6 | CDS | — | — | — | — | — | — | — | — | hypothetical protein |
| Contig1 | 1844238 | 1845356 | + | GENE_01720 | Prodigal: 2.6 | CDS | 1.-.-.- | — | — | — | P32382 | — | — | — | NADH oxidase |
| Contig1 | 1845480 | 1845695 | + | GENE_01721 | Prodigal: 2.6 | CDS | — | — | — | — | O06716 | gerPF_2 | — | — | putative spore germination protein GerPF |
| Contig1 | 1845822 | 1846034 | + | GENE_01722 | Prodigal: 2.6 | CDS | — | — | — | — | O06716 | gerPF_3 | — | — | putative spore germination protein GerPF |
| Contig1 | 1846209 | 1847390 | + | GENE_01723 | Prodigal: 2.6 | CDS | 5.1.1.1 | — | — | — | Q9S5V6 | alr_1 | — | — | Alanine racemase |
| Contig1 | 1847538 | 1848338 | − | GENE_01724 | Prodigal: 2.6 | CDS | — | — | — | — | P06534 | spo0A_1 | — | — | Stage 0 sporulation protein A |
| Contig1 | 1848619 | 1849899 | − | GENE_01725 | Prodigal: 2.6 | CDS | 3.4.21.11 | — | — | — | P17896 | spoIVB | — | — | SpoIVB peptidase precursor |
| Contig1 | 1850063 | 1851793 | − | GENE_01726 | Prodigal: 2.6 | CDS | — | — | — | — | P05824 | recN | — | — | DNA repair protein RecN |
| Contig1 | 1851825 | 1852274 | − | GENE_01727 | Prodigal: 2.6 | CDS | — | — | — | — | P17893 | argR | — | — | Arginine repressor |
| Contig1 | 1852369 | 1853214 | − | GENE_01728 | Prodigal: 2.6 | CDS | — | — | — | — | Q06803 | tlyA | — | — | Hemolysin A |
| Contig1 | 1853211 | 1855112 | − | GENE_01729 | Prodigal: 2.6 | CDS | 2.2.1.7 | — | — | — | P77488 | dxs | — | — | 1-deoxy-D-xylulose-5-phosphate synthase |
| Contig1 | 1855256 | 1856146 | − | GENE_01730 | Prodigal: 2.6 | CDS | 2.5.1.10 | — | — | — | Q08291 | — | — | — | Farnesyl diphosphate synthase |
| Contig1 | 1856136 | 1856390 | − | GENE_01731 | Prodigal: 2.6 | CDS | 3.1.11.6 | — | — | — | P0A8G9 | xseB | — | — | Exodeoxyribonuclease 7 small subunit |
| Contig1 | 1856387 | 1857733 | − | GENE_01732 | Prodigal: 2.6 | CDS | 3.1.11.6 | — | — | — | P04994 | xseA | — | — | Exodeoxyribonuclease 7 large subunit |
| Contig1 | 1857857 | 1858708 | − | GENE_01733 | Prodigal: 2.6 | CDS | — | — | — | — | Q0PA35 | folD | — | — | Bifunctional protein FolD protein |
| Contig1 | 1858720 | 1859112 | − | GENE_01734 | Prodigal: 2.6 | CDS | — | — | — | — | P65578 | — | — | N utilization substance protein B homolog | hypothetical protein |
| Contig1 | 1859377 | 1859784 | − | GENE_01735 | Prodigal: 2.6 | CDS | — | — | — | — | P0A0P8 | — | — | — | Alkaline shock protein 23 |
| Contig1 | 1859806 | 1861158 | − | GENE_01736 | Prodigal: 2.6 | CDS | 6.3.4.14 | — | — | — | P37798 | accC | — | — | Biotin carboxylase |
| Contig1 | 1861173 | 1861652 | − | GENE_01737 | Prodigal: 2.6 | CDS | — | — | — | — | Q06881 | accB | — | — | Biotin carboxyl carrier protein of acetyl-CoA carboxylase |
| Contig1 | 1861806 | 1862456 | − | GENE_01738 | Prodigal: 2.6 | CDS | — | — | — | — | P49785 | spoIIIAH | — | — | Stage III sporulation protein AH |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1862460 | 1863152 | − | GENE_01739 | Prodigal: 2.6 | CDS | — | — | — | — | — | — | — | — | hypothetical protein |
| Contig1 | 1863145 | 1863765 | − | GENE_01740 | Prodigal: 2.6 | CDS | — | — | PF09581.4 | — | — | — | — | — | Stage III sporulation protein AF (Spore_III_AF) |
| Contig1 | 1863782 | 1864990 | − | GENE_01741 | Prodigal: 2.6 | CDS | — | — | — | — | P49782 | spoIIIAE | — | — | Stage III sporulation protein AE precursor |
| Contig1 | 1865023 | 1865355 | − | GENE_01742 | Prodigal: 2.6 | CDS | — | — | PF06686.5 | — | — | — | — | — | Stage III sporulation protein AC/AD protein family protein |
| Contig1 | 1865425 | 1865631 | − | GENE_01743 | Prodigal: 2.6 | CDS | — | — | PF06686.5 | — | — | — | — | — | Stage III sporulation protein AC/AD protein family protein |
| Contig1 | 1865654 | 1866169 | − | GENE_01744 | Prodigal: 2.6 | CDS | — | PRK08307 | — | — | — | — | — | — | stage III sporulation protein SpoAB |
| Contig1 | 1866163 | 1867086 | − | GENE_01745 | Prodigal: 2.6 | CDS | — | — | PF03266.9 | — | — | — | — | — | NTPase |
| Contig1 | 1867163 | 1867444 | − | GENE_01746 | Prodigal: 2.6 | CDS | — | — | — | — | — | — | — | — | hypothetical protein |
| Contig1 | 1867592 | 1868149 | − | GENE_01747 | Prodigal: 2.6 | CDS | — | — | — | — | P99066 | efp | — | — | Elongation factor P |
| Contig1 | 1868174 | 1869235 | − | GENE_01748 | Prodigal: 2.6 | CDS | 3.4.13.9 | — | PF11085.2 | — | Q9S6S1 | pepQ | — | — | Xaa-Pro dipeptidase |
| Contig1 | 1869367 | 1869897 | − | GENE_01749 | Prodigal: 2.6 | CDS | — | — | — | — | — | — | — | Conserved membrane protein YqhR | hypothetical protein |
| Contig1 | 1870119 | 1871075 | + | GENE_01750 | Prodigal: 2.6 | CDS | — | — | — | — | — | — | — | — | hypothetical protein |
| Contig1 | 1871110 | 1871505 | + | GENE_01751 | Prodigal: 2.6 | CDS | — | — | — | — | — | — | — | — | hypothetical protein |
| Contig1 | 1871502 | 1872377 | − | GENE_01752 | Prodigal: 2.6 | CDS | — | — | PF01734.1 | — | — | — | — | — | Patatin-like phospholipase |
| Contig1 | 1872492 | 1872920 | − | GENE_01753 | Prodigal: 2.6 | CDS | — | — | — | — | P54512 | mntR | — | — | Transcriptional regulator MntR |
| Contig1 | 1873020 | 1873856 | − | GENE_01754 | Prodigal: 2.6 | CDS | 2.3.1.181 | — | — | — | P54511 | lipM | — | — | Octanoyltransferase LipM |
| Contig1 | 1874050 | 1874430 | + | GENE_01755 | Prodigal: 2.6 | CDS | — | — | — | — | Q7D5X9 | moeZ | — | — | putative adenylyltransferase/ sulfurtransferase MoeZ |
| Contig1 | 1874483 | 1875958 | − | GENE_01756 | Prodigal: 2.6 | CDS | 1.4.4.2 | — | — | — | P99168 | gcvPB | — | — | putative glycine dehydrogenase (decarboxylating) subunit 2 |
| Contig1 | 1875951 | 1877297 | − | GENE_01757 | Prodigal: 2.6 | CDS | 1.4.4.2 | — | — | — | P64218 | gcvPA | — | — | putative glycine dehydrogenase (decarboxylating) subunit 1 |
| Contig1 | 1877312 | 1878415 | − | GENE_01758 | Prodigal: 2.6 | CDS | 2.1.2.10 | — | — | — | P54378 | gcvT | — | — | Aminomethyltransferase |
| Contig1 | 1878835 | 1880505 | + | GENE_01759 | Prodigal: 2.6 | CDS | 3.6.4.- | — | — | — | P60240 | rapA_3 | — | — | RNA polymerase-associated protein RapA |
| Contig1 | 1880523 | 1881317 | + | GENE_01760 | Prodigal: 2.6 | CDS | — | — | PF11079.2 | — | — | — | — | — | Bacterial protein YqhG of unknown function |
| Contig1 | 1881494 | 1881667 | + | GENE_01761 | Prodigal: 2.6 | CDS | — | — | PF08671.4 | — | — | — | — | — | Anti-repressor SinI |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1881695 | 1881997 | + | GENE_01762 | Prodigal: 2.6 | CDS | — | — | — | — | P06533 | sinR_1 | — | — | HTH-type transcriptional regulator SinR |
| Contig1 | 1882083 | 1882868 | — | GENE_01763 | Prodigal: 2.6 | CDS | — | — | — | — | P54507 | tasA | — | — | Spore coat-associated protein N precursor |
| Contig1 | 1882932 | 1883516 | — | GENE_01764 | Prodigal: 2.6 | CDS | 3.4.21.89 | — | — | — | P54506 | sipW | — | — | Signal peptidase I W |
| Contig1 | 1883488 | 1884159 | — | GENE_01765 | Prodigal: 2.6 | CDS | — | — | — | — | — | — | — | — | hypothetical protein |
| Contig1 | 1884418 | 1884747 | + | GENE_01766 | Prodigal: 2.6 | CDS | — | — | — | — | — | — | — | — | hypothetical protein |
| Contig1 | 1884787 | 1884966 | — | GENE_01767 | Prodigal: 2.6 | CDS | — | — | — | — | — | — | — | — | hypothetical protein |
| Contig1 | 1885023 | 1885400 | — | GENE_01768 | Prodigal: 2.6 | CDS | — | — | — | — | P25959 | comGG | — | — | ComG operon protein 7 precursor |
| Contig1 | 1885401 | 1885796 | — | GENE_01769 | Prodigal: 2.6 | CDS | — | — | — | — | — | — | — | — | hypothetical protein |
| Contig1 | 1885810 | 1886130 | — | GENE_01770 | Prodigal: 2.6 | CDS | — | — | — | — | — | — | — | — | hypothetical protein |
| Contig1 | 1886108 | 1886545 | — | GENE_01771 | Prodigal: 2.6 | CDS | — | — | — | — | — | — | — | — | hypothetical protein |
| Contig1 | 1886535 | 1886801 | — | GENE_01772 | Prodigal: 2.6 | CDS | — | — | — | — | P25955 | comGC | — | — | ComG operon protein 3 precursor |
| Contig1 | 1886848 | 1887885 | — | GENE_01773 | Prodigal: 2.6 | CDS | — | — | — | — | P45780 | epsF_1 | — | — | Type II secretion system protein F |
| Contig1 | 1887872 | 1888942 | — | GENE_01774 | Prodigal: 2.6 | CDS | — | — | — | — | P45759 | gspE | — | — | Putative type II secretion system protein E |
| Contig1 | 1889134 | 1890084 | — | GENE_01775 | Prodigal: 2.6 | CDS | — | — | — | — | P40948 | corA_2 | — | — | Magnesium transport protein CorA |
| Contig1 | 1890230 | 1891531 | + | GENE_01776 | Prodigal: 2.6 | CDS | — | — | — | — | P0A2L3 | corC_2 | — | — | Magnesium and cobalt efflux protein CorC |
| Contig1 | 1891569 | 1892399 | — | GENE_01777 | Prodigal: 2.6 | CDS | — | — | — | — | P54504 | rsbRD_2 | — | — | RsbT co-antagonist protein RsbRD |
| Contig1 | 1892471 | 1892541 | + | GENE_01778 | Aragorn: 1.2 | tRNA | — | — | — | — | — | — | — | — | tRNA-Gln(ttg) |
| Contig1 | 1892605 | 1892985 | + | GENE_01779 | Prodigal: 2.6 | CDS | — | — | — | — | P54503 | mgsR_1 | — | — | Regulatory protein MgsR |
| Contig1 | 1893222 | 1893467 | + | GENE_01780 | Prodigal: 2.6 | CDS | — | — | — | — | — | — | — | — | hypothetical protein |
| Contig1 | 1893508 | 1894146 | — | GENE_01781 | Prodigal: 2.6 | CDS | 3.-.-.- | — | — | — | Q5XD24 | — | — | — | putative metallo-hydrolase |
| Contig1 | 1894301 | 1894474 | + | GENE_01782 | Prodigal: 2.6 | CDS | — | — | — | — | — | — | — | — | hypothetical protein |
| Contig1 | 1894507 | 1894821 | — | GENE_01783 | Prodigal: 2.6 | CDS | — | — | — | — | — | — | — | — | hypothetical protein |
| Contig1 | 1894827 | 1895864 | — | GENE_01784 | Prodigal: 2.6 | CDS | — | — | — | — | — | — | — | — | hypothetical protein |
| Contig1 | 1895937 | 1897064 | — | GENE_01785 | Prodigal: 2.6 | CDS | 3.4.19.11 | — | — | — | Q03415 | — | — | — | Gamma-D-glutamyl-L-diamino acid endopeptidase 1 |
| Contig1 | 1897147 | 1898109 | — | GENE_01786 | Prodigal: 2.6 | CDS | 2.7.1.2 | — | — | — | P54495 | glcK | — | — | Glucokinase |
| Contig1 | 1898145 | 1898354 | — | GENE_01787 | Prodigal: 2.6 | CDS | — | — | — | — | — | — | — | — | hypothetical protein |
| Contig1 | 1898552 | 1899916 | + | GENE_01788 | Prodigal: 2.6 | CDS | — | — | — | — | O07553 | nhaC_2 | — | — | Na(+)/H(+) antiporter NhaC |
| Contig1 | 1899993 | 1900166 | — | GENE_01789 | Prodigal: 2.6 | CDS | — | — | — | — | — | — | — | — | hypothetical protein |
| Contig1 | 1900237 | 1900791 | — | GENE_01790 | Prodigal: 2.6 | CDS | 6.3.3.2 | — | — | — | P75430 | — | — | — | putative 5-formyltetrahydrofolate cyclo-ligase |
| Contig1 | 1900870 | 1901019 | — | GENE_01791 | Prodigal: 2.6 | CDS | — | — | — | — | P23375 | rpmGA | — | — | 50S ribosomal protein L33 1 |
| Contig1 | 1901367 | 1901720 | + | GENE_01792 | Prodigal: 2.6 | CDS | — | — | — | — | — | — | — | — | hypothetical protein |
| Contig1 | 1901717 | 1902181 | + | GENE_01793 | Prodigal: 2.6 | CDS | — | — | PF02618.10 | — | — | — | — | — | YceG-like family protein |
| Contig1 | 1902279 | 1903061 | — | GENE_01794 | Prodigal: 2.6 | CDS | 3.6.3.27 | — | — | — | P0A2V9 | pstB3_2 | — | — | Phosphate import ATP-binding protein PstB 3 |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1903073 | 1903879 | − | GENE_01795 | Prodigal: 2.6 | CDS | 3.6.3.27 | — | — | — | P0A2V9 | pstB3_3 | — | — | Phosphate import ATP-binding protein PstB 3 |
| Contig1 | 1903898 | 1904782 | − | GENE_01796 | Prodigal: 2.6 | CDS | | — | — | — | P07654 | pstA | — | — | Phosphate transport system permease protein PstA |
| Contig1 | 1904782 | 1905711 | − | GENE_01797 | Prodigal: 2.6 | CDS | | — | — | — | P0AGH8 | pstC | — | — | Phosphate transport system permease protein PstC |
| Contig1 | 1905760 | 1906662 | − | GENE_01798 | Prodigal: 2.6 | CDS | | — | — | — | Q8DPB1 | pstS1 | — | — | Phosphate-binding protein PstS 1 precursor |
| Contig1 | 1906818 | 1908965 | − | GENE_01799 | Prodigal: 2.6 | CDS | | — | — | — | Q796K8 | pbpH_2 | — | — | Penicillin-binding protein H |
| Contig1 | 1909067 | 1910356 | − | GENE_01800 | Prodigal: 2.6 | CDS | | — | PF07690.10 | — | — | — | — | — | Major Facilitator Superfamily protein |
| Contig1 | 1910474 | 1911079 | − | GENE_01801 | Prodigal: 2.6 | CDS | 1.15.1.1 | — | — | — | P54375 | sodA_2 | — | — | Superoxide dismutase [Mn] |
| Contig1 | 1911246 | 1911728 | − | GENE_01802 | Prodigal: 2.6 | CDS | | — | — | — | — | — | — | — | hypothetical protein |
| Contig1 | 1911887 | 1912651 | + | GENE_01803 | Prodigal: 2.6 | CDS | | — | — | — | — | — | — | — | hypothetical protein |
| Contig1 | 1912743 | 1913045 | + | GENE_01804 | Prodigal: 2.6 | CDS | | — | — | — | — | — | — | — | hypothetical protein |
| Contig1 | 1913169 | 1914296 | + | GENE_01805 | Prodigal: 2.6 | CDS | 1.17.7.1 | — | — | — | Q81LV7 | ispG | — | — | 4-hydroxy-3-methylbut-2-en-1-yl diphosphate synthase |
| Contig1 | 1914330 | 1914701 | + | GENE_01806 | Prodigal: 2.6 | CDS | | — | — | — | — | — | — | — | hypothetical protein |
| Contig1 | 1914841 | 1915422 | + | GENE_01807 | Prodigal: 2.6 | CDS | | — | — | — | — | — | — | — | hypothetical protein |
| Contig1 | 1915453 | 1915863 | − | GENE_01808 | Prodigal: 2.6 | CDS | | — | — | — | P54479 | zur | — | — | Zinc-specific metallo-regulatory protein |
| Contig1 | 1915987 | 1916868 | − | GENE_01809 | Prodigal: 2.6 | CDS | | — | — | — | — | — | — | — | hypothetical protein |
| Contig1 | 1916987 | 1917241 | + | GENE_01810 | Prodigal: 2.6 | CDS | | — | — | — | — | — | — | — | hypothetical protein |
| Contig1 | 1917270 | 1918163 | + | GENE_01811 | Prodigal: 2.6 | CDS | 3.1.21.2 | — | — | — | Q5KX27 | nfo | — | — | putative endonuclease 4 |
| Contig1 | 1918175 | 1919491 | − | GENE_01812 | Prodigal: 2.6 | CDS | 3.6.4.13 | — | — | — | P54475 | cshB_2 | — | — | DEAD-box ATP-dependent RNA helicase CshB |
| Contig1 | 1919657 | 1920352 | + | GENE_01813 | Prodigal: 2.6 | CDS | | — | — | — | — | — | — | — | hypothetical protein |
| Contig1 | 1920475 | 1921419 | + | GENE_01814 | Prodigal: 2.6 | CDS | 1.17.1.2 | — | — | — | P62623 | ispH | — | — | 4-hydroxy-3-methylbut-2-enyl diphosphate reductase |
| Contig1 | 1921440 | 1922561 | − | GENE_01815 | Prodigal: 2.6 | CDS | 3.5.4.16 | — | — | — | P67272 | — | — | — | Putative GTP cyclohydrolase 1 type 2 |
| Contig1 | 1922554 | 1923309 | − | GENE_01816 | Prodigal: 2.6 | CDS | 2.1.1.217 | — | — | — | P54471 | trmK | — | — | tRNA (adenine(22))-N(1)-methyltransferase |
| Contig1 | 1923384 | 1923746 | − | GENE_01817 | Prodigal: 2.6 | CDS | | — | — | — | P24469 | CCcA2 | — | — | Cytochrome c-550 |
| Contig1 | 1924097 | 1925218 | − | GENE_01818 | Prodigal: 2.6 | CDS | | — | — | — | P06224 | sigA | — | — | RNA polymerase sigma factor SigA |
| Contig1 | 1925410 | 1927221 | − | GENE_01819 | Prodigal: 2.6 | CDS | 2.7.7.- | — | — | — | Q9X4D0 | dnaG | — | — | DNA primase |
| Contig1 | 1927243 | 1927749 | − | GENE_01820 | Prodigal: 2.6 | CDS | | — | — | — | — | — | — | — | hypothetical protein |
| Contig1 | 1928005 | 1928817 | − | GENE_01821 | Prodigal: 2.6 | CDS | 2.7.11.32 | PRK00124 | — | — | P54470 | yqfL | — | — | Putative pyruvate, phosphate dikinase regulatory protein |
| Contig1 | 1928843 | 1929484 | − | GENE_01822 | Prodigal: 2.6 | CDS | | — | — | — | O34994 | ccpN | — | — | Transcriptional repressor CcpN |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1929582 | 1930295 | − | GENE_01823 | Prodigal: 2.6 | CDS | 6.1.1.14 | — | — | — | P00961 | glyS_1 | — | — | Glycine--tRNA ligase beta subunit |
| Contig1 | 1930259 | 1931620 | − | GENE_01824 | Prodigal: 2.6 | CDS | 6.1.1.14 | — | — | — | P00961 | glyS_2 | — | — | Glycine--tRNA ligase beta subunit |
| Contig1 | 1931613 | 1932500 | − | GENE_01825 | Prodigal: 2.6 | CDS | 6.1.1.14 | — | — | — | P00960 | glyQ | — | — | Glycine--tRNA ligase alpha subunit |
| Contig1 | 1932802 | 1933569 | − | GENE_01826 | Prodigal: 2.6 | CDS | — | — | — | — | P42095 | recO | — | — | DNA repair protein RecO |
| Contig1 | 1933606 | 1933749 | − | GENE_01827 | Prodigal: 2.6 | CDS | — | — | — | — | — | — | — | — | hypothetical protein |
| Contig1 | 1933905 | 1934810 | − | GENE_01828 | Prodigal: 2.6 | CDS | — | — | — | — | P42182 | era | — | — | GTPase Era |
| Contig1 | 1934791 | 1935201 | − | GENE_01829 | Prodigal: 2.6 | CDS | 3.5.4.5 | — | — | — | P19079 | cdd | — | — | Cytidine deaminase |
| Contig1 | 1935325 | 1935705 | − | GENE_01830 | Prodigal: 2.6 | CDS | 2.7.1.66 | — | — | — | P19638 | dgkA | — | — | Undecaprenol kinase |
| Contig1 | 1935680 | 1936153 | − | GENE_01831 | Prodigal: 2.6 | CDS | 3.1.-.- | — | — | — | O67367 | ybeY | — | — | Endoribonuclease YbeY |
| Contig1 | 1936154 | 1938286 | − | GENE_01832 | Prodigal: 2.6 | CDS | — | — | PF07697.5 | — | — | — | — | — | 7TM-HD extracellular PhoH-like protein |
| Contig1 | 1938367 | 1939326 | − | GENE_01833 | Prodigal: 2.6 | CDS | — | — | PF06898.5 | — | P0A9K3 | ybeZ_2 | — | — | Putative stage IV sporulation protein YqfD |
| Contig1 | 1939330 | 1940514 | − | GENE_01834 | Prodigal: 2.6 | CDS | — | — | — | — | — | — | — | — | YabP family protein |
| Contig1 | 1940532 | 1940813 | − | GENE_01835 | Prodigal: 2.6 | CDS | — | — | PF07873.5 | — | — | — | — | — | hypothetical protein |
| Contig1 | 1940870 | 1941304 | − | GENE_01836 | Prodigal: 2.6 | CDS | — | — | PF12127.2 | — | — | — | — | — | SigmaW regulon antibacterial |
| Contig1 | 1941332 | 1942324 | − | GENE_01837 | Prodigal: 2.6 | CDS | — | — | — | — | — | — | — | — | hypothetical protein |
| Contig1 | 1942349 | 1943665 | − | GENE_01838 | Prodigal: 2.6 | CDS | — | — | PF01957.12 | — | — | — | — | NfeD-like C-terminal, partner-binding | hypothetical protein |
| Contig1 | 1943788 | 1944234 | − | GENE_01839 | Prodigal: 2.6 | CDS | — | PRK04028 | — | — | — | — | — | — | glutamyl-tRNA(Gln) amidotransferase subunit E |
| Contig1 | 1944249 | 1944422 | − | GENE_01840 | Prodigal: 2.6 | CDS | — | — | — | — | — | — | — | — | 30S ribosomal protein S21 |
| Contig1 | 1944585 | 1945520 | + | GENE_01841 | Prodigal: 2.6 | CDS | 2.-.-.- | — | PF02690.9 | — | P21478 | rpsU | — | — | Na+/Pi-cotransporter |
| Contig1 | 1945558 | 1946913 | − | GENE_01842 | Prodigal: 2.6 | CDS | — | — | — | — | P54462 | mtaB | — | — | Threonylcarbamoyl-adenosine tRNA methylthiotransferase MtaB |
| Contig1 | 1946913 | 1947683 | − | GENE_01843 | Prodigal: 2.6 | CDS | 2.1.1.193 | — | — | — | P54461 | rsmE | — | — | Ribosomal RNA small subunit methyltransferase E |
| Contig1 | 1947706 | 1948641 | − | GENE_01844 | Prodigal: 2.6 | CDS | 2.1.1.- | — | — | — | P0A0P5 | prmA | — | — | Ribosomal protein L11 methyltransferase |
| Contig1 | 1948665 | 1949792 | − | GENE_01845 | Prodigal: 2.6 | CDS | — | — | — | — | P17631 | dnaJ | — | — | Chaperone protein DnaJ |
| Contig1 | 1949978 | 1951816 | − | GENE_01846 | Prodigal: 2.6 | CDS | — | — | — | MF_01151 | P17820 | dnaK | — | — | Chaperone protein DnaK |
| Contig1 | 1951841 | 1952416 | − | GENE_01847 | Prodigal: 2.6 | CDS | — | — | — | — | — | grpE | — | — | Protein GrpE |
| Contig1 | 1952476 | 1953507 | − | GENE_01847 | Prodigal: 2.6 | CDS | — | — | — | — | P30727 | hrcA | — | — | Heat-inducible transcription repressor HrcA |
| Contig1 | 1953588 | 1954727 | − | GENE_01849 | Prodigal: 2.6 | CDS | 1.3.99.22 | — | — | — | P54304 | hemN | — | — | Oxygen-independent coproporphyrinogen-III oxidase 1 |
| Contig1 | 1954787 | 1956622 | − | GENE_01850 | Prodigal: 2.6 | CDS | 3.6.5.- | — | — | — | Q2FXY7 | lepA | — | — | Elongation factor 4 |
| Contig1 | 1956755 | 1957093 | − | GENE_01851 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1957110 | 1958303 | − | GENE_01852 | Prodigal: 2.6 | CDS | — | — | PF07454.5 | — | — | — | — | — | Stage II sporulation protein P (SpoIIP) |
| Contig1 | 1958371 | 1959477 | − | GENE_01853 | Prodigal: 2.6 | CDS | 3.4.24.78 | — | — | — | P22322 | gpr | — | — | Germination protease precursor |
| Contig1 | 1959680 | 1959946 | + | GENE_01854 | Prodigal: 2.6 | CDS | — | — | — | — | P21477 | rpsT | — | — | 30S ribosomal protein S20 |
| Contig1 | 1959982 | 1961004 | − | GENE_01855 | Prodigal: 2.6 | CDS | — | PRK05574 | — | — | — | — | — | — | DNA polymerase III subunit delta |
| Contig1 | 1961392 | 1963743 | − | GENE_01856 | Prodigal: 2.6 | CDS | — | PRK11539 | — | — | — | — | — | — | ComEC family competence protein |
| Contig1 | 1963744 | 1964313 | − | GENE_01857 | Prodigal: 2.6 | CDS | 3.5.4.33 | — | — | MF_00972 | — | tadA_1 | — | — | tRNA-specific adenosine deaminase |
| Contig1 | 1964380 | 1964994 | − | GENE_01858 | Prodigal: 2.6 | CDS | — | — | — | — | P39694 | comEA | — | — | ComE operon protein 1 |
| Contig1 | 1965053 | 1965874 | + | GENE_01859 | Prodigal: 2.6 | CDS | 1.5.1.2 | — | — | — | Q7A5G8 | proC_3 | — | — | Pyrroline-5-carboxylate reductase |
| Contig1 | 1965943 | 1966680 | − | GENE_01860 | Prodigal: 2.6 | CDS | 2.1.1.- | — | — | — | E5KIC0 | cypM_1 | — | — | Cypemycin methyltransferase |
| Contig1 | 1966677 | 1967033 | − | GENE_01861 | Prodigal: 2.6 | CDS | — | — | — | — | Q9KD89 | rsfS | — | — | Ribosomal silencing factor RsfS |
| Contig1 | 1967051 | 1967611 | − | GENE_01862 | Prodigal: 2.6 | CDS | — | PRK07152 | — | — | — | — | — | — | putative nicotinate-nucleotide adenylyltransferase |
| Contig1 | 1967601 | 1968170 | − | GENE_01863 | Prodigal: 2.6 | CDS | 2.7.7.18 | — | — | — | P54455 | nadD | — | — | Nicotinate-nucleotide adenylyltransferase |
| Contig1 | 1968181 | 1968471 | − | GENE_01864 | Prodigal: 2.6 | CDS | — | — | — | — | — | — | — | — | RNA-binding protein |
| Contig1 | 1968465 | 1969307 | − | GENE_01865 | Prodigal: 2.6 | CDS | 1.1.1.25 | — | — | — | P71376 | aroE_2 | — | — | Shikimate dehydrogenase |
| Contig1 | 1969327 | 1970427 | − | GENE_01866 | Prodigal: 2.6 | CDS | — | — | — | MF_00195 | Q5HNV1 | der_2 | — | — | GTPase Der |
| Contig1 | 1970430 | 1970948 | − | GENE_01867 | Prodigal: 2.6 | CDS | 3.1.3.18 | — | — | MF_00495 | — | gph | — | — | Phosphoglycolate phosphatase |
| Contig1 | 1971578 | 1971712 | − | GENE_01868 | Prodigal: 2.6 | CDS | — | — | — | — | — | — | — | — | hypothetical protein |
| Contig1 | 1971787 | 1972518 | − | GENE_01869 | Prodigal: 2.6 | CDS | — | PRK10528 | — | — | — | — | — | — | multifunctional acyl-CoA thioesterase I and protease I and lysophospholipase L1 |
| Contig1 | 1972588 | 1973322 | − | GENE_01870 | Prodigal: 2.6 | CDS | 3.5.1.- | — | — | — | O34798 | pdaC_1 | — | — | Peptidoglycan-N-acetylmuramic acid deacetylase PdaC |
| Contig1 | 1973556 | 1974182 | + | GENE_01871 | Prodigal: 2.6 | CDS | — | — | — | — | P76221 | ydjz2 | — | — | TVP38/TMEM64 family inner membrane protein YdjZ |
| Contig1 | 1974528 | 1974668 | − | GENE_01872 | Prodigal: 2.6 | CDS | — | — | — | — | — | — | — | — | hypothetical protein |
| Contig1 | 1974634 | 1975890 | − | GENE_01873 | Prodigal: 2.6 | CDS | — | PRK10489 | — | — | — | — | — | — | enterobactin exporter EntS |
| Contig1 | 1976345 | 1977070 | + | GENE_01874 | Prodigal: 2.6 | CDS | — | — | — | — | P12254 | sigK | — | — | RNA polymerase sigma-K factor precursor |
| Contig1 | 1977117 | 1977317 | − | GENE_01875 | Prodigal: 2.6 | CDS | — | — | — | — | — | — | — | — | hypothetical protein |
| Contig1 | 1977418 | 1978116 | − | GENE_01876 | Prodigal: 2.6 | CDS | 5.1.1.13 | — | — | — | P29079 | — | — | — | Aspartate racemase |
| Contig1 | 1979158 | 1980009 | − | GENE_01877 | Prodigal: 2.6 | CDS | 1.1.1.- | — | — | — | O32210 | yvgN_1 | — | — | Glyoxal reductase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 1980180 | 1980623 | + | GENE_01878 | Prodigal: 2.6 | CDS | — | — | — | — | O06008 | adhR_1 | — | — | HTH-type transcriptional regulator AdhR |
| Contig1 | 1980787 | 1980963 | − | GENE_01879 | Prodigal: 2.6 | CDS | — | — | — | — | — | — | — | — | hypothetical protein |
| Contig1 | 1981104 | 1982099 | − | GENE_01880 | Prodigal: 2.6 | CDS | — | — | — | — | — | — | — | — | hypothetical protein |
| Contig1 | 1982663 | 1983028 | − | GENE_01881 | Prodigal: 2.6 | CDS | — | — | — | — | — | — | — | — | hypothetical protein |
| Contig1 | 1983104 | 1983214 | − | GENE_01882 | Prodigal: 2.6 | CDS | — | — | — | — | — | — | — | — | hypothetical protein |
| Contig1 | 1983308 | 1983961 | − | GENE_01883 | Prodigal: 2.6 | CDS | — | — | — | — | — | — | — | — | hypothetical protein |
| Contig1 | 1983991 | 1984227 | − | GENE_01884 | Prodigal: 2.6 | CDS | — | — | — | — | — | — | — | — | hypothetical protein |
| Contig1 | 1985108 | 1985914 | + | GENE_01885 | Prodigal: 2.6 | CDS | — | — | — | — | D5EXZ4 | axel-6A | — | — | Carbohydrate acetyl esterase/feruloyl esterase precursor |
| Contig1 | 1985911 | 1986438 | + | GENE_01886 | Prodigal: 2.6 | CDS | — | — | PF03551.8 | — | — | — | — | — | Transcriptional regulator PadR-like family protein |
| Contig1 | 1986493 | 1986918 | + | GENE_01887 | Prodigal: 2.6 | CDS | — | — | PF06445.9 | — | — | — | — | — | Bacterial transcription activator, effector binding domain |
| Contig1 | 1987371 | 1987910 | − | GENE_01888 | Prodigal: 2.6 | CDS | — | PRK06217 | — | — | — | — | — | — | hypothetical protein |
| Contig1 | 1988391 | 1989767 | − | GENE_01889 | Prodigal: 2.6 | CDS | — | — | — | — | P31474 | hsrA_2 | — | — | putative transport protein HsrA |
| Contig1 | 1989976 | 1990500 | − | GENE_01890 | Prodigal: 2.6 | CDS | — | PRK10975 | — | — | — | — | — | — | TDP-fucosamine acetyltransferase |
| Contig1 | 1990657 | 1991157 | − | GENE_01891 | Prodigal: 2.6 | CDS | — | — | PF05163.6 | — | — | — | — | — | DinB family protein |
| Contig1 | 1991353 | 1991637 | − | GENE_01892 | Prodigal: 2.6 | CDS | 3.1.3.- | — | — | — | — | — | — | — | hypothetical protein |
| Contig1 | 1991878 | 1992681 | − | GENE_01893 | Prodigal: 2.6 | CDS | 3.1.3.- | — | — | — | P75809 | ybjI_1 | — | — | Flavin mononucleotide phosphatase YbjI |
| Contig1 | 1992714 | 1993526 | − | GENE_01894 | Prodigal: 2.6 | CDS | — | — | — | — | P75809 | ybjI_2 | — | — | Flavin mononucleotide phosphatase YbjI |
| Contig1 | 1993762 | 1994487 | + | GENE_01895 | Prodigal: 2.6 | CDS | — | — | — | — | Q45581 | ybbH_1 | — | — | putative HTH-type transcriptional regulator YbbH |
| Contig1 | 1994582 | 1995529 | − | GENE_01896 | Prodigal: 2.6 | CDS | 5.3.1.8 | — | — | — | P39841 | yvyI_1 | — | — | Putative mannose-6-phosphate isomerase YvyI |
| Contig1 | 1995544 | 1997502 | − | GENE_01897 | Prodigal: 2.6 | CDS | — | — | — | — | O31645 | manP | — | — | PTS system mannose-specific EIIBCA component |
| Contig1 | 1997655 | 1999607 | − | GENE_01898 | Prodigal: 2.6 | CDS | — | — | — | — | P46321 | licR_1 | — | — | putative licABCH operon regulator |
| Contig1 | 1999835 | 2000752 | − | GENE_01899 | Prodigal: 2.6 | CDS | — | PRK00685 | — | — | — | — | — | — | metal-dependent hydrolase |
| Contig1 | 2000799 | 2001281 | − | GENE_01900 | Prodigal: 2.6 | CDS | 4.2.-.- | — | — | — | P45202 | ybaK | — | — | Cys-tRNA(Pro)/Cys-tRNA(Cys) deacylase YbaK |
| Contig1 | 2001349 | 2002233 | − | GENE_01901 | Prodigal: 2.6 | CDS | — | — | — | — | P20668 | gltC_2 | — | — | HTH-type transcriptional regulator GltC |
| Contig1 | 2002358 | 2003566 | + | GENE_01902 | Prodigal: 2.6 | CDS | — | — | — | — | P43531 | ynfM_2 | — | — | Inner membrane transport protein YnfM |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2003716 | 2006877 | − | GENE_01903 | Prodigal: 2.6 | CDS | — | — | — | — | O08336 | cypE | — | — | putative bifunctional P-450/NADPH-P450 reductase 2 |
| Contig1 | 2006905 | 2007471 | − | GENE_01904 | Prodigal: 2.6 | CDS | — | — | — | — | P43506 | bm3R1_3 | — | — | HTH-type transcriptional repressor Bm3R1 |
| Contig1 | 2007681 | 2008220 | − | GENE_01905 | Prodigal: 2.6 | CDS | 2.1.1.- | — | — | — | O05400 | yrhH | — | — | Putative methyltransferase YrhH |
| Contig1 | 2008722 | 2008862 | − | GENE_01906 | Prodigal: 2.6 | CDS | — | — | PF09501.4 | — | — | — | — | — | putative sporulation protein (Bac_small_yrzI) |
| Contig1 | 2009252 | 2010052 | − | GENE_01907 | Prodigal: 2.6 | CDS | — | — | — | — | P0AC23 | focA | — | — | putative formate transporter 1 |
| Contig1 | 2010317 | 2010685 | − | GENE_01908 | Prodigal: 2.6 | CDS | — | — | — | — | — | — | — | — | hypothetical protein |
| Contig1 | 2010946 | 2013933 | + | GENE_01909 | Prodigal: 2.6 | CDS | 1.2.1.2 | — | — | — | Q99RW4 | — | — | — | Putative formate dehydrogenase |
| Contig1 | 2013951 | 2014442 | + | GENE_01910 | Prodigal: 2.6 | CDS | — | — | — | — | — | — | — | — | hypothetical protein |
| Contig1 | 2014481 | 2014711 | + | GENE_01911 | Prodigal: 2.6 | CDS | — | — | — | — | — | — | — | — | hypothetical protein |
| Contig1 | 2014795 | 2015937 | − | GENE_01912 | Prodigal: 2.6 | CDS | 4.4.1.1 | — | — | — | O05394 | mccB | — | — | Cystathionine gamma-lyase |
| Contig1 | 2015939 | 2016862 | − | GENE_01913 | Prodigal: 2.6 | CDS | 4.2.1.- | — | — | — | O05393 | mccA | — | — | O-acetylserine dependent cystathionine beta-synthase |
| Contig1 | 2016910 | 2017605 | − | GENE_01914 | Prodigal: 2.6 | CDS | 3.2.2.9 | — | — | — | Q9KPI8 | mtnN | — | — | 5′-methylthioadenosine/S-adenosylhomocysteine nucleosidase |
| Contig1 | 2017626 | 2018267 | − | GENE_01915 | Prodigal: 2.6 | CDS | 2.1.1.- | — | — | — | O32029 | yrrT | — | — | putative methyltransferase YrrT |
| Contig1 | 2018451 | 2018654 | + | GENE_01916 | Prodigal: 2.6 | CDS | — | — | — | — | — | — | — | — | hypothetical protein |
| Contig1 | 2018694 | 2019410 | − | GENE_01917 | Prodigal: 2.6 | CDS | — | — | — | — | — | — | — | — | hypothetical protein |
| Contig1 | 2019474 | 2020397 | − | GENE_01918 | Prodigal: 2.6 | CDS | — | — | — | — | O32032 | pbpI_1 | — | — | Penicillin-binding protein 4B |
| Contig1 | 2020424 | 2021227 | − | GENE_01919 | Prodigal: 2.6 | CDS | — | — | — | — | O32032 | pbpI_2 | — | — | Penicillin-binding protein 4B |
| Contig1 | 2021280 | 2021753 | − | GENE_01920 | Prodigal: 2.6 | CDS | — | — | — | — | P80240 | greA | — | — | Transcription elongation factor GreA |
| Contig1 | 2022007 | 2022642 | − | GENE_01921 | Prodigal: 2.6 | CDS | 2.7.1.48 | — | — | — | P67411 | udk | — | — | Uridine kinase |
| Contig1 | 2022649 | 2023917 | − | GENE_01922 | Prodigal: 2.6 | CDS | 3.4.-.- | — | — | — | P45527 | yhbU_1 | — | — | putative protease YhbU precursor |
| Contig1 | 2023935 | 2024864 | − | GENE_01923 | Prodigal: 2.6 | CDS | 3.4.-.- | — | — | — | P45527 | yhbU_2 | — | — | putative protease YhbU precursor |
| Contig1 | 2024871 | 2025524 | − | GENE_01924 | Prodigal: 2.6 | CDS | 2.1.1.- | — | — | — | Q05632 | cbiT | — | — | putative cobalt-precorrin-6Y C(15)-methyltransferase [decarboxylating] |
| Contig1 | 2025676 | 2026767 | − | GENE_01925 | Prodigal: 2.6 | CDS | — | PRK10270 | — | — | — | — | — | — | putative aminodeoxy-chorismate lyase |
| Contig1 | 2026878 | 2027159 | − | GENE_01926 | Prodigal: 2.6 | CDS | — | — | — | — | — | — | — | — | hypothetical protein |
| Contig1 | 2027172 | 2027588 | − | GENE_01927 | Prodigal: 2.6 | CDS | 3.1.-.- | — | — | — | O34634 | yrrK | — | — | Putative Holliday junction resolvase |
| Contig1 | 2027597 | 2027863 | − | GENE_01928 | Prodigal: 2.6 | CDS | — | PRK05473 | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2027948 | 2030584 | – | GENE_01929 | Prodigal: 2.6 | CDS | 6.1.1.7 | — | — | — | P67011 | alaS | — | — | Alanine--tRNA ligase |
| Contig1 | 2030916 | 2031977 | – | GENE_01930 | Prodigal: 2.6 | CDS | — | — | — | — | P0AFS5 | tqsA | — | — | AI-2 transport protein TqsA |
| Contig1 | 2032197 | 2032925 | + | GENE_01931 | Prodigal: 2.6 | CDS | 3.6.3.- | — | — | — | O34677 | glnQ | — | — | Glutamine transport ATP-binding protein GlnQ |
| Contig1 | 2032946 | 2033773 | + | GENE_01932 | Prodigal: 2.6 | CDS | — | — | — | — | O34563 | glnH | — | — | ABC transporter glutamine-binding protein GlnH precursor |
| Contig1 | 2033830 | 2034480 | + | GENE_01933 | Prodigal: 2.6 | CDS | — | — | — | — | O34671 | glnM | — | — | putative glutamine ABC transporter permease protein GlnM |
| Contig1 | 2034499 | 2035155 | + | GENE_01934 | Prodigal: 2.6 | CDS | — | — | — | — | O34606 | glnP | — | — | putative glutamine ABC transporter permease protein GlnP |
| Contig1 | 2035191 | 2035322 | – | GENE_01935 | Prodigal: 2.6 | CDS | — | — | — | — | — | — | — | — | hypothetical protein |
| Contig1 | 2035344 | 2035535 | – | GENE_01936 | Prodigal: 2.6 | CDS | — | — | — | — | — | — | — | — | hypothetical protein |
| Contig1 | 2035548 | 2036006 | – | GENE_01937 | Prodigal: 2.6 | CDS | — | — | PF05239.10 | — | — | — | — | — | PRC-barrel domain protein |
| Contig1 | 2036125 | 2038503 | – | GENE_01938 | Prodigal: 2.6 | CDS | 3.6.4.12 | — | — | — | Q9RT63 | recD2 | — | — | ATP-dependent RecD-like DNA helicase |
| Contig1 | 2038522 | 2039172 | – | GENE_01939 | Prodigal: 2.6 | CDS | — | — | — | — | O34452 | yrrB | — | — | TPR repeat-containing protein YrrB |
| Contig1 | 2039230 | 2040345 | – | GENE_01940 | Prodigal: 2.6 | CDS | 2.8.1.- | — | — | — | Q99TM8 | mnmA | — | — | tRNA-specific 2-thiouridylase MnmA |
| Contig1 | 2040382 | 2041521 | – | GENE_01941 | Prodigal: 2.6 | CDS | 2.8.1.7 | — | — | — | P0A6B7 | iscS_1 | — | — | Cysteine desulfurase |
| Contig1 | 2041540 | 2041917 | + | GENE_01942 | Prodigal: 2.6 | CDS | — | — | — | — | O34527 | cymR | — | — | HTH-type transcriptional regulator CymR |
| Contig1 | 2042151 | 2043419 | + | GENE_01943 | Prodigal: 2.6 | CDS | — | — | — | — | P0AAZ4 | rarA | — | — | Replication-associated recombination protein A |
| Contig1 | 2043495 | 2044259 | – | GENE_01944 | Prodigal: 2.6 | CDS | 6.1.-.- | — | — | — | Q46927 | tcdA | — | — | tRNA threonyl-carbamoyladenosine dehydratase |
| Contig1 | 2044586 | 2046364 | – | GENE_01945 | Prodigal: 2.6 | CDS | 6.1.1.12 | — | — | — | P67015 | aspS | — | — | Aspartate--tRNA ligase |
| Contig1 | 2046379 | 2047653 | – | GENE_01946 | Prodigal: 2.6 | CDS | 6.1.1.21 | — | — | — | P60911 | hisS | — | — | Histidine--tRNA ligase |
| Contig1 | 2047750 | 2047917 | – | GENE_01947 | Prodigal: 2.6 | CDS | — | — | — | — | — | — | — | — | hypothetical protein |
| Contig1 | 2048010 | 2048180 | – | GENE_01948 | Prodigal: 2.6 | CDS | — | — | — | — | — | — | — | — | hypothetical protein |
| Contig1 | 2048311 | 2049873 | + | GENE_01949 | Prodigal: 2.6 | CDS | 3.5.1.28 | — | — | — | Q02114 | lytc_2 | — | — | N-acetylmuramoyl-L-alanine amidase LytC precursor |
| Contig1 | 2049901 | 2050344 | – | GENE_01950 | Prodigal: 2.6 | CDS | 3.1.-.- | — | — | — | O66742 | dtd | — | — | D-tyrosyl-tRNA(Tyr) deacylase |
| Contig1 | 2050357 | 2052561 | – | GENE_01951 | Prodigal: 2.6 | CDS | 27.6.5 | — | — | — | Q99TL8 | relA | — | — | GTP pyrophosphokinase |
| Contig1 | 2052719 | 2053231 | – | GENE_01952 | Prodigal: 2.6 | CDS | 2.4.2.7 | — | — | — | P68779 | apt | — | — | Adenine phosphoribosyltransferase |
| Contig1 | 2053237 | 2055597 | – | GENE_01953 | Prodigal: 2.6 | CDS | 3.1.-.- | — | — | — | P21893 | recJ | — | — | Single-stranded-DNA-specific exonuclease RecJ |
| Contig1 | 2055653 | 2055979 | – | GENE_01954 | Prodigal: 2.6 | CDS | — | — | — | — | — | — | — | — | hypothetical protein |
| Contig1 | 2056043 | 2056540 | – | GENE_01955 | Prodigal: 2.6 | CDS | — | — | — | — | O07535 | khtT_2 | — | — | K(+)/H(+) antiporter subunit KhtT |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2056672 | 2058891 | − | GENE_01956 | Prodigal: 2.6 | CDS | — | — | — | MF_01463_B | — | secD | — | — | Protein translocase subunit SecD |
| Contig1 | 2058928 | 2059224 | − | GENE_01957 | Prodigal: 2.6 | CDS | — | — | — | — | O32049 | comN | — | — | Post-transcriptional regulator ComN |
| Contig1 | 2059340 | 2059582 | + | GENE_01958 | Prodigal: 2.6 | CDS | — | — | — | — | Q00758 | spoVB_1 | — | — | Stage V sporulation protein B |
| Contig1 | 2059579 | 2060895 | + | GENE_01959 | Prodigal: 2.6 | CDS | — | — | — | — | Q00758 | spoVB_2 | — | — | Stage V sporulation protein B |
| Contig1 | 2060903 | 2061559 | − | GENE_01960 | Prodigal: 2.6 | CDS | — | — | — | — | — | — | — | — | hypothetical protein |
| Contig1 | 2061726 | 2062112 | + | GENE_01961 | Prodigal: 2.6 | CDS | — | — | — | — | — | — | — | — | hypothetical protein |
| Contig1 | 2062164 | 2062424 | − | GENE_01962 | Prodigal: 2.6 | CDS | — | PRK05585 | — | — | — | — | — | — | preprotein translocase subunit YajC |
| Contig1 | 2062455 | 2063600 | − | GENE_01963 | Prodigal: 2.6 | CDS | 2.4.2.29 | — | — | — | P66905 | tgt | — | — | Queuine tRNA-ribosyltransferase |
| Contig1 | 2063628 | 2064656 | − | GENE_01964 | Prodigal: 2.6 | CDS | 2.4.99.17 | — | — | — | O32054 | queA | — | — | S-adenosyl-methionine:tRNA ribosyltransferase-isomerase |
| Contig1 | 2064682 | 2064882 | − | GENE_01965 | Prodigal: 2.6 | CDS | — | — | — | — | — | — | — | — | hypothetical protein |
| Contig1 | 2064875 | 2065879 | − | GENE_01966 | Prodigal: 2.6 | CDS | 3.6.4.12 | — | — | — | O32055 | ruvB | — | — | Holliday junction ATP-dependent DNA helicase RuvB |
| Contig1 | 2065890 | 2066495 | − | GENE_01967 | Prodigal: 2.6 | CDS | 3.6.4.12 | — | — | — | P66748 | ruvA | — | — | Holliday junction ATP-dependent DNA helicase RuvA |
| Contig1 | 2066630 | 2067139 | − | GENE_01968 | Prodigal: 2.6 | CDS | — | — | PF08955.4 | — | — | — | — | BofC C-terminal domain | hypothetical protein |
| Contig1 | 2067271 | 2067390 | − | GENE_01969 | Prodigal: 2.6 | CDS | — | — | — | — | — | — | — | — | hypothetical protein |
| Contig1 | 2067541 | 2068116 | − | GENE_01970 | Prodigal: 2.6 | CDS | — | — | — | — | P94446 | coxA | — | — | Sporulation cortex protein CoxA precursor |
| Contig1 | 2068264 | 2069469 | − | GENE_01971 | Prodigal: 2.6 | CDS | — | — | — | — | O32062 | safA | — | — | SpoIVD-associated factor A |
| Contig1 | 2069596 | 2070699 | − | GENE_01972 | Prodigal: 2.6 | CDS | 2.5.1.72 | — | — | — | P11458 | nadA | — | — | Quinolinate synthase A |
| Contig1 | 2070701 | 2071549 | − | GENE_01973 | Prodigal: 2.6 | CDS | 2.4.2.19 | PRK04435 | — | — | P39666 | nadC | — | — | putative nicotinate-nucleotide pyrophosphorylase [carboxylating] |
| Contig1 | 2071531 | 2073096 | − | GENE_01974 | Prodigal: 2.6 | CDS | 1.4.3.16 | — | — | — | P10902 | nadB | — | — | L-aspartate oxidase |
| Contig1 | 2073202 | 2074353 | + | GENE_01975 | Prodigal: 2.6 | CDS | 2.8.1.7 | — | — | — | P38033 | nifS | — | — | Putative cysteine desulfurase NifS |
| Contig1 | 2074350 | 2074892 | + | GENE_01976 | Prodigal: 2.6 | CDS | — | — | — | — | P39667 | nadR | — | — | Transcription repressor NadR |
| Contig1 | 2074918 | 2075775 | − | GENE_01977 | Prodigal: 2.6 | CDS | — | — | — | — | P0A9J8 | pheA | — | — | P-protein |
| Contig1 | 2075789 | 2076232 | − | GENE_01978 | Prodigal: 2.6 | CDS | — | — | — | — | — | — | — | — | hypothetical protein |
| Contig1 | 2076286 | 2077572 | − | GENE_01979 | Prodigal: 2.6 | CDS | — | — | — | — | P20964 | obg | — | — | GTPase ObgE |
| Contig1 | 2077604 | 2078182 | − | GENE_01980 | Prodigal: 2.6 | CDS | 2.7.-.- | — | — | — | P06535 | spo0B | — | — | Sporulation initiation phosphotransferase B |
| Contig1 | 2078500 | 2078784 | − | GENE_01981 | Prodigal: 2.6 | CDS | — | — | — | — | P66133 | rpmA | — | — | 50S ribosomal protein L27 |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2078797 | 2079138 | – | GENE_01982 | Prodigal: 2.6 | CDS | — | — | — | — | — | — | — | — | hypothetical protein |
| Contig1 | 2079141 | 2079449 | – | GENE_01983 | Prodigal: 2.6 | CDS | — | — | — | — | P26908 | rplU | — | — | 50S ribosomal protein L21 |
| Contig1 | 2079595 | 2080461 | – | GENE_01984 | Prodigal: 2.6 | CDS | 3.4.24.- | — | — | — | P26937 | spoIVFB | — | — | Stage IV sporulation protein FB |
| Contig1 | 2080454 | 2081257 | – | GENE_01985 | Prodigal: 2.6 | CDS | — | — | — | — | P26936 | spoIVFA | — | — | Stage IV sporulation protein FA |
| Contig1 | 2081385 | 2082188 | – | GENE_01986 | Prodigal: 2.6 | CDS | — | — | — | — | Q01464 | minD_1 | — | — | Septum site-determining protein MinD |
| Contig1 | 2082191 | 2082871 | – | GENE_01987 | Prodigal: 2.6 | CDS | — | — | — | — | Q01463 | minC | — | — | Septum site-determining protein MinC |
| Contig1 | 2082925 | 2083443 | – | GENE_01988 | Prodigal: 2.6 | CDS | — | — | — | — | Q01467 | mreD | — | — | Rod shape-determining protein MreD |
| Contig1 | 2083440 | 2084303 | – | GENE_01989 | Prodigal: 2.6 | CDS | — | — | — | — | Q01466 | mreC | — | — | Cell shape-determining protein MreC precursor |
| Contig1 | 2084334 | 2085347 | – | GENE_01990 | Prodigal: 2.6 | CDS | — | — | — | — | P0A9X4 | mreB_2 | — | — | Rod shape-determining protein MreB |
| Contig1 | 2085439 | 2086134 | – | GENE_01991 | Prodigal: 2.6 | CDS | — | PRK00024 | — | — | — | — | — | — | hypothetical protein |
| Contig1 | 2086166 | 2086735 | – | GENE_01992 | Prodigal: 2.6 | CDS | — | — | — | — | Q02169 | maf | — | — | Septum formation protein Maf |
| Contig1 | 2086876 | 2087877 | – | GENE_01993 | Prodigal: 2.6 | CDS | — | — | — | — | P37575 | spoIIB | — | — | Stage II sporulation protein B |
| Contig1 | 2088004 | 2088756 | – | GENE_01994 | Prodigal: 2.6 | CDS | — | — | — | — | P15378 | comC | — | — | Type 4 prepilin-like proteins leader peptide-processing enzyme |
| Contig1 | 2088896 | 2090188 | – | GENE_01995 | Prodigal: 2.6 | CDS | 6.3.2.17 | — | — | — | P15925 | fgs | — | — | Folylpolyglutamate synthase |
| Contig1 | 2090247 | 2092889 | – | GENE_01996 | Prodigal: 2.6 | CDS | 6.1.1.9 | — | — | — | Q05873 | valS | — | — | Valine--tRNA ligase |
| Contig1 | 2093342 | 2093533 | + | GENE_01997 | Prodigal: 2.6 | CDS | — | — | — | — | — | — | — | — | hypothetical protein |
| Contig1 | 2093548 | 2094582 | – | GENE_01998 | Prodigal: 2.6 | CDS | — | — | — | — | — | — | — | — | hypothetical protein |
| Contig1 | 2094604 | 2096592 | – | GENE_01999 | Prodigal: 2.6 | CDS | — | — | — | — | P37963 | spoVID | — | — | Stage VI sporulation protein D |
| Contig1 | 2096725 | 2098014 | – | GENE_02000 | Prodigal: 2.6 | CDS | 5.4.3.8 | — | — | — | P30949 | hemL | — | — | Glutamate-1-semialdehyde 2,1-aminomutase |
| Contig1 | 2098043 | 2099020 | – | GENE_02001 | Prodigal: 2.6 | CDS | 4.2.1.24 | — | — | — | P64334 | hemB | — | — | Delta-aminolevulinic acid dehydratase |
| Contig1 | 2099020 | 2099802 | – | GENE_02002 | Prodigal: 2.6 | CDS | — | PRK05928 | — | — | — | — | — | — | uroporphyrinogen-III synthase |
| Contig1 | 2099792 | 2100733 | – | GENE_02003 | Prodigal: 2.6 | CDS | 2.5.1.61 | — | — | — | P64341 | hemC | — | — | Porphobilinogen deaminase |
| Contig1 | 2100768 | 2101598 | – | GENE_02004 | Prodigal: 2.6 | CDS | — | — | — | — | P72978 | ccsA_2 | — | — | Cytochrome c biogenesis protein CcsA |
| Contig1 | 2101606 | 2102973 | – | GENE_02005 | Prodigal: 2.6 | CDS | 1.2.1.70 | — | — | — | P16618 | hemA | — | — | Glutamyl-tRNA reductase |
| Contig1 | 2103168 | 2103659 | + | GENE_02006 | Prodigal: 2.6 | CDS | — | — | — | — | — | — | — | — | hypothetical protein |
| Contig1 | 2103692 | 2104279 | – | GENE_02007 | Prodigal: 2.6 | CDS | — | — | — | — | P38424 | engB | — | — | putative GTP-binding protein EngB |
| Contig1 | 2104276 | 2106600 | – | GENE_02008 | Prodigal: 2.6 | CDS | 3.4.21.53 | — | — | — | P37945 | lon1 | — | — | Lon protease 1 |
| Contig1 | 2106800 | 2108458 | – | GENE_02009 | Prodigal: 2.6 | CDS | 3.4.21.53 | — | — | — | P42425 | lon2 | — | — | Lon protease 2 |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2108608 | 2109870 | − | GENE_02010 | Prodigal: 2.6 | CDS | — | — | — | — | P50866 | clpX | — | — | ATP-dependent Clp protease ATP-binding subunit ClpX |
| Contig1 | 2110142 | 2111416 | − | GENE_02011 | Prodigal: 2.6 | CDS | 5.2.1.8 | — | — | — | P80698 | tig | — | — | Trigger factor |
| Contig1 | 2111633 | 2112637 | − | GENE_02012 | Prodigal: 2.6 | CDS | — | — | PF07719.11 | — | — | — | — | — | Tetratricopeptide repeat protein |
| Contig1 | 2112755 | 2113354 | − | GENE_02013 | Prodigal: 2.6 | CDS | 4.2.1.33 | — | — | — | A5E8Z8 | leuD | — | — | 3-isopropylmalate dehydratase small subunit |
| Contig1 | 2113370 | 2114788 | − | GENE_02014 | Prodigal: 2.6 | CDS | 4.2.1.33 | — | — | — | P80858 | leuC | — | — | 3-isopropylmalate dehydratase large subunit |
| Contig1 | 2114834 | 2115931 | − | GENE_02015 | Prodigal: 2.6 | CDS | 1.1.1.85 | — | — | — | P12010 | leuB | — | — | 3-isopropylmalate dehydrogenase |
| Contig1 | 2115952 | 2117508 | − | GENE_02016 | Prodigal: 2.6 | CDS | 2.3.3.13 | — | — | — | Q71Y35 | leuA | — | — | 2-isopropylmalate synthase |
| Contig1 | 2117495 | 2118523 | − | GENE_02017 | Prodigal: 2.6 | CDS | 1.1.1.86 | — | — | — | P37253 | ilvC | — | — | Ketol-acid reductoisomerase |
| Contig1 | 2118546 | 2119064 | − | GENE_02018 | Prodigal: 2.6 | CDS | 2.2.1.6 | — | — | — | P65161 | ilvH | — | — | Putative acetolactate synthase small subunit |
| Contig1 | 2119061 | 2119411 | − | GENE_02019 | Prodigal: 2.6 | CDS | 2.2.1.6 | — | — | — | P37251 | ilvB_1 | — | — | Acetolactate synthase large subunit |
| Contig1 | 2119408 | 2120535 | − | GENE_02020 | Prodigal: 2.6 | CDS | 2.2.1.6 | — | — | — | P37251 | ilvB_2 | — | — | Acetolactate synthase large subunit |
| Contig1 | 2120532 | 2120783 | − | GENE_02021 | Prodigal: 2.6 | CDS | 2.2.1.6 | — | — | — | P37251 | ilvB_3 | — | — | Acetolactate synthase large subunit |
| Contig1 | 2121577 | 2121927 | + | GENE_02022 | Prodigal: 2.6 | CDS | — | — | — | — | — | — | — | — | hypothetical protein |
| Contig1 | 2121967 | 2122152 | − | GENE_02023 | Prodigal: 2.6 | CDS | — | — | — | — | — | — | — | — | hypothetical protein |
| Contig1 | 2122402 | 2122477 | − | GENE_02024 | Aragorn: 1.2 | tRNA | — | — | — | — | — | — | — | — | tRNA-Arg(tct) |
| Contig1 | 2122598 | 2122673 | − | GENE_02025 | Aragorn: 1.2 | tRNA | — | — | — | — | — | — | — | — | tRNA-Arg(tct) |
| Contig1 | 2122786 | 2123295 | − | GENE_02026 | Prodigal: 2.6 | CDS | — | — | — | — | P75349 | — | — | Putative metallo-phosphoesterase MG207 homolog | hypothetical protein |
| Contig1 | 2123311 | 2123898 | − | GENE_02027 | Prodigal: 2.6 | CDS | 3.6.1.19 | — | — | — | P99094 | — | — | — | Non-canonical purine NTP |
| Contig1 | 2123919 | 2124656 | − | GENE_02028 | Prodigal: 2.6 | CDS | 2.7.7.56 | — | — | — | P28619 | rph | — | — | Ribonuclease PH |
| Contig1 | 2124766 | 2125851 | − | GENE_02029 | Prodigal: 2.6 | CDS | — | — | — | — | P39072 | germ | — | — | Spore germination protein GerM |
| Contig1 | 2125957 | 2126772 | − | GENE_02030 | Prodigal: 2.6 | CDS | 5.1.1.3 | — | — | — | P94556 | racE | — | — | Glutamate racemase 1 |
| Contig1 | 2126783 | 2127223 | − | GENE_02031 | Prodigal: 2.6 | CDS | — | — | — | — | O32181 | yusO_4 | — | — | putative HTH-type transcriptional regulator YusO |
| Contig1 | 2127410 | 2127634 | − | GENE_02032 | Prodigal: 2.6 | CDS | — | — | — | — | P11470 | gerE | — | — | Spore germination protein GerE |
| Contig1 | 2127755 | 2128192 | − | GENE_02033 | Prodigal: 2.6 | CDS | — | — | PF03061.16 | — | — | — | — | — | Thioesterase superfamily protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2128252 | 2129010 | − | GENE_02034 | Prodigal: 2.6 | CDS | 1.3.99.1 | — | — | — | P17596 | frdB | — | — | Fumarate reductase iron-sulfur subunit |
| Contig1 | 2129013 | 2130773 | − | GENE_02035 | Prodigal: 2.6 | CDS | 1.3.5.4 | — | — | — | P00363 | frdA | — | — | Fumarate reductase flavoprotein subunit |
| Contig1 | 2130807 | 2131415 | − | GENE_02036 | Prodigal: 2.6 | CDS | — | — | — | — | P08064 | sdhC | — | — | Succinate dehydrogenase cytochrome b558 subunit |
| Contig1 | 2131711 | 2132157 | + | GENE_02037 | Prodigal: 2.6 | CDS | — | — | — | — | — | — | — | — | hypothetical protein |
| Contig1 | 2132204 | 2133433 | − | GENE_02038 | Prodigal: 2.6 | CDS | 2.7.2.4 | — | — | — | P08495 | lysC_2 | — | — | Aspartokinase 2 |
| Contig1 | 2133800 | 21355 | − | GENE_02039 | Prodigal: 2.6 | CDS | — | — | — | — | Q5KWH6 | uvrC_1 | — | — | UvrABC system protein C |
| Contig1 | 2135716 | 2136030 | − | GENE_02040 | Prodigal: 2.6 | CDS | — | — | — | — | P14949 | trxA_1 | — | — | Thioredoxin |
| Contig1 | 2136183 | 2137673 | − | GENE_02041 | Prodigal: 2.6 | CDS | 3.2.1.55 | — | — | — | P94552 | abf2 | — | — | Intracellular exo-alpha-L-arabinofuranosidase 2 |
| Contig1 | 2137882 | 2138859 | − | GENE_02042 | Prodigal: 2.6 | CDS | — | — | — | — | G3KIM6 | acrA | — | — | Acryloyl-CoA reductase electron transfer subunit beta |
| Contig1 | 2138891 | 2139664 | − | GENE_02043 | Prodigal: 2.6 | CDS | — | — | — | — | P38975 | etfB | — | — | Electron transfer flavoprotein subunit beta |
| Contig1 | 2139678 | 2140457 | − | GENE_02044 | Prodigal: 2.6 | CDS | 4.2.1.17 | — | — | — | P94549 | fadB | — | — | putative enoyl-CoA hydratase |
| Contig1 | 2140471 | 2141061 | − | GENE_02045 | Prodigal: 2.6 | CDS | — | — | — | — | P94548 | fadR | — | — | Fatty acid metabolism regulator protein |
| Contig1 | 2141144 | 2142832 | − | GENE_02046 | Prodigal: 2.6 | CDS | 6.2.1.3 | — | — | — | P69451 | fadD | — | — | Long-chain-fatty-acid-CoA ligase |
| Contig1 | 2142938 | 2143612 | + | GENE_02047 | Prodigal: 2.6 | CDS | — | — | — | — | — | — | — | — | hypothetical protein |
| Contig1 | 2143752 | 2144156 | − | GENE_02048 | Prodigal: 2.6 | CDS | — | — | — | — | — | — | — | — | hypothetical protein |
| Contig1 | 2144173 | 2146530 | − | GENE_02049 | Prodigal: 2.6 | CDS | 3.1.-.- | — | — | — | P65496 | mutS2 | — | — | Endonuclease MutS2 |
| Contig1 | 2146551 | 2148299 | − | GENE_02050 | Prodigal: 2.6 | CDS | — | — | — | — | P94544 | polX | — | — | DNA polymerase/3′-5′ exonuclease PolX |
| Contig1 | 2148369 | 2148902 | − | GENE_02051 | Prodigal: 2.6 | CDS | — | — | PF02674.10 | — | — | — | — | — | Colicin V production protein |
| Contig1 | 2148910 | 2149167 | − | GENE_02052 | Prodigal: 2.6 | CDS | — | — | — | — | P94542 | zapA | — | — | Cell division protein ZapA |
| Contig1 | 2149301 | 2150242 | + | GENE_02053 | Prodigal: 2.6 | CDS | 3.1.26.4 | — | — | — | P94541 | rnhC | — | — | Ribonuclease HIII |
| Contig1 | 2150280 | 2152694 | − | GENE_02054 | Prodigal: 2.6 | CDS | 6.1.1.20 | — | — | — | Q4L5E4 | pheT_1 | — | — | Phenylalanine tRNA ligase beta subunit |
| Contig1 | 2152708 | 2153742 | − | GENE_02055 | Prodigal: 2.6 | CDS | 6.1.1.20 | — | — | — | Q4L5E3 | pheS | — | — | Phenylalanine tRNA ligase alpha subunit |
| Contig1 | 2154104 | 2154850 | − | GENE_02056 | Prodigal: 2.6 | CDS | 2.1.1.- | — | — | — | Q7A794 | — | — | — | Putative TrmH family tRNA/rRNA methyltransferase |
| Contig1 | 2154971 | 2155186 | + | GENE_02057 | Prodigal: 2.6 | CDS | — | — | — | — | P94537 | sspI | — | — | Small, acid-soluble spore protein I |
| Contig1 | 2155248 | 2156333 | + | GENE_02058 | Prodigal: 2.6 | CDS | — | — | — | — | P37047 | cdaR_1 | — | — | Carbohydrate diacid regulator |
| Contig1 | 2156433 | 2157845 | + | GENE_02059 | Prodigal: 2.6 | CDS | 1.-.-.- | — | — | — | Q50685 | — | — | — | putative FAD-linked oxidoreductase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2157842 | 2159170 | + | GENE_02060 | Prodigal: 2.6 | CDS | — | — | — | — | O07020 | lutA_1 | — | — | Lactate utilization protein A |
| Contig1 | 2159240 | 2161036 | − | GENE_02061 | Prodigal: 2.6 | CDS | — | — | — | — | P15078 | cstA | — | — | Carbon starvation protein A |
| Contig1 | 2161149 | 2162648 | − | GENE_02062 | Prodigal: 2.6 | CDS | 3.2.1.55 | — | — | — | P94531 | abfA | — | — | Intracellular exo-alpha-(1->5)-L-arabinofuranosidase 1 |
| Contig1 | 2162667 | 2163509 | − | GENE_02063 | Prodigal: 2.6 | CDS | — | — | — | — | P94530 | araQ_1 | — | — | L-arabinose transport system permease protein AraQ |
| Contig1 | 2163513 | 2164454 | − | GENE_02064 | Prodigal: 2.6 | CDS | — | — | — | — | P94529 | araP_1 | — | — | L-arabinose transport system permease protein AraP |
| Contig1 | 2164496 | 2165791 | − | GENE_02065 | Prodigal: 2.6 | CDS | — | — | — | — | P94528 | araN | — | — | putative arabinose-binding protein precursor |
| Contig1 | 2165823 | 2167007 | − | GENE_02066 | Prodigal: 2.6 | CDS | 1.1.1.261 | — | — | — | P94527 | egsA | — | — | Glycerol-1-phosphate dehydrogenase [NAD(P)+] |
| Contig1 | 2167004 | 2167843 | − | GENE_02067 | Prodigal: 2.6 | CDS | — | — | — | — | P94526 | araL | — | — | Arabinose operon protein AraL |
| Contig1 | 2167788 | 2168477 | − | GENE_02068 | Prodigal: 2.6 | CDS | 5.1.3.4 | — | — | — | P94525 | araD | — | — | L-ribulose-5-phosphate 4-epimerase |
| Contig1 | 2168470 | 2170188 | − | GENE_02069 | Prodigal: 2.6 | CDS | 2.7.1.16 | — | — | — | P94524 | araB_1 | — | — | Ribulokinase |
| Contig1 | 2170157 | 2171656 | − | GENE_02070 | Prodigal: 2.6 | CDS | 5.3.1.4 | — | — | — | P94523 | araA | — | — | L-arabinose isomerase |
| Contig1 | 2171835 | 2172800 | − | GENE_02071 | Prodigal: 2.6 | CDS | 3.2.1.99 | — | — | — | P94522 | abnA | — | — | Extracellular endo-alpha-(1->5)-L-arabinanase 1 precursor |
| Contig1 | 2172944 | 2174029 | − | GENE_02072 | Prodigal: 2.6 | CDS | 3.4.11.- | — | — | — | P94521 | ysdC_2 | — | — | Putative aminopeptidase YsdC |
| Contig1 | 2174213 | 2174605 | + | GENE_02073 | Prodigal: 2.6 | CDS | — | — | — | — | P94520 | ysdB | — | — | Sigma-w pathway protein YsdB |
| Contig1 | 2174619 | 2174885 | − | GENE_02074 | Prodigal: 2.6 | CDS | — | — | — | — | — | — | — | — | hypothetical protein |
| Contig1 | 2174943 | 2175302 | − | GENE_02075 | Prodigal: 2.6 | CDS | — | — | — | — | P55873 | rplT | — | — | 50S ribosomal protein L20 |
| Contig1 | 2175334 | 2175534 | − | GENE_02076 | Prodigal: 2.6 | CDS | — | — | — | — | P75447 | rpmI | — | — | 50S ribosomal protein L35 |
| Contig1 | 2175547 | 2176050 | − | GENE_02077 | Prodigal: 2.6 | CDS | — | — | — | — | P03000 | infC | — | — | Translation initiation factor IF-3 |
| Contig1 | 2176439 | 2177122 | − | GENE_02078 | Prodigal: 2.6 | CDS | — | — | — | — | P60643 | lrgB | — | — | Antiholin-like protein LrgB |
| Contig1 | 2177135 | 2177575 | − | GENE_02079 | Prodigal: 2.6 | CDS | — | — | — | — | P72358 | lrgA | — | — | Antiholin-like protein LrgA |
| Contig1 | 2177705 | 2178439 | − | GENE_02080 | Prodigal: 2.6 | CDS | — | — | — | — | P60611 | lytR_1 | — | — | Sensory transduction protein LytR |
| Contig1 | 2178417 | 2180198 | − | GENE_02081 | Prodigal: 2.6 | CDS | 2.7.13.3 | — | — | — | P0AA93 | ypdA | — | — | Sensor histidine kinase YpdA |
| Contig1 | 2180383 | 2181177 | + | GENE_02082 | Prodigal: 2.6 | CDS | 3.1.3.5 | — | — | — | P0A8Y1 | yjjG | — | — | Pyrimidine 5'-nucleotidase YjjG |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2181231 | 2183162 | − | GENE_02083 | Prodigal: 2.6 | CDS | 6.1.1.3 | — | — | — | P18255 | thrS | — | — | Threonine--tRNA ligase 1 |
| Contig1 | 2183572 | 2184402 | − | GENE_02084 | Prodigal: 2.6 | CDS | — | — | PF08812.5 | — | — | — | — | — | YtxC-like family protein |
| Contig1 | 2184467 | 2185108 | − | GENE_02085 | Prodigal: 2.6 | CDS | — | — | — | — | P76221 | ydjZ_3 | — | — | TVP38/TMEM64 family inner membrane protein YdjZ |
| Contig1 | 2185140 | 2186075 | − | GENE_02086 | Prodigal: 2.6 | CDS | — | — | — | — | P06567 | dnaI | — | — | Primosomal protein DnaI |
| Contig1 | 2186100 | 2187506 | − | GENE_02087 | Prodigal: 2.6 | CDS | — | — | — | — | P07908 | dnaB | — | — | Replication initiation and membrane attachment protein |
| Contig1 | 2187618 | 2188076 | − | GENE_02088 | Prodigal: 2.6 | CDS | — | — | — | — | P0A8D0 | nrdR | — | — | Transcriptional repressor NrdR |
| Contig1 | 2188325 | 2188705 | − | GENE_02089 | Prodigal: 2.6 | CDS | 4.1.1.50 | — | — | — | O34426 | speH | — | — | S-adenosylmethionine decarboxylase proenzyme precursor |
| Contig1 | 2188944 | 2189966 | − | GENE_02090 | Prodigal: 2.6 | CDS | 1.2.1.59 | — | — | — | O34425 | gapB | — | — | Glyceraldehyde-3-phosphate dehydrogenase 2 |
| Contig1 | 2190175 | 2190561 | − | GENE_02091 | Prodigal: 2.6 | CDS | — | — | — | — | O34533 | ytcD_2 | — | — | putative HTH-type transcriptional regulator YteD |
| Contig1 | 2190745 | 2191944 | + | GENE_02092 | Prodigal: 2.6 | CDS | — | — | — | — | P77389 | ydhP_2 | — | — | Inner membrane transport protein YdhP |
| Contig1 | 2192002 | 2192844 | + | GENE_02093 | Prodigal: 2.6 | CDS | 1.-.-.- | — | — | — | O34678 | ytbE | — | — | putative oxidoreductase YtbE |
| Contig1 | 2192883 | 2193476 | − | GENE_02094 | Prodigal: 2.6 | CDS | 2.7.1.24 | — | — | MF_01521 | P63831 | coaE | — | — | Dephospho-CoA kinase |
| Contig1 | 2193492 | 2194124 | − | GENE_02095 | Prodigal: 2.6 | CDS | — | — | — | — | — | mntP_2 | — | — | manganese efflux pump MntP |
| Contig1 | 2194261 | 2195091 | − | GENE_02096 | Prodigal: 2.6 | CDS | 3.2.2.23 | — | — | — | P42371 | mutM | — | — | Formamidopyrimidine-DNA glycosylase |
| Contig1 | 2195116 | 2197755 | − | GENE_02097 | Prodigal: 2.6 | CDS | 2.7.7.7 | — | — | — | P52026 | polA | — | — | DNA polymerase I |
| Contig1 | 2198001 | 2199740 | − | GENE_02098 | Prodigal: 2.6 | CDS | 2.7.13.3 | — | — | — | P23545 | phoR_1 | — | — | Alkaline phosphatase synthesis sensor protein PhoR |
| Contig1 | 2199733 | 2200452 | − | GENE_02099 | Prodigal: 2.6 | CDS | — | — | — | — | P13792 | phoP | — | — | Alkaline phosphatase synthesis transcriptional regulatory protein PhoP |
| Contig1 | 2200668 | 2201606 | − | GENE_02100 | Prodigal: 2.6 | CDS | 1.1.1.37 | — | — | — | P49814 | mdh | — | — | Malate dehydrogenase |
| Contig1 | 2201652 | 2202923 | − | GENE_02101 | Prodigal: 2.6 | CDS | 1.1.1.42 | — | — | — | P39126 | icd | — | — | Isocitrate dehydrogenase [NADP] |
| Contig1 | 2203084 | 2204202 | − | GENE_02102 | Prodigal: 2.6 | CDS | 2.3.3.1 | — | — | — | P39120 | citZ | — | — | Citrate synthase 2 |
| Contig1 | 2205256 | 2205666 | − | GENE_02103 | Prodigal: 2.6 | CDS | — | — | — | — | — | — | — | — | hypothetical protein |
| Contig1 | 2206092 | 2206556 | − | GENE_02104 | Prodigal: 2.6 | CDS | — | — | — | — | — | — | — | — | hypothetical protein |
| Contig1 | 2206654 | 2207769 | − | GENE_02105 | Prodigal: 2.6 | CDS | — | — | — | — | — | — | — | — | hypothetical protein |
| Contig1 | 2207801 | 2208184 | + | GENE_02106 | Prodigal: 2.6 | CDS | — | — | — | — | — | — | — | — | phage T7 F exclusion suppressor FxsA |
| Contig1 | 2208295 | 2210052 | − | GENE_02107 | Prodigal: 2.6 | CDS | 2.7.1.40 | — | — | — | P80885 | pyk | — | — | Pyruvate kinase |
| Contig1 | 2210092 | 2211051 | − | GENE_02108 | Prodigal: 2.6 | CDS | 2.7.1.11 | — | — | — | O34529 | pfkA | — | — | 6-phosphofructokinase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2211243 | 2212220 | − | GENE_02109 | Prodigal: 2.6 | CDS | 6.4.1.2 | — | — | — | O34847 | accA | — | — | Acetyl-coenzyme A carboxylase carboxyl transferase subunit alpha |
| Contig1 | 2212205 | 2213077 | − | GENE_02110 | Prodigal: 2.6 | CDS | 6.4.1.2 | — | — | — | C0SP93 | accD | — | — | Acetyl-coenzyme A carboxylase carboxyl transferase subunit beta |
| Contig1 | 2213406 | 2214638 | − | GENE_02111 | Prodigal: 2.6 | CDS | 1.1.1.38 | — | — | — | P16468 | — | — | — | NAD-dependent malic enzyme |
| Contig1 | 2214778 | 2218119 | − | GENE_02112 | Prodigal: 2.6 | CDS | 2.7.7.7 | — | — | — | P63979 | dnaE | — | — | DNA polymerase III subunit alpha |
| Contig1 | 2218262 | 2218603 | + | GENE_02113 | Prodigal: 2.6 | CDS | — | — | — | — | C0H3P8 | ytrH | — | — | Sporulation membrane protein YtrH |
| Contig1 | 2218600 | 2219103 | + | GENE_02114 | Prodigal: 2.6 | CDS | — | — | — | — | O34460 | ytrI | — | — | Sporulation membrane protein YtrI |
| Contig1 | 2219209 | 2219400 | + | GENE_02115 | Prodigal: 2.6 | CDS | — | — | — | — | — | — | — | — | hypothetical protein |
| Contig1 | 2219418 | 2220359 | − | GENE_02116 | Prodigal: 2.6 | CDS | 3.1.-.- | — | — | — | O34600 | nrnA_1 | — | — | Bifunctional oligoribonuclease and PAP phosphatase NrnA |
| Contig1 | 2220476 | 2220778 | + | GENE_02117 | Prodigal: 2.6 | CDS | — | — | — | — | — | — | — | — | hypothetical protein |
| Contig1 | 2220807 | 2222123 | − | GENE_02118 | Prodigal: 2.6 | CDS | 3.6.1.1 | — | — | — | Q8XIQ9 | — | — | — | Cobalt-dependent inorganic pyrophosphatase |
| Contig1 | 2222262 | 2222948 | − | GENE_02119 | Prodigal: 2.6 | CDS | 3.1.2.6 | — | — | MF_01374 | — | — | — | — | Hydroxyacylglutathione hydrolase |
| Contig1 | 2223009 | 2223776 | − | GENE_02120 | Prodigal: 2.6 | CDS | 1.1.1.100 | — | — | — | P0A2C9 | fabG_5 | — | — | 3-oxoacyl-[acyl-carrier-protein] reductase FabG |
| Contig1 | 2223914 | 2224042 | − | GENE_02121 | Prodigal: 2.6 | CDS | — | — | — | — | — | — | — | — | hypothetical protein |
| Contig1 | 2224117 | 2225493 | − | GENE_02122 | Prodigal: 2.6 | CDS | 4.3.2.1 | — | — | — | P11447 | argH | — | — | Argininosuccinate lyase |
| Contig1 | 2225490 | 2226701 | − | GENE_02123 | Prodigal: 2.6 | CDS | 6.3.4.5 | — | — | — | P77973 | argG | — | — | Argininosuccinate synthase |
| Contig1 | 2226853 | 2227365 | − | GENE_02124 | Prodigal: 2.6 | CDS | — | — | — | — | Q816R0 | moaB | — | — | Molybdenum cofactor biosynthesis protein B |
| Contig1 | 2227465 | 2228652 | − | GENE_02125 | Prodigal: 2.6 | CDS | 2.7.2.1 | — | — | — | P37877 | ackA | — | — | Acetate kinase |
| Contig1 | 2228964 | 2229950 | − | GENE_02126 | Prodigal: 2.6 | CDS | 2.1.11.72 | — | — | — | Q89Z59 | — | — | — | putative type I restriction enzymeP M protein |
| Contig1 | 2230012 | 2230515 | − | GENE_02127 | Prodigal: 2.6 | CDS | 1.11.1.- | — | — | — | P80864 | tpx | — | — | putative thiol peroxidase |
| Contig1 | 2230631 | 2231071 | − | GENE_02128 | Prodigal: 2.6 | CDS | — | — | — | — | O34806 | ytfJ | — | — | putative spore protein YtfJ |
| Contig1 | 2231084 | 2231773 | − | GENE_02129 | Prodigal: 2.6 | CDS | — | — | — | — | — | — | — | — | hypothetical protein |
| Contig1 | 2231851 | 2232342 | − | GENE_02130 | Prodigal: 2.6 | CDS | — | — | PF06271.6 | — | — | — | — | — | RDD family protein |
| Contig1 | 2232356 | 2233363 | − | GENE_02131 | Prodigal: 2.6 | CDS | 3.4.21.- | — | — | — | O34525 | sppA | — | — | Putative signal peptide peptidase SppA |
| Contig1 | 2233521 | 2234351 | + | GENE_02132 | Prodigal: 2.6 | CDS | 2.7.1.23 | — | — | — | Q8Y8D7 | ppnK1 | — | — | putative inorganic polyphosphate/ATP-NAD kinase 1 |
| Contig1 | 2234368 | 2235963 | − | GENE_02133 | Prodigal: 2.6 | CDS | 3.5.1.91 | — | — | — | Q68AP4 | nfdA | — | — | N-substituted formamide deformylase |
| Contig1 | 2235987 | 2237573 | − | GENE_02134 | Prodigal: 2.6 | CDS | 6.2.1.1 | — | — | — | P39062 | acsA_1 | — | — | Acetyl-coenzyme A synthetase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2237722 | 2237940 | − | GENE_02135 | Prodigal: 2.6 | CDS | — | — | — | — | P84583 | — | — | — | Small, acid-soluble spore protein 1 |
| Contig1 | 2238021 | 2239226 | − | GENE_02136 | Prodigal: 2.6 | CDS | 2.8.1.4 | — | — | — | Q81KU0 | thiI | — | — | putative tRNA sulfurtransferase |
| Contig1 | 2239230 | 2240375 | − | GENE_02137 | Prodigal: 2.6 | CDS | 2.8.1.7 | — | — | — | P0A6B7 | iscS_2 | — | — | Cysteine desulfurase |
| Contig1 | 2240569 | 2241909 | + | GENE_02138 | Prodigal: 2.6 | CDS | — | — | — | — | P0AD99 | brnQ | — | — | Branched-chain amino acid transport system 2 carrier protein |
| Contig1 | 2242023 | 2243714 | − | GENE_02139 | Prodigal: 2.6 | CDS | — | — | — | — | O34894 | ezrA | — | — | Septation ring formation regulator EzrA |
| Contig1 | 2243910 | 2244722 | + | GENE_02140 | Prodigal: 2.6 | CDS | 3.1.3.15 | — | — | — | O34411 | hisK | — | — | Histidinol-phosphatase |
| Contig1 | 2244712 | 2245335 | − | GENE_02141 | Prodigal: 2.6 | CDS | — | — | — | — | O34970 | yttP | — | — | putative HTH-type transcriptional regulator YttP |
| Contig1 | 2245461 | 2245943 | + | GENE_02142 | Prodigal: 2.6 | CDS | 1.8.4.14 | — | — | — | P76270 | msrC | — | — | Free methionine-R-sulfoxide reductase |
| Contig1 | 2245978 | 2247726 | − | GENE_02143 | Prodigal: 2.6 | CDS | 2.7.7.65 | — | — | — | P76330 | yedQ_2 | — | — | putative diguanylate cyclase YedQ |
| Contig1 | 2248017 | 2248619 | + | GENE_02144 | Prodigal: 2.6 | CDS | — | — | — | — | P21466 | rpsD | — | — | 30S ribosomal protein S4 |
| Contig1 | 2248961 | 2250331 | + | GENE_02145 | Prodigal: 2.6 | CDS | 1.2.1.3 | — | — | — | P12693 | alkH_1 | — | — | Aldehyde dehydrogenase |
| Contig1 | 2250468 | 2251025 | − | GENE_02146 | Prodigal: 2.6 | CDS | — | — | PF09346.4 | — | — | — | — | — | SMI1/KNR4 family protein |
| Contig1 | 2251566 | 2251766 | − | GENE_02147 | Prodigal: 2.6 | CDS | — | — | — | — | — | — | — | — | hypothetical protein |
| Contig1 | 2251910 | 2252470 | − | GENE_02148 | Prodigal: 2.6 | CDS | — | — | — | — | — | — | — | — | hypothetical protein |
| Contig1 | 2252602 | 2253351 | − | GENE_02149 | Prodigal: 2.6 | CDS | — | — | — | — | — | — | — | — | hypothetical protein |
| Contig1 | 2253958 | 2254623 | − | GENE_02150 | Prodigal: 2.6 | CDS | — | — | — | — | — | — | — | — | hypothetical protein |
| Contig1 | 2255008 | 2255424 | + | GENE_02151 | Prodigal: 2.6 | CDS | — | — | — | — | — | — | — | — | hypothetical protein |
| Contig1 | 2256153 | 2256740 | − | GENE_02152 | Prodigal: 2.6 | CDS | — | — | — | — | — | — | — | — | hypothetical protein |
| Contig1 | 2257500 | 2258690 | − | GENE_02153 | Prodigal: 2.6 | CDS | 1.14.12.17 | — | — | — | P49852 | hmp_1 | — | — | Flavohemoprotein |
| Contig1 | 2258927 | 2259154 | + | GENE_02154 | Prodigal: 2.6 | CDS | — | — | — | — | — | — | — | — | hypothetical protein |
| Contig1 | 2259336 | 2259845 | + | GENE_02155 | Prodigal: 2.6 | CDS | 3.2.-.- | — | — | — | O06006 | yraA_1 | — | — | Putative cysteine protease YraA |
| Contig1 | 2259992 | 2260120 | + | GENE_02156 | Prodigal: 2.6 | CDS | — | — | — | — | — | — | — | — | hypothetical protein |
| Contig1 | 2260136 | 2260888 | − | GENE_02157 | Prodigal: 2.6 | CDS | — | — | PF00657.1 | — | — | — | — | — | GDSL-like Lipase/Acylhydrolase |
| Contig1 | 2261610 | 2262479 | − | GENE_02158 | Prodigal: 2.6 | CDS | — | — | — | — | P69380 | fieF | — | — | Ferrous-iron efflux pump FieF |
| Contig1 | 2262702 | 2263508 | + | GENE_02159 | Prodigal: 2.6 | CDS | — | — | PF01978.13 | — | — | — | — | — | Sugar-specific transcriptional regulator TrmB |
| Contig1 | 2263581 | 2264312 | + | GENE_02160 | Prodigal: 2.6 | CDS | — | — | — | — | P76630 | — | — | — | Inner membrane protein YgaZ |
| Contig1 | 2264309 | 2264632 | + | GENE_02161 | Prodigal: 2.6 | CDS | — | — | PF05437.6 | — | — | ygaZ | — | — | Branched-chain amino acid transport protein (AzlD) |
| Contig1 | 2264918 | 2266182 | − | GENE_02162 | Prodigal: 2.6 | CDS | 6.1.1.1 | — | — | — | P22326 | tyrS1 | — | — | Tyrosine-tRNA ligase 1 |
| Contig1 | 2266520 | 2268238 | − | GENE_02163 | Prodigal: 2.6 | CDS | 6.2.1.1 | — | — | — | P39062 | acsA_2 | — | — | Acetyl-coenzyme A synthetase |
| Contig1 | 2268397 | 2269029 | + | GENE_02164 | Prodigal: 2.6 | CDS | 2.3.1.- | — | — | — | P39065 | acuA | — | — | Acetoin utilization protein AcuA |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2269054 | 2269698 | + | GENE_02165 | Prodigal: 2.6 | CDS | — | — | — | — | O06186 | hrp1_3 | — | — | Hypoxic response protein 1 |
| Contig1 | 2269695 | 2270861 | + | GENE_02166 | Prodigal: 2.6 | CDS | — | — | — | — | P64376 | acuC | — | — | Acetoin utilization protein AcuC |
| Contig1 | 2270870 | 2271559 | − | GENE_02167 | Prodigal: 2.6 | CDS | — | — | — | — | P55892 | motB_2 | — | — | Motility protein B |
| Contig1 | 2271549 | 2272364 | − | GENE_02168 | Prodigal: 2.6 | CDS | — | — | — | — | O06873 | pomA_2 | — | — | Chemotaxis protein PomA |
| Contig1 | 2272433 | 2273437 | − | GENE_02169 | Prodigal: 2.6 | CDS | — | — | — | — | P25144 | ccpA_2 | — | — | Catabolite control protein A |
| Contig1 | 2273716 | 2274792 | − | GENE_02170 | Prodigal: 2.6 | CDS | 2.5.1.54 | — | — | — | Q9WYH8 | aroF_2 | — | — | Phospho-2-dehydro-3-deoxyheptonate aldolase |
| Contig1 | 2275029 | 2275355 | − | GENE_02171 | Prodigal: 2.6 | CDS | — | — | — | — | — | — | — | — | hypothetical protein |
| Contig1 | 2275381 | 2275794 | − | GENE_02172 | Prodigal: 2.6 | CDS | — | — | PF12732.1 | — | — | — | — | — | YtxH-like protein |
| Contig1 | 2275827 | 2276249 | − | GENE_02173 | Prodigal: 2.6 | CDS | — | — | — | — | — | — | — | — | hypothetical protein |
| Contig1 | 2276408 | 2277706 | − | GENE_02174 | Prodigal: 2.6 | CDS | 6.3.2.8 | — | — | — | P65475 | murC | — | — | UDP-N-acetyl-muramate--L-alanine ligase |
| Contig1 | 2277947 | 2280550 | − | GENE_02175 | Prodigal: 2.6 | CDS | — | — | — | — | C0SP86 | sfaA | — | — | DNA translocase SftA |
| Contig1 | 2280718 | 2281323 | − | GENE_02176 | Prodigal: 2.6 | CDS | 6.1.1.20 | — | — | — | Q4L5E4 | pheT_2 | — | — | Phenylalanine tRNA ligase beta subunit |
| Contig1 | 2281338 | 2282147 | − | GENE_02177 | Prodigal: 2.6 | CDS | — | — | — | — | — | — | — | — | hypothetical protein |
| Contig1 | 2282163 | 2282486 | − | GENE_02178 | Prodigal: 2.6 | CDS | — | — | — | — | O34357 | ytpP | — | — | Thioredoxin-like protein YtpP |
| Contig1 | 2282684 | 2283130 | + | GENE_02179 | Prodigal: 2.6 | CDS | — | — | — | — | — | — | — | — | hypothetical protein |
| Contig1 | 2283517 | 2283780 | − | GENE_02180 | Prodigal: 2.6 | CDS | 3.4.11.- | — | — | — | P94521 | ysdC_3 | — | — | Putative aminopeptidase YsdC |
| Contig1 | 2283777 | 2284589 | − | GENE_02181 | Prodigal: 2.6 | CDS | 3.4.11.- | — | — | — | P94521 | ysdC_4 | — | — | Putative aminopeptidase YsdC |
| Contig1 | 2284748 | 2285065 | + | GENE_02182 | Prodigal: 2.6 | CDS | — | — | PF03413.13 | — | — | — | — | — | Peptidase propeptide and YPEB domain protein |
| Contig1 | 2285121 | 2286818 | − | GENE_02183 | Prodigal: 2.6 | CDS | 1.1.1.38 | — | — | — | P45868 | maeA_1 | — | — | putative NAD-dependent malic enzyme 2 |
| Contig1 | 2286897 | 2287742 | − | GENE_02184 | Prodigal: 2.6 | CDS | 3.1.1.- | — | — | — | O34760 | ytnP | — | — | putative quorum-quenching lactonase YtnP |
| Contig1 | 2287801 | 2288454 | − | GENE_02185 | Prodigal: 2.6 | CDS | 2.1.1.33 | — | — | — | O34522 | trmB | — | — | tRNA (guanine-N(7))-methyltransferase |
| Contig1 | 2288641 | 2288919 | + | GENE_02186 | Prodigal: 2.6 | CDS | — | — | — | — | — | — | — | — | hypothetical protein |
| Contig1 | 2288920 | 2289717 | + | GENE_02187 | Prodigal: 2.6 | CDS | — | — | PF01636.17 | — | — | — | — | — | Phosphotransferase enzyme family protein |
| Contig1 | 2289988 | 2290917 | − | GENE_02188 | Prodigal: 2.6 | CDS | 2.7.1.- | — | — | — | O34799 | ytlR | — | — | Putative lipid kinase YtlR |
| Contig1 | 2290969 | 2291901 | − | GENE_02189 | Prodigal: 2.6 | CDS | — | — | — | — | — | — | — | — | hypothetical protein |
| Contig1 | 2291928 | 2292479 | − | GENE_02190 | Prodigal: 2.6 | CDS | 6.5.1.- | — | — | — | P37025 | ligT | — | — | 2'-5'-RNA ligase |
| Contig1 | 2292569 | 2293540 | + | GENE_02191 | Prodigal: 2.6 | CDS | 2.5.1.47 | — | — | — | P63871 | cysK_1 | — | — | Cysteine synthase |
| Contig1 | 2293578 | 2294969 | − | GENE_02192 | Prodigal: 2.6 | CDS | 3.4.13.- | — | — | — | Q7A522 | — | — | — | Putative dipeptidase |
| Contig1 | 2295065 | 2296369 | + | GENE_02193 | Prodigal: 2.6 | CDS | — | — | — | — | O34978 | pbuO | — | — | Guanine/hypoxanthine permease PbuO |
| Contig1 | 2296402 | 2297562 | − | GENE_02194 | Prodigal: 2.6 | CDS | — | — | PF05975.6 | — | — | — | — | — | Bacterial ABC transporter protein EcsB |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2297559 | 2298263 | − | GENE_02195 | Prodigal: 2.6 | CDS | — | — | — | — | P55339 | ecsA_2 | — | — | ABC-type transporter ATP-binding protein EcsA |
| Contig1 | 2298543 | 2298764 | + | GENE_02196 | Prodigal: 2.6 | CDS | — | — | — | — | O32067 | ytzE | — | — | putative HTH-type transcriptional regulator YtzE |
| Contig1 | 2298892 | 2299611 | − | GENE_02197 | Prodigal: 2.6 | CDS | 5.4.99.19 | — | — | — | P0AA43 | rsuA | — | — | Ribosomal small subunit pseudouridine synthase A |
| Contig1 | 2299668 | 2301305 | − | GENE_02198 | Prodigal: 2.6 | CDS | — | — | — | — | O34674 | ytgP_1 | — | — | putative cell division protein YtgP |
| Contig1 | 2301513 | 2302778 | + | GENE_02199 | Prodigal: 2.6 | CDS | 1.18.1.2 | — | — | MF_01685 | — | — | — | — | Ferredoxin–NADP reductase |
| Contig1 | 2302955 | 2304490 | − | GENE_02200 | Prodigal: 2.6 | CDS | — | — | — | — | P54417 | opuD | — | — | Glycine betaine transporter OpuD |
| Contig1 | 2304526 | 2304708 | − | GENE_02201 | Prodigal: 2.6 | CDS | — | — | — | — | P94496 | — | — | — | Sporulation protein cse60 |
| Contig1 | 2304909 | 2305934 | + | GENE_02202 | Prodigal: 2.6 | CDS | — | — | — | — | Q7WTB0 | lacR3 | — | — | HTH-type transcriptional regulator LacR |
| Contig1 | 2305976 | 2307253 | + | GENE_02203 | Prodigal: 2.6 | CDS | — | — | — | — | Q00749 | msmE_1 | — | — | Multiple sugar-binding protein precursor |
| Contig1 | 2307250 | 2308164 | + | GENE_02204 | Prodigal: 2.6 | CDS | — | — | — | — | P29823 | lacF_2 | — | — | Lactose transport system permease protein LacF |
| Contig1 | 2308161 | 2308982 | + | GENE_02205 | Prodigal: 2.6 | CDS | — | — | — | — | P94530 | araQ_2 | — | — | L-arabinose transport system permease protein AraQ |
| Contig1 | 2309005 | 2310303 | + | GENE_02206 | Prodigal: 2.6 | CDS | 3.2.1.22 | — | — | — | P06720 | melA | — | — | Alpha-galactosidase |
| Contig1 | 2310340 | 2310825 | − | GENE_02207 | Prodigal: 2.6 | CDS | 2.3.1.189 | — | — | MF_01698 | — | mshD_1 | — | — | Mycothiol acetyltransferase |
| Contig1 | 2310901 | 2311212 | − | GENE_02208 | Prodigal: 2.6 | CDS | 2.8.1.1 | — | — | — | P0A6V5 | glpE_1 | — | — | Thiosulfate sulfurtransferase GlpE |
| Contig1 | 2311329 | 2313743 | − | GENE_02209 | Prodigal: 2.6 | CDS | 6.1.1.4 | — | — | — | P67513 | leuS | — | — | Leucine--tRNA ligase |
| Contig1 | 2314169 | 2314504 | − | GENE_02210 | Prodigal: 2.6 | CDS | — | — | — | — | — | — | — | — | hypothetical protein |
| Contig1 | 2314894 | 2315679 | + | GENE_02211 | Prodigal: 2.6 | CDS | — | — | — | — | O34627 | pfyP | — | — | Blue-light photoreceptor |
| Contig1 | 2315721 | 2316905 | − | GENE_02212 | Prodigal: 2.6 | CDS | — | — | — | MF_01529 | — | mdtH | — | — | Multidrug resistance protein MdtH |
| Contig1 | 2317101 | 2317811 | − | GENE_02213 | Prodigal: 2.6 | CDS | — | — | PF09529.4 | — | — | — | — | — | Integral membrane protein ( ) |
| Contig1 | 2317919 | 2319859 | − | GENE_02214 | Prodigal: 2.6 | CDS | — | — | — | — | O34741 | bceB | — | — | Bacitracin export permease protein BceB |
| Contig1 | 2319856 | 2320608 | − | GENE_02215 | Prodigal: 2.6 | CDS | — | — | — | — | O34697 | bceA | — | — | Bacitracin export ATP-binding protein BceA |
| Contig1 | 2320714 | 2321676 | − | GENE_02216 | Prodigal: 2.6 | CDS | 2.7.13.3 | — | — | — | Q7A6Z3 | graS_1 | — | — | Sensor histidine kinase GraS |
| Contig1 | 2321711 | 2322406 | − | GENE_02217 | Prodigal: 2.6 | CDS | — | — | — | — | Q5HI09 | graR_1 | — | — | Response regulator protein GraR |
| Contig1 | 2322470 | 2323780 | − | GENE_02218 | Prodigal: 2.6 | CDS | — | — | — | — | O35005 | ytrF | — | — | ABC transporter permease YtrF precursor |
| Contig1 | 2323770 | 2324465 | − | GENE_02219 | Prodigal: 2.6 | CDS | — | — | — | — | O34392 | ytrE | — | — | ABC transporter ATP-binding protein YtrE |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2324481 | 2325464 | − | GENE_02220 | Prodigal: 2.6 | CDS | — | — | — | — | O34898 | ytrC_1 | — | — | putative ABC transporter permease YtrC |
| Contig1 | 2325501 | 2326487 | − | GENE_02221 | Prodigal: 2.6 | CDS | — | — | — | — | O34898 | ytrC_2 | — | — | putative ABC transporter permease YtrC |
| Contig1 | 2326503 | 2327489 | − | GENE_02222 | Prodigal: 2.6 | CDS | — | — | — | — | O34898 | ytrC_3 | — | — | putative ABC transporter permease YtrC |
| Contig1 | 2327483 | 2328361 | − | GENE_02223 | Prodigal: 2.6 | CDS | — | — | — | — | O34641 | ytrB_1 | — | — | ABC transporter ATP-binding protein YtrB |
| Contig1 | 2328354 | 2328746 | − | GENE_02224 | Prodigal: 2.6 | CDS | — | — | — | — | O34712 | ytrA_2 | — | — | HTH-type transcriptional repressor YtrA |
| Contig1 | 2328785 | 2328901 | − | GENE_02225 | Prodigal: 2.6 | CDS | — | — | — | — | — | — | — | — | hypothetical protein |
| Contig1 | 2329094 | 2329366 | − | GENE_02226 | Prodigal: 2.6 | CDS | — | — | — | — | — | — | — | — | hypothetical protein |
| Contig1 | 2329604 | 2330572 | + | GENE_02227 | Prodigal: 2.6 | CDS | 2.8.1.6 | — | — | MF_01694 | — | bioB_2 | — | — | Biotin synthase |
| Contig1 | 2330569 | 2331150 | + | GENE_02228 | Prodigal: 2.6 | CDS | 2.1.1.199 | — | — | MF_01007 | — | rsmH_2 | — | — | Ribosomal RNA small subunit methyltransferase H |
| Contig1 | 2331273 | 2331467 | + | GENE_02229 | Prodigal: 2.6 | CDS | — | — | — | — | — | — | — | — | hypothetical protein |
| Contig1 | 2331521 | 2332603 | − | GENE_02230 | Prodigal: 2.6 | CDS | 4.2.3.130 | — | — | — | — | — | — | — | Tetraprenyl-beta-curcumene synthase |
| Contig1 | 2332621 | 2333400 | − | GENE_02231 | Prodigal: 2.6 | CDS | 3.1.1.- | — | — | — | O34707 | ytpB | — | — | Phospholipase YtpA |
| Contig1 | 2333444 | 2333962 | + | GENE_02232 | Prodigal: 2.6 | CDS | 2.3.1.89 | — | — | — | O34705 | ytpA | — | — | 2,3,4,5-tetrahydropyridine-2,6-dicarboxylate N-acetyltransferase |
| Contig1 | — | — | — | — | — | — | — | — | — | — | Q7A2S0 | dapH_2 | — | — | |
| Contig1 | 2334138 | 2335541 | − | GENE_02233 | Prodigal: 2.6 | CDS | — | — | — | — | P0AAE2 | proY | — | — | Proline-specific permease ProY |
| Contig1 | 2335746 | 2337644 | − | GENE_02234 | Prodigal: 2.6 | CDS | 6.3.5.4 | — | — | — | P54420 | asnB | — | — | Asparagine synthetase [glutamine-hydrolyzing] 1 |
| Contig1 | 2337788 | 2338990 | − | GENE_02235 | Prodigal: 2.6 | CDS | 2.5.1.6 | — | — | — | P66767 | metK | — | — | S-adenosylmethionine synthase |
| Contig1 | 2339497 | 2341080 | + | GENE_02236 | Prodigal: 2.6 | CDS | 4.1.1.49 | — | — | — | P99128 | pckA | — | — | Phosphoenolpyruvate carboxykinase [ATP] |
| Contig1 | 2341123 | 2341365 | − | GENE_02237 | Prodigal: 2.6 | CDS | — | — | — | — | — | — | — | — | hypothetical protein |
| Contig1 | 2341423 | 2342196 | − | GENE_02238 | Prodigal: 2.6 | CDS | — | — | PF00326.1 | — | — | — | — | — | Prolyl oligopeptidase family protein |
| Contig1 | 2342335 | 2343339 | + | GENE_02239 | Prodigal: 2.6 | CDS | — | — | PF09084.5 | — | — | — | — | — | NMT1/THI5 like protein |
| Contig1 | 2343351 | 2344133 | + | GENE_02240 | Prodigal: 2.6 | CDS | 3.6.3.- | — | — | — | P97027 | ssuB_2 | — | — | Aliphatic sulfonates import ATP-binding protein SsuB |
| Contig1 | 2344108 | 2344933 | + | GENE_02241 | Prodigal: 2.6 | CDS | — | — | — | — | P40401 | ssuC_2 | — | — | Putative aliphatic sulfonates transport permease protein SsuC |
| Contig1 | 2344956 | 2345435 | − | GENE_02242 | Prodigal: 2.6 | CDS | 3.6.1.55 | — | — | — | O35013 | ytkD | — | — | Putative 8-oxo-dGTP diphosphatase YtkD |
| Contig1 | 2345568 | 2345972 | − | GENE_02243 | Prodigal: 2.6 | CDS | — | — | PF05105.6 | — | — | — | — | — | Holin family protein |
| Contig1 | 2346124 | 2346561 | − | GENE_02244 | Prodigal: 2.6 | CDS | — | — | — | — | P80879 | dps | — | — | General stress protein 20U |
| Contig1 | 2346686 | 2346835 | + | GENE_02245 | Prodigal: 2.6 | CDS | — | — | — | — | — | — | — | — | hypothetical protein |
| Contig1 | 2346832 | 2347275 | − | GENE_02246 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2347390 | 2347863 | − | GENE_02247 | Prodigal: 2.6 | CDS | 4.4.1.21 | — | — | — | O34667 | luxS | — | — | S-ribosylhomocysteine lyase |
| Contig1 | 2347988 | 2348215 | + | GENE_02248 | Prodigal: 2.6 | CDS | — | — | — | — | P0A8C8 | yidD | — | — | Putative membrane protein insertion efficiency factor |
| Contig1 | 2348212 | 2348781 | − | GENE_02249 | Prodigal: 2.6 | CDS | 4.2.1.1 | — | — | — | P64797 | mtcA1_1 | — | — | Beta-carbonic anhydrase 1 |
| Contig1 | 2348900 | 2349148 | − | GENE_02250 | Prodigal: 2.6 | CDS | — | — | — | — | O34967 | rpmE2 | — | — | 50S ribosomal protein L31 type B |
| Contig1 | 2349346 | 2350677 | + | GENE_02251 | Prodigal: 2.6 | CDS | 1.10.3.- | — | — | — | C0SP90 | ythA | — | — | Putative cytochrome bd menaquinol oxidase subunit I |
| Contig1 | 2350712 | 2351740 | + | GENE_02252 | Prodigal: 2.6 | CDS | — | — | — | — | O34505 | ythB | — | — | Putative cytochrome bd menaquinol oxidase subunit II |
| Contig1 | 2351765 | 2351956 | + | GENE_02253 | Prodigal: 2.6 | CDS | — | — | — | — | — | — | — | — | hypothetical protein |
| Contig1 | 2352344 | 2353459 | − | GENE_02254 | Prodigal: 2.6 | CDS | 4.2.1.113 | — | — | — | O34514 | menC | — | — | o-succinylbenzoate synthase |
| Contig1 | 2353456 | 2354919 | − | GENE_02255 | Prodigal: 2.6 | CDS | 6.2.1.26 | — | — | — | P63526 | menE | — | — | 2-succinylbenzoate-CoA ligase |
| Contig1 | 2355007 | 2355825 | − | GENE_02256 | Prodigal: 2.6 | CDS | 4.1.3.36 | — | — | — | P23966 | menB | — | — | 1,4-Dihydroxy-2-naphthoyl-CoA synthase |
| Contig1 | 2355884 | 2356708 | − | GENE_02257 | Prodigal: 2.6 | CDS | 4.2.99.20 | — | — | — | P37355 | menH | — | — | 2-succinyl-6-hydroxy-2,4-cyclohexadiene-1-carboxylate synthase |
| Contig1 | 2356696 | 2358432 | − | GENE_02258 | Prodigal: 2.6 | CDS | 2.2.1.9 | — | — | — | P23970 | menD | — | — | 2-succinyl-5-enolpyruvyl-6-hydroxy-3-cyclohexene-1-carboxylate synthase |
| Contig1 | 2358429 | 2359844 | − | GENE_02259 | Prodigal: 2.6 | CDS | 5.4.4.2 | — | — | — | Q51508 | pchA | — | — | Salicylate biosynthesis isochorismate synthase |
| Contig1 | 2360127 | 2360846 | + | GENE_02260 | Prodigal: 2.6 | CDS | — | — | PF03073.9 | — | P80872 | yockK3 | — | — | General stress protein 160 TspO/MBR family protein |
| Contig1 | 2361002 | 2361472 | + | GENE_02261 | Prodigal: 2.6 | CDS | — | — | — | — | — | — | — | — | |
| Contig1 | 2361509 | 2361580 | − | GENE_02262 | Aragorn: 1.2 | tRNA | — | — | — | — | — | — | — | — | tRNA-Glu(ttc) |
| Contig1 | 2361584 | 2361674 | − | GENE_02263 | Aragorn: 1.2 | tRNA | — | — | — | — | — | — | — | — | tRNA-Ser(gct) |
| Contig1 | 2361678 | 2361752 | − | GENE_02264 | Aragorn: 1.2 | tRNA | — | — | — | — | — | — | — | — | tRNA-Asn(gtt) |
| Contig1 | 2361763 | 2361839 | − | GENE_02265 | Aragorn: 1.2 | tRNA | — | — | — | — | — | — | — | — | tRNA-Ile(gat) |
| Contig1 | 2361855 | 2361928 | − | GENE_02266 | Aragorn: 1.2 | tRNA | — | — | — | — | — | — | — | — | tRNA-Gly(tcc) |
| Contig1 | 2361937 | 2362012 | − | GENE_02267 | Aragorn: 1.2 | tRNA | — | — | — | — | — | — | — | — | tRNA-His(gtg) |
| Contig1 | 2362033 | 2362108 | − | GENE_02268 | Aragorn: 1.2 | tRNA | — | — | — | — | — | — | — | — | tRNA-Phe(gaa) |
| Contig1 | 2362119 | 2362195 | − | GENE_02269 | Aragorn: 1.2 | tRNA | — | — | — | — | — | — | — | — | tRNA-Asp(gtc) |
| Contig1 | 2362203 | 2362279 | − | GENE_02270 | Aragorn: 1.2 | tRNA | — | — | — | — | — | — | — | — | tRNA-Met(cat) |
| Contig1 | 2362299 | 2362391 | − | GENE_02271 | Aragorn: 1.2 | tRNA | — | — | — | — | — | — | — | — | tRNA-Ser(gga) |
| Contig1 | 2362399 | 2362475 | − | GENE_02272 | Aragorn: 1.2 | tRNA | — | — | — | — | — | — | — | — | tRNA-Met(cat) |
| Contig1 | 2362478 | 2362554 | − | GENE_02273 | Aragorn: 1.2 | tRNA | — | — | — | — | — | — | — | — | tRNA-Met(cat) |
| Contig1 | 2362573 | 2362646 | − | GENE_02274 | Aragorn: 1.2 | tRNA | — | — | — | — | — | — | — | — | tRNA-Ala(tgc) |
| Contig1 | 2362651 | 2362727 | − | GENE_02275 | Aragorn: 1.2 | tRNA | — | — | — | — | — | — | — | — | tRNA-Pro(tgg) |
| Contig1 | 2362745 | 2362821 | − | GENE_02276 | Aragorn: 1.2 | tRNA | — | — | — | — | — | — | — | — | tRNA-Arg(acg) |
| Contig1 | 2362830 | 2362916 | − | GENE_02277 | Aragorn: 1.2 | tRNA | — | — | — | — | — | — | — | — | tRNA-Leu(taa) |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2362936 | 2363010 | − | GENE_02278 | Aragorn: 1.2 | tRNA | — | — | — | — | — | — | — | — | tRNA-Gly(gcc) |
| Contig1 | 2363019 | 2363104 | − | GENE_02279 | Aragorn: 1.2 | tRNA | — | — | — | — | — | — | — | — | tRNA-Ser(cag) |
| Contig1 | 2363114 | 2363189 | − | GENE_02280 | Aragorn: 1.2 | tRNA | — | — | — | — | — | — | — | — | tRNA-Lys(ttt) |
| Contig1 | 2363227 | 2363302 | − | GENE_02281 | Aragorn: 1.2 | tRNA | — | — | — | — | — | — | — | — | tRNA-Thr(tgt) |
| Contig1 | 2363332 | 2363407 | − | GENE_02282 | Aragorn: 1.2 | tRNA | — | — | — | — | — | — | — | — | tRNA-Val(tac) |
| Contig1 | 2363434 | 2363544 | − | GENE_02283 | — | rRNA | — | — | — | — | — | — | — | — | 5S ribosomal RNA |
| Contig1 | 2363599 | 2366524 | − | GENE_02284 | — | rRNA | — | — | — | — | — | — | — | — | 23S ribosomal RNA |
| Contig1 | 2366702 | 2368249 | − | GENE_02285 | — | rRNA | — | — | — | — | — | — | — | — | 16S ribosomal RNA |
| Contig1 | 2368883 | 2369464 | + | GENE_02286 | Prodigal: 2.6 | CDS | — | — | — | — | O37074 | thiT | — | — | Thiamine transporter ThiT |
| Contig1 | 2369495 | 2371024 | − | GENE_02287 | Prodigal: 2.6 | CDS | — | — | — | — | P77306 | yqiK | — | — | Inner membrane protein YqiK |
| Contig1 | 2371044 | 2371574 | − | GENE_02288 | Prodigal: 2.6 | CDS | — | — | — | — | O32077 | yuaF | — | — | putative membrane protein YuaF |
| Contig1 | 2371720 | 2372208 | + | GENE_02289 | Prodigal: 2.6 | CDS | — | — | PF12867.1 | — | — | — | — | — | DinB superfamily protein |
| Contig1 | 2372338 | 2372790 | − | GENE_02290 | Prodigal: 2.6 | CDS | — | — | — | — | O32079 | yuaD | — | — | Putative metal-sulfur cluster biosynthesis proteins YuaD |
| Contig1 | 2372862 | 2374070 | − | GENE_02291 | Prodigal: 2.6 | CDS | 1.1.1.1 | — | — | — | P71017 | gbsB | — | — | Alcohol dehydrogenase |
| Contig1 | 2374087 | 2375559 | − | GENE_02292 | Prodigal: 2.6 | CDS | 1.2.1.8 | — | — | — | P71016 | gbsA | — | — | Betaine aldehyde dehydrogenase |
| Contig1 | 2375760 | 2376314 | + | GENE_02293 | Prodigal: 2.6 | CDS | — | — | — | — | O34709 | opcR_1 | — | — | HTH-type transcriptional repressor OpcR |
| Contig1 | 2376473 | 2377012 | − | GENE_02294 | Prodigal: 2.6 | CDS | — | — | — | — | — | — | — | — | hypothetical protein |
| Contig1 | 2377176 | 2377844 | + | GENE_02295 | Prodigal: 2.6 | CDS | — | — | — | — | O32080 | ktrA_2 | — | — | Ktr system potassium uptake protein A |
| Contig1 | 2377878 | 2378723 | − | GENE_02296 | Prodigal: 2.6 | CDS | 3.2.1.- | — | — | — | O32083 | lytG | — | — | Exo-glucosaminidase LytG precursor |
| Contig1 | 2378866 | 2380047 | − | GENE_02297 | Prodigal: 2.6 | CDS | 1.14.12.17 | — | — | — | P49852 | hmp_2 | — | — | Flavohemoprotein |
| Contig1 | 2380258 | 2380899 | + | GENE_02298 | Prodigal: 2.6 | CDS | — | — | — | — | — | — | — | — | Cupin |
| Contig1 | 2380967 | 2381287 | − | GENE_02299 | Prodigal: 2.6 | CDS | — | — | — | — | — | — | — | — | hypothetical protein |
| Contig1 | 2381520 | 2381756 | − | GENE_02300 | Prodigal: 2.6 | CDS | — | — | — | — | — | — | — | — | hypothetical protein |
| Contig1 | 2382172 | 2382294 | − | GENE_02301 | Prodigal: 2.6 | CDS | — | — | — | — | — | — | — | — | hypothetical protein |
| Contig1 | 2382311 | 2382439 | − | GENE_02302 | Prodigal: 2.6 | CDS | — | — | — | — | — | — | — | — | hypothetical protein |
| Contig1 | 2382429 | 2383559 | − | GENE_02303 | Prodigal: 2.6 | CDS | 3.1.- | — | PF00190.16 | — | Q59HN8 | rapH | — | — | Response regulator aspartate phosphatase H |
| Contig1 | 2383880 | 2384068 | + | GENE_02304 | Prodigal: 2.6 | CDS | — | — | — | — | — | — | — | — | hypothetical protein |
| Contig1 | 2384885 | 2384957 | − | GENE_02305 | Aragorn: 1.2 | tRNA | — | — | — | — | — | — | — | — | tRNA-Ala(ggc) |
| Contig1 | 2385085 | 2385915 | − | GENE_02306 | Prodigal: 2.6 | CDS | 3.6.1.27 | — | — | — | P60932 | uppP | — | — | Undecaprenyl-diphosphatase |
| Contig1 | 2386007 | 2387167 | − | GENE_02307 | Prodigal: 2.6 | CDS | — | PRK12287 | — | — | — | — | — | — | pheromone autoinducer 2 transporter |
| Contig1 | 2387347 | 2388333 | + | GENE_02308 | Prodigal: 2.6 | CDS | 1.1.1.292 | — | — | — | Q2I8V6 | afr | — | — | 1,5-anhydro-D-fructose reductase |
| Contig1 | 2388365 | 2388889 | − | GENE_02309 | Prodigal: 2.6 | CDS | 3.2.-.- | — | — | — | O06006 | yraA_2 | — | — | Putative cysteine protease YraA |
| Contig1 | 2388955 | 2390961 | − | GENE_02310 | Prodigal: 2.6 | CDS | — | — | — | — | P39214 | mcpA_2 | — | — | Methyl-accepting chemotaxis protein McpA |
| Contig1 | 2391077 | 2393062 | − | GENE_02311 | Prodigal: 2.6 | CDS | — | — | — | — | P39214 | mcpA_3 | — | — | Methyl-accepting chemotaxis protein McpA |

TABLE 5-continued

| # ContigID | Start | End | Strand | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|
| Contig1 | 2393190 | 2395178 | − | Prodigal: 2.6 | CDS | — | — | — | — | P39214 | mcpA_4 | — | — | Methyl-accepting chemotaxis protein McpA |
| Contig1 | 2395363 | 2397348 | − | Prodigal: 2.6 | CDS | — | — | — | — | P39215 | mcpB | — | — | Methyl-accepting chemotaxis protein McpB |
| Contig1 | 2397490 | 2398227 | + | Prodigal: 2.6 | CDS | 2.3.2.13 | — | — | — | P40746 | tgl | — | — | Protein-glutamine gamma-glutamyltransferase |
| Contig1 | 2398245 | 2398499 | − | Prodigal: 2.6 | CDS | — | — | — | — | — | — | — | — | hypothetical protein |
| Contig1 | 2398522 | 2399553 | − | Prodigal: 2.6 | CDS | 1.13.12.16 | — | — | — | Q914V0 | — | — | — | Nitronate monooxygenase |
| Contig1 | 2399550 | 2399966 | − | Prodigal: 2.6 | CDS | — | — | — | — | — | — | — | — | hypothetical protein |
| Contig1 | 2400088 | 2401746 | − | Prodigal: 2.6 | CDS | 3.2.1.10 | — | — | — | P29094 | malL | — | — | Oligo-1,6-glucosidase |
| Contig1 | 2401836 | 2403125 | − | Prodigal: 2.6 | CDS | — | — | — | — | P0A2L3 | corC_3 | — | — | Magnesium and cobalt efflux protein CorC |
| Contig1 | 2403168 | 2403845 | − | Prodigal: 2.6 | CDS | — | — | PF04298.6 | — | — | — | — | — | Putative neutral zinc metallopeptidase |
| Contig1 | 2403892 | 2404155 | + | Prodigal: 2.6 | CDS | — | — | — | — | — | — | — | — | hypothetical protein |
| Contig1 | 2404288 | 2404542 | + | Prodigal: 2.6 | CDS | — | — | PF11458.2 | — | — | — | — | — | Membrane-integrating protein Mistic |
| Contig1 | 2404539 | 2405525 | + | Prodigal: 2.6 | CDS | — | — | — | — | Q98GN8 | — | — | — | Cyclic nucleotide-gated potassium channel |
| Contig1 | 2405522 | 2405926 | − | Prodigal: 2.6 | CDS | — | — | PF08868.4 | — | — | — | — | — | YugN-like family protein |
| Contig1 | 2405949 | 2406347 | − | Prodigal: 2.6 | CDS | — | — | — | — | — | — | — | — | hypothetical protein |
| Contig1 | 2406369 | 2407721 | − | Prodigal: 2.6 | CDS | 5.3.1.9 | — | — | — | P80860 | pgi | — | — | Glucose-6-phosphate isomerase |
| Contig1 | 2408119 | 2408685 | + | Prodigal: 2.6 | CDS | 1.7.-.- | — | — | — | O07529 | azr_2 | — | — | FMN-dependent NADPH-azoreductase |
| Contig1 | 2408810 | 2409454 | + | Prodigal: 2.6 | CDS | — | PRK11609 | — | — | — | — | — | — | nicotinamidase/pyrazinamidase |
| Contig1 | 2409756 | 2410928 | − | Prodigal: 2.6 | CDS | 1.1.1.- | — | — | — | Q04944 | bdhA_2 | — | — | NADH-dependent butanol dehydrogenase A |
| Contig1 | 2411014 | 2412177 | − | Prodigal: 2.6 | CDS | 1.1.1.- | — | — | — | Q04944 | bdhA_3 | — | — | NADH-dependent butanol dehydrogenase A |
| Contig1 | 2412407 | 2412643 | + | Prodigal: 2.6 | CDS | — | — | — | — | — | — | — | — | hypothetical protein |
| Contig1 | 2412691 | 2413083 | − | Prodigal: 2.6 | CDS | — | — | — | — | P80870 | yugI_1 | — | — | General stress protein 13 |
| Contig1 | 2413278 | 2414447 | − | Prodigal: 2.6 | CDS | 2.6.1.- | — | — | — | P16524 | patA_2 | — | — | Putative N-acetyl-LL-diaminopimelate aminotransferase |
| Contig1 | 2414448 | 2414948 | − | Prodigal: 2.6 | CDS | — | PRK11169 | — | — | — | — | — | — | leucine-responsive transcriptional regulator |
| Contig1 | 2415101 | 2415922 | + | Prodigal: 2.6 | CDS | 3.7.1.13 | — | — | — | Q9AQM4 | carC | — | — | 2-hydroxy-6-oxo-6-(2'-aminophenyl)hexa-2,4-dienoic acid hydrolase |
| Contig1 | 2415947 | 2416207 | − | Prodigal: 2.6 | CDS | — | — | — | — | — | — | — | — | hypothetical protein |
| Contig1 | 2416294 | 2417457 | + | Prodigal: 2.6 | CDS | 4.4.1.8 | — | — | — | Q08432 | patB | — | — | Cystathionine beta-lyase PatB |
| Contig1 | 2417580 | 2418863 | + | Prodigal: 2.6 | CDS | 2.7.13.3 | — | — | — | P16497 | kinA_3 | — | — | Sporulation kinase A |
| Contig1 | 2418911 | 2419297 | + | Prodigal: 2.6 | CDS | — | — | — | — | Q08429 | kapB | — | — | Kinase-associated lipoprotein B precursor |
| Contig1 | 2419322 | 2419939 | − | Prodigal: 2.6 | CDS | 2.7.7.7 | — | — | MF_00356 | — | polC_3 | — | — | DNA polymerase III PolC-type |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2420090 | 2421334 | + | GENE_02341 | Prodigal: 2.6 | CDS | — | — | — | — | P0A0J9 | qacA_1 | — | — | Antiseptic resistance protein |
| Contig1 | 2421424 | 2423298 | + | GENE_02342 | Prodigal: 2.6 | CDS | — | — | — | — | P40750 | pbpD | — | — | Penicillin-binding protein 4 precursor |
| Contig1 | 2423320 | 2423733 | — | GENE_02343 | Prodigal: 2.6 | CDS | — | — | — | — | — | — | — | — | hypothetical protein |
| Contig1 | 2423748 | 2424305 | + | GENE_02344 | Prodigal: 2.6 | CDS | — | — | — | — | — | — | — | — | hypothetical protein |
| Contig1 | 2424480 | 2426081 | + | GENE_02345 | Prodigal: 2.6 | CDS | 2.7.13.3 | — | — | — | P0AEC8 | dcuS_1 | — | — | Sensor histidine kinase DcuS |
| Contig1 | 2426074 | 2426781 | + | GENE_02346 | Prodigal: 2.6 | CDS | — | — | — | — | P0AD01 | dcuR_1 | — | — | Transcriptional regulatory protein DcuR |
| Contig1 | 2427183 | 2428256 | + | GENE_02347 | Prodigal: 2.6 | CDS | — | — | — | — | P29724 | tmpC_2 | — | — | Membrane lipoprotein TmpC precursor |
| Contig1 | 2428398 | 2429930 | + | GENE_02348 | Prodigal: 2.6 | CDS | 3.6.3.17 | — | — | — | P0AAG8 | mglA | — | — | Galactose/methyl galactoside import ATP-binding protein MglA |
| Contig1 | 2429923 | 2430969 | + | GENE_02349 | Prodigal: 2.6 | CDS | — | — | — | — | — | — | — | — | D-allose transport system permease protein AlsC |
| Contig1 | 2430970 | 2431929 | + | GENE_02350 | Prodigal: 2.6 | CDS | — | — | PF02653.10 | — | P32720 | alsC | — | — | Branched-chain amino acid transport system/permease component |
| Contig1 | 2431974 | 2432192 | — | GENE_02351 | Prodigal: 2.6 | CDS | — | — | — | — | — | — | — | — | hypothetical protein |
| Contig1 | 2432435 | 2434837 | — | GENE_02352 | Prodigal: 2.6 | CDS | — | — | — | — | Q9K2S2 | mrpA | — | — | Na(+)/H(+) antiporter subunit A |
| Contig1 | 2434834 | 2435265 | + | GENE_02353 | Prodigal: 2.6 | CDS | — | — | — | — | O05259 | mrpB | — | — | Na(+)/H(+) antiporter subunit B |
| Contig1 | 2435265 | 2435606 | + | GENE_02354 | Prodigal: 2.6 | CDS | — | — | — | — | O05260 | mrpC | — | — | Na(+)/H(+) antiporter subunit C |
| Contig1 | 2435590 | 2437041 | + | GENE_02355 | Prodigal: 2.6 | CDS | — | — | — | — | O05229 | mrpD | — | — | Na(+)/H(+) antiporter subunit D |
| Contig1 | 2437085 | 2437561 | + | GENE_02356 | Prodigal: 2.6 | CDS | — | — | — | — | Q7WY60 | mrpE | — | — | Na(+)/H(+) antiporter subunit E |
| Contig1 | 2437561 | 2437845 | + | GENE_02357 | Prodigal: 2.6 | CDS | — | — | — | — | O05228 | mrpF | — | — | Na(+)/H(+) antiporter subunit F |
| Contig1 | 2437829 | 2438203 | + | GENE_02358 | Prodigal: 2.6 | CDS | — | — | — | — | O05227 | mrpG | — | — | Na(+)/H(+) antiporter subunit G |
| Contig1 | 2438243 | 2438626 | — | GENE_02359 | Prodigal: 2.6 | CDS | 3.1.2.- | — | — | — | P45083 | — | — | — | Putative esterase |
| Contig1 | 2438648 | 2439292 | — | GENE_02360 | Prodigal: 2.6 | CDS | — | — | — | — | P14204 | comA | — | — | Transcriptional regulatory protein ComA |
| Contig1 | 2439373 | 2441679 | — | GENE_02361 | Prodigal: 2.6 | CDS | 2.7.13.3 | — | — | — | Q99027 | comP | — | — | Sensor histidine kinase ComP |
| Contig1 | 2441698 | 2441874 | — | GENE_02362 | Prodigal: 2.6 | CDS | — | — | — | — | P0CY51 | comX | — | — | Competence pheromone precursor |
| Contig1 | 2441889 | 2442764 | — | GENE_02363 | Prodigal: 2.6 | CDS | — | — | PF00348.11 | — | — | — | — | — | Polyprenyl synthetase |
| Contig1 | 2442916 | 2443056 | — | GENE_02364 | Prodigal: 2.6 | CDS | — | — | — | — | Q99039 | degQ | — | — | Degradation enzyme regulation protein DegQ |
| Contig1 | 2443521 | 2443862 | + | GENE_02365 | Prodigal: 2.6 | CDS | — | — | — | — | — | — | — | — | hypothetical protein |
| Contig1 | 2443869 | 2445089 | — | GENE_02366 | Prodigal: 2.6 | CDS | — | — | PF08668.6 | — | — | — | — | — | HDOD domain protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2445219 | 2446685 | − | GENE_02367 | Prodigal: 2.6 | CDS | 6.3.4.21 | — | — | — | O53770 | pncB2 | — | — | Nicotinate phosphoribosyltransferase pncB2 |
| Contig1 | 2446703 | 2447254 | − | GENE_02368 | Prodigal: 2.6 | CDS | 3.-.-.- | — | — | — | P0ADI7 | yecD_1 | — | — | Isochorismatase family protein YecD |
| Contig1 | 2447351 | 2447749 | − | GENE_02369 | Prodigal: 2.6 | CDS | — | — | — | — | — | — | — | — | hypothetical protein |
| Contig1 | 2447815 | 2448063 | − | GENE_02370 | Prodigal: 2.6 | CDS | — | — | — | — | — | — | — | — | hypothetical protein |
| Contig1 | 2448136 | 2448357 | − | GENE_02371 | Prodigal: 2.6 | CDS | — | — | — | — | O06716 | gerPF_4 | — | — | putative spore germination protein GerPF |
| Contig1 | 2448419 | 2449522 | − | GENE_02372 | Prodigal: 2.6 | CDS | — | PRK12287 | — | — | — | — | — | — | pheromone autoinducer 2 transporter |
| Contig1 | 2449661 | 2449897 | − | GENE_02373 | Prodigal: 2.6 | CDS | — | — | — | — | — | — | — | — | hypothetical protein |
| Contig1 | 2450035 | 2450565 | − | GENE_02374 | Prodigal: 2.6 | CDS | — | — | PF01966.16 | — | — | — | — | — | HD domain protein |
| Contig1 | 2450730 | 2451461 | − | GENE_02375 | Prodigal: 2.6 | CDS | 1.1.1.320 | — | — | — | Q8RJB2 | yueD | — | — | Benzil reductase ((S)-benzoin forming) |
| Contig1 | 2451522 | 2451995 | − | GENE_02376 | Prodigal: 2.6 | CDS | — | — | — | — | — | — | — | — | hypothetical protein |
| Contig1 | 2452003 | 2455143 | − | GENE_02377 | Prodigal: 2.6 | CDS | — | — | PF12698.1 | — | — | — | — | — | ABC-2 family transporter protein |
| Contig1 | 2455140 | 2459615 | − | GENE_02378 | Prodigal: 2.6 | CDS | — | — | — | — | O69735 | eccCa1 | — | — | ESX-1 secretion system protein EccCa1 |
| Contig1 | 2459670 | 2460956 | − | GENE_02379 | Prodigal: 2.6 | CDS | — | — | PF10140.3 | — | — | — | — | — | putative membrane protein essB |
| Contig1 | 2460971 | 2461216 | − | GENE_02380 | Prodigal: 2.6 | CDS | — | — | — | — | P71071 | yukD | — | — | putative ubiquitin-like protein YukD |
| Contig1 | 2461286 | 2461579 | + | GENE_02381 | Prodigal: 2.6 | CDS | — | — | — | — | Q7A7S4 | esxA | — | — | Virulence factor EsxA |
| Contig1 | 2461895 | 2463124 | + | GENE_02382 | Prodigal: 2.6 | CDS | — | — | — | — | P37047 | cdaR_2 | — | — | Carbohydrate diacid regulator |
| Contig1 | 2463228 | 2464358 | + | GENE_02383 | Prodigal: 2.6 | CDS | 1.4.1.1 | — | — | — | Q08352 | ald | — | — | Alanine dehydrogenase |
| Contig1 | 2464475 | 2465152 | + | GENE_02384 | Prodigal: 2.6 | CDS | — | — | — | — | — | — | — | — | hypothetical protein |
| Contig1 | 2465197 | 2465412 | − | GENE_02385 | Prodigal: 2.6 | CDS | — | — | PF03621.7 | — | — | — | — | — | MbtH-like protein |
| Contig1 | 2465431 | 2472558 | − | GENE_02386 | Prodigal: 2.6 | CDS | — | — | — | — | P45745 | dhbF | — | — | Dimodular nonribosomal peptide synthase |
| Contig1 | 2472573 | 2473499 | − | GENE_02387 | Prodigal: 2.6 | CDS | 3.3.2.1 | — | — | — | P45743 | dhbB | — | — | Isochorismatase |
| Contig1 | 2473518 | 2475143 | − | GENE_02388 | Prodigal: 2.6 | CDS | 6.3.2.- | — | — | — | P40871 | dhbE | — | — | 2,3-dihydroxybenzoate-AMP ligase |
| Contig1 | 2475162 | 2476358 | − | GENE_02389 | Prodigal: 2.6 | CDS | 5.4.4.2 | — | — | — | P45744 | dhbC | — | — | Isochorismate synthase DhbC |
| Contig1 | 2476382 | 2477167 | − | GENE_02390 | Prodigal: 2.6 | CDS | 1.3.1.28 | — | — | — | P39071 | dhbA | — | — | 2,3-dihydro-2,3-dihydroxybenzoate dehydrogenase |
| Contig1 | 2477303 | 2478172 | − | GENE_02391 | Prodigal: 2.6 | CDS | 3.1.-.- | — | — | — | O32102 | besA | — | — | Ferri-bacillibactin esterase BesA |
| Contig1 | 2478348 | 2478944 | − | GENE_02392 | Prodigal: 2.6 | CDS | 1.8.-.- | — | — | — | P76342 | yedY | — | — | Sulfoxide reductase catalytic subunit YedY precursor |
| Contig1 | 2479044 | 2479637 | + | GENE_02393 | Prodigal: 2.6 | CDS | — | — | PF03553.8 | — | Q9WZ06 | bioY_2 | — | — | Biotin transporter BioY |
| Contig1 | 2479683 | 2481011 | − | GENE_02394 | Prodigal: 2.6 | CDS | — | — | — | — | — | — | — | — | Na+/H+ antiporter family protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2481144 | 2482634 | − | GENE_02395 | Prodigal: 2.6 | CDS | 3.4.11.1 | — | — | — | Q5H4N2 | pepA | — | — | putative cytosol aminopeptidase |
| Contig1 | 2482782 | 2483258 | + | GENE_02396 | Prodigal: 2.6 | CDS | — | — | PF02681.8 | — | — | — | — | — | Divergent PAP2 family protein |
| Contig1 | 2483287 | 2483928 | − | GENE_02397 | Prodigal: 2.6 | CDS | — | — | — | — | O34669 | yocH_2 | — | — | Cell wall-binding protein YocH precursor |
| Contig1 | 2484029 | 2484349 | − | GENE_02398 | Prodigal: 2.6 | CDS | — | — | — | — | — | — | — | — | hypothetical protein |
| Contig1 | 2484718 | 2485938 | − | GENE_02399 | Prodigal: 2.6 | CDS | 1.6.99.- | — | — | — | Q99VE0 | — | — | — | NADH dehydrogenase-like protein |
| Contig1 | 2486250 | 2487245 | + | GENE_02400 | Prodigal: 2.6 | CDS | 1.18.1.2 | — | — | — | O05268 | yumC_1 | — | — | Ferredoxin—NADP reductase 2 |
| Contig1 | 2487286 | 2487429 | − | GENE_02401 | Prodigal: 2.6 | CDS | — | — | — | — | — | — | — | — | hypothetical protein |
| Contig1 | 2487647 | 2488627 | + | GENE_02402 | Prodigal: 2.6 | CDS | 1.7.1.7 | — | — | — | O05269 | guaC | — | — | GMP reductase |
| Contig1 | 2488690 | 2488911 | − | GENE_02403 | Prodigal: 2.6 | CDS | — | — | — | — | — | — | — | — | hypothetical protein |
| Contig1 | 2488928 | 2489452 | − | GENE_02404 | Prodigal: 2.6 | CDS | — | — | — | — | — | — | — | — | hypothetical protein |
| Contig1 | 2489452 | 2490156 | − | GENE_02405 | Prodigal: 2.6 | CDS | 3.6.3.- | — | — | — | P94374 | yxlF_3 | — | — | putative ABC transporter ATP-binding protein YxlF |
| Contig1 | 2490149 | 2491804 | − | GENE_02406 | Prodigal: 2.6 | CDS | — | — | — | — | — | — | — | — | hypothetical protein |
| Contig1 | 2491887 | 2492225 | − | GENE_02407 | Prodigal: 2.6 | CDS | — | — | PF09221.4 | — | — | — | — | — | Bacteriocin class lid cyclical uberolysin-like protein |
| Contig1 | 2492289 | 2492861 | − | GENE_02408 | Prodigal: 2.6 | CDS | — | — | — | — | — | — | — | — | hypothetical protein |
| Contig1 | 2493610 | 2494371 | + | GENE_02409 | Prodigal: 2.6 | CDS | 1.1.1.- | — | — | — | P39831 | ydfG | — | — | NADP-dependent 3-hydroxy acid dehydrogenase YdfG |
| Contig1 | 2494634 | 2494999 | − | GENE_02410 | Prodigal: 2.6 | CDS | — | — | — | — | — | — | — | — | hypothetical protein |
| Contig1 | 2495449 | 2495811 | − | GENE_02411 | Prodigal: 2.6 | CDS | — | — | — | — | P45344 | erpA | — | — | Iron-sulfur cluster insertion protein ErpA |
| Contig1 | 2495889 | 2496743 | − | GENE_02412 | Prodigal: 2.6 | CDS | 5.1.1.7 | — | — | — | A7Z8D3 | dapF | — | — | Diaminopimelate epimerase |
| Contig1 | 2496867 | 2498084 | − | GENE_02413 | Prodigal: 2.6 | CDS | — | — | — | — | P33021 | nupX | — | — | Nucleoside permease NupX |
| Contig1 | 2498219 | 2498455 | − | GENE_02414 | Prodigal: 2.6 | CDS | — | — | — | — | — | — | — | — | hypothetical protein |
| Contig1 | 2498722 | 2499789 | + | GENE_02415 | Prodigal: 2.6 | CDS | 1.6.99.3 | — | — | — | P00393 | ndh | — | — | NADH dehydrogenase |
| Contig1 | 2499827 | 2500153 | − | GENE_02416 | Prodigal: 2.6 | CDS | — | — | — | — | — | — | — | — | hypothetical protein |
| Contig1 | 2500332 | 2500568 | + | GENE_02417 | Prodigal: 2.6 | CDS | — | — | — | MF_01637 | — | nfuA | — | — | Fe/S biogenesis protein NfuA |
| Contig1 | 2500609 | 2502579 | − | GENE_02418 | Prodigal: 2.6 | CDS | 3.4.14.12 | — | — | — | Q7MUW6 | PtpA | — | — | Prolyl tripeptidyl peptidase precursor |
| Contig1 | 2502683 | 2503612 | − | GENE_02419 | Prodigal: 2.6 | CDS | 2.7.1.39 | — | — | — | Q8Y4A6 | thrB_2 | — | — | Homoserine kinase |
| Contig1 | 2503609 | 2504676 | − | GENE_02420 | Prodigal: 2.6 | CDS | 4.2.3.1 | — | — | — | A0R220 | thrC | — | — | Threonine synthase |
| Contig1 | 2504667 | 2505968 | − | GENE_02421 | Prodigal: 2.6 | CDS | 1.1.1.3 | — | — | — | P08499 | hom | — | — | Homoserine dehydrogenase |
| Contig1 | 2506170 | 2507186 | − | GENE_02422 | Prodigal: 2.6 | CDS | — | — | — | — | — | — | — | — | hypothetical protein |
| Contig1 | 2507305 | 2507841 | + | GENE_02423 | Prodigal: 2.6 | CDS | — | — | PF04608.7 | — | — | — | — | — | Phosphatidylglycero-phosphatase A |
| Contig1 | 2507868 | 2508638 | − | GENE_02424 | Prodigal: 2.6 | CDS | 3.-.-.- | — | — | — | O32125 | yutF_1 | — | — | putative hydrolase YutF |
| Contig1 | 2508672 | 2509106 | − | GENE_02425 | Prodigal: 2.6 | CDS | — | — | — | — | — | — | — | — | hypothetical protein |
| Contig1 | 2509132 | 2509407 | − | GENE_02426 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2509626 | 2510522 | − | GENE_02427 | Prodigal: 2.6 | CDS | 2.8.1.8 | — | — | — | O32129 | lipA | — | — | Lipoyl synthase |
| Contig1 | 2510724 | 2511701 | + | GENE_02428 | Prodigal: 2.6 | CDS | 3.4.-.- | — | — | — | O32130 | lytH | — | — | L-Ala-D-Glu endopeptidase precursor |
| Contig1 | 2511739 | 2512497 | − | GENE_02429 | Prodigal: 2.6 | CDS | — | — | — | — | O32131 | yunB | — | — | Sporulation protein YunB |
| Contig1 | 2512623 | 2514017 | − | GENE_02430 | Prodigal: 2.6 | CDS | 3.1.31.- | — | — | — | P54602 | yhcR_2 | — | — | Endonuclease YhcR precursor |
| Contig1 | 2514035 | 2514856 | − | GENE_02431 | Prodigal: 2.6 | CDS | — | PRK10621 | — | — | — | — | — | — | hypothetical protein |
| Contig1 | 2514876 | 2515727 | − | GENE_02432 | Prodigal: 2.6 | CDS | — | PRK10302 | — | — | — | — | — | — | hypothetical protein |
| Contig1 | 2515754 | 2516107 | − | GENE_02433 | Prodigal: 2.6 | CDS | — | — | — | — | — | — | — | — | hypothetical protein |
| Contig1 | 2516180 | 2517541 | − | GENE_02434 | Prodigal: 2.6 | CDS | 3.5.2.5 | — | — | — | O32137 | allB | — | — | Allantoinase |
| Contig1 | 2517721 | 2519316 | + | GENE_02435 | Prodigal: 2.6 | CDS | — | — | — | — | O32138 | pucR | — | — | Purine catabolism regulatory protein |
| Contig1 | 2519404 | 2519559 | − | GENE_02436 | Prodigal: 2.6 | CDS | — | — | — | — | — | — | — | — | hypothetical protein |
| Contig1 | 2520028 | 2520144 | − | GENE_02437 | Prodigal: 2.6 | CDS | — | — | — | — | — | — | — | — | hypothetical protein |
| Contig1 | 2521183 | 2522379 | − | GENE_02438 | Prodigal: 2.6 | CDS | — | — | — | — | P02980 | tetA_2 | — | — | Tetracycline resistance protein, class B |
| Contig1 | 2522501 | 2523754 | − | GENE_02439 | Prodigal: 2.6 | CDS | 2.-.-.- | — | — | — | O32148 | pucG | — | — | Purine catabolism protein PucG |
| Contig1 | 2523773 | 2525014 | − | GENE_02440 | Prodigal: 2.6 | CDS | 3.5.3.- | — | — | — | O32149 | pucF | — | — | Allantoate amidohydrolase |
| Contig1 | 2525234 | 2526103 | + | GENE_02441 | Prodigal: 2.6 | CDS | 3.1.-.- | — | — | — | Q03091 | bsn | — | — | Extracellular ribonuclease precursor |
| Contig1 | 2526152 | 2527258 | − | GENE_02442 | Prodigal: 2.6 | CDS | 3.6.3.20 | — | — | — | Q8ZLF4 | ugpC | — | — | sn-glycerol-3-phosphate import ATP-binding protein UgpC |
| Contig1 | 2527414 | 2528142 | + | GENE_02443 | Prodigal: 2.6 | CDS | — | — | — | — | O32152 | yurK | — | — | putative HTH-type transcriptional regulator YurK |
| Contig1 | 2528167 | 2529021 | − | GENE_02444 | Prodigal: 2.6 | CDS | 2.7.1.- | — | — | — | O32153 | frlD | — | — | Fructosamine kinase FrlD |
| Contig1 | 2529035 | 2529919 | − | GENE_02445 | Prodigal: 2.6 | CDS | — | — | — | — | P94530 | araQ_3 | — | — | L-arabinose transport system permease protein AraQ |
| Contig1 | 2529923 | 2530813 | − | GENE_02446 | Prodigal: 2.6 | CDS | — | — | — | — | P94529 | araP_2 | — | — | L-arabinose transport system permease protein AraP |
| Contig1 | 2530838 | 2531569 | − | GENE_02447 | Prodigal: 2.6 | CDS | — | — | PF01547.19 | — | — | — | — | — | Bacterial extracellular solute-binding protein |
| Contig1 | 2531587 | 2532123 | − | GENE_02448 | Prodigal: 2.6 | CDS | — | — | — | — | Q00749 | msmE_2 | — | — | Multiple sugar-binding protein precursor |
| Contig1 | 2532176 | 2533162 | − | GENE_02449 | Prodigal: 2.6 | CDS | 3.5.-.- | — | — | — | O32157 | frlB | — | — | Fructosamine deglycase FrlB |
| Contig1 | 2533359 | 2534285 | + | GENE_02450 | Prodigal: 2.6 | CDS | — | — | — | — | P0A9G4 | cueR | — | — | HTH-type transcriptional regulator CueR |
| Contig1 | 2534319 | 2534909 | − | GENE_02451 | Prodigal: 2.6 | CDS | — | — | — | — | O34344 | sdpC | — | — | Killing factor SdpC precursor |
| Contig1 | 2534902 | 2535846 | − | GENE_02452 | Prodigal: 2.6 | CDS | — | — | — | — | O34616 | sdpB | — | — | Sporulation-delaying protein SdpB |
| Contig1 | 2535843 | 2536373 | − | GENE_02453 | Prodigal: 2.6 | CDS | — | — | — | — | O34889 | sdpA | — | — | Sporulation-delaying protein SdpA |

TABLE 5-continued

| # ContigID | Start | End | Strand | Prediction Tool | GeneID | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2536499 | 2536771 | + | Prodigal: 2.6 | GENE_02454 | CDS | — | — | — | — | O31460 | ybgB | — | — | putative membrane protein YbgB |
| Contig1 | 2536810 | 2537184 | — | Prodigal: 2.6 | GENE_02455 | CDS | — | — | — | MF_00203 | — | uvrC_2 | — | — | UvrABC system protein C |
| Contig1 | 2537251 | 2538366 | — | Prodigal: 2.6 | GENE_02456 | CDS | 1.4.99.5 | — | — | — | O85228 | hcnC | — | — | Hydrogen cyanide synthase subunit HcnC precursor |
| Contig1 | 2538404 | 2539105 | — | Prodigal: 2.6 | GENE_02457 | CDS | 2.1.1.- | — | — | — | O31474 | ycgJ | — | — | putative methyltransferase YcgJ |
| Contig1 | 2539183 | 2539644 | + | Prodigal: 2.6 | GENE_02458 | CDS | — | — | — | — | — | — | — | — | hypothetical protein |
| Contig1 | 2539780 | 2540616 | + | Prodigal: 2.6 | GENE_02459 | CDS | 3.2.1.132 | — | — | — | O07921 | csn | — | — | Chitosanase precursor |
| Contig1 | 2540652 | 2542049 | — | Prodigal: 2.6 | GENE_02460 | CDS | — | — | — | — | P77522 | sufB_1 | — | — | FeS cluster assembly protein SufB |
| Contig1 | 2542069 | 2542512 | — | Prodigal: 2.6 | GENE_02461 | CDS | — | — | — | — | O32163 | nifU | — | — | NifU-like protein |
| Contig1 | 2542502 | 2543722 | — | Prodigal: 2.6 | GENE_02462 | CDS | 2.8.1.7 | — | — | — | O32164 | csd_1 | — | — | putative cysteine desulfurase |
| Contig1 | 2543722 | 2545035 | — | Prodigal: 2.6 | GENE_02463 | CDS | — | — | — | — | P77522 | sufB_2 | — | — | FeS cluster assembly protein SufB |
| Contig1 | 2545053 | 2545838 | — | Prodigal: 2.6 | GENE_02464 | CDS | — | — | PF02627.1 | — | P80866 | yurY | — | — | Vegetative protein 296 |
| Contig1 | 2546360 | 2546731 | — | Prodigal: 2.6 | GENE_02465 | CDS | — | — | — | — | — | — | — | — | Carboxymuconolactone decarboxylase family protein |
| Contig1 | 2546831 | 2547646 | — | Prodigal: 2.6 | GENE_02466 | CDS | — | — | — | — | O32167 | metQ_2 | — | — | Methionine-binding lipoprotein MetQ precursor |
| Contig1 | 2547660 | 2548328 | — | Prodigal: 2.6 | GENE_02467 | CDS | — | — | — | — | O32168 | metP | — | — | Methionine import system permease protein MetP |
| Contig1 | 2548321 | 2549346 | — | Prodigal: 2.6 | GENE_02468 | CDS | 3.6.3.- | — | — | — | O32169 | metN | — | — | Methionine import ATP-binding protein MetN |
| Contig1 | 2549669 | 2550019 | — | Prodigal: 2.6 | GENE_02469 | CDS | — | — | PF02036.11 | — | — | — | — | — | SCP-2 sterol transfer family protein |
| Contig1 | 2550116 | 2550436 | — | Prodigal: 2.6 | GENE_02470 | CDS | — | — | — | — | P14949 | trxA_2 | — | — | Thioredoxin |
| Contig1 | 2550439 | 2550804 | — | Prodigal: 2.6 | GENE_02471 | CDS | 3.1.26.8 | — | — | MF_01469 | — | rnmV_1 | — | — | Ribonuclease M5 |
| Contig1 | 2550874 | 2551110 | — | Prodigal: 2.6 | GENE_02472 | CDS | — | — | — | — | — | — | — | — | hypothetical protein |
| Contig1 | 2551165 | 2551548 | — | Prodigal: 2.6 | GENE_02473 | CDS | — | — | — | — | O32174 | gcvH | — | — | Glycine cleavage system H protein |
| Contig1 | 2551608 | 2551964 | — | Prodigal: 2.6 | GENE_02474 | CDS | — | — | — | — | P54503 | mgsR_2 | — | — | Regulatory protein MgsR |
| Contig1 | 2552078 | 2553862 | — | Prodigal: 2.6 | GENE_02475 | CDS | 1.3.99.- | — | — | — | O32176 | fadE | — | — | putative acyl-CoA dehydrogenase |
| Contig1 | 2553881 | 2555056 | — | Prodigal: 2.6 | GENE_02476 | CDS | 2.3.1.16 | — | — | — | O32177 | fadA | — | — | 3-ketoacyl-CoA thiolase |
| Contig1 | 2555067 | 2557436 | — | Prodigal: 2.6 | GENE_02477 | CDS | 1.1.1.35 | — | — | — | O32178 | fadN | — | — | putative 3-hydroxyacyl-CoA dehydrogenase |
| Contig1 | 2557797 | 2558705 | — | Prodigal: 2.6 | GENE_02478 | CDS | 1.5.5.2 | — | — | — | O32179 | fadM_1 | — | — | Proline dehydrogenase 1 |
| Contig1 | 2559315 | 2560919 | + | Prodigal: 2.6 | GENE_02479 | CDS | — | — | — | — | P96712 | bmr3_2 | — | — | Multidrug resistance protein 3 |
| Contig1 | 2561115 | 2561372 | + | Prodigal: 2.6 | GENE_02480 | CDS | — | — | — | — | — | — | — | — | hypothetical protein |
| Contig1 | 2561384 | 2561716 | + | Prodigal: 2.6 | GENE_02481 | CDS | — | — | PF07875.6 | — | — | — | — | — | Coat F domain protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2561854 | 2562315 | + | GENE_02482 | Prodigal: 2.6 | CDS | — | — | — | — | O32181 | yusO_5 | — | — | putative HTH-type transcriptional regulator YusO |
| Contig1 | 2562335 | 2563930 | + | GENE_02483 | Prodigal: 2.6 | CDS | — | — | — | — | P96712 | bmr3_3 | — | — | Multidrug resistance protein 3 |
| Contig1 | 2564039 | 2564926 | − | GENE_02484 | Prodigal: 2.6 | CDS | — | — | — | — | P20668 | gltC_3 | — | — | HTH-type transcriptional regulator GltC |
| Contig1 | 2565048 | 2565794 | + | GENE_02485 | Prodigal: 2.6 | CDS | 4.1.1.4 | — | — | — | P23670 | adc | — | — | Acetoacetate decarboxylase |
| Contig1 | 2565808 | 2566848 | + | GENE_02486 | Prodigal: 2.6 | CDS | — | PRK06522 | — | — | — | — | — | — | 2-dehydropantoate 2-reductase |
| Contig1 | 2567025 | 2567270 | − | GENE_02487 | Prodigal: 2.6 | CDS | — | — | — | — | — | — | — | — | hypothetical protein |
| Contig1 | 2567295 | 2568119 | − | GENE_02488 | Prodigal: 2.6 | CDS | — | — | — | — | O32188 | yusV_1 | — | — | putative siderophore transport system ATP-binding protein YusV |
| Contig1 | 2568275 | 2568712 | − | GENE_02489 | Prodigal: 2.6 | CDS | — | — | — | — | — | — | — | — | hypothetical protein |
| Contig1 | 2568832 | 2570613 | − | GENE_02490 | Prodigal: 2.6 | CDS | 3.4.24.- | — | — | — | P54124 | pepF1_2 | — | — | Oligoendopeptidase F, plasmid |
| Contig1 | 2570746 | 2571588 | + | GENE_02491 | Prodigal: 2.6 | CDS | 1.3.1.- | — | — | — | P16544 | actIII | — | — | Putative ketoacyl reductase |
| Contig1 | 2571677 | 2572141 | − | GENE_02492 | Prodigal: 2.6 | CDS | — | — | — | — | P37960 | mrgA | — | — | Metalloregulation DNA-binding stress protein |
| Contig1 | 2572188 | 2573549 | − | GENE_02493 | Prodigal: 2.6 | CDS | 3.4.21.107 | — | — | — | Q9R9I1 | htrB | — | — | Serine protease Do-like HtrB |
| Contig1 | 2573826 | 2574503 | + | GENE_02494 | Prodigal: 2.6 | CDS | — | — | — | — | O32192 | cssR | — | — | Transcriptional regulatory protein CssR |
| Contig1 | 2574500 | 2575855 | + | GENE_02495 | Prodigal: 2.6 | CDS | 2.7.13.3 | — | — | — | O32193 | cssS | — | — | Sensor histidine kinase CssS |
| Contig1 | 2575883 | 2576047 | − | GENE_02496 | Prodigal: 2.6 | CDS | — | — | — | — | — | — | — | — | hypothetical protein |
| Contig1 | 2576181 | 2577101 | + | GENE_02497 | Prodigal: 2.6 | CDS | — | — | — | — | Q0SV2 | kstR2 | — | — | HTH-type transcriptional repressor KstR2 |
| Contig1 | 2577138 | 2578526 | − | GENE_02498 | Prodigal: 2.6 | CDS | 4.2.1.2 | — | — | — | P64173 | fumC | — | — | Fumarate hydratase class II |
| Contig1 | 2578594 | 2578779 | − | GENE_02499 | Prodigal: 2.6 | CDS | — | — | — | — | — | — | — | — | hypothetical protein |
| Contig1 | 2578896 | 2580338 | + | GENE_02500 | Prodigal: 2.6 | CDS | — | — | — | — | P07868 | gerAA | — | — | Spore germination protein A1 |
| Contig1 | 2580313 | 2581413 | + | GENE_02501 | Prodigal: 2.6 | CDS | — | — | — | — | P07869 | gerAB | — | — | Spore germination protein A2 |
| Contig1 | 2581410 | 2582522 | + | GENE_02502 | Prodigal: 2.6 | CDS | — | — | — | — | P07870 | gerAC | — | — | Spore germination protein A3 precursor |
| Contig1 | 2582565 | 2583197 | − | GENE_02503 | Prodigal: 2.6 | CDS | — | — | — | — | O32197 | liaR_2 | — | — | Transcriptional regulatory protein LiaR |
| Contig1 | 2583175 | 2584257 | − | GENE_02504 | Prodigal: 2.6 | CDS | 2.7.13.3 | — | — | — | O32198 | liaS_2 | — | — | Sensor histidine kinase LiaS |
| Contig1 | 2584254 | 2584985 | − | GENE_02505 | Prodigal: 2.6 | CDS | — | — | — | — | — | — | — | — | hypothetical protein |
| Contig1 | 2585012 | 2585881 | − | GENE_02506 | Prodigal: 2.6 | CDS | — | — | — | — | P54617 | — | — | Phage shock protein A homolog | hypothetical protein |
| Contig1 | 2585987 | 2586664 | − | GENE_02507 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2586678 | 2587058 | − | GENE_02508 | Prodigal: 2.6 | CDS | — | — | — | — | — | — | — | — | hypothetical protein |
| Contig1 | 2587225 | 2588493 | − | GENE_02509 | Prodigal: 2.6 | CDS | — | — | — | — | — | — | — | — | 2-acyl-glycerophospho-ethanolamine acyltransferase |
| Contig1 | 2588657 | 2589226 | − | GENE_02510 | Prodigal: 2.6 | CDS | 2.5.1.17 | PRK08633 | — | — | O34899 | yvqK | — | — | Cob(I)yrinic acid a,c-diamide adenosyltransferase |
| Contig1 | 2589223 | 2590449 | − | GENE_02511 | Prodigal: 2.6 | CDS | 3.6.3.34 | — | — | — | P07821 | fhuC | — | — | Iron(3+)-hydroxamate import ATP-binding protein FhuC |
| Contig1 | 2590446 | 2591513 | − | GENE_02512 | Prodigal: 2.6 | CDS | — | — | — | — | Q56992 | hmuU_1 | — | — | Hemin transport system permease protein HmuU |
| Contig1 | 2591455 | 2592399 | − | GENE_02513 | Prodigal: 2.6 | CDS | — | — | — | — | P37028 | btuF | — | — | Vitamin B12-binding protein precursor |
| Contig1 | 2592587 | 2593378 | + | GENE_02514 | Prodigal: 2.6 | CDS | 1.1.1.100 | — | — | — | O67610 | fabG_6 | — | — | 3-oxoacyl-[acyl-carrier-protein] reductase FabG |
| Contig1 | 2593430 | 2594308 | − | GENE_02515 | Prodigal: 2.6 | CDS | 3.1.1.15 | — | — | — | Q1JUP5 | araB_2 | — | — | L-arabinolactonase |
| Contig1 | 2594372 | 2596114 | − | GENE_02516 | Prodigal: 2.6 | CDS | 2.7.13.3 | — | — | — | O69729 | tcrY_1 | — | — | putative sensor histidine kinase TcrY |
| Contig1 | 2596111 | 2596830 | − | GENE_02517 | Prodigal: 2.6 | CDS | — | — | — | — | Q9RDT5 | walR | — | — | Transcriptional regulatory protein WalR |
| Contig1 | 2597004 | 2597240 | − | GENE_02518 | Prodigal: 2.6 | CDS | — | — | — | — | C0H3R4 | rsoA | — | — | Sigma-O factor regulatory protein RsoA |
| Contig1 | 2597237 | 2597815 | − | GENE_02519 | Prodigal: 2.6 | CDS | — | — | — | — | O34843 | sigO | — | — | RNA polymerase sigma factor SigO |
| Contig1 | 2598016 | 2598171 | + | GENE_02520 | Prodigal: 2.6 | CDS | — | — | PF12841.1 | — | — | — | — | — | YvrJ protein family protein |
| Contig1 | 2598289 | 2599449 | + | GENE_02521 | Prodigal: 2.6 | CDS | 4.1.1.2 | — | — | — | O34714 | oxdC_2 | — | — | Oxalate decarboxylase OxdC |
| Contig1 | 2599516 | 2599938 | + | GENE_02522 | Prodigal: 2.6 | CDS | — | — | — | — | O34686 | yvrL | — | — | Membrane-bound negative regulator YvrL |
| Contig1 | 2599973 | 2600779 | − | GENE_02523 | Prodigal: 2.6 | CDS | — | — | — | — | O32188 | yusV_2 | — | — | putative siderophore transport system ATP-binding protein YusV |
| Contig1 | 2600798 | 2601808 | − | GENE_02524 | Prodigal: 2.6 | CDS | — | — | — | — | P40411 | feuC_1 | — | — | Iron-uptake system permease protein FeuC |
| Contig1 | 2601808 | 2602875 | − | GENE_02525 | Prodigal: 2.6 | CDS | — | — | — | — | P40410 | feuB_1 | — | — | Iron-uptake system permease protein FeuB |
| Contig1 | 2603093 | 2604031 | + | GENE_02526 | Prodigal: 2.6 | CDS | — | — | — | — | P37580 | fhuD | — | — | Iron(3+)-hydroxamate-binding protein FhuD precursor |
| Contig1 | 2604177 | 2605091 | + | GENE_02527 | Prodigal: 2.6 | CDS | — | — | PF04072.8 | — | — | — | — | — | Leucine carboxyl methyltransferase |
| Contig1 | 2605144 | 2606556 | − | GENE_02528 | Prodigal: 2.6 | CDS | — | — | — | — | P0AAE5 | ydgI | — | — | Putative arginine/ornithine antiporter |
| Contig1 | 2606972 | 2607112 | − | GENE_02529 | Prodigal: 2.6 | CDS | — | — | — | — | Q7WY58 | sspJ | — | — | Small, acid-soluble spore protein J |
| Contig1 | 2607296 | 2607778 | + | GENE_02530 | Prodigal: 2.6 | CDS | — | — | — | — | P64481 | ydjM | — | — | Inner membrane protein YdjM |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2607821 | 2609677 | + | GENE_02531 | Prodigal: 2.6 | CDS | — | — | — | — | O34952 | ltaS2_2 | — | — | Lipoteichoic acid synthase 2 |
| Contig1 | 2609708 | 2610634 | − | GENE_02532 | Prodigal: 2.6 | CDS | — | — | PF12727.1 | — | — | — | — | — | PBP superfamily domain protein |
| Contig1 | 2610752 | 2611549 | + | GENE_02533 | Prodigal: 2.6 | CDS | — | — | — | — | P45323 | modA | — | — | Molybdate-binding periplasmic protein precursor |
| Contig1 | 2611530 | 2612213 | + | GENE_02534 | Prodigal: 2.6 | CDS | — | — | — | — | P0AF01 | modB | — | — | Molybdenum transport system permease protein ModB |
| Contig1 | 2612277 | 2612954 | + | GENE_02535 | Prodigal: 2.6 | CDS | — | — | — | — | P13800 | degU_1 | — | — | Transcriptional regulatory protein DegU |
| Contig1 | 2612951 | 2614063 | + | GENE_02536 | Prodigal: 2.6 | CDS | 2.7.13.3 | — | — | — | O34757 | desK_1 | — | — | Sensor histidine kinase DesK |
| Contig1 | 2614183 | 2615118 | + | GENE_02537 | Prodigal: 2.6 | CDS | — | — | — | — | P0A9U1 | ybhF | — | — | putative ABC transporter ATP-binding protein YbhF |
| Contig1 | 2615142 | 2616236 | + | GENE_02538 | Prodigal: 2.6 | CDS | — | — | — | — | P0AFP9 | ybhR_2 | — | — | Inner membrane transport permease YbhR |
| Contig1 | 2616238 | 2617383 | + | GENE_02539 | Prodigal: 2.6 | CDS | — | — | — | — | P0AFQ2 | ybhS | — | — | Inner membrane transport permease YbhS |
| Contig1 | 2617416 | 2618246 | + | GENE_02540 | Prodigal: 2.6 | CDS | 1.1.1.- | — | — | — | O32210 | yvgN_2 | — | — | Glyoxal reductase |
| Contig1 | 2618469 | 2618954 | + | GENE_02541 | Prodigal: 2.6 | CDS | — | — | — | — | O32211 | yvgO_2 | — | — | Stress response protein YvgO precursor |
| Contig1 | 2618991 | 2621006 | − | GENE_02542 | Prodigal: 2.6 | CDS | — | — | — | — | O32212 | nhaK | — | — | Sodium, potassium, lithium and rubidium/H(+) antiporter |
| Contig1 | 2621354 | 2623069 | − | GENE_02543 | Prodigal: 2.6 | CDS | 1.8.1.2 | — | — | — | O32213 | cysI | — | — | Sulfite reductase [NADPH] hemoprotein beta-component |
| Contig1 | 2623097 | 2624905 | − | GENE_02544 | Prodigal: 2.6 | CDS | 1.8.1.2 | — | — | — | O32214 | cysJ | — | — | Sulfite reductase [NADPH] flavoprotein alpha-component |
| Contig1 | 2625080 | 2627395 | − | GENE_02545 | Prodigal: 2.6 | CDS | 3.6.4.12 | PRK10578 | — | — | O32215 | helD | — | — | Helicase IV |
| Contig1 | 2627568 | 2628176 | − | GENE_02547 | Prodigal: 2.6 | CDS | — | — | — | — | — | — | — | — | hypothetical protein |
| Contig1 | 2628399 | 2629199 | + | GENE_02548 | Prodigal: 2.6 | CDS | — | — | — | — | — | — | — | — | hypothetical protein |
| Contig1 | 2629234 | 2629653 | − | GENE_02549 | Prodigal: 2.6 | CDS | — | — | — | — | O32217 | bdbC | — | — | Disulfide bond formation protein C |
| Contig1 | 2629643 | 2630314 | − | GENE_02550 | Prodigal: 2.6 | CDS | — | — | — | — | O32218 | bdbD | — | — | Disulfide bond formation protein D precursor |
| Contig1 | 2630432 | 2632543 | − | GENE_02551 | Prodigal: 2.6 | CDS | 3.63.3 | — | — | — | O32219 | cadA | — | — | Cadmium, zinc and cobalt-transporting ATPase |
| Contig1 | 2632693 | 2635122 | − | GENE_02552 | Prodigal: 2.6 | CDS | 3.6.3.54 | — | — | — | O32220 | copA | — | — | Copper-exporting P-type ATPase A |
| Contig1 | 2635206 | 2635412 | − | GENE_02553 | Prodigal: 2.6 | CDS | — | — | — | — | O32221 | copZ | — | — | Copper chaperone CopZ |
| Contig1 | 2635488 | 2635793 | − | GENE_02553 | Prodigal: 2.6 | CDS | — | — | — | — | O32222 | csoR | — | — | Copper-sensing transcriptional repressor CsoR |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2635932 | 2636972 | + | GENE_02554 | Prodigal: 2.6 | CDS | 1.-.-.- | — | — | — | O32223 | yvaA | — | — | putative oxidoreductase YvaA |
| Contig1 | 2637017 | 2637676 | − | GENE_02555 | Prodigal: 2.6 | CDS | 1.7.-.- | — | — | — | O32224 | azoR2 | — | — | FMN-dependent NADH-azoreductase 2 |
| Contig1 | 2637847 | 2639175 | − | GENE_02556 | Prodigal: 2.6 | CDS | 1.14.-.- | — | — | — | O34974 | moxC | — | — | Putative monooxygenase MoxC |
| Contig1 | 2639172 | 2639459 | − | GENE_02557 | Prodigal: 2.6 | CDS | — | — | PF00462.18 | — | — | — | — | — | Gluta redoxin |
| Contig1 | 2639462 | 2640478 | − | GENE_02558 | Prodigal: 2.6 | CDS | 1.14.13.107 | — | — | — | Q9EUT9 | limB_2 | — | — | Limonene 1,2-monooxygenase |
| Contig1 | 2640475 | 2641254 | − | GENE_02559 | Prodigal: 2.6 | CDS | 3.6.3.- | — | — | — | O34900 | tcyN | — | — | L-cystine import ATP-binding protein TcyN |
| Contig1 | 2641251 | 2641958 | − | GENE_02560 | Prodigal: 2.6 | CDS | — | — | — | — | O34931 | tcyM | — | — | L-cystine transport system permease protein TcyM |
| Contig1 | 2641974 | 2642696 | − | GENE_02561 | Prodigal: 2.6 | CDS | — | — | — | — | O34315 | tcyL | — | — | L-cystine transport system permease protein TcyL |
| Contig1 | 2642719 | 2643531 | − | GENE_02562 | Prodigal: 2.6 | CDS | — | — | — | — | O34852 | tcyK | — | — | L-cystine-binding protein TcyK precursor |
| Contig1 | 2643557 | 2644369 | − | GENE_02563 | Prodigal: 2.6 | CDS | — | — | — | — | O34406 | tcyJ | — | — | L-cystine-binding protein TcyJ precursor |
| Contig1 | 2644366 | 2644905 | − | GENE_02564 | Prodigal: 2.6 | CDS | 2.3.1.- | — | — | — | O34350 | ytmI_1 | — | — | putative N-acetyl-transferase YtmI |
| Contig1 | 2645059 | 2645949 | + | GENE_02565 | Prodigal: 2.6 | CDS | — | — | — | — | Q9F1R2 | cmpR_2 | — | — | HTH-type transcriptional activator CmpR |
| Contig1 | 2645988 | 2646782 | − | GENE_02566 | Prodigal: 2.6 | CDS | 1.1.1.100 | — | — | — | O67610 | fabG_7 | — | — | 3-oxoacyl-[acyl-carrier-protein] reductase FabG |
| Contig1 | 2646897 | 2647202 | − | GENE_02567 | Prodigal: 2.6 | CDS | — | — | — | — | P11540 | — | — | — | Barstar |
| Contig1 | 2647380 | 2648033 | + | GENE_02568 | Prodigal: 2.6 | CDS | — | — | — | — | — | — | — | — | hypothetical protein |
| Contig1 | 2648052 | 2648279 | − | GENE_02569 | Prodigal: 2.6 | CDS | — | — | — | — | — | — | — | — | hypothetical protein |
| Contig1 | 2648980 | 2649339 | − | GENE_02570 | Aragorn: 1.2 | tmRNA | — | — | — | — | — | ssrA | — | — | transfer-messenger RNA, SsrA |
| Contig1 | 2649507 | 2649977 | − | GENE_02571 | Prodigal: 2.6 | CDS | — | — | — | — | O66640 | smpB | — | — | SsrA-binding protein |
| Contig1 | 2650117 | 2652450 | − | GENE_02572 | Prodigal: 2.6 | CDS | 3.1.13.1 | — | — | — | P21499 | rnr | — | — | Ribonuclease R |
| Contig1 | 2652469 | 2653209 | − | GENE_02573 | Prodigal: 2.6 | CDS | 3.1.1.1 | — | — | — | Q06174 | est | — | — | Carboxylesterase |
| Contig1 | 2653328 | 2655558 | − | GENE_02574 | Prodigal: 2.6 | CDS | — | PRK06870 | — | — | — | — | — | — | preprotein translocase subunit SecG |
| Contig1 | 2653682 | 2653912 | − | GENE_02575 | Prodigal: 2.6 | CDS | — | — | PF01381.16 | — | — | — | — | — | Helix-turn-helix |
| Contig1 | 2654063 | 2654443 | + | GENE_02576 | Prodigal: 2.6 | CDS | — | — | — | — | O34844 | yodB_2 | — | — | HTH-type transcriptional regulator YodB |
| Contig1 | 2654528 | 2655931 | − | GENE_02577 | Prodigal: 2.6 | CDS | 2.7.13.3 | — | — | — | P08401 | creC | — | — | Sensor protein CreC |
| Contig1 | 2655922 | 2656584 | − | GENE_02578 | Prodigal: 2.6 | CDS | — | — | — | — | P0C000 | arlR | — | — | Response regulator ArlR |
| Contig1 | 2656606 | 2657376 | − | GENE_02579 | Prodigal: 2.6 | CDS | — | — | PF12730.1 | — | — | — | — | — | ABC-2 family transporter protein |
| Contig1 | 2657373 | 2658107 | − | GENE_02580 | Prodigal: 2.6 | CDS | — | — | PF12730.1 | — | — | — | — | — | ABC-2 family transporter protein |
| Contig1 | 2658104 | 2658817 | − | GENE_02581 | Prodigal: 2.6 | CDS | 3.6.3.- | — | — | — | P94374 | yxlF_4 | — | — | putative ABC transporter ATP-binding protein YxlF |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2658928 | 2659605 | − | GENE_02582 | Prodigal: 2.6 | CDS | — | — | — | — | O34742 | opuCD_1 | — | — | Glycine betaine/carnitine/choline transport system permease protein OpuCD |
| Contig1 | 2659624 | 2660541 | − | GENE_02583 | Prodigal: 2.6 | CDS | — | — | — | — | Q45462 | opuBC | — | — | Choline-binding protein precursor |
| Contig1 | 2660556 | 2661209 | − | GENE_02584 | Prodigal: 2.6 | CDS | — | — | — | — | O34878 | opuCB_1 | — | — | Glycine betaine/carnitine/choline transport system permease protein OpuCB |
| Contig1 | 2661226 | 2662371 | − | GENE_02585 | Prodigal: 2.6 | CDS | — | — | — | — | Q45460 | opuBA | — | — | Choline transport ATP-binding protein OpuBA |
| Contig1 | 2662657 | 2663190 | + | GENE_02586 | Prodigal: 2.6 | CDS | — | — | — | — | O34709 | opcR_2 | — | — | HTH-type transcriptional repressor OpcR |
| Contig1 | 2663224 | 2663898 | − | GENE_02587 | Prodigal: 2.6 | CDS | — | — | — | — | O34742 | opuCD_2 | — | — | Glycine betaine/carnitine/choline transport system permease protein OpuCD |
| Contig1 | 2663916 | 2664833 | − | GENE_02588 | Prodigal: 2.6 | CDS | — | — | — | — | O32243 | opuCC | — | — | Glycine betaine/carnitine/choline-binding protein OpuCC precursor |
| Contig1 | 2664847 | 2665500 | − | GENE_02589 | Prodigal: 2.6 | CDS | — | — | — | — | O34878 | opuCB_2 | — | — | Glycine betaine/carnitine/choline transport system permease protein OpuCB |
| Contig1 | 2665521 | 2666660 | − | GENE_02590 | Prodigal: 2.6 | CDS | — | — | — | — | O34992 | opuCA | — | — | Glycine betaine/carnitine/choline transport ATP-binding protein OpuCA |
| Contig1 | 2666921 | 2667478 | + | GENE_02591 | Prodigal: 2.6 | CDS | — | — | — | — | O34709 | opcR_3 | — | — | HTH-type transcriptional repressor OpcR |
| Contig1 | 2667499 | 2668131 | + | GENE_02592 | Prodigal: 2.6 | CDS | — | PRK11111 | — | — | — | — | — | — | hypothetical protein |
| Contig1 | 2668570 | 2669280 | + | GENE_02593 | Prodigal: 2.6 | CDS | — | — | — | — | — | — | — | — | hypothetical protein |
| Contig1 | 2669319 | 2671097 | + | GENE_02594 | Prodigal: 2.6 | CDS | — | — | — | — | — | — | — | — | hypothetical protein |
| Contig1 | 2671230 | 2671691 | + | GENE_02595 | Prodigal: 2.6 | CDS | 2.3.1.- | — | — | — | O32248 | yvbK | — | — | putative N-acetyl-transferase YvbK |
| Contig1 | 2671734 | 2672969 | − | GENE_02596 | Prodigal: 2.6 | CDS | — | — | — | — | P39642 | bacE_1 | — | — | Putative bacilysin exporter BacE |
| Contig1 | 2672944 | 2673864 | − | GENE_02597 | Prodigal: 2.6 | CDS | — | — | PF01261.18 | — | — | — | — | — | Xylose isomerase-like TIM barrel |
| Contig1 | 2673872 | 2674549 | − | GENE_02598 | Prodigal: 2.6 | CDS | 3.5.1.103 | — | — | MF_01696 | — | mshB_3 | — | — | 1D-myo-inositol 2-acetamido-2-deoxy-alpha-D-glucopyranoside deacetylase |
| Contig1 | 2674512 | 2675246 | − | GENE_02599 | Prodigal: 2.6 | CDS | — | — | PF08889.5 | — | — | — | — | — | WbqC-like protein family protein |
| Contig1 | 2675243 | 2676136 | − | GENE_02600 | Prodigal: 2.6 | CDS | — | — | — | — | — | — | — | — | FemAB family protein |
| Contig1 | 2676136 | 2677392 | − | GENE_02601 | Prodigal: 2.6 | CDS | 2.6.1.100 | — | PF02388.10 | — | Q8G8Y2 | btrR | — | — | L-glutamine:2-deoxy-scyllo-inosose aminotransferase |
| Contig1 | 2677358 | 2678287 | − | GENE_02602 | Prodigal: 2.6 | CDS | 4.2.1.46 | — | — | — | P29782 | strE | — | — | dTDP-glucose 4,6-dehydratase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2678284 | 2679414 | − | GENE_02603 | Prodigal: 2.6 | CDS | 2.6.1.87 | — | — | — | Q8ZNF3 | arnB_1 | — | — | UDP-4-amino-4-deoxy-L-arabinose--oxoglutarate aminotransferase |
| Contig1 | 2679463 | 2680797 | − | GENE_02604 | Prodigal: 2.6 | CDS | 1.1.1.136 | — | — | — | G3XD94 | wbpA | — | — | UDP-N-acetyl-D-glucosamine 6-dehydrogenase |
| Contig1 | 2681064 | 2682344 | − | GENE_02605 | Prodigal: 2.6 | CDS | 3.4.11.6 | — | — | — | P25152 | ywaD | — | — | Aminopeptidase YwaD precursor |
| Contig1 | 2682513 | 2683805 | − | GENE_02606 | Prodigal: 2.6 | CDS | 4.2.1.11 | — | — | — | P37869 | eno | — | — | Enolase |
| Contig1 | 2683833 | 2685368 | − | GENE_02607 | Prodigal: 2.6 | CDS | 5.4.2.12 | — | — | — | P39773 | gpmI | — | — | 2,3-bisphosphoglycerate-independent phosphoglycerate mutase |
| Contig1 | 2685361 | 2686122 | − | GENE_02608 | Prodigal: 2.6 | CDS | 5.3.1.1 | — | — | — | P27876 | tpiA | — | — | Triosephosphate isomerase |
| Contig1 | 2686148 | 2687332 | − | GENE_02609 | Prodigal: 2.6 | CDS | 27.2.3 | — | — | — | P40924 | pgk | — | — | Phosphoglycerate kinase |
| Contig1 | 2687654 | 2688661 | − | GENE_02610 | Prodigal: 2.6 | CDS | 1.2.1.12 | — | — | — | P09124 | gapA | — | — | Glyceraldehyde-3-phosphate dehydrogenase 1 |
| Contig1 | 2688695 | 2689729 | − | GENE_02611 | Prodigal: 2.6 | CDS | — | — | — | — | O32253 | cggR | — | — | Central glycolytic genes regulator |
| Contig1 | 2689857 | 2689997 | − | GENE_02612 | Prodigal: 2.6 | CDS | — | — | — | — | — | — | — | — | hypothetical protein |
| Contig1 | 2689994 | 2691388 | − | GENE_02613 | Prodigal: 2.6 | CDS | — | — | — | — | P96710 | araE | — | — | Arabinose-proton symporter |
| Contig1 | 2691645 | 2692733 | + | GENE_02614 | Prodigal: 2.6 | CDS | — | — | — | — | P96711 | araR | — | — | Arabinose metabolism transcriptional repressor |
| Contig1 | 2692763 | 2694046 | − | GENE_02615 | Prodigal: 2.6 | CDS | — | — | — | — | — | — | — | — | hypothetical protein |
| Contig1 | 2694169 | 2695173 | − | GENE_02616 | Prodigal: 2.6 | CDS | 1.14.14.3 | — | — | — | P07740 | luxA_1 | — | — | Alkanal monooxygenase alpha chain |
| Contig1 | 2695449 | 2695856 | + | GENE_02617 | Prodigal: 2.6 | CDS | — | — | — | — | — | — | — | — | hypothetical protein |
| Contig1 | 2695888 | 2696766 | − | GENE_02618 | Prodigal: 2.6 | CDS | — | — | — | — | P06614 | cysB_2 | — | — | HTH-type transcriptional regulator CysB |
| Contig1 | 2696864 | 2697781 | + | GENE_02619 | Prodigal: 2.6 | CDS | — | — | — | — | P31125 | eamA | — | — | putative amino-acid metabolite efflux pump |
| Contig1 | 2697816 | 2699156 | + | GENE_02620 | Prodigal: 2.6 | CDS | — | — | — | — | P46349 | gabP_2 | — | — | GABA permease |
| Contig1 | 2700090 | 2701397 | + | GENE_02621 | Prodigal: 2.6 | CDS | — | — | — | — | — | — | — | — | hypothetical protein |
| Contig1 | 2701427 | 2702401 | − | GENE_02622 | Prodigal: 2.6 | CDS | — | — | — | — | P25144 | ccpA_3 | — | — | Catabolite control protein A |
| Contig1 | 2702469 | 2703137 | − | GENE_02623 | Prodigal: 2.6 | CDS | — | — | — | — | — | — | — | — | hypothetical protein |
| Contig1 | 2703134 | 2704021 | − | GENE_02624 | Prodigal: 2.6 | CDS | 3.1.3.- | — | — | — | P94592 | ywpJ_1 | — | — | Putative phosphatase YwpJ |
| Contig1 | 2704458 | 2705315 | + | GENE_02625 | Prodigal: 2.6 | CDS | — | — | — | — | Q45581 | ybbH2 | — | — | putative HTH-type transcriptional regulator YbbH |
| Contig1 | 2705488 | 2707032 | + | GENE_02626 | Prodigal: 2.6 | CDS | 2.7.1.17 | — | — | — | P35850 | xylB_2 | — | — | Xylulose kinase |
| Contig1 | 2707059 | 2708387 | + | GENE_02627 | Prodigal: 2.6 | CDS | — | — | — | — | P39344 | idnT | — | — | Gnt-II system L-idonate transporter |
| Contig1 | 2708423 | 2709142 | − | GENE_02628 | Prodigal: 2.6 | CDS | — | — | — | — | O32259 | lutC | — | — | Lactate utilization protein C |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2709145 | 2710575 | − | GENE_02629 | Prodigal: 2.6 | CDS | — | — | — | — | O07021 | lutB | — | — | Lactate utilization protein B |
| Contig1 | 2710603 | 2711319 | − | GENE_02630 | Prodigal: 2.6 | CDS | — | — | — | — | O07020 | lutA_2 | — | — | Lactate utilization protein A |
| Contig1 | 2711500 | 2712690 | − | GENE_02631 | Prodigal: 2.6 | CDS | 2.6.1.39 | — | — | — | Q72LL6 | lysN | — | — | 2-aminoadipate transaminase |
| Contig1 | 2712721 | 2713449 | − | GENE_02632 | Prodigal: 2.6 | CDS | — | — | — | — | O07007 | lutR | — | — | HTH-type transcriptional regulator LutR |
| Contig1 | 2713646 | 2715322 | + | GENE_02633 | Prodigal: 2.6 | CDS | — | — | — | — | P71067 | lutP | — | — | L-lactate permease |
| Contig1 | 2715360 | 2716670 | − | GENE_02634 | Prodigal: 2.6 | CDS | — | — | — | — | P0A171 | rpoN | — | — | RNA polymerase sigma-54 factor |
| Contig1 | 2716748 | 2716966 | + | GENE_02635 | Prodigal: 2.6 | CDS | — | — | PF09628.4 | — | — | — | — | — | YvrG protein |
| Contig1 | 2716980 | 2717945 | − | GENE_02636 | Prodigal: 2.6 | CDS | 2.-.-.- | — | — | — | P71065 | epsO | — | — | Putative pyruvyl transferase EpsO |
| Contig1 | 2717924 | 2719096 | − | GENE_02637 | Prodigal: 2.6 | CDS | 2.6.1.- | — | — | — | Q79SJ3 | epsN | — | — | Putative pyridoxal phosphate-dependent aminotransferase EpsN |
| Contig1 | 2719101 | 2719748 | − | GENE_02638 | Prodigal: 2.6 | CDS | 2.3.1.- | — | — | — | P71063 | epsM | — | — | Putative acetyltransferase EpsM |
| Contig1 | 2719745 | 2720353 | − | GENE_02639 | Prodigal: 2.6 | CDS | 2.-.-.- | — | — | — | P71062 | epsL | — | — | putative sugar transferase EpsL |
| Contig1 | 2720350 | 2721867 | − | GENE_02640 | Prodigal: 2.6 | CDS | — | — | — | — | P71060 | epsK | — | — | putative membrane protein EpsK |
| Contig1 | 2721864 | 2722898 | − | GENE_02641 | Prodigal: 2.6 | CDS | 2.4.-.- | — | — | — | P71059 | epsJ | — | — | putative glycosyltransferase EpsJ |
| Contig1 | 2722895 | 2723971 | − | GENE_02642 | Prodigal: 2.6 | CDS | 2.-.-.- | — | — | — | P71058 | epsI | — | — | Putative pyruvyl transferase EpsI |
| Contig1 | 2723976 | 2725013 | − | GENE_02643 | Prodigal: 2.6 | CDS | 2.4.-.- | — | — | — | P71057 | epsH | — | — | Putative glycosyltransferase EpsH |
| Contig1 | 2725032 | 2726135 | − | GENE_02644 | Prodigal: 2.6 | CDS | — | — | — | — | P71056 | epsG | — | — | Transmembrane protein EpsG |
| Contig1 | 2726139 | 2727275 | − | GENE_02645 | Prodigal: 2.6 | CDS | 2.4.-.- | — | — | — | P71055 | epsF_2 | — | — | Putative glycosyltransferase EpsF |
| Contig1 | 2727268 | 2728110 | − | GENE_02646 | Prodigal: 2.6 | CDS | 2.4.-.- | — | — | — | P71054 | epsE | — | — | Putative glycosyltransferase EpsE |
| Contig1 | 2728107 | 2729246 | − | GENE_02647 | Prodigal: 2.6 | CDS | 2.4.-.- | — | — | — | P71053 | epsD | — | — | Putative glycosyltransferase EpsD |
| Contig1 | 2729262 | 2731079 | − | GENE_02648 | Prodigal: 2.6 | CDS | 4.2.1.135 | — | — | — | Q0P9D4 | pglF | — | — | UDP-N-acetyl-alpha-D-glucosamine C6 dehydratase |
| Contig1 | 2731300 | 2731980 | − | GENE_02649 | Prodigal: 2.6 | CDS | 2.7.10.2 | — | — | — | P96716 | ywqD_1 | — | — | Tyrosine-protein kinase YwqD |
| Contig1 | 2731986 | 2732693 | − | GENE_02650 | Prodigal: 2.6 | CDS | — | — | — | — | P72367 | cap8A_1 | — | — | Capsular polysaccharide type 8 biosynthesis protein cap8A |
| Contig1 | 2732936 | 2733391 | + | GENE_02651 | Prodigal: 2.6 | CDS | — | — | — | — | P06533 | sinR_2 | — | — | HTH-type transcriptional regulator SinR |
| Contig1 | 2733472 | 2734920 | + | GENE_02652 | Prodigal: 2.6 | CDS | 3.1.1.- | — | — | — | P37967 | pnbA | — | — | Para-nitrobenzyl esterase |
| Contig1 | 2735072 | 2735272 | + | GENE_02653 | Prodigal: 2.6 | CDS | — | — | — | — | — | — | — | — | hypothetical protein |
| Contig1 | 2735304 | 2735834 | − | GENE_02654 | Prodigal: 2.6 | CDS | 1.5.1.3 | — | — | — | Q60034 | folA | — | — | Dihydrofolate reductase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2735913 | 2736542 | − | GENE_02655 | Prodigal: 2.6 | CDS | — | — | — | — | — | — | — | — | hypothetical protein |
| Contig1 | 2736677 | 2737195 | + | GENE_02656 | Prodigal: 2.6 | CDS | 2.3.1.- | — | — | — | P21340 | paiA_2 | — | — | Protease synthase and sporulation negative regulatory protein PAI 1 |
| Contig1 | 2737235 | 2737723 | − | GENE_02657 | Prodigal: 2.6 | CDS | 4.1.1.- | — | — | — | O07006 | padC | — | — | Phenolic acid decarboxylase PadC |
| Contig1 | 2738143 | 2738427 | − | GENE_02658 | Prodigal: 2.6 | CDS | — | — | — | — | — | — | — | — | hypothetical protein |
| Contig1 | 2738559 | 2738816 | − | GENE_02659 | Prodigal: 2.6 | CDS | — | — | — | — | — | — | — | — | hypothetical protein |
| Contig1 | 2738966 | 2739277 | + | GENE_02660 | Prodigal: 2.6 | CDS | — | — | — | — | — | — | — | — | hypothetical protein |
| Contig1 | 2739671 | 2739928 | − | GENE_02661 | Prodigal: 2.6 | CDS | — | — | — | — | — | — | — | — | hypothetical protein |
| Contig1 | 2740643 | 2740930 | − | GENE_02662 | Prodigal: 2.6 | CDS | — | — | — | — | — | — | — | — | hypothetical protein |
| Contig1 | 2741133 | 2741330 | + | GENE_02663 | Prodigal: 2.6 | CDS | — | — | — | — | — | — | — | — | hypothetical protein |
| Contig1 | 2741355 | 2741699 | − | GENE_02664 | Prodigal: 2.6 | CDS | — | — | — | — | — | — | — | — | hypothetical protein |
| Contig1 | 2741753 | 2743174 | + | GENE_02665 | Prodigal: 2.6 | CDS | — | — | — | — | — | — | — | — | hypothetical protein |
| Contig1 | 2743191 | 2743502 | + | GENE_02666 | Prodigal: 2.6 | CDS | — | — | — | — | — | — | — | — | hypothetical protein |
| Contig1 | 2743559 | 2743637 | − | GENE_02667 | Aragorn: 1.2 | tRNA | — | — | — | — | — | — | — | — | tRNA-Arg(ccg) |
| Contig1 | 2743851 | 2745320 | − | GENE_02668 | Prodigal: 2.6 | CDS | 3.2.1.26 | — | — | — | P0DJA7 | sacA | — | — | Sucrose-6-phosphate hydrolase |
| Contig1 | 2745335 | 2746567 | − | GENE_02669 | Prodigal: 2.6 | CDS | — | — | — | — | P02920 | lacY | — | — | Lactose permease |
| Contig1 | 2746958 | 2747932 | + | GENE_02670 | Prodigal: 2.6 | CDS | — | — | — | — | P37947 | degA_2 | — | — | HTH-type transcriptional regulator DegA |
| Contig1 | 2748180 | 2748776 | + | GENE_02671 | Prodigal: 2.6 | CDS | 3.4.21.92 | — | — | — | P80244 | dpP | — | — | ATP-dependent Clp protease proteolytic subunit |
| Contig1 | 2748820 | 2749680 | − | GENE_02672 | Prodigal: 2.6 | CDS | — | — | — | — | O34685 | yofA_2 | — | — | HTH-type transcriptional regulator YofA |
| Contig1 | 2749854 | 2750984 | + | GENE_02673 | Prodigal: 2.6 | CDS | 5.3.3.6 | — | — | — | Q0QLE6 | mii | — | — | 3-methylitaconate isomerase |
| Contig1 | 2751027 | 2752403 | + | GENE_02674 | Prodigal: 2.6 | CDS | — | — | — | — | P38055 | ydjE_1 | — | — | Inner membrane metabolite transport protein YdjE |
| Contig1 | 2752615 | 2753190 | − | GENE_02675 | Prodigal: 2.6 | CDS | — | — | — | — | O06986 | yvdD | — | — | LOG family protein YvdD |
| Contig1 | 2753306 | 2753626 | + | GENE_02676 | Prodigal: 2.6 | CDS | — | — | PF03819.11 | — | — | — | — | — | MazG nucleotide pyrophosphohydrolase domain protein |
| Contig1 | 2753671 | 2755260 | − | GENE_02677 | Prodigal: 2.6 | CDS | — | — | — | — | P0AFR2 | dauA_1 | — | — | C4-dicarboxylic acid transporter DauA |
| Contig1 | 2755263 | 2755844 | − | GENE_02678 | Prodigal: 2.6 | CDS | 4.2.1.1 | — | — | — | P64797 | mtcA1_2 | — | — | Beta-carbonic anhydrase 1 |
| Contig1 | 2756245 | 2757210 | + | GENE_02679 | Prodigal: 2.6 | CDS | 1.1.1.79 | — | — | — | P37666 | ghrB | — | — | Glyoxylate/hydroxy-pyruvate reductase B |
| Contig1 | 2757331 | 2757804 | + | GENE_02680 | Prodigal: 2.6 | CDS | 3.1.27.- | — | — | — | P00648 | — | — | — | Ribonuclease precursor |
| Contig1 | 2757864 | 2758055 | − | GENE_02681 | Prodigal: 2.6 | CDS | — | — | — | — | — | — | — | — | hypothetical protein |
| Contig1 | 2758325 | 2759101 | − | GENE_02682 | Prodigal: 2.6 | CDS | — | — | — | — | — | — | — | — | hypothetical protein |
| Contig1 | 2759367 | 2760113 | − | GENE_02683 | Prodigal: 2.6 | CDS | 2.3.1.118 | — | — | — | Q00267 | nhoA | — | — | N-hydroxyarylamine O-acetyltransferase |
| Contig1 | 2760138 | 2760395 | − | GENE_02684 | Prodigal: 2.6 | CDS | — | — | — | — | O06976 | crh | — | — | HPr-like protein Crh |
| Contig1 | 2760419 | 2761369 | − | GENE_02685 | Prodigal: 2.6 | CDS | — | — | — | — | Q9Z515 | whiA | — | — | Sporulation transcription regulator WhiA |
| Contig1 | 2761396 | 2762349 | − | GENE_02686 | Prodigal: 2.6 | CDS | — | — | — | — | Q9K706 | — | — | — | Gluconeogenesis factor |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2762346 | 2763233 | − | GENE_02687 | Prodigal: 2.6 | CDS | — | PRK05416 | — | — | — | — | — | — | glmZ(sRNA)-inactivating NTPase |
| Contig1 | 2763259 | 2763753 | − | GENE_02688 | Prodigal: 2.6 | CDS | 3.6.1.55 | — | — | — | P41354 | mutX | — | — | 8-oxo-dGTP diphosphatase |
| Contig1 | 2764000 | 2764953 | − | GENE_02689 | Prodigal: 2.6 | CDS | 1.8.1.9 | — | — | — | P80880 | trxB | — | — | Thioredoxin reductase |
| Contig1 | 2765157 | 2766569 | − | GENE_02690 | Prodigal: 2.6 | CDS | 3.4.-.- | — | — | — | P40767 | cwlO | — | — | Peptidoglycan DL-endopeptidase CwlO precursor |
| Contig1 | 2766967 | 2768421 | − | GENE_02691 | Prodigal: 2.6 | CDS | — | — | PF07719.11 | — | — | — | — | — | Tetratricopeptide repeat protein |
| Contig1 | 2768537 | 2769598 | − | GENE_02692 | Prodigal: 2.6 | CDS | 2.7.13.3 | — | — | — | P23545 | phoR_2 | — | — | Alkaline phosphatase synthesis sensor protein PhoR |
| Contig1 | 2769595 | 2770272 | − | GENE_02693 | Prodigal: 2.6 | CDS | — | — | — | — | A6QJK3 | hssR | — | — | Heme response regulator HssR |
| Contig1 | 2770309 | 2770926 | − | GENE_02694 | Prodigal: 2.6 | CDS | — | — | — | — | — | — | — | — | hypothetical protein |
| Contig1 | 2771015 | 2772784 | − | GENE_02695 | Prodigal: 2.6 | CDS | 3.6.3.- | — | — | — | O06967 | bmrA | — | — | Multidrug resistance ABC transporter ATP-binding/permease protein BmrA |
| Contig1 | 2772995 | 2773615 | − | GENE_02696 | Prodigal: 2.6 | CDS | 3.6.1.31 | — | — | — | Q81G00 | hisE | — | — | Phosphoribosyl-ATP pyrophosphatase |
| Contig1 | 2773612 | 2774370 | − | GENE_02697 | Prodigal: 2.6 | CDS | 4.1.3.- | — | — | — | Q7SIB9 | hisF | — | — | Imidazole glycerol phosphate synthase subunit HisF |
| Contig1 | 2774367 | 2775104 | − | GENE_02698 | Prodigal: 2.6 | CDS | 5.3.1.16 | — | — | — | Q4KJS5 | hisA | — | — | 1-(5-phosphoribosyl)-5-[(5-phosphoribosylamino) methylideneamino] imidazole-4-carboxamide isomerase |
| Contig1 | 2775101 | 2775739 | − | GENE_02699 | Prodigal: 2.6 | CDS | 2.4.2.- | — | — | — | Q0P8U2 | hisH1 | — | — | Imidazole glycerol phosphate synthase subunit HisH 1 |
| Contig1 | 2775740 | 2776324 | − | GENE_02700 | Prodigal: 2.6 | CDS | 4.2.1.19 | — | — | — | Q98CT7 | hisB | — | — | Imidazoleglycerol-phosphate dehydratase |
| Contig1 | 2776290 | 2777603 | − | GENE_02701 | Prodigal: 2.6 | CDS | 1.1.1.23 | — | — | — | Q4KI73 | hisD | — | — | Histidinol dehydrogenase |
| Contig1 | 2777600 | 2778241 | − | GENE_02702 | Prodigal: 2.6 | CDS | 2.4.2.17 | — | — | — | O34520 | hisG | — | — | ATP phosphoribosyltransferase |
| Contig1 | 2778234 | 2779406 | − | GENE_02703 | Prodigal: 2.6 | CDS | — | — | — | — | Q9K6Z0 | hisZ | — | — | ATP phosphoribosyltransferase regulatory subunit |
| Contig1 | 2779648 | 2780373 | + | GENE_02704 | Prodigal: 2.6 | CDS | — | — | — | — | — | — | — | — | hypothetical protein |
| Contig1 | 2780391 | 2780909 | − | GENE_02705 | Prodigal: 2.6 | CDS | 2.3.1.89 | — | — | — | Q7A2S0 | dapH_3 | — | — | 2,3,4,5-tetrahydro-pyridine-2,6-dicarboxylate N-acetyltransferase |
| Contig1 | 2780913 | 2781563 | − | GENE_02706 | Prodigal: 2.6 | CDS | 3.6.1.1 | — | — | — | Q9JMQ2 | ppaX | — | — | Pyrophosphatase PpaX |
| Contig1 | 2781589 | 2782404 | − | GENE_02707 | Prodigal: 2.6 | CDS | 2.4.99.- | — | — | — | O34752 | lgt | — | — | Prolipoprotein diacylglyceryl transferase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2782419 | 2783351 | − | GENE_02708 | Prodigal: 2.6 | CDS | 2.7.11.- | | | | O34483 | hprK | | | HPr kinase/phosphorylase |
| Contig1 | 2783521 | 2784711 | + | GENE_02709 | Prodigal: 2.6 | CDS | 3.5.1.25 | | | | O34450 | nagA | | | N-acetylglucosamine-6-phosphate deacetylase |
| Contig1 | 2784708 | 2785433 | + | GENE_02710 | Prodigal: 2.6 | CDS | 3.5.99.6 | | | | O35000 | nagB | | | Glucosamine-6-phosphate deaminase 1 |
| Contig1 | 2785447 | 2786178 | + | GENE_02711 | Prodigal: 2.6 | CDS | | | | | O34817 | yvoA_2 | | | HTH-type transcriptional repressor YvoA |
| Contig1 | 2786323 | 2786898 | − | GENE_02712 | Prodigal: 2.6 | CDS | | | | | P42105 | yxaF_1 | | | putative HTH-type transcriptional regulator YxaF |
| Contig1 | 2787056 | 2790925 | − | GENE_02713 | Prodigal: 2.6 | CDS | | | PF00149.22 | | | | | | Calcineurin-like phosphoesterase |
| Contig1 | 2791019 | 2791378 | − | GENE_02714 | Prodigal: 2.6 | CDS | | PRK10697 | PF04020.7 | | | | | | Membrane protein of unknown function |
| Contig1 | 2791379 | 2791573 | − | GENE_02715 | Prodigal: 2.6 | CDS | | | | | | | | | DNA-binding transcriptional activator PspC |
| Contig1 | 2791578 | 2792675 | − | GENE_02716 | Prodigal: 2.6 | CDS | | | | | | | | | hypothetical protein |
| Contig1 | 2792700 | 2793026 | − | GENE_02717 | Prodigal: 2.6 | CDS | | | | | | | | | hypothetical protein |
| Contig1 | 2793225 | 2793464 | + | GENE_02718 | Prodigal: 2.6 | CDS | | | | | | | | | hypothetical protein |
| Contig1 | 2793513 | 2796386 | − | GENE_02719 | Prodigal: 2.6 | CDS | | | | | P63383 | uvrA | | | UvrABC system protein A |
| Contig1 | 2796394 | 2798379 | − | GENE_02720 | Prodigal: 2.6 | CDS | | | | | P37954 | uvrB_1 | | | UvrABC system protein B |
| Contig1 | 2798555 | 2798791 | − | GENE_02721 | Prodigal: 2.6 | CDS | | | | | | | | | hypothetical protein |
| Contig1 | 2799091 | 2801592 | + | GENE_02722 | Prodigal: 2.6 | CDS | | | | | Q0VZ70 | cmdD_2 | | | Chondramide synthase cmdD |
| Contig1 | 2801661 | 2802287 | + | GENE_02723 | Prodigal: 2.6 | CDS | | | | | P28815 | tetC1 | | | Transposon Tn10 TetC protein |
| Contig1 | 2802260 | 2803597 | + | GENE_02724 | Prodigal: 2.6 | CDS | | | | | P0A0J9 | qacA_2 | | | Antiseptic resistance protein |
| Contig1 | 2804265 | 2804888 | − | GENE_02725 | Prodigal: 2.6 | CDS | 1.1.-.- | | | | Q70LM8 | lgrE_1 | | | Linear gramicidin dehydrogenase LgrE |
| Contig1 | 2805053 | 2806120 | − | GENE_02726 | Prodigal: 2.6 | CDS | | | | | | | | | hypothetical protein |
| Contig1 | 2806399 | 2807589 | − | GENE_02727 | Prodigal: 2.6 | CDS | | | | | O34375 | minJ | | | Cell division topological determinant MinJ |
| Contig1 | 2807664 | 2807999 | − | GENE_02728 | Prodigal: 2.6 | CDS | | | | | | | | | hypothetical protein |
| Contig1 | 2808390 | 2809790 | − | GENE_02729 | Prodigal: 2.6 | CDS | 3.4.21.102 | | | | O35002 | ctpB | | | Carboxy-terminal processing protease CtpB precursor |
| Contig1 | 2809958 | 2811364 | + | GENE_02730 | Prodigal: 2.6 | CDS | | | | | | | | | hypothetical protein |
| Contig1 | 2811411 | 2812301 | − | GENE_02731 | Prodigal: 2.6 | CDS | | | | | O34876 | ftsX | | | Cell division protein FtsX |
| Contig1 | 2812294 | 2812980 | − | GENE_02732 | Prodigal: 2.6 | CDS | | | | | O34814 | ftsE | | | Cell division ATP-binding protein FtsE |
| Contig1 | 2813199 | 2813540 | − | GENE_02733 | Prodigal: 2.6 | CDS | | | | | O34594 | cccB | | | Cytochrome c-551 precursor |
| Contig1 | 2813576 | 2814424 | − | GENE_02734 | Prodigal: 2.6 | CDS | | | | | | | | | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2814593 | 2815576 | − | GENE_02735 | Prodigal: 2.6 | CDS | — | — | — | — | Q7A6R4 | prfB | — | — | Peptide chain release factor 2 |
| Contig1 | 2815768 | 2818293 | − | GENE_02736 | Prodigal: 2.6 | CDS | — | — | — | MF_01382 | — | secA | — | — | Protein translocase subunit SecA |
| Contig1 | 2818460 | 2819026 | − | GENE_02737 | Prodigal: 2.6 | CDS | — | — | — | — | P28368 | yvyD | — | — | Putative sigma-54 modulation protein |
| Contig1 | 2819221 | 2819598 | − | GENE_02738 | Prodigal: 2.6 | CDS | — | — | — | — | — | — | — | — | hypothetical protein |
| Contig1 | 2819608 | 2819952 | − | GENE_02739 | Prodigal: 2.6 | CDS | — | — | PF05400.7 | — | — | — | — | — | Flagellar protein FliT |
| Contig1 | 2819952 | 2820353 | − | GENE_02740 | Prodigal: 2.6 | CDS | — | — | — | — | P39739 | fliS | — | — | Flagellar protein FliS |
| Contig1 | 2820373 | 2821893 | − | GENE_02741 | Prodigal: 2.6 | CDS | — | — | — | — | P24216 | fliD | — | — | Flagellar hook-associated protein 2 |
| Contig1 | 2822143 | 2822973 | − | GENE_02742 | Prodigal: 2.6 | CDS | — | — | — | — | P02968 | hag | — | — | Flagellin |
| Contig1 | 2823118 | 2823342 | − | GENE_02743 | Prodigal: 2.6 | CDS | — | — | — | — | P33911 | — | — | Carbon storage regulator homolog | hypothetical protein |
| Contig1 | 2823336 | 2823767 | − | GENE_02744 | Prodigal: 2.6 | CDS | — | — | — | — | — | — | — | — | Flagellar assembly factor FliW |
| Contig1 | 2823797 | 2824366 | − | GENE_02745 | Prodigal: 2.6 | CDS | — | — | — | — | — | — | — | — | hypothetical protein |
| Contig1 | 2824457 | 2825374 | − | GENE_02746 | Prodigal: 2.6 | CDS | — | — | — | — | P96503 | fliW | — | — | Flagellar hook-associated protein 3 |
| Contig1 | 2825386 | 2826903 | − | GENE_02747 | Prodigal: 2.6 | CDS | — | — | — | — | P29744 | flgL | — | — | Flagellar hook-associated protein 1 |
| Contig1 | 2826919 | 2827401 | − | GENE_02748 | Prodigal: 2.6 | CDS | — | — | PF05130.6 | — | P0A1J5 | flgK | — | — | FlgN protein |
| Contig1 | 2827416 | 2827682 | − | GENE_02749 | Prodigal: 2.6 | CDS | — | — | PF04316.7 | — | — | — | — | — | Anti-sigma-28 factor, FlgM |
| Contig1 | 2827752 | 2828171 | − | GENE_02750 | Prodigal: 2.6 | CDS | — | — | — | — | — | — | — | — | hypothetical protein |
| Contig1 | 2828245 | 2828721 | − | GENE_02751 | Prodigal: 2.6 | CDS | — | — | — | MF_00583_A | — | prs_1 | — | — | Ribose-phosphate pyrophosphokinase |
| Contig1 | 2828940 | 2829224 | − | GENE_02752 | Prodigal: 2.6 | CDS | — | — | PF10719.3 | — | — | — | — | — | Late competence development protein ComFB |
| Contig1 | 2829282 | 2830667 | − | GENE_02753 | Prodigal: 2.6 | CDS | — | — | — | MF_00204 | — | uvrB_2 | — | — | UvrABC system protein B |
| Contig1 | 2830775 | 2831623 | − | GENE_02754 | Prodigal: 2.6 | CDS | — | — | — | — | P0A0N0 | — | — | — | DegV domain-containing protein |
| Contig1 | 2831721 | 2832410 | − | GENE_02755 | Prodigal: 2.6 | CDS | — | — | — | — | P13800 | degU_2 | — | — | Transcriptional regulatory protein DegU |
| Contig1 | 2832487 | 2833650 | − | GENE_02756 | Prodigal: 2.6 | CDS | 2.7.13.3 | — | — | — | P13799 | degS | — | — | Signal transduction histidine-protein kinase/phosphatase DegS |
| Contig1 | 2833873 | 2834520 | + | GENE_02757 | Prodigal: 2.6 | CDS | — | — | — | — | P27862 | yigZ | — | — | IMPACT family member YigZ |
| Contig1 | 2834525 | 2835700 | + | GENE_02758 | Prodigal: 2.6 | CDS | — | — | — | — | P96499 | yvhJ | — | — | Putative transcriptional regulator YvhJ |
| Contig1 | 2835790 | 2836866 | − | GENE_02759 | Prodigal: 2.6 | CDS | 2.7.8.33 | — | — | — | O34753 | tagO | — | — | putative undecaprenyl-phosphate N-acetylglucosaminyl 1-phosphate transferase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2836999 | 2838195 | − | GENE_02760 | Prodigal: 2.6 | CDS | 2.4.-.- | — | — | — | O32267 | tuaH | — | — | Putative teichuronic acid biosynthesis glycosyltransferase TuaH |
| Contig1 | 2838215 | 2838973 | − | GENE_02761 | Prodigal: 2.6 | CDS | 2.4.-.- | — | — | — | O32268 | tuaG | — | — | Putative teichuronic acid biosynthesis glycosyltransferase TuaG |
| Contig1 | 2838997 | 2839677 | − | GENE_02762 | Prodigal: 2.6 | CDS | — | — | — | — | O32269 | tuaF | — | — | Teichuronic acid biosynthesis protein TuaF |
| Contig1 | 2839674 | 2841092 | − | GENE_02763 | Prodigal: 2.6 | CDS | — | — | — | — | O32270 | tuaE | — | — | Teichuronic acid biosynthesis protein TuaE |
| Contig1 | 2841229 | 2842569 | − | GENE_02764 | Prodigal: 2.6 | CDS | 1.1.1.22 | — | — | — | O32271 | tuaD | — | — | UDP-glucose 6-dehydrogenase TuaD |
| Contig1 | 2842574 | 2843770 | − | GENE_02765 | Prodigal: 2.6 | CDS | 2.4.-.- | — | — | — | O32272 | tuaC | — | — | Putative teichuronic acid biosynthesis glycosyltransferase TuaC |
| Contig1 | 2843767 | 2845215 | − | GENE_02766 | Prodigal: 2.6 | CDS | — | — | — | — | O32273 | tuaB | — | — | Teichuronic acid biosynthesis protein TuaB |
| Contig1 | 2845252 | 2845911 | − | GENE_02767 | Prodigal: 2.6 | CDS | 2.7.8.- | — | — | — | O32274 | tuaA | — | — | Putative undecaprenyl-phosphate N-acetylgalactosaminyl 1-phosphate transferase |
| Contig1 | 2846165 | 2847655 | − | GENE_02768 | Prodigal: 2.6 | CDS | 3.5.1.28 | — | — | — | Q02114 | lytC_3 | — | — | N-acetylmuramoyl-L-alanine amidase LytC precursor |
| Contig1 | 2847681 | 2849798 | − | GENE_02769 | Prodigal: 2.6 | CDS | — | — | — | — | Q02113 | lytB_1 | — | — | Amidase enhancer precursor |
| Contig1 | 2849821 | 2850123 | − | GENE_02770 | Prodigal: 2.6 | CDS | — | — | — | — | Q02112 | lytA | — | — | Membrane-bound protein LytA precursor |
| Contig1 | 2850229 | 2851221 | + | GENE_02771 | Prodigal: 2.6 | CDS | — | — | — | — | Q02115 | lytR_2 | — | — | Transcriptional regulator LytR |
| Contig1 | 2851273 | 2852412 | − | GENE_02772 | Prodigal: 2.6 | CDS | 5.1.3.14 | — | — | — | P39131 | mnaA | — | — | UDP-N-acetylglucosamine 2-epimerase |
| Contig1 | 2852690 | 2853568 | + | GENE_02773 | Prodigal: 2.6 | CDS | 2.7.7.9 | — | — | — | Q05852 | gtaB_2 | — | — | UTP-glucose-1-phosphate uridylyltransferase |
| Contig1 | 2853602 | 2855155 | − | GENE_02774 | Prodigal: 2.6 | CDS | 3.6.3.40 | — | — | — | P42954 | tagH | — | — | Teichoic acids export ATP-binding protein TagH |
| Contig1 | 2855175 | 2856002 | − | GENE_02775 | Prodigal: 2.6 | CDS | — | — | — | — | P42953 | tagG | — | — | Teichoic acid translocation permease protein TagG |
| Contig1 | 2856157 | 2858322 | − | GENE_02776 | Prodigal: 2.6 | CDS | 2.7.8.12 | — | — | — | P13485 | tagF | — | — | CDP-glycerol-poly (glycerophosphate) glycerophosphotransferase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2858372 | 2860390 | − | GENE_02777 | Prodigal: 2.6 | CDS | 2.4.1.52 | — | — | — | P13484 | tagE | — | — | putative poly(glycerol-phosphate) alpha-glucosyltransferase |
| Contig1 | 2860553 | 2860942 | − | GENE_02778 | Prodigal: 2.6 | CDS | 2.7.7.39 | — | — | — | P27623 | tagD | — | — | Glycerol-3-phosphate cytidylyltransferase |
| Contig1 | 2861298 | 2862068 | + | GENE_02779 | Prodigal: 2.6 | CDS | 2.4.1.187 | — | — | — | P27620 | tagA | — | — | Putative N-acetylmannosaminyl-transferase |
| Contig1 | 2862101 | 2863267 | + | GENE_02780 | Prodigal: 2.6 | CDS | 2.7.8.- | — | — | — | P27621 | tagB | — | — | Putative CDP-glycerol:glycerophosphate glycerophosphotransferase |
| Contig1 | 2863328 | 2865973 | − | GENE_02781 | Prodigal: 2.6 | CDS | 3.2.1.96 | — | — | — | P39848 | lytD | — | — | Beta-N-acetylglucosaminidase precursor |
| Contig1 | 2866114 | 2867064 | − | GENE_02782 | Prodigal: 2.6 | CDS | 5.3.1.8 | — | — | — | P39841 | yvyI_2 | — | — | Putative mannose-6-phosphate isomerase YvyI |
| Contig1 | 2867282 | 2868733 | + | GENE_02783 | Prodigal: 2.6 | CDS | — | — | — | — | P39569 | gerBA_1 | — | — | Spore germination protein B1 |
| Contig1 | 2868739 | 2869845 | + | GENE_02784 | Prodigal: 2.6 | CDS | — | — | — | — | P39570 | gerBB | — | — | Spore germination protein B2 |
| Contig1 | 2869842 | 2870099 | + | GENE_02785 | Prodigal: 2.6 | CDS | — | — | — | — | P39571 | gerBC_1 | — | — | Spore germination protein B3 precursor |
| Contig1 | 2870132 | 2870971 | + | GENE_02786 | Prodigal: 2.6 | CDS | — | — | — | — | P39571 | gerBC_2 | — | — | Spore germination protein B3 precursor |
| Contig1 | 2870975 | 2872354 | − | GENE_02787 | Prodigal: 2.6 | CDS | 2.4.1.289 | — | — | — | Q7D5T2 | wbbL | — | — | N-acetylglucosaminyl-diphospho-decaprenol L-rhamnosyltransferase |
| Contig1 | 2872484 | 2873860 | − | GENE_02788 | Prodigal: 2.6 | CDS | — | — | — | — | P46333 | csbC_1 | — | — | putative metabolite transport protein CsbC |
| Contig1 | 2874165 | 2875151 | + | GENE_02789 | Prodigal: 2.6 | CDS | — | — | — | — | Q7WY78 | ywtF | — | — | Putative transcriptional regulator YwtF |
| Contig1 | 2875306 | 2876163 | + | GENE_02790 | Prodigal: 2.6 | CDS | 3.1.3.- | — | — | — | P94592 | ywpJ_2 | — | — | Putative phosphatase YwpJ |
| Contig1 | 2876270 | 2876362 | + | GENE_02791 | Prodigal: 2.6 | CDS | — | — | — | — | — | — | — | — | hypothetical protein |
| Contig1 | 2876462 | 2876992 | + | GENE_02792 | Prodigal: 2.6 | CDS | — | — | — | — | Q795Q5 | yttA | — | — | putative membrane protein YttA |
| Contig1 | 2877031 | 2878266 | − | GENE_02793 | Prodigal: 2.6 | CDS | 3.4.19.- | — | — | — | P96740 | pgdS | — | — | Gamma-DL-glutamyl hydrolase precursor |
| Contig1 | 2878416 | 2878577 | − | GENE_02794 | Prodigal: 2.6 | CDS | — | — | — | — | — | — | — | — | hypothetical protein |
| Contig1 | 2878585 | 2879733 | − | GENE_02795 | Prodigal: 2.6 | CDS | — | — | — | — | P19579 | capA | — | — | Capsule biosynthesis protein CapA |
| Contig1 | 2879752 | 2880201 | − | GENE_02796 | Prodigal: 2.6 | CDS | — | — | — | — | P19581 | capC | — | — | Capsule biosynthesis protein CapC |
| Contig1 | 2880216 | 2881397 | − | GENE_02797 | Prodigal: 2.6 | CDS | — | — | — | — | P19580 | capB | — | — | Capsule biosynthesis protein CapB |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2882137 | 2883606 | + | GENE_02798 | Prodigal: 2.6 | CDS | — | — | — | — | P39569 | gerBA_2 | — | — | Spore germination protein B1 |
| Contig1 | 2883596 | 2884687 | + | GENE_02799 | Prodigal: 2.6 | CDS | — | — | — | — | O31809 | yndE_1 | — | — | Spore germination protein YndE |
| Contig1 | 2884677 | 2885810 | + | GENE_02800 | Prodigal: 2.6 | CDS | — | — | PF05504.5 | — | — | — | — | Spore germination B3/GerAC like, C-terminal | hypothetical protein |
| Contig1 | 2885904 | 2886893 | + | GENE_02801 | Prodigal: 2.6 | CDS | — | — | — | — | P25144 | ccpA_4 | — | — | Catabolite control protein A |
| Contig1 | 2886886 | 2887767 | + | GENE_02802 | Prodigal: 2.6 | CDS | 2.7.1.15 | — | — | — | P0A9J6 | rbsK | — | — | Ribokinase |
| Contig1 | 2887764 | 2888159 | + | GENE_02803 | Prodigal: 2.6 | CDS | 5.5.1.- | — | — | — | P36946 | rbsD | — | — | D-ribose pyranase |
| Contig1 | 2888176 | 2889669 | + | GENE_02804 | Prodigal: 2.6 | CDS | 3.6.3.17 | — | — | — | P04983 | rbsA | — | — | Ribose import ATP-binding protein RbsA |
| Contig1 | 2889659 | 2890630 | + | GENE_02805 | Prodigal: 2.6 | CDS | — | — | — | — | P0AGI1 | rbsC | — | — | Ribose transport system permease protein RbsC |
| Contig1 | 2890644 | 2891561 | + | GENE_02806 | Prodigal: 2.6 | CDS | — | — | — | — | P0A2C5 | rbsB | — | — | D-ribose-binding periplasmic protein precursor |
| Contig1 | 2891622 | 2892155 | + | GENE_02807 | Prodigal: 2.6 | CDS | — | — | — | — | P96729 | ywsB_2 | — | — | Cell wall-binding protein YwsB precursor |
| Contig1 | 2892280 | 2892804 | - | GENE_02808 | Prodigal: 2.6 | CDS | 1.6.99.- | — | — | — | P80871 | ywrO | — | — | General stress protein 14 |
| Contig1 | 2892907 | 2893674 | - | GENE_02809 | Prodigal: 2.6 | CDS | 4.1.1.5 | — | — | — | Q04777 | alsD | — | — | Alpha-acetolactate decarboxylase |
| Contig1 | 2893735 | 2895450 | - | GENE_02810 | Prodigal: 2.6 | CDS | 2.2.1.6 | — | — | — | Q04789 | alsS | — | — | Acetolactate synthase |
| Contig1 | 2895604 | 2896512 | + | GENE_02811 | Prodigal: 2.6 | CDS | — | — | — | — | Q47141 | hcaR | — | — | Hca operon transcriptional activator |
| Contig1 | 2896707 | 2898038 | + | GENE_02812 | Prodigal: 2.6 | CDS | — | — | — | — | P0AB93 | arsB_1 | — | — | Arsenical pump membrane protein |
| Contig1 | 2898088 | 2898762 | - | GENE_02813 | Prodigal: 2.6 | CDS | — | — | — | — | — | — | — | — | hypothetical protein |
| Contig1 | 2898804 | 2899697 | - | GENE_02814 | Prodigal: 2.6 | CDS | — | — | — | — | — | — | — | — | hypothetical protein |
| Contig1 | 2899820 | 2900914 | - | GENE_02815 | Prodigal: 2.6 | CDS | — | — | — | — | Q45535 | cotH | — | — | Inner spore coat protein H |
| Contig1 | 2901055 | 2901621 | + | GENE_02816 | Prodigal: 2.6 | CDS | — | — | — | — | P39801 | cotG | — | — | Spore coat protein G |
| Contig1 | 2901778 | 2902398 | + | GENE_02817 | Prodigal: 2.6 | CDS | — | — | PF01613.12 | — | — | — | — | — | Flavin reductase like domain protein |
| Contig1 | 2902563 | 2902907 | + | GENE_02818 | Prodigal: 2.6 | CDS | — | — | — | — | — | — | — | — | hypothetical protein |
| Contig1 | 2902919 | 2904496 | - | GENE_02819 | Prodigal: 2.6 | CDS | 2.3.2.2 | — | — | — | O05218 | ywrD | — | — | Putative gamma-glutamyltransferase YwrD |
| Contig1 | 2904704 | 2905180 | + | GENE_02820 | Prodigal: 2.6 | CDS | — | — | — | — | P0ACJ0 | lrp_1 | — | — | Leucine-responsive regulatory protein |
| Contig1 | 2905196 | 2905786 | + | GENE_02821 | Prodigal: 2.6 | CDS | — | — | — | — | P14285 | chrA_1 | — | — | Chromate transport protein |
| Contig1 | 2905783 | 2906319 | + | GENE_02822 | Prodigal: 2.6 | CDS | — | — | — | — | P14285 | chrA_2 | — | — | Chromate transport protein |
| Contig1 | 2906346 | 2906564 | - | GENE_02823 | Prodigal: 2.6 | CDS | — | — | — | — | — | — | — | — | hypothetical protein |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2906561 | 2907106 | − | GENE_02824 | Prodigal: 2.6 | CDS | 1.-.-.- | — | — | — | P96726 | ywqN | — | — | Putative NAD(P)H-dependent FMN-containing oxido-reductase YwqN |
| Contig1 | 2907229 | 2908110 | + | GENE_02825 | Prodigal: 2.6 | CDS | — | — | — | — | — | gltR | — | — | HTH-type transcriptional regulator GltR |
| Contig1 | 2908197 | 2908913 | − | GENE_02826 | Prodigal: 2.6 | CDS | 3.1.21.7 | — | — | — | P94501 | nfi | — | — | Endonuclease V |
| Contig1 | 2909081 | 2909659 | − | GENE_02827 | Prodigal: 2.6 | CDS | — | — | — | — | P96724 | — | — | — | hypothetical protein |
| Contig1 | 2909948 | 2910253 | − | GENE_02828 | Prodigal: 2.6 | CDS | — | — | — | — | — | — | — | — | hypothetical protein |
| Contig1 | 2910270 | 2912015 | − | GENE_02829 | Prodigal: 2.6 | CDS | 3.1.-.- | — | — | — | P96722 | ywqJ | — | — | Putative ribonuclease YwqJ |
| Contig1 | 2912035 | 2912295 | − | GENE_02830 | Prodigal: 2.6 | CDS | — | — | — | — | — | — | — | — | hypothetical protein |
| Contig1 | 2912295 | 2912729 | − | GENE_02831 | Prodigal: 2.6 | CDS | — | — | — | — | — | — | — | — | hypothetical protein |
| Contig1 | 2912801 | 2912914 | − | GENE_02832 | Prodigal: 2.6 | CDS | — | — | — | — | — | — | — | — | hypothetical protein |
| Contig1 | 2913009 | 2913797 | − | GENE_02833 | Prodigal: 2.6 | CDS | — | — | — | — | — | — | — | — | hypothetical protein |
| Contig1 | 2913861 | 2915186 | − | GENE_02834 | Prodigal: 2.6 | CDS | 1.1.1.22 | — | — | — | P96718 | ywqF | — | — | UDP-glucose 6-dehydrogenase YwqF |
| Contig1 | 2915386 | 2916150 | − | GENE_02835 | Prodigal: 2.6 | CDS | 3.1.3.48 | — | — | — | P96717 | ywqE | — | — | Tyrosine-protein phosphatase YwqE |
| Contig1 | 2916196 | 2916885 | − | GENE_02836 | Prodigal: 2.6 | CDS | 2.7.10.2 | — | — | — | P96716 | ywqD_2 | — | — | Tyrosine-protein kinase YwqD |
| Contig1 | 2916872 | 2917618 | − | GENE_02837 | Prodigal: 2.6 | CDS | — | — | — | — | P72367 | cap8A_2 | — | — | Capsular polysaccharide type 8 biosynthesis protein cap8A |
| Contig1 | 2917834 | 2917980 | − | GENE_02838 | Prodigal: 2.6 | CDS | — | — | — | — | — | — | — | — | hypothetical protein |
| Contig1 | 2918181 | 2919791 | + | GENE_02839 | Prodigal: 2.6 | CDS | — | — | — | — | — | — | — | — | hypothetical protein |
| Contig1 | 2919778 | 2922552 | + | GENE_02840 | Prodigal: 2.6 | CDS | — | — | — | MF_01821 | — | rapA_4 | — | — | RNA polymerase-associated protein RapA |
| Contig1 | 2922666 | 2923523 | − | GENE_02841 | Prodigal: 2.6 | CDS | 3.1.3.- | — | — | — | P94592 | ywpJ_3 | — | — | Putative phosphatase YwpJ |
| Contig1 | 2923520 | 2924302 | − | GENE_02842 | Prodigal: 2.6 | CDS | — | — | — | — | P94591 | glcR | — | — | HTH-type transcriptional repressor GlcR |
| Contig1 | 2924512 | 2924853 | − | GENE_02843 | Prodigal: 2.6 | CDS | — | — | — | — | C0SPB6 | ssbB | — | — | Single-stranded DNA-binding protein SsbB |
| Contig1 | 2924951 | 2925304 | − | GENE_02844 | Prodigal: 2.6 | CDS | — | — | — | — | — | — | — | — | hypothetical protein |
| Contig1 | 2925477 | 2925887 | + | GENE_02845 | Prodigal: 2.6 | CDS | — | — | — | — | — | — | — | — | hypothetical protein |
| Contig1 | 2925932 | 2926327 | − | GENE_02846 | Prodigal: 2.6 | CDS | — | — | — | — | P0A742 | mscL | — | — | Large-conductance mechanosensitive channel |
| Contig1 | 2926384 | 2926809 | − | GENE_02847 | Prodigal: 2.6 | CDS | 4.2.1.59 | — | — | — | P64107 | fabZ_1 | — | — | 3-hydroxyacyl-[acyl-carrier-protein] dehydratase FabZ |
| Contig1 | 2927005 | 2928069 | + | GENE_02848 | Prodigal: 2.6 | CDS | 3.1.-.- | — | — | — | P71002 | rapF_1 | — | — | Response regulator aspartate phosphatase F |
| Contig1 | 2928087 | 2928911 | − | GENE_02849 | Prodigal: 2.6 | CDS | — | — | — | — | P0A1J3 | flgG_2 | — | — | Flagellar basal-body rod protein FlgG |
| Contig1 | 2928933 | 2929730 | − | GENE_02850 | Prodigal: 2.6 | CDS | — | — | — | — | P16323 | flgF | — | — | Flagellar basal-body rod protein FlgF |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2929889 | 2930890 | − | GENE_02851 | Prodigal: 2.6 | CDS | — | — | — | — | P0A9X4 | mreB_3 | — | — | Rod shape-determining protein MreB |
| Contig1 | 2931120 | 2931350 | − | GENE_02852 | Prodigal: 2.6 | CDS | — | — | — | — | P15281 | spoIIID | — | — | Stage III sporulation protein D |
| Contig1 | 2931682 | 2932095 | + | GENE_02853 | Prodigal: 2.6 | CDS | — | — | — | — | Q81RU6 | — | — | — | putative HTH-type transcriptional regulator/GBAA_1941/BAS1801 |
| Contig1 | 2932120 | 2933316 | + | GENE_02854 | Prodigal: 2.6 | CDS | — | — | — | — | Q0GQS6 | pbuE_3 | — | — | Purine efflux pump PbuE |
| Contig1 | 2933353 | 2934807 | − | GENE_02855 | Prodigal: 2.6 | CDS | — | — | — | — | P94575 | pucI_1 | — | — | putative allantoin permease |
| Contig1 | 2934971 | 2936335 | − | GENE_02856 | Prodigal: 2.6 | CDS | — | — | — | — | P71879 | stp_2 | — | — | Multidrug resistance protein stp |
| Contig1 | 2936332 | 2936898 | − | GENE_02857 | Prodigal: 2.6 | CDS | 3.-.-.- | — | — | — | P0ADI7 | yecD_2 | — | — | Isochorismatase family protein YecD |
| Contig1 | 2937151 | 2938362 | + | GENE_02858 | Prodigal: 2.6 | CDS | — | — | — | — | Q07429 | nrgA | — | — | Ammonium transporter NrgA |
| Contig1 | 2938380 | 2938730 | + | GENE_02859 | Prodigal: 2.6 | CDS | — | — | — | — | Q07428 | nrgB | — | — | Nitrogen regulatory PII-like protein |
| Contig1 | 2938783 | 2939937 | − | GENE_02860 | Prodigal: 2.6 | CDS | — | — | — | — | O07639 | ftsW_3 | — | — | Lipid II flippase FtsW |
| Contig1 | 2940102 | 2940677 | + | GENE_02861 | Prodigal: 2.6 | CDS | 3.6.1.27 | — | — | — | P94571 | bcrC | — | — | Undecaprenyl-diphosphatase BcrC |
| Contig1 | 2940912 | 2941280 | + | GENE_02862 | Prodigal: 2.6 | CDS | — | — | — | — | — | — | — | — | hypothetical protein |
| Contig1 | 2941252 | 2941731 | − | GENE_02863 | Prodigal: 2.6 | CDS | — | — | — | — | P71045 | ywnJ | — | — | putative membrane protein YwnJ |
| Contig1 | 2941823 | 2942692 | − | GENE_02864 | Prodigal: 2.6 | CDS | — | — | — | — | P71044 | spoIIQ | — | — | Stage II sporulation protein Q |
| Contig1 | 2942825 | 2943322 | + | GENE_02865 | Prodigal: 2.6 | CDS | 2.3.1.183 | — | — | — | P71043 | ywnH | — | — | Putative phosphinothricin acetyltransferase YwnH |
| Contig1 | 2943319 | 2943768 | + | GENE_02866 | Prodigal: 2.6 | CDS | — | — | — | — | — | — | — | — | hypothetical protein |
| Contig1 | 2943800 | 2944237 | + | GENE_02867 | Prodigal: 2.6 | CDS | — | — | — | — | — | — | — | — | hypothetical protein |
| Contig1 | 2944458 | 2945906 | + | GENE_02868 | Prodigal: 2.6 | CDS | 2.7.8.- | — | — | — | P71040 | clsA | — | — | Major cardiolipin synthase ClsA |
| Contig1 | 2946042 | 2946428 | + | GENE_02869 | Prodigal: 2.6 | CDS | — | — | — | — | — | — | — | — | hypothetical protein |
| Contig1 | 2946821 | 2947462 | + | GENE_02870 | Prodigal: 2.6 | CDS | 3.2.1.8 | — | — | — | P18429 | xynA | — | — | Endo-1,4-beta-xylanase A precursor |
| Contig1 | 2947487 | 2947798 | − | GENE_02871 | Prodigal: 2.6 | CDS | — | — | — | — | — | — | — | — | hypothetical protein |
| Contig1 | 2947836 | 2948240 | − | GENE_02872 | Prodigal: 2.6 | CDS | — | — | — | — | P71036 | ywnA_1 | — | — | Putative HTH-type transcriptional regulator YwnA |
| Contig1 | 2948381 | 2950090 | − | GENE_02873 | Prodigal: 2.6 | CDS | 3.5.1.5 | — | — | — | P77837 | ureC | — | — | Urease subunit alpha |
| Contig1 | 2950087 | 2950461 | − | GENE_02874 | Prodigal: 2.6 | CDS | 3.5.1.5 | — | — | — | P71035 | ureB | — | — | Urease subunit beta |
| Contig1 | 2950458 | 2950775 | − | GENE_02875 | Prodigal: 2.6 | CDS | 3.5.1.5 | — | — | — | P75030 | ureA | — | — | Urease subunit gamma |
| Contig1 | 2951129 | 2951317 | − | GENE_02876 | Prodigal: 2.6 | CDS | — | — | — | — | P70964 | csbD | — | — | Stress response protein CsbD |
| Contig1 | 2951391 | 2951870 | − | GENE_02877 | Prodigal: 2.6 | CDS | — | — | — | — | — | — | — | — | hypothetical protein |
| Contig1 | 2951992 | 2953122 | − | GENE_02878 | Prodigal: 2.6 | CDS | 3.1.-.- | — | — | — | Q00828 | rapA_5 | — | — | Response regulator aspartate phosphatase A |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2953313 | 2954338 | − | GENE_02879 | Prodigal: 2.6 | CDS | 4.1.99.18 | — | — | — | P69848 | moaA | — | — | Cyclic pyranopterin monophosphate synthase |
| Contig1 | 2954356 | 2955144 | − | GENE_02880 | Prodigal: 2.6 | CDS | — | — | — | MF_00187 | — | fdhD | — | — | Protein FdhD |
| Contig1 | 2955239 | 2955403 | − | GENE_02881 | Prodigal: 2.6 | CDS | — | — | — | — | — | — | — | — | hypothetical protein |
| Contig1 | 2955490 | 2956170 | − | GENE_02882 | Prodigal: 2.6 | CDS | — | — | PF00092.22 | — | — | — | — | — | von Willebrand factor type A domain protein |
| Contig1 | 2956481 | 2957167 | − | GENE_02883 | Prodigal: 2.6 | CDS | — | — | PF00092.22 | — | — | — | — | — | von Willebrand factor type A domain protein |
| Contig1 | 2957433 | 2958464 | − | GENE_02884 | Prodigal: 2.6 | CDS | — | — | — | — | Q02113 | lytB_2 | — | — | Amidase enhancer precursor |
| Contig1 | 2958664 | 2959974 | − | GENE_02885 | Prodigal: 2.6 | CDS | 2.5.1.7 | — | — | — | P70965 | murAA | — | — | UDP-N-acetylglucosamine 1-carboxyvinyltransferase 1 |
| Contig1 | 2960008 | 2960748 | − | GENE_02886 | Prodigal: 2.6 | CDS | — | — | — | — | — | — | — | — | hypothetical protein |
| Contig1 | 2960890 | 2961120 | − | GENE_02887 | Prodigal: 2.6 | CDS | — | — | — | — | — | — | — | — | hypothetical protein |
| Contig1 | 2961293 | 2961763 | + | GENE_02888 | Prodigal: 2.6 | CDS | — | — | — | — | — | — | — | — | hypothetical protein |
| Contig1 | 2961808 | 2962206 | − | GENE_02889 | Prodigal: 2.6 | CDS | — | — | — | — | P37812 | atpC | — | — | ATP synthase epsilon chain |
| Contig1 | 2962230 | 2963651 | − | GENE_02890 | Prodigal: 2.6 | CDS | 3.6.3.14 | — | — | — | P37809 | atpD | — | — | ATP synthase subunit beta |
| Contig1 | 2963677 | 2964540 | − | GENE_02891 | Prodigal: 2.6 | CDS | — | — | — | — | P37810 | atpG | — | — | ATP synthase gamma chain |
| Contig1 | 2964616 | 2966124 | − | GENE_02892 | Prodigal: 2.6 | CDS | 3.6.3.14 | — | — | — | P37808 | atpA | — | — | ATP synthase subunit alpha |
| Contig1 | 2966141 | 2966686 | − | GENE_02893 | Prodigal: 2.6 | CDS | — | — | — | — | P37811 | atpH | — | — | ATP synthase subunit delta |
| Contig1 | 2966683 | 2967195 | − | GENE_02894 | Prodigal: 2.6 | CDS | — | — | — | — | P37814 | atpF | — | — | ATP synthase subunit b |
| Contig1 | 2967338 | 2967550 | − | GENE_02895 | Prodigal: 2.6 | CDS | — | — | — | — | P37815 | atpE | — | — | ATP synthase subunit c |
| Contig1 | 2967596 | 2968330 | − | GENE_02896 | Prodigal: 2.6 | CDS | — | — | — | — | P37813 | atpB | — | — | ATP synthase subunit a |
| Contig1 | 2968338 | 2968721 | − | GENE_02897 | Prodigal: 2.6 | CDS | — | — | PF03899.9 | — | — | — | — | — | ATP synthase I chain |
| Contig1 | 2969141 | 2969770 | − | GENE_02898 | Prodigal: 2.6 | CDS | 2.4.2.9 | — | — | — | P70881 | upp | — | — | Uracil phosphoribosyltransferase |
| Contig1 | 2969905 | 2971152 | − | GENE_02899 | Prodigal: 2.6 | CDS | 2.1.2.1 | — | — | — | P39148 | glyA | — | — | Serine hydroxymethyltransferase |
| Contig1 | 2971300 | 2971842 | − | GENE_02900 | Prodigal: 2.6 | CDS | — | — | — | — | — | — | — | — | hypothetical protein |
| Contig1 | 2971856 | 2972305 | − | GENE_02901 | Prodigal: 2.6 | CDS | 5.3.1.- | — | — | — | P39156 | ywlF | — | — | Putative sugar phosphate isomerase YwlF |
| Contig1 | 2972439 | 2972894 | − | GENE_02902 | Prodigal: 2.6 | CDS | 3.1.3.48 | — | — | — | P39155 | ywlE | — | — | Low molecular weight protein-tyrosine-phosphatase YwlE |
| Contig1 | 2972968 | 2973525 | − | GENE_02903 | Prodigal: 2.6 | CDS | — | — | — | — | P76264 | mntP_3 | — | — | putative manganese efflux pump MntP |
| Contig1 | 2973593 | 2974633 | − | GENE_02904 | Prodigal: 2.6 | CDS | 2.7.7.87 | — | — | — | P39153 | ywlC | — | — | Threonylcarbamoyl-AMP synthase |
| Contig1 | 2974790 | 2975233 | − | GENE_02905 | Prodigal: 2.6 | CDS | — | — | PF09551.4 | — | — | — | — | — | hypothetical protein |
| Contig1 | 2975304 | 2975984 | − | GENE_02906 | Prodigal: 2.6 | CDS | — | — | — | — | — | — | — | — | Stage II sporulation protein R (spore_II_R) |
| Contig1 | 2976145 | 2976519 | + | GENE_02907 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 2976506 | 2976784 | − | GENE_02908 | Prodigal: 2.6 | CDS | — | — | — | — | — | — | — | — | hypothetical protein |
| Contig1 | 2976855 | 2977715 | − | GENE_02909 | Prodigal: 2.6 | CDS | 2.1.1.- | — | — | — | B0B9D1 | prmC | — | — | Release factor glutamine methyltransferase |
| Contig1 | 2977717 | 2978787 | − | GENE_02910 | Prodigal: 2.6 | CDS | — | — | — | — | P66018 | prfA | — | — | Peptide chain release factor 1 |
| Contig1 | 2978899 | 2979282 | + | GENE_02911 | Prodigal: 2.6 | CDS | — | — | — | — | — | — | — | — | putative lyase |
| Contig1 | 2979393 | 2979956 | + | GENE_02912 | Prodigal: 2.6 | CDS | — | PRK11478 | — | — | P45870 | racA | — | — | Chromosome-anchoring protein RacA |
| Contig1 | 2979990 | 2980946 | − | GENE_02913 | Prodigal: 2.6 | CDS | — | — | — | — | — | — | — | — | putative transporter YfdV |
| Contig1 | 2981032 | 2982729 | − | GENE_02914 | Prodigal: 2.6 | CDS | 1.1.1.38 | PRK09903 | — | — | P45868 | maeA_2 | — | — | putative NAD-dependent malic enzyme 2 |
| Contig1 | 2983006 | 2983596 | − | GENE_02915 | Prodigal: 2.6 | CDS | 2.7.1.21 | — | — | — | Q81JX0 | tdk | — | — | Thymidine kinase |
| Contig1 | 2983681 | 2983881 | − | GENE_02916 | Prodigal: 2.6 | CDS | — | — | — | — | Q03223 | rpmE | — | — | 50S ribosomal protein L31 |
| Contig1 | 2984004 | 2985290 | − | GENE_02917 | Prodigal: 2.6 | CDS | — | — | — | — | P0AG30 | — | — | Transcription termination factor Rho | hypothetical protein |
| Contig1 | 2985697 | 2986662 | − | GENE_02918 | Prodigal: 2.6 | CDS | 3.1.3.11 | — | — | — | Q03224 | glpX | — | — | Fructose-1,6-bisphosphatase class 2 |
| Contig1 | 2986696 | 2987985 | − | GENE_02919 | Prodigal: 2.6 | CDS | 2.5.1.7 | — | — | — | P19670 | murAB | — | — | UDP-N-acetylglucosamine 1-carboxyvinyltransferase 2 |
| Contig1 | 2988295 | 2988933 | − | GENE_02920 | Prodigal: 2.6 | CDS | 2.2.1.2 | — | — | — | P19669 | tal | — | — | Transaldolase |
| Contig1 | 2989052 | 2989909 | − | GENE_02921 | Prodigal: 2.6 | CDS | 4.1.2.13 | — | — | — | P13243 | fbaA | — | — | putative fructose-bisphosphate aldolase |
| Contig1 | 2990085 | 2990459 | − | GENE_02922 | Prodigal: 2.6 | CDS | 2.7.-.- | — | — | — | P06628 | spo0F | — | — | Sporulation initiation phosphotransferase F |
| Contig1 | 2990624 | 2991145 | + | GENE_02923 | Prodigal: 2.6 | CDS | — | — | — | — | — | — | — | — | hypothetical protein |
| Contig1 | 2991193 | 2992800 | − | GENE_02924 | Prodigal: 2.6 | CDS | 6.3.4.2 | — | — | — | P99072 | pyrG | — | — | CTP synthase |
| Contig1 | 2993041 | 2993568 | − | GENE_02925 | Prodigal: 2.6 | CDS | — | — | — | — | P12464 | rpoE | — | — | DNA-directed RNA polymerase subunit delta |
| Contig1 | 2993796 | 2995904 | − | GENE_02926 | Prodigal: 2.6 | CDS | — | — | — | MF_02105 | — | lutA_3 | — | — | Lactate utilization protein A |
| Contig1 | 2996043 | 2997242 | + | GENE_02927 | Prodigal: 2.6 | CDS | — | — | — | — | P45865 | clsB | — | — | Minor cardiolipin synthase ClsB |
| Contig1 | 2997255 | 2998217 | + | GENE_02928 | Prodigal: 2.6 | CDS | 3.-.-.- | — | — | — | Q9RTE6 | uvsE | — | — | UV DNA damage endonuclease |
| Contig1 | 2998286 | 2998558 | + | GENE_02929 | Prodigal: 2.6 | CDS | — | — | — | — | — | — | — | — | hypothetical protein |
| Contig1 | 2998625 | 3000352 | − | GENE_02930 | Prodigal: 2.6 | CDS | 3.6.3.- | — | — | — | Q99T13 | — | — | — | Putative multidrug export ATP-binding/permease protein |
| Contig1 | 3000433 | 3001998 | − | GENE_02931 | Prodigal: 2.6 | CDS | 2.7.8.- | — | — | — | P45860 | ywiE | — | — | putative cardiolipin synthase YwiE |
| Contig1 | 3002032 | 3002661 | − | GENE_02932 | Prodigal: 2.6 | CDS | — | — | — | — | — | — | — | — | hypothetical protein |
| Contig1 | 3002800 | 3003471 | − | GENE_02933 | Prodigal: 2.6 | CDS | 1.7.99.4 | — | — | — | P71994 | narX_1 | — | — | Nitrate reductase-like protein NarX |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3003468 | 3004025 | − | GENE_02934 | Prodigal: 2.6 | CDS | 1.7.99.4 | — | — | — | P71994 | narX_2 | — | — | Nitrate reductase-like protein NarX |
| Contig1 | 3004051 | 3005514 | − | GENE_02935 | Prodigal: 2.6 | CDS | 1.7.99.4 | — | — | — | P11349 | narH | — | — | Respiratory nitrate reductase 1 beta chain |
| Contig1 | 3005504 | 3009190 | − | GENE_02936 | Prodigal: 2.6 | CDS | 1.7.99.4 | — | — | — | P09152 | narG | — | — | Respiratory nitrate reductase 1 alpha chain |
| Contig1 | 3009366 | 3009842 | − | GENE_02937 | Prodigal: 2.6 | CDS | — | — | — | — | P46910 | arfM | — | — | putative transcription regulator ArfM |
| Contig1 | 3009985 | 3010704 | + | GENE_02938 | Prodigal: 2.6 | CDS | — | — | — | — | — | — | — | — | hypothetical protein |
| Contig1 | 3010735 | 3011451 | − | GENE_02939 | Prodigal: 2.6 | CDS | — | — | — | — | P46908 | fnr | — | — | Anaerobic regulatory protein |
| Contig1 | 3011549 | 3012739 | − | GENE_02940 | Prodigal: 2.6 | CDS | — | — | — | — | O33854 | narT | — | — | putative nitrate transporter NarT |
| Contig1 | 3012874 | 3014544 | − | GENE_02941 | Prodigal: 2.6 | CDS | 6.1.1.19 | — | — | — | Q99W05 | argS | — | — | Arginine--tRNA ligase |
| Contig1 | 3014541 | 3014969 | − | GENE_02942 | Prodigal: 2.6 | CDS | — | — | — | — | O07624 | ywiB | — | — | putative beta-barrel protein YwiB |
| Contig1 | 3015261 | 3016406 | + | GENE_02943 | Prodigal: 2.6 | CDS | 3.1.-.- | — | — | — | P71002 | rapF_2 | — | — | Response regulator aspartate phosphatase F |
| Contig1 | 3016390 | 3016509 | + | GENE_02944 | Prodigal: 2.6 | CDS | — | PRK04140 | PF1131.2 | — | — | — | — | — | Rap-phr extracellular signalling |
| Contig1 | 3016710 | 3016913 | + | GENE_02945 | Prodigal: 2.6 | CDS | — | — | — | — | — | — | — | — | hypothetical protein |
| Contig1 | 3016927 | 3017130 | + | GENE_02946 | Prodigal: 2.6 | CDS | — | — | — | — | — | — | — | — | hypothetical protein |
| Contig1 | 3017537 | 3017818 | + | GENE_02947 | Prodigal: 2.6 | CDS | — | — | — | — | — | — | — | — | hypothetical protein |
| Contig1 | 3017877 | 3018374 | + | GENE_02948 | Prodigal: 2.6 | CDS | — | — | — | — | — | — | — | — | hypothetical protein |
| Contig1 | 3018379 | 3018918 | + | GENE_02949 | Prodigal: 2.6 | CDS | — | — | — | — | — | — | — | — | hypothetical protein |
| Contig1 | 3018965 | 3019183 | − | GENE_02950 | Prodigal: 2.6 | CDS | — | — | PF00196.13 | — | — | — | — | — | Bacterial regulatory proteins, luxR family |
| Contig1 | 3019353 | 3020225 | − | GENE_02951 | Prodigal: 2.6 | CDS | 3.5.3.11 | — | — | — | P70999 | speB | — | — | Agmatinase |
| Contig1 | 3020285 | 3021115 | − | GENE_02952 | Prodigal: 2.6 | CDS | 2.5.1.16 | — | — | — | P70998 | speE | — | — | Spermidine synthase |
| Contig1 | 3021315 | 3023387 | + | GENE_02953 | Prodigal: 2.6 | CDS | — | — | — | — | P70997 | pbpG | — | — | Penicillin-binding protein 2D |
| Contig1 | 3023412 | 3023843 | − | GENE_02954 | Prodigal: 2.6 | CDS | — | — | — | — | — | — | — | — | hypothetical protein |
| Contig1 | 3023987 | 3024505 | − | GENE_02955 | Prodigal: 2.6 | CDS | — | — | PF08741.4 | — | — | — | — | — | YwhD family protein |
| Contig1 | 3024518 | 3025177 | − | GENE_02956 | Prodigal: 2.6 | CDS | — | — | PF02163.16 | — | — | — | — | — | Peptidase family M50 |
| Contig1 | 3025283 | 3025471 | + | GENE_02957 | Prodigal: 2.6 | CDS | 5.3.2.6 | — | — | — | P70994 | ywhB | — | — | 2-hydroxymuconate tautomerase |
| Contig1 | 3025509 | 3025928 | − | GENE_02958 | Prodigal: 2.6 | CDS | — | — | — | — | O32181 | yusO_6 | — | — | putative HTH-type transcriptional regulator YusO |
| Contig1 | 3026316 | 3027698 | + | GENE_02959 | Prodigal: 2.6 | CDS | — | — | — | — | O07576 | yhdG_3 | — | — | putative amino acid permease YhdG |
| Contig1 | 3027763 | 3028263 | − | GENE_02960 | Prodigal: 2.6 | CDS | — | — | — | — | — | — | — | — | hypothetical protein |
| Contig1 | 3028303 | 3029604 | − | GENE_02961 | Prodigal: 2.6 | CDS | — | — | — | MF_01212 | — | — | — | — | Deoxyguanosine-triphosphate triphosphohydrolase-like protein |
| Contig1 | 3029765 | 3029989 | − | GENE_02962 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3030194 | 3030967 | + | GENE_02963 | Prodigal: 2.6 | CDS | — | — | — | — | P39650 | rsfA_2 | — | — | Prespore-specific transcriptional regulator RsfA |
| Contig1 | 3031229 | 3031543 | + | GENE_02964 | Prodigal: 2.6 | CDS | — | — | PF03551.8 | — | — | — | — | — | Transcriptional regulator PadR-like family protein |
| Contig1 | 3031544 | 3032098 | + | GENE_02965 | Prodigal: 2.6 | CDS | — | — | — | — | — | — | — | — | hypothetical protein |
| Contig1 | 3032196 | 3033116 | + | GENE_02966 | Prodigal: 2.6 | CDS | 3.6.3.- | — | — | — | O07190 | — | — | — | Fluoroquinolones export ATP-binding protein/MT2762 |
| Contig1 | 3033113 | 3034066 | + | GENE_02967 | Prodigal: 2.6 | CDS | — | — | PF12730.1 | — | — | — | — | — | ABC-2 family transporter protein |
| Contig1 | 3034056 | 3034892 | − | GENE_02968 | Prodigal: 2.6 | CDS | — | — | — | — | — | — | — | — | hypothetical protein |
| Contig1 | 3034883 | 3035647 | − | GENE_02969 | Prodigal: 2.6 | CDS | — | — | — | — | — | — | — | — | hypothetical protein |
| Contig1 | 3035649 | 3036572 | − | GENE_02970 | Prodigal: 2.6 | CDS | — | — | — | — | — | — | — | — | hypothetical protein |
| Contig1 | 3036621 | 3036800 | − | GENE_02971 | Prodigal: 2.6 | CDS | — | — | — | — | — | — | — | — | hypothetical protein |
| Contig1 | 3036953 | 3037816 | − | GENE_02972 | Prodigal: 2.6 | CDS | 2.3.1.204 | — | — | — | P39648 | lipL | — | — | Octanoyl-[GcvH]:protein N-octanoyltransferase |
| Contig1 | 3037863 | 3038762 | − | GENE_02973 | Prodigal: 2.6 | CDS | — | — | — | — | P39647 | cysL_2 | — | — | HTH-type transcriptional regulator CysL |
| Contig1 | 3038884 | 3039855 | + | GENE_02974 | Prodigal: 2.6 | CDS | — | — | — | — | — | — | — | — | hypothetical protein |
| Contig1 | 3039893 | 3040864 | − | GENE_02975 | Prodigal: 2.6 | CDS | 2.3.1.8 | — | — | — | P39646 | pta_2 | — | — | Phosphate acetyltransferase |
| Contig1 | 3041127 | 3041891 | + | GENE_02976 | Prodigal: 2.6 | CDS | 1.-.-.- | PRK12276 | — | — | — | — | — | — | putative heme peroxidase |
| Contig1 | 3041990 | 3042790 | + | GENE_02977 | Prodigal: 2.6 | CDS | — | — | — | — | P39644 | ywfH | — | — | Bacilysin biosynthesis oxidoreductase YwfH |
| Contig1 | 3042807 | 3044006 | − | GENE_02978 | Prodigal: 2.6 | CDS | 2.6.1.83 | — | — | — | A0LEA5 | dapL_2 | — | — | LL-diaminopimelate aminotransferase |
| Contig1 | 3044019 | 3045200 | − | GENE_02979 | Prodigal: 2.6 | CDS | — | — | — | — | P39642 | bacE_2 | — | — | Putative bacilysin exporter BacE |
| Contig1 | 3045197 | 3046615 | − | GENE_02980 | Prodigal: 2.6 | CDS | 6.3.2.28 | — | — | — | P39641 | bacD | — | — | Alanine-anticapsin ligase BacD |
| Contig1 | 3046633 | 3047394 | − | GENE_02981 | Prodigal: 2.6 | CDS | 1.1.1.47 | — | — | — | P12310 | gdh_2 | — | — | Glucose 1-dehydrogenase |
| Contig1 | 3047391 | 3048101 | − | GENE_02982 | Prodigal: 2.6 | CDS | — | — | — | — | P39639 | bacB | — | — | Bacilysin biosynthesis protein BacB |
| Contig1 | 3048091 | 3048705 | − | GENE_02983 | Prodigal: 2.6 | CDS | — | — | — | — | — | — | — | — | prephenate dehydratase |
| Contig1 | 3048867 | 3049316 | − | GENE_02984 | Prodigal: 2.6 | CDS | — | PRK11898 | — | MF_00517 | — | sotB | — | — | sugar efflux transporter |
| Contig1 | 3049319 | 3050104 | − | GENE_02985 | Prodigal: 2.6 | CDS | — | — | — | — | P77389 | ydhP_3 | — | — | Inner membrane transport protein YdhP |
| Contig1 | 3050327 | 3051529 | + | GENE_02986 | Prodigal: 2.6 | CDS | — | — | — | — | P28246 | bcr_2 | — | — | Bicyclomycin resistance protein |
| Contig1 | 3051562 | 3052980 | − | GENE_02987 | Prodigal: 2.6 | CDS | — | — | — | — | P39636 | rocC_1 | — | — | Amino-acid permease RocC |
| Contig1 | 3053005 | 3054687 | − | GENE_02988 | Prodigal: 2.6 | CDS | 3.5.1.18 | — | — | MF_01690 | — | dapE | — | — | Succinyl-diaminopimelate desuccinylase |
| Contig1 | 3054758 | 3056305 | − | GENE_02989 | Prodigal: 2.6 | CDS | 1.2.1.88 | — | — | — | P39634 | rocA_1 | — | — | 1-pyrroline-5-carboxylate dehydrogenase |
| Contig1 | 3056503 | 3057789 | − | GENE_02990 | Prodigal: 2.6 | CDS | 1.4.1.2 | — | — | — | P39633 | rocG | — | — | Catabolic NAD-specific glutamate dehydrogenase RocG |
| Contig1 | 3057079 | 3058439 | − | GENE_02991 | Prodigal: 2.6 | CDS | — | — | — | — | — | — | — | — | hypothetical protein |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3058653 | 3059108 | − | GENE_02992 | Prodigal: 2.6 | CDS | 5.1.3.13 | — | — | — | P37745 | rfbC | — | — | dTDP-4-dehydrorhamnose 3,5-epimerase |
| Contig1 | 3059105 | 3059953 | − | GENE_02993 | Prodigal: 2.6 | CDS | 1.1.1.133 | — | — | — | A0QTF8 | rmlD | — | — | dTDP-4-dehydrorhamnose reductase |
| Contig1 | 3059974 | 3060921 | − | GENE_02994 | Prodigal: 2.6 | CDS | 4.2.1.46 | — | — | — | P39630 | rfbB | — | — | dTDP-glucose 4,6-dehydratase |
| Contig1 | 3060924 | 3061661 | − | GENE_02995 | Prodigal: 2.6 | CDS | 2.7.7.24 | — | — | — | P39629 | rmlA | — | — | Glucose-1-phosphate thymidylyltransferase |
| Contig1 | 3061689 | 3062693 | − | GENE_02996 | Prodigal: 2.6 | CDS | 2.4.1.227 | — | — | MF_00033 | — | murG_2 | — | — | UDP-N-acetylglucosamine--N-acetylmuramyl-(penta peptide) pyrophosphoryl-undecaprenol N-acetylglucosamine transferase |
| Contig1 | 3062695 | 3063438 | − | GENE_02997 | Prodigal: 2.6 | CDS | 2.7.7.38 | — | — | — | P42216 | kpsU | — | — | 3-deoxy-manno-octulosonate cytidylyltransferase |
| Contig1 | 3063428 | 3064549 | − | GENE_02998 | Prodigal: 2.6 | CDS | — | — | — | — | P39625 | spsE | — | — | Spore coat polysaccharide biosynthesis protein SpsE |
| Contig1 | 3064549 | 3065412 | − | GENE_02999 | Prodigal: 2.6 | CDS | — | PRK10975 | — | — | — | — | — | — | TDP-fucosamine acetyltransferase |
| Contig1 | 3065413 | 3066582 | − | GENE_03000 | Prodigal: 2.6 | CDS | 2.6.1.87 | — | — | — | Q8ZNF3 | arnB_2 | — | — | UDP-4-amino-4-deoxy-L-arabinose--oxoglutarate aminotransferase |
| Contig1 | 3066604 | 3068028 | − | GENE_03001 | Prodigal: 2.6 | CDS | — | — | PF05159.8 | — | — | — | — | — | Capsule polysaccharide biosynthesis protein |
| Contig1 | 3068033 | 3068803 | − | GENE_03002 | Prodigal: 2.6 | CDS | — | — | — | — | P39621 | spsA_2 | — | — | Spore coat polysaccharide biosynthesis protein SpsA |
| Contig1 | 3069085 | 3069630 | + | GENE_03003 | Prodigal: 2.6 | CDS | — | PRK10873 | — | — | P39620 | gerQ | — | — | Spore coat protein GerQ |
| Contig1 | 3069677 | 3070048 | − | GENE_03004 | Prodigal: 2.6 | CDS | — | — | — | — | — | — | — | — | hypothetical protein |
| Contig1 | 3070112 | 3071431 | − | GENE_03005 | Prodigal: 2.6 | CDS | — | — | — | — | P39618 | ywdJ | — | — | Putative purine permease YwdJ |
| Contig1 | 3071450 | 3071776 | − | GENE_03006 | Prodigal: 2.6 | CDS | — | — | — | — | — | — | — | — | hypothetical protein |
| Contig1 | 3071931 | 3072614 | − | GENE_03007 | Prodigal: 2.6 | CDS | 3.2.2.27 | — | — | — | P39615 | ung | — | — | Uracil-DNA glycosylase |
| Contig1 | 3072629 | 3073435 | − | GENE_03008 | Prodigal: 2.6 | CDS | 2.4.1.- | — | — | — | P0A599 | — | — | — | PGL/p-HBAD biosynthesis glycosyltransferase/MT3031 |
| Contig1 | 3073520 | 3074047 | − | GENE_03009 | Prodigal: 2.6 | CDS | — | — | — | — | — | — | — | — | hypothetical protein |
| Contig1 | 3074092 | 3074727 | − | GENE_03010 | Prodigal: 2.6 | CDS | — | — | — | — | — | — | — | — | hypothetical protein |
| Contig1 | 3074720 | 3075058 | − | GENE_03011 | Prodigal: 2.6 | CDS | — | PRK09416 | — | — | — | — | — | — | lineage-specific thermal regulator protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3075208 | 3076020 | + | GENE_03012 | Prodigal: 2.6 | CDS | 2.7.1.35 | — | — | — | P39610 | pdxK | — | — | Pyridoxine kinase |
| Contig1 | 3076051 | 3076290 | − | GENE_03013 | Prodigal: 2.6 | CDS | — | — | — | — | — | — | — | — | hypothetical protein |
| Contig1 | 3076390 | 3077829 | − | GENE_03014 | Prodigal: 2.6 | CDS | 3.2.1.26 | — | — | — | P27217 | scrB | — | — | Sucrose-6-phosphate hydrolase |
| Contig1 | 3077826 | 3079208 | − | GENE_03015 | Prodigal: 2.6 | CDS | — | — | — | — | P15400 | sacX | — | — | Negative regulator of SacY activity |
| Contig1 | 3079426 | 3080256 | − | GENE_03016 | Prodigal: 2.6 | CDS | — | — | — | — | P15401 | sacY | — | — | Levansucrase and sucrase synthesis operon antiterminator |
| Contig1 | 3080280 | 3080594 | − | GENE_03017 | Prodigal: 2.6 | CDS | — | — | — | — | — | — | — | — | hypothetical protein |
| Contig1 | 3081120 | 3083531 | + | GENE_03018 | Prodigal: 2.6 | CDS | 3.4.21.- | — | — | — | P29141 | vpr | — | — | Minor extracellular protease vpr precursor |
| Contig1 | 3083573 | 3084574 | − | GENE_03019 | Prodigal: 2.6 | CDS | 1.14.14.3 | — | — | — | P07740 | luxA_2 | — | — | Alkanal monooxygenase alpha chain |
| Contig1 | 3084738 | 3085487 | − | GENE_03020 | Prodigal: 2.6 | CDS | 1.5.1.38 | — | — | — | P39605 | nfrA1 | — | — | FMN reductase (NADPH) |
| Contig1 | 3085591 | 3086778 | − | GENE_03021 | Prodigal: 2.6 | CDS | — | — | — | — | P39604 | rodA | — | — | Rod shape-determining protein RodA |
| Contig1 | 3086980 | 3087438 | − | GENE_03022 | Prodigal: 2.6 | CDS | 2.3.1.- | — | — | — | P94562 | ysnE_1 | — | — | putative N-acetyltransferase YsnE |
| Contig1 | 3087732 | 3087992 | + | GENE_03023 | Prodigal: 2.6 | CDS | — | — | — | — | P39603 | ywcE | — | — | Spore morphogenesis and germination protein YwcE |
| Contig1 | 3088036 | 3088404 | − | GENE_03024 | Prodigal: 2.6 | CDS | 1.10.3.- | — | — | — | E0TW64 | qoxD | — | — | Quinol oxidase subunit 4 |
| Contig1 | 3088406 | 3089020 | − | GENE_03025 | Prodigal: 2.6 | CDS | 1.10.3.- | — | — | — | E0TW65 | qoxC | — | — | Quinol oxidase subunit 3 |
| Contig1 | 3089035 | 3090984 | − | GENE_03026 | Prodigal: 2.6 | CDS | 1.10.3.- | — | — | — | E0TW66 | qoxB | — | — | Quinol oxidase subunit 1 |
| Contig1 | 3091012 | 3091977 | − | GENE_03027 | Prodigal: 2.6 | CDS | 1.10.3.- | — | — | — | E0TW67 | qoxA | — | — | Quinol oxidase subunit 2 precursor |
| Contig1 | 3092480 | 3092725 | + | GENE_03028 | Prodigal: 2.6 | CDS | — | — | PF04226.7 | — | — | — | — | — | Transglycosylase associated protein |
| Contig1 | 3092742 | 3094283 | − | GENE_03029 | Prodigal: 2.6 | CDS | 2.7.7.12 | — | — | — | E8MF11 | galT_2 | — | — | Galactose-1-phosphate uridylyltransferase |
| Contig1 | 3094525 | 3094932 | − | GENE_03030 | Prodigal: 2.6 | CDS | — | — | PF04138.8 | — | — | — | — | — | GtrA-like protein |
| Contig1 | 3094991 | 3095614 | − | GENE_03031 | Prodigal: 2.6 | CDS | — | — | — | — | P28815 | tetC_2 | — | — | Transposon Tn10 TetC protein |
| Contig1 | 3095950 | 3096111 | + | GENE_03032 | Prodigal: 2.6 | CDS | — | — | — | — | P0C8M5 | slrA | — | — | Transcriptional regulator SlrA |
| Contig1 | 3096329 | 3097009 | + | GENE_03033 | Prodigal: 2.6 | CDS | 2.1.1.222 | — | — | — | Q4K8M4 | ubiG | — | — | Ubiquinone biosynthesis O-methyltransferase |
| Contig1 | 3097009 | 3097683 | + | GENE_03034 | Prodigal: 2.6 | CDS | — | — | — | — | — | — | — | — | hypothetical protein |
| Contig1 | 3097704 | 3098306 | − | GENE_03035 | Prodigal: 2.6 | CDS | — | — | PF01323.14 | — | — | — | — | — | DSBA-like thioredoxin domain protein |
| Contig1 | 3098393 | 3099649 | − | GENE_03036 | Prodigal: 2.6 | CDS | 1.11.1.- | — | — | — | P39597 | efeN | — | — | putative deferrochelatase/peroxidase EfeN precursor |
| Contig1 | 3100061 | 3100735 | − | GENE_03037 | Prodigal: 2.6 | CDS | 2.5.1.3 | — | — | — | P39594 | thiE | — | — | Thiamine-phosphate synthase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3100732 | 3101550 | − | GENE_03038 | Prodigal: 2.6 | CDS | 2.7.1.50 | | | | P39593 | thiM | | | Hydroxyethylthiazole kinase |
| Contig1 | 3101553 | 3102461 | − | GENE_03039 | Prodigal: 2.6 | CDS | | | | | P27111 | cynR | | | HTH-type transcriptional regulator CynR |
| Contig1 | 3102568 | 3102954 | + | GENE_03040 | Prodigal: 2.6 | CDS | | | | | P60647 | cidA_1 | | | Holin-like protein CidA |
| Contig1 | 3102936 | 3103616 | + | GENE_03041 | Prodigal: 2.6 | CDS | | | | | P0AD19 | yohK | | | Inner membrane protein YohK |
| Contig1 | 3103746 | 3103940 | + | GENE_03042 | Prodigal: 2.6 | CDS | | | | | | | | | hypothetical protein |
| Contig1 | 3104095 | 3104856 | + | GENE_03043 | Prodigal: 2.6 | CDS | | | | | P71039 | mta | | | HTH-type transcriptional activator mta |
| Contig1 | 3105040 | 3106227 | − | GENE_03044 | Prodigal: 2.6 | CDS | 2.1.1.191 | | | | P75876 | rlmI | | | Ribosomal RNA large subunit methyltransferase I |
| Contig1 | 3106322 | 3106705 | + | GENE_03045 | Prodigal: 2.6 | CDS | 4.4.1.5 | | | | P44638 | gloA | | | Lactoylglutathione lyase |
| Contig1 | 3106734 | 3108068 | − | GENE_03046 | Prodigal: 2.6 | CDS | | | | | P46317 | licC_1 | | | Lichenan permease IIC component |
| Contig1 | 3108230 | 3109975 | + | GENE_03047 | Prodigal: 2.6 | CDS | 3.4.21.- | | | | P16396 | epr | | | Minor extracellular protease Epr precursor |
| Contig1 | 3110032 | 3110892 | − | GENE_03048 | Prodigal: 2.6 | CDS | | | | | P25148 | gspA | | | General stress protein A |
| Contig1 | 3111152 | 3111784 | − | GENE_03049 | Prodigal: 2.6 | CDS | 2.7.6.5 | | | | P39583 | ywaC | | | GTP pyrophosphokinase YwaC |
| Contig1 | 3111916 | 3112851 | − | GENE_03050 | Prodigal: 2.6 | CDS | 2.5.1.74 | | | | P32166 | menA | | | 1,4-dihydroxy-2-naphthoate octaprenyltransferase |
| Contig1 | 3113295 | 3113444 | + | GENE_03051 | Prodigal: 2.6 | CDS | | | PF12459.2 | | | | | | D-Ala-teichoic acid biosynthesis protein |
| Contig1 | 3113460 | 3114971 | + | GENE_03052 | Prodigal: 2.6 | CDS | 6.1.1.13 | | | | P39581 | dltA | | | D-alanine--poly(phosphoribitol) ligase subunit 1 |
| Contig1 | 3114968 | 3116149 | + | GENE_03053 | Prodigal: 2.6 | CDS | 2.3.1.- | | | | O25526 | patA_3 | | | Peptidoglycan O-acetyltransferase |
| Contig1 | 3116166 | 3116402 | + | GENE_03054 | Prodigal: 2.6 | CDS | 6.1.1.13 | | | | P39579 | dltC | | | D-alanine--poly(phosphoribitol) ligase subunit 2 |
| Contig1 | 3116403 | 3117587 | + | GENE_03055 | Prodigal: 2.6 | CDS | | | PF0491406 | | | | | DltD C-terminal region | hypothetical protein |
| Contig1 | 3117774 | 3118862 | + | GENE_03056 | Prodigal: 2.6 | CDS | 2.6.1.42 | | | | P39576 | ilvK | | | Branched-chain-amino-acid aminotransferase 2 |
| Contig1 | 3118903 | 3120231 | − | GENE_03057 | Prodigal: 2.6 | CDS | 3.2.1.86 | | | | P46320 | licH | | | putative 6-phospho-beta-glucosidase |
| Contig1 | 3120228 | 3120560 | − | GENE_03058 | Prodigal: 2.6 | CDS | 2.7.1.- | | | | P46319 | licA | | | Lichenan-specific phosphotransferase enzyme IIA component |
| Contig1 | 3120579 | 3121937 | − | GENE_03059 | Prodigal: 2.6 | CDS | | | | | P46317 | licC_2 | | | Lichenan permease IIC component |
| Contig1 | 3121953 | 3122261 | − | GENE_03060 | Prodigal: 2.6 | CDS | 2.7.1.69 | | | | P46318 | licB | | | Lichenan-specific phosphotransferase enzyme IIB component |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3122360 | 3124300 | − | GENE_03061 | Prodigal: 2.6 | CDS | — | — | — | — | P46321 | licR_2 | — | — | putative licABCH operon regulator |
| Contig1 | 3124633 | 3125223 | − | GENE_03062 | Prodigal: 2.6 | CDS | — | — | — | MF_00527 | — | — | — | — | Putative 3-methyladenine DNA glyosylase |
| Contig1 | 3125435 | 3126463 | + | GENE_03063 | Prodigal: 2.6 | CDS | — | — | — | — | P40410 | feuB_2 | — | — | Iron-uptake system permease protein FeuB |
| Contig1 | 3126464 | 3127477 | + | GENE_03064 | Prodigal: 2.6 | CDS | — | — | — | — | P40411 | feuC2 | — | — | Iron-uptake system permease protein FeuC |
| Contig1 | 3127494 | 3128390 | + | GENE_03065 | Prodigal: 2.6 | CDS | — | — | — | — | O31567 | yfiY | — | — | putative siderophore-binding lipoprotein YfiY precursor |
| Contig1 | 3128493 | 3128843 | + | GENE_03066 | Prodigal: 2.6 | CDS | — | — | — | — | P96677 | aseR | — | — | HTH-type transcriptional repressor AseR |
| Contig1 | 3128857 | 3130155 | + | GENE_03067 | Prodigal: 2.6 | CDS | — | — | — | — | P0AB93 | arsB_2 | — | — | Arsenical pump membrane protein |
| Contig1 | 3130308 | 3130619 | + | GENE_03068 | Prodigal: 2.6 | CDS | 2.7.1.69 | — | — | — | O05505 | gmuB | — | — | Oligo-beta-mannoside-specific phosphotransferase enzyme IIB component |
| Contig1 | 3130634 | 3130951 | + | GENE_03069 | Prodigal: 2.6 | CDS | 2.7.1.- | — | — | — | O05506 | gmuA | — | — | Oligo-beta-mannoside-specific phosphotransferase enzyme IIA component |
| Contig1 | 3130970 | 3132289 | + | GENE_03070 | Prodigal: 2.6 | CDS | — | — | — | — | O05507 | gmuC | — | — | Oligo-beta-mannoside permease IIC component |
| Contig1 | 3132319 | 3133719 | + | GENE_03071 | Prodigal: 2.6 | CDS | 3.2.1.86 | — | — | — | O05508 | gmuD | — | — | 6-phospho-beta-glucosidase GmuD |
| Contig1 | 3133739 | 3134620 | + | GENE_03072 | Prodigal: 2.6 | CDS | 2.7.1.4 | — | — | — | O05510 | gmuE | — | — | Putative fructokinase |
| Contig1 | 3134617 | 3135561 | + | GENE_03073 | Prodigal: 2.6 | CDS | 5.3.1.8 | — | — | — | O05511 | gmuF | — | — | putative mannose-6-phosphate isomerase GmuF |
| Contig1 | 3135581 | 3136663 | + | GENE_03074 | Prodigal: 2.6 | CDS | 3.2.1.78 | — | — | — | O05512 | gmuG | — | — | Mannan endo-1,4-beta-mannosidase precursor |
| Contig1 | 3136741 | 3138354 | + | GENE_03075 | Prodigal: 2.6 | CDS | 1.11.1.6 | — | — | — | Q59337 | katA_2 | — | — | Catalase |
| Contig1 | 3138394 | 3139380 | − | GENE_03076 | Prodigal: 2.6 | CDS | 3.5.1.11 | — | — | — | P12256 | — | — | — | Penicillin acylase precursor |
| Contig1 | 3139697 | 3141055 | + | GENE_03077 | Prodigal: 2.6 | CDS | — | — | — | — | P94575 | puc_2 | — | — | putative allantoin permease |
| Contig1 | 3141069 | 3141899 | − | GENE_03078 | Prodigal: 2.6 | CDS | 4.2.1.136 | — | — | — | P94368 | nnrD | — | — | ADP-dependent (S)-NAD(P)H-hydrate dehydratase |
| Contig1 | 3141990 | 3143720 | − | GENE_03079 | Prodigal: 2.6 | CDS | — | — | — | — | Q57538 | — | — | — | putative ABC transporter ATP-binding protein |
| Contig1 | 3143717 | 3145420 | − | GENE_03080 | Prodigal: 2.6 | CDS | — | — | — | — | P29018 | cydD | — | — | ATP-binding/permease protein CydD |
| Contig1 | 3145420 | 3146436 | − | GENE_03081 | Prodigal: 2.6 | CDS | 1.10.3.10 | — | — | — | P0ABK2 | cydB | — | — | Cytochrome bd-I ubiquinol oxidase subunit 2 |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3146420 | 3147826 | − | GENE_03082 | Prodigal: 2.6 | CDS | 1.10.3.- | — | — | — | Q09049 | cydA | — | — | Cytochrome bd ubiquinol oxidase subunit 1 |
| Contig1 | 3148329 | 3149672 | + | GENE_03083 | Prodigal: 2.6 | CDS | — | — | — | — | P94363 | cimH | — | — | Citrate/malate transporter |
| Contig1 | 3149708 | 3150550 | − | GENE_03084 | Prodigal: 2.6 | CDS | 3.5.1.- | — | — | — | Q6TYB1 | icaB | — | — | Poly-beta-1,6-N-acetyl-D-glucosamine N-deacetylase precursor |
| Contig1 | 3150650 | 3151750 | − | GENE_03085 | Prodigal: 2.6 | CDS | 3.6.3.- | — | — | — | O50454 | sugC | — | — | Trehalose import ATP-binding protein SugC |
| Contig1 | 3151868 | 3152761 | − | GENE_03086 | Prodigal: 2.6 | CDS | — | PRK04164 | — | — | Q54087 | lrp_2 | — | — | Leucine-rich protein |
| Contig1 | 3152928 | 3153764 | − | GENE_03087 | Prodigal: 2.6 | CDS | — | — | — | — | — | — | — | — | hypothetical protein |
| Contig1 | 3154179 | 3154817 | + | GENE_03088 | Prodigal: 2.6 | CDS | — | — | PF11611.2 | — | — | — | — | — | Telomeric repeat-binding factor 2 |
| Contig1 | 3154864 | 3155880 | − | GENE_03089 | Prodigal: 2.6 | CDS | 5.1.3.2 | — | — | — | E8MF10 | lnpD | — | — | UDP-glucose 4-epimerase |
| Contig1 | 3156091 | 3157323 | + | GENE_03090 | Prodigal: 2.6 | CDS | 3.4.11.4 | — | — | — | Q81WU4 | pepT_2 | — | — | Peptidase T |
| Contig1 | 3157422 | 3157538 | + | GENE_03091 | Prodigal: 2.6 | CDS | — | — | — | — | — | — | — | — | hypothetical protein |
| Contig1 | 3157900 | 3158067 | + | GENE_03092 | Prodigal: 2.6 | CDS | — | — | — | — | — | — | — | — | hypothetical protein |
| Contig1 | 3158170 | 3158646 | + | GENE_03093 | Prodigal: 2.6 | CDS | — | — | — | — | — | — | — | — | hypothetical protein |
| Contig1 | 3158896 | 3160032 | + | GENE_03094 | Prodigal: 2.6 | CDS | 2.1.1.14 | — | — | — | P80877 | metE_2 | — | — | 5-methyltetra-hydropteroyl-triglutamate--homocysteine methyltransferase |
| Contig1 | 3160066 | 3160947 | − | GENE_03095 | Prodigal: 2.6 | CDS | 2.1.1.187 | — | — | — | P36999 | rlmA | — | — | 23S rRNA (guanine(745)-N(1))-methyltransferase |
| Contig1 | 3161551 | 3162744 | + | GENE_03096 | Prodigal: 2.6 | CDS | — | — | — | — | P42312 | nupG | — | — | Purine nucleoside transport protein NupG |
| Contig1 | 3162792 | 3163466 | − | GENE_03097 | Prodigal: 2.6 | CDS | 3.5.1.- | — | — | — | O34798 | pdaC_2 | — | — | Peptidoglycan-N-acetylmuramic acid deacetylase PdaC |
| Contig1 | 3163607 | 3163909 | − | GENE_03098 | Prodigal: 2.6 | CDS | — | — | — | — | — | — | — | — | hypothetical protein |
| Contig1 | 3163930 | 3164613 | − | GENE_03099 | Prodigal: 2.6 | CDS | — | — | — | — | — | — | — | — | hypothetical protein |
| Contig1 | 3164799 | 3166850 | + | GENE_03100 | Prodigal: 2.6 | CDS | 1.11.1.6 | — | — | — | P21179 | katE | — | — | Catalase HPH |
| Contig1 | 3167051 | 3168331 | + | GENE_03101 | Prodigal: 2.6 | CDS | — | — | — | — | P42308 | citN | — | — | Citrate transporter |
| Contig1 | 3168373 | 3169104 | + | GENE_03102 | Prodigal: 2.6 | CDS | 3.2.1.73 | — | — | — | P04957 | bglS | — | — | Beta-glucanase precursor |
| Contig1 | 3169354 | 3170187 | − | GENE_03103 | Prodigal: 2.6 | CDS | — | — | — | — | P39805 | licT | — | — | Transcription antiterminator LicT |
| Contig1 | 3170362 | 3171609 | + | GENE_03104 | Prodigal: 2.6 | CDS | — | — | PF11700.2 | — | — | — | — | — | Vacuole effluxer Atg22 like protein |
| Contig1 | 3171641 | 3173080 | − | GENE_03105 | Prodigal: 2.6 | CDS | 3.6.4.13 | — | — | — | P42305 | dbpA_2 | — | — | ATP-dependent RNA helicase DbpA |
| Contig1 | 3173232 | 3173510 | − | GENE_03106 | Prodigal: 2.6 | CDS | — | — | — | — | — | — | — | — | hypothetical protein |
| Contig1 | 3173566 | 3173826 | − | GENE_03107 | Prodigal: 2.6 | CDS | — | — | — | — | — | — | — | — | hypothetical protein |
| Contig1 | 3173843 | 3174208 | − | GENE_03108 | Prodigal: 2.6 | CDS | — | — | — | — | D4G3R3 | wapI | — | — | Immunity protein WapI |
| Contig1 | 3174202 | 3174363 | − | GENE_03109 | Prodigal: 2.6 | CDS | — | — | — | — | — | — | — | — | hypothetical protein |
| Contig1 | 3174466 | 3175293 | − | GENE_03110 | Prodigal: 2.6 | CDS | — | — | — | — | — | — | — | — | hypothetical protein |
| Contig1 | 3175336 | 3175812 | − | GENE_03111 | Prodigal: 2.6 | CDS | — | — | — | — | — | — | — | — | hypothetical protein |
| Contig1 | 3175879 | 3176286 | − | GENE_03112 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3177258 | 3178322 | − | GENE_03113 | Prodigal: 2.6 | CDS | 4.2.2.10 | — | — | — | P94449 | pelB | — | — | Pectin lyase precursor |
| Contig1 | 3178464 | 3179375 | − | GENE_03114 | Prodigal: 2.6 | CDS | — | — | PF00892.14 | — | — | — | — | — | EamA-like transporter family protein |
| Contig1 | 3179524 | 3179970 | − | GENE_03115 | Prodigal: 2.6 | CDS | — | — | — | — | O07552 | nhaX_2 | — | — | Stress response protein NhaX |
| Contig1 | 3180222 | 3183353 | + | GENE_03116 | Prodigal: 2.6 | CDS | — | — | — | MF_00204 | — | uvrB_3 | — | — | UvrABC system protein B |
| Contig1 | 3183342 | 3183731 | − | GENE_03117 | Prodigal: 2.6 | CDS | 3.6.1.65 | — | — | — | P77788 | nudG | — | — | CTP pyrophosphohydrolase |
| Contig1 | 3183916 | 3184734 | − | GENE_03118 | Prodigal: 2.6 | CDS | 3.2.1.99 | — | — | — | P42293 | abn2_1 | — | — | Extracellular endo-alpha-(1−>5)-L-arabinanase 2 precursor |
| Contig1 | 3184731 | 3185321 | − | GENE_03119 | Prodigal: 2.6 | CDS | 3.2.1.99 | — | — | — | P42293 | abn2_2 | — | — | Extracellular endo-alpha-(1−>5)-L-arabinanase 2 precursor |
| Contig1 | 3185563 | 3186009 | + | GENE_03120 | Prodigal: 2.6 | CDS | — | — | — | — | P10943 | hutP | — | — | Hut operon positive regulatory protein |
| Contig1 | 3186117 | 3187660 | + | GENE_03121 | Prodigal: 2.6 | CDS | 4.3.1.3 | — | — | — | P10944 | hutH | — | — | Histidine ammonia-lyase |
| Contig1 | 3187657 | 3189321 | + | GENE_03122 | Prodigal: 2.6 | CDS | 4.2.1.49 | — | — | — | P25503 | hutU | — | — | Urocanate hydratase |
| Contig1 | 3189323 | 3190588 | + | GENE_03123 | Prodigal: 2.6 | CDS | 3.5.2.7 | — | — | — | P42084 | hutI | — | — | Imidazolonepropionase |
| Contig1 | 3190581 | 3191531 | + | GENE_03124 | Prodigal: 2.6 | CDS | 3.5.3.8 | — | — | — | P42068 | hutG | — | — | Formimidoylglutamase |
| Contig1 | 3191602 | 3193020 | + | GENE_03125 | Prodigal: 2.6 | CDS | — | — | — | — | P39137 | rocE_1 | — | — | Amino-acid permease RocE |
| Contig1 | 3193061 | 3194362 | − | GENE_03126 | Prodigal: 2.6 | CDS | 2.4.2.2 | — | — | — | Q7A4D0 | pdp | — | — | Pyrimidine-nucleoside phosphorylase |
| Contig1 | 3194390 | 3195571 | − | GENE_03127 | Prodigal: 2.6 | CDS | — | — | — | — | P0AFF2 | nupC | — | — | Nucleoside permease NupC |
| Contig1 | 3195664 | 3196332 | − | GENE_03128 | Prodigal: 2.6 | CDS | 4.1.2.4 | — | — | — | P99102 | deoC1 | — | — | Deoxyribose-phosphate aldolase 1 |
| Contig1 | 3196423 | 3197364 | − | GENE_03129 | Prodigal: 2.6 | CDS | — | — | — | — | P39140 | deoR | — | — | Deoxyribonucleoside regulator |
| Contig1 | 3197435 | 3198247 | − | GENE_03130 | Prodigal: 2.6 | CDS | 3.1.3.23 | — | — | — | P0A8Y5 | yidA_2 | — | — | Sugar phosphatase YidA |
| Contig1 | 3198316 | 3198840 | − | GENE_03131 | Prodigal: 2.6 | CDS | — | — | — | — | — | — | — | — | hypothetical protein |
| Contig1 | 3198830 | 3199249 | − | GENE_03132 | Prodigal: 2.6 | CDS | — | — | — | — | — | — | — | — | hypothetical protein |
| Contig1 | 3199361 | 3199747 | + | GENE_03133 | Prodigal: 2.6 | CDS | — | — | — | — | — | — | — | — | hypothetical protein |
| Contig1 | 3199905 | 3200270 | + | GENE_03134 | Prodigal: 2.6 | CDS | — | — | — | — | — | — | — | — | hypothetical protein |
| Contig1 | 3200321 | 3200713 | + | GENE_03135 | Prodigal: 2.6 | CDS | — | — | — | — | — | — | — | — | hypothetical protein |
| Contig1 | 3200843 | 3201805 | + | GENE_03136 | Prodigal: 2.6 | CDS | — | — | — | — | P54941 | yxeB | — | — | Iron(3+)-hydroxamate-binding protein YxeB precursor |
| Contig1 | 3201846 | 3202193 | − | GENE_03137 | Prodigal: 2.6 | CDS | — | — | — | — | — | — | — | — | hypothetical protein |
| Contig1 | 3202207 | 3204075 | − | GENE_03138 | Prodigal: 2.6 | CDS | — | — | — | — | P42424 | yxdM | — | — | ABC transporter permease protein YxdM |
| Contig1 | 3204050 | 3204823 | − | GENE_03139 | Prodigal: 2.6 | CDS | — | — | — | — | P42423 | yxdL | — | — | ABC transporter ATP-binding protein YxdL |
| Contig1 | 3204968 | 3205945 | − | GENE_03140 | Prodigal: 2.6 | CDS | 2.7.13.3 | — | — | — | Q5H108 | graS_2 | — | — | Sensor histidine kinase GraS |
| Contig1 | 3205942 | 3206673 | − | GENE_03141 | Prodigal: 2.6 | CDS | — | — | — | — | Q932F1 | graR_2 | — | — | Response regulator protein GraR |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3206781 | 3208220 | − | GENE_03142 | Prodigal: 2.6 | CDS | 2.7.13.3 | — | — | — | P08400 | phoR_3 | — | — | Phosphate regulon sensor protein PhoR |
| Contig1 | 3208217 | 3208939 | − | GENE_03143 | Prodigal: 2.6 | CDS | — | — | — | — | Q9L524 | srrA_2 | — | — | Transcriptional regulatory protein SrrA |
| Contig1 | 3209182 | 3210093 | + | GENE_03144 | Prodigal: 2.6 | CDS | 3.6.3.- | — | — | — | P94374 | yxlF_5 | — | — | putative ABC transporter ATP-binding protein YxlF |
| Contig1 | 3210090 | 3210848 | + | GENE_03145 | Prodigal: 2.6 | CDS | — | — | PF12730.1 | — | — | — | — | — | ABC-2 family transporter protein |
| Contig1 | 3210865 | 3211599 | + | GENE_03146 | Prodigal: 2.6 | CDS | — | — | PF12730.1 | — | — | — | — | — | ABC-2 family transporter protein |
| Contig1 | 3211885 | 3212091 | + | GENE_03147 | Prodigal: 2.6 | CDS | — | — | — | — | P43683 | mrsA | — | — | Lantibiotic mersacidin precursor |
| Contig1 | 3212187 | 3212828 | + | GENE_03148 | Prodigal: 2.6 | CDS | — | — | — | — | P0AA16 | ompR | — | — | Transcriptional regulatory protein OmpR |
| Contig1 | 3212877 | 3213461 | − | GENE_03149 | Prodigal: 2.6 | CDS | 4.1.1.- | — | — | — | Q9RC23 | mrsD | — | — | Mersacidin decarboxylase |
| Contig1 | 3213672 | 3216860 | + | GENE_03150 | Prodigal: 2.6 | CDS | — | — | PF05147.7 | — | — | — | — | — | Lanthionine synthetase C-like protein |
| Contig1 | 3216913 | 3219113 | + | GENE_03151 | Prodigal: 2.6 | CDS | 3.4.22.- | — | — | — | P59852 | lagD | — | — | Lactococcin-G-processing and transport ATP-binding protein LagD |
| Contig1 | 3219392 | 3220264 | − | GENE_03152 | Prodigal: 2.6 | CDS | 4.1.2.29 | — | — | — | P42420 | iolJ | — | — | 6-phospho-5-dehydro-2-deoxy-D-gluconate aldolase |
| Contig1 | 3220267 | 3221163 | − | GENE_03153 | Prodigal: 2.6 | CDS | 5.3.99.- | PRK09856 | — | — | P42419 | iolI | — | — | Inosose isomerase |
| Contig1 | 3221197 | 3222066 | − | GENE_03154 | Prodigal: 2.6 | CDS | — | — | — | — | — | — | — | — | fructoselysine 3-epimerase |
| Contig1 | 3222085 | 3223119 | − | GENE_03155 | Prodigal: 2.6 | CDS | 1.1.1.18 | — | — | — | P26935 | iolG | — | — | Inositol 2-dehydrogenase/D-chiro-inositol 3-dehydrogenase |
| Contig1 | 3223142 | 3224437 | − | GENE_03156 | Prodigal: 2.6 | CDS | — | — | — | — | Q46909 | ygcS | — | — | Inner membrane metabolite transport protein YgcS |
| Contig1 | 3224450 | 3225346 | − | GENE_03157 | Prodigal: 2.6 | CDS | 4.2.1.44 | — | — | — | P42416 | iolE | — | — | Inosose dehydratase |
| Contig1 | 3225362 | 3227275 | − | GENE_03158 | Prodigal: 2.6 | CDS | 3.7.1.- | — | — | — | P42415 | iolD | — | — | 3D-(3,5/4)-trihydroxy-cyclohexane-1,2-dione hydrolase |
| Contig1 | 3227300 | 3228292 | − | GENE_03159 | Prodigal: 2.6 | CDS | 2.7.1.92 | — | — | — | P42414 | iolC_2 | — | — | 5-dehydro-2-deoxygluconokinase |
| Contig1 | 3228316 | 3229131 | − | GENE_03160 | Prodigal: 2.6 | CDS | 5.3.1.- | — | — | — | P42413 | iolB | — | — | 5-deoxy-glucuronate isomerase |
| Contig1 | 3229205 | 3230668 | − | GENE_03161 | Prodigal: 2.6 | CDS | 1.2.1.27 | — | — | — | P42412 | iolA | — | — | Methylmalonate semialdehyde dehydrogenase [acylating] |
| Contig1 | 3231112 | 3231867 | + | GENE_03162 | Prodigal: 2.6 | CDS | — | — | — | — | P15082 | srlR | — | — | Glucitol operon repressor |
| Contig1 | 3231945 | 3232877 | + | GENE_03163 | Prodigal: 2.6 | CDS | 1.1.1.- | — | — | — | P80874 | yhdN_2 | — | — | General stress protein 69 |
| Contig1 | 3232997 | 3234385 | + | GENE_03164 | Prodigal: 2.6 | CDS | — | — | — | — | P46333 | csbC2 | — | — | putative metabolite transport protein CsbC |

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3234428 | 3236308 | − | GENE_03165 | Prodigal: 2.6 | CDS | — | — | — | — | P0A6Z3 | htpG | — | — | Chaperone protein HtpG |
| Contig1 | 3236480 | 3236728 | − | GENE_03166 | Prodigal: 2.6 | CDS | — | — | — | — | — | — | — | — | hypothetical protein |
| Contig1 | 3236857 | 3237678 | + | GENE_03167 | Prodigal: 2.6 | CDS | 1.1.1.- | — | — | — | Q9LBG2 | lvr | — | — | Levodione reductase |
| Contig1 | 3237738 | 3238337 | − | GENE_03168 | Prodigal: 2.6 | CDS | — | — | — | — | P13800 | degU_3 | — | — | Transcriptional regulatory protein DegU |
| Contig1 | 3238334 | 3239470 | − | GENE_03169 | Prodigal: 2.6 | CDS | 2.7.13.3 | — | — | — | O34757 | desK_2 | — | — | Sensor histidine kinase DesK |
| Contig1 | 3239593 | 3240642 | − | GENE_03170 | Prodigal: 2.6 | CDS | 1.14.19.- | — | — | MF_01839 | O34653 | des | — | — | Fatty acid desaturase |
| Contig1 | 3240864 | 3242021 | − | GENE_03171 | Prodigal: 2.6 | CDS | — | — | — | — | — | slmA | — | — | Nucleoid occlusion factor SlmA |
| Contig1 | 3242163 | 3243500 | + | GENE_03172 | Prodigal: 2.6 | CDS | 1.2.1.3 | — | — | — | P12693 | alkH_2 | — | — | Aldehyde dehydrogenase |
| Contig1 | 3243552 | 3244779 | − | GENE_03173 | Prodigal: 2.6 | CDS | 2.7.11.1 | — | — | — | P54741 | afsK | — | — | Serine/threonine-protein kinase AfsK |
| Contig1 | 3244883 | 3245302 | − | GENE_03174 | Prodigal: 2.6 | CDS | — | — | — | — | — | — | — | — | hypothetical protein |
| Contig1 | 3245457 | 3245756 | + | GENE_03175 | Prodigal: 2.6 | CDS | — | PRK10141 | — | — | — | — | — | — | DNA-binding transcriptional repressor ArsR |
| Contig1 | 3245835 | 3247001 | + | GENE_03176 | Prodigal: 2.6 | CDS | — | — | — | — | Q0GQS6 | pbuE_4 | — | — | Purine efflux pump PbuE |
| Contig1 | 3247071 | 3247526 | + | GENE_03177 | Prodigal: 2.6 | CDS | — | — | PF06271.6 | — | — | — | — | — | RDD family protein |
| Contig1 | 3247562 | 3248248 | − | GENE_03178 | Prodigal: 2.6 | CDS | — | — | PF12681.1 | — | — | — | — | — | Glyoxalase-like domain protein |
| Contig1 | 3248371 | 3250269 | − | GENE_03179 | Prodigal: 2.6 | CDS | 3.6.4.12 | — | — | MF_01451 | — | addA_2 | — | — | ATP-dependent helicase/nuclease subunit A |
| Contig1 | 3250339 | 3251229 | − | GENE_03180 | Prodigal: 2.6 | CDS | — | — | — | MF_00188 | — | htpX_3 | — | — | Protease HtpX |
| Contig1 | 3251377 | 3252288 | − | GENE_03181 | Prodigal: 2.6 | CDS | — | — | — | — | P24202 | mrr | — | — | Mrr restriction system protein |
| Contig1 | 3252850 | 3253413 | + | GENE_03182 | Prodigal: 2.6 | CDS | 1.11.1.15 | — | — | — | P80239 | ahpC | — | — | Alkyl hydroperoxide reductase subunit C |
| Contig1 | 3253427 | 3254956 | + | GENE_03183 | Prodigal: 2.6 | CDS | 1.6.99.3 | — | — | — | P42974 | ahpF | — | — | NADH dehydrogenase |
| Contig1 | 3255047 | 3256393 | − | GENE_03184 | Prodigal: 2.6 | CDS | — | — | — | — | P0AAE0 | cycA | — | — | D-serine/D-alanine/glycine transporter |
| Contig1 | 3256917 | 3258842 | + | GENE_03185 | Prodigal: 2.6 | CDS | 3.1.3.11 | — | — | — | Q45597 | fbp | — | — | Fructose-1,6-bisphosphatase class 3 |
| Contig1 | 3258895 | 3259359 | − | GENE_03186 | Prodigal: 2.6 | CDS | 1.17.2.1 | — | — | — | Q88FX9 | nicA | — | — | Nicotinate dehydrogenase subunit A |
| Contig1 | 3259352 | 3260194 | − | GENE_03187 | Prodigal: 2.6 | CDS | 1.17.1.5 | — | — | — | Q0QLF4 | ndhF | — | — | Nicotinate dehydrogenase FAD-subunit |
| Contig1 | 3260181 | 3260492 | − | GENE_03188 | Prodigal: 2.6 | CDS | 1.17.1.4 | — | — | — | Q46799 | xdhA_1 | — | — | Xanthine dehydrogenase molybdenum-binding subunit |
| Contig1 | 3260495 | 3262510 | − | GENE_03189 | Prodigal: 2.6 | CDS | 1.17.1.4 | — | — | — | Q46799 | xdhA_2 | — | — | Xanthine dehydrogenase molybdenum-binding subunit |
| Contig1 | 3262516 | 3263136 | − | GENE_03190 | Prodigal: 2.6 | CDS | — | — | — | — | O32146 | pucB | — | — | Purine catabolism protein PucB |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3263133 | 3264149 | − | GENE_03191 | Prodigal: 2.6 | CDS | 1.17.1.4 | — | — | — | O32147 | pucA | — | — | putative xanthine dehydrogenase subunit A |
| Contig1 | 3264218 | 3265231 | − | GENE_03192 | Prodigal: 2.6 | CDS | — | — | PF04632.6 | — | — | — | — | — | Fusaric acid resistance protein family protein |
| Contig1 | 3266489 | 3267529 | + | GENE_03193 | Prodigal: 2.6 | CDS | — | — | — | — | — | — | — | — | hypothetical protein |
| Contig1 | 3267545 | 3268357 | + | GENE_03194 | Prodigal: 2.6 | CDS | — | — | — | — | — | — | — | — | hypothetical protein |
| Contig1 | 3268631 | 3269320 | − | GENE_03195 | Prodigal: 2.6 | CDS | — | — | — | — | — | — | — | — | hypothetical protein |
| Contig1 | 3269339 | 3270742 | − | GENE_03196 | Prodigal: 2.6 | CDS | 3.1.5.1 | — | — | — | P15723 | dgt | — | — | Deoxyguanosine-triphosphate triphosphohydrolase |
| Contig1 | 3270823 | 3271302 | − | GENE_03197 | Prodigal: 2.6 | CDS | 2.1.1.177 | — | — | — | Q45601 | rlmH | — | — | Ribosomal RNA large subunit methyltransferase H |
| Contig1 | 3271383 | 3271553 | − | GENE_03198 | Prodigal: 2.6 | CDS | — | — | — | — | — | — | — | — | hypothetical protein |
| Contig1 | 3271707 | 3271877 | − | GENE_03199 | Prodigal: 2.6 | CDS | — | — | — | — | — | — | — | — | hypothetical protein |
| Contig1 | 3272194 | 3272889 | − | GENE_03200 | Prodigal: 2.6 | CDS | — | — | — | — | — | — | — | — | hypothetical protein |
| Contig1 | 3273017 | 3274180 | − | GENE_03201 | Prodigal: 2.6 | CDS | — | — | — | — | — | — | — | — | hypothetical protein |
| Contig1 | 3274191 | 3274940 | − | GENE_03202 | Prodigal: 2.6 | CDS | — | — | — | — | — | — | — | — | hypothetical protein |
| Contig1 | 3275122 | 3276102 | + | GENE_03203 | Prodigal: 2.6 | CDS | 1.1.1.- | — | — | — | P80874 | yhdN_3 | — | — | General stress protein 69 |
| Contig1 | 3276132 | 3276605 | − | GENE_03204 | Prodigal: 2.6 | CDS | 2.3.1.- | — | — | — | O32292 | yycN | — | — | putative N-acetyl-transferase YycN |
| Contig1 | 3276643 | 3276777 | − | GENE_03205 | Prodigal: 2.6 | CDS | — | — | — | — | — | — | — | — | hypothetical protein |
| Contig1 | 3276764 | 3277879 | − | GENE_03206 | Prodigal: 2.6 | CDS | 3.1.-.- | — | — | — | P96649 | rapI | — | — | Response regulator aspartate phosphatase I |
| Contig1 | 3278010 | 3278900 | − | GENE_03207 | Prodigal: 2.6 | CDS | 3.5.3.1 | — | — | — | P39138 | rocF | — | — | Arginase |
| Contig1 | 3278974 | 3280374 | − | GENE_03208 | Prodigal: 2.6 | CDS | — | — | — | — | P39137 | rocE_2 | — | — | Amino-acid permease RocE |
| Contig1 | 3280598 | 3281803 | − | GENE_03209 | Prodigal: 2.6 | CDS | 2.6.1.13 | — | — | — | P38021 | rocD | — | — | Ornithine aminotransferase |
| Contig1 | 3282033 | 3282668 | − | GENE_03210 | Prodigal: 2.6 | CDS | — | — | — | — | O32241 | sdpI | — | — | Immunity protein SdpI |
| Contig1 | 3282665 | 3282952 | − | GENE_03211 | Prodigal: 2.6 | CDS | — | — | — | — | O32242 | sdpR | — | — | Transcriptional repressor SdpR |
| Contig1 | 3283125 | 3284540 | + | GENE_03212 | Prodigal: 2.6 | CDS | — | — | — | — | P38022 | rocR_2 | — | — | Arginine utilization regulatory protein RocR |
| Contig1 | 3284582 | 3285301 | − | GENE_03213 | Prodigal: 2.6 | CDS | — | — | PF02373.16 | — | — | — | — | — | JmjC domain protein |
| Contig1 | 3285315 | 3286940 | − | GENE_03214 | Prodigal: 2.6 | CDS | — | — | — | — | P0A9W3 | yjjK | — | — | putative ABC transporter ATP-binding protein YjjK |
| Contig1 | 3286968 | 3288158 | − | GENE_03215 | Prodigal: 2.6 | CDS | — | PRK11551 | — | — | — | — | — | — | putative 3-hydroxyphenylpropionic transporter MhpT |
| Contig1 | 3288177 | 3289499 | − | GENE_03216 | Prodigal: 2.6 | CDS | — | — | PF00496.16 | — | — | — | — | — | Bacterial extracellular solute-binding proteins, family 5 Middle |
| Contig1 | 3289496 | 3290503 | − | GENE_03217 | Prodigal: 2.6 | CDS | 2.7.7.80 | — | — | — | P12282 | moeB | — | — | Molybdopterin-synthase adenylyltransferase |
| Contig1 | 3290735 | 3292153 | − | GENE_03218 | Prodigal: 2.6 | CDS | 2.7.13.3 | — | — | — | O69729 | tcrY_2 | — | — | putative sensor histidine kinase TcrY |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3292150 | 3292362 | − | GENE_03219 | Prodigal: 2.6 | CDS | — | — | PF00486.22 | — | — | — | — | Transcriptional protein, C regulatory terminal | hypothetical protein |
| Contig1 | 3292854 | 3294050 | − | GENE_03220 | Prodigal: 2.6 | CDS | 3.4.21.107 | — | — | — | Q9LA06 | htrA_2 | — | — | Serine protease Do-like HtrA |
| Contig1 | 3294137 | 3294931 | − | GENE_03221 | Prodigal: 2.6 | CDS | 3.-.-.- | — | — | — | C0SP91 | yycJ | — | — | Putative metallo-hydrolase YycJ |
| Contig1 | 3294946 | 3295785 | − | GENE_03222 | Prodigal: 2.6 | CDS | — | — | — | — | Q45612 | yycI | — | — | Two-component system YycFG regulatory protein |
| Contig1 | 3295772 | 3297130 | − | GENE_03223 | Prodigal: 2.6 | CDS | — | — | — | — | Q794W0 | yycH | — | — | Two-component system YycF/YycG regulatory protein YycH |
| Contig1 | 3297120 | 3298955 | − | GENE_03224 | Prodigal: 2.6 | CDS | 2.7.13.3 | — | — | — | Q45614 | yycG_2 | — | — | Sensor histidine kinase YycG |
| Contig1 | 3298962 | 3299672 | − | GENE_03225 | Prodigal: 2.6 | CDS | — | — | — | — | P37478 | yycF | — | — | Transcriptional regulatory protein YycF |
| Contig1 | 3300004 | 3300077 | − | GENE_03226 | Aragorn: 1.2 | tRNA | — | — | — | — | — | — | — | — | tRNA-Phe(gaa) |
| Contig1 | 3300114 | 3300190 | − | GENE_03227 | Aragorn: 1.2 | tRNA | — | — | — | — | — | — | — | — | tRNA-Asp(gtc) |
| Contig1 | 3300274 | 3300347 | − | GENE_03228 | Aragorn: 1.2 | tRNA | — | — | — | — | — | — | — | — | tRNA-Glu(ttc) |
| Contig1 | 3300355 | 3300430 | − | GENE_03229 | Aragorn: 1.2 | tRNA | — | — | — | — | — | — | — | — | tRNA-Lys(ttt) |
| Contig1 | 3300632 | 3301924 | − | GENE_03230 | Prodigal: 2.6 | CDS | 6.3.4.4 | — | — | — | Q8LJI9 | purA | — | — | Adenylosuccinate synthetase |
| Contig1 | 3302163 | 3302576 | − | GENE_03231 | Prodigal: 2.6 | CDS | — | — | PF12681.1 | — | — | — | — | — | Glyoxalase-like domain protein |
| Contig1 | 3302694 | 3304067 | − | GENE_03232 | Prodigal: 2.6 | CDS | 3.6.4.12 | — | — | — | P37469 | dnaC | — | — | Replicative DNA helicase |
| Contig1 | 3304228 | 3304425 | + | GENE_03233 | Prodigal: 2.6 | CDS | — | — | — | — | — | — | — | — | hypothetical protein |
| Contig1 | 3304457 | 3304666 | + | GENE_03234 | Prodigal: 2.6 | CDS | — | — | — | — | — | — | — | — | hypothetical protein |
| Contig1 | 3304785 | 3304928 | + | GENE_03235 | Prodigal: 2.6 | CDS | — | — | — | — | — | — | — | — | hypothetical protein |
| Contig1 | 3305315 | 3306607 | − | GENE_03236 | Prodigal: 2.6 | CDS | 2.4.1.11 | — | — | — | O53279 | — | — | — | Glycogen synthase |
| Contig1 | 3306630 | 3307685 | − | GENE_03237 | Prodigal: 2.6 | CDS | — | — | PF01636.17 | — | — | — | — | — | Phosphotransferase enzyme familyprotein |
| Contig1 | 3307678 | 3308556 | − | GENE_03238 | Prodigal: 2.6 | CDS | 6.3.1.12 | — | — | — | H8L902 | — | — | — | D-aspartate ligase |
| Contig1 | 3308532 | 3308864 | − | GENE_03239 | Prodigal: 2.6 | CDS | — | — | — | — | — | — | — | — | hypothetical protein |
| Contig1 | 3308854 | 3310188 | − | GENE_03240 | Prodigal: 2.6 | CDS | 2.4.1.250 | — | — | — | Q8NTA6 | mshA_2 | — | — | D-inositol 3-phosphate glycosyltransferase |
| Contig1 | 3310185 | 3310841 | − | GENE_03241 | Prodigal: 2.6 | CDS | — | — | PF02585.11 | — | — | — | — | — | GlcNAc-PI de-N-acetylase |
| Contig1 | 3310929 | 3311594 | − | GENE_03242 | Prodigal: 2.6 | CDS | — | — | — | — | — | — | — | — | hypothetical protein |
| Contig1 | 3311633 | 3312082 | − | GENE_03243 | Prodigal: 2.6 | CDS | — | — | — | — | P02417 | rplI | — | — | 50S ribosomal protein L9 |
| Contig1 | 3312079 | 3314058 | − | GENE_03244 | Prodigal: 2.6 | CDS | 3.1.-.- | — | — | — | Q5SM25 | nrnA_2 | — | — | Bifunctional oligoribonuclease and PAP phosphatase NrnA |
| Contig1 | 3314089 | 3315024 | − | GENE_03245 | Prodigal: 2.6 | CDS | — | — | — | — | — | — | — | — | hypothetical protein |
| Contig1 | 3315268 | 3315420 | − | GENE_03246 | Prodigal: 2.6 | CDS | — | — | — | — | — | — | — | — | hypothetical protein |
| Contig1 | 3315512 | 3316039 | + | GENE_03247 | Prodigal: 2.6 | CDS | — | — | — | — | P23261 | cotF_3 | — | — | Spore coat protein F precursor |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3316076 | 3316447 | − | GENE_03248 | Prodigal: 2.6 | CDS | — | — | — | — | P37486 | yybR | — | — | putative HTH-type transcriptional regulator YybR |
| Contig1 | 3316654 | 3317583 | + | GENE_03249 | Prodigal: 2.6 | CDS | 3.6.1.1 | — | — | — | P37487 | PPaC | — | — | Manganese-dependent inorganic pyrophosphatase |
| Contig1 | 3317827 | 3318684 | + | GENE_03250 | Prodigal: 2.6 | CDS | — | — | — | — | P31437 | yicL | — | — | putative inner membrane transporter YicL |
| Contig1 | 3319032 | 3320453 | + | GENE_03251 | Prodigal: 2.6 | CDS | 2.4.1.10 | — | — | — | P21130 | sacB | — | — | Levansucrase precursor |
| Contig1 | 3320470 | 3322071 | + | GENE_03252 | Prodigal: 2.6 | CDS | 3.2.1.64 | — | — | — | O07003 | levB | — | — | Levanbiose-producing levanase |
| Contig1 | 3322151 | 3322813 | + | GENE_03253 | Prodigal: 2.6 | CDS | — | — | — | — | P0ACM2 | ydfH_2 | — | — | putative HTH-type transcriptional regulator YdfH |
| Contig1 | 3322891 | 3323400 | − | GENE_03254 | Prodigal: 2.6 | CDS | — | — | PF05163.6 | — | — | — | — | — | DinB family protein |
| Contig1 | 3323451 | 3324677 | − | GENE_03255 | Prodigal: 2.6 | CDS | — | — | PF07690.10 | — | — | — | — | — | Major Facilitator Superfamily protein |
| Contig1 | 3325016 | 3325384 | − | GENE_03256 | Prodigal: 2.6 | CDS | — | — | — | — | — | — | — | — | hypothetical protein |
| Contig1 | 3325415 | 3326053 | − | GENE_03257 | Prodigal: 2.6 | CDS | 1.-.-.- | — | — | — | P81102 | yodC_2 | — | — | Putative NAD(P)H nitroreductase YodC |
| Contig1 | 3326067 | 3326501 | − | GENE_03258 | Prodigal: 2.6 | CDS | — | — | — | — | B1JJ73 | slyA | — | — | Transcriptional regulator SlyA |
| Contig1 | 3326639 | 3327517 | − | GENE_03259 | Prodigal: 2.6 | CDS | — | PRK04164 | — | — | — | — | — | — | hypothetical protein |
| Contig1 | 3327700 | 3328152 | − | GENE_03260 | Prodigal: 2.6 | CDS | — | — | — | — | P69782 | hosA | — | — | Transcriptional regulator HosA |
| Contig1 | 3328273 | 3328707 | + | GENE_03261 | Prodigal: 2.6 | CDS | 2.3.1.- | — | — | — | O31628 | yjcF_2 | — | — | putative N-acetyltransferase YjcF |
| Contig1 | 3328907 | 3330361 | − | GENE_03262 | Prodigal: 2.6 | CDS | — | — | — | — | Q2G1P1 | norG_2 | — | — | HTH-type transcriptional regulator NorG |
| Contig1 | 3330497 | 3331408 | + | GENE_03263 | Prodigal: 2.6 | CDS | — | — | — | — | P0AA70 | yedA | — | — | putative inner membrane transporter YedA |
| Contig1 | 3331877 | 3332689 | + | GENE_03264 | Prodigal: 2.6 | CDS | — | — | — | — | P39075 | bmrR | — | — | Multidrug-efflux transporter 1 regulator |
| Contig1 | 3332758 | 3333447 | + | GENE_03265 | Prodigal: 2.6 | CDS | — | — | — | — | P96689 | ydiK | — | — | putative membrane protein YdfK |
| Contig1 | 3333594 | 3333755 | + | GENE_03266 | Prodigal: 2.6 | CDS | — | — | — | — | — | — | — | — | hypothetical protein |
| Contig1 | 3333785 | 3335674 | + | GENE_03267 | Prodigal: 2.6 | CDS | 5.1.3.11 | — | — | — | — | — | — | — | Cellobiose 2-epimerase |
| Contig1 | 3335671 | 3336567 | − | GENE_03268 | Prodigal: 2.6 | CDS | — | — | PF02517.10 | MF_00929 | — | — | — | — | CAAX amino terminal protease self-immunity |
| Contig1 | 3336782 | 3338113 | + | GENE_03269 | Prodigal: 2.6 | CDS | — | — | — | — | P38055 | ydjE_2 | — | — | Inner membrane metabolite transport protein YdjE |
| Contig1 | 3338144 | 3338524 | − | GENE_03270 | Prodigal: 2.6 | CDS | — | — | PF12681.1 | — | — | — | — | — | Glyoxalase-like domain protein |
| Contig1 | 3338580 | 3339518 | − | GENE_03271 | Prodigal: 2.6 | CDS | — | — | — | — | P37517 | ccpB_2 | — | — | Catabolite control protein B |
| Contig1 | 3339581 | 3340339 | − | GENE_03272 | Prodigal: 2.6 | CDS | 3.1.11.2 | — | — | — | P37454 | exoA | — | — | Exodeoxyribonuclease |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3340378 | 3340734 | − | GENE_03273 | Prodigal: 2.6 | CDS | 2.1.1.63 | — | — | — | P19220 | adaB_1 | — | — | Methylated-DNA--protein-cysteine methyltransferase, inducible |
| Contig1 | 3340741 | 3340893 | − | GENE_03274 | Prodigal: 2.6 | CDS | 2.1.1.63 | — | — | — | P19220 | adaB_2 | — | — | Methylated-DNA--protein-cysteine methyltransferase, inducible |
| Contig1 | 3340890 | 3341471 | − | GENE_03275 | Prodigal: 2.6 | CDS | 2.1.1.- | — | — | — | P19219 | adaA | — | — | Bifunctional transcriptional activator/DNA repair enzyme AdaA |
| Contig1 | 3341660 | 3341899 | − | GENE_03276 | Prodigal: 2.6 | CDS | — | — | — | — | P21475 | rpsR | — | — | 30S ribosomal protein S18 |
| Contig1 | 3341943 | 3342461 | − | GENE_03277 | Prodigal: 2.6 | CDS | — | — | — | — | P37455 | ssb | — | — | Single-stranded DNA-binding protein ssb |
| Contig1 | 3342501 | 3342788 | − | GENE_03278 | Prodigal: 2.6 | CDS | — | — | — | — | P21468 | rpsF | — | — | 30S ribosomal protein S6 |
| Contig1 | 3342900 | 3344000 | − | GENE_03279 | Prodigal: 2.6 | CDS | — | — | — | — | P44681 | ychF | — | — | Ribosome-binding ATPase YchF |
| Contig1 | 3344127 | 3346130 | − | GENE_03280 | Prodigal: 2.6 | CDS | 1.8.5.3 | — | — | — | P18775 | dmsA_2 | — | — | Dimethyl sulfoxide reductase DmsA precursor |
| Contig1 | 3346177 | 3346383 | − | GENE_03281 | Prodigal: 2.6 | CDS | — | — | — | — | — | — | — | — | hypothetical protein |
| Contig1 | 3346469 | 3347473 | − | GENE_03282 | Prodigal: 2.6 | CDS | — | — | — | — | — | — | — | — | hypothetical protein |
| Contig1 | 3347662 | 3348129 | + | GENE_03283 | Prodigal: 2.6 | CDS | 2.3.1.189 | — | — | MF_01698 | — | mshD_2 | — | — | Mycothiol acetyltransferase |
| Contig1 | 3348303 | 3348917 | + | GENE_03284 | Prodigal: 2.6 | CDS | — | — | — | — | — | — | — | — | hypothetical protein |
| Contig1 | 3348946 | 3349797 | − | GENE_03285 | Prodigal: 2.6 | CDS | — | — | — | — | Q72H91 | — | — | — | Chromosome-partitioning protein SpoOJ |
| Contig1 | 3349790 | 3350551 | − | GENE_03286 | Prodigal: 2.6 | CDS | 3.6.-.- | — | — | — | P37522 | soj | — | — | Sporulation initiation inhibitor protein Soj |
| Contig1 | 3350850 | 3351701 | − | GENE_03287 | Prodigal: 2.6 | CDS | — | — | — | — | P37524 | noc | — | — | Nucleoid occlusion protein |
| Contig1 | 3351823 | 3352542 | − | GENE_03288 | Prodigal: 2.6 | CDS | 2.1.1 | — | — | — | P25813 | rsmG | — | — | Ribosomal RNA small subunit methyltransferase G |
| Contig1 | 3352556 | 3354442 | − | GENE_03289 | Prodigal: 2.6 | CDS | 3.6.-.- | — | — | — | P64230 | mnmG | — | — | tRNA uridine 5-carboxymethylamino-methyl modification enzyme MnmG |
| Contig1 | 3354459 | 3355838 | − | GENE_03290 | Prodigal: 2.6 | CDS | — | — | — | — | Q8YN91 | mnmE | — | — | tRNA modification GTPase MnmE |
| Contig1 | 3356128 | 3356769 | − | GENE_03291 | Prodigal: 2.6 | CDS | — | — | PF01424.16 | — | — | — | — | — | R3H domain protein |
| Contig1 | 3356766 | 3357545 | − | GENE_03292 | Prodigal: 2.6 | CDS | — | — | — | — | Q01625 | misCA | — | — | Membrane protein insertase MisCA precursor |
| Contig1 | 3357676 | 3358026 | − | GENE_03293 | Prodigal: 2.6 | CDS | 3.1.26.5 | — | — | — | P25814 | rnpA | — | — | Ribonuclease P protein component |
| Contig1 | 3358949 | 3360277 | + | GENE_03294 | Prodigal: 2.6 | CDS | — | — | — | — | P05648 | dnaA_2 | — | — | Chromosomal replication initiator protein DnaA |
| Contig1 | 3360462 | 3361598 | + | GENE_03295 | Prodigal: 2.6 | CDS | 2.7.7.7 | — | — | — | P99103 | dnaN | — | — | DNA polymerase III subunit beta |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3361733 | 3361948 | + | GENE_03296 | Prodigal: 2.6 | CDS | — | — | — | — | — | — | — | — | hypothetical protein |
| Contig1 | 3361964 | 3363076 | + | GENE_03297 | Prodigal: 2.6 | CDS | — | — | — | — | Q9RVE0 | recF | — | — | DNA replication and repair protein RecF |
| Contig1 | 3363094 | 3363339 | + | GENE_03298 | Prodigal: 2.6 | CDS | — | — | — | — | — | — | — | — | hypothetical protein |
| Contig1 | 3363393 | 3365315 | + | GENE_03299 | Prodigal: 2.6 | CDS | 5.99.1.3 | — | — | — | P0A0K8 | gyrB | — | — | DNA gyrase subunit B |
| Contig1 | 3365530 | 3367989 | + | GENE_03300 | Prodigal: 2.6 | CDS | 5.99.1.3 | — | — | — | P05653 | gyrA | — | — | DNA gyrase subunit A |
| Contig1 | 3368354 | 3369901 | + | GENE_03301 | — | rRNA | — | — | — | — | — | — | — | — | 16S ribosomal RNA |
| Contig1 | 3370002 | 3370078 | + | GENE_03302 | Aragorn: 1.2 | tRNA | — | — | — | — | — | — | — | — | tRNA-Ile(gat) |
| Contig1 | 3370093 | 3370168 | + | GENE_03303 | Aragorn: 1.2 | tRNA | — | — | — | — | — | — | — | — | tRNA-Ala(tgc) |
| Contig1 | 3370253 | 3373178 | + | GENE_03304 | — | rRNA | — | — | — | — | — | — | — | — | 23S ribosomal RNA |
| Contig1 | 3373233 | 3373343 | + | GENE_03305 | — | rRNA | — | — | — | — | — | — | — | — | 5S ribosomal RNA |
| Contig1 | 3373391 | 3374380 | − | GENE_03306 | Prodigal: 2.6 | CDS | — | — | — | — | — | — | — | — | hypothetical protein |
| Contig1 | 3374462 | 3375928 | + | GENE_03307 | Prodigal: 2.6 | CDS | 1.1.1.205 | — | — | — | P218799 | guaB | — | — | Inosine-5'-monophosphate dehydrogenase |
| Contig1 | 3376081 | 3377412 | + | GENE_03308 | Prodigal: 2.6 | CDS | 3.4.16.4 | — | — | — | P08750 | dacA | — | — | D-alanyl-D-alanine carboxypeptidase DacA precursor |
| Contig1 | 3377610 | 3378494 | + | GENE_03309 | Prodigal: 2.6 | CDS | 4.-.-.- | — | — | — | P37527 | pdxS | — | — | Pyridoxal biosynthesis lyase PdxS |
| Contig1 | 3378516 | 3379106 | + | GENE_03310 | Prodigal: 2.6 | CDS | 2.6.-.- | — | — | — | P37528 | pdxT | — | — | Glutamine amidotransferase subunit PdxT |
| Contig1 | 3379426 | 3380703 | − | GENE_03311 | Prodigal: 2.6 | CDS | 6.1.1.11 | — | — | — | O66647 | serS | — | — | Serine—tRNA ligase |
| Contig1 | 3380715 | 3381860 | − | GENE_03312 | Prodigal: 2.6 | CDS | 2.7.1.165 | — | — | — | P23524 | garK | — | — | Glycerate 2-kinase |
| Contig1 | 3382078 | 3382170 | + | GENE_03313 | Aragorn: 1.2 | tRNA | — | — | — | — | — | — | — | — | tRNA-Ser(tga) |
| Contig1 | 3382301 | 3382954 | + | GENE_03314 | Prodigal: 2.6 | CDS | 2.7.1.74 | — | — | — | P37529 | dck | — | — | Deoxyadenosine/deoxycytidine kinase |
| Contig1 | 3382951 | 3383574 | − | GENE_03315 | Prodigal: 2.6 | CDS | 2.7.1.113 | — | — | — | P37530 | dgk | — | — | Deoxyguanosine kinase |
| Contig1 | 3383670 | 3384950 | − | GENE_03316 | Prodigal: 2.6 | CDS | — | — | — | — | P37531 | yaaH | — | — | Spore germination protein YaaH |
| Contig1 | 3385025 | 3385576 | − | GENE_03317 | Prodigal: 2.6 | CDS | 3.3.2.1 | — | — | — | P0ADI4 | entB | — | — | Isochorismatase |
| Contig1 | 3385659 | 3386141 | + | GENE_03318 | Prodigal: 2.6 | CDS | 3.5.4.33 | — | — | — | P21335 | tadA_2 | — | — | tRNA-specific adenosine deaminase |
| Contig1 | 3386624 | 3388315 | + | GENE_03319 | Prodigal: 2.6 | CDS | 2.7.7.7 | — | — | — | P06710 | dnaX_1 | — | — | DNA polymerase III subunit tau |
| Contig1 | 3388340 | 3388663 | + | GENE_03320 | Prodigal: 2.6 | CDS | — | — | — | — | A3DHB8 | — | — | — | Nucleoid-associated protein |
| Contig1 | 3388678 | 3389274 | + | GENE_03321 | Prodigal: 2.6 | CDS | — | — | — | — | Q932G3 | recR | — | — | Recombination protein RecR |
| Contig1 | 3389293 | 3389517 | + | GENE_03322 | Prodigal: 2.6 | CDS | — | — | — | — | — | — | — | — | hypothetical protein |
| Contig1 | 3389578 | 3389841 | + | GENE_03323 | Prodigal: 2.6 | CDS | — | — | — | — | P24282 | bofA | — | — | Sigma-K factor-processing regulatory protein BofA |
| Contig1 | 3390157 | 3391703 | + | GENE_03324 | — | rRNA | — | — | — | — | — | — | — | — | 16S ribosomal RNA |
| Contig1 | 3391804 | 3391880 | + | GENE_03325 | Aragorn: 1.2 | tRNA | — | — | — | — | — | — | — | — | tRNA-Ile(gat) |
| Contig1 | 3391895 | 3391970 | + | GENE_03326 | Aragorn: 1.2 | tRNA | — | — | — | — | — | — | — | — | tRNA-Ala(tgc) |
| Contig1 | 3392055 | 3394980 | + | GENE_03327 | — | rRNA | — | — | — | — | — | — | — | — | 23S ribosomal RNA |
| Contig1 | 3395035 | 3395145 | + | GENE_03328 | — | rRNA | — | — | — | — | — | — | — | — | 5S ribosomal RNA |
| Contig1 | 3395323 | 3395517 | + | GENE_03329 | Prodigal: 2.6 | CDS | — | — | PF10764.3 | — | — | — | — | — | Inhibitor of sigma-G Gin |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3395666 | 3396280 | + | GENE_03330 | Prodigal: 2.6 | CDS | — | — | PF10112.3 | — | — | — | — | — | 5-bromo-4-chloroindolyl phosphate hydrolysis protein |
| Contig1 | 3396296 | 3397414 | + | GENE_03331 | Prodigal: 2.6 | CDS | — | — | — | — | P60108 | — | — | — | TelA-like protein |
| Contig1 | 3397492 | 3398925 | + | GENE_03332 | Prodigal: 2.6 | CDS | 4.1.1.19 | — | — | — | P21885 | speA_2 | — | — | Arginine decarboxylase |
| Contig1 | 3398922 | 3399560 | + | GENE_03333 | Prodigal: 2.6 | CDS | 2.7.4.9 | — | — | — | Q97R91 | tmk | — | — | Thymidylate kinase |
| Contig1 | 3399631 | 3399960 | + | GENE_03334 | Prodigal: 2.6 | CDS | — | — | — | — | — | — | — | — | hypothetical protein |
| Contig1 | 3399973 | 3400413 | + | GENE_03335 | Prodigal: 2.6 | CDS | — | — | — | — | — | — | — | — | hypothetical protein |
| Contig1 | 3400425 | 3401414 | + | GENE_03336 | Prodigal: 2.6 | CDS | 2.7.7.7 | — | — | — | P06710 | dnaX_2 | — | — | DNA polymerase III subunit tau |
| Contig1 | 3401417 | 3402244 | + | GENE_03337 | Prodigal: 2.6 | CDS | — | — | PF04468.6 | — | — | — | — | PSP1 C-terminal | hypothetical protein |
| Contig1 | 3402259 | 3402618 | + | GENE_03338 | Prodigal: 2.6 | CDS | — | — | — | — | Q99WB7 | — | — | — | Initiation-control protein YabA |
| Contig1 | 3402679 | 3403422 | + | GENE_03339 | Prodigal: 2.6 | CDS | 2.1.1.223 | — | — | MF_01872 | — | yfiC | — | — | tRNA1(Val) (adenine(37)-N6)-methyltransferase |
| Contig1 | 3403409 | 3403708 | + | GENE_03340 | Prodigal: 2.6 | CDS | — | PRK00329 | — | — | — | — | — | — | GIY-YIG nuclease superfamily protein |
| Contig1 | 3403683 | 3404564 | + | GENE_03341 | Prodigal: 2.6 | CDS | 2.1.1.198 | — | — | — | P67087 | rsmI | — | — | Ribosomal RNA small subunit methyltransferase I |
| Contig1 | 3404614 | 3404898 | − | GENE_03342 | Prodigal: 2.6 | CDS | — | — | — | — | P08874 | abrB | — | — | Transition state regulatory protein AbrB |
| Contig1 | 3405387 | 3407378 | + | GENE_03343 | Prodigal: 2.6 | CDS | 6.1.1.10 | — | — | — | P67579 | metG_2 | — | — | Methionine-tRNA ligase |
| Contig1 | 3407454 | 3408221 | + | GENE_03344 | Prodigal: 2.6 | CDS | 3.1.21.- | — | — | — | P0AFQ7 | ycfH | — | — | putative deoxyribonuclease YcfH |
| Contig1 | 3408320 | 3409681 | + | GENE_03345 | Prodigal: 2.6 | CDS | 3.1.26.8 | — | — | — | O34669 | yocH3 | — | — | Cell wall-binding protein YocH precursor |
| Contig1 | 3409816 | 3410379 | + | GENE_03346 | Prodigal: 2.6 | CDS | 2.1.1.182 | — | — | — | P3754 | mmV_2 | — | — | Ribonuclease M5 |
| Contig1 | 3410369 | 3411250 | + | GENE_03347 | Prodigal: 2.6 | CDS | — | — | — | — | P66662 | rsmA | — | — | Ribosomal RNA small subunit methyltransferase A |
| Contig1 | 3411423 | 3412298 | + | GENE_03348 | Prodigal: 2.6 | CDS | 3.4.-.- | — | — | — | P37548 | yabG | — | — | Sporulation-specific protease YabG |
| Contig1 | 3412510 | 3412770 | + | GENE_03349 | Prodigal: 2.6 | CDS | — | — | — | — | — | — | — | — | hypothetical protein |
| Contig1 | 3412933 | 3413121 | + | GENE_03350 | Prodigal: 2.6 | CDS | — | — | PF00269.14 | — | — | — | — | — | Small, acid-soluble spore proteins, alpha/beta type |
| Contig1 | 3413265 | 3414134 | + | GENE_03351 | Prodigal: 2.6 | CDS | 2.7.1.148 | — | — | — | P65178 | ispE | — | — | 4-diphosphocytidyl-2-C-methyl-D-erythritol kinase |
| Contig1 | 3414190 | 3415047 | + | GENE_03352 | Prodigal: 2.6 | CDS | — | — | — | — | P37551 | purR | — | — | Pur operon repressor |
| Contig1 | 3415044 | 3415424 | + | GENE_03353 | Prodigal: 2.6 | CDS | 3.5.4.- | — | — | — | P37552 | yabJ | — | — | Enamine/imine deaminase |
| Contig1 | 3415620 | 3415913 | + | GENE_03354 | Prodigal: 2.6 | CDS | — | — | — | — | P28015 | spoVG | — | — | Putative septation protein SpoVG |
| Contig1 | 3416105 | 3417475 | + | GENE_03355 | Prodigal: 2.6 | CDS | — | — | — | — | Q7A7B4 | glmU | — | — | Bifunctional protein GlmU |
| Contig1 | 3417497 | 3418450 | + | GENE_03356 | Prodigal: 2.6 | CDS | 2.7.6.1 | — | — | — | P14193 | prs_2 | — | — | Ribose-phosphate pyrophosphokinase |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3418535 | 3419143 | + | GENE_03357 | Prodigal: 2.6 | CDS | — | — | — | — | P14194 | ctc | — | — | General stress protein CTC |
| Contig1 | 3419228 | 3419794 | + | GENE_03358 | Prodigal: 2.6 | CDS | 3.1.1.29 | — | — | — | Q6YP15 | pth | — | — | Peptidyl-tRNA hydrolase |
| Contig1 | 3419856 | 3420086 | + | GENE_03359 | Prodigal: 2.6 | CDS | — | — | — | — | — | — | — | — | hypothetical protein |
| Contig1 | 3420156 | 3423689 | + | GENE_03360 | Prodigal: 2.6 | CDS | 3.6.4.- | — | — | — | Q7A7B2 | mfd | — | — | Transcription-repair-coupling factor |
| Contig1 | 3423826 | 3424362 | + | GENE_03361 | Prodigal: 2.6 | CDS | — | — | — | — | P37554 | spoVT | — | — | Stage V sporulation protein T |
| Contig1 | 3424530 | 3426110 | + | GENE_03362 | Prodigal: 2.6 | CDS | — | — | — | — | O34674 | ytgP_2 | — | — | putative cell division protein YtgP |
| Contig1 | 3426100 | 3427575 | + | GENE_03363 | Prodigal: 2.6 | CDS | 3.6.1.8 | — | — | — | P0AEY3 | mazG | — | — | Nucleoside triphosphate pyrophosphohydrolase |
| Contig1 | 3427577 | 3427837 | + | GENE_03364 | Prodigal: 2.6 | CDS | — | — | — | — | P0ACG8 | hslR | — | — | Heat shock protein 15 |
| Contig1 | 3427916 | 3428218 | + | GENE_03365 | Prodigal: 2.6 | CDS | — | — | — | — | P37558 | yabP | — | — | Spore protein YabP |
| Contig1 | 3428215 | 3428850 | + | GENE_03366 | Prodigal: 2.6 | CDS | — | — | — | — | P37559 | yabQ | — | — | Spore protein YabQ |
| Contig1 | 3428868 | 3429245 | + | GENE_03367 | Prodigal: 2.6 | CDS | — | — | — | — | P37471 | divIC | — | — | Cell division protein DivIC |
| Contig1 | 3429326 | 3429712 | + | GENE_03368 | Prodigal: 2.6 | CDS | — | — | — | — | P80870 | yugI_2 | — | — | General stress protein 13 |
| Contig1 | 3429870 | 3429946 | + | GENE_03369 | Aragorn: 1.2 | tRNA | — | — | — | — | — | — | — | — | tRNA-Met(cat) |
| Contig1 | 3429955 | 3430029 | + | GENE_03370 | Aragorn: 1.2 | tRNA | — | — | — | — | — | — | — | — | tRNA-Glu(ttc) |
| Contig1 | 3430237 | 3432726 | + | GENE_03371 | Prodigal: 2.6 | CDS | 3.1.3.16 | — | — | — | P37475 | spoIIE | — | — | Stage II sporulation protein E |
| Contig1 | 3432794 | 3433531 | + | GENE_03372 | Prodigal: 2.6 | CDS | — | — | PF00092.22 | — | — | — | — | — | von Willebrand factor type A domain protein |
| Contig1 | 3433497 | 3434498 | + | GENE_03373 | Prodigal: 2.6 | CDS | 2.7.11.1 | — | — | — | A6QGC0 | prkC_2 | — | — | Serine/threonine-protein kinase PrkC |
| Contig1 | 3434603 | 3436021 | + | GENE_03374 | Prodigal: 2.6 | CDS | 6.3.4.19 | — | — | — | P37563 | tilS | — | — | tRNA(Ile)-lysidine synthase |
| Contig1 | 3436018 | 3436557 | + | GENE_03375 | Prodigal: 2.6 | CDS | 2.4.2.8 | — | — | — | Q5XEL6 | hpt | — | — | Hypoxanthine-guanine phosphoribosyltransferase |
| Contig1 | 3436655 | 3438574 | + | GENE_03376 | Prodigal: 2.6 | CDS | 3.4.24.- | — | — | — | P37476 | ftsH | — | — | ATP-dependent zinc metalloprotease FtsH |
| Contig1 | 3438723 | 3439499 | + | GENE_03377 | Prodigal: 2.6 | CDS | 2.7.1.33 | — | — | — | P37564 | coaX | — | — | Type III pantothenate kinase |
| Contig1 | 3439510 | 3440385 | + | GENE_03378 | Prodigal: 2.6 | CDS | — | — | — | — | P37565 | hslO | — | — | 33 kDa chaperonin |
| Contig1 | 3440449 | 3441321 | + | GENE_03379 | Prodigal: 2.6 | CDS | 5.2.1.8 | — | — | — | Q81TU1 | prsA2 | — | — | Foldase protein PrsA 2 precursor |
| Contig1 | 3441397 | 3442323 | + | GENE_03380 | Prodigal: 2.6 | CDS | 2.5.1.47 | — | — | — | P37887 | cysK_2 | — | — | Cysteine synthase |
| Contig1 | 3442488 | 3443912 | + | GENE_03381 | Prodigal: 2.6 | CDS | 2.6.1.85 | — | — | — | P28820 | pabB | — | — | Aminodeoxychorismate synthase component 1 |
| Contig1 | 3443919 | 3444506 | + | GENE_03382 | Prodigal: 2.6 | CDS | 2.6.1.85 | — | — | — | P28819 | pabA | — | — | Aminodeoxychorismate/anthranilate synthase component 2 |
| Contig1 | 3444503 | 3445387 | + | GENE_03383 | Prodigal: 2.6 | CDS | 2.6.1.21 | — | — | — | P99090 | dat_2 | — | — | D-alanine aminotransferase |
| Contig1 | 3445368 | 3446225 | + | GENE_03384 | Prodigal: 2.6 | CDS | 2.5.1.15 | — | — | — | Q5XCA8 | folP | — | — | Dihydropteroate synthase |
| Contig1 | 3446218 | 3446680 | + | GENE_03385 | Prodigal: 2.6 | CDS | 4.1.2.25 | — | — | — | P56740 | folB | — | — | Dihydroneopterin aldolase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3446577 | 3447080 | + | GENE_03386 | Prodigal: 2.6 | CDS | — | — | — | — | P59657 | sulD | — | — | Bifunctional folate synthesis protein |
| Contig1 | 3447032 | 3447241 | + | GENE_03387 | Prodigal: 2.6 | CDS | — | — | PF01381.16 | — | — | — | — | — | Helix-turn-helix |
| Contig1 | 3447263 | 3448264 | + | GENE_03388 | Prodigal: 2.6 | CDS | 1.-.-.- | — | — | — | P33371 | dusC | — | — | tRNA-dihydrouridine synthase C |
| Contig1 | 3448354 | 3449853 | + | GENE_03389 | Prodigal: 2.6 | CDS | 6.1.1.6 | — | — | — | Q9RHV9 | lysS | — | — | Lysine–tRNA ligase |
| Contig1 | 3450184 | 3451731 | + | GENE_03390 | — | rRNA | — | — | — | — | — | — | — | — | 16S ribosomal RNA |
| Contig1 | 3451909 | 3454834 | + | GENE_03391 | — | rRNA | — | — | — | — | — | — | — | — | 23S ribosomal RNA |
| Contig1 | 3454889 | 3454999 | + | GENE_03392 | — | rRNA | — | — | — | — | — | — | — | — | 5S ribosomal RNA |
| Contig1 | 3455026 | 3455101 | + | GENE_03393 | Aragorn: 1.2 | tRNA | — | — | — | — | — | — | — | — | tRNA-Val(tac) |
| Contig1 | 3455107 | 3455182 | + | GENE_03394 | Aragorn: 1.2 | tRNA | — | — | — | — | — | — | — | — | tRNA-Thr(tgt) |
| Contig1 | 3455219 | 3455294 | + | GENE_03395 | Aragorn: 1.2 | tRNA | — | — | — | — | — | — | — | — | tRNA-Lys(ttt) |
| Contig1 | 3455301 | 3455382 | + | GENE_03396 | Aragorn: 1.2 | tRNA | — | — | — | — | — | — | — | — | tRNA-Leu(tag) |
| Contig1 | 3455407 | 3455481 | + | GENE_03397 | Aragorn: 1.2 | tRNA | — | — | — | — | — | — | — | — | tRNA-Gly(gcc) |
| Contig1 | 3455496 | 3455581 | + | GENE_03398 | Aragorn: 1.2 | tRNA | — | — | — | — | — | — | — | — | tRNA-Leu(taa) |
| Contig1 | 3455593 | 3455669 | + | GENE_03399 | Aragorn: 1.2 | tRNA | — | — | — | — | — | — | — | — | tRNA-Arg(acg) |
| Contig1 | 3455686 | 3455762 | + | GENE_03400 | Aragorn: 1.2 | tRNA | — | — | — | — | — | — | — | — | tRNA-Pro(tgg) |
| Contig1 | 3455767 | 3455842 | + | GENE_03401 | Aragorn: 1.2 | tRNA | — | — | — | — | — | — | — | — | tRNA-Ala(tgc) |
| Contig1 | 3456010 | 3457557 | + | GENE_03402 | — | rRNA | — | — | — | — | — | — | — | — | 16S ribosomal RNA |
| Contig1 | 3457735 | 3460659 | + | GENE_03403 | — | rRNA | — | — | — | — | — | — | — | — | 23S ribosomal RNA |
| Contig1 | 3460714 | 3460824 | + | GENE_03404 | — | rRNA | — | — | — | — | — | — | — | — | 5S ribosomal RNA |
| Contig1 | 3461055 | 3461519 | + | GENE_03405 | Prodigal: 2.6 | CDS | — | — | — | — | P37568 | ctsR | — | — | Transcriptional regulator CtsR |
| Contig1 | 3461710 | 3462090 | + | GENE_03406 | Prodigal: 2.6 | CDS | — | — | PF02151.13 | — | — | — | — | — | UvrB/uvrC motif protein |
| Contig1 | 3462090 | 3463181 | + | GENE_03407 | Prodigal: 2.6 | CDS | 2.7.3.- | — | — | — | P65205 | — | — | — | Putative ATP:guanido phosphotransferase |
| Contig1 | 3463178 | 3465610 | + | GENE_03408 | Prodigal: 2.6 | CDS | — | — | — | — | P37571 | clpC | — | — | Negative regulator of genetic competence ClpC/MecB |
| Contig1 | 3465704 | 3467083 | + | GENE_03409 | Prodigal: 2.6 | CDS | — | — | — | — | A0R563 | — | — | DNA repair protein RadA homolog | hypothetical protein |
| Contig1 | 3467087 | 3468169 | + | GENE_03410 | Prodigal: 2.6 | CDS | 2.7.7.85 | — | — | — | P37573 | disA_2 | — | — | DNA integrity scanning protein DisA |
| Contig1 | 3468283 | 3469383 | + | GENE_03411 | Prodigal: 2.6 | CDS | 3.1.-.- | — | — | — | Q5SKV3 | — | — | — | putative PIN and TRAM-domain containing protein precursor |
| Contig1 | 3469396 | 3470094 | + | GENE_03412 | Prodigal: 2.6 | CDS | 2.7.7.60 | — | — | — | Q46893 | ispD | — | — | 2-C-methyl-D-erythritol 4-phosphate cytidylyltransferase |
| Contig1 | 3470087 | 3470563 | + | GENE_03413 | Prodigal: 2.6 | CDS | 4.6.1.12 | — | — | — | Q06756 | ispF | — | — | 2-C-methyl-D-erythritol 2,4-cyclodiphosphate synthase |
| Contig1 | 3470655 | 3472106 | + | GENE_03414 | Prodigal: 2.6 | CDS | 6.1.1.17 | — | — | — | P99170 | gltX | — | — | Glutamate-tRNA ligase |
| Contig1 | 3472417 | 3473070 | + | GENE_03415 | Prodigal: 2.6 | CDS | 2.3.1.30 | — | — | — | Q06750 | cysE | — | — | Serine acetyltransferase |
| Contig1 | 3473067 | 3474467 | + | GENE_03416 | Prodigal: 2.6 | CDS | 6.1.1.16 | — | — | — | Q06752 | cysS | — | — | Cysteine-tRNA ligase |
| Contig1 | 3474472 | 3474903 | + | GENE_03417 | Prodigal: 2.6 | CDS | 3.1.26.- | — | — | — | O31418 | mrnC | — | — | Mini-ribonuclease 3 |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3474887 | 3475636 | + | GENE_03718 | Prodigal: 2.6 | CDS | 2.1.1.- | — | — | — | Q7A794 | — | — | — | Putative TrmH family tRNA/rRNA |
| Contig1 | 3475643 | 3476155 | + | GENE_03419 | Prodigal: 2.6 | CDS | — | — | PF05991.5 | — | — | — | — | — | YacP-like NYN domain protein |
| Contig1 | 3476218 | 3476874 | + | GENE_03420 | Prodigal: 2.6 | CDS | — | — | — | — | P17869 | sigH | — | — | RNA polymerase sigma-H factor |
| Contig1 | 3477142 | 3477321 | + | GENE_03421 | Prodigal: 2.6 | CDS | — | — | — | MF_00422 | — | secE | — | — | Protein translocase subunit SecE |
| Contig1 | 3477429 | 3478019 | + | GENE_03422 | Prodigal: 2.6 | CDS | — | — | — | — | Q06795 | — | — | Transcription termination/anti-termination protein NusG | hypothetical protein |
| Contig1 | 3478187 | 3478612 | + | GENE_03423 | Prodigal: 2.6 | CDS | — | — | — | — | Q06796 | rplK | — | — | 50S ribosomal protein L11 |
| Contig1 | 3478707 | 3479405 | + | GENE_03424 | Prodigal: 2.6 | CDS | — | — | — | — | Q06797 | rplA | — | — | 50S ribosomal protein L1 |
| Contig1 | 3479660 | 3480160 | + | GENE_03425 | Prodigal: 2.6 | CDS | — | — | — | — | P42923 | rplJ | — | — | 50S ribosomal protein L10 |
| Contig1 | 3480202 | 3480573 | + | GENE_03426 | Prodigal: 2.6 | CDS | — | — | — | — | P02394 | rplL | — | — | 50S ribosomal protein L7/L12 |
| Contig1 | 3480665 | 3481270 | + | GENE_03427 | Prodigal: 2.6 | CDS | 2.1.1.174 | — | — | — | P42596 | rlmG | — | — | Ribosomal RNA large subunit methyltransferase G |
| Contig1 | 3481515 | 3485096 | + | GENE_03428 | Prodigal: 2.6 | CDS | 2.7.7.6 | — | — | — | P37870 | rpoB | — | — | DNA-directed RNA polymerase subunit beta |
| Contig1 | 3485159 | 3488758 | + | GENE_03429 | Prodigal: 2.6 | CDS | 2.7.7.6 | — | — | — | P37871 | rpoC | — | — | DNA-directed RNA polymerase subunit beta' |
| Contig1 | 3488926 | 3489174 | + | GENE_03430 | Prodigal: 2.6 | CDS | — | — | — | — | P46350 | rplGB | — | — | Ribosome-associated protein L7Ae-like protein |
| Contig1 | 3489290 | 3489706 | + | GENE_03431 | Prodigal: 2.6 | CDS | — | — | — | — | P21472 | rpsL | — | — | 30S ribosomal protein S12 |
| Contig1 | 3489747 | 3490217 | + | GENE_03432 | Prodigal: 2.6 | CDS | — | — | — | — | P21469 | rpsG | — | — | 30S ribosomal protein S7 |
| Contig1 | 3490270 | 3492348 | + | GENE_03433 | Prodigal: 2.6 | CDS | — | — | — | — | P80868 | fusA | — | — | Elongation factor G |
| Contig1 | 3492468 | 3493658 | + | GENE_03434 | Prodigal: 2.6 | CDS | — | — | — | — | P99152 | tuf | — | — | Elongation factor Tu |
| Contig1 | 3493762 | 3494727 | + | GENE_03435 | Prodigal: 2.6 | CDS | 3.4.11.5 | — | — | — | P46541 | pip | — | — | Proline iminopeptidase |
| Contig1 | 3494976 | 3495284 | + | GENE_03436 | Prodigal: 2.6 | CDS | — | — | — | — | P21471 | rpsJ | — | — | 30S ribosomal protein S10 |
| Contig1 | 3495324 | 3495953 | + | GENE_03437 | Prodigal: 2.6 | CDS | — | — | — | — | P42920 | rplC | — | — | 50S ribosomal protein L3 |
| Contig1 | 3495981 | 3496604 | + | GENE_03438 | Prodigal: 2.6 | CDS | — | — | — | — | P42921 | rplD | — | — | 50S ribosomal protein L4 |
| Contig1 | 3496604 | 3496891 | + | GENE_03439 | Prodigal: 2.6 | CDS | — | — | — | — | P42924 | rplW | — | — | 50S ribosomal protein L23 |
| Contig1 | 3496923 | 3497756 | + | GENE_03440 | Prodigal: 2.6 | CDS | — | — | — | — | P42919 | rplB | — | — | 50S ribosomal protein L2 |
| Contig1 | 3497814 | 3498092 | + | GENE_03441 | Prodigal: 2.6 | CDS | — | — | — | — | P21476 | rpsS | — | — | 30S ribosomal protein S19 |
| Contig1 | 3498109 | 3498450 | + | GENE_03442 | Prodigal: 2.6 | CDS | — | — | — | — | P42060 | rplV | — | — | 50S ribosomal protein L22 |
| Contig1 | 3498454 | 3499110 | + | GENE_03443 | Prodigal: 2.6 | CDS | — | — | — | — | P21465 | rpsC | — | — | 30S ribosomal protein S3 |
| Contig1 | 3499112 | 3499546 | + | GENE_03444 | Prodigal: 2.6 | CDS | — | — | — | — | Q7A461 | rplP | — | — | 50S ribosomal protein L16 |
| Contig1 | 3499536 | 3499736 | + | GENE_03445 | Prodigal: 2.6 | CDS | — | — | — | — | P12873 | rpmC | — | — | 50S ribosomal protein L29 |
| Contig1 | 3499759 | 3500022 | + | GENE_03446 | Prodigal: 2.6 | CDS | — | — | — | — | P12874 | rpsQ | — | — | 30S ribosomal protein S17 |
| Contig1 | 3500063 | 3500431 | + | GENE_03447 | Prodigal: 2.6 | CDS | — | — | — | — | P12875 | rplN | — | — | 50S ribosomal protein L14 |
| Contig1 | 3500468 | 3500779 | + | GENE_03448 | Prodigal: 2.6 | CDS | — | — | — | — | P0CI78 | rplX | — | — | 50S ribosomal protein L24 |
| Contig1 | 3500806 | 3501345 | + | GENE_03449 | Prodigal: 2.6 | CDS | — | — | — | — | P12877 | rplE | — | — | 50S ribosomal protein L5 |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3501368 | 3501553 | + | GENE_03450 | Prodigal: 2.6 | CDS | — | — | — | — | P12878 | rpsN1 | — | — | 30S ribosomal protein S14 |
| Contig1 | 3501585 | 3501983 | + | GENE_03451 | Prodigal: 2.6 | CDS | — | — | — | — | P12879 | rpsH | — | — | 30S ribosomal protein S8 |
| Contig1 | 3502014 | 3502553 | + | GENE_03452 | Prodigal: 2.6 | CDS | — | — | — | — | P46898 | rplF | — | — | 50S ribosomal protein L6 |
| Contig1 | 3502588 | 3502950 | + | GENE_03453 | Prodigal: 2.6 | CDS | — | — | — | — | P46899 | rplR | — | — | 50S ribosomal protein L18 |
| Contig1 | 3502969 | 3503475 | + | GENE_03454 | Prodigal: 2.6 | CDS | — | — | — | — | P21467 | rpsE | — | — | 30S ribosomal protein S5 |
| Contig1 | 3503489 | 3503668 | + | GENE_03455 | Prodigal: 2.6 | CDS | — | — | — | — | P19947 | rpmD | — | — | 50S ribosomal protein L30 |
| Contig1 | 3503699 | 3504139 | + | GENE_03456 | Prodigal: 2.6 | CDS | — | — | — | — | P19946 | rplO | — | — | 50S ribosomal protein L15 |
| Contig1 | 3504141 | 3505436 | + | GENE_03457 | Prodigal: 2.6 | CDS | — | — | — | MF_01465 | — | secY | — | — | Protein translocase subunit SecY |
| Contig1 | 3505488 | 3506141 | + | GENE_03458 | Prodigal: 2.6 | CDS | 27.4.3 | — | — | — | P16304 | adk | — | — | Adenylate kinase |
| Contig1 | 3506135 | 3506884 | + | GENE_03459 | Prodigal: 2.6 | CDS | 3.4.11.18 | — | — | — | P19994 | map | — | — | Methionine aminopeptidase 1 |
| Contig1 | 3507209 | 3507427 | + | GENE_03460 | Prodigal: 2.6 | CDS | — | — | — | — | P20458 | infA | — | — | Translation initiation factor IF-1 |
| Contig1 | 3507461 | 3507574 | + | GENE_03461 | Prodigal: 2.6 | CDS | — | — | — | — | P07841 | rpmJ | — | — | 50S ribosomal protein L36 |
| Contig1 | 3507597 | 3507962 | + | GENE_03462 | Prodigal: 2.6 | CDS | — | — | — | — | P20282 | rpsM | — | — | 30S ribosomal protein S13 |
| Contig1 | 3507983 | 3508378 | + | GENE_03463 | Prodigal: 2.6 | CDS | — | — | — | — | P66357 | rpsK | — | — | 30S ribosomal protein S11 |
| Contig1 | 3508555 | 3509499 | + | GENE_03464 | Prodigal: 2.6 | CDS | 2.7.7.6 | — | — | — | P20429 | rpoA | — | — | DNA-directed RNA polymerase subunit alpha |
| Contig1 | 3509577 | 3509939 | + | GENE_03465 | Prodigal: 2.6 | CDS | — | — | — | — | P20277 | rplQ | — | — | 50S ribosomal protein L17 |
| Contig1 | 3510071 | 3510916 | + | GENE_03466 | Prodigal: 2.6 | CDS | 3.6.3.- | — | — | — | Q035B2 | ecfA1 | — | — | Energy-coupling factor transporter ATP-binding protein EcfA1 |
| Contig1 | 3510892 | 3511761 | + | GENE_03467 | Prodigal: 2.6 | CDS | 3.6.3.- | — | — | — | A2RI02 | ecfA2 | — | — | Energy-coupling factor transporter ATP-binding protein EcfA2 |
| Contig1 | 3511758 | 3512555 | + | GENE_03468 | Prodigal: 2.6 | CDS | — | — | — | — | P70972 | ecfT | — | — | Energy-coupling factor transporter transmembrane protein EcfT |
| Contig1 | 3512568 | 3513311 | + | GENE_03469 | Prodigal: 2.6 | CDS | 5.4.99.12 | — | — | — | Q5SHU9 | truA | — | — | tRNA pseudouridine synthase A |
| Contig1 | 3513471 | 3513908 | + | GENE_03470 | Prodigal: 2.6 | CDS | — | — | — | — | P70974 | rplM | — | — | 50S ribosomal protein L13 |
| Contig1 | 3513929 | 3514321 | + | GENE_03471 | Prodigal: 2.6 | CDS | — | — | — | — | P21470 | rpsI | — | — | 30S ribosomal protein S9 |
| Contig1 | 3514459 | 3515226 | + | GENE_03472 | Prodigal: 2.6 | CDS | — | — | PF08241.6 | — | — | — | — | — | Methyltransferase domain protein |
| Contig1 | 3515240 | 3515713 | − | GENE_03473 | Prodigal: 2.6 | CDS | — | — | PF05163.6 | — | — | — | — | — | DinB family protein |
| Contig1 | 3515844 | 3516287 | + | GENE_03474 | Prodigal: 2.6 | CDS | — | — | — | — | — | — | — | — | hypothetical protein |
| Contig1 | 3516348 | 3517061 | − | GENE_03475 | Prodigal: 2.6 | CDS | 3.5.1.28 | — | — | — | P50864 | cwlD | — | — | Germination-specific N-acetylmuramoyl-L-alanine amidase precursor |
| Contig1 | 3517141 | 3518193 | + | GENE_03476 | Prodigal: 2.6 | CDS | — | — | — | — | Q01464 | minD_2 | — | — | Septum site-determining protein MinD |
| Contig1 | 3518226 | 3518381 | − | GENE_03477 | Prodigal: 2.6 | CDS | — | — | — | — | P16450 | gerD_1 | — | — | Spore germination protein GerD precursor |
| Contig1 | 3518444 | 3518782 | − | GENE_03478 | Prodigal: 2.6 | CDS | — | — | — | — | P16450 | gerD_2 | — | — | Spore germination protein GerD precursor |
| Contig1 | 3518890 | 3519486 | + | GENE_03479 | Prodigal: 2.6 | CDS | — | — | — | — | — | — | — | — | hypothetical protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3519487 | 3520251 | − | GENE_03480 | Prodigal: 2.6 | CDS | 3.5.1.104 | — | — | — | Q8DP63 | pgdA_2 | — | — | Peptidoglycan-N-acetylglucosamine deacetylase |
| Contig1 | 3520595 | 3522142 | + | GENE_03481 | — | rRNA | — | — | — | — | — | — | — | — | 16S ribosomal RNA |
| Contig1 | 3522320 | 3525243 | + | GENE_03482 | — | rRNA | — | — | — | — | — | — | — | — | 23S ribosomal RNA |
| Contig1 | 3525298 | 3525408 | + | GENE_03483 | — | rRNA | — | — | — | — | — | — | — | — | 5S ribosomal RNA |
| Contig1 | 3525457 | 3525531 | + | GENE_03484 | Aragorn: 1.2 | tRNA | — | — | — | — | — | — | — | — | tRNA-Asn(gtt) |
| Contig1 | 3525534 | 3525606 | + | GENE_03485 | Aragorn: 1.2 | tRNA | — | — | — | — | — | — | — | — | tRNA-Thr(ggt) |
| Contig1 | 3525903 | 3525977 | + | GENE_03486 | Aragorn: 1.2 | tRNA | — | — | — | — | — | — | — | — | tRNA-Gly(gcc) |
| Contig1 | 3526010 | 3526086 | + | GENE_03487 | Aragorn: 1.2 | tRNA | — | — | — | — | — | — | — | — | tRNA-Arg(acg) |
| Contig1 | 3526103 | 3526179 | + | GENE_03488 | Aragorn: 1.2 | tRNA | — | — | — | — | — | — | — | — | tRNA-Pro(tgg) |
| Contig1 | 3526483 | 3528030 | + | GENE_03489 | — | rRNA | — | — | — | — | — | — | — | — | 16S ribosomal RNA |
| Contig1 | 3528208 | 3531133 | + | GENE_03490 | — | rRNA | — | — | — | — | — | — | — | — | 23S ribosomal RNA |
| Contig1 | 3531188 | 3531298 | + | GENE_03491 | — | rRNA | — | — | — | — | — | — | — | — | 5S ribosomal RNA |
| Contig1 | 3531397 | 3532611 | − | GENE_03492 | Prodigal: 2.6 | CDS | — | — | — | — | O07563 | glcP | — | — | Glucose/mannose transporter GlcP |
| Contig1 | 3532837 | 3534105 | + | GENE_03493 | Prodigal: 2.6 | CDS | 2.6.1.- | — | — | — | Q5SHH5 | argD_2 | — | — | Acetylornithine/acetyl-lysine aminotransferase |
| Contig1 | 3534102 | 3535052 | + | GENE_03494 | Prodigal: 2.6 | CDS | — | — | — | — | — | — | — | — | bifunctional inositol-1 monophosphatase/fructose-1,6-bisphosphatase |
| Contig1 | 3535027 | 3536073 | + | GENE_03495 | Prodigal: 2.6 | CDS | 1.1.1.14 | — | — | — | Q06004 | gutB_3 | — | — | Sorbitol dehydrogenase |
| Contig1 | 3536305 | 3537738 | + | GENE_03496 | Prodigal: 2.6 | CDS | — | PRK12676 | — | — | P0AFR2 | dauA_2 | — | — | C4-dicarboxylic acid transporter DauA |
| Contig1 | 3537847 | 3538830 | + | GENE_03497 | Prodigal: 2.6 | CDS | — | — | PF01758.10 | — | — | — | — | — | Sodium Bile acid symporter family protein |
| Contig1 | 3538819 | 3539571 | − | GENE_03498 | Prodigal: 2.6 | CDS | — | PRK10439 | — | — | — | — | — | — | enterobactin/ferric enterobactin esterase |
| Contig1 | 3539568 | 3540590 | − | GENE_03499 | Prodigal: 2.6 | CDS | — | — | — | — | P40411 | feuC_3 | — | — | Iron-uptake system permease protein FeuC |
| Contig1 | 3540580 | 3541587 | − | GENE_03500 | Prodigal: 2.6 | CDS | — | — | — | — | P40410 | feuB_3 | — | — | Iron-uptake system permease protein FeuB |
| Contig1 | 3541607 | 3542563 | − | GENE_03501 | Prodigal: 2.6 | CDS | — | — | — | — | P40409 | feuA | — | — | Iron-uptake system-binding protein precursor |
| Contig1 | 3542651 | 3544246 | − | GENE_03502 | Prodigal: 2.6 | CDS | — | — | — | — | P40408 | btr_2 | — | — | HTH-type transcriptional activator Btr |
| Contig1 | 3544384 | 3545628 | − | GENE_03503 | Prodigal: 2.6 | CDS | — | — | — | — | — | — | — | — | hypothetical protein |
| Contig1 | 3545644 | 3547557 | − | GENE_03504 | Prodigal: 2.6 | CDS | — | — | — | — | — | ybbD | — | — | putative lipoprotein YbbD precursor |
| Contig1 | 3547604 | 3548887 | − | GENE_03505 | Prodigal: 2.6 | CDS | 3.1.1 | — | — | — | Q9KX40 | estB | — | — | Esterase EstB |
| Contig1 | 3548906 | 3550273 | − | GENE_03506 | Prodigal: 2.6 | CDS | — | — | — | — | Q7A804 | — | — | — | PTS system EIIBC component |
| Contig1 | 3550402 | 3551331 | − | GENE_03507 | Prodigal: 2.6 | CDS | 4.2.1.126 | — | — | — | Q45582 | murQ | — | — | N-acetylmuramic acid 6-phosphate etherase |
| Contig1 | 3551431 | 3551907 | − | GENE_03508 | Prodigal: 2.6 | CDS | — | — | PF00583.18 | — | — | — | — | — | Acetyltransferase (GNAT) family protein |
| Contig1 | 3551926 | 3552378 | − | GENE_03509 | Prodigal: 2.6 | CDS | — | — | — | — | — | — | — | — | hypothetical protein |
| Contig1 | 3552559 | 3552630 | + | GENE_03510 | Aragorn: 1.2 | tRNA | — | — | — | — | — | — | — | — | tRNA-Glu(ttc) |
| Contig1 | 3552634 | 3552709 | + | GENE_03511 | Aragorn: 1.2 | tRNA | — | — | — | — | — | — | — | — | tRNA-Val(tac) |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3552715 | 3552788 | + | GENE_03512 | Aragorn: 1.2 | tRNA | — | — | — | — | — | — | — | — | tRNA-Thr(tgt) |
| Contig1 | 3552807 | 3552891 | + | GENE_03513 | Aragorn: 1.2 | tRNA | — | — | — | — | — | — | — | — | tRNA-Tyr(tgta) |
| Contig1 | 3552895 | 3552969 | + | GENE_03514 | Aragorn: 1.2 | tRNA | — | — | — | — | — | — | — | — | tRNA-Gln(ttg) |
| Contig1 | 3553199 | 3553762 | + | GENE_03515 | Prodigal: 2.6 | CDS | — | — | — | — | Q45585 | sigW | — | — | ECF RNA polymerase sigma factor SigW |
| Contig1 | 3553776 | 3554402 | + | GENE_03516 | Prodigal: 2.6 | CDS | — | — | — | — | Q45588 | rsiW | — | — | Anti-sigma-W factor RsiW |
| Contig1 | 3554570 | 3555391 | + | GENE_03517 | Prodigal: 2.6 | CDS | 2.7.7.85 | — | — | MF_01438 | — | disA_3 | — | — | DNA integrity scanning protein DisA |
| Contig1 | 3555384 | 3556823 | + | GENE_03518 | Prodigal: 2.6 | CDS | — | — | PF07949.6 | — | — | — | — | — | YbbR-like protein |
| Contig1 | 3556841 | 3558187 | + | GENE_03519 | Prodigal: 2.6 | CDS | 5.4.2.10 | — | — | — | O34824 | glmM | — | — | Phosphoglucosamine mutase |
| Contig1 | 3558619 | 3560421 | + | GENE_03520 | Prodigal: 2.6 | CDS | 2.6.1.16 | — | — | — | P64228 | glmS | — | — | Glutamine-fructose-6-phosphate aminotransferase [isomerizing] |
| Contig1 | 3560845 | 3561717 | + | GENE_03521 | Prodigal: 2.6 | CDS | — | — | — | — | O34641 | ytrB_2 | — | — | ABC transporter ATP-binding protein YtrB |
| Contig1 | 3561695 | 3562348 | − | GENE_03522 | Prodigal: 2.6 | CDS | — | — | — | — | — | — | — | — | hypothetical protein |
| Contig1 | 3562463 | 3563371 | − | GENE_03523 | Prodigal: 2.6 | CDS | — | — | — | — | — | — | — | — | hypothetical protein |
| Contig1 | 3563473 | 3564639 | + | GENE_03524 | Prodigal: 2.6 | CDS | — | — | — | — | — | — | — | — | hypothetical protein |
| Contig1 | 3564692 | 3565537 | − | GENE_03525 | Prodigal: 2.6 | CDS | 1.1.1.274 | — | — | — | P15339 | dkgB | — | — | 2,5-diketo-D-gluconic acid reductase B |
| Contig1 | 3565648 | 3566340 | − | GENE_03526 | Prodigal: 2.6 | CDS | — | — | — | — | P60639 | cidB | — | — | Holin-like protein CidB |
| Contig1 | 3566310 | 3566807 | − | GENE_03527 | Prodigal: 2.6 | CDS | — | — | — | — | P60647 | cidA_2 | — | — | Holin-like protein CidA |
| Contig1 | 3566906 | 3567340 | + | GENE_03528 | Prodigal: 2.6 | CDS | — | — | PF01047.16 | — | — | — | — | — | MarR family protein |
| Contig1 | 3567340 | 3567444 | + | GENE_03529 | Prodigal: 2.6 | CDS | — | — | — | — | — | — | — | — | hypothetical protein |
| Contig1 | 3567766 | 3569151 | + | GENE_03530 | Prodigal: 2.6 | CDS | — | — | — | — | P27837 | yifK | — | — | putative transport protein YifK |
| Contig1 | 3569244 | 3569948 | + | GENE_03531 | Prodigal: 2.6 | CDS | 3.-.-.- | — | — | — | O06480 | yfnB | — | — | Putative HAD-hydrolase YfnB |
| Contig1 | 3570004 | 3571161 | + | GENE_03532 | Prodigal: 2.6 | CDS | 2.7.13.3 | — | — | — | O32198 | liaS_3 | — | — | Sensor histidine kinase LiaS |
| Contig1 | 3571185 | 3571838 | + | GENE_03533 | Prodigal: 2.6 | CDS | — | — | — | — | P13800 | degU_4 | — | — | Transcriptional regulatory protein DegU |
| Contig1 | 3572056 | 3572988 | + | GENE_03534 | Prodigal: 2.6 | CDS | 3.6.3.- | — | — | — | P32010 | drrA_3 | — | — | Daunorubicin/doxorubicin resistance ATP-binding protein DrrA |
| Contig1 | 3573004 | 3574212 | + | GENE_03535 | Prodigal: 2.6 | CDS | — | — | PF12698.1 | — | — | — | — | — | ABC-2 family transporter protein |
| Contig1 | 3574215 | 3575378 | + | GENE_03536 | Prodigal: 2.6 | CDS | — | — | PF12698.1 | — | — | — | — | — | ABC-2 family transporter protein |
| Contig1 | 3575434 | 3575607 | + | GENE_03537 | Prodigal: 2.6 | CDS | — | — | — | — | — | — | — | — | hypothetical protein |
| Contig1 | 3575679 | 3576374 | + | GENE_03538 | Prodigal: 2.6 | CDS | 1.1.-.- | — | — | — | Q70LM8 | lgrE_2 | — | — | Linear gramicidin dehydrogenase LgrE |
| Contig1 | 3576746 | 3584368 | + | GENE_03539 | Prodigal: 2.6 | CDS | — | — | — | — | P27206 | srfAA_1 | — | — | Surfactin synthase subunit 1 |
| Contig1 | 3584328 | 3595085 | + | GENE_03540 | Prodigal: 2.6 | CDS | — | — | — | — | Q70LM4 | lgrD_2 | — | — | Linear gramicidin synthase subunit D |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3595168 | 3596421 | + | GENE_03541 | Prodigal: 2.6 | CDS | 2.3.1.39 | — | — | — | Q9R9J2 | fenF_2 | — | — | Malonyl CoA-acyl carrier protein transacylase |
| Contig1 | 3596465 | 3601237 | + | GENE_03542 | Prodigal: 2.6 | CDS | — | — | — | — | P40872 | pksM_3 | — | — | Polyketide synthase PksM |
| Contig1 | 3601423 | 3606213 | + | GENE_03543 | Prodigal: 2.6 | CDS | 2.3.1.- | — | — | — | O31782 | pksN_7 | — | — | Polyketide synthase PksN |
| Contig1 | 3606292 | 3607758 | + | GENE_03544 | Prodigal: 2.6 | CDS | 1.3.99.28 | — | — | — | P17054 | crtI | — | — | Phytoene desaturase (neurosporene-forming) |
| Contig1 | 3607853 | 3614473 | + | GENE_03545 | Prodigal: 2.6 | CDS | 2.3.1.- | — | — | — | P39846 | ppsB_2 | — | — | Plipastatin synthase subunit B |
| Contig1 | 3614494 | 3615537 | + | GENE_03546 | Prodigal: 2.6 | CDS | 2.1.1.- | — | — | — | P16559 | tcmN | — | — | Multifunctional cyclase-dehydratase-3-O-methyl transferase TcmN |
| Contig1 | 3615694 | 3616170 | + | GENE_03547 | Prodigal: 2.6 | CDS | — | — | — | — | O31994 | yolA | — | — | SPBc2 prophage-derived uncharacterized protein YolA precursor |
| Contig1 | 3616248 | 3616499 | + | GENE_03548 | Prodigal: 2.6 | CDS | — | — | — | — | — | — | — | — | hypothetical protein |
| Contig1 | 3616609 | 3617307 | - | GENE_03549 | Prodigal: 2.6 | CDS | — | — | — | — | — | — | — | — | hypothetical protein |
| Contig1 | 3617353 | 3617613 | - | GENE_03550 | Prodigal: 2.6 | CDS | — | — | — | — | — | — | — | — | hypothetical protein |
| Contig1 | 3617781 | 3619418 | + | GENE_03551 | Prodigal: 2.6 | CDS | — | — | — | — | — | — | — | — | Aspartate-proton symporter |
| Contig1 | 3619981 | 3620277 | + | GENE_03552 | Prodigal: 2.6 | CDS | — | — | — | — | — | — | — | — | hypothetical protein |
| Contig1 | 3620234 | 3621184 | + | GENE_03553 | Prodigal: 2.6 | CDS | — | — | — | — | — | — | — | — | hypothetical protein |
| Contig1 | 3621252 | 3621500 | + | GENE_03554 | Prodigal: 2.6 | CDS | — | — | — | — | — | — | — | — | hypothetical protein |
| Contig1 | 3621684 | 3622568 | - | GENE_03555 | Prodigal: 2.6 | CDS | 3.1.4.46 | — | — | — | O07002 | yveE_2 | — | — | putative glycerophosphoryl diester phosphodiesterase 1 |
| Contig1 | 3622664 | 3623998 | - | GENE_03556 | Prodigal: 2.6 | CDS | — | — | — | — | P96236 | glpQ1 | — | — | Glycerol-3-phosphate transporter |
| Contig1 | 3624333 | 3624575 | + | GENE_03557 | Prodigal: 2.6 | CDS | — | — | — | — | P08194 | glpT | — | — | hypothetical protein |
| Contig1 | 3624631 | 3626079 | - | GENE_03558 | Prodigal: 2.6 | CDS | 1.14.14.9 | — | — | — | Q5SJP8 | — | — | — | 4-hydroxyphenylacetate 3-monooxygenase oxygenase component |
| Contig1 | 3626228 | 3626653 | - | GENE_03559 | Prodigal: 2.6 | CDS | — | — | PF01471.12 | — | — | — | — | — | hypothetical protein |
| Contig1 | 3626726 | 3628900 | - | GENE_03560 | Prodigal: 2.6 | CDS | — | — | — | — | — | — | — | — | Putative peptidoglycan binding domain protein |
| Contig1 | 3629280 | 3629723 | + | GENE_03561 | Prodigal: 2.6 | CDS | — | — | PF12844.1 | — | — | — | — | — | hypothetical protein |
| Contig1 | 3629986 | 3630456 | + | GENE_03562 | Prodigal: 2.6 | CDS | — | — | — | — | — | — | — | — | Helix-turn-helix domain protein |
| Contig1 | 3630529 | 3631599 | + | GENE_03563 | Prodigal: 2.6 | CDS | 1.1.1.6 | — | — | — | Q9WYQ4 | gldA_2 | — | — | Glycerol dehydrogenase |
| Contig1 | 3631681 | 3632835 | + | GENE_03564 | Prodigal: 2.6 | CDS | 2.1.2.- | — | — | — | P33221 | purT | — | — | Phosphoribosyl-glycinamide formyltransferase 2 |
| Contig1 | 3633312 | 3633845 | + | GENE_03565 | Prodigal: 2.6 | CDS | 27.8.5 | — | — | MF_01437 | — | pgsA_2 | — | — | CDP-diacylglycerol--glycerol-3-phosphate 3-phosphatidyltransferase |
| Contig1 | 3633836 | 3634324 | + | GENE_03566 | Prodigal: 2.6 | CDS | — | — | — | — | P33366 | yohD | — | — | Inner membrane protein YohD |
| Contig1 | 3634317 | 3635132 | + | GENE_03567 | Prodigal: 2.6 | CDS | 4.1.1.65 | — | — | — | P0A8K1 | psd | — | — | Phosphatidylserine decarboxylase proenzyme |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3635175 | 3635450 | + | GENE_03568 | Prodigal: 2.6 | CDS | — | — | — | — | — | — | — | — | hypothetical protein |
| Contig1 | 3635557 | 3636525 | + | GENE_03569 | Prodigal: 2.6 | CDS | 2.8.1.1 | — | — | MF_01009 | P24943 | glpE_2 | — | — | Thiosulfate sulfurtransferase GlpE |
| Contig1 | 3636562 | 3637812 | — | GENE_03570 | Prodigal: 2.6 | CDS | — | — | — | — | — | gltT_2 | — | — | Proton/sodium-glutamate symport protein |
| Contig1 | 3638183 | 3639250 | + | GENE_03571 | Prodigal: 2.6 | CDS | 2.6.1.42 | — | — | — | O31461 | ilvE | — | — | Branched-chain-amino-acid transaminase 1 |
| Contig1 | 3639291 | 3640754 | — | GENE_03572 | Prodigal: 2.6 | CDS | — | — | — | — | P39636 | rocC_2 | — | — | Amino-acid permease RocC |
| Contig1 | 3640808 | 3641755 | — | GENE_03573 | Prodigal: 2.6 | CDS | 2.1.1.10 | — | — | — | Q47690 | mmuM | — | — | Homocysteine S-methyltransferase |
| Contig1 | 3641871 | 3643307 | — | GENE_03574 | Prodigal: 2.6 | CDS | — | — | — | — | Q45068 | alsT_2 | — | — | Amino-acid carrier protein AlsT |
| Contig1 | 3643332 | 3644315 | — | GENE_03575 | Prodigal: 2.6 | CDS | 3.5.1.2 | — | — | — | O31465 | glsA1 | — | — | Glutaminase 1 |
| Contig1 | 3644559 | 3645851 | + | GENE_03576 | Prodigal: 2.6 | CDS | 2.7.13.3 | — | — | — | P40758 | glnK | — | — | Sensor histidine kinase GlnK |
| Contig1 | 3645853 | 3646800 | + | GENE_03577 | Prodigal: 2.6 | CDS | — | — | — | — | P06534 | spo0A_2 | — | — | Stage 0 sporulation protein A |
| Contig1 | 3647097 | 3648017 | + | GENE_03578 | Prodigal: 2.6 | CDS | — | — | PF01636.17 | — | — | — | — | — | Phosphotransferase enzyme family protein |
| Contig1 | 3648405 | 3648569 | + | GENE_03579 | Prodigal: 2.6 | CDS | — | — | — | — | O31466 | rtpA | — | — | Tryptophan RNA-binding attenuator protein inhibitory protein |
| Contig1 | 3648649 | 3649542 | — | GENE_03580 | Prodigal: 2.6 | CDS | — | — | — | — | O07084 | czcD_1 | — | — | Cadmium, cobalt and zinc/H(+)-K(+) antiporter |
| Contig1 | 3649940 | 3650560 | + | GENE_03581 | Prodigal: 2.6 | CDS | 1.-.-.- | — | — | — | P96692 | mhqN | — | — | Putative NAD(P)H nitroreductase MhqN |
| Contig1 | 3650585 | 3651523 | + | GENE_03582 | Prodigal: 2.6 | CDS | 1.13.11.- | — | — | — | P96693 | mhqO | — | — | Putative ring-cleaving dioxygenase MhqO |
| Contig1 | 3651659 | 3652048 | + | GENE_03583 | Prodigal: 2.6 | CDS | 1.-.-.- | — | — | — | P96694 | mhqP | — | — | Putative oxidoreductase MhqP |
| Contig1 | 3652228 | 3652566 | — | GENE_03584 | Prodigal: 2.6 | CDS | — | — | PF00085.14 | — | — | — | — | — | Thioredoxin |
| Contig1 | 3652905 | 3653288 | — | GENE_03585 | Prodigal: 2.6 | CDS | — | — | — | — | — | — | — | — | hypothetical protein |
| Contig1 | 3653442 | 3653870 | + | GENE_03586 | Prodigal: 2.6 | CDS | — | — | — | — | P42249 | cwlJ | — | — | Cell wall hydrolase CwlJ |
| Contig1 | 3654134 | 3655885 | + | GENE_03587 | Prodigal: 2.6 | CDS | 3.1.3.1 | — | — | — | P42251 | phoD | — | — | Alkaline phosphatase D precursor |
| Contig1 | 3655898 | 3656095 | + | GENE_03588 | Prodigal: 2.6 | CDS | — | — | — | — | O31467 | tatAd | — | — | Sec-independent protein translocase protein TatAd |
| Contig1 | 3656157 | 3656882 | + | GENE_03589 | Prodigal: 2.6 | CDS | — | — | — | — | P42252 | tatC1 | — | — | Sec-independent protein translocase protein TatCd |
| Contig1 | 3656879 | 3657526 | — | GENE_03590 | Prodigal: 2.6 | CDS | 3.4.19.3 | — | — | — | P46107 | pcp | — | — | Pyrrolidone-carboxylate peptidase |
| Contig1 | 3657598 | 3658725 | + | GENE_03591 | Prodigal: 2.6 | CDS | 2.8.1.7 | — | — | — | P99177 | csd_2 | — | — | putative cysteine desulfurase |
| Contig1 | 3658762 | 3660195 | — | GENE_03592 | Prodigal: 2.6 | CDS | — | — | — | — | P0AEJ0 | emrB_3 | — | — | Multidrug export protein EmrB |
| Contig1 | 3660238 | 3660804 | — | GENE_03593 | Prodigal: 2.6 | CDS | — | — | — | — | P42105 | yxaF_2 | — | — | putative HTH-type transcriptional regulator YxaF |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3660982 | 3662097 | + | GENE_03594 | Prodigal: 2.6 | CDS | 3.5.1.1 | — | — | — | O34482 | ansZ | — | — | L-asparaginase 2 precursor |
| Contig1 | 3662294 | 3662938 | + | GENE_03595 | Prodigal: 2.6 | CDS | 3.1.1.3 | PRK05590 | — | — | P37957 | estA | — | — | Lipase EstA precursor |
| Contig1 | 3663076 | 3664146 | + | GENE_03596 | Prodigal: 2.6 | CDS | — | — | — | — | — | — | — | — | hypothetical protein |
| Contig1 | 3664277 | 3665209 | + | GENE_03597 | Prodigal: 2.6 | CDS | 1.1.1.- | — | — | — | P80874 | yhdN_4 | — | — | General stress protein 69 |
| Contig1 | 3665253 | 3666248 | - | GENE_03598 | Prodigal: 2.6 | CDS | — | — | PF11611.2 | — | — | — | — | — | Telomeric repeat-binding factor 2 |
| Contig1 | 3666377 | 3667777 | + | GENE_03599 | Prodigal: 2.6 | CDS | — | — | — | — | — | — | — | — | hypothetical protein |
| Contig1 | 3667978 | 3669336 | + | GENE_03600 | Prodigal: 2.6 | CDS | — | — | — | — | — | — | — | — | hypothetical protein |
| Contig1 | 3669333 | 3669836 | - | GENE_03601 | Prodigal: 2.6 | CDS | 3.4.-.- | — | — | — | O34360 | cwlK | — | — | Peptidoglycan L-alanyl-D-glutamate endopeptidase CwlK precursor |
| Contig1 | 3669946 | 3671067 | + | GENE_03602 | Prodigal: 2.6 | CDS | 3.1.-.- | — | — | — | O34327 | rapJ | — | — | Response regulator aspartate phosphatase J |
| Contig1 | 3671183 | 3671962 | + | GENE_03603 | Prodigal: 2.6 | CDS | 1.1.1.47 | — | — | — | P80869 | yedF | — | — | Glucose 1-dehydrogenase 2 |
| Contig1 | 3672046 | 3673725 | + | GENE_03604 | Prodigal: 2.6 | CDS | 3.2.1.10 | — | — | — | O34364 | yedG | — | — | putative oligo-1,6-glucosidase 2 |
| Contig1 | 3673865 | 3674869 | + | GENE_03605 | Prodigal: 2.6 | CDS | — | — | — | — | O34966 | znuA | — | — | High-affinity zinc uptake system binding-protein ZnuA precursor |
| Contig1 | 3674924 | 3675619 | + | GENE_03606 | Prodigal: 2.6 | CDS | 3.6.3.- | — | — | — | O34946 | znuC | — | — | High-affinity zinc uptake system ATP-binding protein ZnuC |
| Contig1 | 3675583 | 3676416 | + | GENE_03607 | Prodigal: 2.6 | CDS | — | — | — | — | O34610 | znuB | — | — | High-affinity zinc uptake system membrane protein ZnuB |
| Contig1 | 3676461 | 3677456 | - | GENE_03608 | Prodigal: 2.6 | CDS | 1.14.14.3 | — | — | — | P07740 | luxA_3 | — | — | Alkanal monooxygenase alpha chain |
| Contig1 | 3677732 | 3678328 | + | GENE_03609 | Prodigal: 2.6 | CDS | — | — | — | — | P81100 | yceC | — | — | Stress response protein SCP2 |
| Contig1 | 3678352 | 3678933 | + | GENE_03610 | Prodigal: 2.6 | CDS | — | — | — | — | P80875 | yceD_1 | — | — | General stress protein 16U |
| Contig1 | 3678967 | 3679545 | + | GENE_03611 | Prodigal: 2.6 | CDS | — | — | — | — | P80875 | yceD_2 | — | — | General stress protein 16U |
| Contig1 | 3679584 | 3680357 | + | GENE_03612 | Prodigal: 2.6 | CDS | — | — | — | — | P42601 | alx | — | — | Inner membrane protein alx |
| Contig1 | 3680430 | 3682052 | + | GENE_03613 | Prodigal: 2.6 | CDS | — | — | — | — | — | — | — | — | hypothetical protein |
| Contig1 | 3682059 | 3683147 | + | GENE_03614 | Prodigal: 2.6 | CDS | — | — | — | — | P60108 | — | — | — | TelA-like protein |
| Contig1 | 3683262 | 3684464 | + | GENE_03615 | Prodigal: 2.6 | CDS | — | — | — | — | O34691 | naiP | — | — | Putative niacin/nicotinamide transporter NaiP |
| Contig1 | 3684847 | 3686103 | + | GENE_03616 | Prodigal: 2.6 | CDS | 3.6.3.32 | — | — | — | P46920 | opuAA | — | — | Glycine betaine transport ATP-binding protein OpuAA |
| Contig1 | 3686104 | 3686952 | + | GENE_03617 | Prodigal: 2.6 | CDS | — | — | — | — | P46921 | opuAB | — | — | Glycine betaine transport system permease protein OpuAB |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3686952 | 3687833 | + | GENE_03618 | Prodigal: 2.6 | CDS | — | — | — | — | P46922 | opuAC | — | — | Glycine betaine-binding protein OpuAC precursor |
| Contig1 | 3687869 | 3688990 | + | GENE_03619 | Prodigal: 2.6 | CDS | 3.-.-.- | PRK11588 | — | — | P54955 | yxeP_1 | — | — | putative hydrolase YxeP |
| Contig1 | 3689125 | 3690558 | + | GENE_03620 | Prodigal: 2.6 | CDS | — | — | — | — | — | — | — | — | hypothetical protein |
| Contig1 | 3690650 | 3691132 | + | GENE_03621 | Prodigal: 2.6 | CDS | — | — | — | — | — | — | — | — | hypothetical protein |
| Contig1 | 3691380 | 3693359 | + | GENE_03622 | Prodigal: 2.6 | CDS | 3.2.1.1 | — | — | — | P00691 | amyE | — | — | Alpha-amylase precursor |
| Contig1 | 3693630 | 3694583 | + | GENE_03623 | Prodigal: 2.6 | CDS | 1.1.1.27 | — | — | — | P13714 | ldh_2 | — | — | L-lactate dehydrogenase |
| Contig1 | 3694625 | 3696157 | − | GENE_03624 | Prodigal: 2.6 | CDS | — | — | — | — | P96712 | bmr3_4 | — | — | Multidrug resistance protein 3 |
| Contig1 | 3696272 | 3696733 | + | GENE_03625 | Prodigal: 2.6 | CDS | — | — | — | — | O31672 | mhqR_3 | — | — | HTH-type transcriptional regulator MhqR |
| Contig1 | 3696797 | 3697426 | + | GENE_03626 | Prodigal: 2.6 | CDS | — | — | — | — | — | — | — | — | leucine export protein LeuE |
| Contig1 | 3697491 | 3698252 | + | GENE_03627 | Prodigal: 2.6 | CDS | — | — | PF08892.5 | — | — | — | — | — | YqcI/YcgG family protein |
| Contig1 | 3698254 | 3699582 | − | GENE_03628 | Prodigal: 2.6 | CDS | — | PRK10958 | — | — | P15993 | aroP | — | — | Aromatic amino acid transport protein AroP |
| Contig1 | 3699707 | 3700303 | + | GENE_03629 | Prodigal: 2.6 | CDS | — | — | — | — | — | — | — | — | hypothetical protein |
| Contig1 | 3700438 | 3701256 | + | GENE_03630 | Prodigal: 2.6 | CDS | 6.3.1.5 | — | — | — | P08164 | nadE | — | — | NH(3)-dependent NAD(+) synthetase |
| Contig1 | 3701304 | 3701588 | − | GENE_03631 | Prodigal: 2.6 | CDS | — | — | — | — | P82243 | — | — | — | Antimicrobial peptide LCI |
| Contig1 | 3701769 | 3702362 | − | GENE_03632 | Prodigal: 2.6 | CDS | — | — | — | — | P12921 | tmrB | — | — | Tunicamycin resistance protein |
| Contig1 | 3702418 | 3703206 | − | GENE_03633 | Prodigal: 2.6 | CDS | 4.2.1.118 | — | — | — | Q81RQ4 | asbF | — | — | 3-dehydroshikimate dehydratase |
| Contig1 | 3703409 | 3704719 | + | GENE_03634 | Prodigal: 2.6 | CDS | — | — | — | — | P0AA76 | dgoT | — | — | D-galactonate transporter |
| Contig1 | 3704845 | 3705405 | + | GENE_03635 | Prodigal: 2.6 | CDS | 2.7.1.71 | — | — | — | O67925 | aroK | — | — | Shikimate kinase |
| Contig1 | 3705550 | 3706506 | + | GENE_03636 | Prodigal: 2.6 | CDS | 3.1.1.41 | — | — | — | P94388 | cah | — | — | Cephalosporin-C deacetylase |
| Contig1 | 3706572 | 3707357 | + | GENE_03637 | Prodigal: 2.6 | CDS | — | — | PF10127.3 | — | — | — | — | — | putative nucleotidyltransferase |
| Contig1 | 3707545 | 3708456 | + | GENE_03638 | Prodigal: 2.6 | CDS | 1.5.5.2 | — | — | — | O32179 | fadM_2 | — | — | Proline dehydrogenase 1 |
| Contig1 | 3708474 | 3710021 | + | GENE_03639 | Prodigal: 2.6 | CDS | 1.2.1.88 | — | — | — | Q65NN2 | rocA_2 | — | — | 1-pyrroline-5-carboxylate dehydrogenase |
| Contig1 | 3710137 | 3711567 | + | GENE_03640 | Prodigal: 2.6 | CDS | — | — | — | — | Q7A4Q7 | putP_2 | — | — | Sodium/proline symporter |
| Contig1 | 3711725 | 3712960 | + | GENE_03641 | Prodigal: 2.6 | CDS | — | — | — | — | P37047 | cdaR_3 | — | — | Carbohydrate diacid regulator |
| Contig1 | 3713159 | 3714169 | + | GENE_03642 | Prodigal: 2.6 | CDS | 1.18.1.2 | — | — | — | O05268 | yumC_2 | — | — | Ferredoxin--NADP reductase 2 |
| Contig1 | 3714224 | 3714895 | − | GENE_03643 | Prodigal: 2.6 | CDS | 2.1.1.107 | — | — | — | P42437 | nasF_1 | — | — | Uroporphyrinogen-III C-methyltransferase |
| Contig1 | 3714859 | 3715662 | − | GENE_03644 | Prodigal: 2.6 | CDS | 2.1.1.107 | — | — | — | P42437 | nasF_2 | — | — | Uroporphyrinogen-III C-methyltransferase |
| Contig1 | 3715729 | 3716049 | − | GENE_03645 | Prodigal: 2.6 | CDS | 1.7.1.4 | — | — | — | P42436 | nasE | — | — | Assimilatory nitrite reductase [NAD(P)H] small subunit |
| Contig1 | 3716070 | 3718487 | − | GENE_03646 | Prodigal: 2.6 | CDS | 1.7.1.4 | — | — | — | P42435 | nasD | — | — | Nitrite reductase [NAD(P)H] |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3718879 | 3720081 | + | GENE_03647 | Prodigal: 2.6 | CDS | — | — | — | — | P94400 | yciC | — | — | Putative metal chaperone YciC |
| Contig1 | 3720146 | 3721282 | + | GENE_03648 | Prodigal: 2.6 | CDS | 1.2.1.46 | — | — | — | P46154 | fdhA | — | — | Glutathione-independent formaldehyde dehydrogenase |
| Contig1 | 3721294 | 3721731 | + | GENE_03649 | Prodigal: 2.6 | CDS | — | — | PF06271.6 | — | — | — | — | — | RDD family protein |
| Contig1 | 3721804 | 3722124 | + | GENE_03650 | Prodigal: 2.6 | CDS | — | — | — | — | — | — | — | — | hypothetical protein |
| Contig1 | 3722332 | 3722469 | + | GENE_03651 | Prodigal: 2.6 | CDS | 3.2.1.86 | — | — | — | P42403 | bglC | — | — | Aryl-phospho-beta-D-glucosidase BglC |
| Contig1 | 3722599 | 3722997 | − | GENE_03652 | Prodigal: 2.6 | CDS | — | — | — | — | P12669 | nin | — | — | DNA-entry nuclease inhibitor |
| Contig1 | 3723019 | 3723456 | − | GENE_03653 | Prodigal: 2.6 | CDS | 3.-.-.- | — | — | — | P42983 | nucB_2 | — | — | Sporulation-specific extracellular nuclease precursor |
| Contig1 | 3723815 | 3724372 | − | GENE_03654 | Prodigal: 2.6 | CDS | 5.3.1.27 | — | — | — | P42404 | hxlB | — | — | 3-hexulose-6-phosphate isomerase |
| Contig1 | 3724369 | 3725004 | − | GENE_03655 | Prodigal: 2.6 | CDS | 4.1.2.43 | — | — | — | P42405 | hxlA | — | — | 3-hexulose-6-phosphate synthase |
| Contig1 | 3725236 | 3725598 | + | GENE_03656 | Prodigal: 2.6 | CDS | — | — | — | — | P42406 | hxlR | — | — | HTH-type transcriptional activator HxlR |
| Contig1 | 3726187 | 3736941 | + | GENE_03657 | Prodigal: 2.6 | CDS | — | — | — | — | P27206 | srfAA_2 | — | — | Surfactin synthase subunit 1 |
| Contig1 | 3736963 | 3747726 | + | GENE_03658 | Prodigal: 2.6 | CDS | — | — | — | — | Q04747 | srfAB | — | — | Surfactin synthase subunit 2 |
| Contig1 | 3747761 | 3751597 | + | GENE_03659 | Prodigal: 2.6 | CDS | — | — | — | — | Q08787 | srfAC | — | — | Surfactin synthase subunit 3 |
| Contig1 | 3751617 | 3752348 | + | GENE_03660 | Prodigal: 2.6 | CDS | 3.1.2.- | — | — | — | Q08788 | srfAD | — | — | Surfactin synthase thioesterase subunit |
| Contig1 | 3752470 | 3753780 | + | GENE_03661 | Prodigal: 2.6 | CDS | 2.6.1.1 | — | — | — | P23034 | — | — | — | Aspartate aminotransferase |
| Contig1 | 3753816 | 3754490 | − | GENE_03662 | Prodigal: 2.6 | CDS | 2.7.8.- | — | — | — | P39135 | sfp | — | — | 4′-phosphopantetheinyl transferase sfp |
| Contig1 | 3754589 | 3755218 | − | GENE_03663 | Prodigal: 2.6 | CDS | — | — | — | — | — | — | — | — | hypothetical protein |
| Contig1 | 3755318 | 3756061 | − | GENE_03664 | Prodigal: 2.6 | CDS | 3.6.3.- | — | — | — | P39456 | — | — | — | L-cystine import ATP-binding protein TcyC |
| Contig1 | 3756074 | 3756763 | − | GENE_03665 | Prodigal: 2.6 | CDS | — | — | — | — | P42200 | tcyB | — | — | L-cystine transport system permease protein TcyB |
| Contig1 | 3756765 | 3757562 | − | GENE_03666 | Prodigal: 2.6 | CDS | — | — | — | — | P42199 | tcyA | — | — | L-cystine-binding protein TcyA precursor |
| Contig1 | 3757691 | 3758563 | − | GENE_03667 | Prodigal: 2.6 | CDS | — | — | — | — | P20668 | gltC_4 | — | — | HTH-type transcriptional regulator GltC |
| Contig1 | 3758693 | 3759271 | + | GENE_03668 | Prodigal: 2.6 | CDS | 4.1.1.- | — | — | — | P94404 | bsdB | — | — | Phenolic acid decarboxylase subunit B |
| Contig1 | 3759274 | 3760695 | + | GENE_03669 | Prodigal: 2.6 | CDS | 4.1.1.- | — | — | — | P94405 | bsdC | — | — | Phenolic acid decarboxylase subunit C |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3760713 | 3760940 | + | GENE_03670 | Prodigal: 2.6 | CDS | 4.1.1.- | — | — | — | C0H3U9 | bsdD | — | — | Phenolic acid decarboxylase subunit D |
| Contig1 | 3760940 | 3761401 | + | GENE_03671 | Prodigal: 2.6 | CDS | — | — | — | — | — | — | — | — | hypothetical protein |
| Contig1 | 3761444 | 3762922 | − | GENE_03672 | Prodigal: 2.6 | CDS | — | — | — | — | P0C2U3 | dtpT | — | — | Di-/tripeptide transporter |
| Contig1 | 3763201 | 3764946 | + | GENE_03673 | Prodigal: 2.6 | CDS | — | — | PF12708.1 | — | — | — | — | — | Pectate lyase superfamily protein |
| Contig1 | 3765039 | 3765260 | − | GENE_03674 | Prodigal: 2.6 | CDS | — | — | — | — | — | — | — | — | hypothetical protein |
| Contig1 | 3765382 | 3767022 | + | GENE_03675 | Prodigal: 2.6 | CDS | — | — | — | — | P39569 | gerBA_3 | — | — | Spore germination protein B1 |
| Contig1 | 3767009 | 3768235 | + | GENE_03676 | Prodigal: 2.6 | CDS | — | — | — | — | P39571 | gerBC_3 | — | — | Spore germination protein B3 precursor |
| Contig1 | 3768260 | 3769378 | + | GENE_03677 | Prodigal: 2.6 | CDS | — | — | — | — | O31809 | yndE_2 | — | — | Spore germination protein YndE |
| Contig1 | 3769550 | 3770872 | + | GENE_03678 | Prodigal: 2.6 | CDS | 1.14.14.10 | — | — | — | P54989 | ntaA | — | — | Nitrilotriacetate monooxygenase component A |
| Contig1 | 3770886 | 3771377 | + | GENE_03679 | Prodigal: 2.6 | CDS | 2.3.1.- | — | — | — | O34350 | ytmI_2 | — | — | putative N-acetyl-transferase YtmI |
| Contig1 | 3771406 | 3772197 | + | GENE_03680 | Prodigal: 2.6 | CDS | — | — | — | — | P54952 | yxeM | — | — | putative amino-acid-binding protein YxeM precursor |
| Contig1 | 3772220 | 3772894 | + | GENE_03681 | Prodigal: 2.6 | CDS | — | — | — | — | P54953 | yxeN | — | — | putative amino-acid permease protein YxeN |
| Contig1 | 3772908 | 3773657 | + | GENE_03682 | Prodigal: 2.6 | CDS | 3.6.3.- | — | — | — | P54954 | yxeO | — | — | putative amino-acid import ATP-binding protein YxeO |
| Contig1 | 3773675 | 3774826 | + | GENE_03683 | Prodigal: 2.6 | CDS | 3.-.-.- | — | PF03972.8 | — | P54955 | yxeP_2 | — | — | putative hydrolase YxeP |
| Contig1 | 3774823 | 3776169 | + | GENE_03684 | Prodigal: 2.6 | CDS | — | — | — | — | — | — | — | — | MngE/PrpD family protein |
| Contig1 | 3776273 | 3776956 | − | GENE_03685 | Prodigal: 2.6 | CDS | 3.6.3.- | — | — | — | P75957 | lolD | — | — | Lipoprotein-releasing system ATP-binding protein LolD |
| Contig1 | 3776971 | 3778407 | − | GENE_03686 | Prodigal: 2.6 | CDS | 3.6.3.- | — | — | — | Q5MK06 | macB_2 | — | — | Macrolide export ATP-binding/permease protein MacB |
| Contig1 | 3778620 | 3779303 | + | GENE_03687 | Prodigal: 2.6 | CDS | — | — | — | — | Q9L524 | srrA_3 | — | — | Transcriptional regulatory protein SrrA |
| Contig1 | 3779293 | 3780723 | + | GENE_03688 | Prodigal: 2.6 | CDS | 2.7.13.3 | — | — | — | P23545 | phoR_4 | — | — | Alkaline phosphatase synthesis sensor protein PhoR |
| Contig1 | 3780876 | 3782024 | + | GENE_03689 | Prodigal: 2.6 | CDS | 3.1.-.- | — | — | — | P71002 | rapF_3 | — | — | Response regulator aspartate phosphatase F |
| Contig1 | 3782008 | 3782127 | + | GENE_03690 | Prodigal: 2.6 | CDS | — | — | PF11131.2 | — | — | — | — | — | Rap-phr extracellular signalling |
| Contig1 | 3782467 | 3783831 | − | GENE_03691 | Prodigal: 2.6 | CDS | 2.7.2.4 | — | — | — | P94417 | yclM | — | — | Aspartokinase 3 |
| Contig1 | 3784246 | 3785199 | + | GENE_03692 | Prodigal: 2.6 | CDS | — | — | — | — | P40410 | feuB_4 | — | — | Iron-uptake system permease protein FeuB |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3785189 | 3786136 | + | GENE_03693 | Prodigal: 2.6 | CDS | — | — | — | — | Q56992 | hmuU_2 | — | — | Hemin transport system permease protein HmuU |
| Contig1 | 3786130 | 3786888 | + | GENE_03694 | Prodigal: 2.6 | CDS | — | — | — | — | O32188 | yusV_3 | — | — | putative siderophore transport system ATP-binding protein YusV |
| Contig1 | 3786910 | 3787854 | + | GENE_03695 | Prodigal: 2.6 | CDS | — | — | — | — | P94421 | yclQ | — | — | putative ABC transporter solute-binding protein YclQ precursor |
| Contig1 | 3787896 | 3789320 | − | GENE_03696 | Prodigal: 2.6 | CDS | — | — | — | — | P52600 | emrY | — | — | putative multidrug resistance protein EmrY |
| Contig1 | 3789338 | 3790213 | − | GENE_03697 | Prodigal: 2.6 | CDS | — | — | PF00440.17 | — | — | — | — | — | Bacterial regulatory proteins, tetR family |
| Contig1 | 3790374 | 3791120 | − | GENE_03698 | Prodigal: 2.6 | CDS | 1.5.1.39 | — | — | — | P94424 | nfrA2 | — | — | FMN reductase [NAD(P)H] |
| Contig1 | 3791137 | 3791424 | − | GENE_03699 | Prodigal: 2.6 | CDS | 1.-.-.- | — | — | — | P94425 | ycnE | — | — | Putative monooxygenase YcnE |
| Contig1 | 3791566 | 3791880 | + | GENE_03700 | Prodigal: 2.6 | CDS | — | — | — | — | Q55940 | — | — | Transcriptional repressor SmtB homolog | hypothetical protein |
| Contig1 | 3791908 | 3793317 | − | GENE_03701 | Prodigal: 2.6 | CDS | — | — | — | — | P94426 | gabR_2 | — | — | HTH-type transcriptional regulatory protein GabR |
| Contig1 | 3793425 | 3794732 | + | GENE_03702 | Prodigal: 2.6 | CDS | 2.6.1.48 | — | — | — | Q9I6M4 | davT | — | — | 5-aminovalerate aminotransferase DavT |
| Contig1 | 3794838 | 3796226 | + | GENE_03703 | Prodigal: 2.6 | CDS | 1.2.1.79 | — | — | — | P94428 | gabD | — | — | Succinate-semialdehyde dehydrogenase [NADP(+)] |
| Contig1 | 3796381 | 3797244 | + | GENE_03704 | Prodigal: 2.6 | CDS | — | — | — | — | P40420 | glcU | — | — | Glucose uptake protein GlcU |
| Contig1 | 3797265 | 3798050 | + | GENE_03705 | Prodigal: 2.6 | CDS | 1.1.1.47 | — | — | — | P12310 | gdh_3 | — | — | Glucose 1-dehydrogenase |
| Contig1 | 3798096 | 3798707 | − | GENE_03706 | Prodigal: 2.6 | CDS | — | — | — | — | — | — | — | — | hypothetical protein |
| Contig1 | 3798720 | 3800348 | − | GENE_03707 | Prodigal: 2.6 | CDS | — | — | — | — | C0SP95 | ycnJ | — | — | Copper transport protein YcnJ precursor |
| Contig1 | 3800381 | 3800953 | − | GENE_03708 | Prodigal: 2.6 | CDS | — | — | — | — | P94433 | ycnK | — | — | HTH-type transcriptional repressor YcnK |
| Contig1 | 3801130 | 3801471 | + | GENE_03709 | Prodigal: 2.6 | CDS | — | — | — | — | — | — | — | — | hypothetical protein |
| Contig1 | 3801653 | 3803086 | + | GENE_03710 | Prodigal: 2.6 | CDS | — | — | — | — | P00550 | mtlA | — | — | PTS system mannitol-specific EIICBA component |
| Contig1 | 3803112 | 3803543 | + | GENE_03711 | Prodigal: 2.6 | CDS | 2.7.1.- | — | — | — | C0H3V2 | mtlF | — | — | Mannitol-specific phosphotransferase enzyme IIA component |
| Contig1 | 3803545 | 3804666 | + | GENE_03712 | Prodigal: 2.6 | CDS | 1.1.1.17 | — | — | — | P09424 | mtlD | — | — | Mannitol-1-phosphate 5-dehydrogenase |
| Contig1 | 3804736 | 3805131 | + | GENE_03713 | Prodigal: 2.6 | CDS | 4.2.1.59 | — | — | — | P64107 | fabZ_2 | — | — | 3-hydroxyacyl-[acyl-carrier-protein] dehydratase FabZ |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3805170 | 3805334 | − | GENE_03714 | Prodigal: 2.6 | CDS | — | — | — | — | — | — | — | — | hypothetical protein |
| Contig1 | 3805462 | 3806211 | + | GENE_03715 | Prodigal: 2.6 | CDS | 3.1.3.- | PRK05406 | — | — | Q5XD45 | — | — | — | Putative phosphatase |
| Contig1 | 3806417 | 3807181 | + | GENE_03716 | Prodigal: 2.6 | CDS | — | — | — | — | — | — | — | — | LamB/YcsF family protein |
| Contig1 | 3807204 | 3808418 | + | GENE_03717 | Prodigal: 2.6 | CDS | — | — | — | MF_00221 | — | mntH_1 | — | — | Divalent metal cation transporter MntH |
| Contig1 | 3808423 | 3809217 | + | GENE_03718 | Prodigal: 2.6 | CDS | — | — | — | — | — | — | — | — | hypothetical protein |
| Contig1 | 3809247 | 3809978 | + | GENE_03719 | Prodigal: 2.6 | CDS | — | — | — | — | P60495 | kipI | — | — | Kinase A inhibitor KipI |
| Contig1 | 3809975 | 3810988 | + | GENE_03720 | Prodigal: 2.6 | CDS | — | — | — | — | Q7WY77 | kipA | — | — | KipI antagonist |
| Contig1 | 3810976 | 3811755 | + | GENE_03721 | Prodigal: 2.6 | CDS | — | — | — | — | P42968 | kipR | — | — | HTH-type transcriptional regulator KipR |
| Contig1 | 3811820 | 3812461 | + | GENE_03722 | Prodigal: 2.6 | CDS | 3.-.-.- | — | — | — | P42969 | lipC_2 | — | — | Spore germination lipase LipC |
| Contig1 | 3812628 | 3812873 | + | GENE_03723 | Prodigal: 2.6 | CDS | — | — | — | — | — | — | — | — | hypothetical protein |
| Contig1 | 3812844 | 3813164 | − | GENE_03724 | Prodigal: 2.6 | CDS | — | — | PF03992.10 | — | — | — | — | — | Antibiotic biosynthesis monooxygenase |
| Contig1 | 3813321 | 3815324 | + | GENE_03725 | Prodigal: 2.6 | CDS | — | — | — | — | P07944 | pbp | — | — | Beta-lactam-inducible penicillin-binding protein |
| Contig1 | 3815438 | 3816340 | + | GENE_03726 | Prodigal: 2.6 | CDS | 1.-.-.- | — | — | — | P76187 | ydhF | — | — | Oxidoreductase YdhF |
| Contig1 | 3816642 | 3818726 | + | GENE_03727 | Prodigal: 2.6 | CDS | — | — | — | — | P96574 | mtlR | — | — | Transcriptional regulator MtlR |
| Contig1 | 3818948 | 3820462 | + | GENE_03728 | Prodigal: 2.6 | CDS | 6.2.1.3 | — | — | — | O07610 | lcfB_4 | — | — | Long-chain-fatty-acid-CoA ligase |
| Contig1 | 3820621 | 3821481 | + | GENE_03729 | Prodigal: 2.6 | CDS | 1.-.-.- | — | — | — | P80873 | ydaD_3 | — | — | General stress protein 39 |
| Contig1 | 3821494 | 3821997 | + | GENE_03730 | Prodigal: 2.6 | CDS | 5.3.1.- | — | — | — | P96578 | ydaE | — | — | putative D-lyxose ketol-isomerase |
| Contig1 | 3822084 | 3822707 | + | GENE_03731 | Prodigal: 2.6 | CDS | 2.3.1.- | — | — | — | P96579 | ydaF | — | — | Putative ribosomal N-acetyltransferase YdaF |
| Contig1 | 3822714 | 3823136 | + | GENE_03732 | Prodigal: 2.6 | CDS | — | — | — | — | P80238 | ydaG | — | — | General stress protein 26 |
| Contig1 | 3823635 | 3824444 | + | GENE_03733 | Prodigal: 2.6 | CDS | — | — | — | — | — | — | — | — | hypothetical protein |
| Contig1 | 3824482 | 3824772 | + | GENE_03734 | Prodigal: 2.6 | CDS | — | — | — | — | — | — | — | — | putative diguanylate cyclase AdrA |
| Contig1 | 3824949 | 3825383 | + | GENE_03735 | Prodigal: 2.6 | CDS | — | — | — | — | P96582 | lrpC | — | — | HTH-type transcriptional regulator LrpC |
| Contig1 | 3825423 | 3827633 | + | GENE_03736 | Prodigal: 2.6 | CDS | 5.99.1.2 | — | — | — | P14294 | topB | — | — | DNA topoisomerase 3 |
| Contig1 | 3827866 | 3828951 | + | GENE_03737 | Prodigal: 2.6 | CDS | — | — | — | — | — | — | — | — | hypothetical protein |
| Contig1 | 3828932 | 3829780 | + | GENE_03738 | Prodigal: 2.6 | CDS | 2.7.7.65 | — | — | — | P0AAP1 | adrA | — | — | putative diguanylate cyclase AdrA |
| Contig1 | 3829770 | 3831497 | + | GENE_03739 | Prodigal: 2.6 | CDS | — | — | — | — | — | — | — | — | hypothetical protein |
| Contig1 | 3831490 | 3832752 | + | GENE_03740 | Prodigal: 2.6 | CDS | 2.4.1.- | — | — | — | Q3MB01 | — | — | — | Beta-monoglucosyldiacyl-glycerol synthase |
| Contig1 | 3832749 | 3834863 | + | GENE_03741 | Prodigal: 2.6 | CDS | — | PRK11114 | — | — | — | — | — | — | cellulose synthase regulator protein |
| Contig1 | 3835301 | 3837121 | + | GENE_03742 | Prodigal: 2.6 | CDS | — | — | — | — | — | — | — | — | hypothetical protein |
| Contig1 | 3837175 | 3837621 | + | GENE_03743 | Prodigal: 2.6 | CDS | 3.6.1.- | — | — | — | Q9ZDT9 | rppH | — | — | RNA pyrophospho-hydrolase |
| Contig1 | 3837679 | 3839400 | + | GENE_03744 | Prodigal: 2.6 | CDS | — | — | — | — | P96591 | ydaP | — | — | Putative thiamine pyrophosphate-containing protein YdaP |
| Contig1 | 3839661 | 3839891 | − | GENE_03745 | Prodigal: 2.6 | CDS | — | — | — | — | — | — | — | — | hypothetical protein |

TABLE 5-continued

| #ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3840078 | 3840257 | − | GENE_03746 | Prodigal: 2.6 | CDS | — | — | — | — | — | — | — | — | hypothetical protein |
| Contig1 | 3840274 | 3840897 | − | GENE_03747 | Prodigal: 2.6 | CDS | — | — | — | — | — | — | — | — | hypothetical protein |
| Contig1 | 3840927 | 3841505 | − | GENE_03748 | Prodigal: 2.6 | CDS | — | — | — | — | — | — | — | — | hypothetical protein |
| Contig1 | 3841729 | 3841995 | − | GENE_03749 | Prodigal: 2.6 | CDS | — | — | — | — | — | — | — | — | hypothetical protein |
| Contig1 | 3842101 | 3843375 | − | GENE_03750 | Prodigal: 2.6 | CDS | — | — | — | — | P96593 | mntH_2 | — | — | Divalent metal cation transporter MntH |
| Contig1 | 3844015 | 3844368 | + | GENE_03751 | Prodigal: 2.6 | CDS | — | — | PF08239.5 | — | — | — | — | — | Bacterial SH3 domain protein |
| Contig1 | 3844418 | 3844642 | − | GENE_03752 | Prodigal: 2.6 | CDS | — | — | — | — | — | — | — | — | hypothetical protein |
| Contig1 | 3844700 | 3845107 | − | GENE_03753 | Prodigal: 2.6 | CDS | — | — | — | — | — | — | — | — | hypothetical protein |
| Contig1 | 3845104 | 3845469 | − | GENE_03754 | Prodigal: 2.6 | CDS | — | — | — | — | P23895 | emrE | — | — | Multidrug transporter EmrE |
| Contig1 | 3845636 | 3846442 | + | GENE_03755 | Prodigal: 2.6 | CDS | — | — | PF12787.1 | — | — | — | — | — | EcsC protein family protein |
| Contig1 | 3846543 | 3846914 | + | GENE_03756 | Prodigal: 2.6 | CDS | — | — | — | — | P26907 | gsiB | — | — | Glucose starvation-inducible protein B |
| Contig1 | 3847049 | 3847390 | + | GENE_03757 | Prodigal: 2.6 | CDS | — | — | PF07883.5 | — | — | — | — | — | Cupin domain protein |
| Contig1 | 3847384 | 3847743 | + | GENE_03758 | Prodigal: 2.6 | CDS | — | — | — | — | — | — | — | — | hypothetical protein |
| Contig1 | 3847768 | 3848589 | − | GENE_03759 | Prodigal: 2.6 | CDS | 1.11.1.6 | — | — | — | P80878 | — | — | — | putative manganese catalase |
| Contig1 | 3848674 | 3849726 | − | GENE_03760 | Prodigal: 2.6 | CDS | — | — | — | — | P37735 | dctP | — | — | C4-dicarboxylate-binding periplasmic protein precursor |
| Contig1 | 3849807 | 3851429 | + | GENE_03761 | Prodigal: 2.6 | CDS | 2.7.13.3 | — | — | — | P0AEC8 | dcuS_2 | — | — | Sensor histidine kinase DcuS |
| Contig1 | 3851404 | 3852075 | + | GENE_03762 | Prodigal: 2.6 | CDS | — | — | — | — | P0AD01 | dcuR_2 | — | — | Transcriptional regulatory protein DcuR |
| Contig1 | 3852184 | 3853440 | + | GENE_03763 | Prodigal: 2.6 | CDS | — | — | — | — | P96603 | dctA | — | — | C4-dicarboxylate transport protein |
| Contig1 | 3853626 | 3854675 | + | GENE_03764 | Prodigal: 2.6 | CDS | 3.6.3.- | — | — | — | — | — | — | — | hypothetical protein |
| Contig1 | 3854777 | 3855703 | + | GENE_03765 | Prodigal: 2.6 | CDS | — | — | — | — | P94374 | yxlF_6 | — | — | putative ABC transporter ATP-binding protein YxlF |
| Contig1 | 3855696 | 3856463 | + | GENE_03766 | Prodigal: 2.6 | CDS | — | — | PF12730.1 | — | — | — | — | — | ABC-2 family transporter protein |
| Contig1 | 3856558 | 3856893 | − | GENE_03767 | Prodigal: 2.6 | CDS | — | — | — | — | — | — | — | — | hypothetical protein |
| Contig1 | 3857009 | 3858151 | + | GENE_03768 | Prodigal: 2.6 | CDS | 1.3.99.- | — | — | — | P96608 | ydbM | — | — | Putative acyl-CoA dehydrogenase YdbM |
| Contig1 | 3858180 | 3858326 | − | GENE_03769 | Prodigal: 2.6 | CDS | — | — | — | — | — | — | — | — | hypothetical protein |
| Contig1 | 3858313 | 3858492 | − | GENE_03770 | Prodigal: 2.6 | CDS | — | — | — | — | — | — | — | — | hypothetical protein |
| Contig1 | 3858705 | 3859598 | + | GENE_03771 | Prodigal: 2.6 | CDS | — | — | — | — | O53471 | — | — | — | putative cation efflux system protein/MT2084 |
| Contig1 | 3859595 | 3859912 | − | GENE_03772 | Prodigal: 2.6 | CDS | — | — | — | — | P96611 | ydbP | — | — | Thioredoxin-like protein YdbP |
| Contig1 | 3860065 | 3861150 | + | GENE_03773 | Prodigal: 2.6 | CDS | 6.3.2.4 | — | — | — | P63892 | ddl | — | — | D-alanine—D-alanine ligase |
| Contig1 | 3861227 | 3862597 | + | GENE_03774 | Prodigal: 2.6 | CDS | 6.3.2.10 | — | — | — | P11880 | murF | — | — | UDP-N-acetylmuramoyl-tripeptide-D-alanyl-D-alanine ligase |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3862928 | 3864412 | + | GENE_03775 | Prodigal: 2.6 | CDS | 3.6.4.13 | — | — | — | P96614 | cshA | — | — | DEAD-box ATP-dependent RNA helicase CshA |
| Contig1 | 3864524 | 3865006 | + | GENE_03776 | Prodigal: 2.6 | CDS | — | — | PF03703.8 | — | — | — | — | — | Bacterial membrane flanked domain protein |
| Contig1 | 3864999 | 3866462 | + | GENE_03777 | Prodigal: 2.6 | CDS | — | — | PF03703.8 | — | — | — | — | — | Bacterial membrane flanked domain protein |
| Contig1 | 3866459 | 3867058 | - | GENE_03778 | Prodigal: 2.6 | CDS | 3.4.21.105 | — | — | — | P54493 | gluP | — | — | Rhomboid protease GluP |
| Contig1 | 3867151 | 3867516 | + | GENE_03779 | Prodigal: 2.6 | CDS | 2.7.8.7 | — | — | — | P96618 | acpS | — | — | Holo-[acyl-carrier-protein] synthase |
| Contig1 | 3867681 | 3868688 | + | GENE_03780 | Prodigal: 2.6 | CDS | — | — | — | — | P96619 | ydcC | — | — | Sporulation protein YdcC |
| Contig1 | 3868805 | 3869974 | + | GENE_03781 | Prodigal: 2.6 | CDS | 5.1.1.1 | — | — | — | P10724 | alr_2 | — | — | Alanine racemase |
| Contig1 | 3870094 | 3870375 | + | GENE_03782 | Prodigal: 2.6 | CDS | — | — | — | — | P96621 | ndoAI | — | — | Antitoxin EndoAI |
| Contig1 | 3870381 | 3870731 | + | GENE_03783 | Prodigal: 2.6 | CDS | 3.1.-.- | — | — | — | P96622 | ndoA | — | — | mRNA interferase EndoA |
| Contig1 | 3870849 | 3871670 | + | GENE_03784 | Prodigal: 2.6 | CDS | — | — | — | — | P42409 | rsbRA | — | — | RsbT co-antagonist protein RsbRA |
| Contig1 | 3871675 | 3872040 | + | GENE_03785 | Prodigal: 2.6 | CDS | — | — | — | — | P42410 | rsbS | — | — | RsbT antagonist protein RsbS |
| Contig1 | 3872043 | 3872444 | + | GENE_03786 | Prodigal: 2.6 | CDS | 2.7.11.1 | — | — | — | P42411 | rsbT | — | — | Serine/threonine-protein kinase RsbT |
| Contig1 | 3872456 | 3873463 | + | GENE_03787 | Prodigal: 2.6 | CDS | 3.1.3.3 | — | — | — | P40399 | rsbU_1 | — | — | Phosphoserine phosphatase RsbU |
| Contig1 | 3873527 | 3873856 | + | GENE_03788 | Prodigal: 2.6 | CDS | — | — | — | — | P17903 | rsbV | — | — | Anti-sigma-B factor antagonist |
| Contig1 | 3873853 | 3874335 | + | GENE_03789 | Prodigal: 2.6 | CDS | 2.7.11.1 | — | — | — | P17904 | rsbW | — | — | Serine-protein kinase RsbW |
| Contig1 | 3874301 | 3875089 | + | GENE_03790 | Prodigal: 2.6 | CDS | — | — | — | — | P06574 | sigB | — | — | RNA polymerase sigma-B factor |
| Contig1 | 3875089 | 3875691 | + | GENE_03791 | Prodigal: 2.6 | CDS | 3.1.3.3 | — | — | — | P40399 | rsbU_2 | — | — | Phosphoserine phosphatase RsbU |
| Contig1 | 3875764 | 3877923 | + | GENE_03792 | Prodigal: 2.6 | CDS | — | — | — | — | P0AG67 | rpsA | — | — | 30S ribosomal protein S1 |
| Contig1 | 3877933 | 3878046 | - | GENE_03793 | Prodigal: 2.6 | CDS | — | — | — | — | — | — | — | — | hypothetical protein |
| Contig1 | 3878263 | 3878595 | + | GENE_03794 | Prodigal: 2.6 | CDS | — | — | — | MF_00745 | — | — | — | — | Protein SprT-like protein |
| Contig1 | 3878731 | 3878805 | + | GENE_03795 | Aragorn: 1.2 | tRNA | — | — | — | — | — | — | — | — | tRNA-Asn(gtt) |
| Contig1 | 3878810 | 3878900 | + | GENE_03796 | Aragorn: 1.2 | tRNA | — | — | — | — | — | — | — | — | tRNA-Ser(gct) |
| Contig1 | 3878920 | 3878994 | + | GENE_03797 | Aragorn: 1.2 | tRNA | — | — | — | — | — | — | — | — | tRNA-Glu(ttc) |
| Contig1 | 3879006 | 3879080 | + | GENE_03798 | Aragorn: 1.2 | tRNA | — | — | — | — | — | — | — | — | tRNA-Gln(ttg) |
| Contig1 | 3879114 | 3879189 | + | GENE_03799 | Aragorn: 1.2 | tRNA | — | — | — | — | — | — | — | — | tRNA-Lys(ttt) |
| Contig1 | 3879198 | 3879280 | + | GENE_03800 | Aragorn: 1.2 | tRNA | — | — | — | — | — | — | — | — | tRNA-Leu(tag) |
| Contig1 | 3879348 | 3879431 | + | GENE_03801 | Aragorn: 1.2 | tRNA | — | — | — | — | — | — | — | — | tRNA-Leu(gag) |
| Contig1 | 3879937 | 3880386 | - | GENE_03802 | Prodigal: 2.6 | CDS | — | — | — | — | — | — | — | — | hypothetical protein |
| Contig1 | 3881525 | 3882319 | + | GENE_03803 | Prodigal: 2.6 | CDS | 3.1.1.2 | — | — | — | P22862 | — | — | — | Arylesterase |
| Contig1 | 3883358 | 3884761 | + | GENE_03804 | Prodigal: 2.6 | CDS | — | — | — | — | P0C0L7 | proP | — | — | Proline/betaine transporter |
| Contig1 | 3885322 | 3886269 | - | GENE_03805 | Prodigal: 2.6 | CDS | — | — | — | — | P71667 | nlhH | — | — | Carboxylesterase NlhH |
| Contig1 | 3886360 | 3886779 | - | GENE_03806 | Prodigal: 2.6 | CDS | 3.1.1.1 | — | — | — | P80242 | ohrB_2 | — | — | Organic hydroperoxide resistance protein OhrB |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3887121 | 3887558 | + | GENE_03807 | Prodigal: 2.6 | CDS | — | — | — | — | O34777 | ohrR_3 | — | — | Organic hydroperoxide resistance transcriptional regulator |
| Contig1 | 3888042 | 3888446 | − | GENE_03808 | Prodigal: 2.6 | CDS | — | — | — | — | P71036 | ywnA_2 | — | — | Putative HTH-type transcriptional regulator YwnA |
| Contig1 | 3888684 | 3889322 | + | GENE_03809 | Prodigal: 2.6 | CDS | — | — | — | — | — | — | — | — | NmrA-like family protein |
| Contig1 | 3889884 | 3890087 | + | GENE_03810 | Prodigal: 2.6 | CDS | — | — | PF05368.7 | — | P39158 | cspC | — | — | Cold shock protein CspC |
| Contig1 | 3890689 | 3891150 | − | GENE_03811 | Prodigal: 2.6 | CDS | — | — | — | — | A0R561 | carD | — | — | RNA polymerase-binding transcription factor CarD |
| Contig1 | 3891690 | 3892370 | + | GENE_03812 | Prodigal: 2.6 | CDS | 5.1.1.- | — | — | — | P32960 | racX | — | — | putative amino-acid racemase |
| Contig1 | 3892477 | 3893046 | − | GENE_03813 | Prodigal: 2.6 | CDS | — | — | — | — | — | — | — | — | hypothetical protein |
| Contig1 | 3893033 | 3893350 | − | GENE_03814 | Prodigal: 2.6 | CDS | — | — | PF03551.8 | — | — | — | — | — | Transcriptional regulator PadR-like family protein |
| Contig1 | 3893703 | 3894608 | + | GENE_03815 | Prodigal: 2.6 | CDS | 2.3.1.- | — | — | — | P94562 | ysnE_2 | — | — | putative N-acetyltransferase YsnE |
| Contig1 | 3894625 | 3895914 | − | GENE_03816 | Prodigal: 2.6 | CDS | — | — | — | — | Q51330 | oxlT | — | — | Oxalate:formate antiporter |
| Contig1 | 3896006 | 3896974 | − | GENE_03817 | Prodigal: 2.6 | CDS | 3.1.1.- | — | — | — | O06996 | cotR | — | — | Putative sporulation hydrolase CotR |
| Contig1 | 3897178 | 3897654 | + | GENE_03818 | Prodigal: 2.6 | CDS | — | — | PF12867.1 | — | — | — | — | — | DinB superfamily protein |
| Contig1 | 3897690 | 3898055 | + | GENE_03819 | Prodigal: 2.6 | CDS | 1.13.11.6 | — | — | MF_00825 | — | HAAO | — | — | 3-hydroxyanthranilate 3,4-dioxygenase |
| Contig1 | 3898702 | 3899022 | + | GENE_03820 | Prodigal: 2.6 | CDS | — | — | — | — | — | — | — | — | hypothetical protein |
| Contig1 | 3899413 | 3900759 | + | GENE_03821 | Prodigal: 2.6 | CDS | 1.21.-.- | — | — | — | O06997 | yvdP_2 | — | — | putative FAD-linked oxidoreductase YvdP |
| Contig1 | 3900837 | 3901136 | − | GENE_03822 | Prodigal: 2.6 | CDS | — | — | PF12681.1 | — | — | — | — | — | Glyoxalase-like domain protein |
| Contig1 | 3901331 | 3902272 | + | GENE_03823 | Prodigal: 2.6 | CDS | — | — | — | — | O07084 | czcD_2 | — | — | Cadmium, cobalt and zinc/H(+)-K(+) antiporter |
| Contig1 | 3902335 | 3903372 | + | GENE_03824 | Prodigal: 2.6 | CDS | 1.-.-.- | — | — | — | O07085 | czcO | — | — | putative oxidoreductase CzcO |
| Contig1 | 3903720 | 3904253 | + | GENE_03825 | Prodigal: 2.6 | CDS | — | — | PF07883.5 | — | — | — | — | — | Cupin domain protein |
| Contig1 | 3904511 | 3905038 | − | GENE_03826 | Prodigal: 2.6 | CDS | — | — | PF12867.1 | — | — | — | — | — | DinB superfamily protein |
| Contig1 | 3905136 | 3905678 | + | GENE_03827 | Prodigal: 2.6 | CDS | 4.3.3.7 | — | — | — | O67216 | dapA_2 | — | — | 4-hydroxy-tetrahydrodipicolinate synthase |
| Contig1 | 3905734 | 3906114 | + | GENE_03828 | Prodigal: 2.6 | CDS | — | — | PF05014.9 | — | — | — | — | — | hypothetical protein |
| Contig1 | 3906413 | 3906874 | + | GENE_03829 | Prodigal: 2.6 | CDS | — | — | — | — | — | — | — | — | Nucleoside 2-deoxyribosyltransferase |
| Contig1 | 3906874 | 3907884 | + | GENE_03830 | Prodigal: 2.6 | CDS | 2.1.1.45 | — | — | — | Q8NS38 | thyA | — | — | Thymidylate synthase |
| Contig1 | 3907881 | 3908639 | + | GENE_03831 | Prodigal: 2.6 | CDS | 2.1.1.- | — | — | — | E5KIC0 | cypM_2 | — | — | Cypemycin methyltransferase |
| Contig1 | 3908654 | 3909502 | + | GENE_03832 | Prodigal: 2.6 | CDS | 2.7.1.49 | — | — | — | P99124 | thiD_2 | — | — | Hydroxymethyl pyrimidine/phosphomethylpyrimidine kinase |
| Contig1 | 3909483 | 3910718 | + | GENE_03833 | Prodigal: 2.6 | CDS | 3.-.-.- | — | — | — | O32125 | yutF_2 | — | — | putative hydrolase YutF |
| Contig1 | 3910907 | 3911869 | + | GENE_03834 | Prodigal: 2.6 | CDS | — | — | PF01758.10 | — | — | — | — | — | Sodium Bile acid symporter family protein |

TABLE 5-continued

| # ContigID | Start | End | Strand | GeneID | Prediction Tool | Type | EC_Number | CLUSTERS | Pfam | HAMAP | UniProt | GeneName | Repeat-Family | Note | Description |
|---|---|---|---|---|---|---|---|---|---|---|---|---|---|---|---|
| Contig1 | 3911928 | 3912977 | − | GENE_03835 | Prodigal: 2.6 | CDS | 1.1.1 | — | — | — | C0SPA5 | adhA | — | — | putative formaldehyde dehydrogenase AdhA |
| Contig1 | 3913137 | 3913541 | + | GENE_03836 | Prodigal: 2.6 | CDS | — | — | — | — | O06008 | adhR_2 | — | — | HTH-type transcriptional regulator AdhR |
| Contig1 | 3913765 | 3915054 | + | GENE_03837 | Prodigal: 2.6 | CDS | — | — | — | — | O07553 | nhaC_3 | — | — | Na(+)/H(+) antiporter NhaC |
| Contig1 | 3915092 | 3916474 | − | GENE_03838 | Prodigal: 2.6 | CDS | — | — | — | — | P94426 | gabR_3 | — | — | HTH-type transcriptional regulatory protein GabR |
| Contig1 | 3916593 | 3917213 | + | GENE_03839 | Prodigal: 2.6 | CDS | — | — | — | — | P21341 | paiB_2 | — | — | Protease synthase and sporulation protein PAI 2 |
| Contig1 | 3917262 | 3917624 | − | GENE_03840 | Prodigal: 2.6 | CDS | — | — | — | — | — | — | — | — | hypothetical protein |
| Contig1 | 3917841 | 3919031 | − | GENE_03841 | Prodigal: 2.6 | CDS | — | — | — | — | P43531 | ynfM_3 | — | — | Inner membrane transport protein YnfM |
| Contig1 | 3919276 | 3919854 | + | GENE_03842 | Prodigal: 2.6 | CDS | — | — | — | — | P43506 | bm3R1_4 | — | — | HTH-type transcriptional repressor Bm3R1 |
| Contig1 | 3920047 | 3920346 | − | GENE_03843 | Prodigal: 2.6 | CDS | — | — | — | — | P23261 | cotF_4 | — | — | Spore coat protein F precursor |
| Contig1 | 3920361 | 3920558 | − | GENE_03844 | Prodigal: 2.6 | CDS | — | — | — | — | — | — | — | — | hypothetical protein |
| Contig1 | 3920577 | 3921713 | − | GENE_03845 | Prodigal: 2.6 | CDS | 1.2.99.4 | — | — | — | Q52078 | fdm_2 | — | — | Formaldehyde dismutase |
| Contig1 | 3921732 | 3922100 | − | GENE_03846 | Prodigal: 2.6 | CDS | — | — | — | — | P23261 | cotF_5 | — | — | Spore coat protein F precursor |
| Contig1 | 3922118 | 3922363 | − | GENE_03847 | Prodigal: 2.6 | CDS | — | — | — | — | — | — | — | — | hypothetical protein |
| Contig1 | 3922714 | 3923991 | + | GENE_03848 | Prodigal: 2.6 | CDS | 2.7.13.3 | — | — | — | O32198 | liaS_4 | — | — | Sensor histidine kinase LiaS |
| Contig1 | 3923984 | 3924619 | + | GENE_03849 | Prodigal: 2.6 | CDS | — | — | — | — | Q7A4R9 | vraR_2 | — | — | Response regulator protein VraR |
| Contig1 | 3924718 | 3925566 | + | GENE_03850 | Prodigal: 2.6 | CDS | — | — | — | — | P96687 | ydfJ_2 | — | — | Membrane protein YdfJ |
| Contig1 | 3925569 | 3926837 | + | GENE_03851 | Prodigal: 2.6 | CDS | — | — | — | — | P96687 | ydfJ_3 | — | — | Membrane protein YdfJ |
| Contig1 | 3926906 | 3927274 | − | GENE_03852 | Prodigal: 2.6 | CDS | 2.4.2.- | — | — | — | O33341 | — | — | — | Putative glutamine amidotransferase |
| Contig1 | 3927268 | 3927507 | − | GENE_03853 | Prodigal: 2.6 | CDS | 2.4.2.- | — | — | — | O33341 | — | — | — | Putative glutamine amidotransferase |
| Contig1 | 3927763 | 3928221 | − | GENE_03854 | Prodigal: 2.6 | CDS | — | — | — | — | P63389 | yheS_5 | — | — | putative ABC transporter ATP-binding protein YheS |

Although the invention has been described in conjunction with specific embodiments thereof, it is evident tint many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

1. Cho, K.-M. (2008). "Characterization of potential probiotics *Bacillus subtilis* CS90 from soybean paste (doenjang) and its antimicrobial activity against food-borne pathogens." Journal of Applied Biological Chemistry 51(6): 285-291.
2. FRANZ, C. M., A. HUMMEL and W. H. HOLZAPFEL (2005). "Problems related to the safety assessment of lactic acid bacteria starter cultures and probiotics." Mitteilungen aus Lebensmitteluntersuchung und Hygiene 96(1): 39-65.
3. Ginsberg, H. S., L. L. Moldawer, P. B. Sehgal, M. Redington, P. L. Kilian, R. M. Chanock and G. A. Prince (1991). "A mouse model for investigating the molecular pathogenesis of adenovirus pneumonia." Proceedings of the National Academy of Sciences 88(5): 1651-1655.
4. Holzapfel, W. H. and U. Schillinger (2002). "Introduction to pre- and probiotics." Food Research International 35(2): 109-116.
5. Hong, H., J. M. Huang, R. Khaneja, L. Hiep, M. Urdaci and S. Cutting (2008). "The safety of *Bacillus subtilis* and *Bacillus indicus* as food probiotics." Journal of applied microbiology 105(2): 510-520.
6. Jeon, H. H., J. Y. Jung, B.-H. Chun, M.-D. Kim, S. Y. Baek, J. Y. Moon, S.-H. Yeo and C. O. Jeon (2016). "Screening and characterization of potential *Bacillus* starter cultures for fermenting low salt soybean paste (doenjang)." J. Microbiol. Biotechnol 26(4): 666-674.
7. Jorgensen, J. H. and J. D. Turnidge (2015). Susceptibility test methods: dilution and disk diffusion methods. Manual of Clinical Microbiology, Eleventh Edition, American Society of Microbiology: 1253-1273.
8. Kong, X., G. R. Hellermann, G. Patton, M. Kumar, A. Behera, T. S. Randall, J. Zhang, R. F. Lockey and S. S. Mohapatra (2005). "An immunocompromised BALB/c mouse model for respiratory syncytial virus infection." Virology journal 2(1): 3.
9. Leuschner, R. G., T. P. Robinson, M. Hugas, P. S. Cocconcelli, F. Richard-Forget, G. Klein, T. R. Licht, C. Nguyen-The, A. Querol and M. Richardson (2010). "Qualified presumption of safety (QPS): a generic risk assessment approach for biological agents notified to the European Food Safety Authority (EFSA)." Trends in Food Science & Technology 21(9): 425-435.
10. Reysenbach, A.-L., L. J. Giver, G. S. Wickham and N. R. Pace (1992). "Differential amplification of rRNA genes by polymerase chain reaction." Applied and Environmental Microbiology 58(10): 3417-3418.
11. Sorokulova, I. B., I. V. Pinchuk, M. Denayrolles, I. G. Osipova, J. M. Huang, S. M. Cutting and M. C. Urdaci (2008). "The safety of two *Bacillus* probiotic strains for human use." Digestive diseases and sciences 53(4): 954-963.
12. Wang, L.-T., F.-L. Lee, C.-J. Tai and H. Kasai (2007). "Comparison of gyrB gene sequences, 16S rRNA gene sequences and DNA-DNA hybridization in the *Bacillus subtilis* group." International Journal of Systematic and Evolutionary Microbiology 57(8): 1846-1850.
13. Xu, S. J., D. H. Park, J.-Y. Kim and B.-S. Kim (2016). "Biological control of gray mold and growth promotion of tomato using *Bacillus* spp. isolated from soil." Tropical Plant Pathology 41(3): 169-176.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11618880B2). An electronic copy of the "Sequence Listing" will also be available from the USPTO upon request and payment of the fee set forth in 37 CFR 1.19(b)(3).

What is claimed is:

1. A method of controlling a population of pathogenic bacteria and/or fungi, the method comprising providing an effective amount of the isolated bacterial strain *Bacillus amyloliquefaciens* 298, a sample of which having been deposited as KCTC 13469BP at the Korean Collection for Type Cultures, thereby controlling the population of pathogenic bacteria and/or fungi.

2. The method of claim 1, wherein said isolated microbial strain is purified to a level of at least 99%.

* * * * *